(12) United States Patent
Chaudhary et al.

(10) Patent No.: US 7,642,339 B2
(45) Date of Patent: Jan. 5, 2010

(54) ANTIVIRAL COMPOUNDS

(75) Inventors: Kleem Chaudhary, Hayward, CA (US); Melissa Fleury, Redwood City, CA (US); Choung U. Kim, San Carlos, CA (US); Darren J. McMurtrie, San Mateo, CA (US); Xiaoning C. Sheng, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 192 days.

(21) Appl. No.: 11/184,429

(22) Filed: Jul. 18, 2005

(65) Prior Publication Data

US 2006/0122123 A1 Jun. 8, 2006

Related U.S. Application Data

(60) Provisional application No. 60/588,633, filed on Jul. 16, 2004, provisional application No. 60/591,635, filed on Jul. 27, 2004.

(51) Int. Cl.
*A61K 38/00* (2006.01)
(52) U.S. Cl. .......................................... 530/340; 514/9
(58) Field of Classification Search ....................... None
See application file for complete search history.

(56) References Cited

FOREIGN PATENT DOCUMENTS

WO    WO 03/064416    *    8/2003

* cited by examiner

*Primary Examiner*—Cecilia Tsang
*Assistant Examiner*—Thomas S Heard
(74) *Attorney, Agent, or Firm*—Barry F. McGurl; Gilead Sciences, Inc.

(57) ABSTRACT

The invention is related to phosphorus substituted anti-viral inhibitory compounds, compositions containing such compounds, and therapeutic methods that include the administration of such compounds, as well as to processes and intermediates useful for preparing such compounds.

9 Claims, No Drawings

ANTIVIRAL COMPOUNDS

This application claims the benefit of U.S. Provisional Application Nos. 60/588,633 filed Jul. 16, 2004 60/591,635 filed Jul. 27, 2004

FIELD OF THE INVENTION

The invention relates generally to compounds with HCV inhibitory activity.

BACKGROUND OF THE INVENTION

Improving the delivery of drugs and other agents to target cells and tissues has been the focus of considerable research for many years. Though many attempts have been made to develop effective methods for importing biologically active molecules into cells, both in vivo and in vitro, none has proved to be entirely satisfactory. Optimizing the association of the inhibitory drug with its intracellular target, while minimizing intercellular redistribution of the drug, e.g., to neighboring cells, is often difficult or inefficient.

Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., glucocorticoids and other anti-inflammatory drugs) that can be administered. By comparison, although oral administration of drugs is generally recognized as a convenient and economical method of administration, oral administration can result in either (a) uptake of the drug through the cellular and tissue barriers, e.g., blood/brain, epithelial, cell membrane, resulting in undesirable systemic distribution, or (b) temporary residence of the drug within the gastrointestinal tract. Accordingly, a major goal has been to develop methods for specifically targeting agents to cells and tissues. Benefits of such treatment includes avoiding the general physiological effects of inappropriate delivery of such agents to other cells and tissues, such as uninfected cells.

Hepatitis C is recognized as a chronic viral disease of the liver which is characterized by liver disease. Although drugs targeting the liver are in wide use and have shown effectiveness, toxicity and other side effects have limited their usefulness.

Assay methods capable of determining the presence, absence or amounts of HCV are of practical utility in the search for inhibitors as well as for diagnosing the presence of HCV.

Inhibitors of HCV are useful to limit the establishment and progression of infection by HCV as well as in diagnostic assays for HCV.

There is a need for HCV therapeutic agents, i.e. drugs, having improved inhibitory and pharmacokinetic properties, including enhanced activity against development of viral resistance, improved oral bioavailability, greater potency and extended effective half-life in vivo. New HCV inhibitors should have fewer side effects, less complicated dosing schedules, and be orally active. In particular, there is a need for a less onerous dosage regimen, such as one pill, once per day.

SUMMARY OF THE INVENTION

Intracellular targeting may be achieved by methods and compositions that allow accumulation or retention of biologically active agents inside cells. The present invention provides compositions and methods for inhibition of HCV or therapeutic activity against HCV.

The present invention relates generally to the accumulation or retention of therapeutic compounds inside cells. The invention is more particularly related to attaining high concentrations of phosphonate molecules in liver cells. Such effective targeting may be applicable to a variety of therapeutic formulations and procedures.

Compositions of the invention include anti-viral compounds having usually at least one phosphonate group. Accordingly, in one embodiment, the invention provides a compound of the invention which is linked to one or more phosphonate groups.

In another embodiment, the invention provides a conjugate, or a pharmaceutically acceptable salt or solvate thereof.

The present invention provides a compound of formula I:

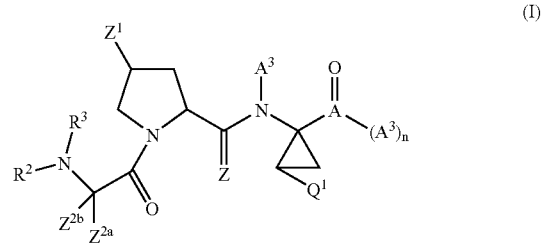

(I)

or a pharmaceutically acceptable salt, enantiomer, solvate or prodrug thereof, wherein, $R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH$_2$, —NH((C1-4)alkyl) and —N((C1-4)alkyl)$_2$, —CONH$_2$ and —CONH—(C1-4)alkyl;

$R^3$ is H or (C1-6)alkyl;

Z is O, S, or N;

$Z^1$ is O, N, C, or S, optionally substituted with one or more $A^3$;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with $R^1$, $R^2$, $Q^1$, or any $A^3$;

$Z^{2b}$ is H, (C1-6)alkyl, (C2-8)alkenyl, (C2-8)alkynyl;

$Q^1$ is (C1-8)alkyl, (C2-8)alkenyl, or (C2-8)alkynyl.

In one embodiment of the invention A is C or P.

In another embodiment of the invention A is P.

In another embodiment of the invention A is P or C, optionally substituted with one or two $A^3$, with the proviso that when A is C, then $A^3$ is selected from —P($Y^1$)($A^2$)($A^2$), —P($Y^1$)($Y^1A^2$)($Y^1A^2$), —P($Y^1$)($Y^1A^2$)($A^2$), —P($Y^1$)(N$A^2$) ($A^2$), —P($Y^1$)(N$A^2$)(N$A^2$), —P($Y^1$)($Y^1A^2$)(N$A^2$), —N—P($Y^1$)($A^2$)($A^2$), —NS(O)$_2$$A^2Y^1$(CH$_2$)$_r$P($Y^1$)($A^2$)$_2$, or —NS(O)$_2$($A^2$), or when either $Z^{2a}$ or $Z^{2b}$ forms a 7-membered chain ring with $Q^1$, one of $Z^{2a}$ and $Z^{2b}$ is H and $R^2$ is not —C(O)OCH$_3$, —C(O)O$^t$Bu, or —C(O)O-cyclopentyl, or at least one $A^3$ is P($Y^1$)($A^2$)($A^2$), —P($Y^1$)($Y^1A^2$)($Y^1A^2$), —P($Y^1$)($Y^1A^2$)($A^2$), —P($Y^1$)(N$A^2$)($A^2$), —P($Y^1$)(N$A^2$)(N$A^2$), —P($Y^1$)($Y^1A^2$)(N$A^2$) or —N—P($Y^1$)($A^2$)($A^2$);

n is 1 or 2;

$A^3$ is independently selected from H, —OH, —C(O), —C(O)OH, cyano, alkyl, alkenyl, alkynyl, amino, amido, imido, imino, halogen, CF$_3$, CH$_2$CF$_3$, cycloalkyl, nitro, aryl aralkyl, alkoxy, aryloxy, heterocycle, heteroaryl, —C($A^2$)$_2$, C(O)$A^2$, —C(O)O$A^2$, —O($A^2$), —N($A^2$)$_2$, —S($A^2$), —CH$_2$P(O)($A^2$)(O$A^2$), —CH$_2$P(O)($A^2$)(N($A^2$)$_2$), —CH$_2$P(O)(O$A^2$)(O$A^2$), —OCH$_2$P(O)(O$A^2$)(O$A^2$), —OCH$_2$P(O)($A^2$)(O$A^2$), —OCH$_2$P(O)($A^2$)(N($A^2$)$_2$), —C(O)OCH$_2$P(O)(O$A^2$)(O$A^2$), —C(O)OCH$_2$P(O)($A^2$) (O$A^2$), —C(O)OCH$_2$P(O)($A^2$)(N($A^2$)$_2$), —CH$_2$P(O)(O$A^2$)(N($A^2$)$_2$), —OCH$_2$P(O)(O$A^2$)(N($A^2$)$_2$), —C(O)OCH$_2$P(O)(O$A^2$)(N($A^2$)$_2$), —CH$_2$P(O)(N($A^2$)$_2$)(N($A^2$)$_2$), —C(O)OCH$_2$P(O)(N($A^2$)$_2$)(N($A^2$)$_2$), —OCH$_2$P(O)(N($A^2$)$_2$)(N($A^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C(O)—O-alkyl, —(CH$_2$)$_m$O—C(O)—O-cyclokyl, —N(H)C(Me)C(O)O-alkyl, or alkoxy arylsulfonamide, whereas each maybe optionally substituted with —R$^1$, —P(O)(O$A^2$)(O$A^2$), —P(O)(O$A^2$)(N($A^2$)$_2$), —P(O)($A^2$)(O$A^2$), —P(O)($A^2$)(N($A^2$)$_2$), or P(O)(N($A^2$)$_2$)(N($A^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cyclopentyl, —N(H)C(CH$_3$)C(O)O-alkyl, or alkoxy arylsulfonamide, optionally substituted with R$^1$; or $A^3$ is independently selected from —(CH$_2$)$_m$—, —C(O)O—, —NH—, —C($A^2$)$_2$—, to form a carbocyclic or heterocyclic ring with any other $A^3$ or $Q^1$;

$A^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with $A^3$; and m is 0 to 6.

The present invention provides a compound of formula 1, wherein the compound is an enantiomer.

The present invention provides a compound of formula I:

(I)

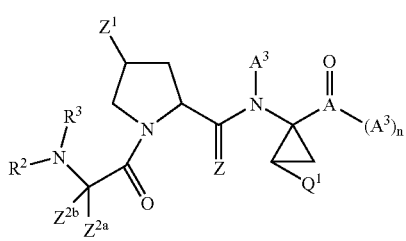

or a pharmaceutically acceptable salt, enantiomer, solvate or prodrug thereof, wherein, $R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which R$^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH$_2$, —NH((C1-4)alkyl) and —N((C1-4)alkyl)$_2$, —CONH$_2$ and —CONH—(C1-4)alkyl;

$R^3$ is H or (C1-6)alkyl;

Z is O, S, or N;

$Z^1$ is O, N, C, or S, optionally substituted with one or more $A^3$;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with $R^1$, $R^2$, $Q^1$, or any $A^3$;

$Z^{2b}$ is H, (C1-6)alkyl, (C2-8)alkenyl, (C2-8)alkynyl;

$Q^1$ is (C1-8)alkyl, (C2-8)alkenyl, or (C2-8)alkynyl;

A is C or P;

n is 1 or 2;

$A^3$ is independently selected from H, —OH, —C(O), —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, heteroaryl, —C($A^2$)$_2$, C(O)$A^2$, —C(O)O$A^2$, —O($A^2$), —N($A^2$)$_2$, —S($A^2$), —CH$_2$P(O)($A^2$)(O$A^2$), —CH$_2$P(O)($A^2$)(N($A^2$)$_2$), —CH$_2$P(O)(O$A^2$)(O$A^2$), —OCH$_2$P(O)(O$A^2$)(O$A^2$), —OCH$_2$P(O)($A^2$)(O$A^2$), —OCH$_2$P(O)($A^2$)(N($A^2$)$_2$), —C(O)OCH$_2$P(O)(O$A^2$)(O$A^2$), —C(O)OCH$_2$P(O)($A^2$)(O$A^2$), —C(O)OCH$_2$P(O)($A^2$)(N($A^2$)$_2$), —CH$_2$P(O)(O$A^2$)(N($A^2$)$_2$), —OCH$_2$P(O)(O$A^2$)(N($A^2$)$_2$), —C(O)OCH$_2$P(O)(O$A^2$)(N($A^2$)$_2$), —CH$_2$P(O)(N($A^2$)$_2$)(N($A^2$)$_2$), —C(O)OCH$_2$P(O)(N($A^2$)$_2$)(N($A^2$)$_2$), —OCH$_2$P(O)(N($A^2$)$_2$) (N($A^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C(O)—O-alkyl, —(CH$_2$)$_m$O—C(O)—O-cyclokyl, —N(H)C(Me)C(O)O-alkyl, or alkoxy arylsulfonamide, whereas each maybe optionally substituted with —R$^1$, —P(O)(O$A^2$)(O$A^2$), —P(O)(O$A^2$)(N($A^2$)$_2$), —P(O)($A^2$)(O$A^2$), —P(O)($A^2$)(N($A^2$)$_2$), or P(O)(N($A^2$)$_2$)(N($A^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—

O—C(O)—O-cycloalkyl, —N(H)C(CH$_3$)C(O)O-alkyl, or alkoxy arylsulfonamide, optionally substituted with R$^1$; or A$^3$ is independently selected from —(CH$_2$)$_m$—, —C(O)O—, —NH—, —C(A$^2$)$_2$—, to form a carbocyclic or heterocyclic ring with any other A$^3$ or Q$^1$;

A$^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A$^3$; and m is 0 to 6.

The present invention provides a compound of formula 1 wherein A is C, and n is 1.

The present invention provides a compound of formula 1 wherein A is P, and n is 2.

The present invention provides a compound of formula III:

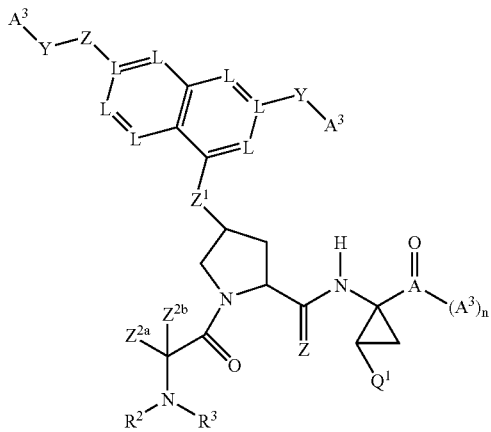

(III)

or a pharmaceutically acceptable salt, enantiomer, solvate or prodrug thereof, wherein, R$^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more A$^3$;

R$^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which R$^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH$_2$, —NH((C1-4)alkyl) and —N((C1-4)alkyl)$_2$, —CONH$_2$ and —CONH—(C1-4)alkyl;

R$^3$ is H or (C1-6)alkyl;

A is C or P;

n is 1 or 2;

L is independently selected from C or N, providing there are no more than three consecutive N, each optionally substituted with one or more A$^3$;

Y is a bond, N, or C, each optionally substituted with R$^1$ or R$^2$;

Z is O, N or S;

Z$^1$ is O, N, C, or S, optionally substituted with one or more A$^3$;

Z$^{2a}$ is H, (C1-10)alkyl, (C2-10)alkenyl, (C2-10)alkynyl, wherein any carbon atom may be replaced with a heteroatom selected from O, S or N, or Z$^{2a}$ optionally forms a carbocycle or heterocycle with R$^1$, R$^2$, Q$^1$, or any A$^3$;

Z$^{2b}$ is H, (C1-6)alkyl, (C2-8)alkenyl, (C2-8)alkynyl;

Q$^1$ is (C1-8)alkyl, (C2-8)alkenyl, or (C2-8)alkynyl;

A$^3$ is independently selected from H, —OH, —C(O), —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, heteroaryl, —C(A$^2$)$_2$, C(O)A$^2$, —C(O)OA$^2$, —O(A$^2$), —N(A$^2$)$_2$, —S(A$^2$), —CH$_2$P(O)(A$^2$)(OA$^2$), —CH$_2$P(O)(A$^2$)(N(A$^2$)$_2$), —CH$_2$P(O)(OA$^2$)(OA$^2$), —OCH$_2$P(O)(OA$^2$)(OA$^2$), —OCH$_2$P(O)(A$^2$)(OA$^2$), —OCH$_2$P(O)(A$^2$)(N(A$^2$)$_2$), —C(O)OCH$_2$P(O)(OA$^2$)(OA$^2$), —C(O)OCH$_2$P(O)(A$^2$)(OA$^2$), —C(O)OCH$_2$P(O)(A$^2$)(N(A$^2$)$_2$), —CH$_2$P(O)(OA$^2$)(N(A$^2$)$_2$), —OCH$_2$P(O)(OA$^2$)(N(A$^2$)$_2$), —C(O)OCH$_2$P(O)(OA$^2$)(N(A$^2$)$_2$), —CH$_2$P(O)(N(A$^2$)$_2$)(N(A$^2$)$_2$), —C(O)OCH$_2$P(O)(N(A$^2$)$_2$)(N(A$^2$)$_2$), —OCH$_2$P(O)(N(A$^2$)$_2$)(N(A$^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C(O)—O-alkyl, —(CH$_2$)$_m$O—C(O)—O-cycloalkyl, —N(H)C(Me)C(O)O-alkyl, or alkoxy arylsulfonamide, whereas each maybe optionally substituted with —R$^1$, —P(O)(OA$^2$)(OA$^2$), —P(O)(OA$^2$)(N(A$^2$)$_2$), —P(O)(A$^2$)(OA$^2$), —P(O)(A$^2$)(N(A$^2$)$_2$), or P(O)(N(A$^2$)$_2$)(N(A$^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with R$^1$; or A$^3$ is independently selected from —(CH$_2$)$_m$—, —C(O)O—, —NH—, —C(A$^2$)$_2$—, to form a carbocyclic or heterocyclic ring with any other A$^3$ or Q$^1$;

A$^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A$^3$; and m is 0 to 6.

The present invention provides a compound of formula III wherein A is C, and n is 1.

The present invention provides a compound of formula III wherein A is P, and n is 2.

The present invention provides a compound of formula VII,

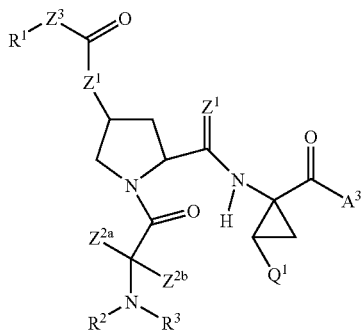

(VII)

or a pharmaceutically acceptable salt, enantiomer, solvate or prodrug thereof, wherein, $R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH$_2$, —NH((C1-4)alkyl) and —N((C1-4)alkyl)$_2$, —CONH$_2$ and —CONH—(C1-4)alkyl;

$R^3$ is H or (C1-6)alkyl;

$Z^1$ is O, N, C, or S, optionally substituted with one or more $A^3$;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with $R^1$, $R^2$, $Q^1$, or any $A^3$;

$Z^{2b}$ is H, (C1-6)alkyl, (C2-8)alkenyl, (C2-8)alkynyl;

$Z^3$ is O or N, wherein said N may be optionally substituted with $A^3$;

$Q^1$ is (C1-8)alkyl, (C2-8)alkenyl, or (C2-8)alkynyl;

$A^3$ is independently selected from H, —OH, —C(O), —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, heteroaryl, —C(A$^2$)$_2$, C(O)A$^2$, —C(O)OA$^2$, —O(A$^2$), —N(A$^2$)$_2$, —S(A$^2$), —CH$_2$P(O)(A$^2$)(OA$^2$), —CH$_2$P(O)(A$^2$)(N(A$^2$)$_2$), —CH$_2$P(O)(OA$^2$)(OA$^2$), —OCH$_2$P(O)(OA$^2$)(OA$^2$), —OCH$_2$P(O)(A$^2$)(OA$^2$), —OCH$_2$P(O)(A$^2$)(N(A$^2$)$_2$), —OCH$_2$P(O)(OA$^2$)(OA$^2$), —C(O)OCH$_2$P(O)(A$^2$)(OA$^2$), —C(O)OCH$_2$P(O)(A$^2$)(N(A$^2$)$_2$), —CH$_2$P(O)(OA$^2$)(N(A$^2$)$_2$), —OCH$_2$P(O)(OA$^2$)(N(A$^2$)$_2$), —C(O)OCH$_2$P(O)(OA$^2$)(N(A$^2$)$_2$), —CH$_2$P(O)(N(A$^2$)$_2$)(N(A$^2$)$_2$), —C(O)OCH$_2$P(O)(N(A$^2$)$_2$)(N(A$^2$)$_2$), —OCH$_2$P(O)(N(A$^2$)$_2$)(N(A$^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C(O)—O-alkyl, —(CH$_2$)$_m$O—C(O)—O-cycloalkyl, —N(H)C(Me)C(O)O-alkyl, or alkoxy arylsulfonamide, whereas each maybe optionally substituted with —R$^1$, —P(O)(OA$^2$)(OA$^2$), —P(O)(OA$^2$)(N(A$^2$)$_2$), —P(O)(A$^2$)(OA$^2$), —P(O)(A$^2$)(N(A$^2$)$_2$), or P(O)(N(A$^2$)$_2$)(N(A$^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with R$^1$; or $A^3$ is independently selected from —(CH$_2$)$_m$—, —C(O)O—, —NH—, —C(A$^2$)$_2$—, to form a carbocyclic or heterocyclic ring with any other $A^3$ or $Q^1$;

$A^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with $A^3$; and m is 0 to 6.

The present invention provides a compound of formula VII wherein $Z^3$ is N.

The present invention provides a compound of formula VII wherein said N is further substituted with $A^3$.

The present invention provides a compound of formula VII wherein $Z^1$ is N.

The present invention provides a compound of formula VII wherein $Z^3$ is O.

The present invention provides a compound of formula XI,

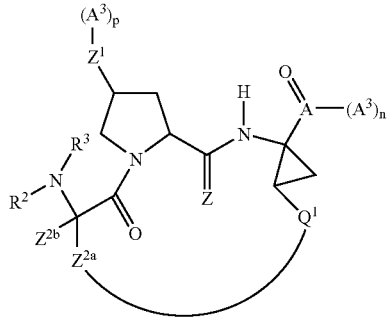

(XI)

or a pharmaceutically acceptable salt, enantiomer, solvate or prodrug thereof, wherein, $R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which R² is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH₂, —NH((C1-4)alkyl) and —N((C1-4)alkyl)₂, —CONH₂ and —CONH—(C1-4)alkyl;

R³ is H or (C1-6)alkyl;

A is C or P;

n is 1 or 2;

Y is a bond, N, or C, each optionally substituted with R¹ or R²;

Z is O, N or S;

Z¹ is O, N, C, or S, optionally substituted with one or more A³;

Z²ᵃ forms a (C1-10)alkyl, (C2-10)alkenyl, (C2-10)alkynyl carbocycle with Q¹, wherein any carbon atom may be replaced with a heteroatom selected from O, S or N to form a heterocycle, further each atom may be substituted with A³;

Z²ᵇ is H, (C1-6)alkyl, (C2-8)alkenyl, (C2-8)alkynyl;

Q¹ is (C1-8)alkyl, (C2-8)alkenyl, or (C2-8)alkynyl;

A³ is independently selected from H, —OH, —C(O), —C(O)OH, cyano, alkyl, alkenyl, alkynyl, amino, amido, imido, imino, halogen, CF₃, CH₂CF₃, cycloalkyl, nitro, aryl, aralkyl, alkoxy, aryloxy, heterocycle, heteroaryl, —C(A²)₂, C(O)A², —C(O)OA², —O(A²), —N(A²)₂, —S(A²), —CH₂P(O)(A²)(OA²), —CH₂P(O)(A²)(N(A²)₂), —CH₂P(O)(OA²)(OA²), —OCH₂P(O)(OA²)(OA²), —OCH₂P(O)(A²)(OA²), —OCH₂P(O)(A²)(N(A²)₂), —C(O)OCH₂P(O)(OA²)(OA²), —C(O)OCH₂P(O)(A²)(OA²), —C(O)OCH₂P(O)(A²)(N(A²)₂), —CH₂P(O)(OA²)(N(A²)₂), —C(O)OCH₂P(O)(OA²)(N(A²)₂), —CH₂P(O)(N(A²)₂)(N(A²)₂), —C(O)OCH₂P(O)(N(A²)₂)(N(A²)₂), —OCH₂P(O)(N(A²)₂)(N(A²)₂), —(CH₂)ₘ-heterocycle, —(CH₂)ₘC(O)Oalkyl, —O—(CH₂)ₘ—O—C(O)—Oalkyl, —O—(CH₂)ᵣ—O—C(O)—(CH₂)ₘ-alkyl, —(CH₂)ₘO—C(O)—O-alkyl, —(CH₂)ₘO—C(O)—O-cycloalkyl, —N(H)C(Me)C(O)O-alkyl, or alkoxy arylsulfonamide, whereas each maybe optionally substituted with —R¹, —P(O)(OA²)(OA²), —P(O)(OA²)(N(A²)₂), —P(O)(A²)(OA²), —P(O)(A²)(N(A²)₂), or P(O)(N(A²)₂)(N(A²)₂), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH₂)ₘheterocycle, —(CH₂)ₘ—C(O)O-alkyl, —O(CH₂)ₘOC(O)Oalkyl, —O—(CH₂)ₘ—O—C(O)—(CH₂)ₘ-alkyl, —(CH₂)ₘ—O—C(O)—O-alkyl, —(CH₂)ₘ—O—C(O)—O-cycloalkyl, —N(H)C(CH₃)C(O)O-alkyl, or alkoxy arylsulfonamide, optionally substituted with R¹; or A³ is independently selected from —(CH₂)ₘ—, —C(O)O—, —NH—, —C(A²)₂—, to form a carbocyclic or heterocyclic ring with any other A³ or Q¹;

p is 0 to 3;

A² is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A³; and m is 0 to 6.

The present invention provides a compound of formula XI wherein A is C, and n is 1.

The present invention provides a compound of formula XI wherein A is P, and n is 2.

The present invention provides a compound of formula XI wherein Z¹ is O.

The present invention provides a compound of formula XII,

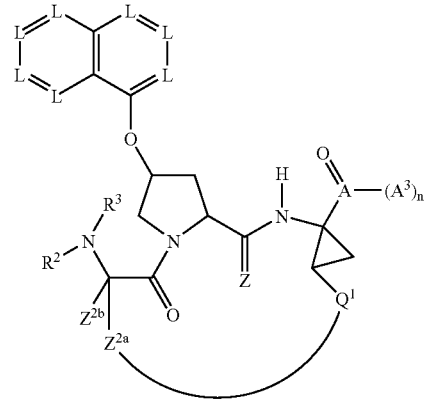

(XII)

or a pharmaceutically acceptable salt, enantiomer, solvate or prodrug thereof wherein, R¹ is independently selected from H, alkyl, alkenyl, alkynyl, aryl, cycloalkyl, heterocycle, halogen, haloalkyl, alkylsulfonamido, arylsulfonamido, —C(O)NHS(O)₂—, or —S(O)₂—, optionally substituted with one or more A³;

R² is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH₂-groups not being directly linked to each other may be optionally substituted replaced by —O— such that the O-atom is linked to the N atom to which R² is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH₂, —NH((C1-4)alkyl) and —N((C1-4)alkyl)₂, —CONH₂ and —CONH—(C1-4)alkyl;

R³ is H or (C1-6)alkyl;

A is C or P;

n is 1 or 2;

L is independently selected from C or N, providing there are no more than three consecutive N, each optionally substituted with one or more A³;

Z is O, N or S;

Z²ᵃ forms a (C1-10)alkyl, (C2-10)alkenyl, (C2-10)alkynyl carbocycle with Q¹, wherein any carbon atom may be replaced with a heteroatom selected from O, S or N to form a heterocycle, further each atom may be substituted with A³;

Z²ᵇ is H, (C1-6)alkyl, (C2-8)alkenyl, (C2-8)alkynyl;

Q¹ is (C1-8)alkyl, (C2-8)alkenyl, or (C2-8)alkynyl;

A³ is independently selected from H, —OH, —C(O), —C(O)OH, cyano, alkyl, alkenyl, alkynyl, amino, amido, imido, imino, halogen, CF₃, CH₂CF₃, cycloalkyl, nitro, aryl, aralkyl, alkoxy, aryloxy, heterocycle, heteroaryl, —C(A²)₂, $C(O)A^2$, $-C(O)OA^2$, $-O(A^2)$, $-N(A^2)_2$, $-S(A^2)$, $-CH_2P(O)(A^2)(OA^2)$, $-CH_2P(O)(A^2)(N(A^2)_2)$, $-CH_2P(O)(OA^2)(OA^2)$, $-OCH_2P(O)(OA^2)(OA^2)$, $-OCH_2P(O)(A^2)(OA^2)$, $-OCH_2P(O)(A^2)(N(A^2)_2)$, $-C(O)OCH_2P(O)(OA^2)(OA^2)$, $-C(O)OCH_2P(O)(A^2)(OA^2)$, $-C(O)OCH_2P(O)(A^2)(N(A^2)_2)$, $-CH_2P(O)(OA^2)(N(A^2)_2)$, $-OCH_2P(O)(OA^2)(N(A^2)_2)$, $-C(O)OCH_2P(O)(OA^2)(N(A^2)_2)$, $-CH_2P(O)(N(A^2)_2)(N(A^2)_2)$, $-C(O)OCH_2P(O)(N(A^2)_2)(N(A^2)_2)$, $-OCH_2P(O)(N(A^2)_2)(N(A^2)_2)$, $-(CH_2)_m$-heterocycle, $-(CH_2)_mC(O)Oalkyl$, $-O-(CH_2)_m-O-C(O)-Oalkyl$, $-O-(CH_2)_r-O-C(O)-(CH_2)_m$-alkyl, $-(CH_2)_mO-C(O)-O$-alkyl, $-(CH_2)_mO-C(O)-O$-cycloalkyl, $-N(H)C(Me)C(O)O$-alkyl, or alkoxy arylsulfonamide, whereas each maybe optionally substituted with $-R^1$, $-P(O)(OA^2)(OA^2)$, $-P(O)(OA^2)(N(A^2)_2)$, $-P(O)(A^2)(OA^2)$, $-P(O)(A^2)(N(A^2)_2)$, or $P(O)(N(A^2)_2)(N(A^2)_2)$, halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, $-(CH_2)_m$heterocycle, $-(CH_2)_m-C(O)O$-alkyl, $-O(CH_2)_mOC(O)Oalkyl$, $-O-(CH_2)_m-O-C(O)-(CH_2)_m$-alkyl, $-(CH_2)_m-O-C(O)-O$-alkyl, $-(CH_2)_m-O-C(O)-O$-cycloalkyl, $-N(H)C(CH_3)C(O)O$-alkyl, or alkoxy arylsulfonamide, optionally substituted with $R^1$; or $A^3$ is independently selected from $-(CH_2)_m-$, $-C(O)O-$, $-NH-$, $-C(A^2)_2-$, to form a carbocyclic or heterocyclic ring with any other $A^3$ or $Q^1$;

$A^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with $A^3$; and m is 0 to 6.

The present invention provides a compound of formula XIII,

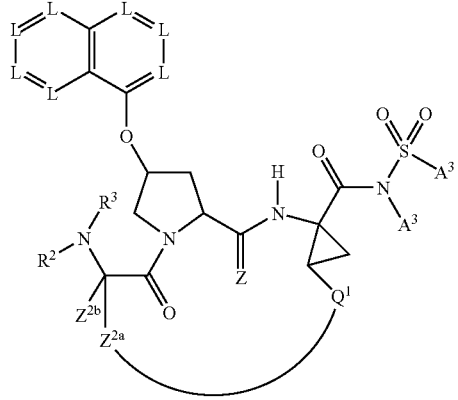

(XIII)

or a pharmaceutically acceptable salt, enantiomer, solvate or prodrug thereof wherein, $R^1$ is independently selected from H, alkyl, alkenyl, alkynyl, aryl, cycloalkyl, heterocycle, halogen, haloalkyl, alkylsulfonamido, arylsulfonamido, $-C(O)NHS(O)_2-$, or $-S(O)_2-$, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and $O-(C1-4)$alkyl, or where each of said alkyl-groups may be optionally substituted with mono-, di- or tri-substituted with halogen, or where each of said cycloalkyl groups being 5-, 6- or 7-membered, one or two $-CH_2$-groups not being directly linked to each other may be optionally substituted replaced by $-O-$ such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, $-OH$, (C1-4)alkyl, $O-(C1-4)$alkyl, $S-(C1-4)$alkyl, $-NH_2$, $-NH((C1-4)$alkyl) and $-N((C1-4)$alkyl)$_2$, $-CONH_2$ and $-CONH-(C1-4)$alkyl;

$R^3$ is H or (C1-6)alkyl;

L is independently selected from C or N, providing there are no more than three consecutive N, each optionally substituted with one or more $A^3$;

Z is O, N or S;

$Z^{2a}$ forms a (C1-10)alkyl, (C2-10)alkenyl, (C2-10)alkynyl carbocycle with $Q^1$, wherein any carbon atom may be replaced with a heteroatom selected from O, S or N to form a heterocycle, further each atom may be substituted with $A^3$;

$Z^{2b}$ is H, (C1-6)alkyl, (C2-8)alkenyl, (C2-8)alkynyl;

$Q^1$ is (C1-8)alkyl, (C2-8)alkenyl, or (C2-8)alkynyl;

$A^3$ is independently selected from H, $-OH$, $-C(O)$, $-C(O)OH$, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, heteroaryl, $-C(A^2)_2$, $C(O)A^2$, $-C(O)OA^2$, $-O(A^2)$, $-N(A^2)_2$, $-S(A^2)$, $-CH_2P(O)(A^2)(OA^2)$, $-CH_2P(O)(A^2)(N(A^2)_2)$, $-CH_2P(O)(OA^2)(OA^2)$, $-OCH_2P(O)(OA^2)(OA^2)$, $-OCH_2P(O)(A^2)(OA^2)$, $-OCH_2P(O)(A^2)(N(A^2)_2)$, $-C(O)OCH_2P(O)(OA^2)(OA^2)$, $-C(O)OCH_2P(O)(A^2)(OA^2)$, $-C(O)OCH_2P(O)(A^2)(N(A^2)_2)$, $-CH_2P(O)(OA^2)(N(A^2)_2)$, $-OCH_2P(O)(OA^2)(N(A^2)_2)$, $-C(O)OCH_2P(O)(OA^2)(N(A^2)_2)$, $-CH_2P(O)(N(A^2)_2)(N(A^2)_2)$, $-C(O)OCH_2P(O)(N(A^2)_2)(N(A^2)_2)$, $-OCH_2P(O)(N(A^2)_2)(N(A^2)_2)$, $-(CH_2)_m$-heterocycle, $-(CH_2)_mC(O)Oalkyl$, $-O-(CH_2)_m-O-C(O)-Oalkyl$, $-O-(CH_2)_r-O-C(O)-(CH_2)_m$-alkyl, $-(CH_2)_mO-C(O)-O$-alkyl, $-(CH_2)_mO-C(O)-O$-cycloalkyl, $-N(H)C(Me)C(O)O$-alkyl, or alkoxy arylsulfonamide, whereas each maybe optionally substituted with $-R^1$, $-P(O)(OA^2)(OA^2)$, $-P(O)(OA^2)(N(A^2)_2)$, $-P(O)(A^2)(OA^2)$, $-P(O)(A^2)(N(A^2)_2)$, or $P(O)(N(A^2)_2)(N(A^2)_2)$, halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, $-(CH_2)_m$heterocycle, $-(CH_2)_m-C(O)O$-alkyl, $-O(CH_2)_mOC(O)Oalkyl$, $-O-(CH_2)_m-O-C(O)-(CH_2)_m$-alkyl, $-(CH_2)_m-O-C(O)-O$-alkyl, $-(CH_2)_m-O-C(O)-O$-cycloalkyl, $-N(H)C(CH_3)C(O)O$-alkyl, or alkoxy arylsulfonamide, optionally substituted with $R^1$; or $A^3$ is independently selected from $-(CH_2)_m-$, $-C(O)O-$, $-NH-$, $-C(A^2)_2-$, to form a carbocyclic or heterocyclic ring with any other $A^3$ or $Q^1$;

$A^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with $A^3$; and m is 0 to 6.

The present invention provides a compound of formula XIV:

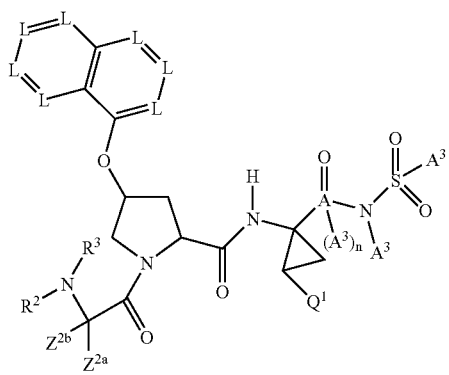

(XIV)

or a pharmaceutically acceptable salt, enantiomer, solvate or prodrug thereof wherein, $R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH$_2$—, —NH((C1-4)alkyl) and —N((C1-4)alkyl)$_2$, —CONH$_2$ and —CONH—(C1-4)alkyl;

$R^3$ is H or (C1-6)alkyl;

A is C or P;

n is 1 or 2;

L is independently selected from C or N, providing there are no more than three consecutive N, each optionally substituted with one or more $A^3$;

Z is O, N or S;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with $R^1$, $R^2$, $Q^1$, or any $A^3$;

$Z^{2b}$ is H, (C1-6)alkyl, (C2-8)alkenyl, (C2-8)alkynyl;

$Q^1$ is (C1-8)alkyl, (C2-8)alkenyl, or (C2-8)alkynyl;

$A^3$ is independently selected from H, —OH, —C(O), —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, heteroaryl, —C($A^2$)$_2$, C(O)$A^2$, —C(O)O$A^2$, —O($A^2$), —N($A^2$)$_2$, —S($A^2$), —CH$_2$P(O)($A^2$)($A^2$), —CH$_2$P(O)($A^2$)(N($A^2$)$_2$), —CH$_2$P(O)(O$A^2$)(O$A^2$), —OCH$_2$P(O)(O$A^2$)(O$A^2$), —OCH$_2$P(O)($A^2$)(O$A^2$), —OCH$_2$P(O)($A^2$)(N($A^2$)$_2$), —C(O)OCH$_2$P(O) (O$A^2$)(O$A^2$), —C(O)OCH$_2$P(O)($A^2$)(O$A^2$), —C(O)OCH$_2$P (O)($A^2$)(N($A^2$)$_2$), —CH$_2$P(O)(O$A^2$)(N($A^2$)$_2$), —OCH$_2$P(O) (O$A^2$)(N($A^2$)$_2$), —C(O)OCH$_2$P(O)(O$A^2$)(N($A^2$)$_2$), —CH$_2$P (O) (N($A^2$)$_2$)(N($A^2$)$_2$), —C(O)OCH$_2$P(O)(N($A^2$)$_2$)(N($A^2$)$_2$), —OCH$_2$P(O)(N($A^2$)$_2$)(N($A^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C (O)—O-alkyl, —(CH$_2$)$_m$O—C(O)—O-cycloalkyl, —N(H)C (Me)C(O)O-alkyl, or alkoxy arylsulfonamide, whereas each maybe optionally substituted with —R$^1$, —P(O)(O$A^2$) (O$A^2$), —P(O)(O$A^2$)(N($A^2$)$_2$), —P(O)($A^2$)(O$A^2$) —P(O) ($A^2$)(N($A^2$)$_2$), or P(O)(N($A^2$)$_2$)(N($A^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with $R^1$; or $A^3$ is independently selected from —(CH$_2$)$_m$—, —C(O) O—, —NH—, —C($A^2$)$_2$—, to form a carbocyclic or heterocyclic ring with any other $A^3$ or $Q^1$;

$A^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with $A^3$; and m is 0 to 6.

The present invention provides a compound of formula XV (XV)

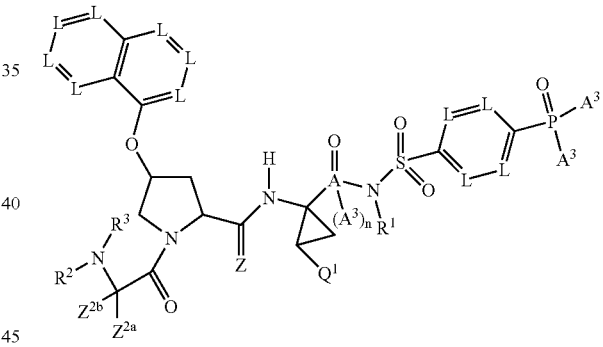

or a pharmaceutically acceptable salt, enantiomer, solvate or prodrug thereof wherein, $R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4) alkyl, —NH$_2$, —NH((C1-4)alkyl) and —N((C1-4)alkyl)$_2$, —CONH$_2$ and —CONH—(C1-4)alkyl;

$R^3$ is H or (C1-6)alkyl;

A is C or P;

n is 1 or 2;

L is independently selected from C or N, providing there are no more than three consecutive N, each optionally substituted with one or more $A^3$;

Z is O, N or S;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with $R^1$, $R^2$, $Q^1$, or any $A^3$;

$Z^{2b}$ is H, (C1-6)alkyl, (C2-8)alkenyl, (C2-8)alkynyl;

$Q^1$ is (C1-8)alkyl, (C2-8)alkenyl, or (C2-8)alkynyl;

$A^3$ is independently selected from H, —OH, —C(O), —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, heteroaryl, —C(A$^2$)$_2$, C(O)A$^2$, —C(O)OA$^2$, —O(A$^2$), —N(A$^2$)$_2$, —S(A$^2$), —CH$_2$P(O)(A$^2$)(OA$^2$), —CH$_2$P(O)(A$^2$)(N(A$^2$)$_2$), —CH$_2$P(O)(OA$^2$)(OA$^2$), —OCH$_2$P(O)(OA$^2$)(OA$^2$), —OCH$_2$P(O)(A$^2$)(OA$^2$), —OCH$_2$P(O)(A$^2$)(N(A$^2$)$_2$), —C(O)OCH$_2$P(O)(OA$^2$)(OA$^2$), —C(O)OCH$_2$P(O)(A$^2$)(OA$^2$), —C(O)OCH$_2$P(O)(A$^2$)(N(A$^2$)$_2$), —CH$_2$P(O)(OA$^2$)(N(A$^2$)$_2$), —OCH$_2$P(O)(OA$^2$)(N(A$^2$)$_2$), —C(O)OCH$_2$P(O)(OA$^2$)(N(A$^2$)$_2$), —CH$_2$P(O)(N(A$^2$)$_2$)(N(A$^2$)$_2$), —C(O)OCH$_2$P(O)(N(A$^2$)$_2$)(N(A$^2$)$_2$), —OCH$_2$P(O)(N(A$^2$)$_2$)(N(A$^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C(O)—O-alkyl, —(CH$_2$)$_m$O—C(O)—O-cycloalkyl, —N(H)C(Me)C(O)O-alkyl, or alkoxy arylsulfonamide, whereas each maybe optionally substituted with —R$^1$, —P(O)(OA$^2$)(OA$^2$), —P(O)(OA$^2$)(N(A$^2$)$_2$), —P(O)(A$^2$)(OA$^2$), —P(O)(A$^2$)(N(A$^2$)$_2$), or P(O)(N(A$^2$)$_2$)(N(A$^2$)$_2$), halogen; alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with R$^1$; or $A^3$ is independently selected from —(CH$_2$)$_m$—, —C(O)O—, —NH—, —C(A$^2$)$_2$—, to form a carbocyclic or heterocyclic ring with any other $A^3$ or $Q^1$;

$A^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A$^3$; and m is 0 to 6.

The present invention provides a compound of formula XVI,

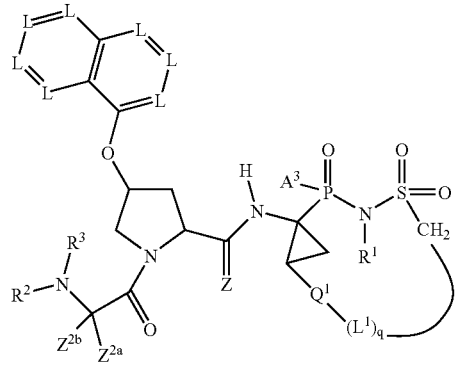

(XVI)

or a pharmaceutically acceptable salt, enantiomer, solvate or prodrug thereof wherein, $R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4) alkyl, —NH$_2$, —NH((C1-4)alkyl) and —N((C1-4)alkyl)$_2$, —CONH$_2$ and —CONH—(C1-4)alkyl;

$R^3$ is H or (C1-6)alkyl;

L is independently selected from C or N, providing there are no more than three consecutive N, each optionally substituted with one or more $A^3$;

$L^1$ is independently selected from C, O, S, or N, providing there are no more than three consecutive N, each optionally substituted with one or more $A^3$;

Z is O, N or S;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with $R^1$, $R^2$, $Q^1$, or any $A^3$;

$Z^{2b}$ is H, (C1-6)alkyl, (C2-8)alkenyl, (C2-8)alkynyl;

$Q^1$ is (C1-8)alkyl, (C2-8)alkenyl, or (C2-8)alkynyl;

$A^3$ is independently selected from H, —OH, —C(O), —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, heteroaryl, —C(A$^2$)$_2$, C(O)A$^2$, —C(O)OA$^2$, —O(A$^2$), —N(A$^2$)$_2$, —S(A$^2$), —CH$_2$P(O)(A$^2$)(OA$^2$), —CH$_2$P(O)(A$^2$)(N(A$^2$)$_2$), —CH$_2$P(O)(OA$^2$)(OA$^2$), —OCH$_2$P(O)(OA$^2$)(OA$^2$), —OCH$_2$P(O)

($A^2$)($OA^2$), —$OCH_2P(O)(A^2)(N(A^2)_2)$, —$C(O)OCH_2P(O)(OA^2)(OA^2)$, —$C(O)OCH_2P(O)(A^2)(OA^2)$, —$C(O)OCH_2P(O)(A^2)(N(A^2)_2)$, —$CH_2P(O)(OA^2)(N(A^2)_2)$, —$OCH_2P(O)(OA^2)(N(A^2)_2)$, —$C(O)OCH_2P(O)(OA^2)(N(A^2)_2)$, —$CH_2P(O)(N(A^2)_2)(N(A^2)_2)$, —$C(O)OCH_2P(O)(N(A^2)_2)(N(A^2)_2)$, —$OCH_2P(O)(N(A^2)_2)(N(A^2)_2)$, —$(CH_2)_m$-heterocycle, —$(CH_2)_mC(O)Oalkyl$, —O—$(CH_2)_m$—O—C(O)—Oalkyl, —O—$(CH_2)_r$—O—C(O)—$(CH_2)_m$-alkyl, —$(CH_2)_m$O—C(O)—O-alkyl, —$(CH_2)_m$O—C(O)—O-cycloalkyl, —N(H)C(Me)C(O)O-alkyl, or alkoxy arylsulfonamide, whereas each maybe optionally substituted with —$R^1$, —$P(O)(OA^2)(OA^2)$, —$P(O)(OA^2)(N(A^2)_2)$, —$P(O)(A^2)(OA^2)$, —$P(O)(A^2)(N(A^2)_2)$, or $P(O)(N(A^2)_2)(N(A^2)_2)$, halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —$(CH_2)_m$heterocycle, —$(CH_2)_m$—C(O)O-alkyl, —$O(CH_2)_m$OC(O)Oalkyl, —O—$(CH_2)_m$—O—C(O)—$(CH_2)_m$-alkyl, —$(CH_2)_m$—O—C(O)—O-alkyl, —$(CH_2)_m$—O—C(O)—O-cycloalkyl, —$N(H)C(CH_3)C(O)O$-alkyl, or alkoxy arylsulfonamide, optionally substituted with $R^1$; or $A^3$ is independently selected from —$(CH_2)_m$—, —C(O)O—, —NH—, —$C(A^2)_2$—, to form a carbocyclic or heterocyclic ring with any other $A^3$ or $Q^1$;

$A^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with $A^3$;

m is 0 to 6; and q is 1 to 10.

The present invention provides a compound of formula XVIII,

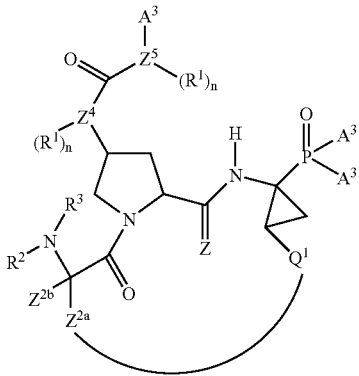

(XVIII)

or a pharmaceutically acceptable salt, enantiomer, solvate or prodrug thereof wherein, $R^1$ is independently selected from H, alkyl, alkenyl, alkynyl, aryl, cycloalkyl, heterocycle, halogen, haloalkyl, alkylsulfonamido, arylsulfonamido, —$C(O)NHS(O)_2$—, or —$S(O)_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —$CH_2$-groups not being directly linked to each other may be optionally substituted replaced by —O— such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —$NH_2$, —NH((C1-4)alkyl) and —$N((C1-4)alkyl)_2$, —$CONH_2$ and —CONH—(C1-4)alkyl;

$R^3$ is H or (C1-6)alkyl;

n is independently 0, 1 or 2;

Y is a bond, N, or C, each optionally substituted with $R^1$ or $R^2$;

Z is O, N or S;

$Z^{2a}$ forms a (C1-10)alkyl, (C2-10)alkenyl, (C2-10)alkynyl carbocycle with $Q^1$, wherein any carbon atom may be replaced with a heteroatom selected from O, S or N, and each atom may be substituted with $A^3$;

$Z^{2b}$ is H, (C1-6)alkyl, (C2-8)alkenyl, (C2-8)alkynyl;

$Z^4$ and $Z^5$ are independently a bond, O or N;

$Q^1$ is (C1-8)alkyl, (C2-8)alkenyl, or (C2-8)alkynyl;

$A^3$ is independently selected from H, —OH, —C(O), —C(O)OH, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, heteroaryl, —$C(A^2)_2$, $C(O)A^2$, —$C(O)OA^2$, —$O(A^2)$, —$N(A^2)_2$, —$S(A^2)$, —$CH_2P(O)(A^2)(OA^2)$, —$CH_2P(O)(A^2)(N(A^2)_2)$, —$CH_2P(O)(OA^2)(OA^2)$, —$OCH_2P(O)(OA^2)(OA^2)$, —$OCH_2P(O)(A^2)(OA^2)$, —$OCH_2P(O)(A^2)(N(A^2)_2)$, —$C(O)OCH_2P(O)(OA^2)(OA^2)$, —$C(O)OCH_2P(O)(A^2)(OA^2)$, —$C(O)OCH_2P(O)(A^2)(N(A^2)_2)$, —$CH_2P(O)(OA^2)(N(A^2)_2)$, —$OCH_2P(O)(OA^2)(N(A^2)_2)$, —$C(O)OCH_2P(O)(OA^2)(N(A^2)_2)$, —$CH_2P(O)(N(A^2)_2)(N(A^2)_2)$, —$C(O)OCH_2P(O)(N(A^2)_2)(N(A^2)_2)$, —$OCH_2P(O)(N(A^2)_2)(N(A^2)_2)$, —$(CH_2)_m$-heterocycle, —$(CH_2)_mC(O)Oalkyl$, —O—$(CH_2)_m$—O—C(O)—Oalkyl, —O—$(CH_2)_r$—O—C(O)—$(CH_2)_m$-alkyl, —$(CH_2)_m$O—C(O)—O-alkyl, —$(CH_2)_m$O—C(O)—O-cycloalkyl, —N(H)C(Me)C(O)O-alkyl, or alkoxy arylsulfonamide, whereas each maybe optionally substituted with —$R^1$, —$P(O)(OA^2)(OA^2)$, —$P(O)(OA^2)(N(A^2)_2)$, —$P(O)(A^2)(OA^2)$, —$P(O)(A^2)(N(A^2)_2)$, or $P(O)(N(A^2)_2)(N(A^2)_2)$, halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —$(CH_2)_m$heterocycle, —$(CH_2)_n$—C(O)O-alkyl, —$O(CH_2)_m$OC(O)Oalkyl, —O—$(CH_2)_m$—O—C(O)—$(CH_2)_m$-alkyl, —$(CH_2)_m$—O—C(O)—O-alkyl, —$(CH_2)_m$—O—C(O)—O-cycloalkyl, —$N(H)C(CH_3)C(O)O$-alkyl, or alkoxy arylsulfonamide, optionally substituted with $R^1$; or $A^3$ is independently selected from —$(CH_2)_m$—, —C(O)O—, —NH—, —$C(A^2)_2$—, to form a carbocyclic or heterocyclic ring with any other $A^3$ or $Q^1$;

$A^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with $A^3$; and m is 0 to 6.

The present invention provides a compound of formula XIX,

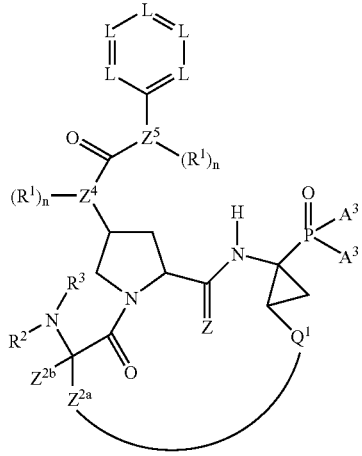

(XIX)

or a pharmaceutically acceptable salt, enantiomer, solvate or prodrug thereof wherein, $R^1$ is independently selected from H, alkyl alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH$_2$, —NH((C1-4)alkyl) and —N((C1-4)alkyl)$_2$, —CONH$_2$ and —CONH—(C1-4)alkyl;

$R^3$ is H or (C1-6)alkyl;

n is independently 0, 1 or 2;

L is independently selected from C or N, providing there are no more than three consecutive N, each optionally substituted with one or more $A^3$;

Z is O, N or S;

$Z^{2a}$ forms a (C1-10)alkyl, (C2-10)alkenyl, (C2-10)alkynyl carbocycle with $Q^1$, wherein any carbon atom may be replaced with a heteroatom selected from O, S or N, and each atom may be substituted with $A^3$;

$Z^{2b}$ is H, (C1-6)alkyl, (C2-8)alkenyl, (C2-8)alkynyl;

$Z^4$ and $Z^5$ are independently a bond, O or N;

$Q^1$ is (C1-8)alkyl, (C2-8)alkenyl, or (C2-8)alkynyl;

$A^3$ is independently selected from H, —OH, —C(O), —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, heteroaryl, —C(A$^2$)$_2$, C(O)A$^2$, —C(O)OA$^2$, —O(A$^2$), —N(A$^2$)$_2$, —S(A$^2$), —CH$_2$P(O)(A$^2$)(OA$^2$), —CH$_2$P(O)(A$^2$)(N(A$^2$)$_2$), —CH$_2$P(O)(OA$^2$)(OA$^2$), —OCH$_2$P(O)(A$^2$)(OA$^2$), —OCH$_2$P(O)(A$^2$)(OA$^2$), —OCH$_2$P(O)(A$^2$)(N(A$^2$)$_2$), —C(O)OCH$_2$P(O)(OA$^2$)(OA$^2$), —C(O)OCH$_2$P(O)(A$^2$)(OA$^2$), —C(O)OCH$_2$P(O)(A$^2$)(N(A$^2$)$_2$), —CH$_2$P(O)(OA$^2$)(N(A$^2$)$_2$), —OCH$_2$P(O)(OA$^2$)(N(A$^2$)$_2$), —C(O)OCH$_2$P(O)(OA$^2$)(N(A$^2$)$_2$), —CH$_2$P(O)(N(A$^2$)$_2$)(N(A$^2$)$_2$), —C(O)OCH$_2$P(O)(N(A$^2$)$_2$)(N(A$^2$)$_2$), —OCH$_2$P(O)(N(A$^2$)$_2$)(N(A$^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C(O)—O-alkyl, —(CH$_2$)$_m$O—C(O)—O-cycloalkyl, —N(H)C(Me)C(O)O-alkyl, or alkoxy arylsulfonamide, whereas each maybe optionally substituted with —R$^1$, —P(O)(OA$^2$)(OA$^2$), —P(O)(OA$^2$)(N(A$^2$)$_2$), —P(O)(A$^2$)(OA$^2$), —P(O)(A$^2$)(N(A$^2$)$_2$), or P(O)(N(A$^2$)$_2$)(N(A$^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with R$^1$; or $A^3$ is independently selected from —(CH$_2$)$_m$—, —C(O)O—, —NH—, —C(A$^2$)$_2$—, to form a carbocyclic or heterocyclic ring with any other $A^3$ or $Q^1$;

$A^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with $A^3$; and m is 0 to 6.

The present invention provides a compound having the general structure shown in formula XXI,

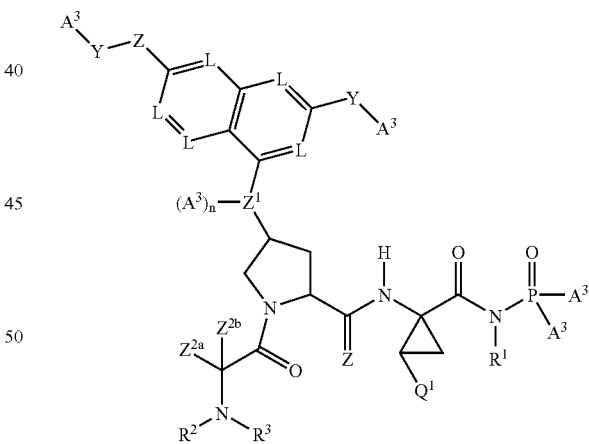

(XXI)

or a pharmaceutically acceptable salt, enantiomer, solvate or prodrug thereof wherein, $R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which R$^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH$_2$, —NH((C1-4)alkyl) and —N((C1-4)alkyl)$_2$, —CONH$_2$ and —CONH—(C1-4)alkyl;

R$^3$ is H or (C1-6)alkyl;

n is 0, 1, or 2;

L is independently selected from C or N, providing there are no more than three consecutive N, each optionally substituted with one or more A$^3$;

Y is a bond, N, or C, each optionally substituted with R$^1$ or R$^2$;

Z is independently O, N or S;

Z$^1$ is O, N, C, or S, optionally substituted with one or more A$^3$;

Z$^{2a}$ is H, (C1-10)alkyl, (C2-10)alkenyl, (C2-10)alkynyl, wherein any carbon atom may be replaced with a heteroatom selected from O, S or N, or Z$^{2a}$ optionally forms a carbocycle or heterocycle with R$^1$, R$^2$, Q$^1$, or any A$^3$;

Z$^{2b}$ is H, (C1-6)alkyl, (C2-8)alkenyl, (C2-8)alkynyl;

Q$^1$ is (C1-8)alkyl, (C2-8)alkenyl, or (C2-8)alkynyl;

A$^3$ is independently selected from H, —OH, —C(O), —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, heteroaryl, —C(A$^2$)$_2$, C(O)A$^2$, —C(O)OA$^2$, —O(A$^2$), —N(A$^2$)$_2$, —S(A$^2$), —CH$_2$P(O)(A$^2$)(OA$^2$), —CH$_2$P(O)(A$^2$)(N(A$^2$)$_2$), —CH$_2$P(O)(OA$^2$)(OA$^2$), —OCH$_2$P(O)(OA$^2$)(OA$^2$), —OCH$_2$P(O)(A$^2$)(OA$^2$), —OCH$_2$P(O)(A$^2$)(N(A$^2$)$_2$), —C(O)OCH$_2$P(O)(OA$^2$)(OA$^2$), —C(O)OCH$_2$P(O)(A$^2$)(OA$^2$), —C(O)OCH$_2$P(O)(A$^2$)(N(A$^2$)$_2$), —CH$_2$P(O)(OA$^2$)(N(A$^2$)$_2$), —OCH$_2$P(O)(OA$^2$)(N(A$^2$)$_2$), —C(O)OCH$_2$P(O)(OA$^2$)(N(A$^2$)$_2$), —CH$_2$P(O)(N(A$^2$)$_2$)(N(A$^2$)$_2$), —C(O)OCH$_2$P(O)(N(A$^2$)$_2$)(N(A$^2$)$_2$), —OCH$_2$P(O)(N(A$^2$)$_2$)(N(A$^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, (CH$_2$)$_m$O—C(O)—O-alkyl, —(CH$_2$)$_m$O—C(O)—O-cycloalkyl, —N(H)C(Me)C(O)O-alkyl, or alkoxy arylsulfonamide, whereas each maybe optionally substituted with —R$^1$, —P(O)(OA$^2$)(OA$^2$), —P(O)(OA$^2$)(N(A$^2$)$_2$), —P(O)(A$^2$)(OA$^2$), —P(O)(A$^2$)(N(A$^2$)$_2$), or P(O)(N(A$^2$)$_2$)(N(A$^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with R$^1$; or A$^3$ is independently selected from —(CH$_2$)$_m$—, —C(O)O—, —NH—, —C(A$^2$)$_2$—, to form a carbocyclic or heterocyclic ring with any other A$^3$ or Q$^1$;

A$^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A$^3$; and m is 0 to 6.

The present invention provides a compound of formula XXII,

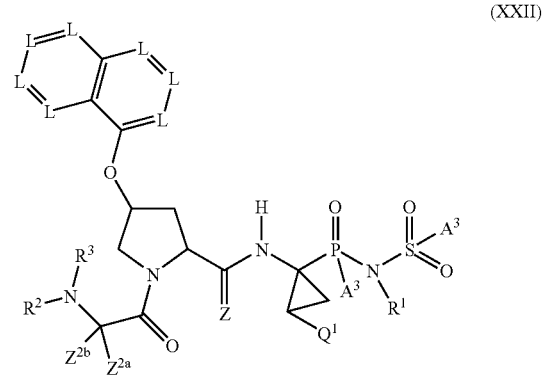

(XXII)

or a pharmaceutically acceptable salt, enantiomer, solvate or prodrug thereof wherein, R$^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more A$^3$;

R$^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which R$^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH$_2$, —NH((C1-4)alkyl) and —N((C1-4)alkyl)$_2$, —CONH$_2$ and —CONH—(C1-4)alkyl;

R$^3$ is H or (C1-6)alkyl;

L is independently selected from C or N, providing there are no more than three consecutive N, each optionally substituted with one or more A$^3$;

Z is O, N or S;

Z$^{2a}$ is H, (C1-10)alkyl, (C2-10)alkenyl, (C2-10)alkynyl, wherein any carbon atom may be replaced with a heteroatom selected from O, S or N, or Z$^{2a}$ optionally forms a carbocycle or heterocycle with R$^1$, R$^2$, Q$^1$, or any A$^3$;

Z$^{2b}$ is H, (C1-6)alkyl, (C2-8)alkenyl, (C2-8)alkynyl;

Q$^1$ is (C1-8)alkyl, (C2-8)alkenyl, or (C2-8)alkynyl;

A$^3$ is independently selected from H, —OH, —C(O), —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, heteroaryl, —C(A$^2$)$_2$, C(O)A$^2$, —C(O)OA$^2$, —O(A$^2$), —N(A$^2$)$_2$, —S(A$^2$), —CH$_2$P(O)(A$^2$)(OA$^2$), —CH$_2$P(O)(A$^2$)(N(A$^2$)$_2$), —CH$_2$P(O)(OA$^2$)(OA$^2$), —OCH$_2$P(O)(OA$^2$)(OA$^2$), —OCH$_2$P(O)

(A²)(OA²), —OCH₂P(O)(A²)(N(A²)₂), —C(O)OCH₂P(O)(OA²)(OA²), —C(O)OCH₂P(O)(A²)(OA²), —C(O)OCH₂P(O)(A²)(N(A²)₂), —CH₂P(O)(OA²)(N(A²)₂), —OCH₂P(O)(OA²)(N(A²)₂), —C(O)OCH₂P(O)(N(A²)₂)(N(A²)₂), —CH₂P(O)(N(A²)₂)(N(A²)₂), —C(O)OCH₂P(O)(N(A²)₂)(N(A²)₂), —OCH₂P(O)(N(A²)₂)(N(A²)₂), —(CH₂)$_m$-heterocycle, —(CH₂)$_m$C(O)Oalkyl, —O—(CH₂)$_m$—O—C(O)—Oalkyl, —O—(CH₂)$_r$—O—C(O)—(CH₂)$_m$-alkyl, —(CH₂)$_m$O—C(O)—O-alkyl, —(CH₂)$_m$O—C(O)—O-cycloalkyl, —N(H)C(Me)C(O)O-alkyl, or alkoxy arylsulfonamide, whereas each maybe optionally substituted with —R¹, —P(O)(OA²)(OA²), —P(O)(OA²)(N(A²)₂), —P(O)(A²)(OA²), —P(O)(A²)(N(A²)₂), or P(O)(N(A²)₂)(N(A²)₂), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH₂)$_m$heterocycle, —(CH₂)$_m$—C(O)O-alkyl, —O(CH₂)$_m$OC(O)Oalkyl, —O—(CH₂)$_m$—O—C(O)—(CH₂)$_m$-alkyl, —(CH₂)$_m$—O—C(O)—O-alkyl, —(CH₂)$_m$—O—C(O)—O-cycloalkyl, —N(H)C(CH₃)C(O)O-alkyl, or alkoxy arylsulfonamide, optionally substituted with R¹; or A³ is independently selected from —(CH₂)$_m$—, —C(O)O—, —NH—, —C(A²)₂—, to form a carbocyclic or heterocyclic ring with any other A³ or Q¹;

A² is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A³; and m is 0 to 6.

The present invention provides a compound of formula XXIII,

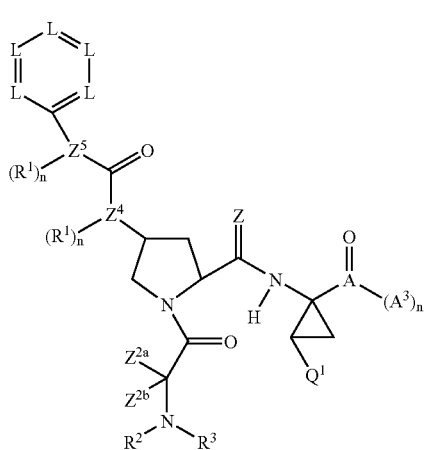

(XXIII)

or a pharmaceutically acceptable salt, enantiomer, solvate or prodrug thereof wherein, R¹ is independently selected from H, alkyl, alkenyl, alkynyl, aryl, cycloalkyl, heterocycle, halogen, haloalkyl, alkylsulfonamido, arylsulfonamido, —C(O)NHS(O)₂—, or —S(O)₂—, optionally substituted with one or more A³;

R² is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6-, or 7-membered, one or two —CH₂-groups not being directly linked to each other may be optionally substituted replaced by —O— such that the O-atom is linked to the N atom to which R² is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH₂, —NH((C1-4)alkyl) and —N((C1-4)alkyl)₂, —CONH₂ and —CONH—(C1-4)alkyl;

R³ is H or (C1-6)alkyl;

A is C or P;

n is independently 0, 1 or 2;

L is independently selected from C or N, providing there are no more than three consecutive N, each optionally substituted with one or more A³;

Z is O, N or S;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with R¹, R², Q¹, or any A³;

$Z^{2b}$ is H, (C1-6)alkyl, (C2-8)alkenyl, (C2-8)alkynyl;

$Z^4$ and $Z^5$ are independently a bond, O or N;

Q¹ is (C1-8)alkyl, (C2-8)alkenyl, or (C2-8)alkynyl;

A³ is independently selected from H, —OH, —C(O), —C(O)OH, cyano, alkyl, alkenyl, alkynyl, amino, amido, imido, imino, halogen, CF₃, CH₂CF₃, cycloalkyl, nitro, aryl, aralkyl, alkoxy, aryloxy, heterocycle, heteroaryl, —C(A²)₂, C(O)A², —C(O)OA², —O(A²), —N(A²)₂, —S(A²), —CH₂P(O)(A²)(OA²), —CH₂P(O)(A²)(N(A²)₂), —CH₂P(O)(OA²)(OA²), —OCH₂P(O)(OA²)(OA²), —OCH₂P(O)(A²)(OA²), —OCH₂P(O)(A²)(N(A²)₂), —C(O)OCH₂P(O)(OA²)(OA²), —C(O)OCH₂P(O)(A²)(OA²), —C(O)OCH₂P(O)(A²)(N(A²)₂), —CH₂P(O)(OA²)(N(A²)₂), —OCH₂P(O)(OA²)(N(A²)₂), —C(O)OCH₂P(O)(OA²)(N(A²)₂), —CH₂P(O)(N(A²)₂)(N(A²)₂), —C(O)OCH₂P(O)(N(A²)₂)(N(A²)₂), —OCH₂P(O)(N(A²)₂)(N(A²)₂), —(CH₂)$_m$-heterocycle, —(CH₂)$_m$C(O)Oalkyl, —O—(CH₂)$_m$—O—C(O)—Oalkyl, —O—(CH₂)$_r$—O—C(O)—(CH₂)$_m$-alkyl, —(CH₂)$_m$O—C(O)—O-alkyl, —(CH₂)$_m$O—C(O)—O-cycloalkyl, —N(H)C(Me)C(O)O-alkyl, or alkoxy arylsulfonamide, whereas each maybe optionally substituted with —R¹, —P(O)(OA²)(OA²), —P(O)(OA²)(N(A²)₂), —P(O)(A²)(OA²), —P(O)(A²)(N(A²)₂), or P(O)(N(A²)₂)(N(A²)₂), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH₂)$_m$heterocycle, —(CH₂)$_m$—C(O)O-alkyl, —O(CH₂)$_m$OC(O)Oalkyl, —O—(CH₂)$_m$—O—C(O)—(CH₂)$_m$-alkyl, —(CH₂)$_m$—O—C(O)—O-alkyl, —(CH₂)$_m$—O—C(O)—O-cycloalkyl, —N(H)C(CH₃)C(O)O-alkyl, or alkoxy arylsulfonamide, optionally substituted with R¹; or A³ is independently selected from —(CH₂)$_m$—, —C(O)O—, —NH—, —C(A²)₂—, to form a carbocyclic or heterocyclic ring with any other A³ or Q¹;

A² is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A³; and m is 0 to 6.

The present invention provides a compound of formula XXIV, (XXIV)

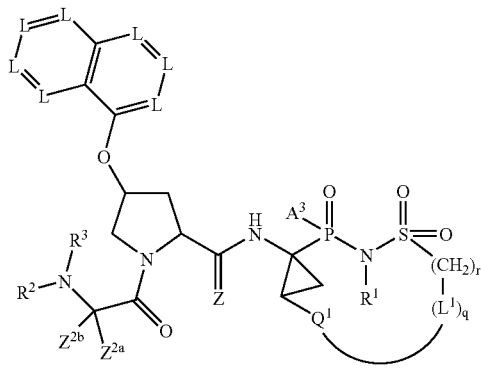

or a pharmaceutically acceptable salt, enantiomer, solvate or prodrug thereof wherein, R¹ is independently selected from H, alkyl, alkenyl, alkynyl, aryl, cycloalkyl, heterocycle, halogen, haloalkyl, alkylsulfonamido, arylsulfonamido, —C(O)NHS(O)₂—, or —S(O)₂—, optionally substituted with one or more A³;

R² is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH₂-groups not being directly linked to each other may be optionally substituted replaced by —O— such that the O-atom is linked to the N atom to which R² is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH₂, —NH((C1-4)alkyl) and —N((C1-4)alkyl)₂, —CONH₂ and —CONH—(C1-4)alkyl;

R³ is H or (C1-6)alkyl;

L is independently selected from C or N, providing there are no more than three consecutive N, each optionally substituted with one or more A³;

L¹ is independently selected from C, O, S, or N, providing there are no more than three consecutive N, each optionally substituted with one or more A³;

Z is O, N or S;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with R¹, R², Q¹, or any A³.

$Z^{2b}$ is H, (C1-6)alkyl, (C2-8)alkenyl, (C2-8)alkynyl;

Q¹ is (C1-8)alkyl, (C2-8)alkenyl, or (C2-8)alkynyl;

A³ is independently selected from H, —OH, —C(O), —C(O)OH, cyano, alkyl, alkenyl, alkynyl, amino, amido, imido, imino, halogen, CF₃, CH₂CF₃, cycloalkyl, nitro, aryl, aralkyl, alkoxy, aryloxy, heterocycle, heteroaryl, —C(A²)₂, C(O)A², —C(O)OA², —O(A²), —N(A²)₂, —S(A²), —CH₂P(O)(A²)(OA²), —CH₂P(O)(A²)(N(A²)₂), —CH₂P (O)(OA²)(OA²), —OCH₂P(O)(OA²)(OA²), —OCH₂P(O)(A²)(OA²), —OCH₂P(O)(A²)(N(A²)₂), —C(O)OCH₂P(O)(OA²)(OA²), —C(O)OCH₂P(O)(A²)(OA²), —C(O)OCH₂P(O)(A²)(N(A²)₂), —CH₂P(O)(OA²)(N(A²)₂), —OCH₂P(O)(A²)(N(A²)₂), —C(O)OCH₂P(O)(OA²)(N(A²)₂), —CH₂P(O)(N(A²)₂)(N(A²)₂), —C(O)OCH₂P(O)(N(A²)₂)(N(A²)₂), —OCH₂P(O)(N(A²)₂)(N(A²)₂), —(CH₂)ₘ-heterocycle, —(CH₂)ₘC(O)Oalkyl, —O—(CH₂)ₘ—O—C(O)—Oalkyl, —O—(CH₂)ᵣ—O—C(O)—(CH₂)ₘ-alkyl, —(CH₂)ₘO—C(O)—O-alkyl, —(CH₂)ₘO—C(O)—O-cycloalkyl, —N(H)C(Me)C(O)O-alkyl, or alkoxy arylsulfonamide, whereas each maybe optionally substituted with —R¹, —P(O)(OA²)(OA²), —P(O)(OA²)(N(A²)₂), —P(O)(A²)(OA²), —P(O)(A²)(N(A²)₂), or P(O)(N(A²)₂)(N(A²)₂), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH₂)ₘheterocycle, —(CH₂)ₘ—C(O)O-alkyl, —O(CH₂)ₘOC(O)Oalkyl, —O—(CH₂)ₘ—O—C(O)—(CH₂)ₘ-alkyl, —(CH₂)ₘ—O—C(O)—O-alkyl, —(CH₂)ₘ—O—C(O)—O-cycloalkyl, —N(H)C(CH₃)C(O)O-alkyl, or alkoxy arylsulfonamide, optionally substituted with R¹; or A³ is independently selected from —(CH₂)ₘ—, —C(O)O—, —NH—, —C(A²)₂—, to form a carbocyclic or heterocyclic ring with any other A³ or Q¹;

A² is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A³;

q is 1 to 10;

r is 1 to 2; and m is 0 to 6.

The present invention provides a compound of formula XXV, (XXV)

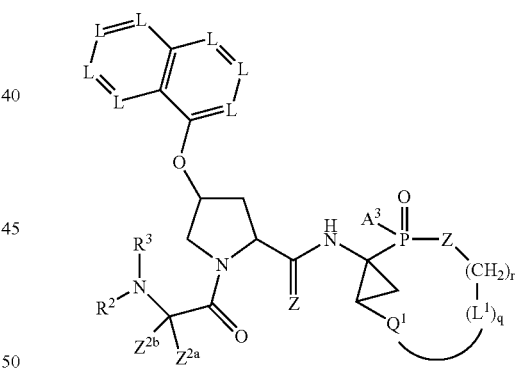

or a pharmaceutically acceptable salt, enantiomer, solvate or prodrug thereof wherein, R¹ is independently selected from H, alkyl, alkenyl, alkynyl, aryl, cycloalkyl, heterocycle, halogen, haloalkyl, alkylsulfonamido, arylsulfonamido, —C(O)NHS(O)₂—, or —S(O)₂—, optionally substituted with one or more A³;

R² is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —$CH_2$-groups not being directly linked to each other may be optionally substituted replaced by —O— such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —$NH_2$, —NH((C1-4)alkyl) and —N((C1-4)alkyl)$_2$, —$CONH_2$ and —CONH—(C1-4)alkyl;

$R^3$ is H or (C1-6)alkyl;

L is independently selected from C or N, providing there are no more than three consecutive N, each optionally substituted with one or more $A^3$;

$L^1$ is independently selected from C, O, S, or N, providing there are no more than three consecutive N, each optionally substituted with one or more $A^3$;

Z is independently O, N or S;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with $R^1$, $R^2$, $Q^1$, or any $A^3$;

$Z^{2b}$ is H, (C1-6)alkyl, (C2-8)alkenyl, (C2-8)alkynyl;

$Q^1$ is (C1-8)alkyl, (C2-8)alkenyl, or (C2-8)alkynyl;

$A^3$ is independently selected from H, —OH, —C(O), —C(O)OH, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, heteroaryl, —C($A^2$)$_2$, C(O)$A^2$, —C(O)O$A^2$, —O($A^2$), —N($A^2$)$_2$, —S($A^2$), —$CH_2$P(O) ($A^2$)(O$A^2$), —$CH_2$P(O)($A^2$)(N($A^2$)$_2$), —$CH_2$P(O)(O$A^2$)(O$A^2$), —O$CH_2$P(O)(O$A^2$)(O$A^2$), —O$CH_2$P(O)($A^2$)(O$A^2$), —O$CH_2$P(O)($A^2$)(N($A^2$)$_2$), —C(O)O$CH_2$P(O)(O$A^2$)(O$A^2$), —C(O)O$CH_2$P(O)($A^2$)(O$A^2$), —C(O)O$CH_2$P(O)($A^2$)(N($A^2$)$_2$), —$CH_2$P(O)(O$A^2$)(N($A^2$)$_2$), —O$CH_2$P(O)(O$A^2$)(N($A^2$)$_2$), —C(O)O$CH_2$P(O)(O$A^2$)(N($A^2$)$_2$), —$CH_2$P(O)(N($A^2$)$_2$)(N($A^2$)$_2$), —C(O)O$CH_2$P(O)(N($A^2$)$_2$)(N($A^2$)$_2$), —O$CH_2$P(O) (N($A^2$)$_2$) (N($A^2$)$_2$), —($CH_2$)$_m$-heterocycle, —($CH_2$)$_m$C(O)Oalkyl, —O—($CH_2$)$_m$—O—C(O)—Oalkyl, —O—($CH_2$)$_r$—O—C(O)—($CH_2$)$_m$-alkyl, —($CH_2$)$_m$O—C(O)—O-alkyl, —($CH_2$)$_m$O—C(O)—O-cycloalkyl, —N(H)C(Me)C(O)O-alkyl, or alkoxy arylsulfonamide, whereas each maybe optionally substituted with —$R^1$, —P(O)(O$A^2$)(O$A^2$), —P(O)(O$A^2$)(N($A^2$)$_2$), —P(O)($A^2$)(O$A^2$), —P(O)($A^2$)(N($A^2$)$_2$), or P(O)(N($A^2$)$_2$)(N($A^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —($CH_2$)$_m$heterocycle, —($CH_2$)$_m$—C(O)O-alkyl, —O($CH_2$)$_m$OC(O)Oalkyl, —O—($CH_2$)$_m$—O—C(O)—($CH_2$)$_m$-alkyl, —($CH_2$)$_m$—O—C(O)—O-alkyl, —($CH_2$)$_m$—O—C(O)—O-cycloalkyl, —N(H)C($CH_3$)C(O)O-alkyl, or alkoxy arylsulfonamide, optionally substituted with $R^1$; or $A^3$ is independently selected from —($CH_2$)$_m$—, —C(O)O—, —NH—, —C($A^2$)$_2$—, to form a carbocyclic or heterocyclic ring with any other $A^3$ or $Q^1$;

$A^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with $A^3$;

q is 1 to 10;
r is 1 to 2; and
m is 0 to 6.

The present invention provides a compound of formula XXVI,

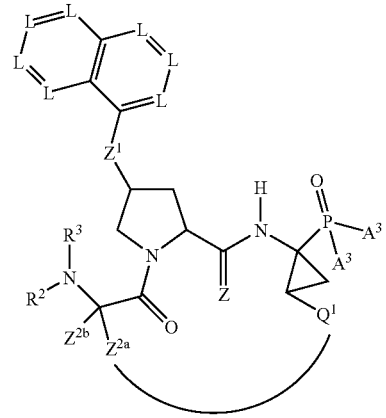

(XXVI)

or a pharmaceutically acceptable salt, enantiomer, solvate or prodrug thereof wherein, $R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —$CH_2$-groups not being directly linked to each other may be optionally substituted replaced by —O— such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —$NH_2$, —NH((C1-4)alkyl) and —N((C1-4)alkyl)$_2$, —$CONH_2$ and —CONH—(C1-4)alkyl;

$R^3$ is H or (C1-6)alkyl;

L is independently selected from C or N, providing there are no more than three consecutive N, each optionally substituted with one or more $A^3$;

Z is O, N or S;

$Z^1$ is O, N, C, or S, optionally substituted with one or more $A^3$;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with $R^1$, $R^2$, $Q^1$, or any $A^3$;

$Z^{2b}$ is H, (C1-6)alkyl, (C2-8)alkenyl, (C2-8)alkynyl;

$Q^1$ is (C1-8)alkyl, (C2-8)alkenyl, or (C2-8)alkynyl;

$A^3$ is independently selected from H, —OH, —C(O), —C(O)OH, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, heteroaryl, —C($A^2$)$_2$, C(O)$A^2$, —C(O)O$A^2$, —O($A^2$), —N($A^2$)$_2$, —S($A^2$), —$CH_2$P(O)($A^2$)(O$A^2$), —$CH_2$P(O)($A^2$)(N($A^2$)$_2$), —$CH_2$P (O)(OA²)(OA²), —OCH₂P(O)(OA²)(OA²), —OCH₂P(O)(A²)(OA²), —OCH₂P(O)(A²)(N(A²)₂), —C(O)OCH₂P(O)(OA²)(OA²), —C(O)OCH₂P(O)(A²)(OA²), —C(O)OCH₂P(O)(A²)(N(A²)₂), —OCH₂P(O)(OA²)(N(A²)₂), —C(O)OCH₂P(O)(OA²)(N(A²)₂), —CH₂P(O)(N(A²)₂)(N(A²)₂), —C(O)OCH₂P(O)(N(A²)₂)(N(A²)₂), —OCH₂P(O)(N(A²)₂)(N(A²)₂), —(CH₂)$_m$-heterocycle, —(CH₂)$_m$C(O)Oalkyl, —O—(CH₂)$_m$—O—C(O)—Oalkyl, —O—(CH₂)$_r$—O—C(O)—(CH₂)$_m$-alkyl, —(CH₂)$_m$O—C(O)—O-alkyl, —(CH₂)$_m$O—C(O)—O-cycloalkyl, —N(H)C(Me)C(O)O-alkyl, or alkoxy arylsulfonamide, whereas each maybe optionally substituted with —R¹, —P(O)(OA²)(OA²), —P(O)(OA²)(N(A²)₂), —P(O)(A²)(OA²), —P(O)(A²)(N(A²)₂), or P(O)(N(A²)₂)(N(A²)₂), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH₂)$_m$heterocycle, —(CH₂)$_m$—C(O)O-alkyl, —O(CH₂)$_m$OC(O)Oalkyl, —O—(CH₂)$_m$—O—C(O)—(CH₂)$_m$-alkyl, —(CH₂)$_m$—O—C(O)—O-alkyl, —(CH₂)$_m$—O—C(O)—O-cycloalkyl, —N(H)C(CH₃)C(O)O-alkyl, or alkoxy arylsulfonamide, optionally substituted with R¹; or A³ is independently selected from —(CH₂)$_m$—, —C(O)O—, —NH—, —C(A²)₂—, to form a carbocyclic or heterocyclic ring with any other A³ or Q¹;

A² is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A³; and m is 0 to 6.

The present invention provides a compound of formula XXVII,

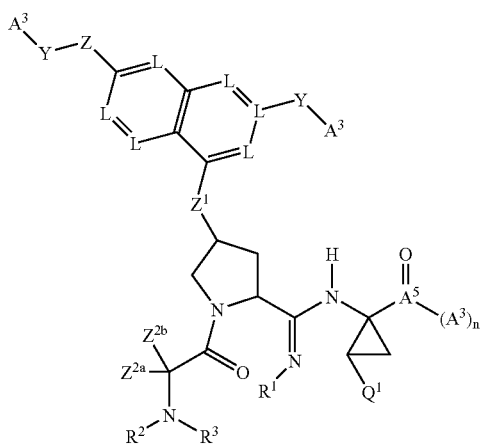

(XXVII)

or a pharmaceutically acceptable salt, enantiomer, solvate or prodrug thereof wherein, R¹ is independently selected from H, alkyl, alkenyl, alkynyl, aryl, cycloalkyl, heterocycle, halogen, haloalkyl, alkylsulfonamido, arylsulfonamido, —C(O)NHS(O)₂—, or —S(O)₂—, optionally substituted with one or more A³;

R² is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH₂-groups not being directly linked to each other may be optionally substituted replaced by —O— such that the O-atom is linked to the N atom to which R² is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH₂, —NH((C1-4)alkyl) and —N((C1-4)alkyl)₂, —CONH₂ and —CONH—(C1-4)alkyl;

R³ is H or (C1-6)alkyl;

n is 1 or 2;

L is independently selected from C or N, providing there are no more than three consecutive N, each optionally substituted with one or more A³;

Y is a bond, N, or C, each optionally substituted with R¹ or R²;

Z is O, N or S;

Z¹ is O, N, C, or S, optionally substituted with one or more A³;

Z$^{2a}$ is H, (C1-10)alkyl, (C2-10)alkenyl, (C2-10)alkynyl, wherein any carbon atom may be replaced with a heteroatom selected from O, S or N, or Z$^{2a}$ optionally forms a carbocycle or heterocycle with R¹, R², Q¹, or any A³.

Z$^{2b}$ is H, (C1-6)alkyl, (C2-8)alkenyl, (C2-8)alkynyl;

Q¹ is (C1-8)alkyl, (C2-8)alkenyl, or (C2-8)alkynyl;

A³ is independently selected from H, —OH, —C(O), —C(O)OH, cyano, alkyl, alkenyl, alkynyl, amino, amido, imido, imino, halogen, CF₃, CH₂CF₃, cycloalkyl, nitro, aryl, aralkyl, alkoxy, aryloxy, heterocycle, heteroaryl, —C(A²)₂, C(O)A², —C(O)OA², —O(A²), —N(A²)₂, —S(A²), —CH₂P(O)(A²)(OA²), —CH₂P(O)(A²)(N(A²)₂), —CH₂P(O)(OA²)(OA²), —OCH₂P(O)(OA²)(OA²), —OCH₂P(O)(A²)(OA²), —OCH₂P(O)(A²)(N(A²)₂), —C(O)OCH₂P(O)(OA²)(OA²), —C(O)OCH₂P(O)(A²)(OA²), —C(O)OCH₂P(O)(A²)(N(A²)₂), —CH₂P(O)(OA²)(N(A²)₂), —OCH₂P(O)(OA²)(N(A²)₂), —C(O)OCH₂P(O)(OA²)(N(A²)₂), —CH₂P(O)(N(A²)₂)(N(A²)₂), —C(O)OCH₂P(O)(N(A²)₂)(N(A²)₂), —OCH₂P(O)(N(A²)₂)(N(A²)₂), —(CH₂)$_m$-heterocycle, —(CH₂)$_m$C(O)Oalkyl, —O—(CH₂)$_m$—O—C(O)—Oalkyl, —O—(CH₂)$_r$—O—C(O)—(CH₂)$_m$-alkyl, —(CH₂)$_m$O—C(O)—O-alkyl, —(CH₂)$_m$O—C(O)—O-cycloalkyl, —N(H)C(Me)C(O)O-alkyl, or alkoxy arylsulfonamide, whereas each maybe optionally substituted with —R¹, —P(O)(OA²)(OA²), —P(O)(OA²)(N(A²)₂), —P(O)(A²)(OA²), —P(O)(A²)(N(A²)₂), or P(O)(N(A²)₂)(N(A²)₂), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH₂)$_m$heterocycle, —(CH₂)$_m$—C(O)O-alkyl, —O(CH₂)$_m$OC(O)Oalkyl, —O—(CH₂)$_n$—O—C(O)—(CH₂)$_m$-alkyl, —(CH₂)$_m$—O—C(O)—O-alkyl, —(CH₂)$_m$—O—C(O)—O-cycloalkyl, —N(H)C(CH₃)C(O)O-alkyl, or alkoxy arylsulfonamide, optionally substituted with R¹; or A³ is independently selected from —(CH₂)$_m$—, —C(O)O—, —NH—, —C(A²)₂—, to form a carbocyclic or heterocyclic ring with any other A³ or Q¹;

A² is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A³;

A⁵ is C or P, optionally substituted with A³;

n is 1 or 2; and m is 0 to 6.

The present invention provides a compound of formula XXVIII,

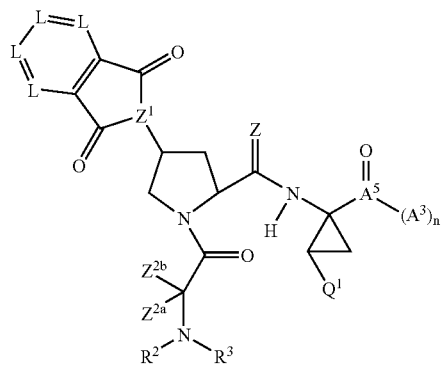

(XXVIII)

or a pharmaceutically acceptable salt, enantiomer, solvate or prodrug thereof wherein, $R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH$_2$, —NH((C1-4)alkyl) and —N((C1-4)alkyl)$_2$, —CONH$_2$ and —CONH—(C1-4)alkyl;

$R^3$ is H or (C1-6)alkyl;

L is independently selected from C or N, providing there are no more than three consecutive N, each optionally substituted with one or more $A^3$;

n is 1 or 2;

Z is O, N or S;

$Z^1$ is N, or C;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with $R^1$, $R^2$, $Q^1$, or any $A^3$;

$Z^{2b}$ is H, (C1-6)alkyl, (C2-8)alkenyl, (C2-8)alkynyl;

$Q^1$ is (C1-8)alkyl, (C2-8)alkenyl, or (C2-8)alkynyl;

$A^3$ is independently selected from H, —OH, —C(O), —C(O)OH, cyano, alkyl, alkenyl, alkynyl, amino, amido, imido, imino, halogen, CF$_3$, CH$_2$CF$_3$, cycloalkyl, nitro, aryl, aralkyl, alkoxy, aryloxy, heterocycle, heteroaryl, —C($A^2$)$_2$, C(O)$A^2$, —C(O)O$A^2$, —O($A^2$), —N($A^2$)$_2$, —S($A^2$), —CH$_2$P(O)($A^2$)(O$A^2$), —CH$_2$P(O)($A^2$)(N($A^2$)$_2$), —CH$_2$P (O)(O$A^2$)(O$A^2$), —OCH$_2$P(O)(O$A^2$)(O$A^2$), —OCH$_2$P(O)($A^2$)(O$A^2$), —OCH$_2$P(O)($A^2$)(N($A^2$)$_2$), —C(O)OCH$_2$P(O)(O$A^2$)(O$A^2$), —C(O)OCH$_2$P(O)($A^2$)(O$A^2$), —C(O)OCH$_2$P(O)($A^2$) (N($A^2$)$_2$), —CH$_2$P(O)(O$A^2$) (N($A^2$)$_2$), —OCH$_2$P(O) (O$A^2$)(N($A^2$)$_2$), —C(O)OCH$_2$P(O)(O$A^2$)(N($A^2$)$_2$), —CH$_2$P (O)(N($A^2$)$_2$)(N($A^2$)$_2$), —C(O)OCH$_2$P(O)(N($A^2$)$_2$)(N($A^2$)$_2$), —OCH$_2$P(O)(N($A^2$)$_2$)(N($A^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C (O)—O-alkyl, —(CH$_2$)$_m$O—C(O)—O-cycloalkyl, —N(H)C (Me)C(O)O-alkyl, or alkoxy arylsulfonamide, whereas each maybe optionally substituted with —R$^1$, —P(O)(O$A^2$) (O$A^2$), —P(O)(O$A^2$)(N($A^2$)$_2$), —P(O)($A^2$)(O$A^2$), —P(O) ($A^2$)(N($A^2$)$_2$), or P(O)(N($A^2$)$_2$)(N($A^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with R$^1$; or $A^3$ is independently selected from —(CH$_2$)$_m$—, —C(O) O—, —NH—, —C($A^2$)$_2$—, to form a carbocyclic or heterocyclic ring with any other $A^3$ or $Q^1$;

$A^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with $A^3$;

$A^5$ is C or P, optionally substituted with $A^3$; and m is 0 to 6.

The present invention provides a compound of formula XXIX,

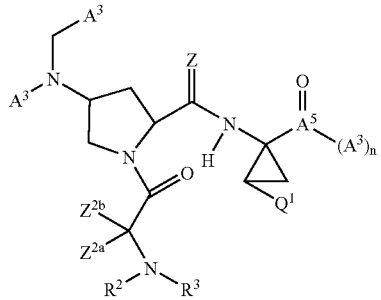

(XXIX)

or a pharmaceutically acceptable salt, enantiomer, solvate or prodrug thereof wherein, $R^1$ is independently selected from H, alkyl, alkenyl, alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NH$_2$, —NH((C1-4)alkyl) and —N((C1-4)alkyl)$_2$, —CONH$_2$ and —CONH—(C1-4)alkyl;

$R^3$ is H or (C1-6)alkyl;

n is 1 or 2;

L is independently selected from C or N, providing there are no more than three consecutive N, each optionally substituted with one or more $A^3$;

Z is O, N or S;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with $R^1$, $R^2$, $Q^1$, or any $A^3$;

$Z^{2b}$ is 14 (C1-6)alkyl, (C2-8)alkenyl, (C2-8)alkynyl;

$Q^1$ is (C1-8)alkyl, (C2-8)alkenyl, or (C2-8)alkynyl;

$A^3$ is independently selected from H, —OH, —C(O), —C(O)OH, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, heteroaryl, —C($A^2$)$_2$, C(O)$A^2$, —C(O)O$A^2$, —O($A^2$), —N($A^2$)$_2$, —S($A^2$), —CH$_2$P(O)($A^2$)(O$A^2$), —CH$_2$P(O)($A^2$)(N($A^2$)$_2$), —CH$_2$P(O)(O$A^2$)(O$A^2$), —OCH$_2$P(O)(O$A^2$)(O$A^2$), —OCH$_2$P(O)($A^2$)(O$A^2$), —OCH$_2$P(O)($A^2$)(N($A^2$)$_2$), —C(O)OCH$_2$P(O)(O$A^2$)(O$A^2$), —C(O)OCH$_2$P(O)($A^2$)(O$A^2$), —C(O)OCH$_2$P(O)($A^2$)(N($A^2$)$_2$), —CH$_2$P(O)(O$A^2$)(N($A^2$)$_2$), —OCH$_2$P(O)(O$A^2$)(N($A^2$)$_2$), —C(O)OCH$_2$P(O)(O$A^2$)(N($A^2$)$_2$), —CH$_2$P(O)(N($A^2$)$_2$)(N($A^2$)$_2$), —C(O)OCH$_2$P(O)(N($A^2$)$_2$)(N($A^2$)$_2$), —OCH$_2$P(O)(N($A^2$)$_2$)(N($A^2$)$_2$), —(CH$_2$)$_m$-heterocycle, —(CH$_2$)$_m$C(O)Oalkyl, —O—(CH$_2$)$_m$—O—C(O)—Oalkyl, —O—(CH$_2$)$_r$—O—C(O)—(CH$_2$)$_m$-alkyl, —(CH$_2$)$_m$O—C(O)—O-alkyl, —(CH$_2$)$_m$O—C(O)—O-cycloalkyl, —N(H)C(Me)C($A^2$)C(O)O-alkyl, or alkoxy arylsulfonamide, whereas each maybe optionally substituted with —$R^1$, —P(O)(O$A^2$)(O$A^2$), —P(O)(O$A^2$)(N($A^2$)$_2$), —P(O)($A^2$)(O$A^2$), —P(O)($A^2$)(N($A^2$)$_2$), or P(O)(N($A^2$)$_2$)(N($A^2$)$_2$), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH$_2$)$_m$heterocycle, —(CH$_2$)$_m$—C(O)O-alkyl, —O(CH$_2$)$_m$OC(O)Oalkyl, —O—(CH$_2$)$_m$—O—C(O)—(CH$_2$)$_m$-alkyl, —(CH$_2$)$_m$—O—C(O)—O-alkyl, —(CH$_2$)$_m$—O—C(O)—O-cycloalkyl, —N(H)C(CH$_3$)C(O)O-alkyl, or alkoxy arylsulfonamide, optionally substituted with $R^1$; or $A^3$ is independently selected from —(CH$_2$)$_m$—, —C(O)O—, —NH—, —C($A^2$)$_2$—, to form a carbocyclic or heterocyclic ring with any other $A^3$ or $Q^1$;

$A^2$ is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with $A^3$;

$A^5$ is C or P, optionally substituted with $A^3$; and m is 0 to 6.

The present invention provides a compound of formula XXXVI,

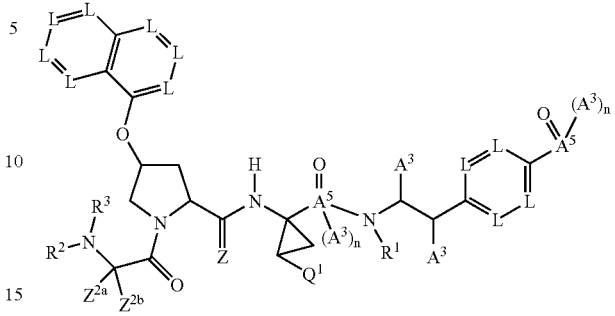

(XXXVI)

or a pharmaceutically acceptable salt, enantiomer, solvate or prodrug thereof wherein, $R^1$ is independently selected from H, alkyl alkenyl alkynyl, aryl, cycloalkyl, heterocycle, halogen, haloalkyl, alkylsulfonamido, arylsulfonamido, —C(O)NHS(O)$_2$—, or —S(O)$_2$—, optionally substituted with one or more $A^3$;

$R^2$ is (C2-10)alkyl, (C3-7)cycloalkyl or (C1-4)alkyl-(C3-7)cycloalkyl, where said cycloalkyl and alkyl-cycloalkyl may be optionally substituted with mono-, di- or tri-substituted with (C1-3)alkyl, or where said alkyl, cycloalkyl and alkyl-cycloalkyl may be optionally substituted with mono- or di-substituted with substituents selected from hydroxy and O—(C1-4)alkyl, or where each of said alkyl-groups may be optionally substituted with mono-, di- or tri-substituted with halogen, or where each of said cycloalkyl groups being 5-, 6- or 7-membered, one or two —CH$_2$-groups not being directly linked to each other may be optionally substituted replaced by —O— such that the O-atom is linked to the N atom to which $R^2$ is attached via at least two C-atoms, phenyl, (C1-3)alkyl-phenyl, heteroaryl or (C1-3)alkyl-heteroaryl, wherein the heteroaryl-groups are 5- or 6-membered having from 1 to 3 heteroatoms selected from N, O and S; wherein said phenyl and heteroaryl groups may be optionally substituted with mono-, di- or trisubstituted with substituents selected from halogen, —OH, (C1-4)alkyl, O—(C1-4)alkyl, S—(C1-4)alkyl, —NFL, —NH((C1-4)alkyl) and —N((C1-4)alkyl)$_2$, —CONH$_2$ and —CONH—(C1-4)alkyl;

$R^3$ is H or (C1-6)alkyl;

L is independently selected from C or N, providing there are no more than three consecutive N, each optionally substituted with one or more $A^3$;

Z is O, N or S;

$Z^{2a}$ is H, (C1-10)alkyl, (C2-10)alkenyl, (C2-10)alkynyl, wherein any carbon atom may be replaced with a heteroatom selected from O, S or N, or $Z^{2a}$ optionally forms a carbocycle or heterocycle with $R^1$, $R^2$, $Q^1$, or any $A^3$;

$Z^{2b}$ is H, (C1-6)alkyl, (C2-8)alkenyl, (C2-8)alkynyl;

$Q^1$ is (C1-8)alkyl, (C2-8)alkenyl, or (C2-8)alkynyl;

$A^3$ is independently selected from H, —OH, —C(O), —C(O)OH, cyano, alkyl, alkenyl, alkynyl, amino, amido, imido, imino, halogen, $CF_3$, $CH_2CF_3$, cycloalkyl, nitro, aryl, aralkyl, alkoxy, aryloxy, heterocycle, heteroaryl, —C($A^2$)$_2$, C(O)$A^2$, —C(O)O$A^2$, —O($A^2$), —N($A^2$)$_2$, —S($A^2$), —CH$_2$P(O)($A^2$)(O$A^2$), —CH$_2$P(O)($A^2$)(N($A^2$)$_2$), —CH$_2$P(O)(O$A^2$)(O$A^2$), —OCH$_2$P(O)(O$A^2$)(O$A^2$), —OCH$_2$P(O)($A^2$)(O$A^2$), —OCH$_2$P(O)($A^2$)(N($A^2$)$_2$), —C(O)OCH$_2$P(O)($A^2$)(O$A^2$), —C(O)OCH$_2$P(O)($A^2$)(N($A^2$)$_2$), —CH$_2$P(O)(O$A^2$)(N($A^2$)$_2$), —OCH$_2$P(O)(O$A^2$)(N($A^2$)$_2$), —C(O)OCH$_2$P(O)(O$A^2$)(N($A^2$)$_2$), —CH$_2$P (O)(N(A²)₂)(N(A²)₂), —C(O)OCH₂P(O)(N(A²)₂)(N(A²)₂), —OCH₂P(O) (N(A²)₂) (N(A²)₂), —(CH₂)ₘ-heterocycle, —(CH₂)ₘC(O)Oalkyl, —O—(CH₂)ₘ—O—C(O)—Oalkyl, —O—(CH₂)ᵣ—O—C(O)—(CH₂)ₘ-alkyl, —(CH₂)ₘO—C(O)—O-alkyl, —(CH₂)ₘO—C(O)—O-cycloalkyl, —N(H)C(Me)C(O)O-alkyl, or alkoxy arylsulfonamide, whereas each maybe optionally substituted with —R¹, —P(O)(OA²)(OA²), —P(O)(OA²)(N(A²)₂), —P(O)(A²)(OA²), —P(O)(A²)(N(A²)₂), or P(O)(N(A²)₂)(N(A²)₂), halogen, alkyl, alkenyl, alkynyl, aryl, carbocycle, heterocycle, aralkyl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, —(CH₂)ₘheterocycle, —(CH₂)ₘ—C(O)O-alkyl, —O(CH₂)ₘOC(O)Oalkyl, —O—(CH₂)ₘ—O—C(O)—(CH₂)ₘ-alkyl, —(CH₂)ₘ—O—C(O)—O-alkyl, —(CH₂)ₘ—O—C(O)—O-cycloalkyl, —N(H)C(CH₃)C(O)O-alkyl, or alkoxy arylsulfonamide, optionally substituted with R¹; or A³ is independently selected from —(CH₂)ₘ—, —C(O)O—, —NH—, —C(A²)₂—, to form a carbocyclic or heterocyclic ring with any other A³ or Q¹;

A² is independently selected from H, alkyl, alkenyl, alkynyl, amino, amino acid, alkoxy, aryloxy, cyano, haloalkyl, cycloalkyl, aryl, heteroaryl, alkylsulfonamide, or arylsulfonamide, optionally substituted with A³;

A⁵ is C or P, optionally substituted with A³;

n is independently 0, 1, or 2; and m is 0 to 6.

The present invention provides a compound selected from the group consisting of:

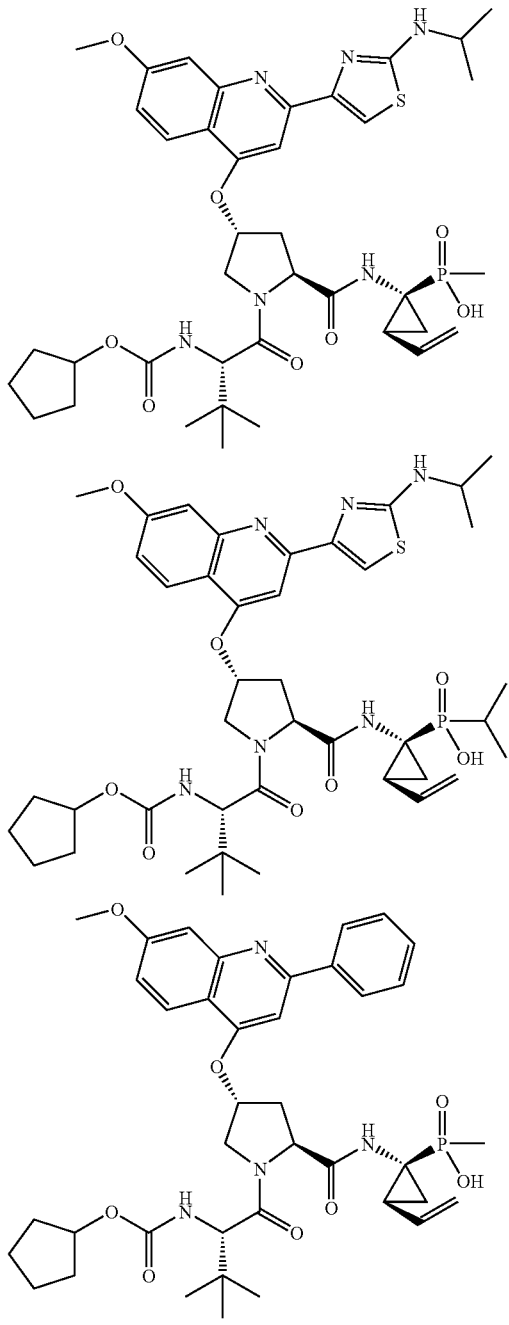
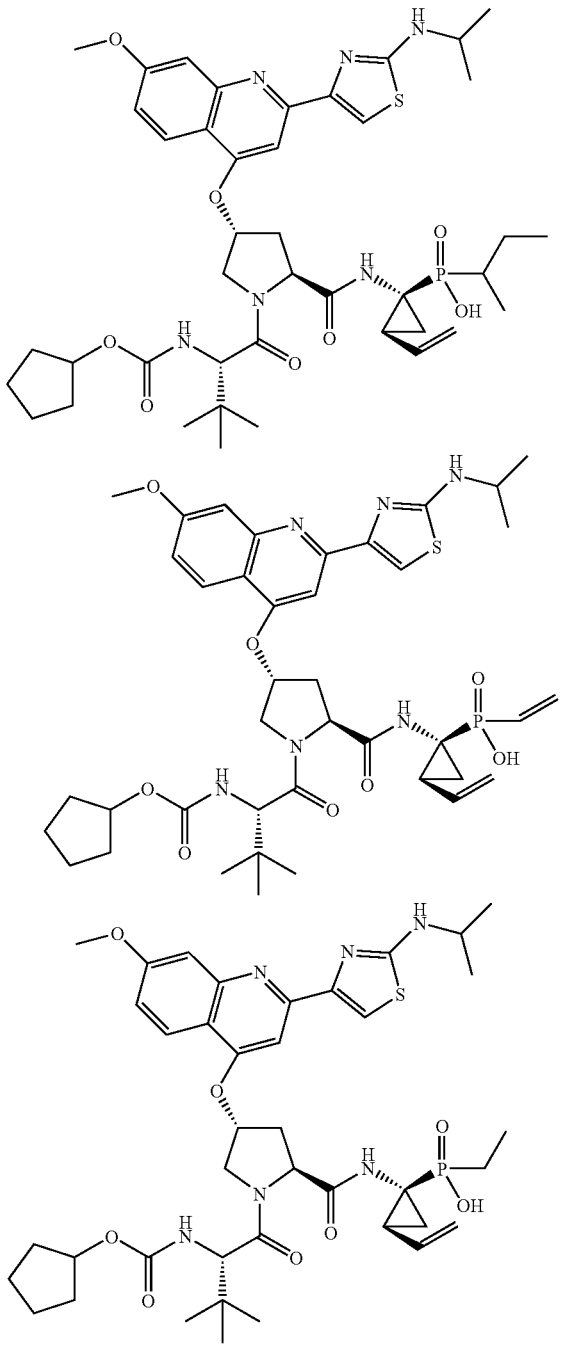

37 38
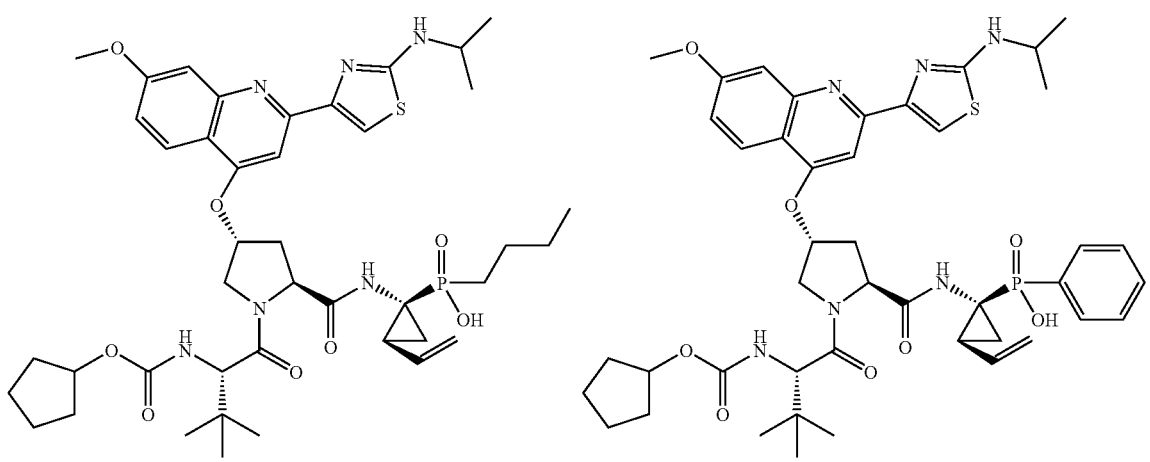
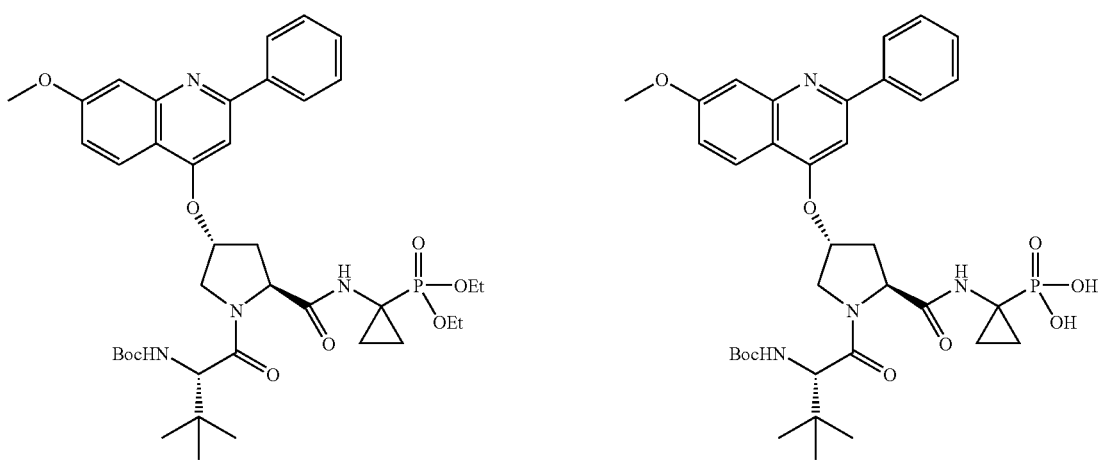
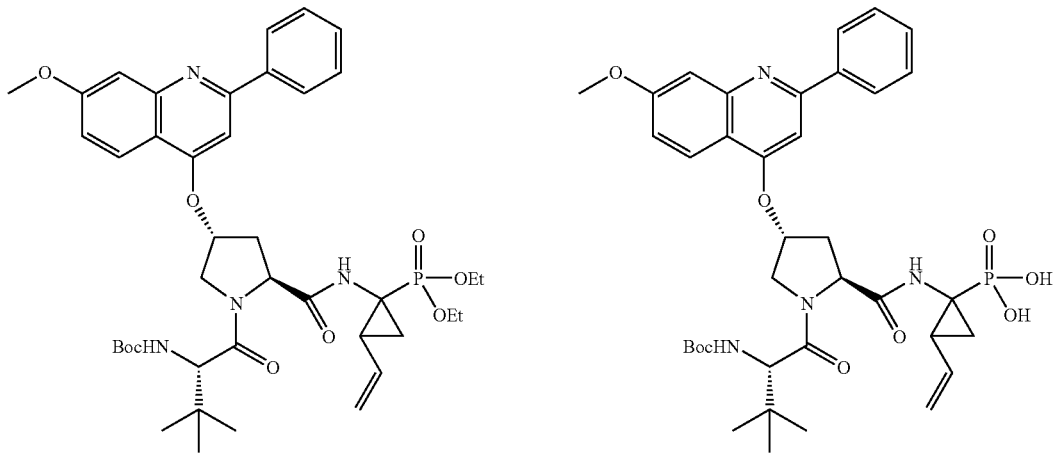

39
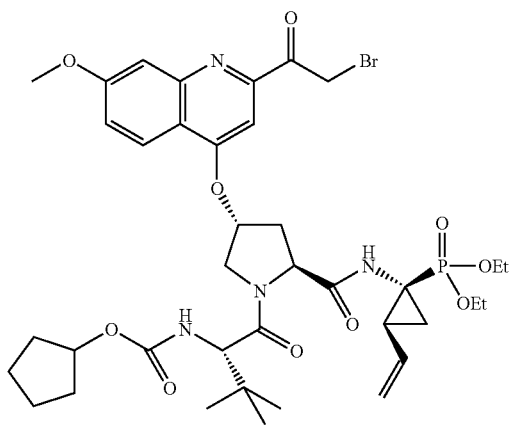
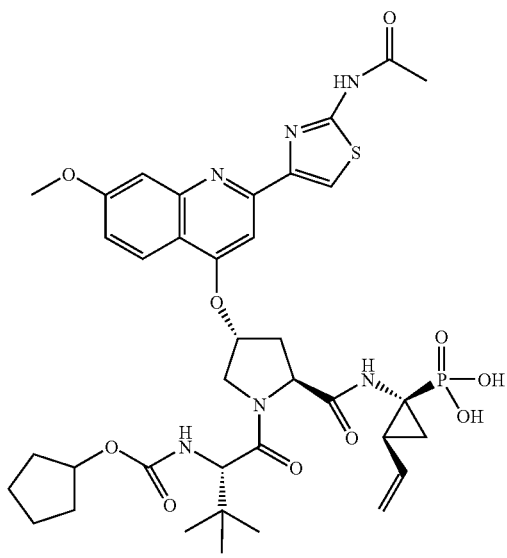
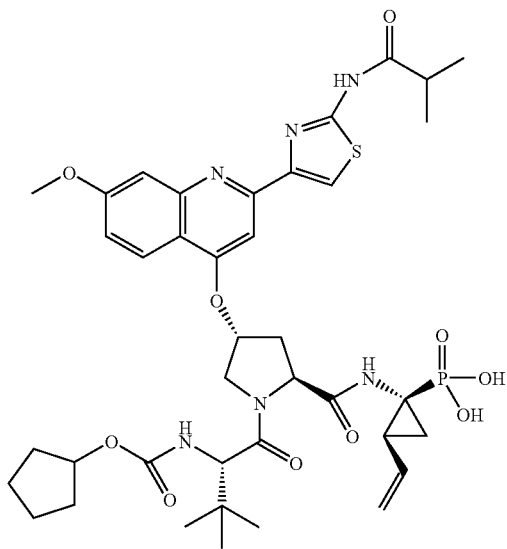
40
-continued
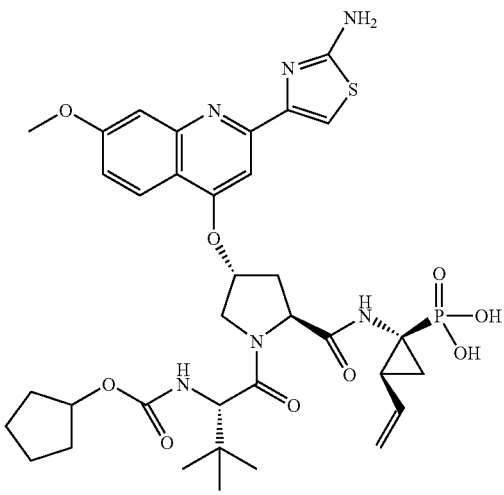
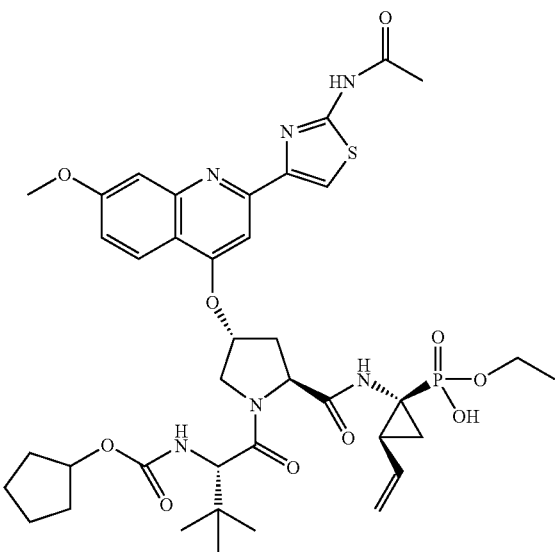
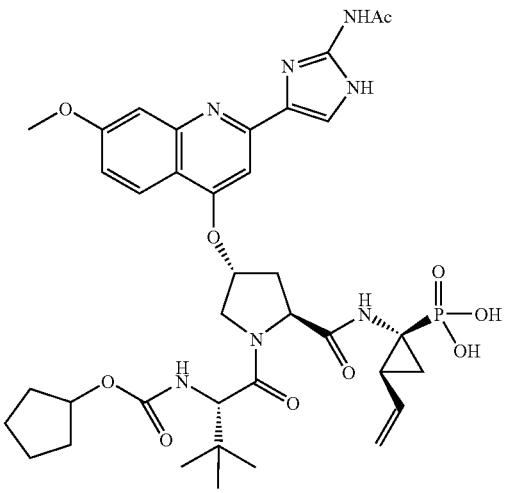

41
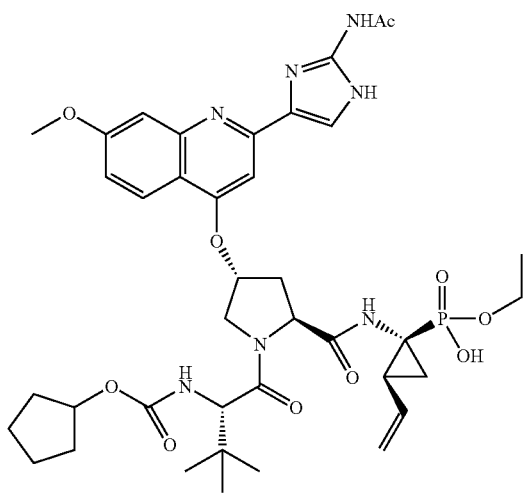
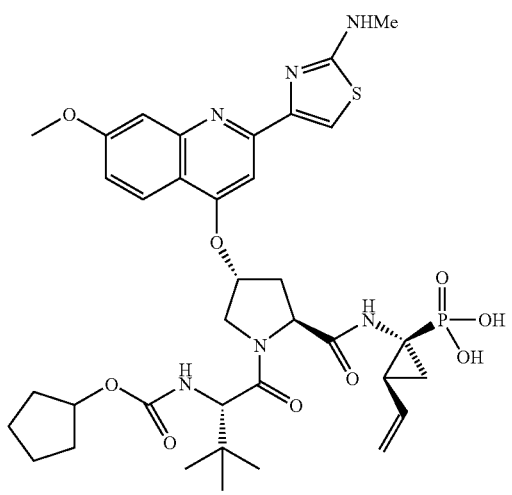
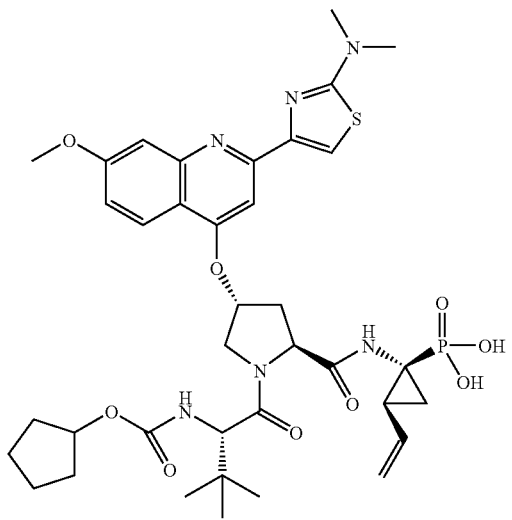
42
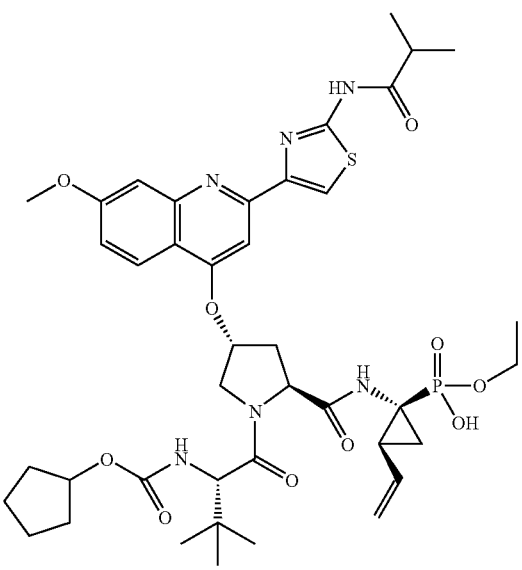
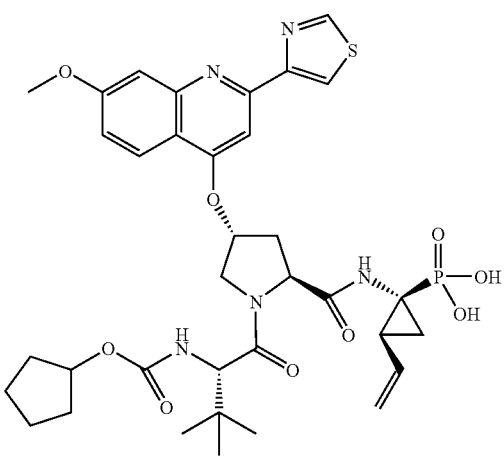
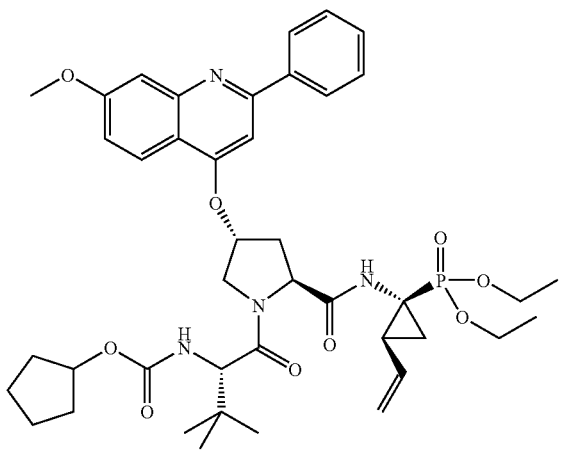

-continued
43
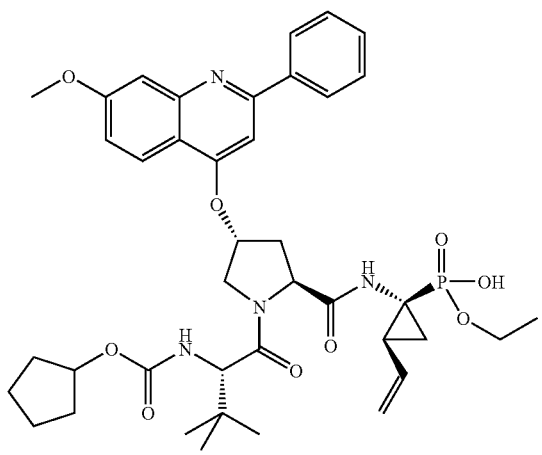
44
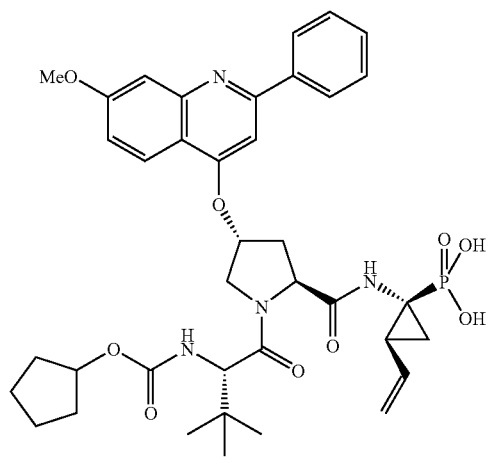
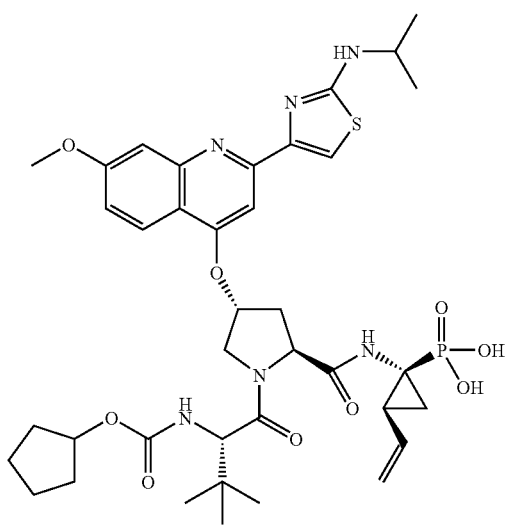
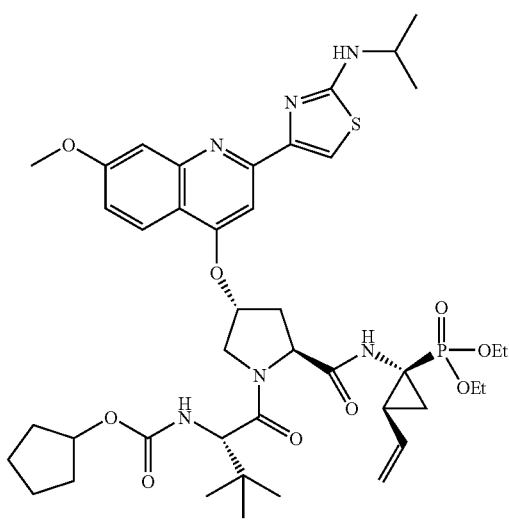
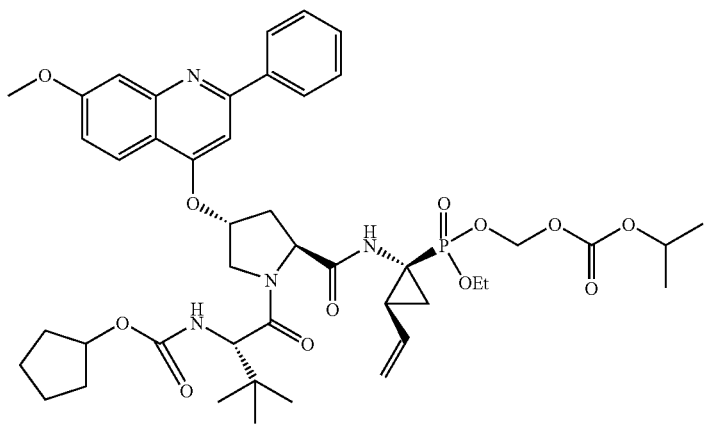

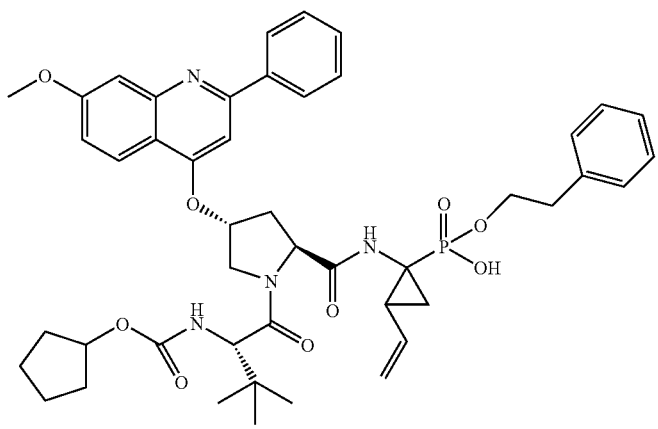
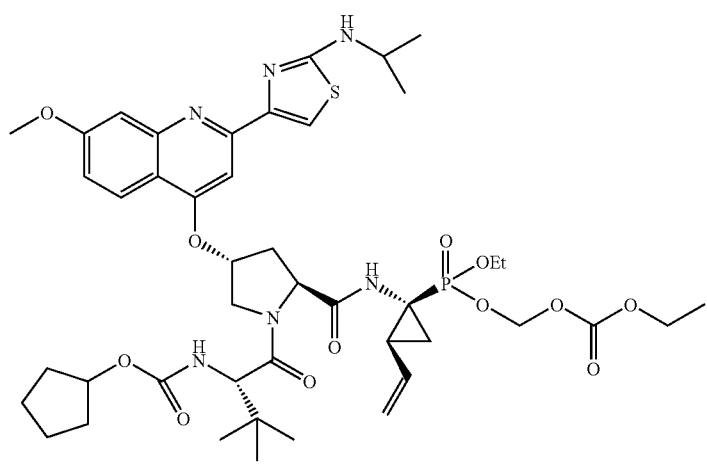
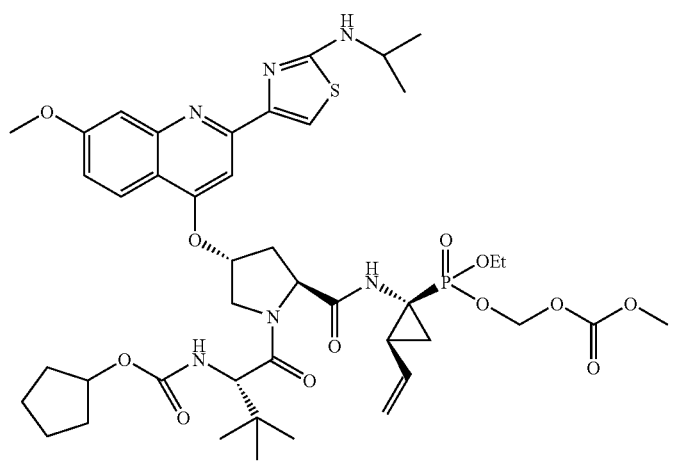

-continued
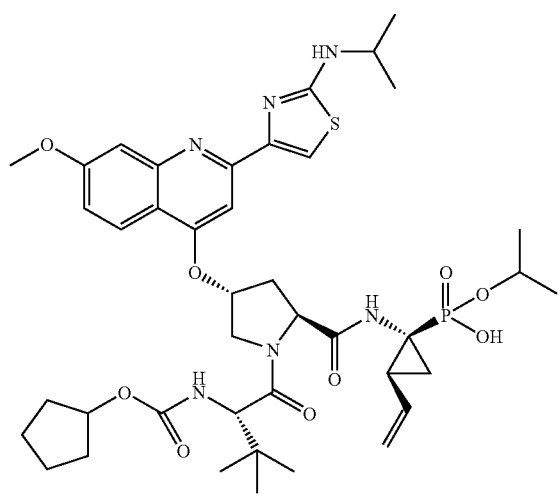
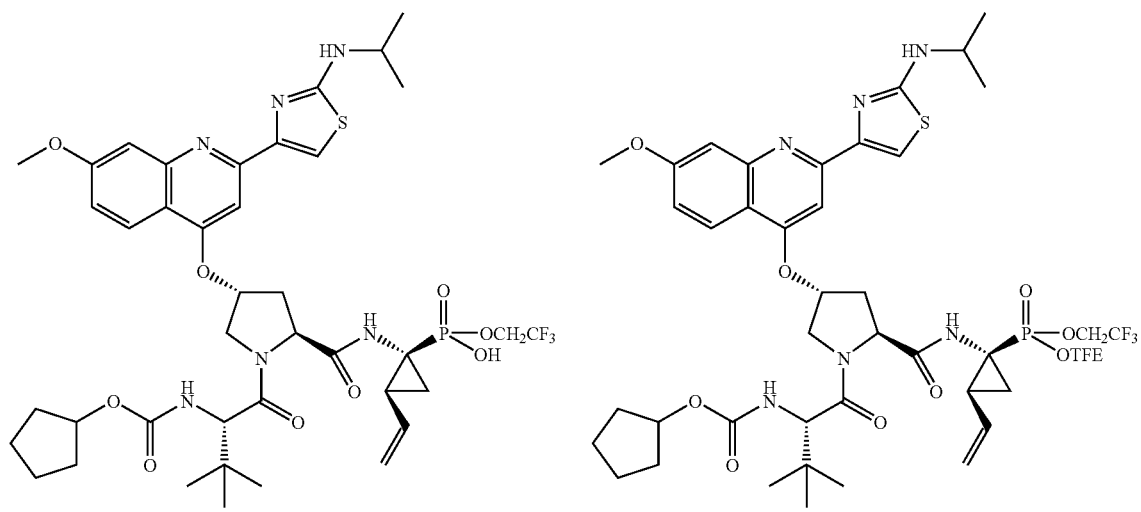
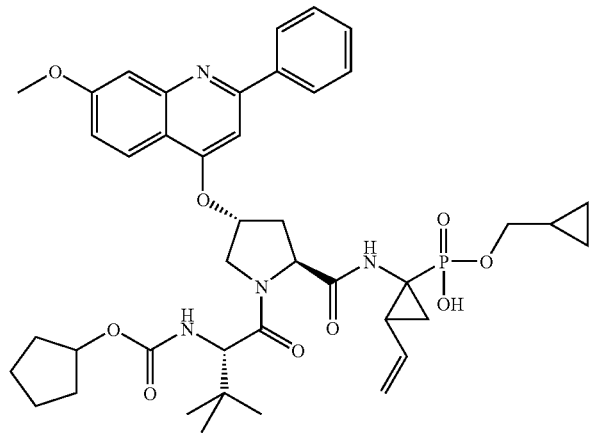

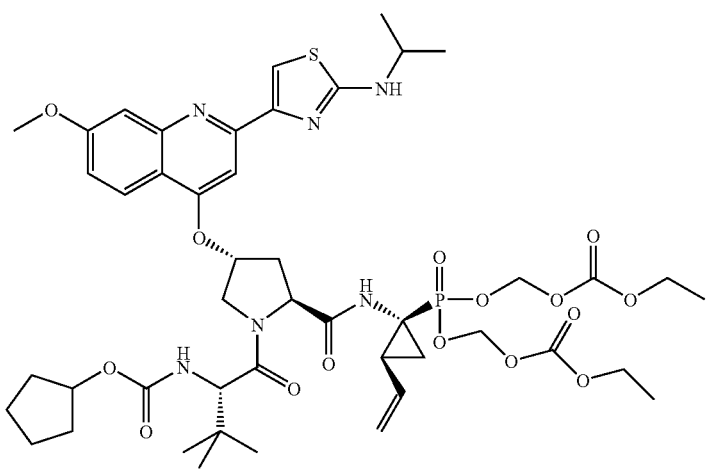
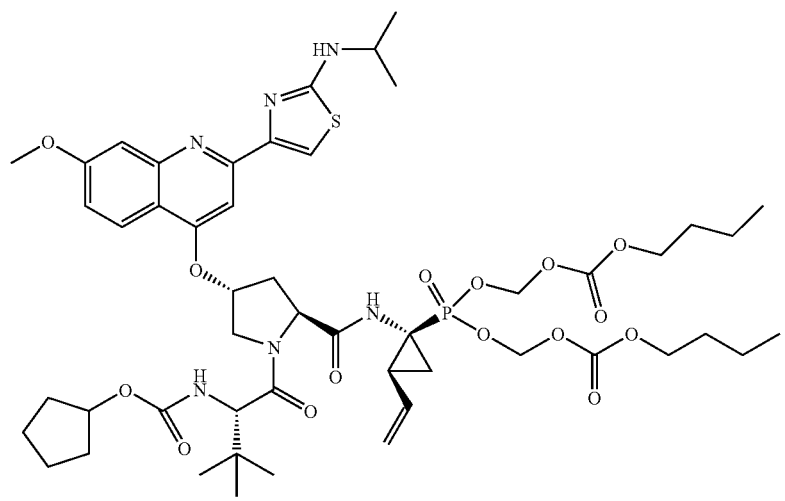
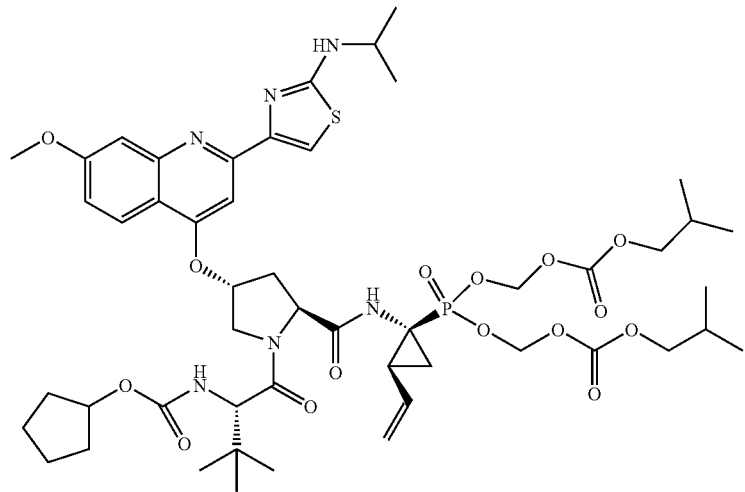

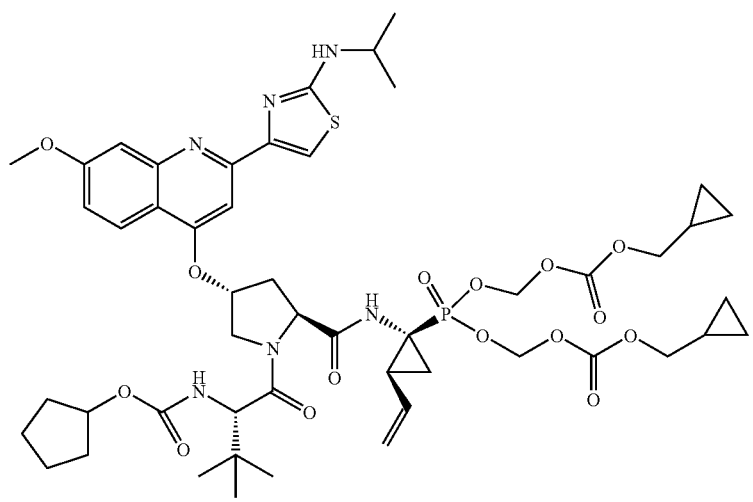
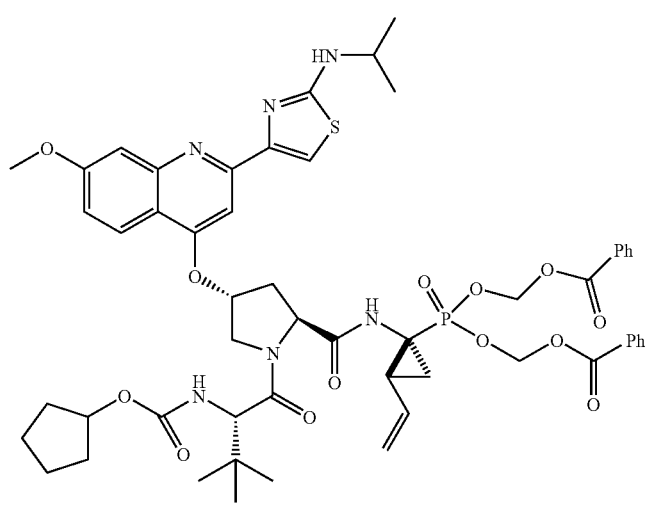
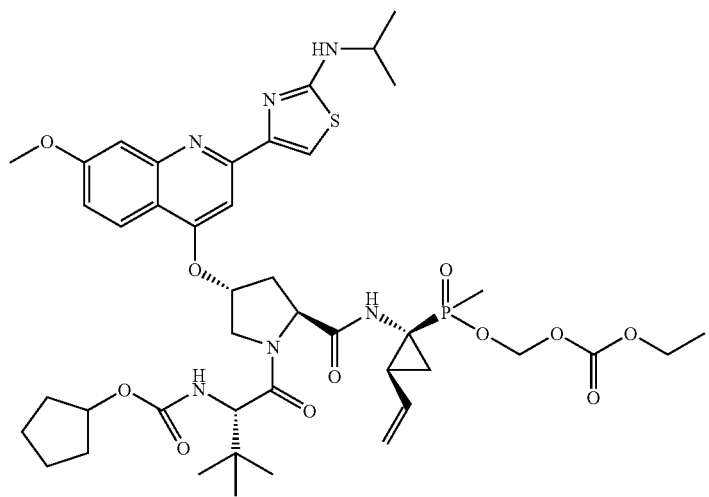

-continued
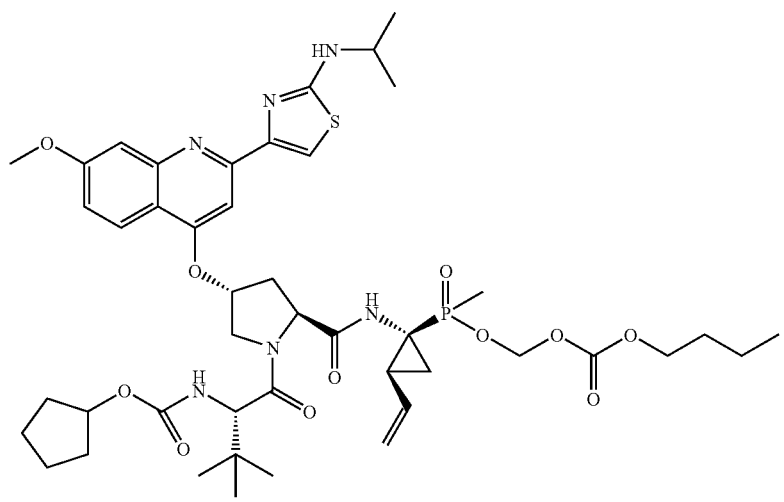
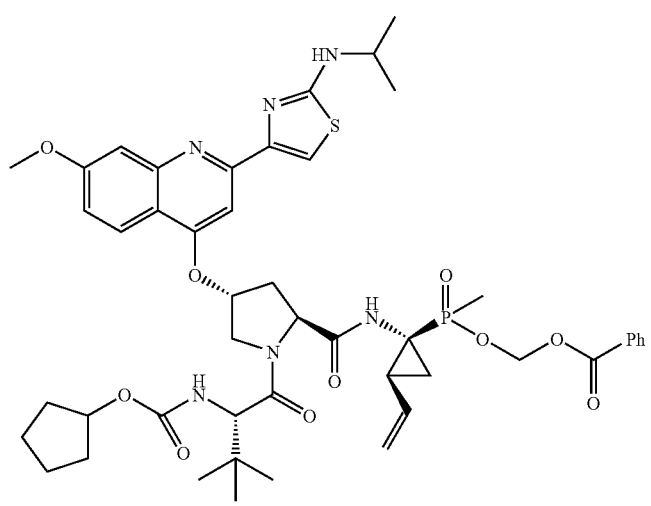
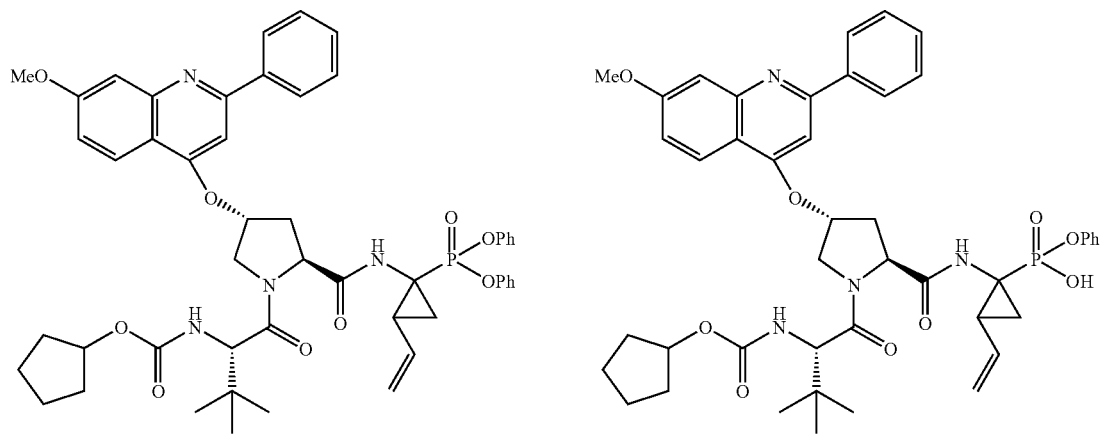

55
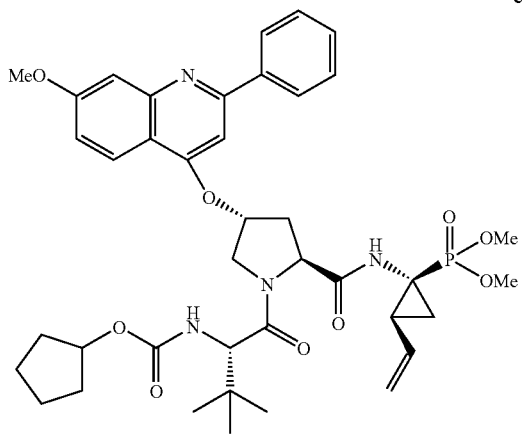
56
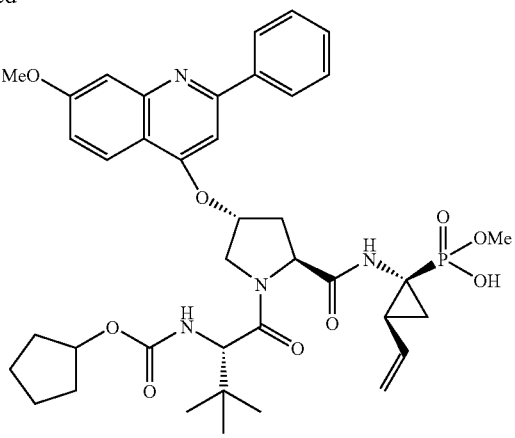
-continued
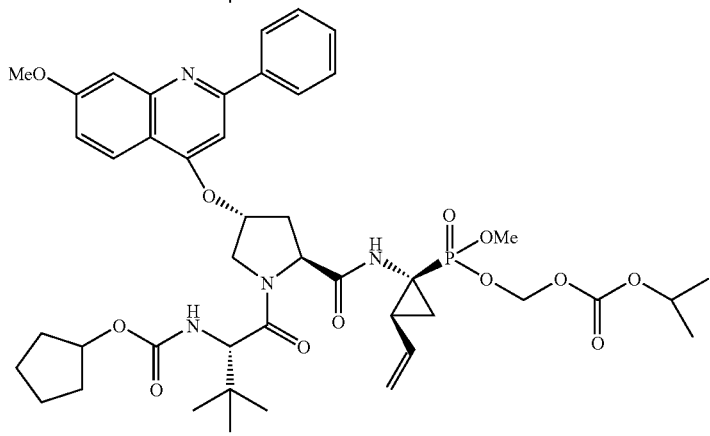
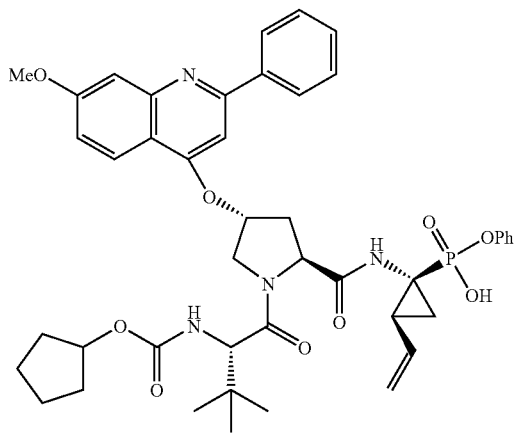
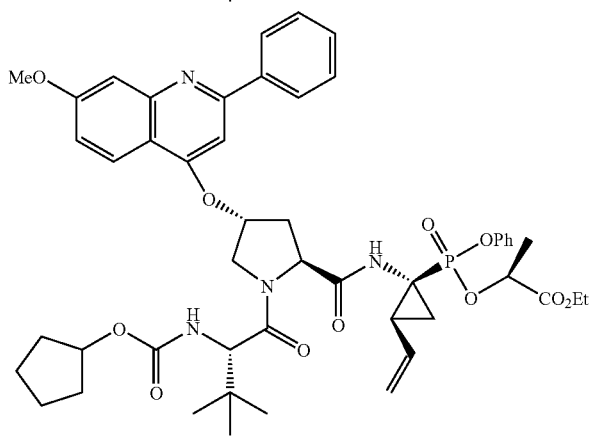

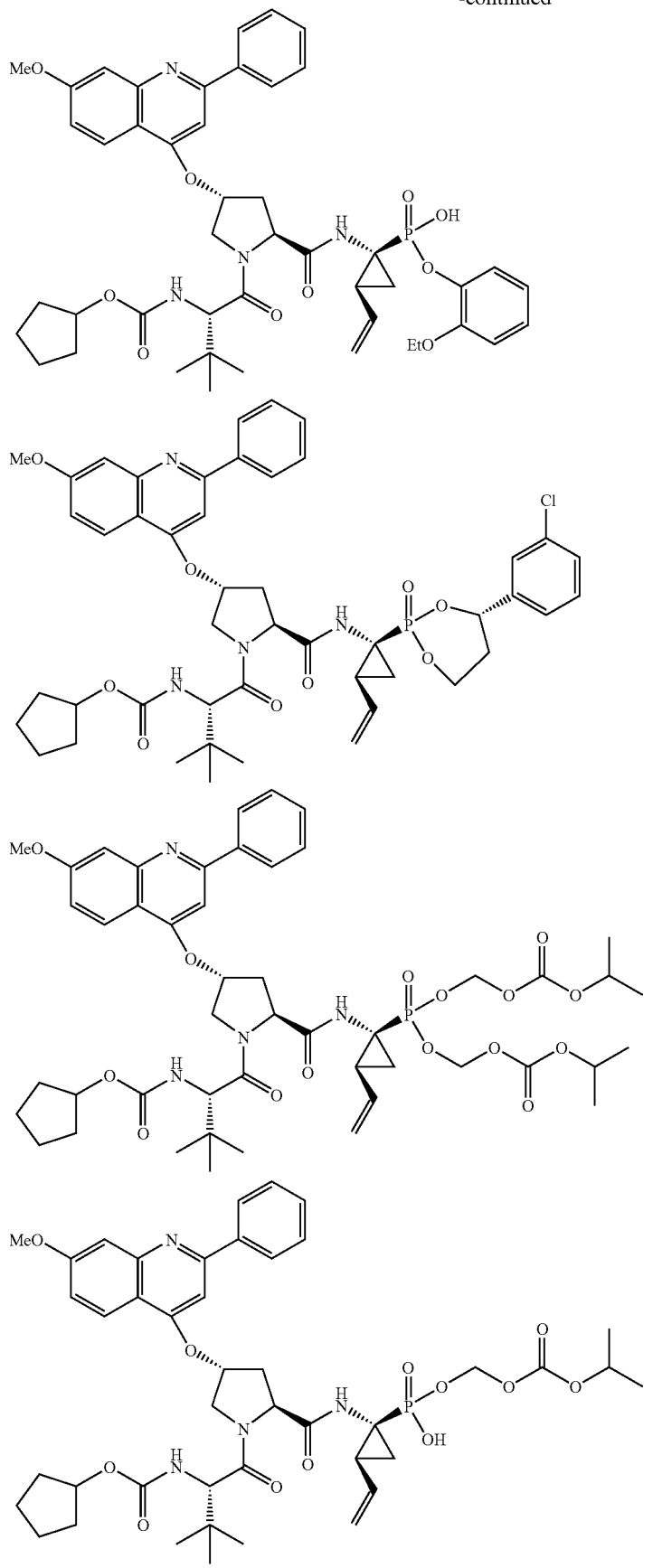

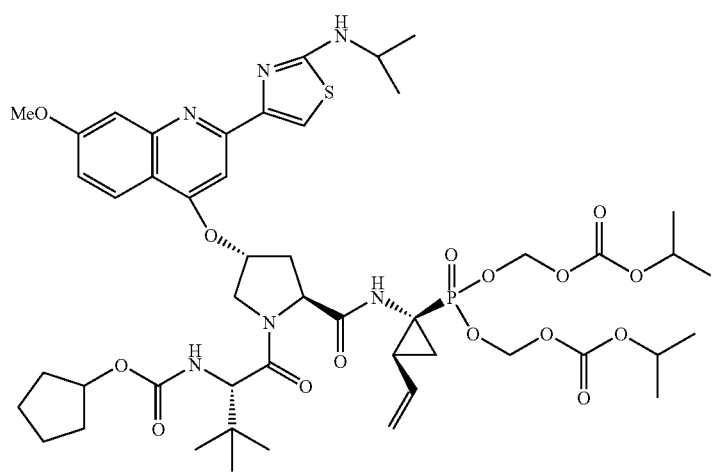
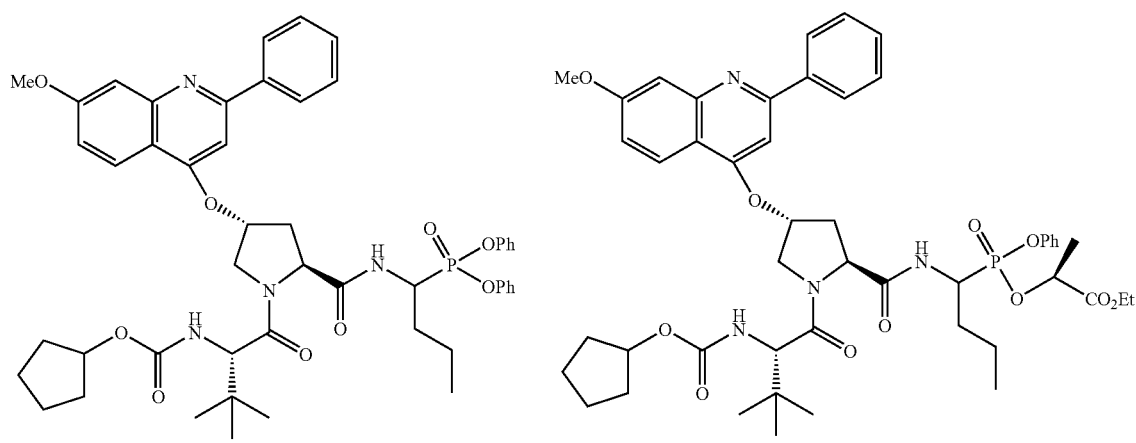
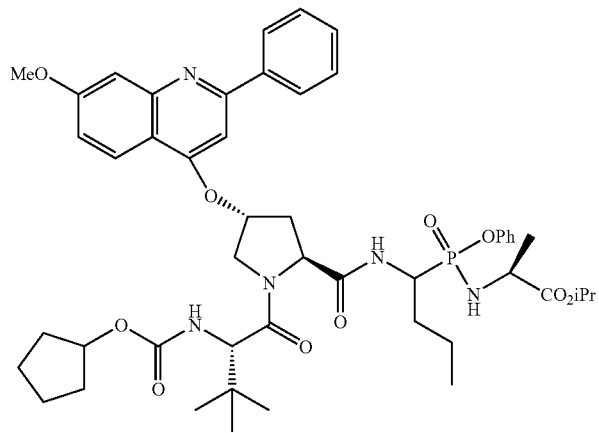

-continued
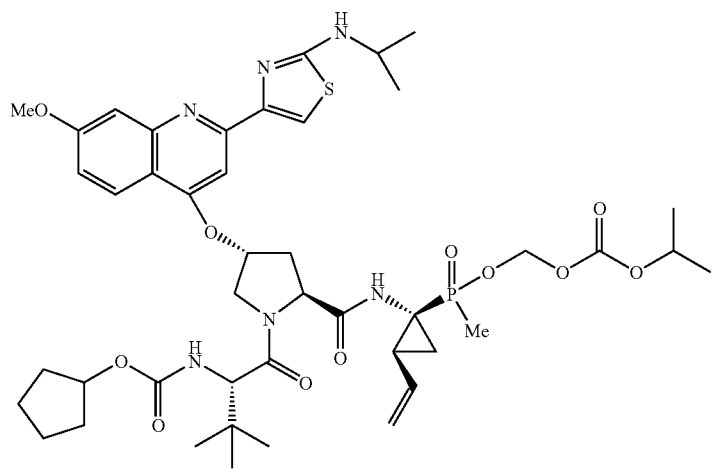
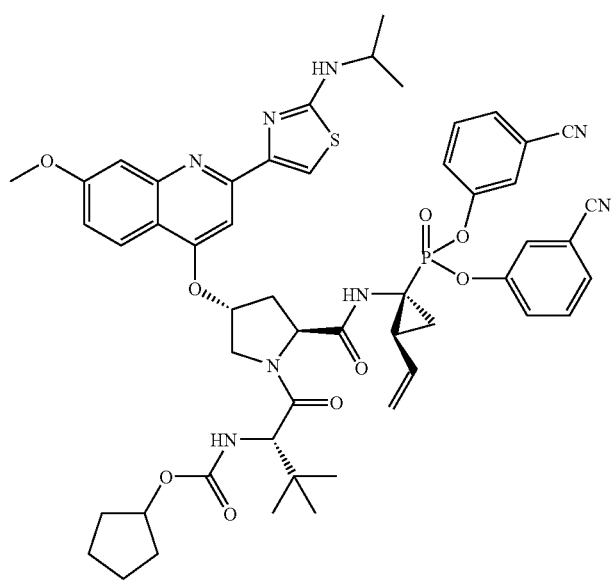
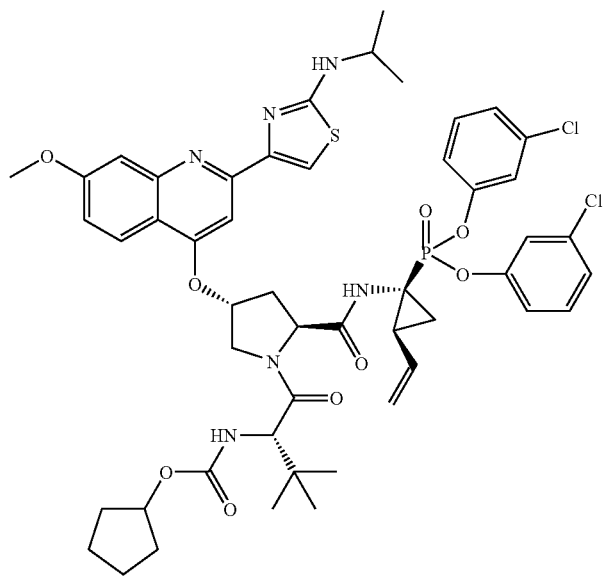

-continued
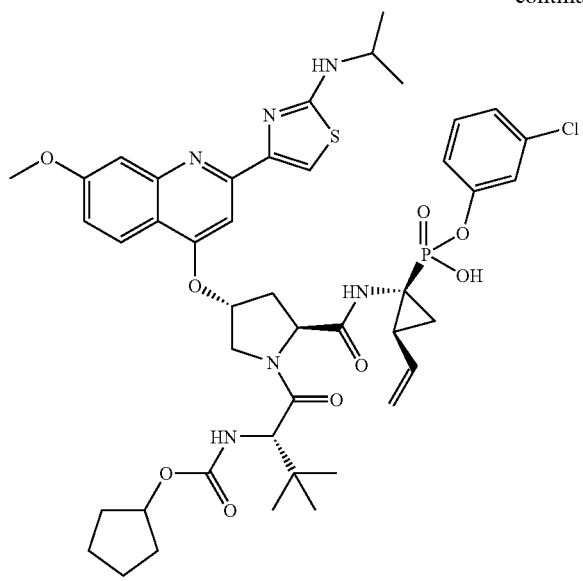
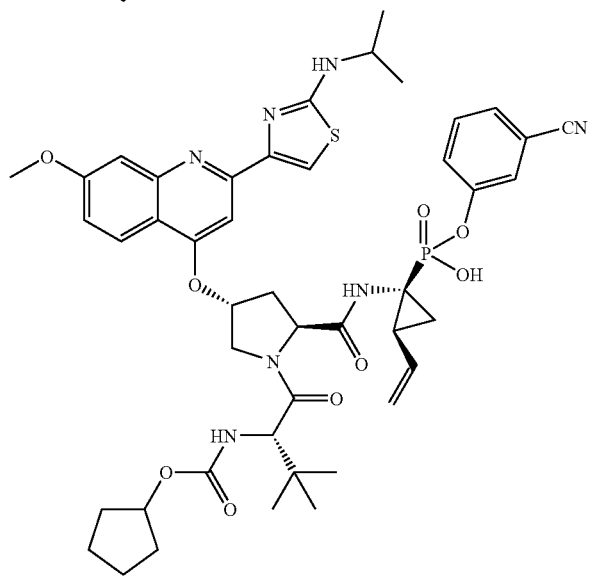
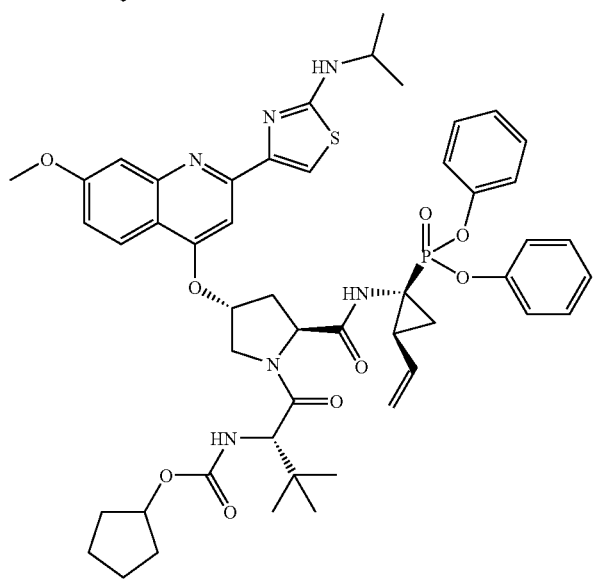

-continued
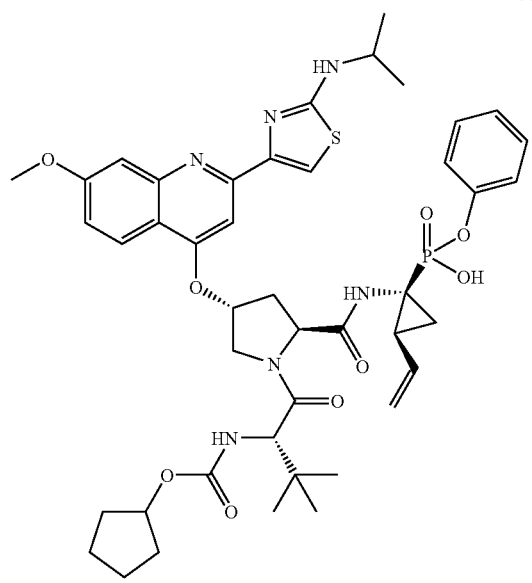
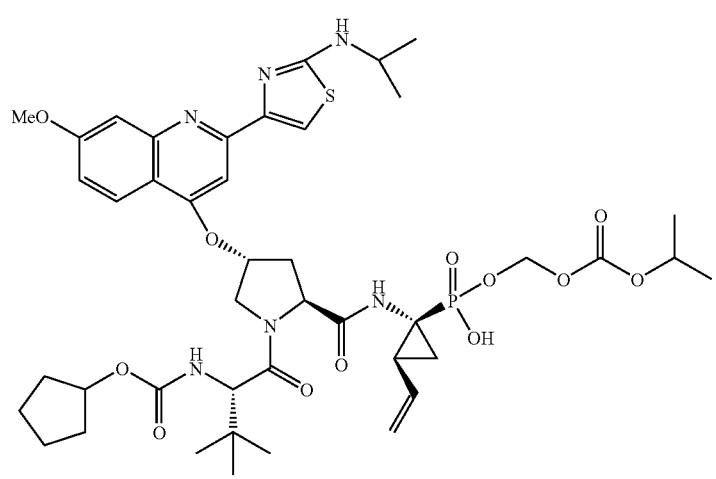
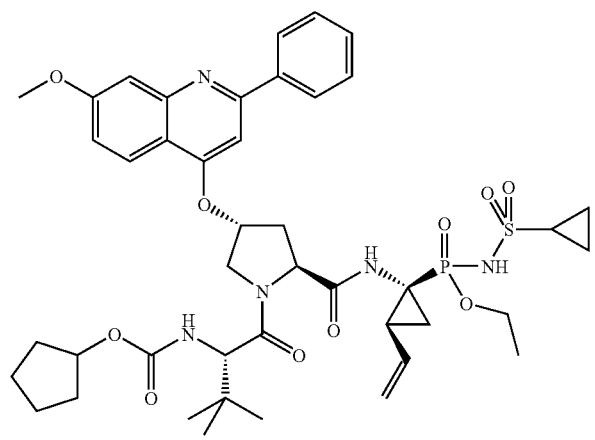

-continued
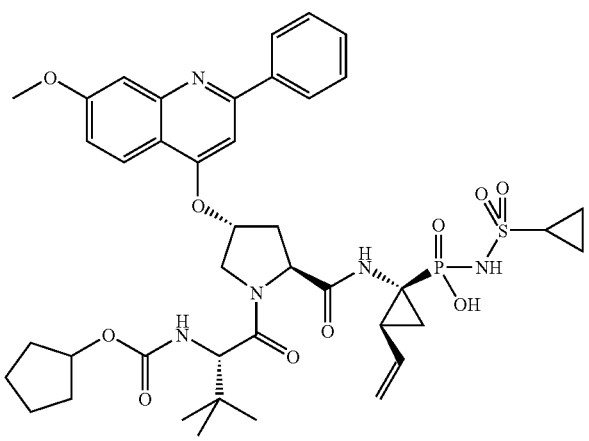
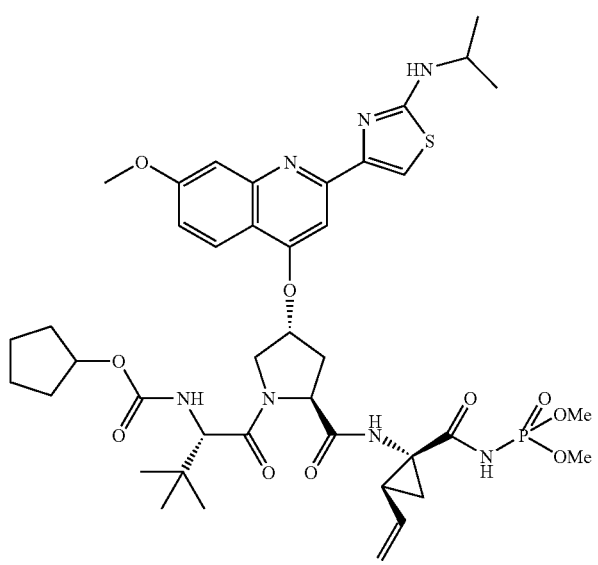
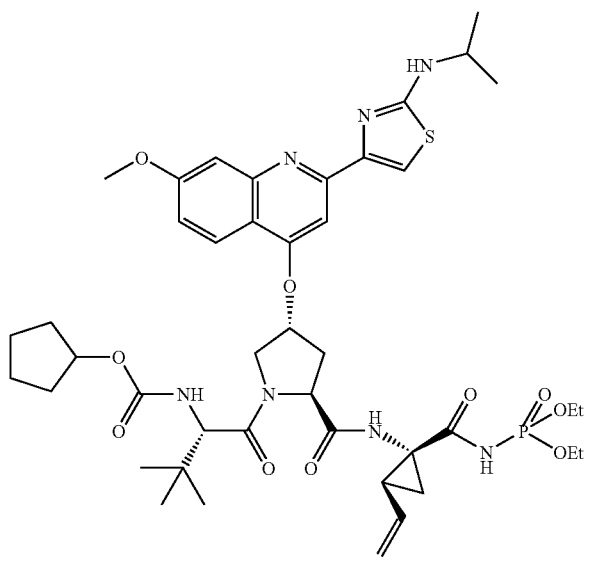

-continued
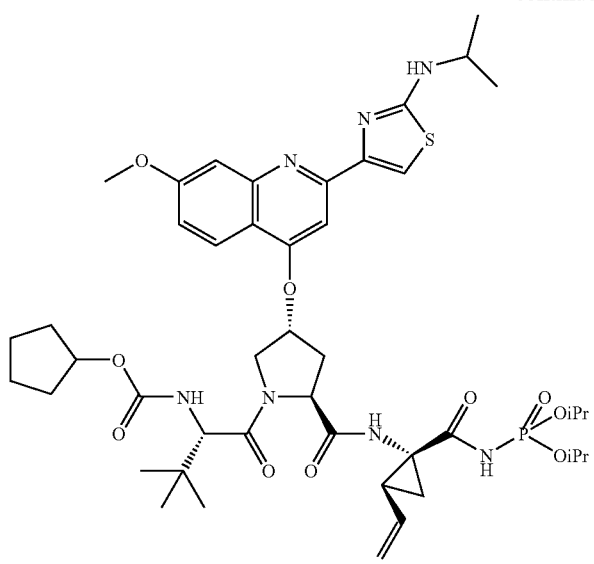
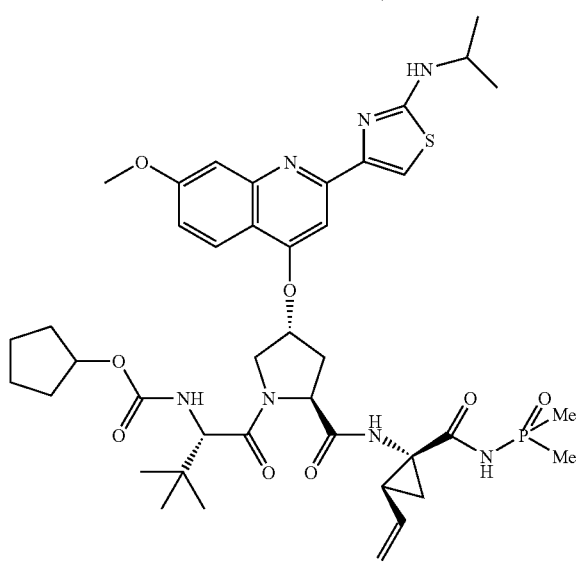
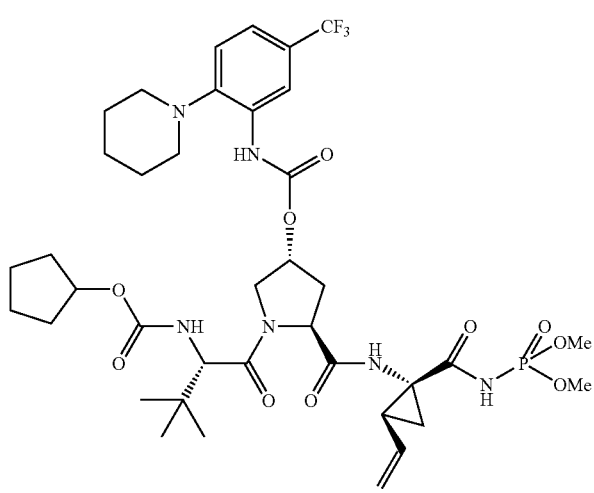

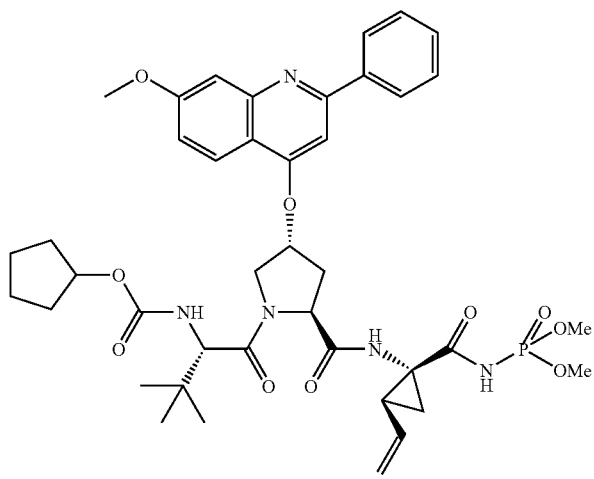
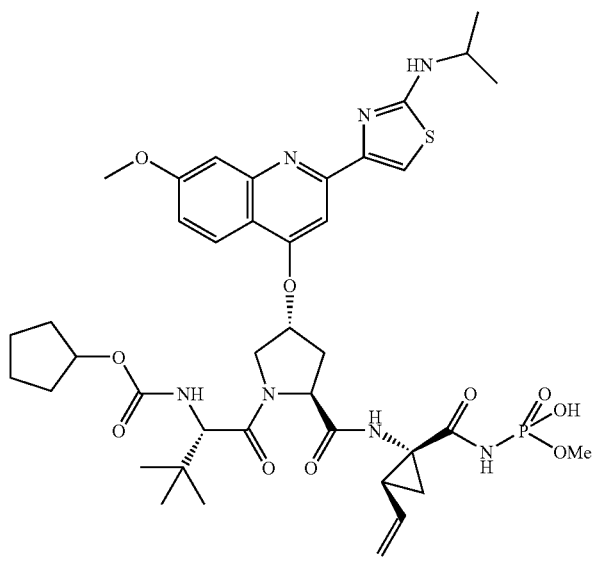
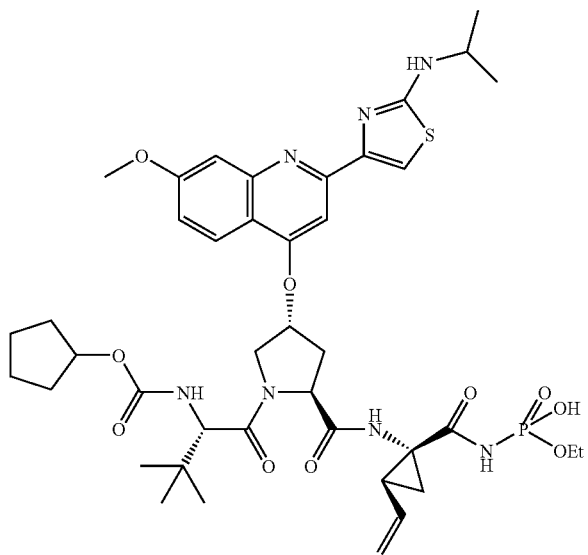

73
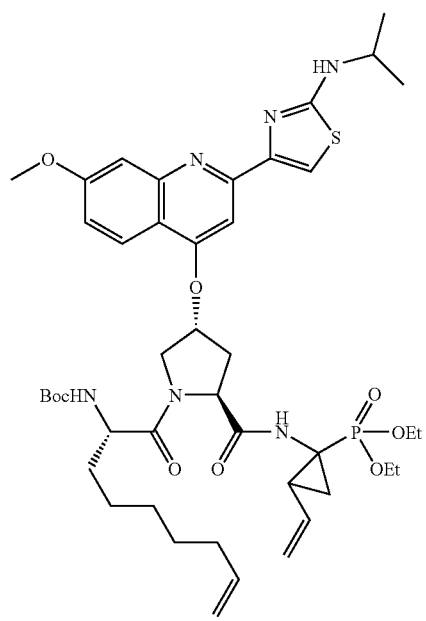
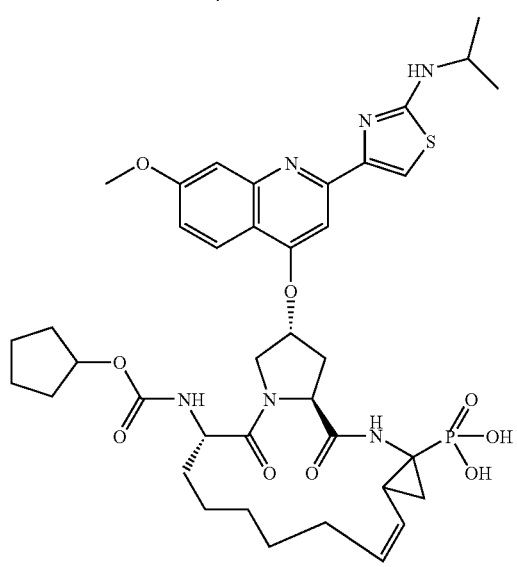
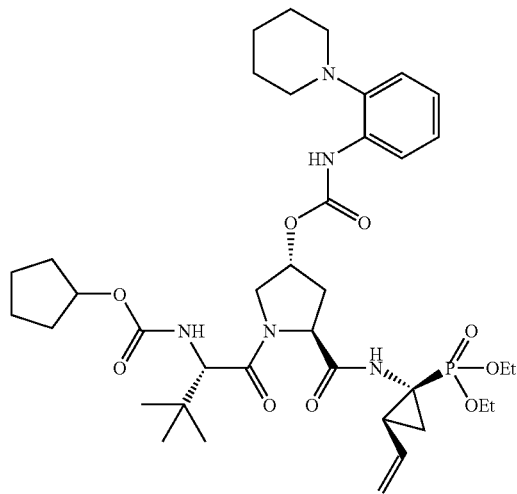
-continued
74
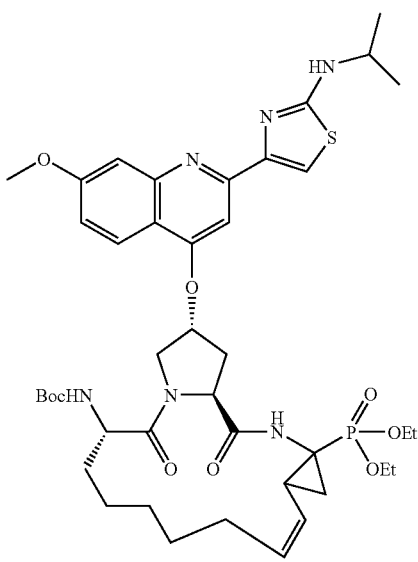
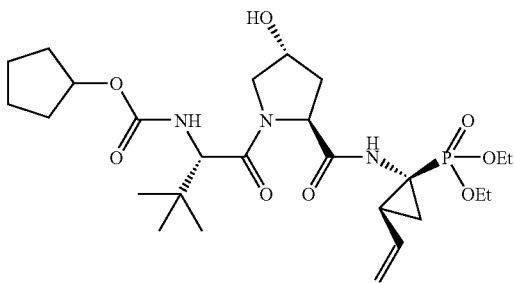
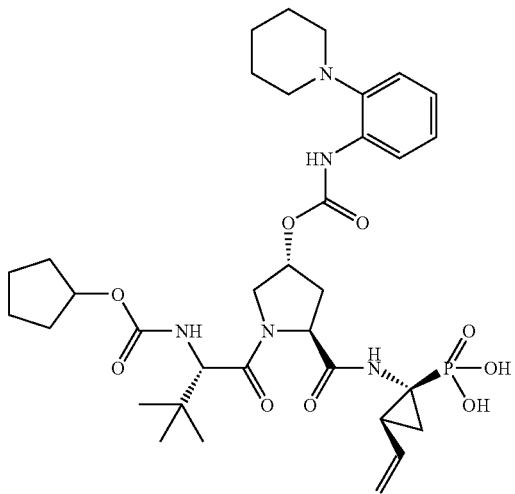

75
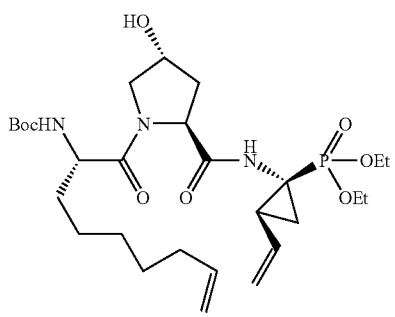
76
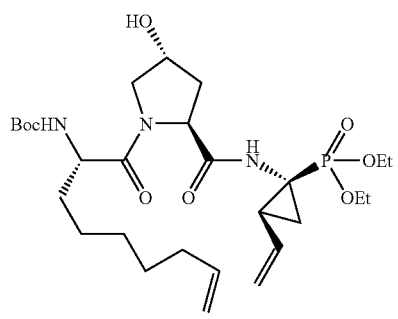
-continued
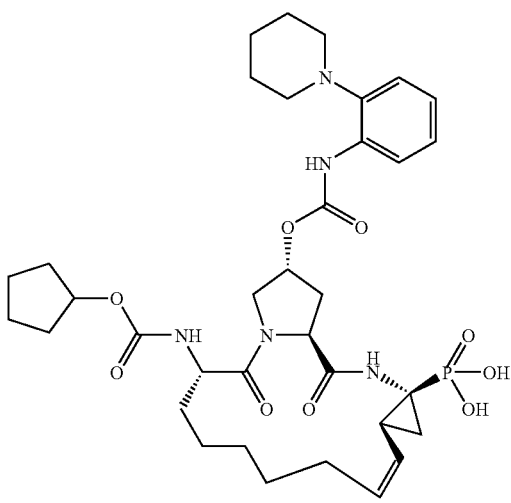
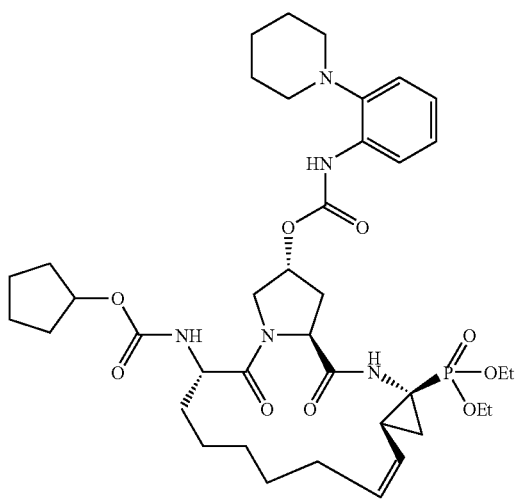
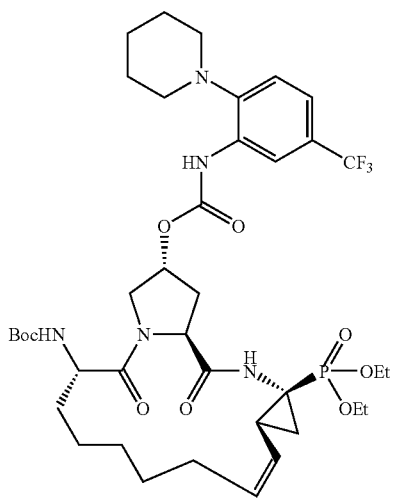
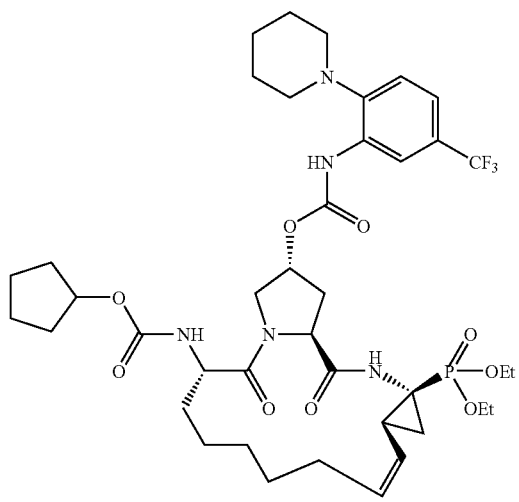

-continued
| 77 | 78 |
|---|---|
| 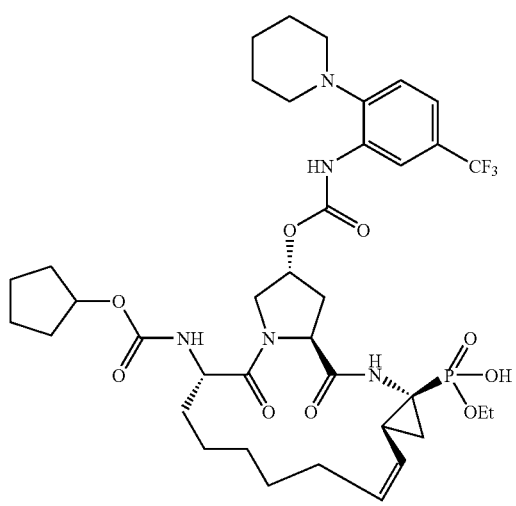 | 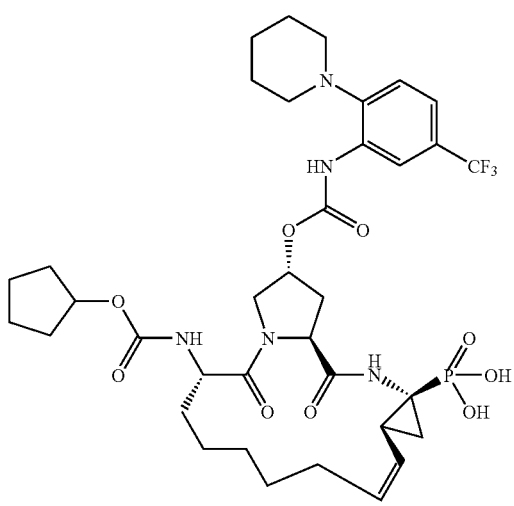 |
| 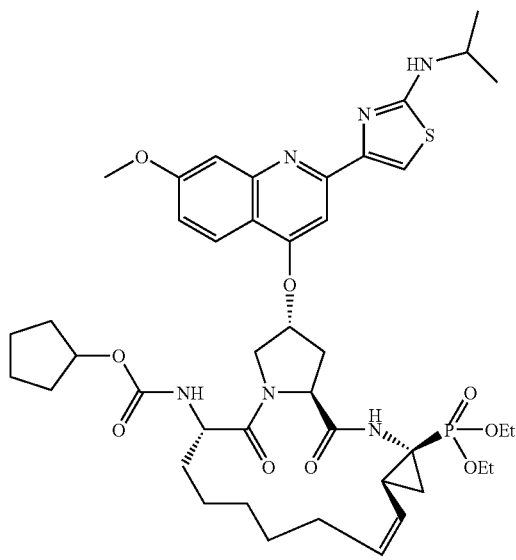 | 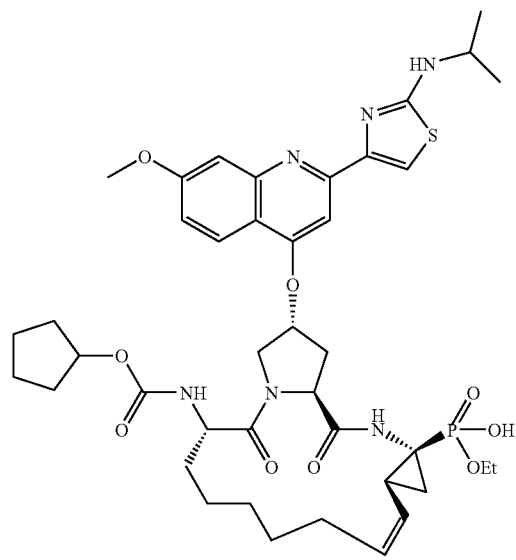 |
| 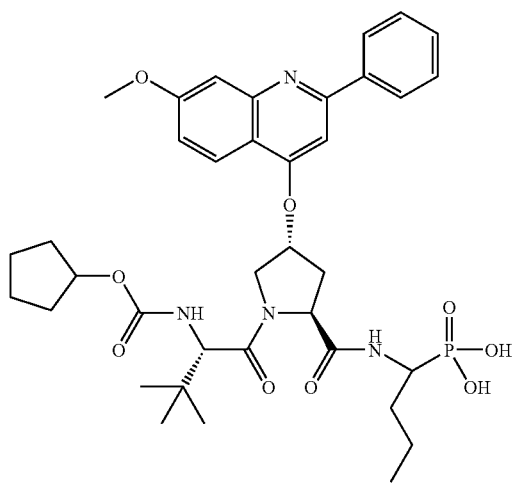 | 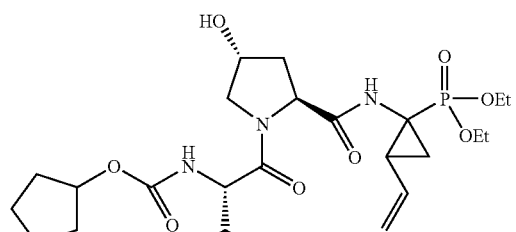 |

| 79 | 80 |
|---|---|
| 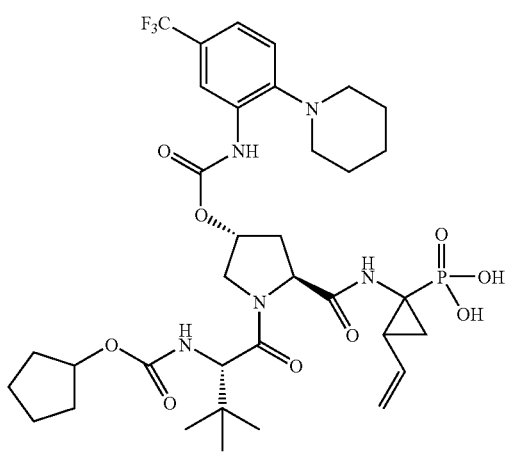 | 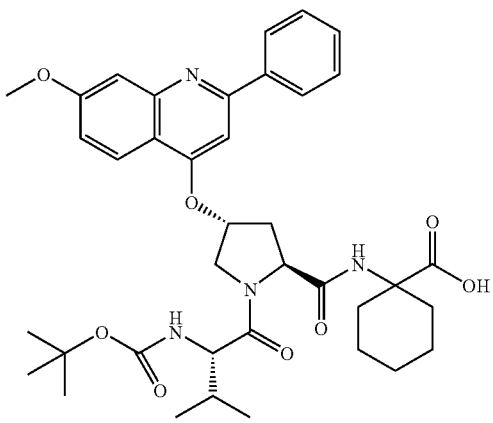 |
| 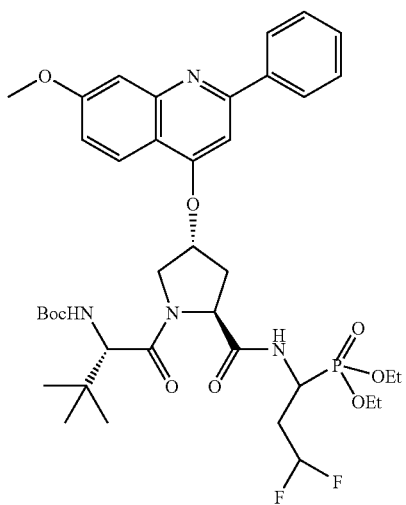 | 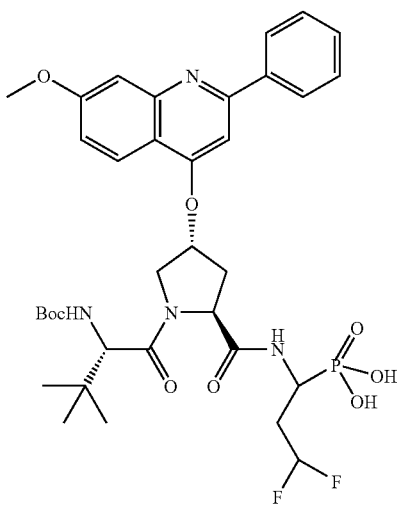 |
| 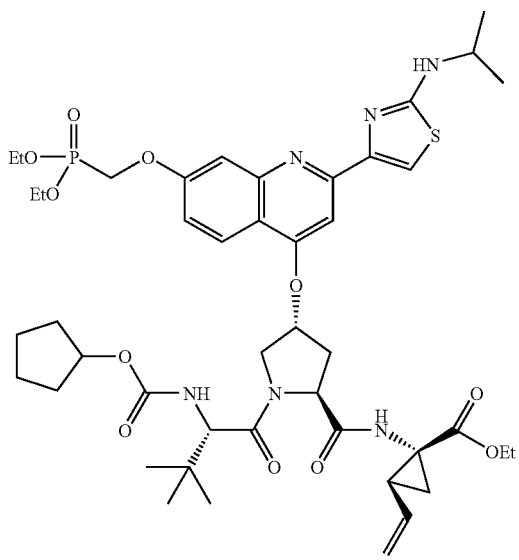 | 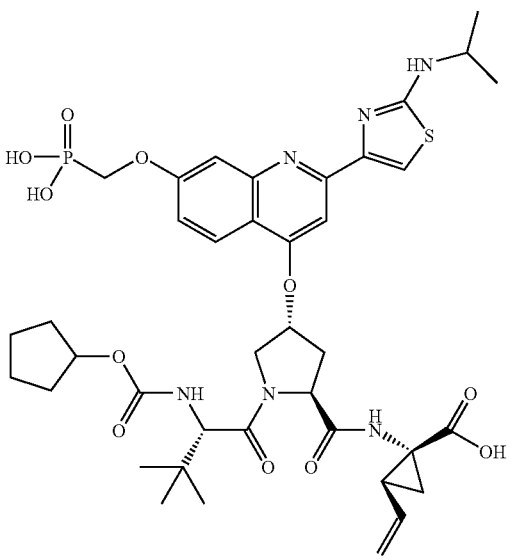 |

-continued
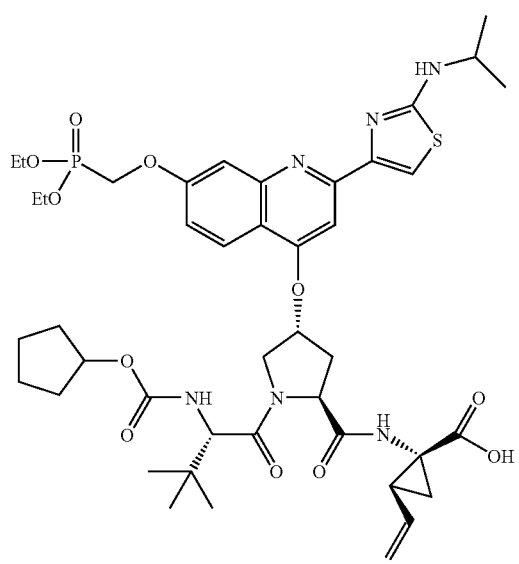
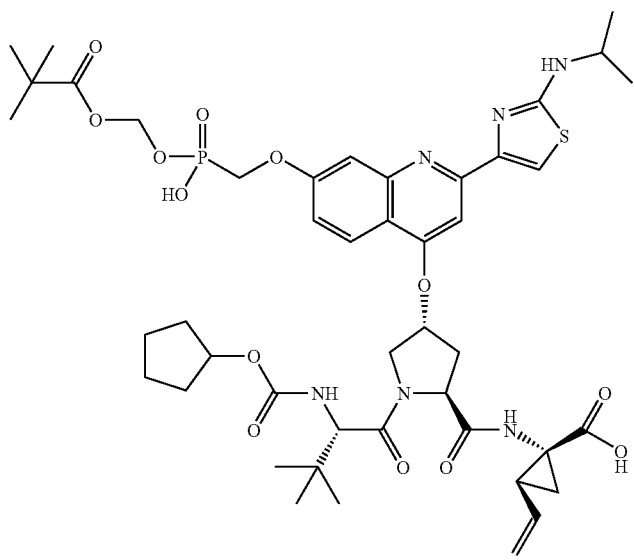
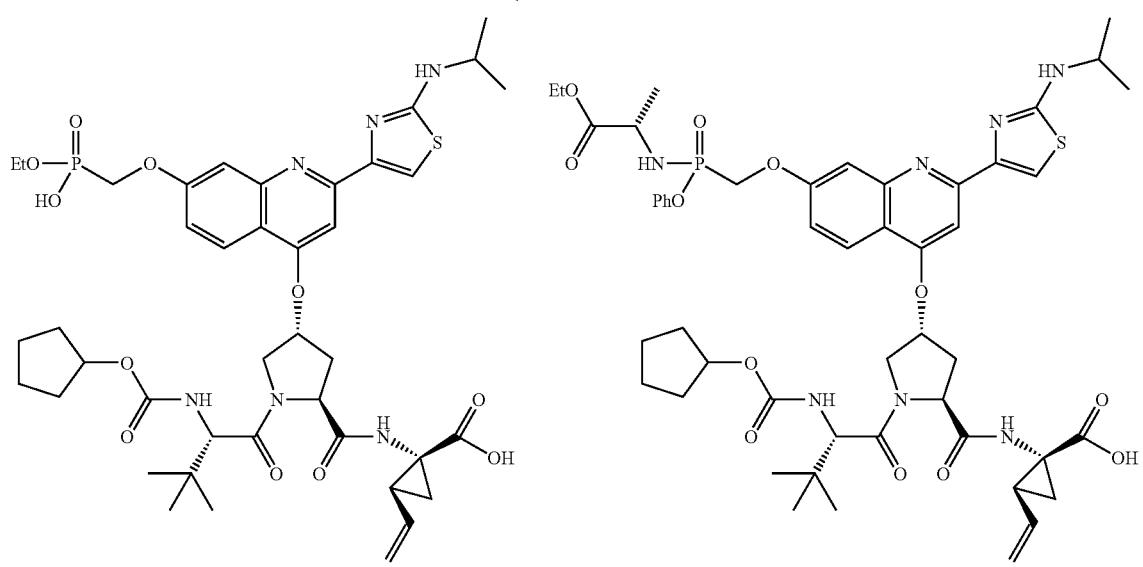

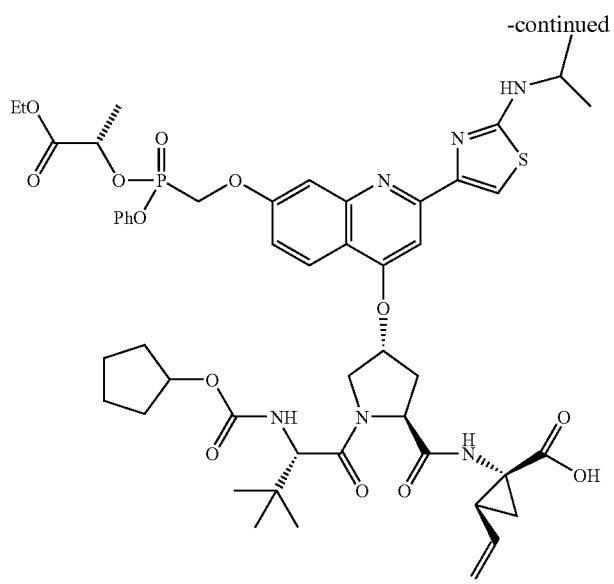
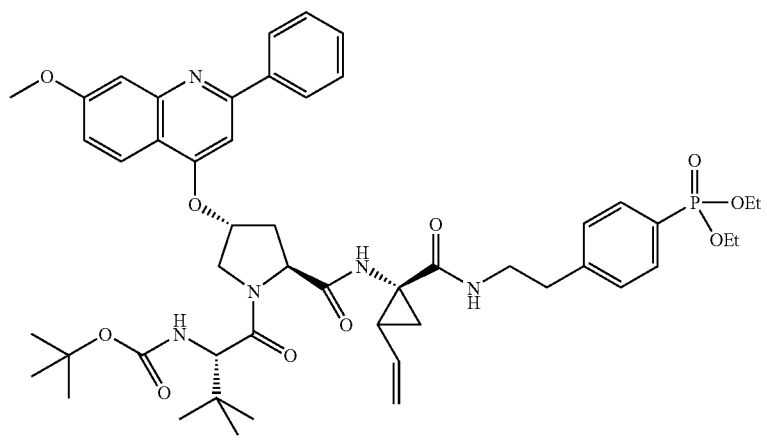
The present invention provides a compound selected from the group consisting of:
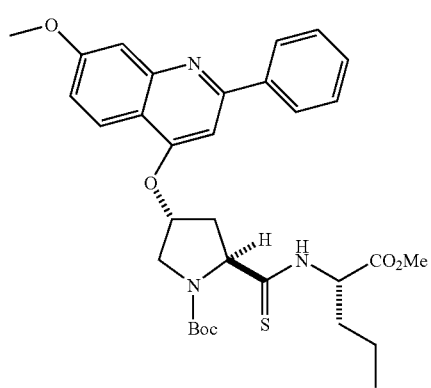
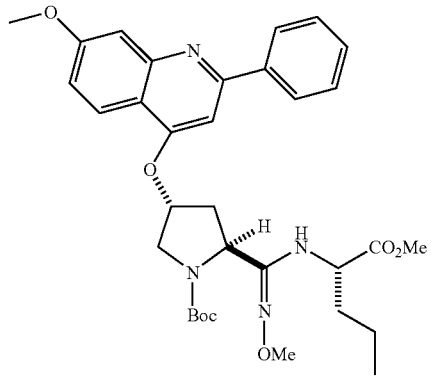

85
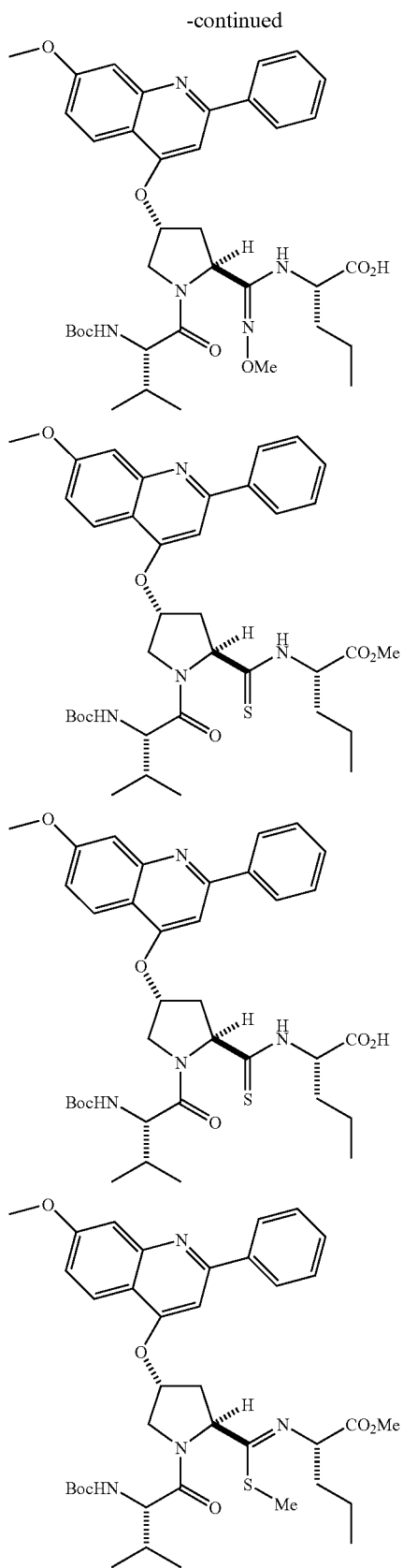
86
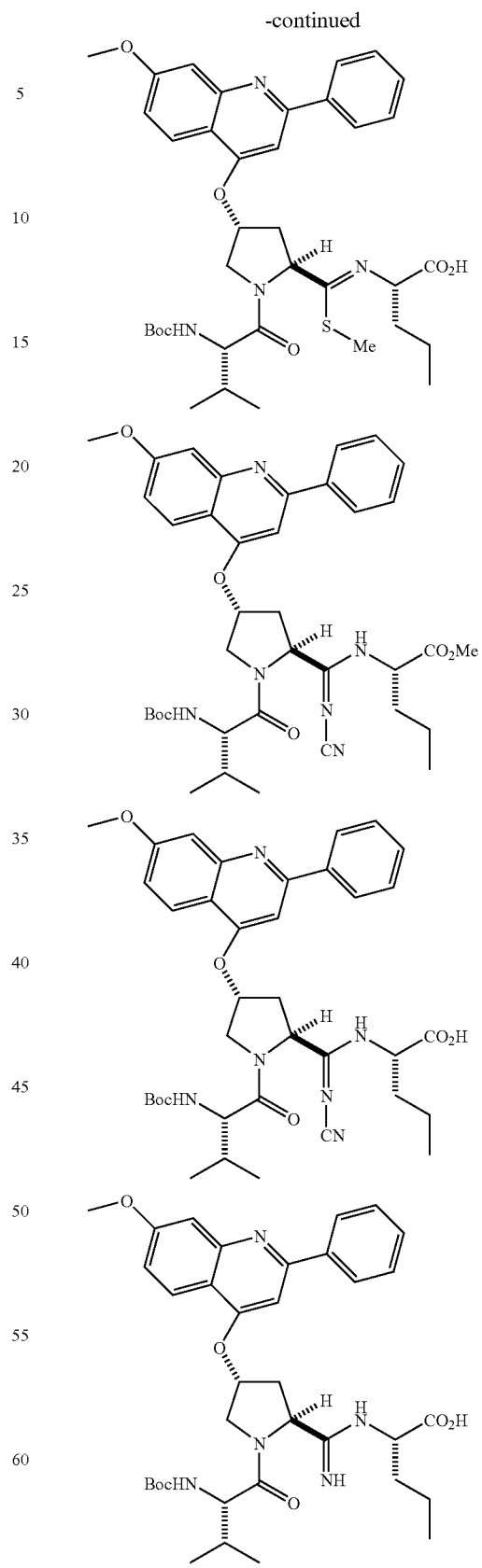

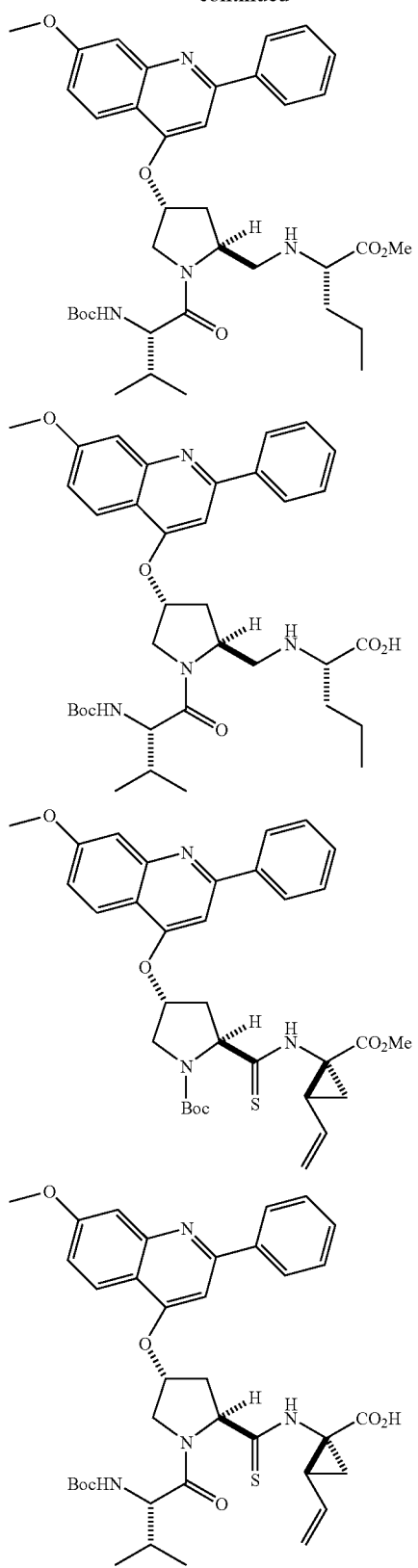
The present invention provides a compound selected from the group consisting of:
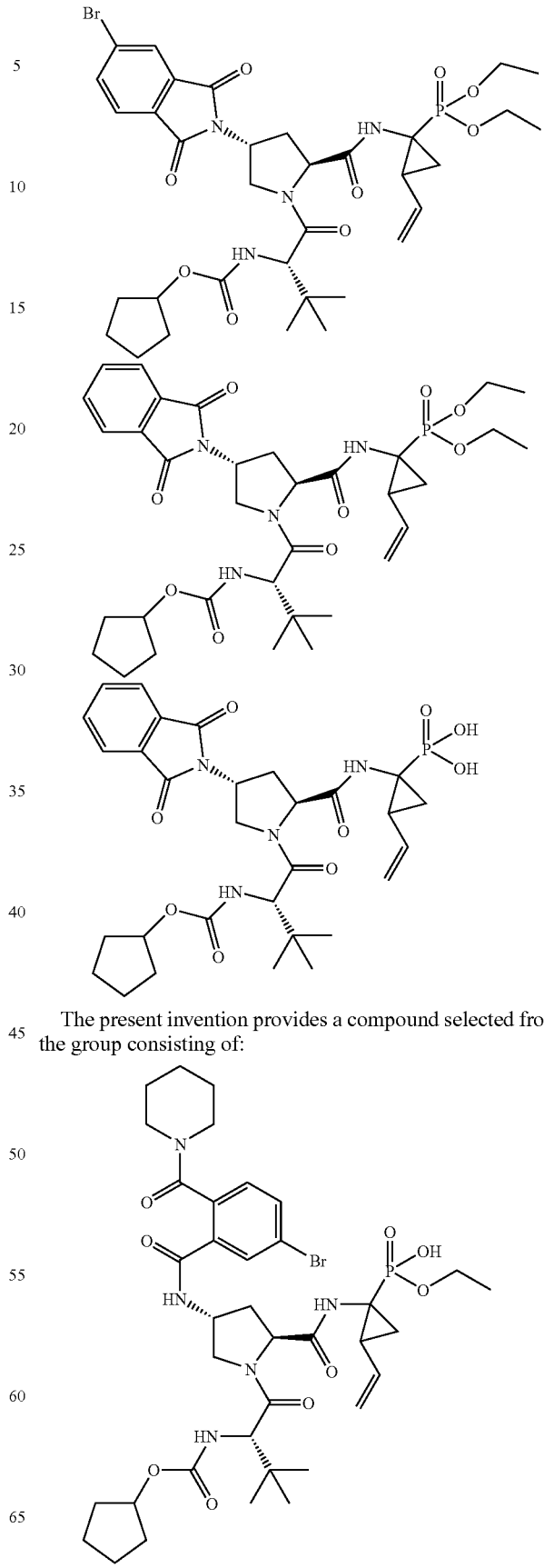
The present invention provides a compound selected from the group consisting of:

-continued

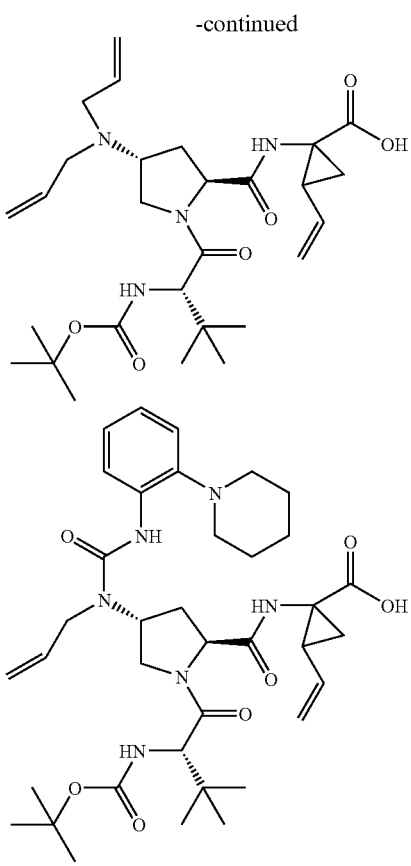

The present invention also provides for a pharmaceutical composition comprising a compound described above and at least one pharmaceutically acceptable carrier.

The present invention also provides for a pharmaceutical composition for use in treating disorders associated with HCV.

The present invention also provides for a pharmaceutical composition additionally containing a nucleoside analogue.

The present invention also provides for a pharmaceutical composition additionally containing an interferon or pegylated interferon.

The present invention also provides for a pharmaceutical composition wherein said nucleoside analogue is selected from ribavirin, viramidine levovirin, a L-nucleoside, and isatoribine and said interferon is α-interferon or pegylated interferon.

The present invention also provides for a method of treating disorders associated with hepatitis C, said method comprising administering to an individual a pharmaceutical composition which comprises a therapeutically effective amount of the compounds, including enantiomers thereof, described above.

The present invention also provides a pharmaceutical composition comprising an effective amount of a compound or conjugate of the invention, or a pharmaceutically acceptable salt or solvate thereof, in combination with a pharmaceutically acceptable excipient.

The present invention also pertains to a method of increasing cellular accumulation and retention of a drug compound, thus improving their therapeutic and diagnostic value, comprising linking the compound to one or more phosphonate groups.

The present invention also provides a method of inhibiting HCV, comprising administering to a mammal afflicted with a condition associated with HCV activity, an amount of a compound of the invention, effective to inhibit HCV.

The present invention also provides a compound of the invention for use in medical therapy (preferably for use in inhibiting HCV or treating a condition associated with HCV activity), as well as the use of a compound of the invention for the manufacture of a medicament useful for inhibiting HCV or the treatment of a condition associated with HCV activity in a mammal.

The present invention also provides processes and novel intermediates disclosed herein which are useful for preparing compounds, including enantiomers thereof, of the invention. Some of the compounds of the invention are useful to prepare other compounds of the invention.

In another aspect the invention provides a method of inhibiting HCV activity in a sample comprising treating the sample with a compound or conjugate of the invention.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the embodiments.

Compositions of the Invention

The compounds of this invention exclude compounds heretofore known. However, as will be further apparent below in other embodiments it is within the invention to use for antiviral purposes known compounds heretofore only produced and used as intermediates in the preparation of antiviral compounds. With respect to the United States, the compounds or compositions herein exclude compounds that are anticipated under 35 USC §102 or obvious under 35 USC §103.

Whenever a compound described herein is substituted with more than one of the same designated group, e.g., "$R^1$" or "$A^3$", then it will be understood that the groups may be the same or different, i.e., each group is independently selected.

"Heterocycle" as used herein includes by way of example and not limitation these heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and "J. Am. Chem. Soc.", 82:5566 (1960).

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Groups $A^3$ and $A^2$ are not critical functionalities and may vary widely. When not H, their function is to serve as intermediates for the parental drug substance. This does not mean that they are biologically inactive. On the contrary, a principal function of these groups is to convert the parental drug into a prodrug, whereby the parental drug is released upon conversion of the prodrug in vivo. Because active prodrugs are absorbed more effectively than the parental drug they in fact often possess greater potency in vivo than the parental drug. $A^3$ or $A^2$ are removed either in vitro, in the instance of chemical intermediates, or in vivo, in the case of prodrugs. With chemical intermediates, it is not particularly important that the resulting pro-functionality products, e.g. alcohols, be physiologically acceptable, although in general it is more desirable if the products are pharmacologically innocuous.

The term "PRT" is selected from the terms "prodrugs" and "protecting groups" as defined herein.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^9$ and acyloxymethyl carbonates —$CH_2OC(=O)OR^9$ where $R^9$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC) —$CH_2C(=O)OC(CH_3)_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group.

Aryl esters of phosphorus groups, especially phenyl esters, are reported to enhance oral bioavailability (De Lombaert et al. (1994) *J. Med. Chem.* 37:498). Phenyl esters containing a carboxylic ester ortho to the phosphate have also been described (Khamnei and Torrence, (1996) *J. Med. Chem.* 39:4109-4115). Benzyl esters are reported to generate the parent phosphonic acid. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate the phosphoric acid and the quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958). Cyclic phosphonate esters have also been described as prodrugs of phosphorus-containing compounds (Erion et al., U.S. Pat. No. 6,312,662).

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Any reference to any of the compounds of the invention also includes a reference to a physiologically acceptable salt thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound of an hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to, ethylene or vinyl (—$CH=CH_2$), allyl (—$CH_2CH=CH_2$), cyclopentenyl (—$C_5H_7$), and 5-hexenyl (—$CH_2CH_2CH_2CH_2CH=CH_2$).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—$CH_2$C≡CH), "Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—$CH_2$C≡C—), and 4-pentynyl (—$CH_2CH_2CH_2$C≡CH—).

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to, —X, —R, —O—; —OR, —SR, —S—, —$NR_2$, —$NR_3$, =NR, —$CX_3$, —CN, —OCN, —SCN, —N=C=O, —NCS, —NO, —$NO_2$, =$N_2$, —$N_3$, NC(=O)R, —C(=O)R, —C(=O)NRR, —S(=O)$_2$O—; —S(=O)$_2$OH, —S(=O)$_2$R, —OS(=O)$_2$ OR, —S(=O)₂NR, —S(=O)R, —OP(=O)O₂RR, —P(=O)O₂RR, —P(=O)(O—)₂, —P(=O)(OH)₂, —C(=O)R, —C(=O)X, —C(S)R, —C(O)OR, —C(O)O—, —C(S)OR, —C(O)SR, —C(S)SR, —C(O)NRR, —C(S)NRR, —C(NR)NRR, where each X is independently a halogen: F, Cl, Br, or I; and each R is independently —H, alkyl, aryl, heterocycle, protecting group or prodrug moiety. Alkylene, alkenylene, and alkynylene groups may also be similarly substituted.

"Heterocycle" as used herein includes by way of example and not limitation these heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S).

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

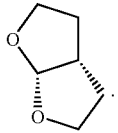

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

"Linker" or "link" refers to a chemical moiety comprising a covalent bond or a chain or group of atoms that covalently attaches a phosphonate group to a drug. Linkers include portions of substituents A¹ and A³, which include moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereo-selection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

$A^3$ and $A^2$ may be H, alkyl, or an ether- or ester-forming group. "Ether-forming group" means a group which is capable of forming a stable, covalent bond between the parental molecule and a group having the formula:

$$\int\!\!-O-V_a(V_1)_3, \int\!\!-O-V_a(V_1)(V_2), \int\!\!-O-V_a(V_3)$$

$$\int\!\!-O-V_b(V_1)_2, \int\!\!-O-V_b(V_2), \text{ or } \int\!\!-O-V_c(V_1)$$

Wherein $V_a$ is a tetravalent atom typically selected from C and Si; $V_b$ is a trivalent atom typically selected from B, Al, N, and P, more typically N and P; $V_c$ is a divalent atom typically selected from O, S, and Se, more typically S; $V_1$ is a group bonded to $V_a$, $V_b$ or $V_c$ by a stable, single covalent bond, typically $V_1$ is $A^2$ groups; $V_2$ is a group bonded to $V_a$ or $V_b$ by a stable, double covalent bond, provided that $V_2$ is not =O, =S or =N—, typically $V_2$ is =C(V_1)_2 wherein $V_1$ is as described above; and $V_3$ is a group bonded to $V_a$ by a stable, triple covalent bond, typically $V_3$ is $\int\!C(V_1)$ wherein $V_1$ is as described above.

"Ester-forming group" means a group which is capable of forming a stable, covalent bond between the parental molecule and a group having the formula:

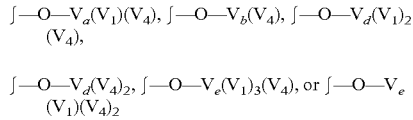

Wherein $V_a$, $V_b$, and $V_1$, are as described above; $V_d$ is a pentavalent atom typically selected from P and N; $V_e$ is a hexavalent atom typically S; and $V_4$ is a group bonded to $V_a$, $V_b$, $V_d$ or $V_e$ by a stable, double covalent bond, provided that at least one $V_4$ is =O, =S or =N—$V_1$, typically $V_4$, when other than =O, =S or =N—, is =C(V_1)_2 wherein $V_1$ is as described above.

Protecting groups for —OH functions (whether hydroxy, acid or other functions) are embodiments of "ether- or ester-forming groups".

Particularly of interest are ether- or ester-forming groups that are capable of functioning as protecting groups in the synthetic schemes set forth herein. However, some hydroxyl and thio protecting groups are neither ether- nor ester-forming groups, as will be understood by those skilled in the art, and are included with amides, discussed below, and are capable of protecting hydroxyl or thio groups such that hydrolysis from the parental molecule yields hydroxyl or thio.

In its ester-forming role, $A^3$ or $A^2$ typically is bound to any acidic group such as, by way of example and not limitation, a —CO_2H or —C(S)OH group, thereby resulting in —CO_2A^2 or —CO_2A^3. $A^2$ for example is deduced from the enumerated ester groups of WO 95/07920.

Examples of $A^2$ include $C_3$-$C_{12}$ heterocycle (described above) or aryl. These aromatic groups optionally are polycyclic or monocyclic. Examples include phenyl, spiryl, 2- and 3-pyrrolyl, 2- and 3-thienyl, 2- and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl, $C_3$-$C_{12}$ heterocycle or aryl substituted with halo, $R^1$, $R_1$—O—$C_1$-$C_{12}$ alkylene, $C_1$-$C_{12}$ alkoxy, CN, NO_2, OH, carboxy, carboxyester, thiol, thioester, $C_1$-$C_{12}$ haloalkyl (1-6 halogen atoms), $C_2$-$C_{12}$ alkenyl or $C_2$-$C_{12}$ alkynyl. Such groups include 2-, 3- and 4-alkoxyphenyl ($C_1$-$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl), 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3- and 4-haloalkylphenyl (1 to 5 halogen atoms, $C_1$-$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$-$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_1$-$C_4$ alkyl, including 2-, 3- and 4-ethylsalicylphenyl), 2-, 3- and 4-acetylphenyl, 1,8-dihydroxynaphthyl (—$C_{10}H_6$—OH) and aryloxy ethyl [$C_6$-$C_9$ aryl (including phenoxy ethyl)], 2,2'-dihydroxybiphenyl, 2-, 3- and 4-N,N-dialkylaminophenol, —$C_6H_4CH_2$—N($CH_3$)$_2$, trimethoxybenzyl, triethoxybenzyl, 2-alkyl pyridinyl ($C_{1-4}$ alkyl);

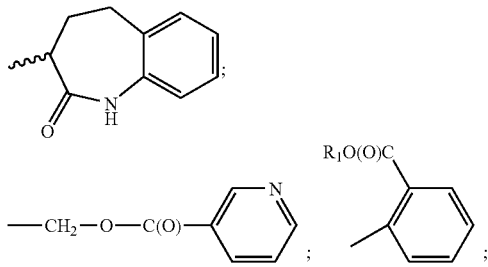

$C_4$-$C_8$ esters of 2-carboxyphenyl; and $C_1$-$C_4$ alkylene-$C_3$-$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$-$C_{12}$ alkoxy (including methoxy and ethoxy), cyano, nitro, OH, $C_1$-$C_{12}$ haloalkyl (1 to 6 halogen atoms; including —$CH_2$—$CCl_3$), $C_1$-$C_{12}$ alkyl (including methyl and ethyl), $C_2$-$C_{12}$ alkenyl or $C_2$-$C_{12}$ alkynyl;

alkoxy ethyl [$C_1$-$C_6$ alkyl including —$CH_2$—$CH_2$—O—$CH_3$ (methoxy ethyl)];

alkyl substituted by any of the groups set forth above for aryl, in particular OH or by 1 to 3 halo atoms (including —$CH_3$, —$CH(CH_3)_2$, —$C(CH_3)_3$, —$CH_2CH_3$, —$(CH_2)_2CH_3$, —$(CH_2)_3CH_3$, —$(CH_2)_4CH_3$, —$(CH_2)_5CH_3$, —$CH_2CH_2F$, —$CH_2CH_2Cl$, —$CH_2CF_3$, and —$CH_2CCl_3$);

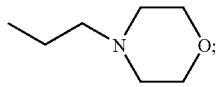

—N-2-propylmorpholino, 2,3-dihydro-6-hydroxyindene, sesamol, catechol monoester, —$CH_2$—C(O)—N($R^1$)$_2$, —$CH_2$—S(O)($R^1$), —$CH_2$—S(O)$_2$($R^1$), —$CH_2$—CH(OC(O)$CH_2R^1$)—$CH_2$(OC(O)$CH_2R^1$), cholesteryl, enolpyruvate (HOOC—C(=$CH_2$)—), glycerol;

a 5 or 6 carbon monosaccharide, disaccharide or oligosaccharide (3 to 9 monosaccharide residues);

triglycerides such as α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids) linked to acyl of the parental compounds herein through a glyceryl oxygen of the triglyceride;

phospholipids linked to the carboxyl group through the phosphate of the phospholipid;

phthalidyl (shown in FIG. 1 of Clayton et al., *Antimicrob. Agents Chemo.* 5(6):670-671 [1974]);

cyclic carbonates such as (5-$R_d$-2-oxo-1,3-dioxolen-4-yl) methyl esters (Sakamoto et al., *Chem. Pharm. Bull.* 32(6) 2241-2248 [1984]) where $R_d$ is $R_1$, $R_4$ or aryl; and

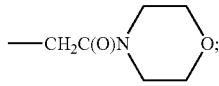

The hydroxyl groups of the compounds of this invention optionally are substituted with one of groups III, IV or V disclosed in WO94/21604, or with isopropyl.

As further embodiments, Table A lists examples of $A^2$ ester moieties that for example can be bonded via oxygen to —C(O)O— and —P(O)(O—)$_2$ groups. Several amidates also are shown, which are bound directly to —C(O)— or —P(O)$_2$. Esters of structures 1-5, 8-10 and 16, 17, 19-22 are synthesized by reacting the compound herein having a free hydroxyl with the corresponding halide (chloride or acyl chloride and the like) and N,N-dicylohexyl-N-morpholine carboxamidine (or another base such as DBU, triethylamine, $CsCO_3$, N,N-dimethylaniline and the like) in DMF (or other solvent such as acetonitrile or N-methylpyrrolidone). When $A^3$ is phosphonate, the esters of structures 5-7, 11, 12, 21, and 23-26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE A

| | |
|---|---|
| 1. | —$CH_2$—C(O)—N($R_1$)$_2$* |
| 2. | —$CH_2$—S(O)($R_1$) |
| 3. | —$CH_2$—S(O)$_2$($R_1$) |
| 4. | —$CH_2$—O—C(O)—$CH_2$—$C_6H_5$ |
| 5. | 3-cholesteryl |
| 6. | 3-pyridyl |
| 7. | N-ethylmorpholino |
| 8. | —$CH_2$—O—C(O)—$C_6H_5$ |
| 9. | —$CH_2$—O—C(O)—$CH_2CH_3$ |
| 10. | —$CH_2$—O—C(O)—C($CH_3$)$_3$ |
| 11. | —$CH_2$—$CCl_3$ |
| 12. | —$C_6H_5$ |
| 13. | —NH—$CH_2$—C(O)O—$CH_2CH_3$ |
| 14. | —N($CH_3$)—$CH_2$—C(O)O—$CH_2CH_3$ |
| 15. | —$NHR_1$ |
| 16. | —$CH_2$—O—C(O)—$C_{10}H_{15}$ |
| 17. | —$CH_2$—O—C(O)—CH($CH_3$)$_2$ |
| 18. | —$CH_2$—C#H(OC(O)$CH_2R_1$)—$CH_2$—(OC(O)$CH_2R_1$)* |
| 19. | ![morpholine structure] |
| 20. | ![benzazepinone structure] |
| 21. | ![sugar structure] |
| 22. | ![pyridyl carbonate structure] |

TABLE A-continued

23. 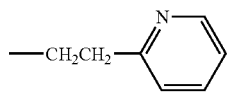

24. 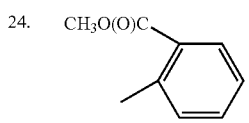

25. 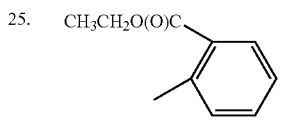

26. 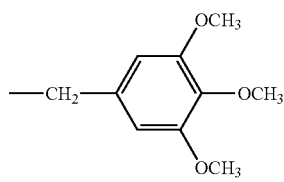

—chiral center is (R), (S) or racemate.

Other esters that are suitable for use herein are described in European Patent No. 632,048.

$A^2$ also includes "double ester" forming profunctionalities such as —$CH_2OC(O)OCH_3$,

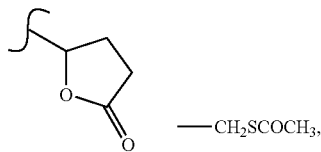
—$CH_2SCOCH_3$,

—$CH_2OCON(CH_3)_2$, or alkyl- or aryl-acyloxyalkyl groups of the structure —$CH(R^1)O((CO)R_{37})$ or —$CH(R^1)((CO)OR_{38})$ (linked to oxygen of the acidic group) wherein $R_{37}$ and $R_{38}$ are alkyl, aryl, or alkylaryl groups (see U.S. Pat. No. 4,968,788). Frequently $R_{37}$ and $R_{38}$ are bulky groups such as branched alkyl, ortho-substituted aryl, meta-substituted aryl, or combinations thereof, including normal, secondary, iso- and tertiary alkyls of 1-6 carbon atoms. An example is the pivaloyloxymethyl group. These are of particular use with prodrugs for oral administration. Examples of such useful $A^2$ groups are alkylacyloxymethyl esters and their derivatives, including —$CH(CH_2CH_2OCH_3)OC(O)C(CH_3)_3$,

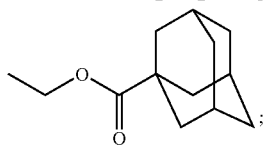;

—$CH_2OC(O)C_{10}H_{15}$, —$CH_2OC(O)C(CH_3)_3$, —$CH(CH_2OCH_3)OC(O)C(CH_3)_3$, —$CH(CH(CH_3)_2)OC(O)C(CH_3)_3$, —$CH_2OC(O)CH_2CH(CH_3)_2$, —$CH_2OC(O)C_6H_{11}$, —$CH_2OC(O)C_6H_5$, —$CH_2OC(O)C_{10}H_{15}$, —$CH_2OC(O)CH_2CH_3$, —$CH_2OC(O)CH(CH_3)_2$, —$CH_2OC(O)C(CH_3)_3$ and —$CH_2OC(O)CH_2C_6H_5$.

For prodrug purposes, the ester typically chosen is one heretofore used for antiviral drugs, in particular the cyclic carbonates, double esters, or the phthalidyl, aryl or alkyl esters.

As noted $A^3$ or $A^2$ groups optionally are used to prevent side reactions with the protected group during synthetic procedures, so they function as protecting groups (PRT) during synthesis. For the most part the decision as to which groups to protect, when to do so, and the nature of the PRT will be dependent upon the chemistry of the reaction to be protected against (e.g., acidic, basic, oxidative, reductive or other conditions) and the intended direction of the synthesis. The PRT groups do not need to be, and generally are not, the same if the compound is substituted with multiple PRT. In general, PRT will be used to protect carboxyl, hydroxyl or amino groups. The order of deprotection to yield free groups is dependent upon the intended direction of the synthesis and the reaction conditions to be encountered, and may occur in any order as determined by the artisan.

A very large number of $A^3$ or $A^2$ hydroxy protecting groups and amide-forming groups and corresponding chemical cleavage reactions are described in "Protective Groups in Organic Chemistry", Theodora W. Greene (John Wiley & Sons, Inc., New York, 1991, ISBN 0-471-62301-6) ("Greene"). See also Kocienski, Philip J.; "Protecting Groups" (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For $A^2$ carboxylic acid, phosphonic acid, phosphonate, sulfonic acid and other protecting groups for $A^3$ acids see Greene as set forth below. Such groups include by way of example and not limitation, esters, amides, hydrazides, and the like.

In some embodiments the $A^2$ protected acidic group is an ester of the acidic group and $A^2$ is the residue of a hydroxyl-containing functionality. In other embodiments, an amino compound is used to protect the acid functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11-18 and related text of WO 95/07920 as groups L1 or L2. WO 95/07920 expressly teaches the amidates of phosphonic acids, but it will be understood that such amidates are formed with any of the acid groups set forth herein and the amino acid residues set forth in WO 95/07920.

Typical $A^2$ esters for protecting $A^3$ acidic functionalities are also described in WO 95/07920, again understanding that the same esters can be formed with the acidic groups herein as with the phosphonate of the '920 publication. Typical ester groups are defined at least on WO 95/07920 pages 89-93 (under $R^{31}$ or $R^{35}$), the table on page 105, and pages 21-23 (as $R^1$). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or $C_1$-$C_4$ alkylestercarboxyphenyl (salicylate $C_1$-$C_{12}$ alkylesters).

The protected acidic groups $A^3$, particularly when using the esters or amides of WO 95/07920, are useful as prodrugs for oral administration. However, it is not essential that the $A^3$ acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate and ester may be used.

Typical $A^2$ hydroxy protecting groups described in Greene (pages 14-118) include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy) methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy) methyl, 2-(Trimethylsilyl)ethoxymethyl, Tetrahydropyranyl, 3-Bromotetrahydropyranyl, Tetrahydropthiopyranyl, 1-Methoxycyclohexyl, 4-Methoxytetrahydropyranyl, 4-Methoxytetrahydrothiopyranyl, 4-Methoxytetrahydropthiopyranyl S,S-Dioxido, 1-[(2-Chloro-4-methyl)phenyl]-4-methoxypiperidin-4-yl, 35, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl)); Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, ⊕-Naphthyldiphenylmethyl, p-methoxyphenyldiphenylmethyl, Di(p-methoxyphenyl) phenylmethyl, Tri(p-methoxyphenyl)methyl, 4-(4'-Bromophenacyloxy)phenyldiphenylmethyl, 4,4',4"-Tris(4,5-dichlorophthalimidophenyl)methyl, 4,4',4"-Tris(levulinoyloxyphenyl)methyl, 4,4',4"-Tris(benzoyloxyphenyl)methyl, 3-(Imidazol-1-ylmethyl)bis(4', 4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4-(Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate)); Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate); Groups With Assisted Cleavage (2-Iodobenzoate, 4-Azidobutyrate, 4-Niotro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3 tetramethylbutyl)phenoxyacetate, 2,4-Bis(1,1-dimethylpropyl)phenoxyacetate, Chorodiphenylacetate, Isobutyrate, Monosuccinoate, (E)-2-Methyl-2-butenoate (Tigloate), o-(Methoxycarbonyl)benzoate, p-poly-Benzoate, ⊕-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

More typically, $A^2$ hydroxy protecting groups include substituted methyl ethers, substituted benzyl ethers, silyl ethers, and esters including sulfonic acid esters, still more typically, trialkylsilyl ethers, tosylates and acetates.

Typical 1,2-diol protecting groups (thus, generally where two OH groups are taken together with the $A^2$ protecting functionality) are described in Greene at pages 118-142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, ⊕-Methoxybenzylidene, 1-(N,N-Dimethylamino)ethylidene Derivative, ⊕-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table B, still more typically, epoxides, acetonides, cyclic ketals and aryl acetals.

TABLE B

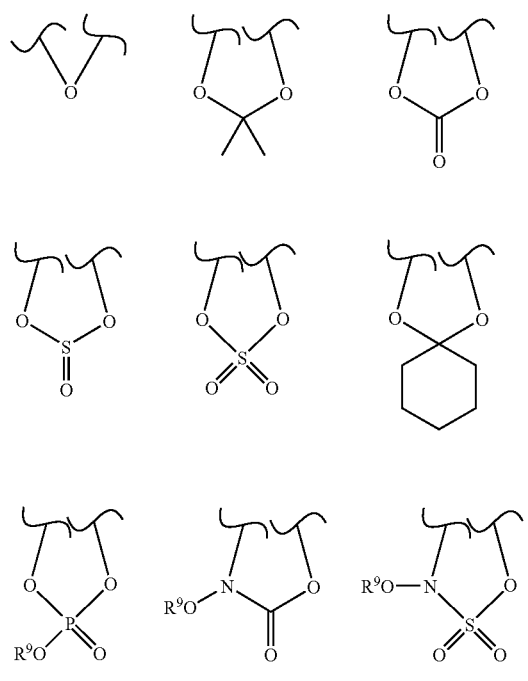

TABLE B-continued

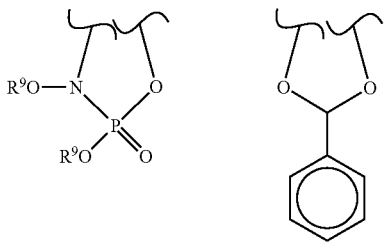

wherein $R^9$ is $C_1$—$C_6$ alkyl.

$A^2$ is also H, a protecting group for amino or the residue of a carboxyl-containing compound, in particular H, —C(O)$R_4$, an amino acid, a polypeptide or a protecting group not —C(O)$R_4$, amino acid or polypeptide. Amide-forming $A^2$ are found for instance in group $A^3$. When $A^2$ is an amino acid or polypeptide it has the structure $R_{15}$NHCH($R_{16}$)C(O)—, where $R_{15}$ is H, an amino acid or polypeptide residue, or $R_{15}$, and $R_{16}$ is defined below.

$R_{16}$ is lower alkyl or lower alkyl ($C_1$-$C_6$) substituted with amino, carboxyl, amide, carboxyl ester, hydroxyl, $C_6$-$C_7$ aryl, guanidinyl, imidazolyl, indolyl, sulfhydryl, sulfoxide, and/or alkylphosphate. $R_{10}$ also is taken together with the amino acid αN to form a proline residue ($R_{10}$=—$CH_2)_3$—). However, $R_{10}$ is generally the side group of a naturally-occurring amino acid such as H, —$CH_3$, —CH($CH_3)_2$, —$CH_2$—CH($CH_3)_2$—CH$CH_3$—$CH_2$—$CH_3$, —$CH_2$—$C_6H_5$, —$CH_2CH_2$—S—$CH_3$, —$CH_2$OH, —CH(OH)—$CH_3$, —$CH_2$—SH, —$CH_2$—$C_6H_4$OH, —$CH_2$—CO—$NH_2$, —$CH_2$—$CH_2$—CO—$NH_2$, —$CH_2$—COOH, —$CH_2$—$CH_2$—COOH, —($CH_2)_4$—$NH_2$ and —($CH_2)_3$—NH—C($NH_2$)—$NH_2$. $R_{10}$ also includes 1-guanidinoprop-3-yl, benzyl, 4-hydroxybenzyl, imidazol-4-yl, indol-3-yl, methoxyphenyl and ethoxyphenyl. $A^2$ are residues of carboxylic acids for the most part, but any of the typical amino protecting groups described by Greene at pages 315-385 are useful. They include Carbamates (methyl and ethyl, 9-fluorenylmethyl, 9(2-sulfo)fluoroenylmethyl, 9-(2, 7-dibromo)fluorenylmethyl, 2,7-di-t-buthyl-[9-(10,10-dioxo-10,10,10,10-tetrahydrothioxanthyl)]methyl, 4-methoxyphenacyl); Substituted Ethyl (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chorobenzyl, 2,4-dichlorobenzyl, 4-methylsulfinylbenzyl, 9-anthrylmethyl, diphenylmethyl); Groups With Assisted Cleavage (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl)benzyl, 5-benzisoxazolylmethyl, 2-(trifluoromethyl)-6-chromonylmethyl); Groups Capable of Photolytic Cleavage (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl); Miscellaneous Carbamates (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido) propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl) ethyl, phenyl, p-(phenylazo)benzyl, 2,4,6-tri-t-butylphenyl, 4-(trimethylammonium)benzyl, 2,4,6-trimethylbenzyl); Amides (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl); Amides With Assisted Cleavage (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy) propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one); Cyclic Imide Derivatives (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl); N-Alkyl and N-Aryl Amines (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide), Imine Derivatives (N-1,1-dimethylthiomethylene, N-benzylidene, N-p-methoxybenzylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene); Enamine Derivatives (N-(5,5-dimethyl-3-oxo-1-cyclohexenyl)); N-Metal Derivatives (N-borane derivatives, N-diphenylborinic acid derivatives, N-[phenyl(pentacarbonylchromium- or -tungsten)]carbenyl, N-copper or N-zinc chelate); N—N Derivatives (N-nitro, N-nitroso, N-oxide); N—P Derivatives (N-diphenylphosphinyl, N-dimethylthiophosphinyl, N-diphenylthiophosphinyl, N-dialkyl phosphoryl, N-dibenzyl phosphoryl, N-diphenyl phosphoryl); N—Si Derivatives; N—S Derivatives; N-Sulfenyl Derivatives (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-ɷ-trimethylsilyethanesulfonyl, N-9-anthracenesulfonyl, N-4-(4',8'- dimethoxynaphthylmethyl)benzenesulfonyl, N-benzylsulfonyl, N-trifluoromethylsulfonyl, N-phenacylsulfonyl).

More typically, protected amino groups include carbamates and amides, still more typically, —NHC(O)R$_1$ or —N═CR$_1$N(R$_1$)$_2$. Another protecting group, also useful as a prodrug at the A$^3$ site, particularly for amino or —NH(R$_5$), is:

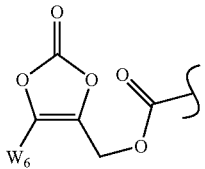

see for example Alexander, J. et al.; J. Med. Chem. 1996, 39, 480-486.

A$^2$ is also H or the residue of an amino-containing compound, in particular an amino acid, a polypeptide, a protecting group, —NHSO$_2$R$_4$, NHC(O)R$_4$, —N(R$_4$)$_2$, NH$_2$ or —NH(R$_4$)(H), whereby for example the carboxyl or phosphonic acid groups of A$^3$ are reacted with the amine to form an amide, as in —C(O)A$^2$, —P(O)(A$^2$)$_2$ or —P(O)(OH)(A$^2$). In general, A$^2$ has the structure R$_{17}$C(O)CH(R$_{16}$)NH—, where R$_{17}$ is OH, OA$^2$, OR$_5$, an amino acid or a polypeptide residue.

Amino acids are low molecular weight compounds, on the order of less than about 1,000 MW, that contain at least one amino or imino group and at least one carboxyl group. Generally the amino acids will be found in nature, i.e., can be detected in biological material such as bacteria or other microbes, plants, animals or man. Suitable amino acids typically are alpha amino acids, i.e. compounds characterized by one amino or imino nitrogen atom separated from the carbon atom of one carboxyl group by a single substituted or unsubstituted alpha carbon atom. Of particular interest are hydrophobic residues such as mono- or di-alkyl or aryl amino acids, cycloalkylamino acids and the like. These residues contribute to cell permeability by increasing the partition coefficient of the parental drug. Typically, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline.

When A$^2$ are single amino acid residues or polypeptides they usually are substituted at A$^3$. These conjugates are produced by forming an amide bond between a carboxyl group of the amino acid (or C-terminal amino acid of a polypeptide for example) and amino nitrogen. Similarly, conjugates are formed between A$^3$ and an amino group of an amino acid or polypeptide. Generally, only one of any site in the parental molecule is amidated with an amino acid as described herein, although it is within the scope of this invention to introduce amino acids at more than one permitted site. Usually, a carboxyl group of A$^3$ is amidated with an amino acid. In general, the ⊕-amino or ⊕-carboxyl group of the amino acid or the terminal amino or carboxyl group of a polypeptide are bonded to the parental functionalities, i.e., carboxyl or amino groups in the amino acid side chains generally are not used to form the amide bonds with the parental compound (although these groups may need to be protected during synthesis of the conjugates as described further below).

With respect to the carboxyl-containing side chains of amino acids or polypeptides it will be understood that the carboxyl group optionally will be blocked, e.g. by A$^2$, esterified with A$^2$ or amidated with A$^2$. Similarly, the amino side chains R$_{16}$ optionally will be blocked with A$^2$ or substituted with R$_5$.

Such ester or amide bonds with side chain amino or carboxyl groups, like the esters or amides with the parental molecule, optionally are hydrolyzable in vivo or in vitro under acidic (pH<3) or basic (pH>10) conditions. Alternatively, they are substantially stable in the gastrointestinal tract of humans but are hydrolyzed enzymatically in blood or in intracellular environments. The esters or amino acid or polypeptide amidates also are useful as intermediates for the preparation of the parental molecule containing free amino or carboxyl groups. The free acid or base of the parental compound, for example, is readily formed from the esters or amino acid or polypeptide conjugates of this invention by conventional hydrolysis procedures.

When an amino acid residue contains one or more chiral centers, any of the D, L, meso, threo or erythro (as appropriate) racemates, scalemates or mixtures thereof may be used. In general, if the intermediates are to be hydrolyzed non-enzymatically (as would be the case where the amides are used as chemical intermediates for the free acids or free amines), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable amino acids whose residues are represented by A$^2$ include the following:

Glycine;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid;

Amino acid amides such as glutamine and asparagine;

Polyamino- or polybasic-monocarboxylic acids such as arginine, lysine, β-aminoalanine, γ-aminobutyrine, ornithine, citruline, homoarginine, homocitrulline, hydroxylysine, allohydroxylsine and diaminobutyric acid;

Other basic amino acid residues such as histidine;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid;

Imino acids such as proline, hydroxyproline, allohydroxyproline, γ-methylproline, pipecolic acid, 5-hydroxypipecolic acid, and azetidine-2-carboxylic acid;

A mono- or di-alkyl (typically C$_1$-C$_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid, isoleucine, alloisoleucine, tert-leucine, β-methyltryptophan and α-amino-β-ethyl-β-phenylpropionic acid; β-phenylserinyl;

Aliphatic α-amino-β-hydroxy acids such as serine, β-hydroxyleucine, β-hydroxynorleucine, β-hydroxynorvaline, and α-amino-β-hydroxystearic acid;

α-Amino, α-, γ-, δ- or ε-hydroxy acids such as homoserine, γ-hydroxynorvaline, δ-hydroxynorvaline and epsilon-hydroxynorleucine residues; canavine and canaline; γ-hydroxyornithine;

2-hexosaminic acids such as D-glucosaminic acid or D-galactosaminic acid;

α-Amino-β-thiols such as penicillamine, β-thiolnorvaline or β-thiolbutyrine;

Other sulfur containing amino acid residues including cysteine; homocystine, β-phenylmethionine, methionine, S-allyl-L-cysteine sulfoxide, 2-thiolhistidine, cystathionine, and thiol ethers of cysteine or homocysteine;

Phenylalanine, tryptophan and ring-substituted α-amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halo-substituted phenyl (e.g., tyrosine, methyltyrosine and o-chloro-, p-chloro-3,4-dichloro, o-, m- or p-methyl-, 2,4,6-trimethyl-, 2-ethoxy-5-nitro-, 2-hydroxy-5-nitro- and p-nitro-phenylalanine); furyl-, thienyl-, pyridyl-, pyrimidinyl-, purinyl- or naphthyl-alanines; and tryptophan analogues and derivatives including kynurenine, 3-hydroxykynurenine, 2-hydroxytryptophan and 4-carboxytryptophan;

α-Amino substituted amino acids including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acids including serine, threonine, allothreonine, phosphoserine and phosphothreonine.

Polypeptides are polymers of amino acids in which a carboxyl group of one amino acid monomer is bonded to an amino or imino group of the next amino acid monomer by an amide bond. Polypeptides include dipeptides, low molecular weight polypeptides (about 1500-5000 MW) and proteins. Proteins optionally contain 3, 5, 10, 50, 75, 100 or more residues, and suitably are substantially sequence-homologous with human, animal, plant or microbial proteins. They include enzymes (e.g., hydrogen peroxidase) as well as immunogens such as KLH, or antibodies or proteins of any type against which one wishes to raise an immune response. The nature and identity of the polypeptide may vary widely.

The polypeptide amidates are useful as immunogens in raising antibodies against either the polypeptide (if it is not immunogenic in the animal to which it is administered) or against the epitopes on the remainder of the compound of this invention.

Antibodies capable of binding to the parental non-peptidyl compound are used to separate the parental compound from mixtures, for example in diagnosis or manufacturing of the parental compound. The conjugates of parental compound and polypeptide generally are more immunogenic than the polypeptides in closely homologous animals, and therefore make the polypeptide more immunogenic for facilitating raising antibodies against it. Accordingly, the polypeptide or protein may not need to be immunogenic in an animal typically used to raise antibodies, e.g., rabbit, mouse, horse, or rat, but the final product conjugate should be immunogenic in at least one of such animals. The polypeptide optionally contains a peptidolytic enzyme cleavage site at the peptide bond between the first and second residues adjacent to the acidic heteroatom. Such cleavage sites are flanked by enzymatic recognition structures, e.g. a particular sequence of residues recognized by a peptidolytic enzyme.

Peptidolytic enzymes for cleaving the polypeptide conjugates of this invention are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its ε-amino group to the phosphorus or carbon atoms of the compounds herein. In embodiments where $A^3$ is phosphonate it is expected that this peptide will be cleaved by the appropriate peptidolytic enzyme, leaving the carboxyl of the proximal amino acid residue to autocatalytically cleave the phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, EI, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FI, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptide residues are also useful as $A^2$. When $A^3$ is phosphonate, the sequence —$X^4$-pro-$X^5$— (where $X^4$ is any amino acid residue and $X^5$ is an amino acid residue, a carboxyl ester of proline, or hydrogen) will be cleaved by luminal carboxypeptidase to yield $X^4$ with a free carboxyl, which in turn is expected to autocatalytically cleave the phosphonoamidate bond. The carboxy group of $X^5$ optionally is esterified with benzyl.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., "Pharm Res." 9:969-978 (1992). Transport competent peptides can thus be used to enhance bioavailability of the amidate compounds. Di- or tripeptides having one or more amino acids in the D configuration are also compatible with peptide transport and can be utilized in the amidate compounds of this invention. Amino acids in the D configuration can be used to reduce the susceptibility of a di- or tripeptide to hydrolysis by proteases common to the brush border such as aminopeptidase N (EC 3.4.11.2). In addition, di- or tripeptides alternatively are selected on the basis of their relative resistance to hydrolysis by proteases found in the lumen of the intestine. For example, tripeptides or polypeptides lacking asp and/or glu are poor substrates for aminopeptidase A (EC 3.4.11.7), di- or tripeptides lacking amino acid residues on the N-terminal side of hydrophobic amino acids (leu, tyr, phe, val, trp) are poor substrates for endopeptidase 24.11 (EC 3.4.24.11), and peptides lacking a pro residue at the penultimate position at a free carboxyl terminus are poor substrates for carboxypeptidase P (EC 3.4.17). Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

HCV-Inhibitory Compounds

The compounds of the invention include those with HCV-inhibitory activity. The compounds of the inventions optionally bear one or more (e.g. 1, 2, 3, or 4) phosphonate groups, which may be a prodrug moiety.

The term "HCV-inhibitory compound" includes those compounds that inhibit HCV.

Typically, compounds of the invention have a molecular weight of from about 400 amu to about 10,000 amu; in a specific embodiment of the invention, compounds have a molecular weight of less than about 5000 amu; in another specific embodiment of the invention, compounds have a molecular weight of less than about 2500 amu; in another specific embodiment of the invention, compounds have a molecular weight of less than about 1000 amu; in another specific embodiment of the invention, compounds have a molecular weight of less than about 800 amu; in another specific embodiment of the invention, compounds have a molecular weight of less than about 600 amu; and in another specific embodiment of the invention, compounds have a molecular weight of less than about 600 amu and a molecular weight of greater than about 400 amu.

The compounds of the invention also typically have a log D (polarity) less than about 5. In one embodiment the invention provides compounds having a log D less than about 4; in another one embodiment the invention provides compounds having a log D less than about 3; in another one embodiment the invention provides compounds having a log D greater than about −5; in another one embodiment the invention provides compounds having a log D greater than about −3; and in another one embodiment the invention provides compounds having a log D greater than about 0 and less than about 3.

Selected substituents within the compounds of the invention are present to a recursive degree. In this context, "recursive substituent" means that a substituent may recite another instance of itself. Because of the recursive nature of such substituents, theoretically, a large number may be present in any given embodiment. For example, $R^x$ contains a $R^y$ substituent. $R^y$ can be $R^2$, which in turn can be $R^3$. If $R^3$ is selected to be $R^{3c}$, then a second instance of $R^x$ can be selected. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

By way of example and not limitation, $A^3$, $A^2$ and $R^1$ are all recursive substituents in certain embodiments. Typically, each of these may independently occur 20, 19, 18, 17, 16, 15, 14, 13, 12, 11, 10, 9, 8, 7, 6, 5, 4, 3, 2, 1, or 0, times in a given embodiment. More typically, each of these may independently occur 12 or fewer times in a given embodiment. More typically yet, $W^3$ will occur 0 to 8 times, $R^y$ will occur 0 to 6 times and $R^3$ will occur 0 to 10 times in a given embodiment. Even more typically, $W^3$ will occur 0 to 6 times, $R^y$ will occur 0 to 4 times and $R^3$ will occur 0 to 8 times in a given embodiment.

Recursive substituents are an intended aspect of the invention. One of ordinary skill in the art of medicinal chemistry understands the versatility of such substituents. To the degree that recursive substituents are present in an embodiment of the invention, the total number will be determined as set forth above.

Whenever a compound described herein is substituted with more than one of the same designated group, e.g., "$R^1$" or "$A^3$", then it will be understood that the groups may be the same or different, i.e., each group is independently selected. Wavy lines indicate the site of covalent bond attachments to the adjoining groups, moieties, or atoms.

In one embodiment of the invention, the compound is in an isolated and purified form. Generally, the term "isolated and purified" means that the compound is substantially free from biological materials (e.g. blood, tissue, cells, etc.). In one specific embodiment of the invention, the term means that the compound or conjugate of the invention is at least about 50 wt. % free from biological materials; in another specific embodiment, the term means that the compound or conjugate of the invention is at least about 75 wt. % free from biological materials; in another specific embodiment, the term means that the compound or conjugate of the invention is at least about 90 wt. % free from biological materials; in another specific embodiment, the term means that the compound or conjugate of the invention is at least about 98 wt. % free from biological materials; and in another embodiment, the term means that the compound or conjugate of the invention is at least about 99 wt. % free from biological materials. In another specific embodiment, the invention provides a compound or conjugate of the invention that has been synthetically prepared (e.g., ex vivo).

Cellular Accumulation

In one embodiment, the invention is provides compounds capable of accumulating in human PBMC (peripheral blood mononuclear cells). PBMC refer to blood cells having round lymphocytes and monocytes. Physiologically, PBMC are critical components of the mechanism against infection. PBMC may be isolated from heparinized whole blood of normal healthy donors or buffy coats, by standard density gradient centrifugation and harvested from the interface, washed (e.g. phosphate-buffered saline) and stored in freezing medium. PBMC may be cultured in multi-well plates. At various times of culture, supernatant may be either removed for assessment, or cells may be harvested and analyzed (Smith R. et al (2003) *Blood* 102(7):2532-2540). The compounds of this embodiment may further comprise a phosphonate or phosphonate prodrug. More typically, the phosphonate or phosphonate prodrug can have the structure $A^3$ as described herein.

Typically, compounds of the invention demonstrate improved intracellular half-life of the compounds or intracellular metabolites of the compounds in human PBMC when compared to analogs of the compounds not having the phosphonate or phosphonate prodrug. Typically, the half-life is improved by at least about 50%, more typically at least in the range 50-100%, still more typically at least about 100%, more typically yet greater than about 100%.

In one embodiment of the invention the intracellular half-life of a metabolite of the compound in human PBMCs is improved when compared to an analog of the compound not having the phosphonate or phosphonate prodrug. In such embodiments, the metabolite may be generated intracellularly, e.g. generated within human PBMC. The metabolite may be a product of the cleavage of a phosphonate prodrug within human PBMCs. The phosphonate prodrug may be cleaved to form a metabolite having at least one negative charge at physiological pH. The phosphonate prodrug may be enzymatically cleaved within human PBMC to form a phosphonate having at least one active hydrogen atom of the form P—OH.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. All though only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

The compositions of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. Monovalent salts are preferred if a water soluble salt is desired.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the amino acids described above are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Methods of Inhibition of HCV

Another aspect of the invention relates to methods of inhibiting the activity of HCV comprising the step of treating a sample suspected of containing HCV with a composition of the invention.

Compositions of the invention may act as inhibitors of HCV, as intermediates for such inhibitors or have other utilities as described below. The inhibitors will generally bind to locations on the surface or in a cavity of the liver. Compositions binding in the liver may bind with varying degrees of reversibility. Those compounds binding substantially irreversibly are ideal candidates for use in this method of the invention. Once labeled, the substantially irreversibly binding compositions are useful as probes for the detection of HCV. Accordingly, the invention relates to methods of detecting NS3 in a sample suspected of containing HCV comprising the steps of: treating a sample suspected of containing HCV with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino.

Within the context of the invention samples suspected of containing HCV include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing HCV. Samples can be contained in any medium including water and organic solvent/water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of HCV after application of the composition can be observed by any method including direct and indirect methods of detecting HCV activity. Quantitative, qualitative, and semiquantitative methods of determining HCV activity are all contemplated. Typically one of the screening methods described above are applied, however, any other method such as observation of the physiological properties of a living organism are also applicable.

Many organisms contain HCV. The compounds of this invention are useful in the treatment or prophylaxis of conditions associated with HCV activation in animals or in man.

However, in screening compounds capable of inhibiting HCV it should be kept in mind that the results of enzyme assays may not correlate with cell culture assays. Thus, a cell based assay should be the primary screening tool.

Screens for HCV Inhibitors

Compositions of the invention are screened for inhibitory activity against HCV by any of the conventional techniques for evaluating enzyme activity. Within the context of the invention, typically compositions are first screened for inhibition of HCV in vitro and compositions showing inhibitory activity are then screened for activity in vivo. Compositions having in vitro Ki (inhibitory constants) of less then about $5 \times 10^{-6}$ M, typically less than about $1 \times 10^{-7}$ M and preferably less than about $5 \times 10^{-8}$ M are preferred for in vivo use. Useful in vitro screens have been described in detail.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents.

Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of conditions associated with HCV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies. It can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Active ingredients of the invention are also used in combination with other active ingredients. Such combinations are selected based on the condition to be treated, cross-reactivities of ingredients and pharmaco-properties of the combination.

It is also possible to combine any compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HCV-inhibitory activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The phosphonate prodrugs of the invention typically will be stable in the digestive system but are substantially hydrolyzed to the parental drug in the digestive lumen, liver or other metabolic organ, or within cells in general.

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry, Third Edition*, (John Wiley & Sons, New York, 1985), *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing).

A number of exemplary methods for the preparation of the compositions of the invention are provided below. These methods are intended to illustrate the nature of such preparations and are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis are used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (*Stereochemistry of Carbon Compounds*, (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) *Stereochemistry of Organic Compounds*, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (*Chiral Liquid Chromatography* (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

SCHEMES AND EXAMPLES

General aspects of these exemplary methods are described below and in the Examples. Each of the products of the following processes is optionally separated, isolated, and/or purified prior to its use in subsequent processes.

A number of exemplary methods for the preparation of compounds of the invention are provided herein, for example, in the Examples hereinbelow. These methods are intended to illustrate the nature of such preparations are not intended to limit the scope of applicable methods. Certain compounds of the invention can be used as intermediates for the preparation of other compounds of the invention. For example, the interconversion of various phosphonate compounds of the invention is illustrated below.

Interconversions of the Phosphonates R-Link-P(O)(OR$^1$)$_2$, R-Link-P(O)(OR$^1$)(OH) and R-Link-P(O)(OH)$_2$.

The following schemes 32-38 describe the preparation of phosphonate esters of the general structure R-link-P(O)(OR$^1$)$_2$, in which the groups R$^1$ may be the same or different. The R$^1$ groups attached to a phosphonate ester, or to precursors thereto, may be changed using established chemical transformations. The interconversion reactions of phosphonates are illustrated in Scheme S32. The group R in Scheme 32 represents the substructure, i.e. the drug "scaffold, to which the substituent link-P(O)(OR$^1$)$_2$ is attached, either in the compounds of the invention, or in precursors thereto. At the point in the synthetic route of conducting a phosphonate interconversion, certain functional groups in R may be protected. The methods employed for a given phosphonate transformation depend on the nature of the substituent R$^1$, and of the substrate to which the phosphonate group is attached. The preparation and hydrolysis of phosphonate esters is described in *Organic Phosphorus Compounds*, G. M. Kosolapoff, L. Maeir, eds, Wiley, 1976, p. 9ff.

In general, synthesis of phosphonate esters is achieved by coupling a nucleophile amine or alcohol with the corresponding activated phosphonate electrophilic precursor. For example, chlorophosphonate addition on to 5′-hydroxy of nucleoside is a well known method for preparation of nucleoside phosphate monoesters. The activated precursor can be prepared by several well known methods. Chlorophosphonates useful for synthesis of the prodrugs are prepared from the substituted-1,3-propanediol (Wissner, et al, (1992) *J. Med Chem.* 35:1650). Chlorophosphonates are made by oxidation of the corresponding chlorophospholanes (Anderson, et al, (1984) *J. Org. Chem.* 49:1304) which are obtained by reaction of the substituted diol with phosphorus trichloride. Alternatively, the chlorophosphonate agent is made by treating substituted-1,3-diols with phosphorusoxychloride (Patois, et al, (1990) *J. Chem. Soc. Perkin Trans. I,* 1577). Chlorophosphonate species may also be generated in situ from corresponding cyclic phosphites (Silverburg, et al., (1996) *Tetrahedron lett.*, 37:771-774), which in turn can be either made from chlorophospholane or phosphoramidate intermediate. Phosphoroflouridate intermediate prepared either from pyrophosphate or phosphoric acid may also act as precursor in preparation of cyclic prodrugs (Watanabe et al., (1988) *Tetrahedron lett.*, 29:5763-66).

Phosphonate prodrugs of the present invention may also be prepared from the free acid by Mitsunobu reactions (Mitsunobu, (1981) *Synthesis*, 1; Campbell, (1992) *J. Org. Chem.* 57:6331), and other acid coupling reagents including, but not limited to, carbodiimides (Alexander, et al, (1994) *Collect. Czech. Chem. Commun.* 59:1853; Casara et al, (1992) *Bioorg. Med. Chem. Lett.* 2:145; Ohashi et al, (1988) *Tetrahedron Lett.*, 29:1189), and benzotriazolyloxytris-(dimethylamino) phosphonium salts (Campagne et al (1993) *Tetrahedron Lett.* 34:6743).

Aryl halides undergo Ni$^{+2}$ catalyzed reaction with phosphite derivatives to give aryl phosphonate containing compounds (Balthazar, et al (1980) *J. Org. Chem.* 45:5425). Phosphonates may also be prepared from the chlorophosphonate in the presence of a palladium catalyst using aromatic triflates (Petrakis et al (1987) *J. Am. Chem. Soc.* 109:2831; Lu et al (1987) *Synthesis* 726). In another method, aryl phosphonate esters are prepared from aryl phosphates under anionic rearrangement conditions (Melvin (1981) *Tetrahedron Lett.* 22:3375; Casteel et al (1991) *Synthesis,* 691). N-Alkoxy aryl salts with alkali metal derivatives of cyclic alkyl phosphonate provide general synthesis for heteroaryl-2-phosphonate linkers (Redmore (1970) *J. Org. Chem.* 35:4114). These above mentioned methods can also be extended to compounds where the $W^5$ group is a heterocycle. Cyclic-1,3-propanyl prodrugs of phosphonates are also synthesized from phosphonic diacids and substituted propane-1,3-diols using a coupling reagent such as 1,3-dicyclohexylcarbodiimide (DCC) in presence of a base (e.g., pyridine). Other carbodiimide based coupling agents like 1,3-disopropylcarbodiimide or water soluble reagent, 1-(3-dimethylaminopropyl)-3-ethylcarbodiimide hydrochloride (EDCI) can also be utilized for the synthesis of cyclic phosphonate prodrugs.

The conversion of a phosphonate diester S32.1 into the corresponding phosphonate monoester S32.2 (Scheme 32, Reaction 1) is accomplished by a number of methods. For example, the ester S32.1 in which $R^1$ is an aralkyl group such as benzyl, is converted into the monoester compound S32.2 by reaction with a tertiary organic base such as diazabicyclooctane (DABCO) or quinuclidine, as described in *J. Org. Chem.* (1995) 60:2946. The reaction is performed in an inert hydrocarbon solvent such as toluene or xylene, at about 110° C. The conversion of the diester S32.1 in which $R^1$ is an aryl group such as phenyl, or an alkenyl group such as allyl, into the monoester S32.2 is effected by treatment of the ester S32.1 with a base such as aqueous sodium hydroxide in acetonitrile or lithium hydroxide in aqueous tetrahydrofuran. Phosphonate diesters S32.1 in which one of the groups $R^1$ is aralkyl, such as benzyl, and the other is alkyl, is converted into the monoesters S32.2 in which $R^1$ is alkyl by hydrogenation, for example using a palladium on carbon catalyst. Phosphonate diesters in which both of the groups $R^1$ are alkenyl, such as allyl, is converted into the monoester S32.2 in which $R^1$ is alkenyl, by treatment with chlorotris(triphenylphosphine) rhodium (Wilkinson's catalyst) in aqueous ethanol at reflux, optionally in the presence of diazabicyclooctane, for example by using the procedure described in *J. Org. Chem.* (1973) 38:3224, for the cleavage of allyl carboxylates.

The conversion of a phosphonate diester S32.1 or a phosphonate monoester S32.2 into the corresponding phosphonic acid S32.3 (Scheme 32, Reactions 2 and 3) can be effected by reaction of the diester or the monoester with trimethylsilyl bromide, as described in *J. Chem. Soc., Chem. Comm.,* (1979) 739. The reaction is conducted in an inert solvent such as, for example, dichloromethane, optionally in the presence of a silylating agent such as bis(trimethylsilyl)trifluoroacetamide, at ambient temperature. A phosphonate monoester S32.2 in which $R^1$ is aralkyl such as benzyl, is converted into the corresponding phosphonic acid S32.3 by hydrogenation over a palladium catalyst, or by treatment with hydrogen chloride in an ethereal solvent such as dioxane. A phosphonate monoester S32.2 in which $R^1$ is alkenyl such as, for example, allyl, is converted into the phosphonic acid S32.3 by reaction with Wilkinson's catalyst in an aqueous organic solvent, for example in 15% aqueous acetonitrile, or in aqueous ethanol, for example using the procedure described in *Helv. Chim. Acta.* (1985) 68:618. Palladium catalyzed hydrogenolysis of phosphonate esters S32.1 in which $R^1$ is benzyl is described in *J. Org. Chem.* (1959) 24:434. Platinum-catalyzed hydrogenolysis of phosphonate esters S32.1 in which $R^1$ is phenyl is described in *J. Am. Chem. Soc.* (1956) 78:2336.

The conversion of a phosphonate monoester S32.2 into a phosphonate diester S32.1 (Scheme 32, Reaction 4) in which the newly introduced $R^1$ group is alkyl, aralkyl, haloalkyl such as chloroethyl, or aralkyl is effected by a number of reactions in which the substrate S32.2 is reacted with a hydroxy compound $R^1OH$, in the presence of a coupling agent. Typically, the second phosphonate ester group is different than the first introduced phosphonate ester group, i.e. $R^1$ is followed by the introduction of $R^2$ where each of $R^1$ and $R^2$ is alkyl, aralkyl, haloalkyl such as chloroethyl, or aralkyl (Scheme 32, Reaction 4a) whereby S32.2 is converted to S32.1a. Suitable coupling agents are those employed for the preparation of carboxylate esters, and include a carbodiimide such as dicyclohexylcarbodiimide, in which case the reaction is preferably conducted in a basic organic solvent such as pyridine, or (benzotriazol-1-yloxy)tripyrrolidinophosphonium hexafluorophosphate (PYBOP, Sigma), in which case the reaction is performed in a polar solvent such as dimethylformamide, in the presence of a tertiary organic base such as diisopropylethylamine, or Aldrithiol-2 (Aldrich) in which case the reaction is conducted in a basic solvent such as pyridine, in the presence of a triaryl phosphine such as triphenylphosphine. Alternatively, the conversion of the phosphonate monoester S32.2 to the diester S32.1 is effected by the use of the Mitsunobu reaction, as described above. The substrate is reacted with the hydroxy compound $R^1OH$, in the presence of diethyl azodicarboxylate and a triarylphosphine such as triphenyl phosphine. Alternatively, the phosphonate monoester S32.2 is transformed into the phosphonate diester S32.1, in which the introduced $R^1$ group is alkenyl or aralkyl, by reaction of the monoester with the halide $R^1Br$, in which $R^1$ is as alkenyl or aralkyl. The alkylation reaction is conducted in a polar organic solvent such as dimethylformamide or acetonitrile, in the presence of a base such as cesium carbonate. Alternatively, the phosphonate monoester is transformed into the phosphonate diester in a two step procedure. In the first step, the phosphonate monoester S32.2 is transformed into the chloro analog $RP(O)(OR^1)Cl$ by reaction with thionyl chloride or oxalyl chloride and the like, as described in *Organic Phosphorus Compounds,* G. M. Kosolapoff, L. Maeir, eds, Wiley, 1976, p. 17, and the thus-obtained product $RP(O)(OR^1)Cl$ is then reacted with the hydroxy compound $R^1OH$, in the presence of a base such as triethylamine, to afford the phosphonate diester S32.1.

A phosphonic acid R-link-$P(O)(OH)_2$ is transformed into a phosphonate monoester $RP(O)(OR^1)(OH)$ (Scheme 32, Reaction 5) by means of the methods described above of for the preparation of the phosphonate diester R-link-P(O) $(OR^1)_2$ S32.1, except that only one molar proportion of the component $R^1OH$ or $R^1Br$ is employed. Dialkyl phosphonates may be prepared according to the methods of: Quast et al (1974) *Synthesis* 490; Stowell et al (1990) *Tetrahedron Lett.* 3261; U.S. Pat. No. 5,663,159.

A phosphonic acid R-link-$P(O)(OH)_2$ S32.3 is transformed into a phosphonate diester R-link-$P(O)(OR^1)_2$ S32.1 (Scheme 32, Reaction 6) by a coupling reaction with the hydroxy compound $R^1OH$, in the presence of a coupling agent such as Aldrithiol-2 (Aldrich) and triphenylphosphine. The reaction is conducted in a basic solvent such as pyridine. Alternatively, phosphonic acids S32.3 are transformed into phosphonic esters S32.1 in which $R^1$ is aryl, by means of a coupling reaction employing, for example, dicyclohexylcarbodiimide in pyridine at ca 70° C. Alternatively, phosphonic acids S32.3 are transformed into phosphonic esters S32.1 in which $R^1$ is alkenyl, by means of an alkylation reaction. The phosphonic acid is reacted with the alkenyl bromide $R^1Br$ in a polar organic solvent such as acetonitrile solution at reflux temperature, the presence of a base such as cesium carbonate, to afford the phosphonic ester S32.1.

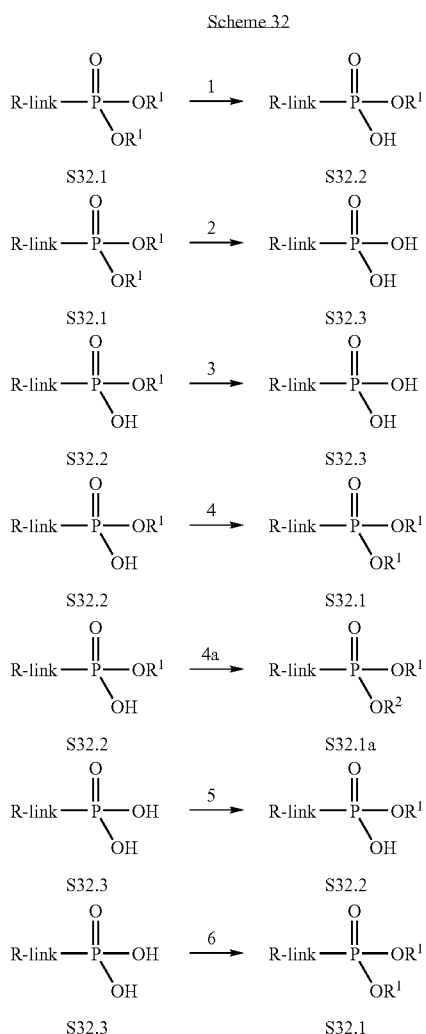

Scheme 32

Preparation of Phosphonate Carbamates.

Phosphonate esters may contain a carbamate linkage. The preparation of carbamates is described in *Comprehensive Organic Functional Group Transformations*, A. R. Katritzky, ed., Pergamon, 1995, Vol. 6, p. 416ff, and in *Organic Functional Group Preparations*, by S. R. Sandler and W. Karo, Academic Press, 1986, p. 260ff. The carbamoyl group may be formed by reaction of a hydroxy group according to the methods known in the art, including the teachings of Ellis, US 2002/0103378 A1 and Hajima, U.S. Pat. No. 6,018,049.

Scheme 33 illustrates various methods by which the carbamate linkage is synthesized. As shown in Scheme 33, in the general reaction generating carbamates, an alcohol S33.1, is converted into the activated derivative S33.2 in which Lv is a leaving group such as halo, imidazolyl, benztriazolyl and the like, as described herein. The activated derivative S33.2 is then reacted with an amine S33.3, to afford the carbamate product S33.4. Examples 1-7 in Scheme 33 depict methods by which the general reaction is effected. Examples 8-10 illustrate alternative methods for the preparation of carbamates.

Scheme 33, Example 1 illustrates the preparation of carbamates employing a chloroformyl derivative of the alcohol S33.5. In this procedure, the alcohol S33.5 is reacted with phosgene, in an inert solvent such as toluene, at about 0° C., as described in *Org. Syn. Coll. Vol.* 3, 167, 1965, or with an equivalent reagent such as trichloromethoxy chloroformate, as described in *Org. Syn. Coll. Vol.* 6, 715, 1988, to afford the chloroformate S33.6. The latter compound is then reacted with the amine component S33.3, in the presence of an organic or inorganic base, to afford the carbamate S33.7. For example, the chloroformyl compound S33.6 is reacted with the amine S33.3 in a water-miscible solvent such as tetrahydrofuran, in the presence of aqueous sodium hydroxide, as described in *Org. Syn. Coll. Vol.* 3, 167, 1965, to yield the carbamate S33.7. Alternatively, the reaction is performed in dichloromethane in the presence of an organic base such as diisopropylethylamine or dimethylaminopyridine.

Scheme 33, Example 2 depicts the reaction of the chloroformate compound S33.6 with imidazole to produce the imidazolide S33.8. The imidazolide product is then reacted with the amine S33.3 to yield the carbamate S33.7. The preparation of the imidazolide is performed in an aprotic solvent such as dichloromethane at 0°, and the preparation of the carbamate is conducted in a similar solvent at ambient temperature, optionally in the presence of a base such as dimethylaminopyridine, as described in *J. Med. Chem.*, 1989, 32, 357.

Scheme 33 Example 3, depicts the reaction of the chloroformate S33.6 with an activated hydroxyl compound R"OH, to yield the mixed carbonate ester S33.10. The reaction is conducted in an inert organic solvent such as ether or dichloromethane, in the presence of a base such as dicyclohexylamine or triethylamine. The hydroxyl component R"OH is selected from the group of compounds S33.19-S33.24 shown in Scheme 33, and similar compounds. For example, if the component R"OH is hydroxybenztriazole S33.19, N-hydroxysuccinimide S33.20, or pentachlorophenol, S33.21, the mixed carbonate S33.10 is obtained by the reaction of the chloroformate with the hydroxyl compound in an ethereal solvent in the presence of dicyclohexylamine, as described in *Can. J. Chem.*, 1982, 60, 976. A similar reaction in which the component R"OH is pentafluorophenol S33.22 or 2-hydroxypyridine S33.23 is performed in an ethereal solvent in the presence of triethylamine, as described in *Syn.*, 1986, 303, and *Chem. Ber.* 118, 468, 1985.

Scheme 33 Example 4 illustrates the preparation of carbamates in which an alkyloxycarbonylimidazole S33.8 is employed. In this procedure, an alcohol S33.5 is reacted with an equimolar amount of carbonyl diimidazole S33.11 to prepare the intermediate S33.8. The reaction is conducted in an aprotic organic solvent such as dichloromethane or tetrahydrofuran. The acyloxyimidazole S33.8 is then reacted with an equimolar amount of the amine R'NH$_2$ to afford the carbamate S33.7. The reaction is performed in an aprotic organic solvent such as dichloromethane, as described in *Tet. Lett.*, 42, 2001, 5227, to afford the carbamate S33.7.

Scheme 33, Example 5 illustrates the preparation of carbamates by means of an intermediate alkoxycarbonylbenztriazole S33.13. In this procedure, an alcohol ROH is reacted at ambient temperature with an equimolar amount of benztriazole carbonyl chloride S33.12, to afford the alkoxycarbonyl product S33.13. The reaction is performed in an organic solvent such as benzene or toluene, in the presence of a tertiary organic amine such as triethylamine, as described in *Synthesis.*, 1977, 704. The product is then reacted with the amine R'NH$_2$ to afford the carbamate S33.7. The reaction is conducted in toluene or ethanol, at from ambient temperature to about 80° C. as described in *Synthesis.*, 1977, 704.

Scheme 33, Example 6 illustrates the preparation of carbamates in which a carbonate (R"O)$_2$CO, S33.14, is reacted with an alcohol S33.5 to afford the intermediate alkyloxycarbonyl intermediate S33.15. The latter reagent is then reacted with the amine R'NH$_2$ to afford the carbamate S33.7. The procedure in which the reagent S33.15 is derived from hydroxybenztriazole S33.19 is described in Synthesis, 1993, 908; the procedure in which the reagent S33.15 is derived from N-hydroxysuccinimide S33.20 is described in *Tet. Lett.*, 1992, 2781; the procedure in which the reagent S33.15 is derived from 2-hydroxypyridine S33.23 is described in *Tet. Lett.*, 1991, 4251; the procedure in which the reagent S33.15 is derived from 4-nitrophenol S33.24 is described in *Synthesis.* 1993, 103. The reaction between equimolar amounts of the alcohol ROH and the carbonate S33.14 is conducted in an inert organic solvent at ambient temperature.

Scheme 33, Example 7 illustrates the preparation of carbamates from alkoxycarbonyl azides S33.16. In this procedure, an alkyl chloroformate S33.6 is reacted with an azide, for example sodium azide, to afford the alkoxycarbonyl azide S33.16. The latter compound is then reacted with an equimolar amount of the amine R'NH$_2$ to afford the carbamate S33.7. The reaction is conducted at ambient temperature in a polar aprotic solvent such as dimethylsulfoxide, for example as described in *Synthesis.*, 1982, 404.

Scheme 33, Example 8 illustrates the preparation of carbamates by means of the reaction between an alcohol ROH and the chloroformyl derivative of an amine S33.17. In this procedure, which is described in *Synthetic Organic Chemistry*, R. B. Wagner, H. D. Zook, Wiley, 1953, p. 647, the reactants are combined at ambient temperature in an aprotic solvent such as acetonitrile, in the presence of a base such as triethylamine, to afford the carbamate S33.7.

Scheme 33, Example 9 illustrates the preparation of carbamates by means of the reaction between an alcohol ROH and an isocyanate S33.18. In this procedure, which is described in *Synthetic Organic Chemistry*, R. B. Wagner, H. D. Zook, Wiley, 1953, p. 645, the reactants are combined at ambient temperature in an aprotic solvent such as ether or dichloromethane and the like, to afford the carbamate S33.7.

Scheme 33, Example 10 illustrates the preparation of carbamates by means of the reaction between an alcohol ROH and an amine R'NH$_2$. In this procedure, which is described in *Chem. Lett.* 1972, 373, the reactants are combined at ambient temperature in an aprotic organic solvent such as tetrahydrofuran, in the presence of a tertiary base such as triethylamine, and selenium. Carbon monoxide is passed through the solution and the reaction proceeds to afford the carbamate S33.7.

Scheme 33.
Preparation of carbamates.

General Reaction

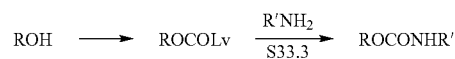

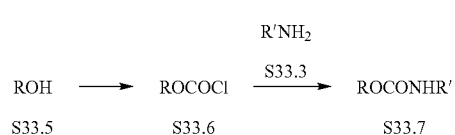

-continued $$ROH \xrightarrow[S33.17]{R'NHCOCl} ROCONHR' \quad (8)$$
S33.5 S33.7

$$ROH \xrightarrow[S33.18]{R'NCO} ROCONHR' \quad (9)$$
S33.5 S33.7

$$ROH \xrightarrow[S33.3]{R'NH_2} ROCONHR' \quad (10)$$
S33.5 S33.7

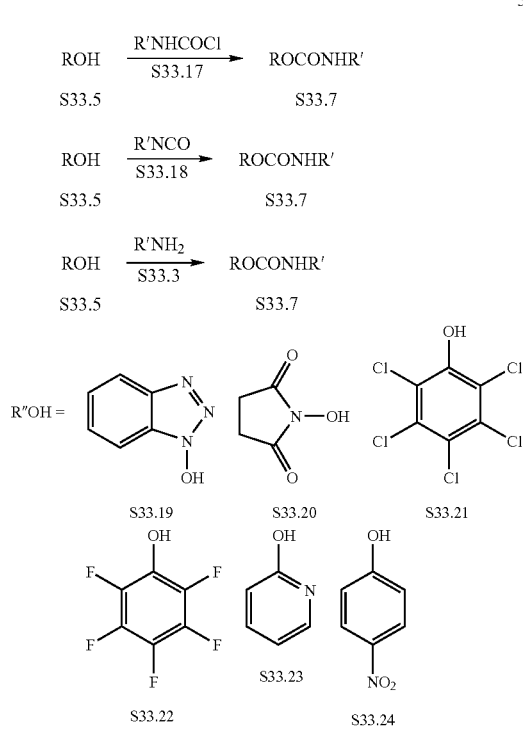

R"OH = S33.19, S33.20, S33.21, S33.22, S33.23, S33.24

Preparation of Carboalkoxy-Substituted Phosphonate Bisamidates, Monoamidates, Diesters and Monoesters.

A number of methods are available for the conversion of phosphonic acids into amidates and esters. In one group of methods, the phosphonic acid is either converted into an isolated activated intermediate such as a phosphoryl chloride, or the phosphonic acid is activated in situ for reaction with an amine or a hydroxy compound.

The conversion of phosphonic acids into phosphoryl chlorides is accomplished by reaction with thionyl chloride, for example as described in *J. Gen. Chem. USSR*, 1983, 53, 480, *Zh. Obschei Khim.*, 1958, 28, 1063, or *J. Org. Chem.*, 1994, 59, 6144, or by reaction with oxalyl chloride, as described in *J. Am. Chem. Soc.*, 1994, 116, 3251, or *J. Org. Chem.*, 1994, 59, 6144, or by reaction with phosphorus pentachloride, as described in *J. Org. Chem.*, 2001, 66, 329, or in *J. Med. Chem.*, 1995, 38, 1372. The resultant phosphoryl chlorides are then reacted with amines or hydroxy compounds in the presence of a base to afford the amidate or ester products.

Phosphonic acids are converted into activated imidazolyl derivatives by reaction with carbonyl diimidazole, as described in *J. Chem. Soc., Chem. Comm.* (1991) 312, or *Nucleosides & Nucleotides* (2000) 19:1885. Activated sulfonyloxy derivatives are obtained by the reaction of phosphonic acids with trichloromethylsulfonyl chloride or with triisopropylbenzenesulfonyl chloride, as described in *Tet. Lett.* (1996) 7857, or *Bioorg. Med. Chem. Lett.* (1998) 8.663. The activated sulfonyloxy derivatives are then reacted with amines or hydroxy compounds to afford amidates or esters.

Alternatively, the phosphonic acid and the amine or hydroxy reactant are combined in the presence of a diimide coupling agent. The preparation of phosphonic amidates and esters by means of coupling reactions in the presence of dicyclohexyl carbodiimide is described, for example, in *J. Chem. Soc., Chem. Comm.* (1991) 312 or *Coll. Czech. Chem. Comm.* (1987) 52:2792. The use of ethyl dimethylaminopropyl carbodiimide for activation and coupling of phosphonic acids is described in *Tet. Lett.*, (2001) 42:8841, or *Nucleosides & Nucleotides* (2000) 19:1885.

A number of additional coupling reagents have been described for the preparation of amidates and esters from phosphonic acids. The agents include Aldrithiol-2, and PYBOP and BOP, as described in *J. Org. Chem.*, 1995, 60, 5214, and *J. Med. Chem.* (1997) 40:3842, mesitylene-2-sulfonyl-3-nitro-1,2,4-triazole (MSNT), as described in *J. Med. Chem.* (1996) 39:4958, diphenylphosphoryl azide, as described in *J. Org. Chem.* (1984) 49:1158, 1-(2,4,6-triisopropylbenzenesulfonyl-3-nitro-1,2,4-triazole (TPSNT) as described in *Bioorg. Med. Chem. Lett.* (1998) 8:1013, bromotris(dimethylamino)phosphonium hexafluorophosphate (BroP), as described in *Tet. Lett.*, (1996) 37:3997, 2-chloro-5,5-dimethyl-2-oxo-1,3,2-dioxaphosphinane, as described in *Nucleosides Nucleotides* 1995, 14, 871, and diphenyl chlorophosphate, as described in *J. Med. Chem.*, 1988, 31, 1305.

Phosphonic acids are converted into amidates and esters by means of the Mitsunobu reaction, in which the phosphonic acid and the amine or hydroxy reactant are combined in the presence of a triaryl phosphine and a dialkyl azodicarboxylate. The procedure is described in *Org. Lett.*, 2001, 3, 643, or *J. Med. Chem.*, 1997, 40, 3842.

Phosphonic esters are also obtained by the reaction between phosphonic acids and halo compounds, in the presence of a suitable base. The method is described, for example, in *Anal. Chem.*, 1987, 59, 1056, or *J. Chem. Soc. Perkin Trans., I*, 1993, 19, 2303, or *J. Med. Chem.*, 1995, 38, 1372, or *Tet. Lett.*, 2002, 43, 1161.

Schemes 34-37 illustrate the conversion of phosphonate esters and phosphonic acids into carboalkoxy-substituted phosphonbisamidates (Scheme 34), phosphonamidates (Scheme 35), phosphonate monoesters (Scheme 36) and phosphonate diesters, (Scheme 37). Scheme 38 illustrates synthesis of gem-dialkyl amino phosphonate reagents.

Scheme 34 illustrates various methods for the conversion of phosphonate diesters S34.1 into phosphonbisamidates S34.5. The diester S34.1, prepared as described previously, is hydrolyzed, either to the monoester S34.2 or to the phosphonic acid S34.6. The methods employed for these transformations are described above. The monoester S34.2 is converted into the monoamidate S34.3 by reaction with an aminoester S34.9, in which the group $R^2$ is H or alkyl; the group $R^{4b}$ is a divalent alkylene moiety such as, for example, $CHCH_3$, $CHCH_2CH_3$, $CH(CH(CH_3)_2)$, $CH(CH_2Ph)$, and the like, or a side chain group present in natural or modified aminoacids; and the group $R^{5b}$ is $C_1$-$C_{12}$ alkyl, such as methyl, ethyl, propyl, isopropyl, or isobutyl; $C_6$-$C_{20}$ aryl, such as phenyl or substituted phenyl; or $C_6$-$C_{20}$ arylalkyl, such as benzyl or benzyhydryl. The reactants are combined in the presence of a coupling agent such as a carbodiimide, for example dicyclohexyl carbodiimide, as described in *J. Am. Chem. Soc.*, (1957) 79:3575, optionally in the presence of an activating agent such as hydroxybenztriazole, to yield the amidate product S34.3. The amidate-forming reaction is also effected in the presence of coupling agents such as BOP, as described in *J. Org. Chem.* (1995) 60:5214, Aldrithiol, PYBOP and similar coupling agents used for the preparation of amides and esters. Alternatively, the reactants S34.2 and S34.9 are transformed into the monoamidate S34.3 by means of a Mitsunobu reaction. The preparation of amidates by means of the Mitsunobu reaction is described in *J. Med. Chem.* (1995) 38:2742. Equimolar amounts of the reactants are combined in an inert solvent such as tetrahydrofuran in the presence of a triaryl phosphine and a dialkyl azodicarboxylate. The thus-obtained monoamidate ester S34.3 is then transformed into amidate phosphonic acid S34.4. The conditions used for the hydrolysis reaction depend on the nature of the $R^1$ group, as described previously. The phosphonic acid amidate S34.4 is then reacted with an aminoester S34.9, as described above, to yield the bisamidate product S34.5, in which the amino substituents are the same or different. Alternatively, the phosphonic acid S34.6 may be treated with two different amino ester reagents simulataneously, i.e. S34.9 where $R^2$, $R^{4b}$ or $R^{5b}$ are different. The resulting mixture of bisamidate products S34.5 may then be separable, e.g. by chromatography.

the monoacid product S34.18 which may be unstable according to J. Med. Chem. (1997) 40(23):3842. This compound S34.18 is then reacted in a Mitsunobu reaction with ethyl leucinate S34.19, triphenyl phosphine and diethylazodicarboxylate, as described in J. Med. Chem., 1995, 38, 2742, to produce the bisamidate product S34.20.

Using the above procedures, but employing in place of ethyl leucinate S34.19 or ethyl alaninate S34.16, different aminoesters S34.9, the corresponding products S34.5 are obtained.

Alternatively, the phosphonic acid S34.6 is converted into the bisamidate S34.5 by use of the coupling reactions described above. The reaction is performed in one step, in

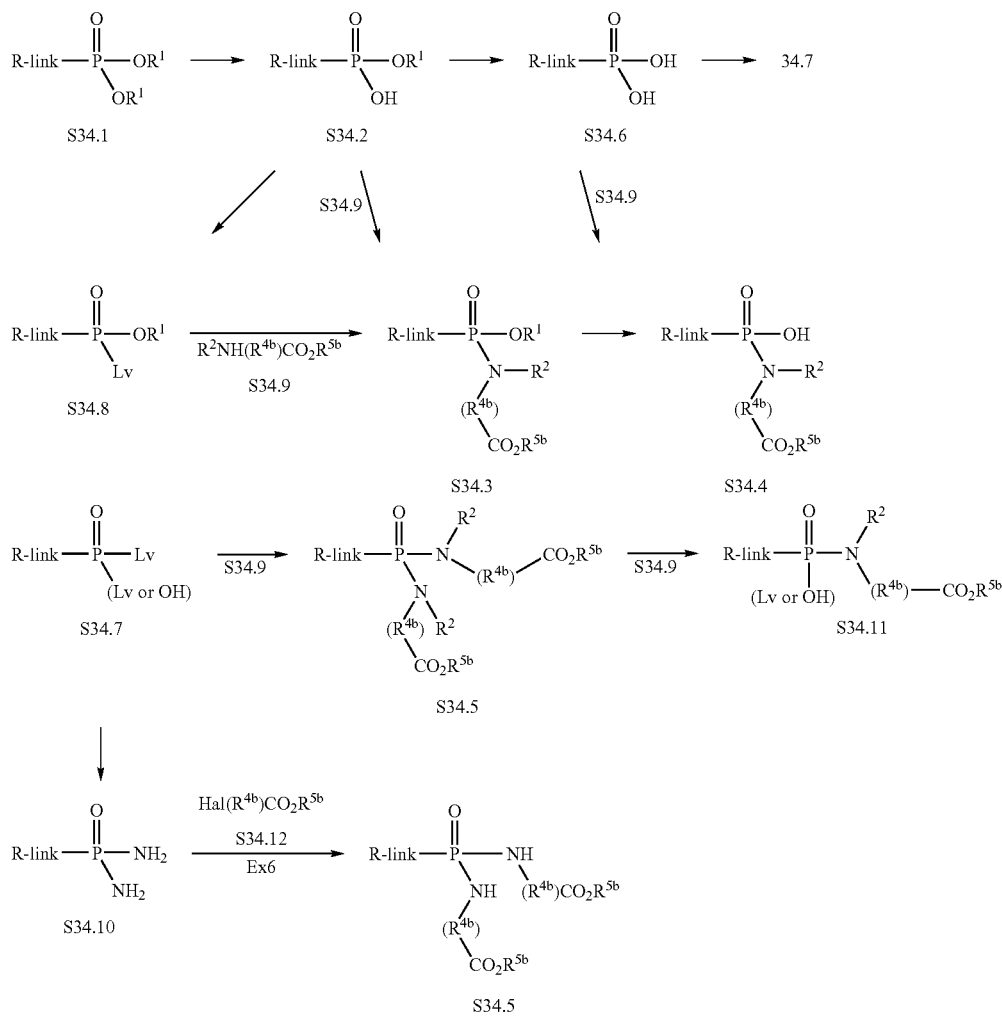

Scheme 34

An example of this procedure is shown in Scheme 34, Example 1. In this procedure, a dibenzyl phosphonate S34.14 is reacted with diazabicyclooctane (DABCO) in toluene at reflux, as described in J. Org. Chem., 1995, 60, 2946, to afford the monobenzyl phosphonate S34.15. The product is then reacted with equimolar amounts of ethyl alaninate S34.16 and dicyclohexyl carbodiimide in pyridine, to yield the amidate product S34.17. The benzyl group is then removed, for example by hydrogenolysis over a palladium catalyst, to give which case the nitrogen-related substituents present in the product S34.5 are the same, or in two steps, in which case the nitrogen-related substituents can be different.

An example of the method is shown in Scheme 34, Example 2. In this procedure, a phosphonic acid S34.6 is reacted in pyridine solution with excess ethyl phenylalaninate S34.21 and dicyclohexylcarbodiimide, for example as described in J. Chem. Soc., Chem. Comm., 1991, 1063, to give the bisamidate product S34.22.

Using the above procedures, but employing, in place of ethyl phenylalaninate, different aminoesters S34.9, the corresponding products S34.5 are obtained.

As a further alternative, the phosphonic acid S34.6 is converted into the mono or bis-activated derivative S34.7, in which Lv is a leaving group such as chloro, imidazolyl, triisopropylbenzenesulfonyloxy etc.

The conversion of phosphonic acids into chlorides S34.7 (Lv=Cl) is effected by reaction with thionyl chloride or oxalyl chloride and the like, as described in *Organic Phosphorus Compounds*. M. Kosolapoff, L.

Maeir, eds, Wiley, 1976, p. 17. The conversion of phosphonic acids into monoimidazolides S34.7 (Lv=imidazolyl) is described in *J. Med. Chem.*, 2002, 45, 1284 and in *J. Chem. Soc. Chem. Comm.*, 1991, 312. Alternatively, the phosphonic acid is activated by reaction with triisopropylbenzenesulfonyl chloride, as described in *Nucleosides and Nucleotides*, 2000, 10, 1885. The activated product is then reacted with the aminoester S34.9, in the presence of a base, to give the bisamidate S34.5. The reaction is performed in one step, in which case the nitrogen substituents present in the product S34.5 are the same, or in two steps, via the intermediate S34.11, in which case the nitrogen substituents can be different.

Examples of these methods are shown in Scheme 34, Examples 3 and 5. In the procedure illustrated in Scheme 34, Example 3, a phosphonic acid S34.6 is reacted with ten molar equivalents of thionyl chloride, as described in *Zh. Obschei Khim.*, 1958, 28, 1063, to give the dichloro compound S34.23. The product is then reacted at reflux temperature in a polar aprotic solvent such as acetonitrile, and in the presence of a base such as triethylamine, with butyl serinate S34.24 to afford the bisamidate product S34.25.

Using the above procedures, but employing, in place of butyl serinate S34.24, different aminoesters S34.9, the corresponding products S34.5 are obtained.

In the procedure illustrated in Scheme 34, Example 5, the phosphonic acid S34.6 is reacted, as described in *J. Chem. Soc. Chem. Comm.*, 1991, 312, with carbonyl diimidazole to give the imidazolide S34.S32. The product is then reacted in acetonitrile solution at ambient temperature, with one molar equivalent of ethyl alaninate S34.33 to yield the monodisplacement product S34.S34. The latter compound is then reacted with carbonyl diimidazole to produce the activated intermediate S34.35, and the product is then reacted, under the same conditions, with ethyl N-methylalaninate S34.33a to give the bisamidate product S34.36.

Using the above procedures, but employing, in place of ethyl alaninate S34.33 or ethyl N-methylalaninate S34.33a, different aminoesters S34.9, the corresponding products S34.5 are obtained.

The intermediate monoamidate S34.3 is also prepared from the monoester S34.2 by first converting the monoester into the activated derivative S34.8 in which Lv is a leaving group such as halo, imidazolyl etc, using the procedures described above. The product S34.8 is then reacted with an aminoester S34.9 in the presence of a base such as pyridine, to give an intermediate monoamidate product S34.3. The latter compound is then converted, by removal of the $R^1$ group and coupling of the product with the aminoester S34.9, as described above, into the bisamidate S34.5.

An example of this procedure, in which the phosphonic acid is activated by conversion to the chloro derivative S34.26, is shown in Scheme 34, Example 4. In this procedure, the phosphonic monobenzyl ester S34.15 is reacted, in dichloromethane, with thionyl chloride, as described in *Tet. Letters.*, 1994, 35, 4097, to afford the phosphoryl chloride S34.26. The product is then reacted in acetonitrile solution at ambient temperature with one molar equivalent of ethyl 3-amino-2-methylpropionate S34.27 to yield the monoamidate product S34.28. The latter compound is hydrogenated in ethylacetate over a 5% palladium on carbon catalyst to produce the monoacid product S34.29. The product is subjected to a Mitsunobu coupling procedure, with equimolar amounts of butyl alaninate S34.30, triphenyl phosphine, diethylazodicarboxylate and triethylamine in tetrahydrofuran, to give the bisamidate product S34.31.

Using the above procedures, but employing, in place of ethyl 3-amino-2-methylpropionate S34.27 or butyl alaninate S34.30, different aminoesters S34.9, the corresponding products S34.5 are obtained.

The activated phosphonic acid derivative S34.7 is also converted into the bisamidate S34.5 via the diamino compound S34.10. The conversion of activated phosphonic acid derivatives such as phosphoryl chlorides into the corresponding amino analogs S34.10, by reaction with ammonia, is described in *Organic Phosphorus Compounds*, G. M. Kosolapoff, L. Maeir, eds, Wiley, 1976. The bisamino compound S34.10 is then reacted at elevated temperature with a haloester S34.12 (Hal=halogen, i.e. F, Cl, Br, I), in a polar organic solvent such as dimethylformamide, in the presence of a base such as 4,4-dimethylaminopyridine (DMAP) or potassium carbonate, to yield the bisamidate S34.5. Alternatively, S34.6 may be treated with two different amino ester reagents simulataneously, i.e. S34.12 where $R^{4b}$ or $R^{5b}$ are different. The resulting mixture of bisamidate products S34.5 may then be separable, e.g. by chromatography.

An example of this procedure is shown in Scheme 34, Example 6. In this method, a dichlorophosphonate S34.23 is reacted with ammonia to afford the diamide S34.37. The reaction is performed in aqueous, aqueous alcoholic or alcoholic solution, at reflux temperature. The resulting diamino compound is then reacted with two molar equivalents of ethyl 2-bromo-3-methylbutyrate S34.38, in a polar organic solvent such as N-methylpyrrolidinone at ca. 150° C., in the presence of a base such as potassium carbonate, and optionally in the presence of a catalytic amount of potassium iodide, to afford the bisamidate product S34.39.

Using the above procedures, but employing, in place of ethyl 2-bromo-3-methylbutyrate S34.38, different haloesters S34.12 the corresponding products S34.5 are obtained.

The procedures shown in Scheme 34 are also applicable to the preparation of bisamidates in which the aminoester moiety incorporates different functional groups. Scheme 34, Example 7 illustrates the preparation of bisamidates derived from tyrosine. In this procedure, the monoimidazolide S34.32 is reacted with propyl tyrosinate S34.40, as described in Example 5, to yield the monoamidate S34.41. The product is reacted with carbonyl diimidazole to give the imidazolide S34.42, and this material is reacted with a further molar equivalent of propyl tyrosinate to produce the bisamidate product S34.43.

Using the above procedures, but employing, in place of propyl tyrosinate S34.40, different aminoesters S34.9, the corresponding products S34.5 are obtained. The aminoesters employed in the two stages of the above procedure can be the same or different, so that bisamidates with the same or different amino substituents are prepared.

Scheme 35 illustrates methods for the preparation of phosphonate monoamidates.

In one procedure, a phosphonate monoester S34.1 is converted, as described in Scheme 34, into the activated derivative S34.8. This compound is then reacted, as described above, with an aminoester S34.9, in the presence of a base, to afford the monoamidate product S35.1.

The procedure is illustrated in Scheme 35, Example 1. In this method, a monophenyl phosphonate S35.7 is reacted with, for example, thionyl chloride, as described in *J. Gen. Chem. USSR.*, 1983, 32, 367, to give the chloro product S35.8. The product is then reacted, as described in Scheme 34, with ethyl alaninateS3, to yield the amidate S35.10.

Using the above procedures, but employing, in place of ethyl alaninate S35.9, different aminoesters S34.9, the corresponding products S35.1 are obtained.

Alternatively, the phosphonate monoester S34.1 is coupled, as described in Scheme 34, with an aminoester S34.9 to produce the amidateS335.1. If necessary, the $R^1$ substituent is then altered, by initial cleavage to afford the phosphonic acid S35.2. The procedures for this transformation depend on the nature of the $R^1$ group, and are described above. The phosphonic acid is then transformed into the ester amidate product S35.3, by reaction with the hydroxy compound $R^3OH$, in which the group $R^3$ is aryl, heterocycle, alkyl, cycloalkyl, haloalkyl etc, using the same coupling procedures (carbodiimide, Aldrithiol-2, PYBOP, Mitsunobu reaction etc) described in Scheme 34 for the coupling of amines and phosphonic acids.

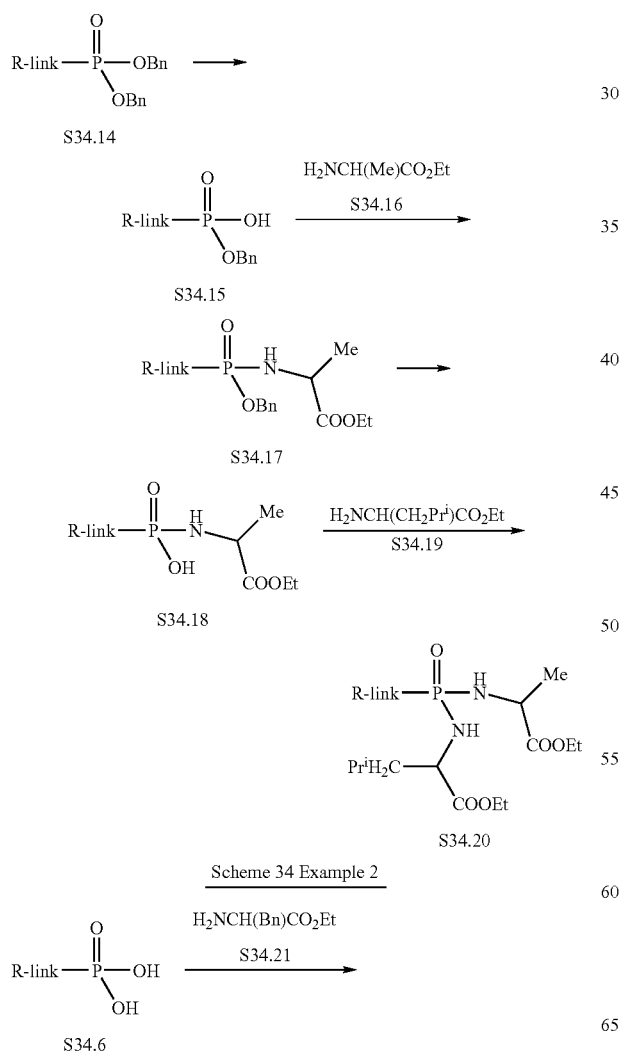

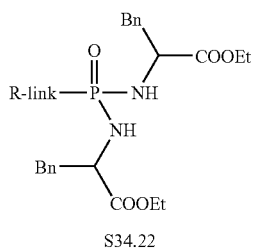

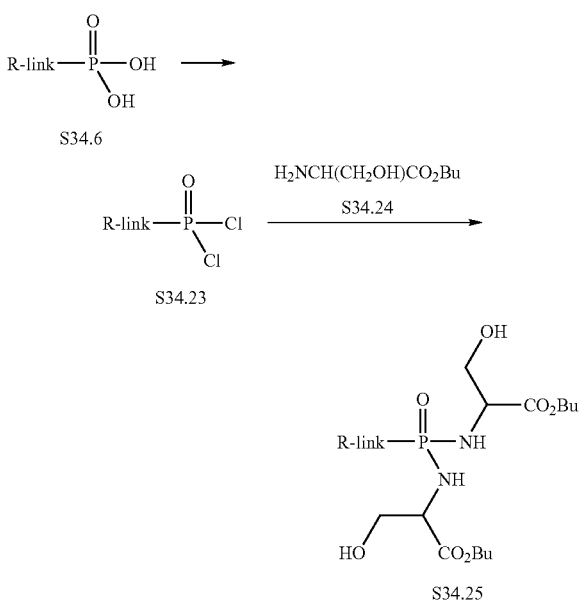

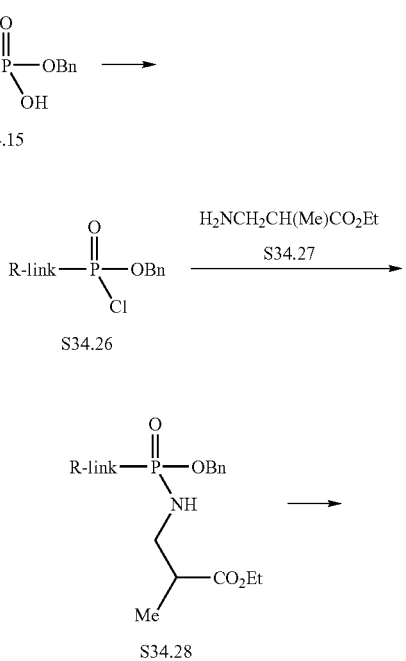

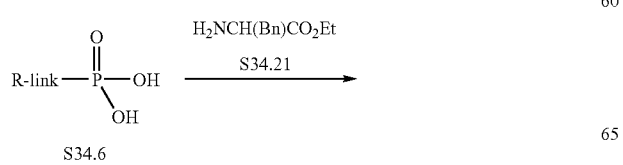

-continued
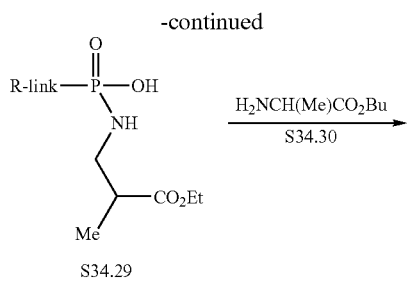
S34.29
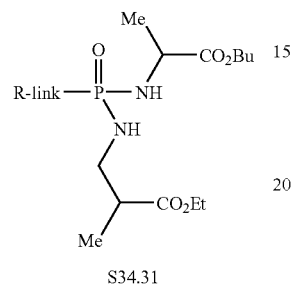
S34.31
Scheme 34 Example 5
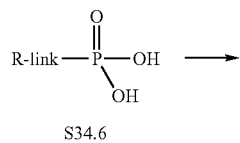
S34.6
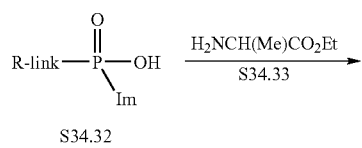
S34.32
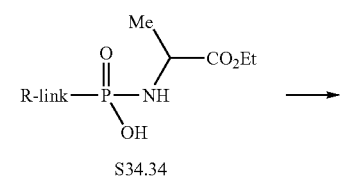
S34.34
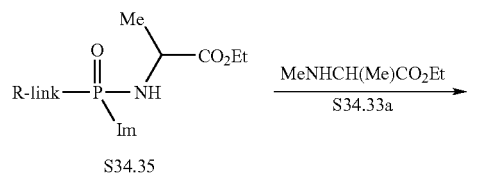
S34.35
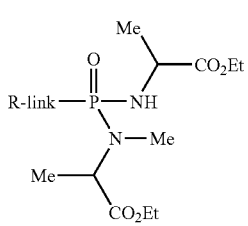
S34.36
-continued
Scheme 34 Example 6
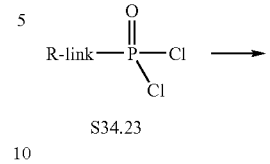
S34.23
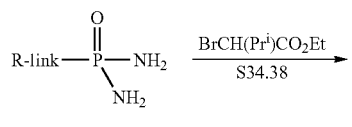
S34.37
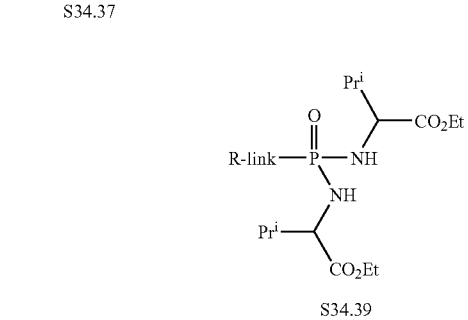
S34.39
Scheme 34 Example 7
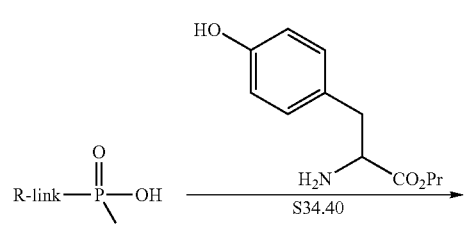
S34.32
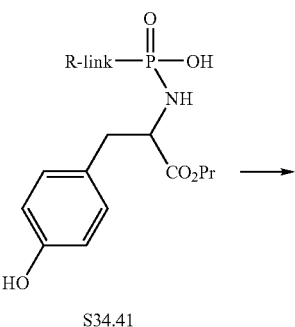
S34.41
S34.42

-continued

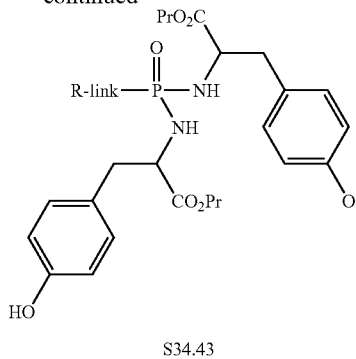

S34.43

Examples of this method are shown in Scheme 35, Examples 2 and 53. In the sequence shown in Example 2, a monobenzyl phosphonate S35.11 is transformed by reaction with ethyl alaninate, using one of the methods described above, into the monoamidate S35.12. The benzyl group is then removed by catalytic hydrogenation in ethylacetate solution over a 5% palladium on carbon catalyst, to afford the phosphonic acid amidate S35.13. The product is then reacted in dichloromethane solution at ambient temperature with equimolar amounts of 1-(dimethylaminopropyl)-3-ethylcarbodiimide and trifluoroethanol S35.14, for example as described in Tet. Lett., 2001, 42, 8841, to yield the amidate ester S35.15.

In the sequence shown in Scheme 35, Example 3, the monoamidate S35.13 is coupled, in tetrahydrofuran solution at ambient temperature, with equimolar amounts of dicyclohexyl carbodiimide and 4-hydroxy-N-methylpiperidine S35.16, to produce the amidate ester product S35.17.

Using the above procedures, but employing, in place of the ethyl alaninate product S35.12 different monoacids S35.2, and in place of trifluoroethanol S35.14 or 4-hydroxy-N-methylpiperidine S35.16, different hydroxy compounds $R^3OH$, the corresponding products S35.3 are obtained.

Alternatively, the activated phosphonate ester S34.8 is reacted with ammonia to yield the amidate S35.4. The product is then reacted, as described in Scheme 34, with a haloester S35.5, in the presence of a base, to produce the amidate product S35.6. If appropriate, the nature of the $R^1$ group is changed, using the procedures described above, to give the product S35.3. The method is illustrated in Scheme 35, Example 4. In this sequence, the monophenyl phosphoryl chloride S35.18 is reacted, as described in Scheme 34, with ammonia, to yield the amino product S35.19. This material is then reacted in N-methylpyrrolidinone solution at 170° with butyl 2-bromo-3-phenylpropionate S35.20 and potassium carbonate, to afford the amidate product S35.21.

Using these procedures, but employing, in place of butyl 2-bromo-3-phenylpropionate S35.20, different haloesters S35.5, the corresponding products S35.6 are obtained.

The monoamidate products S35.3 are also prepared from the doubly activated phosphonate derivatives S34.7. In this procedure, examples of which are described in Synlett., 1998, 1, 73, the intermediate S34.7 is reacted with a limited amount of the aminoester S34.9 to give the mono-displacement product S34.11. The latter compound is then reacted with the hydroxy compound $R^3OH$ in a polar organic solvent such as dimethylformamide, in the presence of a base such as diisopropylethylamine, to yield the monoamidate ester S35.3.

The method is illustrated in Scheme 35, Example 5. In this method, the phosphoryl dichloride S35.22 is reacted in dichloromethane solution with one molar equivalent of ethyl N-methyl tyrosinate S35.23 and dimethylaminopyridine, to generate the monoamidate S35.24. The product is then reacted with phenol S35.25 in dimethylformamide containing potassium carbonate, to yield the ester amidate product S35.26.

Using these procedures, but employing, in place of ethyl N-methyl tyrosinate S35.23 or phenol S35.25, the aminoesters 34.9 and/or the hydroxy compounds $R^3OH$, the corresponding products S35.3 are obtained.

Scheme 35

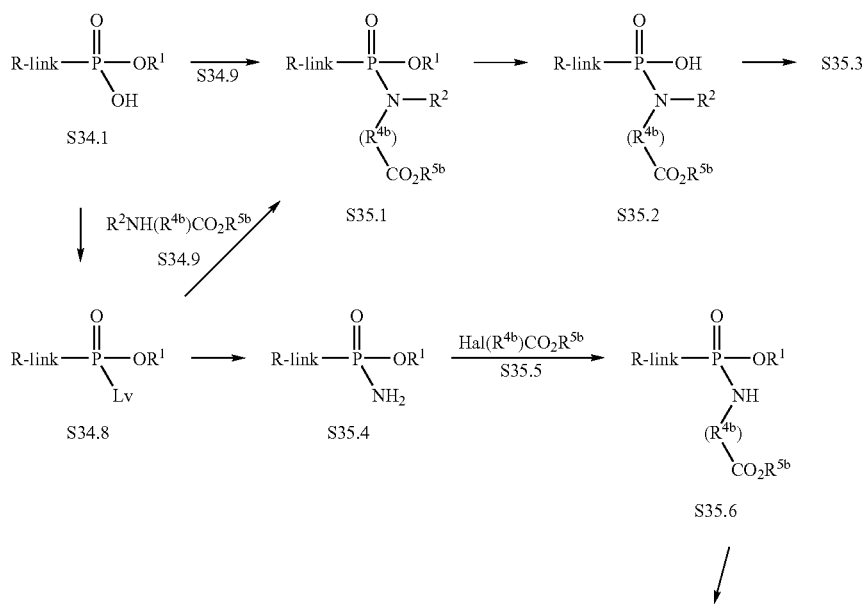

-continued
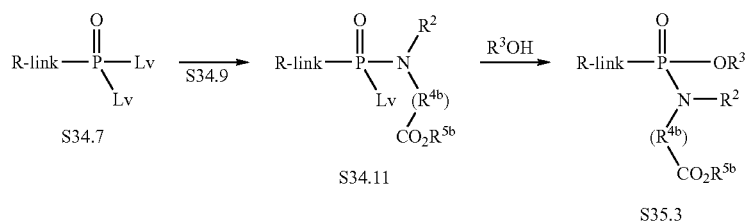
Scheme 35 Example 1
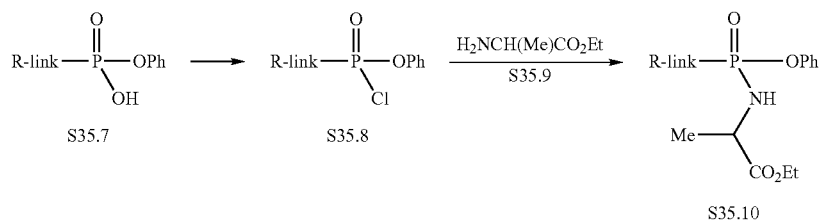
Scheme 35 Example 2
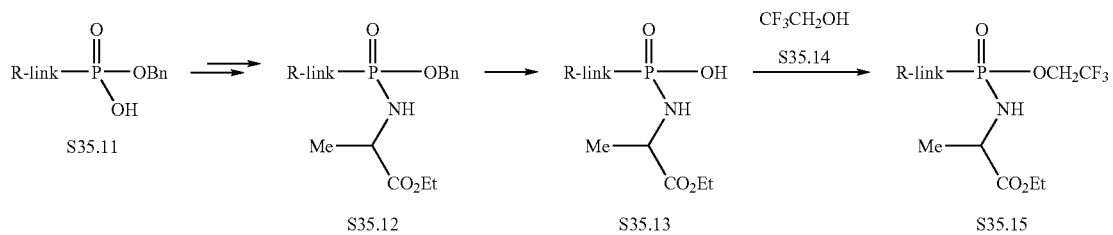
Scheme 35 Example 3
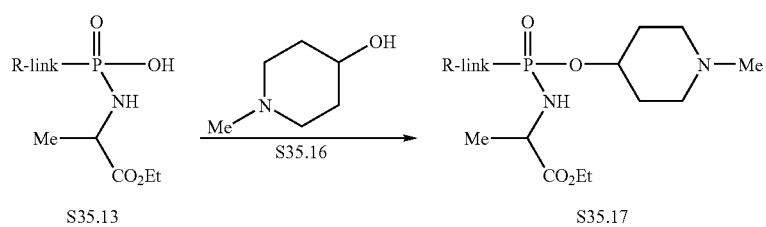
Scheme 35 Example 4
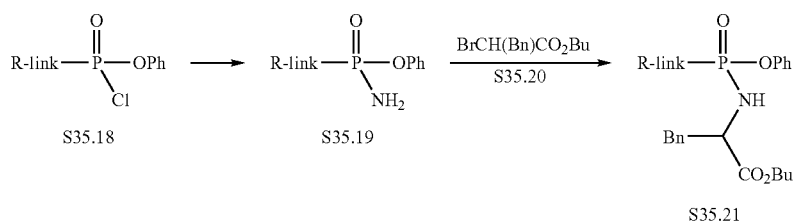

-continued
Scheme 35 Example 5

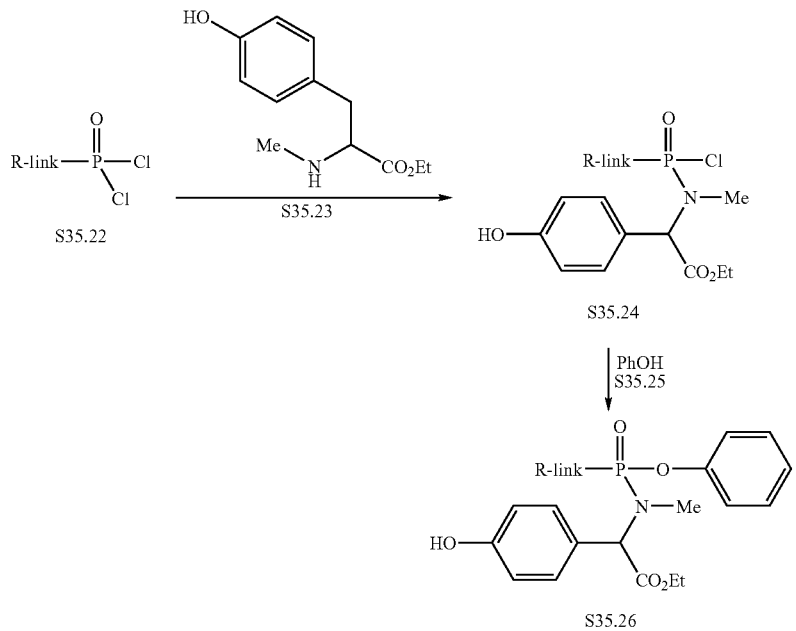

Scheme 36 illustrates methods for the preparation of carboalkoxy-substituted phosphonate diesters in which one of the ester groups incorporates a carboalkoxy substituent.

In one procedure, a phosphonate monoester S34.1, prepared as described above, is coupled, using one of the methods described above, with a hydroxyester S36.1, in which the groups $R^{4b}$ and $R^{5b}$ are as described in Scheme 34. For example, equimolar amounts of the reactants are coupled in the presence of a carbodiimide such as dicyclohexyl carbodiimide, as described in *Aust. J. Chem.*, 1963, 609, optionally in the presence of dimethylaminopyridine, as described in *Tet.*, 1999, 55, 12997. The reaction is conducted in an inert solvent at ambient temperature.

The procedure is illustrated in Scheme 36, Example 1. In this method, a monophenyl phosphonate S36.9 is coupled, in dichloromethane solution in the presence of dicyclohexyl carbodiimide, with ethyl 3-hydroxy-2-methylpropionate S36.10 to yield the phosphonate mixed diester S36.11.

Using this procedure, but employing, in place of ethyl 3-hydroxy-2-methylpropionate S36.10, different hydroxyesters S33.1, the corresponding products S33.2 are obtained.

The conversion of a phosphonate monoester S34.1 into a mixed diester S36.2 is also accomplished by means of a Mitsunobu coupling reaction with the hydroxyester S36.1, as described in *Org. Lett.*, 2001, 643. In this method, the reactants 34.1 and S36.1 are combined in a polar solvent such as tetrahydrofuran, in the presence of a triarylphosphine and a dialkyl azodicarboxylate, to give the mixed diester S36.2. The $R^1$ substituent is varied by cleavage, using the methods described previously, to afford the monoacid product S36.3. The product is then coupled, for example using methods described above, with the hydroxy compound $R^3OH$, to give the diester product S36.4.

The procedure is illustrated in Scheme 36, Example 2. In this method, a monoallyl phosphonate S36.12 is coupled in tetrahydrofuran solution, in the presence of triphenylphosphine and diethylazodicarboxylate, with ethyl lactate S36.13 to give the mixed diester S36.14. The product is reacted with tris(triphenylphosphine) rhodium chloride (Wilkinson catalyst) in acetonitrile, as described previously, to remove the allyl group and produce the monoacid product S36.15. The latter compound is then coupled, in pyridine solution at ambient temperature, in the presence of dicyclohexyl carbodiimide, with one molar equivalent of 3-hydroxypyridine S36.16 to yield the mixed diester S36.17.

Using the above procedures, but employing, in place of the ethyl lactate S36.13 or 3-hydroxypyridine, a different hydroxyester S36.1 and/or a different hydroxy compound $R^3OH$, the corresponding products S36.4 are obtained.

The mixed diesters S36.2 are also obtained from the monoesters S34.1 via the intermediacy of the activated monoesters S36.5. In this procedure, the monoester S34.1 is converted into the activated compound S36.5 by reaction with, for example, phosphorus pentachloride, as described in *J. Org. Chem.*, 2001, 66, 329, or with thionyl chloride or oxalyl chloride (Lv=Cl), or with triisopropylbenzenesulfonyl chloride in pyridine, as described in *Nucleosides and Nucleotides*, 2000, 19, 1885, or with carbonyl diimidazole, as described in *J. Med. Chem.*, 2002, 45, 1284. The resultant activated monoester is then reacted with the hydroxyester S36.1, as described above, to yield the mixed diester S36.2.

The procedure is illustrated in Scheme 36, Example 3. In this sequence, a monophenyl phosphonate S36.9 is reacted, in acetonitrile solution at 70° C., with ten equivalents of thionyl chloride, so as to produce the phosphoryl chloride S36.19. The product is then reacted with ethyl 4-carbamoyl-2-hydroxybutyrate S36.20 in dichlorometnane containing triethylamine, to give the mixed diester S36.21.

Using the above procedures, but employing, in place of ethyl 4-carbamoyl-2-hydroxybutyrate S36.20, different hydroxyesters S36.1, the corresponding products S36.2 are obtained.

The mixed phosphonate diesters are also obtained by an alternative route for incorporation of the $R^3O$ group into intermediates S36.3 in which the hydroxyester moiety is already incorporated. In this procedure, the monoacid intermediate S36.3 is converted into the activated derivative S36.6 in which Lv is a leaving group such as chloro, imidazole, and the like, as previously described. The activated intermediate is then reacted with the hydroxy compound $R^3OH$, in the presence of a base, to yield the mixed diester product S36.4.

The method is illustrated in Scheme 36, Example 4. In this sequence, the phosphonate monoacid S36.22 is reacted with trichloromethanesulfonyl chloride in tetrahydrofuran containing collidine, as described in *J. Med. Chem.*, 1995, 38, 4648, to produce the trichloromethanesulfonyloxy product S36.23. This compound is reacted with 3-(morpholinomethyl)phenol S36.24 in dichloromethane containing triethylamine, to yield the mixed diester product S36.25.

Using the above procedures, but employing, in place of with 3-(morpholinomethyl)phenol S36.24, different alcohols $R^3OH$, the corresponding products S36.4 are obtained.

The phosphonate esters S36.4 are also obtained by means of alkylation reactions performed on the monoesters S34.1. The reaction between the monoacid S34.1 and the haloester S36.7 is performed in a polar solvent in the presence of a base such as diisopropylethylamine, as described in *Anal. Chem.*, 1987, 59, 1056, or triethylamine, as described in *J. Med. Chem.*, 1995, 38, 1372, or in a non-polar solvent such as benzene, in the presence of 18-crown-6, as described in *Syn. Comm.*, 1995, 25, 3565.

The method is illustrated in Scheme. 36, Example 5. In this procedure, the monoacid S36.26 is reacted with ethyl 2-bromo-3-phenylpropionate S36.27 and diisopropylethylamine in dimethylformamide at 80° C. to afford the mixed diester product S36.28.

Using the above procedure, but employing, in place of ethyl 2-bromo-3-phenylpropionate S36.27, different haloesters S36.7, the corresponding products S36.4 are obtained.

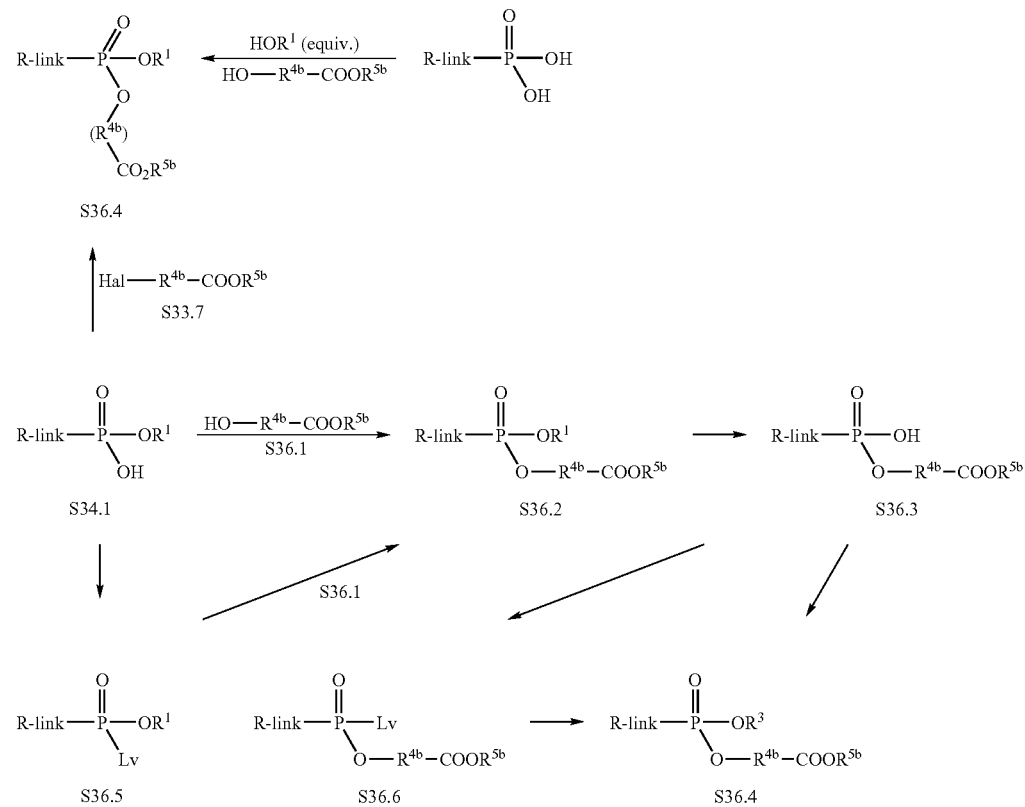

Scheme 36

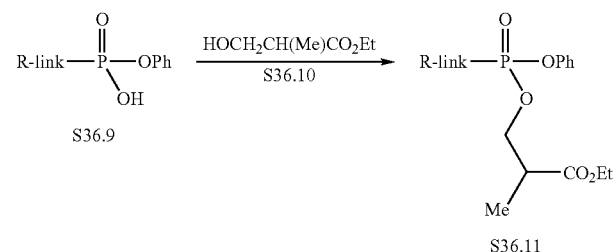

Scheme 36 Example 1

-continued
Scheme 36 Example 2
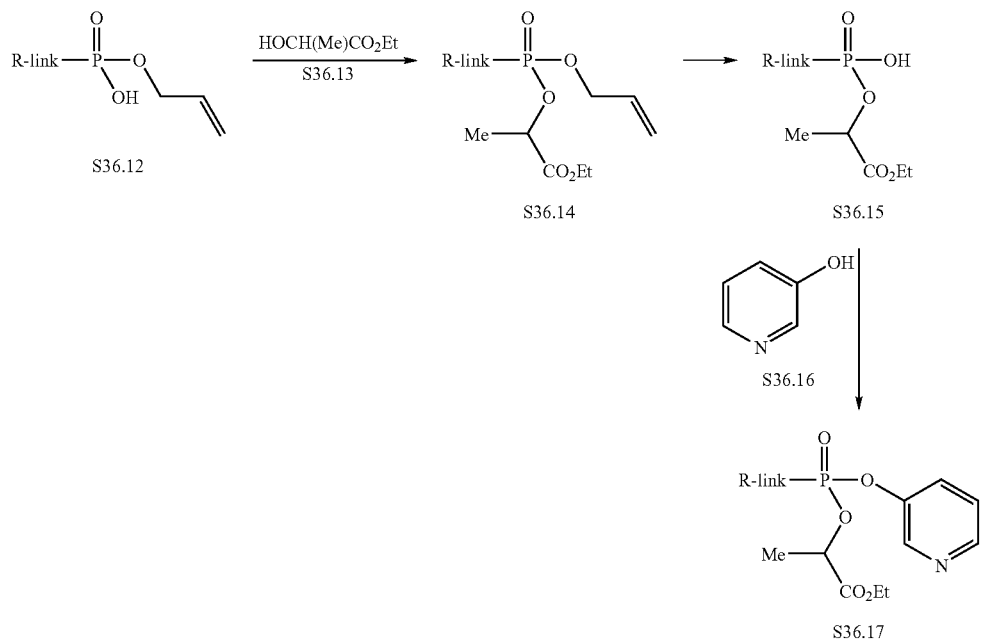
Scheme 36 Example 3
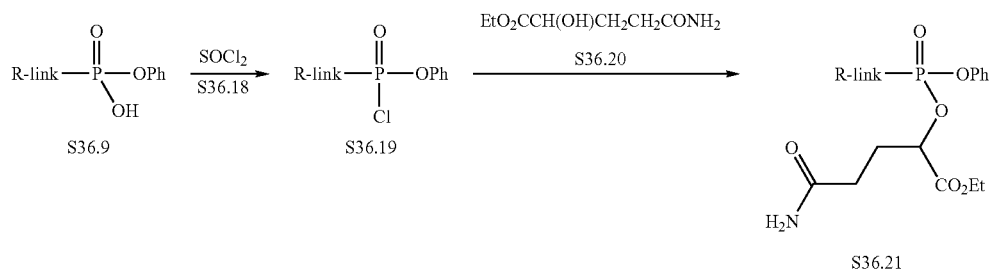
Scheme 36 Example 4
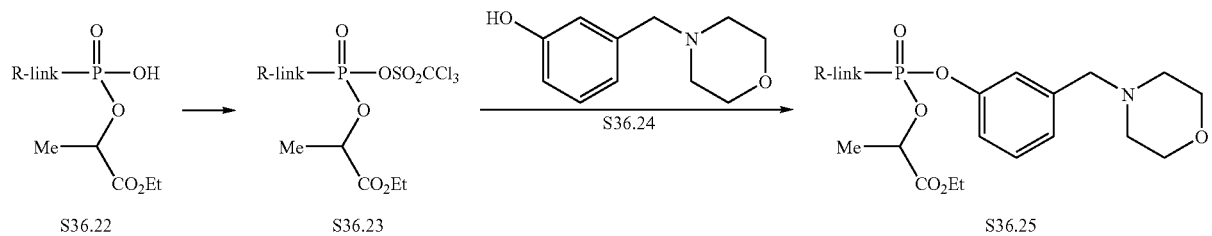
Scheme 36 Example 5
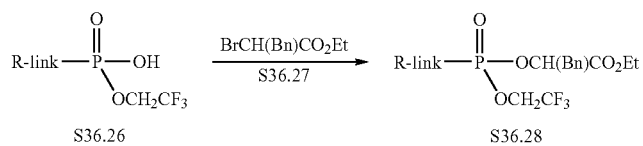

Scheme 37 illustrates methods for the preparation of phosphonate diesters in which both the ester substituents incorporate carboalkoxy groups.

The compounds are prepared directly or indirectly from the phosphonic acids S34.6. In one alternative, the phosphonic acid is coupled with the hydroxyester S37.2, using the conditions described previously in Schemes 34-36, such as coupling reactions using dicyclohexyl carbodiimide or similar reagents, or under the conditions of the Mitsunobu reaction, to afford the diester product S37.3 in which the ester substituents are identical.

This method is illustrated in Scheme 37, Example 1. In this procedure, the phosphonic acid S34.6 is reacted with three molar equivalents of butyl lactate S37.5 in the presence of Aldrithiol-2 and triphenyl phosphine in pyridine at ca. 70° C., to afford the diester S37.6.

Using the above procedure, but employing, in place of butyl lactate S37.5, different hydroxyesters S37.2, the corresponding products S37.3 are obtained.

Alternatively, the diesters S37.3 are obtained by alkylation of the phosphonic acid S34.6 with a haloester S37.1. The alkylation reaction is performed as described in Scheme 36 for the preparation of the esters S36.4.

This method is illustrated in Scheme 37, Example 2. In this procedure, the phosphonic acid S34.6 is reacted with excess ethyl 3-bromo-2-methylpropionate S37.7 and diisopropylethylamine in dimethylformamide at ca. 80° C., as described in *Anal. Chem.*, 1987, 59, 1056, to produce the diester S37.8.

Using the above procedure, but employing, in place of ethyl 3-bromo-2-methylpropionate S37.7, different haloesters S37.1, the corresponding products S37.3 are obtained.

The diesters S37.3 are also obtained by displacement reactions of activated derivatives S34.7 of the phosphonic acid with the hydroxyesters S37.2. The displacement reaction is performed in a polar solvent in the presence of a suitable base, as described in Scheme 36. The displacement reaction is performed in the presence of an excess of the hydroxyester, to afford the diester product S37.3 in which the ester substituents are identical, or sequentially with limited amounts of different hydroxyesters, to prepare diesters S37.3 in which the ester substituents are different.

The methods are illustrated in Scheme 37, Examples 3 and 4. As shown in Example 3, the phosphoryl dichloride S35.22 is reacted with three molar equivalents of ethyl 3-hydroxy-2-(hydroxymethyl)propionate S37.9 in tetrahydrofuran containing potassium carbonate, to obtain the diester product S37.10.

Using the above procedure, but employing, in place of ethyl 3-hydroxy-2-(hydroxymethyl)propionate S37.9, different hydroxyesters S37.2, the corresponding products S37.3 are obtained.

Scheme 37, Example 4 depicts the displacement reaction between equimolar amounts of the phosphoryl dichloride S35.22 and ethyl 2-methyl-3-hydroxypropionate S37.11, to yield the monoester product S37.12. The reaction is conducted in acetonitrile at 70° in the presence of diisopropylethylamine. The product S37.12 is then reacted, under the same conditions, with one molar equivalent of ethyl lactate S37.13, to give the diester product S37.14.

Using the above procedures, but employing, in place of ethyl 2-methyl-3-hydroxypropionate 537.11 and ethyl lactate S37.13, sequential reactions with different hydroxyesters S37.2, the corresponding products S37.3 are obtained.

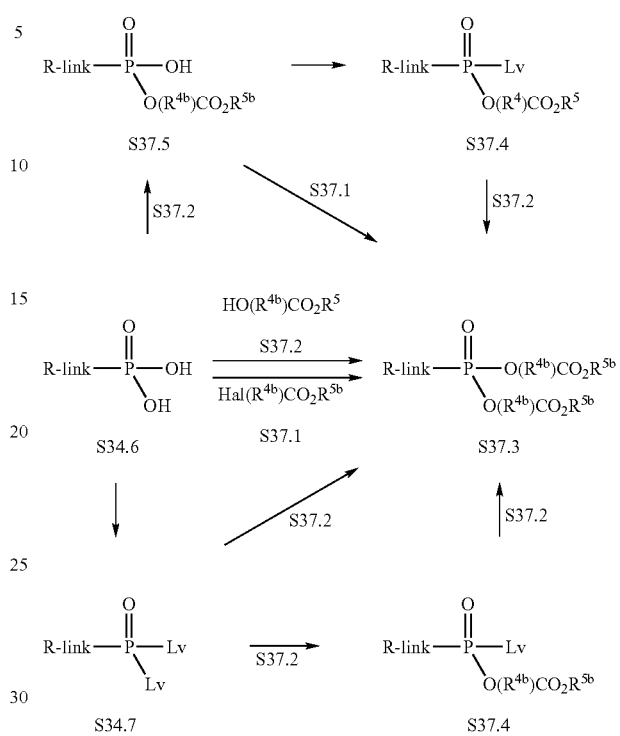

Scheme 37


Scheme 37 Example 1

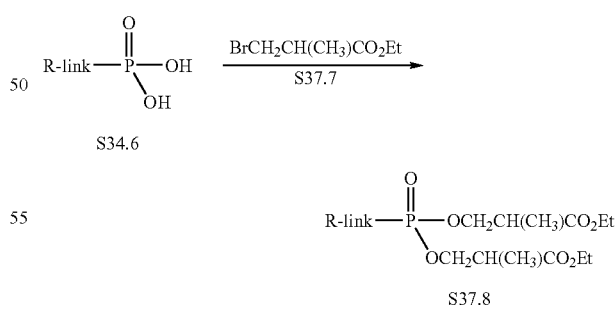

Scheme 37 Example 2

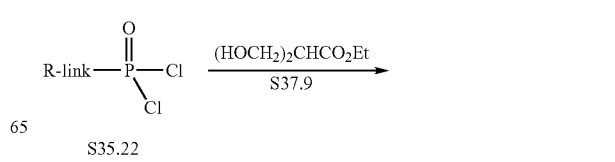

Scheme 37 Example 3

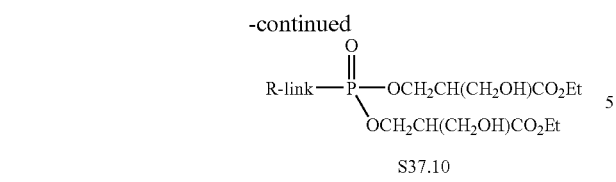

S37.10

Scheme 37 Example 4

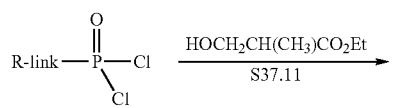

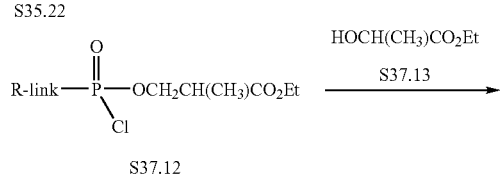

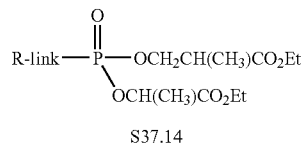

S37.14

2,2-Dimethyl-2-aminoethylphosphonic acid intermediates can be prepared by the route in Scheme 5. Condensation of 2-methyl-2-propanesulfinamide with acetone give sulfinyl imine S38.11 (*J. Org. Chem.* 1999, 64, 12). Addition of dimethyl methylphosphonate lithium to S38.11 afford S38.12. Acidic methanolysis of S38.12 provide amine S38.13. Protection of amine with Cbz group and removal of methyl groups yield phosphonic acid S38.14, which can be converted to desired S38.15 (Scheme 38a) using methods reported earlier on. An alternative synthesis of compound S38.14 is also shown in Scheme 38b. Commercially available 2-amino-2-methyl-1-propanol is converted to aziridines S38.16 according to literature methods (*J. Org. Chem.* 1992, 57, 5813; *Syn. Lett.* 1997, 8, 893). Aziridine opening with phosphite give S38.17 (*Tetrahedron Lett.* 1980, 21, 1623). Reprotection) of S38.17 affords S38.14.

Scheme 38a

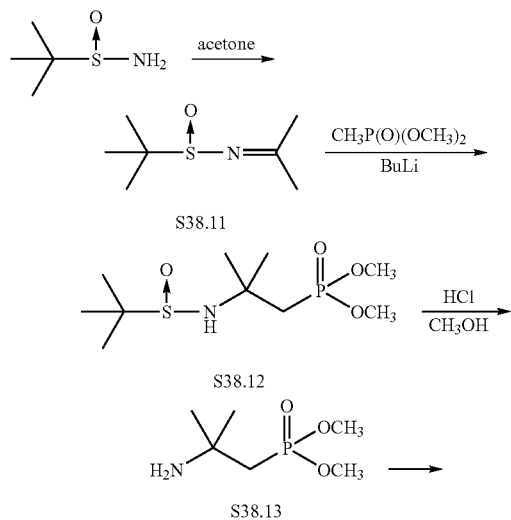

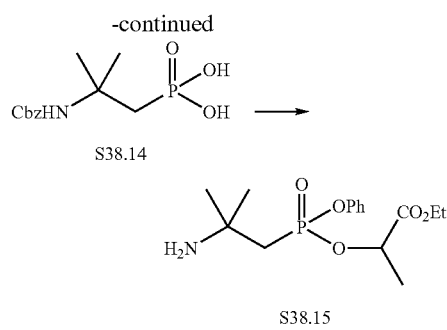

Scheme 38b

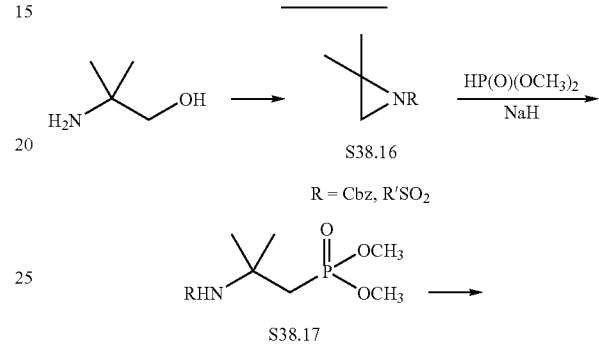

EXAMPLES

Preparation of P1 Intermediates

1. Synthesis and Resolution of diethyl (1S,2R)-1-amino-2-ethenylcyclopropane-1-phosphonate dibenzoyl-L-tartaric acid salt

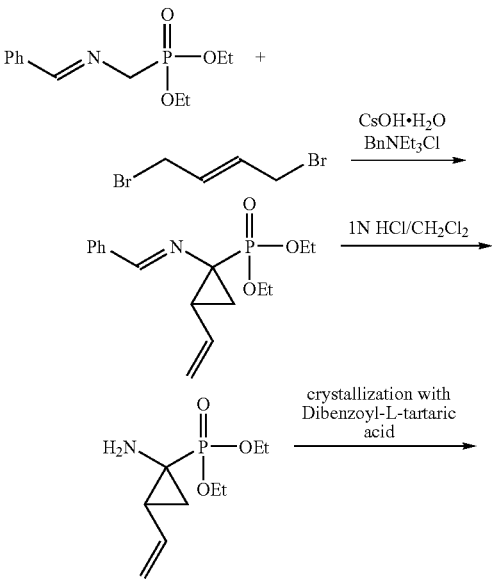

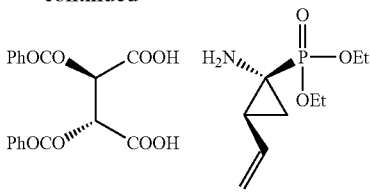

A solution of diethyl-(N-benzylideneaminomethyl)phosphonate (50 g, 196 mmole), trans-1,4-dibromo-2-butene (50 g, 235 mmole), and benzyltriethylammonium chloride (4.5 g, 19.6 mmole) in dichloromethane (1.0 L) was stirred at room temperature using a mechanical stirrer when cesium hydroxide monohydrate (82 g, 490 mmole) was added. The resulting mixture was stirred for 18 hr after which another portion of cesium hydroxide monohydrate (82 g, 490 mmole) was added. The resulting mixture was stirred for 24 hr. The salts were then filtered off through celite 521 pad and the filtrate was allowed to stir with 1 N aq. HCl at room temperature for 3 h. The resulting mixture was filtered through celite 521 pad and the two phases of the filtrate were separated. The organic fraction was extracted with 1 N aq. HCl (250 mL×1). The aqueous fractions were washed with dichloromethane (250 mL×1) and the combined aq. fractions were stirred with ethyl acetate (500 mL) while 84 g (1 mol) of NaHCO$_3$ was added cautiously followed by excess NaCl until saturated. After the resulting mixture was filtered through celite 521 pad to remove excess NaCl and some black tar, two layers were separated and the aqueous fraction was extracted further with ethyl acetate (250 mL×2). The organic extracts were washed with saturated NaCl solution (250 mL×1), combined, dried (MgSO$_4$), and concentrated to obtain ~16.5-17 g of the crude amine.

The crude amine was partially purified by column chromatography using 165-170 g of silica gel by eluting ethyl acetate (100%, ~500 mL) followed by 5% methanol in ethyl acetate (~1200 mL). The product containing fractions were pooled and concentrated, which resulted 11.5-12 g of partially purified amine.

To this amine was added a solution of 18.8-19.6 g (1 mole eq.) of dibenzoyl-L-tartaric acid in 151.5-158 mL of acetonitrile (5 times of the amount of the salt). The mixture was heated until it became a solution and cooled slowly at room temperature to obtain solids. After: overnight, the solids were collected by filtration and washed with acetonitrile. The solids were recrystallized from the same amount of acetonitrile again at room temperature to afford 10.5-11.5 g of optically pure salt: $^1$H NMR (300 MHz, CD$_3$OD) δ 8.14 (br, 2H), 8.11 (d, J=1.2 Hz, 2H), 7.64 (tt, J=7.5 and 1.2 Hz, 2H), 7.51 (br t, J=7.5 Hz, 4H), 5.94 (s, 2H), 5.82 (dt, J=17.1 and 9.9 Hz, 1H), 5.32 (dd, J=17.1 and 1.2 Hz, 1H), 5.13 (dd, J=10.5 and 1.2 Hz, 1H), 4.11-4.26 (m, 4H), 2.11 (m, 1H), 1.33-1.47 (m, 2H), 1.37 (dt, J=10.2 and 7.2 Hz, 6H); $^{31}$P NMR (75 MHz, CD$_3$OD) δ 22.55.

Analytical: The optical purity of the amine can be determined by $^{31}$P NMR of Mosher's amide in DMSO-d$_6$. The recrystallized material (25 mg) was dissolved in a mixture of saturated aq. NaHCO$_3$ (5 mL) and saturated aq. NaCl (5 mL), and the free amine was extracted by dichloromethane (10 mL×2). The extracts were washed once with a mixture of saturated aq. NaHCO$_3$ (5 mL) and saturated aq. NaCl (5 mL), dried (MgSO$_4$), and concentrated. To a solution of the residue and N,N-dimethylaminopyridine (~3.5 mg) in pyridine (0.1 mL) was added (R)-(−)-α-methoxy-α-(trifluoromethyl)phenylacetyl chloride at room temperature. After stirring for 1.5 h, the pyridine was evaporated and the residue was dissolved in 0.5 N HCl (10 mL) and ethyl acetate (10 mL). After the separation of two fractions, the organic fraction was washed with water (10 mL×1) and saturated aq. NaHCO$_3$ (10 mL×1), dried (MgSO$_4$), and concentrated. On the $^{31}$P NMR of the residue in DMSO-d$_6$, the desired amide appears at 23.00 ppm whereas the undesired amide comes at 22.79 ppm.

2. Preparation of P1 Phosphonic Acid Intermediates

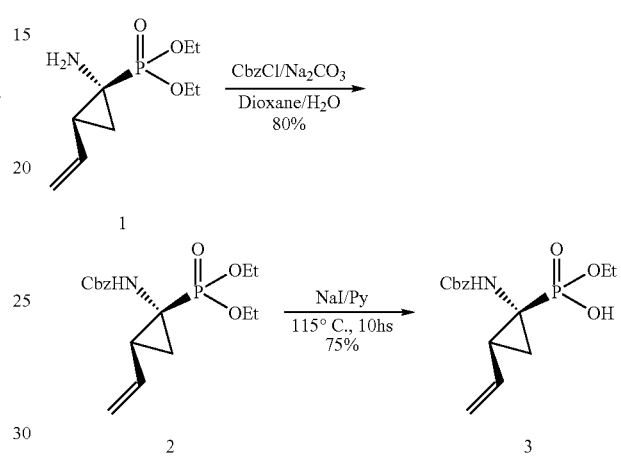

Amine 1 (9.0 g, 41.1 mmol) was dissolved in Dioxane (100 mL). A solution of Na$_2$CO$_3$ (13.1 g, 123.3 mmol) in H$_2$O (50 mL) was added to the reaction mixture and stirred for 5 minutes at room temperature. After Benzyl chloroformate (8.4 g, 49.3 mmol) was added, the reaction solution was stirred at room temperature for overnight. The organic phase was diluted with EtOAc and extracted with H$_2$O and brine. The organic phase was dried over MgSO$_4$. Concentration of the filtrate from vacuum filtration removal of the MgSO$_4$ yielded an oil from which 2 was isolated by column chromatography (SiO$_2$, 20% EtOAc in hexane) as a clear oil (11.6 g, 80%).

$^1$H NMR (300 MHz, CDCl$_3$) δ 7.33 (s, 5H), 6.05 (dt, J=9.9, 17.1 Hz, 1H), 5.65 (d, J=23.7 Hz, 1H), 5.31 (d, J=17.1 Hz, 1H), 5.06 (m, 3H), 4.06 (m, 4H), 2.09 (m, 1H), 1.73 (m, 2H), 1.15 (dt, J=8.1, 26.4 Hz, 6H) $^{31}$P NMR (121.4 MHz, CDCl$_3$) δ 23.7

Intermediate 2 (11.6 g, 32.9 mmol) and NaI (24.5 g, 164.3 mmol) were dissolved in pyridine (110 mL). The reaction solution was heated to 115° C. for 10 hours. After cooling back to room temperature, the reaction solution was concentrated to remove pyridine. H$_2$O (50 mL) was added to the crude. The aqueous was washed by diethyl ether (2×100 mL). Then the aqueous phase was adjusted to pH=2 by adding 1 M HCl$_{(aq.)}$. Product 3 (7.5 g, 23.0 mmol) was isolated by extracting with dichloromethane and used for next step without further purification.

$^1$H NMR (300 MHz, CDCl$_3$) δ 8.63 (br, 1H), 7.33 (s, 5H), 5.95 (dt, J=9.9, 17.1 Hz, 1H), 5.65 (d, J=23.7 Hz, 1H), 5.31 (d, J=17.1 Hz, 1H), 5.06 (m, 3H), 4.06 (m, 2H), 2.09 (m, 1H), 1.73 (m, 2H), 1.23 (dt, J=8.1, 26.4 Hz, 3H) $^{31}$P NMR (121.4 MHz, CDCl$_3$) δ 24.6

LC/MS=326 (M$^+$+1), 348 (M$^+$+Na)

3. Preparation of P1 Phosphinic Acid Intermediates

A. Preparation of (1-benzyloxycarbonylamino-2-vinyl-cyclopropyl)-methyl-phosphinic acid ethyl ester

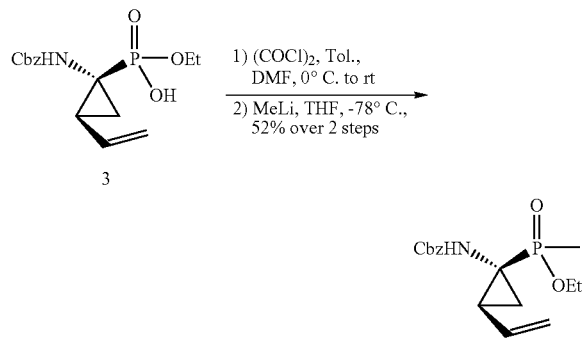

Phosphonic acid intermediate (1-Benzyloxycarbonylamino-2-vinyl-cyclopropyl)-phosphonic acid monoethyl ester (415 mg, 1.28 mmol) was dissolved in toluene (8 mL). This solution was cooled to 0° C. and (COCl)$_2$ (222 µL, 2.56 mmol) was added in a drop-wise fashion. DMF (44 µL, 0.56 mmol) was then added. Reaction was run for 2 h at 0° C. and determined to be complete by $^{31}$P NMR.

$^{31}$P NMR (121.4 MHz, CDCl$_3$) δ=39.0, 38.5, 37.4, 36.5, 17.0, 16.2, 16.0, 15.4.

The reaction was concentrated to orange-yellow oil and then placed under high vacuum for 1 h. The resulting residue was dissolved in THF (6.4 mL) and this solution was cooled to −78° C. A 1.4M solution of Methyllithium in diethyl ether (1.37 mL, 1.92 mmol) was added drop-wise. After 40 min more Methyllithium (456 µL, 0.64 mmol) was added drop-wise. After 10 min the reaction was quenched at −78° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$. Concentration of the filtrate from vacuum filtration removal of the MgSO$_4$ yielded an orange oil from which product was isolated by column chromatography (SiO$_2$, 100% EtOAc) as a clear oil (214 mg, 52% over 2 steps).

$^1$H NMR (300 MHz, CDCl$_3$) δ 7.33 (s, 5H), 6.09 (dt, J=9.9, 17.1 Hz, 1H), 5.65 (d, J=23.7 Hz, 1H), 5.31 (d, J=17.1 Hz, 1H), 5.06 (m, 3H), 4.06 (m, 2H), 2.09 (m, 1H), 1.73 (m, 2H), 1.40 (d, 3H), 1.13 (dt, J=8.1, 26.4 Hz, 3H) $^{31}$P NMR (121.4 MHz, CDCl$_3$) δ 53.7, 50.8 LC/MS=324 (M$^+$+1), 346 (M$^+$+Na)

B. Preparation of (1-benzyloxycarbonylamino-2-vinyl-cyclopropyl)-sec-butyl-phosphinic acid ethyl ester

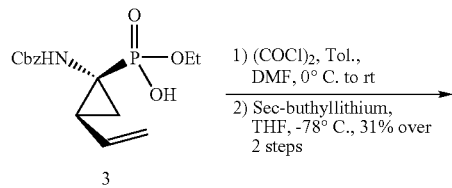

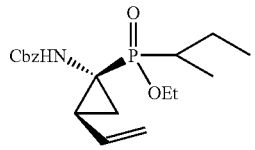

Phosphonic acid intermediate 3 (415 mg, 1.28 mmol) was dissolved in toluene (8 mL). This solution was cooled to 0° C. and (COCl)$_2$ (222 µL, 2.56 mmol) was added in a drop-wise fashion. DMF (44 µL, 0.56 mmol) was then added. Reaction was run for 2 h at 0° C. and determined to be complete by $^{31}$P NMR. $^{31}$P NMR (121.4 MHz, CDCl$_3$) δ=39.0, 38.5, 37.4, 36.5, 17.0, 16.2, 16.0, 15.4.

The reaction was concentrated to orange-yellow oil and then placed under high vacuum for 1 h. The resulting residue was dissolved in THF (6.4 mL) and this solution was cooled to −78° C. A 1.4M solution of Sec-Butyllithium in cyclohexane (1.37 mL, 1.92 mmol) was added drop-wise. After 40 min more Sec-Butyllithium in cyclohexane (456 µL, 0.64 mmol) was added drop-wise. After 10 min the reaction was quenched at −78° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$. Concentration of the filtrate from vacuum filtration removal of the MgSO$_4$ yielded an orange oil from which product was isolated by column chromatography (SiO$_2$, 60% EtOAc in Hexane) as a clear oil (146 mg, 31% over 2 steps).

$^1$H NMR (300 MHz, CDCl$_3$) δ 7.33 (s, 5H), 6.07 (dt, J=9.9, 17.1 Hz, 1H), 5.55 (d, J=23.7 Hz, 1H), 5.31 (d, J=17.1 Hz, 1H), 5.06 (m, 3H), 4.06 (m, 2H), 2.09 (m, 1H), 1.65-1.83 (m, 3H), 1.58 (m, 1H) 1.41 (m, 1H), 1.03-1.32 (m, 6H), 0.97 (dt, J=8.1, 26.4 Hz, 3H)

$^{31}$P NMR (121.4 MHz, CDCl$_3$) δ 54.9, 54.3, 50.8, 50.0 LC/MS=366 (M$^+$+1), 388 (M$^+$+Na)

C. Preparation of (1-benzyloxycarbonylamino-2-vinyl-cyclopropyl)-isopropyl-phosphinic acid ethyl ester

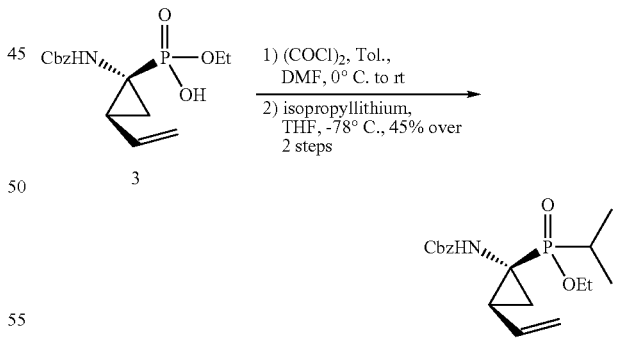

Phosphonic acid intermediate 3 (415 mg, 1.28 mmol) was dissolved in toluene (8 mL). This solution was cooled to 0° C. and (COCl)$_2$ (222 µL, 2.56 mmol) was added in a drop-wise fashion. DMF (44 µL, 0.56 mmol) was then added. Reaction was run for 2 h at 0° C. and determined to be complete by $^{31}$P NMR. $^{31}$P NMR (121.4 MHz, CDCl$_3$) δ 39.0, 38.5, 37.4, 36.5, 17.0, 16.2, 16.0, 15.4.

The reaction was concentrated to orange-yellow oil and then placed under high vacuum for 1 h. The resulting residue was dissolved in THF (6.4 mL) and this solution was cooled to −78° C. A 0.7M solution of isopropyllithium in pentane (2.74 mL, 1.92 mmol) was added drop-wise. After 40 min more isopropyllithium (912 ⊕L, 0.64 mmol) was added drop-wise. After 10 min the reaction was quenched at −78° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$. Concentration of the filtrate from vacuum filtration removal of the MgSO$_4$ yielded an orange oil from which product was isolated by column chromatography (SiO$_2$, 100% EtOAc) as a clear oil (200 mg, 45% over 2 steps).

$^1$H NMR (300 MHz, CD$_3$CN) δ=7.38 (s, 5H), 6.69 (m, 1H), 6.12 (m, 1H), 5.35 (m, 1H), 5.06 (m, 4H), 4.06 (m, 2H), 2.09 (m, 1H), 1.55 (m, 1H) 1.41 (m, 1H), 1.02-1.35 (m, 9H)

$^{31}$P NMR (121.4 MHz, CD$_3$CN) δ 56.0, 53.8

LC/MS=352 (M$^+$+1), 374 (M$^+$+Na)

D. Preparation of (1-benzyloxycarbonylamino-2-vinyl-cyclopropyl)-vinyl-phosphinic acid ethyl ester

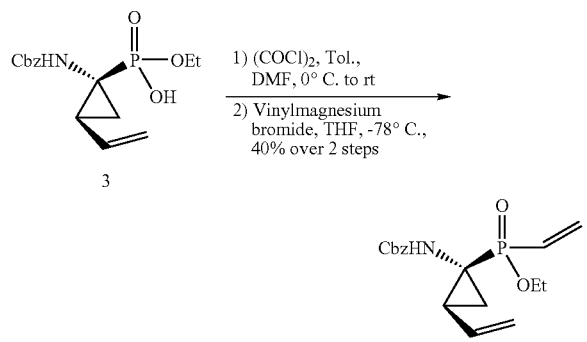

Phosphonic acid intermediate 3 (415 mg, 1.28 mmol) was dissolved in toluene (8 mL). This solution was cooled to 0° C. and (COCl)$_2$ (222 μL, 2.56 mmol) was added in a drop-wise fashion. DMF (44 μL, 0.56 mmol) was then added. Reaction was run for 2 h at 0° C. and determined to be complete by $^{31}$P NMR. $^{31}$P NMR (121.4 MHz, CDCl$_3$) δ 39.0, 38.5, 37.4, 36.5, 17.0, 16.2, 16.0, 15.4.

The reaction was concentrated to orange-yellow oil and then placed under high vacuum for 1 h. The resulting residue was dissolved in THF (6.4 mL) and this solution was cooled to −78° C. A 1.0M solution of Vinylmagnesium bromide in tetrahydrofuran (2.6 mL, 2.6 mmol) was added drop-wise. After 40 min more Vinylmagnesium bromide (2.6 mL, 2.6 mmol) was added drop-wise. After 10 min the reaction was quenched at −78° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$. Concentration of the filtrate from vacuum filtration removal of the MgSO$_4$ yielded an orange oil from which product was isolated by column chromatography (SiO$_2$, 100% EtOAc) as a clear oil (214 mg, 40% over 2 steps).

$^1$H NMR (300 MHz, CDCl$_3$) δ 7.33 (s, 5H), 6.09-6.15 (m, 2H), 5.55 (m, 1H), 5.31 (m, 1H), 5.05 (m, 4H), 4.06 (m, 2H), 2.09 (m, 1H), 1.73 (m, 1H), 1.60 (m, 1H), 1.43 (m, 1H), 1.13 (dt, J=8.1, 26.4 Hz, 3H) $^{31}$P NMR (121.4 MHz, CDCl$_3$) δ 36.5, 34.6

LC/MS=336 (M$^+$+1), 358 (M$^+$+Na)

E. Preparation of (1-benzyloxycarbonylamino-2-vinyl-cyclopropyl)-ethyl phosphinic acid ethyl ester

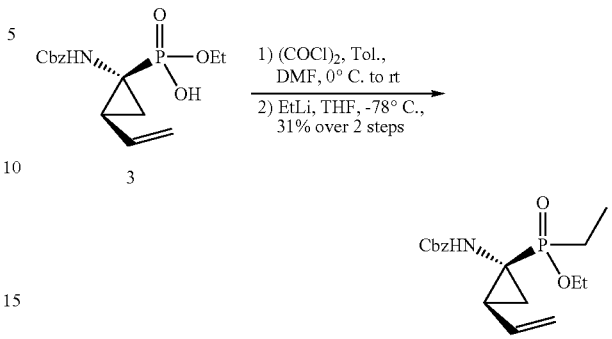

Phosphonic acid intermediate 3 (208 mg, 0.64 mmol) was dissolved in toluene (8 mL). This solution was cooled to 0° C. and (COCl)$_2$ (111 μL/1.28 mmol) was added in a drop-wise fashion. DMF (22 μL, 0.28 mmol) was then added. The reaction was run for 2 h at 0° C. and determined to be complete by $^{31}$P NMR. $^{31}$P NMR (121.4 MHz, CDCl$_3$) δ=39.0, 38.5, 37.4, 36.5, 17.0; 16.2, 16.0, 15.4.

The reaction was concentrated to orange-yellow oil and then placed under high vacuum for 1 h. The resulting residue was dissolved in THF (6.4 mL) and this solution was cooled to −78° C. A 1.7M solution of EtLi in dibutyl ether (566 ⊕L, 0.96 mmol) was added drop-wise. After 40 min more EtLi (189 ⊕L, 0.32 mmol) was added drop-wise. After 10 min the reaction was quenched at −78° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$. Concentration of the filtrate from vacuum filtration removal of the MgSO$_4$ yielded an orange oil from which the desired product was isolated by column chromatography (SiO$_2$, 100% EtOAc) as a clear oil (67 mg, 31% over 2 steps).

$^1$H NMR (300 MHz, CDCl$_3$) δ 7.33 (s, 5H), 6.09 (dt, J=9.9, 17.1 Hz, 1H Diastereomer 1), 5.94 (dt, J=9.9, 17.1 Hz, 1H Diastereomer 2), 5.65 (d, J=23.7 Hz, 1H), 5.31 (d, J=17.1 Hz, 1H), 5.06 (m, 3H), 4.06 (m, 2H), 2.09 (m, 1H), 1.73 (m, 2H), 1.50 (m, 2H), 1.25 (m, 4H), 1.13 (dt, J=8.1, 26.4 Hz, 3H)

$^{31}$P NMR (121.4 MHz, CDCl$_3$) δ 54.0, 53.6, 51.3, 50.8

LC/MS=338 (M$^+$+1), 360 (M$^+$+Na)

F. Preparation of (1-Benzyloxycarbonylamino-2-vinyl-cyclopropyl)-butyl-phosphinic acid ethyl ester

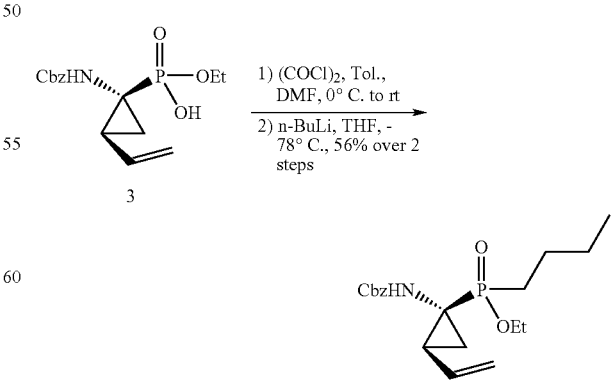

Phosphonic acid intermediate 3 (386 mg, 1.19 mmol) was dissolved in toluene (14.9 mL). This solution was cooled to 0° C. and (COCl)$_2$ (155 μL, 1.78 mmol) was added in a dropwise fashion. DMF (20 μL, 0.26 mmol) was then added. The reaction was run for 2 h at 0° C. and determined to be complete by $^{31}$P NMR.

$^{31}$P NMR (121.4 MHz, CDCl$_3$) δ 39.0, 38.5, 37.4, 36.6, 17.0, 16.2, 16.1, 15.4.

The reaction was concentrated to orange-yellow oil and then placed under high vacuum for 1 h. The resulting residue was dissolved in THF (11.9 mL) and this solution was cooled to −78° C. A 2M solution of n-BuLi in pentane (595 μL, 1.19 mmol) was added drop-wise. After 40 min more n-BuLi (520 μL, 1.04 mmol) was added drop-wise. After 10 min the reaction was quenched at −78° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$. Concentration of the filtrate from vacuum filtration removal of the MgSO$_4$ yielded an orange oil from which product was isolated by column chromatography (SiO$_2$, 7/3 EtOAc:hexane) as a clear oil (243 mg, 56% over 2 steps).

$^1$H NMR (300 MHz, CDCl$_3$) δ 7.35 (s, 5H), 6.12 (dt, J=9.9, 16.8 Hz, 1H Diastereomer 1), 5.96 (dt, J=10.2, 16.8 Hz, 1H Diastereomer 2), 5.33 (m, 2H), 5.09 (m, 3H), 4.11 (m, 2H), 2.01 (brd, J=6.6 Hz, 1H), 1.50-1.90 (m, 6H), 1.37 (brd, J=5.1 Hz, 2H), 1.26 (quart., J=6.2 Hz, 3H), 0.9 (m, 3H)

$^{31}$P NMR (121.4 MHz, CDCl$_3$) δ 52.8, 52.4, 50.2, 49.7

LC/MS=366 (M$^+$+1), 388 (M$^+$+Na)

G. Preparation of (1-benzyloxycarbonylamino-2-vinyl-cyclopropyl)-phenyl-phosphinic acid ethyl ester

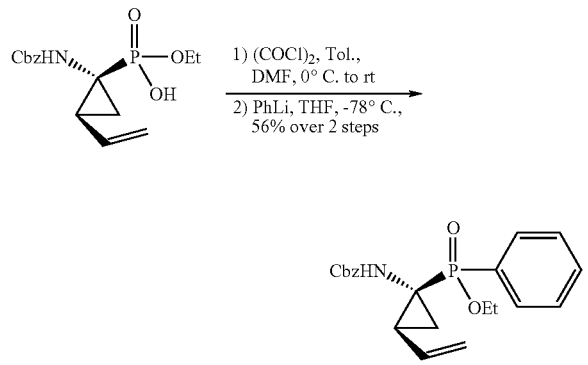

Phosphonic acid intermediate 3 (451 mg, 1.39 mmol) was dissolved in toluene (17.4 mL). This solution was cooled to 0° C. and (COCl)$_2$ (1.21 mL, 13.87 mmol) was added in a drop-wise fashion. DMF (24 μL, 0.306 mmol) was then added. The reaction was run for 2 h at 0° C. and then 18 h at rt. The reaction was determined to be complete by $^{31}$P NMR.

$^{31}$P NMR (121.4 MHz, CDCl$_3$) δ 39.3, 38.8, 37.6, 36.8, 17.2, 16.4, 16.3, 15.6.

The reaction was concentrated to an orange-yellow oil and then placed under high vacuum for 1 h. The resulting residue was dissolved in THF (13.9 mL) and this solution was cooled to −78° C. A 1.8M solution of PhLi in Et$_2$O (1.2 mL, 2.17 mmol) was added drop-wise. After 30 min the reaction was quenched at −78° C. by the addition of sat. NH$_4$Cl$_{(aq.)}$. The organic phase was diluted with EtOAc and extracted with sat. NH$_4$Cl$_{(aq.)}$ and brine. The organic phase was dried over MgSO$_4$ which was subsequently removed by vacuum filtration. Concentration of the filtrate yielded an orange oil from which the desired product was isolated by column chromatography (SiO$_2$, 7/3 EtOAc:hexane) as a clear oil (243 mg, 56% over 2 steps) in 73% purity by $^{31}$P NMR.

$^1$H NMR (300 MHz, CDCl$_3$) δ=7.75 (m, 2H), 7.56 (m, 1H), 7.20-7.44 (m, 7H), 6.18 (m, 1H), 5.39 (d, J=17.1 Hz, 1H), 4.80-5.30 (m, 4H), 4.0-4.3 (m, 2H), 1.91 (m, 1H), 1.69 (m, 1H), 1.2-1.4 (m, 4H)

$^{31}$P NMR (121.4 MHz, CDCl$_3$) δ 37.8, 37.4, 36.2, 36.0, 35.0, 34.7, 33.4, 33.3

LC/MS=386 (M$^+$+1), 408 (M$^+$+Na)

4. Preparation of Dipeptide Intermediates

A. Synthesis of Phenyl Quinoline Dipeptide Intermediate

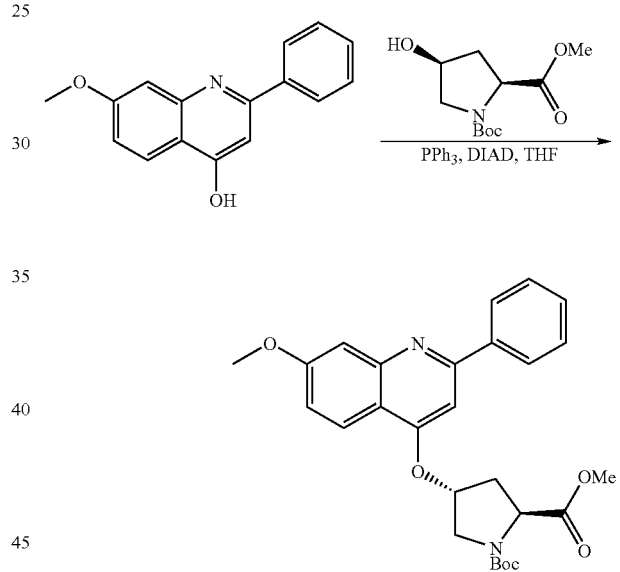

Step 1. Quinoline (7.6 g, 30.1 mmol), N-t-Boc-cis-4-Hydroxy-L-Proline methyl ester (8.9 g, 36.3 mm) and triphenylphosphine (17.4 g, 66.3 mmol) were dissolved in THF (250 mL). After cooling the reaction solution to 0° C., DIAD (13.4 g, 66.3 mmol) was added in 15 minutes. The reaction solution was stirred at room temperature for 12 hours and was diluted with EtOAc (700 mL) and washed by NaHCO$_3$ $_{(aq.)}$, H$_2$O and brine. The organic phase was dried over MgSO$_4$. After concentration, the crude was crystallized to remove most of the triphenylphosphine oxide by using EtOAc (100 mL) and hexane (50 mL) and desired product was isolated by column chromatography (SiO$_2$, 70% EtOAc in hexane) as an oil (11.9 g, 85%).

$^1$H NMR (300 MHz, CDCl$_3$) δ 8.03 (m, 2H), 7.50 (m, 5H), 7.18 (m, 1H), 6.97 (m, 1H), 5.15 (m, 1H), 4.99 (m, 2H), 4.06 (s, 3H), 3.99 (m, 1H), 3.75 (s, 3H), 2.79 (dd, J=8.7, 14.3 Hz, 1H), 2.45 (ddd, J=3.5, 10.7, 13.8 Hz, 1H), 1.15 (s, 9H)

LC/MS=479 (M$^+$+1), 501 (M$^+$+Na)

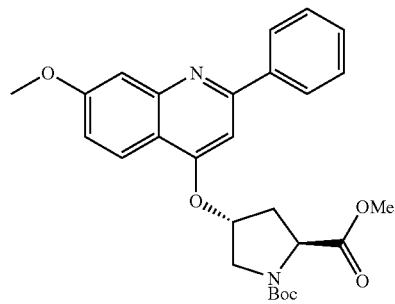
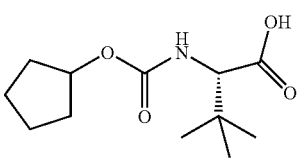
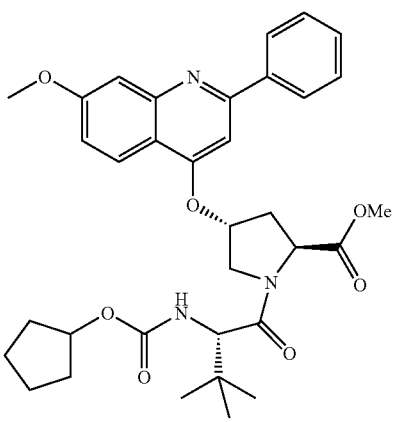

Step 2. Product from the above reaction (9.6 g, 20.8 mmol) was dissolved in dichloromethane (20 mL). 4.0 M HCl in Dioxane (50 mL) was added to the reaction solution slowly and the reaction solution was allowed to stir at room temperature for 5 hours. After concentration under high vacuum for 30 minutes, the crude was dissolved in DMF (70 mL). 3 (6.1 g, 25.0 mmol), HATU (11.9 g, 31.2 mmol) and N-methylmorpholine (10.5 g, 104.0 mmol) were added to the reaction solution. The reaction solution was stirred at room temperature for overnight and was diluted with EtOAc (500 mL) and washed by $NH_4Cl_{(aq.)}$, $NaHCO_{3\ (aq.)}$ and brine. The organic phase was dried over $MgSO_4$. After concentration, desired product (10.0 g, 80%) was isolated by column chromatography ($SiO_2$, 90% EtOAc in hexane) as a solid.

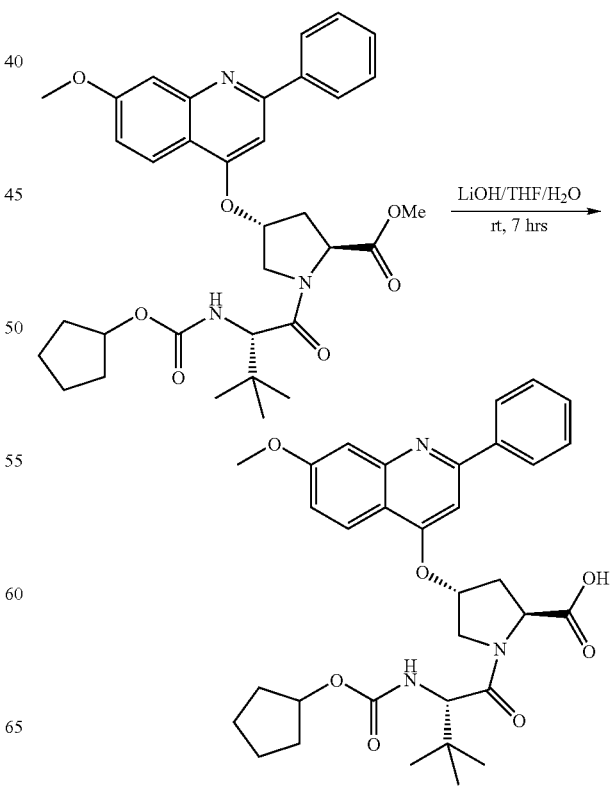

$^1$H NMR (300 MHz, $CD_3OD$) δ 8.33 (d, J=9.6 Hz, 1H), 8.09 (m, 2H), 7.74 (m, 3H), 7.65 (m 1H), 7.52 (m 1H), 7.24 (dd, J=2.1, 9.6 Hz, 1H), 5.91 (m, 1H), 5.04 (m, 1H), 4.81 (d, J=9.0 Hz, 1H), 4.76 (d, J=9.0 Hz, 1H), 4.46 (m, 1H), 4.23 (m, 1H), 4.06 (s, 3H), 3.99 (m, 1H), 3.75 (s, 3H), 2.99 (dd, J=9.0, 14.7 Hz, 1H), 2.53 (ddd, J=3.3, 10.5, 13.8 Hz, 1H), 1.42-1.78 (m, 8H), 1.05 (s, 9H)

LC/MS=604 ($M^+$+1), 626($M^+$+Na)

Step 3. The methyl ester (9.2 g, 15.3 mmol) was dissolved in THF (30 mL), MeOH (10 mL) and H$_2$O (10 mL). LiOH (1.8 g, 76.5 mmol) was added to the reaction solution and the reaction solution was allowed to stir at room temperature for 7 hours. After EtOAc (150 mL) was added to dilute the reaction solution, the aqueous phase was adjusted to pH=2 by adding 1 M HCl$_{(aq.)}$. Dipeptide acid (8.6 g, 95%) was isolated by extracting with EtOAc (2×100 mL) and used for next step without further purification.

$^1$H NMR (300 MHz, CD$_3$OD) δ 8.38 (d, J=9.6 Hz, 1H), 8.11 (m, 2H), 7.76 (m, 3H), 7.65 (m 1H), 7.55 (m 1H), 7.24 (dd, J=2.1, 9.6 Hz, 1H), 5.89 (m, 1H), 5.04 (m, 1H), 4.81 (d, j=8.7 Hz, 1H), 4.76 (d, j=8.7 Hz, 1H), 4.46 (m, 1H), 4.23 (m, 1H), 4.06 (s, 3H), 3.99 (m, 1H), 2.99 (dd, J=9.0, 14.7 Hz, 1H), 2.53 (ddd, J=3.3, 10.5, 13.8 Hz, 1H), 1.42-1.78 (m, 8H), 1.05 (s, 9H)

LC/MS=590 (M$^+$+1), 612 (M$^+$+Na)

B. Synthesis of 1-(2-cyclopentyloxycarbonylamino-3,3-dimethyl-butyryl)-4-[2-(2-isopropylamino-thiazol-4-yl)-7-methoxy-quinolin-4-yloxy]-pyrrolidine-2-carboxylic acid

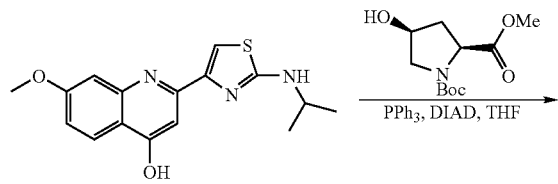

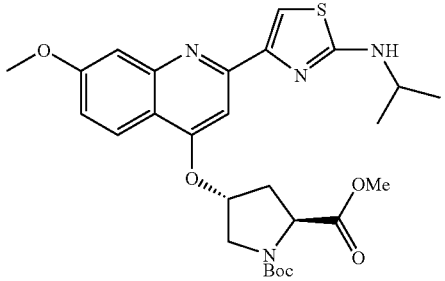

Step 1. To a solution of hydroxythiazole quinoline (20.0 g, 63.5 mmol) in THF (400 mL), was added cis-Boc-hydroxyproline methyl ester (18.7 g, 76.2 mmol), and triphenyl phosphine (36.6 g, 139.7 mmol). The solution was cooled to 0° C. and DIAD (27 mL, 139.7 mmol) was added slowly. The solution was allowed to warm to room temperature over a period of 1 h and stirred overnight. The solvent was removed under reduced pressure and the crude reaction mixture was dissolved in ethyl acetate and extracted with water followed by brine. The organics were dried over MgSO$_4$, filtered and the solvent was removed under reduced pressure. The crude material was eluted through a plug of silica using a quick gradient of (25%-100%) ethyl acetate/hexane to afford 32.5 g of desired product as a yellow solid that has 10%-15% triphenylphosphineoxide contamination. $^1$H NMR (300 MHz, CDCl$_3$): δ 7.98, (d, J=9.2 Hz, 1H), 7.46 (m, 2H), 7.37 (d, J=2.4 Hz, 1H), 7.31 (s, 1H), 7.09 (d, J=9.1 Hz, 1H), 5.26 (m, 1H), 4.96 (m, 1H), 4.62 (t, J=7.3 Hz, 1H), 5.57 (t, J=15 Hz, 1H), 3.97-3.84 (bs, 5H), 3.76-3.66 (bs, 5H), 2.77 (m, 1H), 2.42 (m, 1H), 2.03 (s, 1H), 1.43 (s, 9H), 1.33 (d, J=6.4 Hz, 6H). LC/MS: 543 (M$^+$+1).

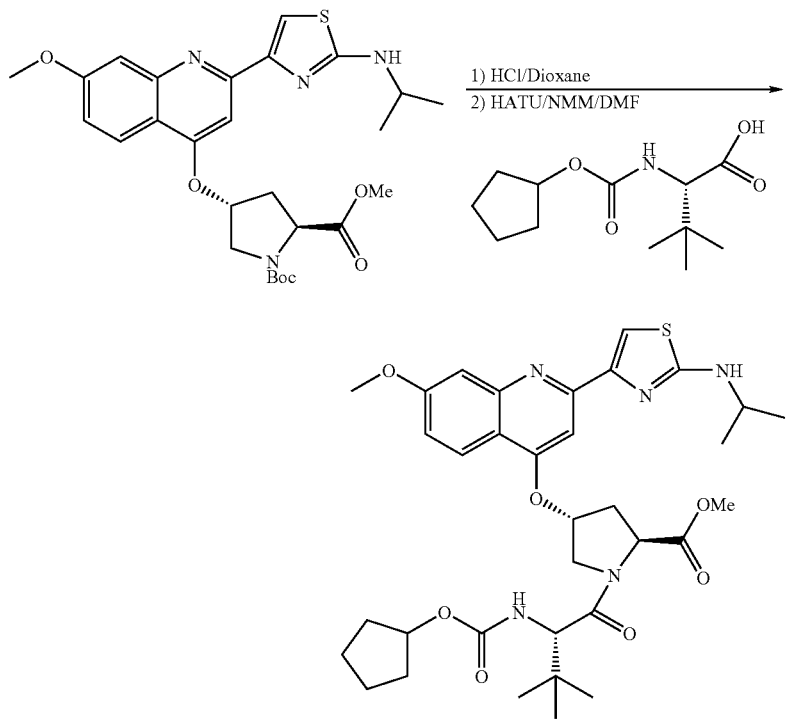

Step 2. To a solution of methyl ester (30.0 g, 55 mmol) in methylene chloride (150 mL) at 0° C., was added 4 N HCl in dioxane (150 mL). Stir cold to room temperature over 1 h. As the reaction proceeds, the product precipitates out of solution. Filter the solids and wash repeatedly with diethyl ether to afford HCL salt of the amine (20.67 g, 78%) as a crystalline yellow solid. $^1$H NMR (300 MHz, CD$_3$OD): δ 8.45 (d, J=9.2 Hz, 1H), 8.35 (s, 1H), 7.85 (s, 1H), 7.79 (s, 1H), 7.45 (d, J=9.5 Hz, 1H), 6.02 (m, 1H), 4.22 (m, 1H), 4.07 (s, 3H), 4.02 (d, J=3.9 Hz, 1H), 3.98 (s, 1H), 3.92 (s, 3H), 3.66 (s, 1H), 3.03 (m, 1H), 2.82 (m, 1H), 1.36 (d, J=6.4 Hz, 6H), 1.33 (d, J=6.4 Hz, 6H). LC/MS: 443 (M$^+$+1).

To a solution of HCl amine salt (20.96 g, 43.8 mmol) in DMF (300 mL) at room temperature was added cyclopentyl-carbamate-tert-leucine carboxylic acid (13.0 g, 52.6 mmol), and HATU (25.0 g, 65.7 mmol). The reaction was stirred for 10 min at room temperature then Hunig's base (45 mL, 262 mmol) was added over 5 min. The reaction was stirred at room temperature for 1 h, monitoring by LCMS. Remove solvent under reduced pressure and dilute with ethyl acetate. Extract the reaction mixture with sat. NaHCO$_3$, followed by water and brine. Dry organics over MgSO$_4$, filter solids and remove solvent under reduced pressure. Elute crude material through silica plug to remove excess salts, remove solvent, and recrystallize the product with ethyl acetate and hexane to afford dipeptide methyl ester (23.5 g, 81%) as a yellow crystalline solid. $^1$H NMR (300 MHz, CDCl$_3$): δ 7.98, (d, J=9.1 Hz, 1H), 7.67 (s, 1H), 7.51 (s, 1H), 7.27 (s, 1H), 7.16 (d, J=7.3 Hz, 1H), 5.62 (m, 1H), 5.54 (m, 1H), 5.27 (d, J=9.7 Hz, 1H), 4.81-4.71 (bs, 2H), 4.49 (d, J=12.5 Hz, 1H), 4.28 (d, J=10 Hz, 1H), 4.14 (m, 1H), 4.04 (s, 3H), 3.78 (s, 3H), 3.60 (m, 1H), 2.76 (m, 2H), 2.51 (m, 2H) 1.63-1.50 (m, 10H) 1.26 (d, J=6.4 Hz, 6H), 1.07 (s, 9H). LC/MS: 668 (M$^+$+1).

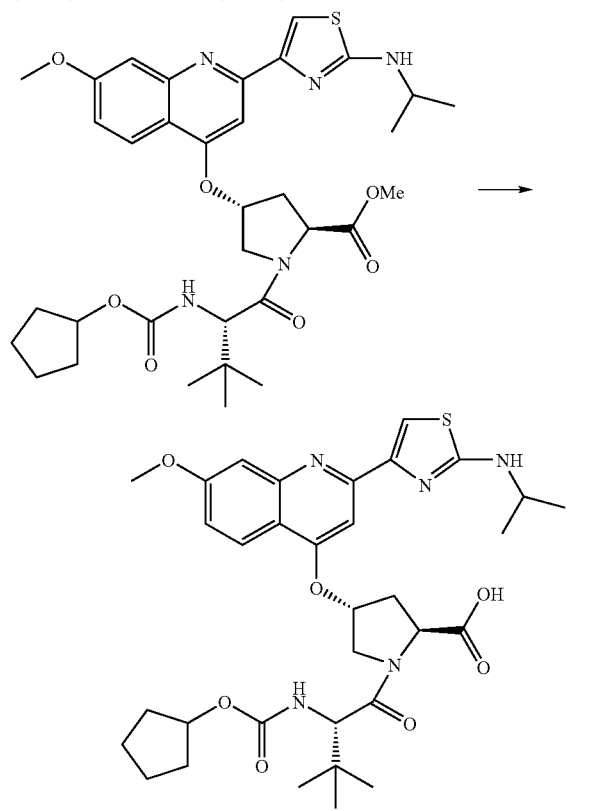

Step 3. To a solution of methyl ester (21.0 g, 31.5 mmol) in THF (300 mL) and Remove organic solvents under reduced pressure and adjust the pH to 2-3 with 10% HCl in water. Extract the solution with ethyl acetate, 2×250 mL. Combine organics and dry over MgSO$_4$, filter and remove the solvent under reduced pressure to afford dipeptide carboxylic acid (19.3 g, 94%) as a yellow solid. $^1$H NMR (300 MHz, CD$_3$OD: δ 8.29 (d, J=9.5 Hz, 1H), 8.17 (s, 1H), 7.72 (s, 2H), 7.33 (d, J=7.6 Hz, 1H), 5.77 (s, 1H), 4.80 (t, J=9.1 Hz, 1H), 4.77 (d, J=12 Hz, 1H), 4.44 (m, 1H), 4.19-4.04 (bs, 6H), 2.96 (m, 1H), 2.50 (m, 1H), 1.62-1.50 (bs, 8H), 1.35 (d, J=6.7 Hz, 6H), 1.05 (s, 9H). LC/MS: 655 (M$^+$+1).

Section B:

Example 1

Preparation of Compound 1

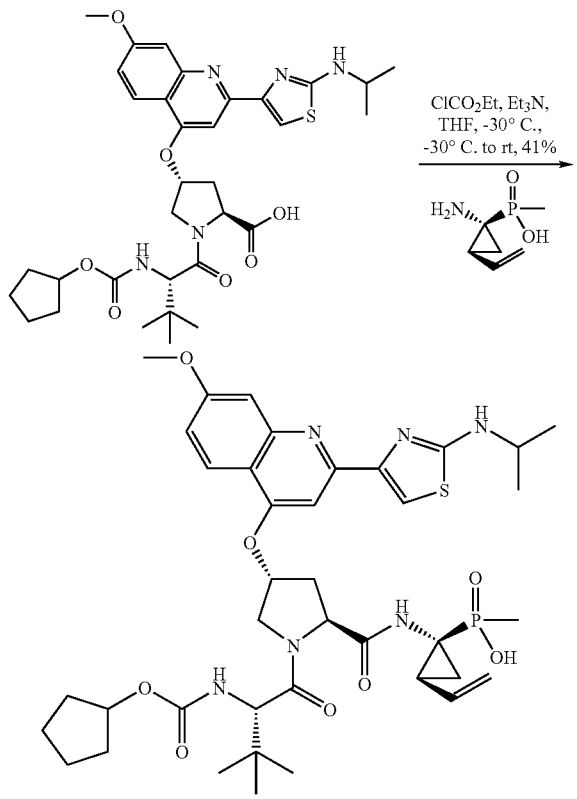

Step 1. A solution of (1-Benzyloxycarbonylamino-2-vinyl-cyclopropyl)-methyl-phosphinic acid ethyl ester (100 mg, 0.308 mmol) in ACN (7.7 mL) was cooled to 0° C. and TMSI (220 μL, 1.54 mmol) was added in a drop-wise fashion. The reaction was warmed to rt and stirred for an hour. The reaction was then cooled to 0° C. and additional TMSI (110 μL, 0.77 mmol) was added in a drop-wise fashion. The reaction was warmed to rt and stirred for 30 min. The reaction was cooled back to 0° C. and 2,6-lutidine (360 μL, 3.1 mmol) was added in a drop-wise fashion. This was followed by the addition of Et$_3$N (1 mL, 7.2 mmol) and MeOH (4 mL). The reaction was then concentrated in vacuum and crude intermediate was used directly in the next reaction. Step 2. A solution of dipeptide (81 mg, 0.123 mmol) in THF (2 mL) was cooled to −30° C. Et$_3$N (34 μL, 0.246 mmol) was added to this solution followed by ClCO$_2$Et (18 μL, 0.185 mmol). The reaction was stirred at a temperature between −20° C. and −30° C. for 30 min. Additional Et$_3$N (34 μL, 0.246 mmol) and ClCO$_2$Et (18 μL, 0.185 mmol) was added to the reaction. The reaction was stirred for an additional 30 min at a temperature between −20° C. and −30° C. A solution of crude product from step 1 in CH$_2$Cl$_2$ (2 mL) was added in a drop-wise fashion at −30° C. and the reaction was warmed to rt and stirred for 2 hours. The reaction was quenched by the addition of sat. NH$_4$Cl$_{(aq.)}$. The organic phase was diluted with EtOAc and extracted with sat. NH$_4$Cl$_{(aq.)}$, H$_2$O, and brine. The organic phase was then dried over Na$_2$SO$_4$, which was subsequently removed by vacuum filtration. The filtrate was concentrated in vacuum and the residue was dissolved in MeOH (1.5 mL). Compound 1 was isolated from this solution by reverse-phase HPLC as a yellow solid (37 mg, 37%).

$^1$H NMR (300 MHz, CD$_3$CN) δ=8.50 (m, 1H), 8.11 (d, J=9.6 Hz, 1H), 8.02 (s, 1H), 7.75 (s, 1H), 7.38 (s, 1H), 7.21 (dd, J=2.1, 9.3 Hz, 1H), 7.00 (m, 1H), 6.03 (m, 1H), 5.97 (dt; J=6.9, 17.1 Hz, 1H), 5.67 (s, 1H), 5.14 (d, J=17.1 Hz, 1H), 5.01 (d, J=11.4 Hz, 1H), 4.63 (m, 2H), 4.44 (s, 1H), 4.17 (m, 2H), 4.08 (s, 1H), 4.04 (s, 3H), 2.74 (dd, J=7.2, 14.1 Hz, 1H), 2.43 (ddd, J=3.3, 10.5, 13.8 Hz, 1H), 2.08 (m, 1H), 1.24-1.75 (m, 19H), 1.15 (m, 1H), 1.04 (s, 9H)

$^{31}$P NMR (121.4 MHz, CD$_3$CN) δ 46.6

LC/MS=797 (M$^+$+1), 819 (M$^+$+Na)

Example 2

Preparation of Compound 2

Step 1. A solution of (1-Benzyloxycarbonylamino-2-vinyl-cyclopropyl)-sec-butyl-phosphinic acid ethyl ester (112 mg, 0.308 mmol) in ACN (7.7 mL) was cooled to 0° C. and TMSI (220 ⊕L, 1.54 mmol) was added in a drop-wise fashion. The reaction was warmed to rt and stirred for an hour. The reaction was then cooled to 0° C. and additional TMSI (110 ⊕L, 0.77 mmol) was added in a drop-wise fashion. The reaction was warmed to rt and stirred for 30 min. The reaction was cooled back to 0° C. and 2,6-lutidine (360 ⊕L, 3.1 mmol) was added in a drop-wise fashion. This was followed by the addition of Et$_3$N (1 mL, 7.2 mmol) and MeOH (4 mL). The reaction was then concentrated in vacuum and crude was used directly in the next reaction.

Step 2. A solution of dipeptide (81 mg, 0.123 mmol) in THF (2 mL) was cooled to −30° C. Et$_3$N (34 ⊕L, 0.246 mmol) was added to this solution followed by ClCO$_2$Et (18 ⊕L, 0.185 mmol). The reaction was stirred at a temperature between −20° C. and −30° C. for 30 min. Additional Et$_3$N (34 ⊕L, 0.246 mmol) and ClCO$_2$Et (18 ⊕L, 0.185 mmol) was added to the reaction. The reaction was stirred for an additional 30 min at a temperature between −20° C. and −30° C. A solution of crude product from step 1 in CH$_2$Cl$_2$ (2 mL) was added in a drop-wise fashion at −30° C. and the reaction was warmed to rt and stirred for 2 hours. The reaction was quenched by the addition of sat. NH$_4$Cl$_{(aq.)}$. The organic phase was diluted with EtOAc and extracted with sat. NH$_4$

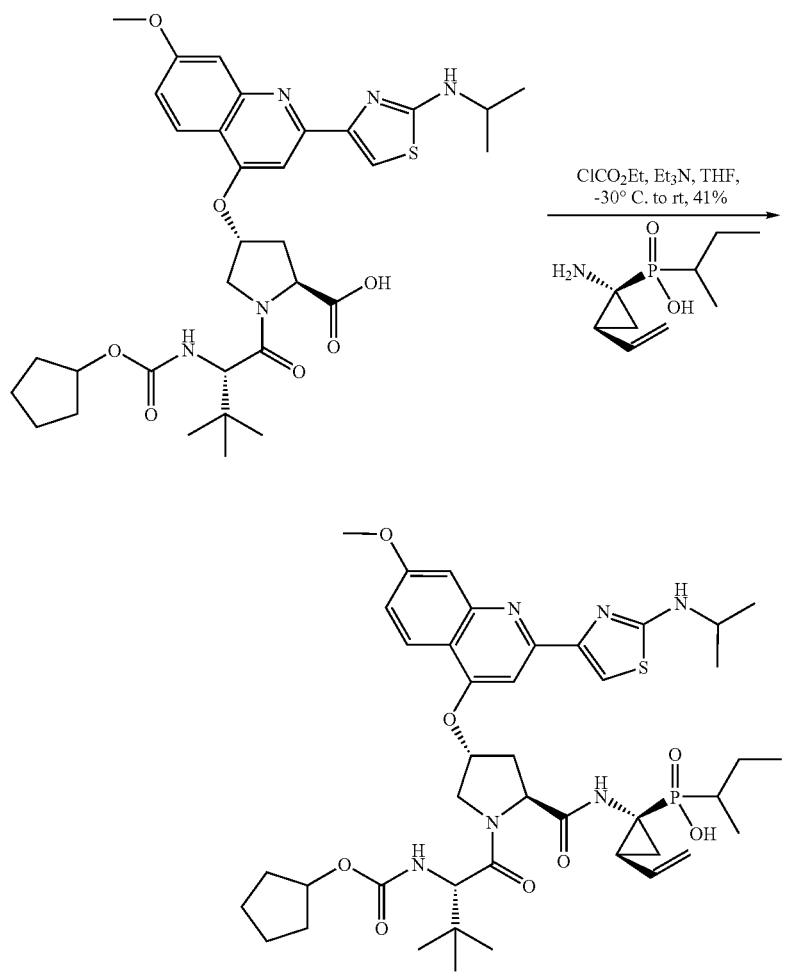

Cl$_{(aq.)}$, H$_2$O, and brine. The organic phase was then dried over Na$_2$SO$_4$, which was subsequently removed by vacuum filtration. The filtrate was concentrated in vacuum and the residue was dissolved in MeOH (1.5 mL). Compound 2 was isolated from this solution by reverse-phase HPLC as a yellow solid (42 mg, 41%).

$^1$H NMR (300 MHz, CD$_3$OD) δ 8.27 (d, J=9.6 Hz, 1H), 8.18 (s, 1H), 7.75 (d, J=2.1 Hz, 1H), 7.39 (d, J=3.9 Hz, 1H), 7.31 (dd, J=2.1, 9.3 Hz, 1H), 6.01 (dt, J=6.9, 17.1 Hz, 1H), 5.77 (s, 1H), 5.26 (d, J=17.1 Hz, 1H), 5.08 (d, J=11.4 Hz, 1H), 4.63 (m, 2H), 4.44 (s, 1H), 4.17 (m, 2H), 4.08 (s, 1H), 4.04 (s, 3H), 2.76 (dd, J=7.2, 14.1 Hz, 1H), 2.43 (ddd, J=3.3, 10.5, 13.8 Hz, 1H), 2.08 (m, 1H), 1.96 (m, 2H), 1.60-1.82 (m, 9H), 1.34 (d, J=6.3 Hz, 6H), 1.22 (m, 6H), 1.04 (s, 9H), 0.99 (m, 3H)

$^{31}$P NMR (121.4 MHz, CD$_3$OD) δ 52.4, 52.2

LC/MS=839 (M$^+$+1), 861 (M$^+$+Na)

Example 3

Preparation of Compound 3

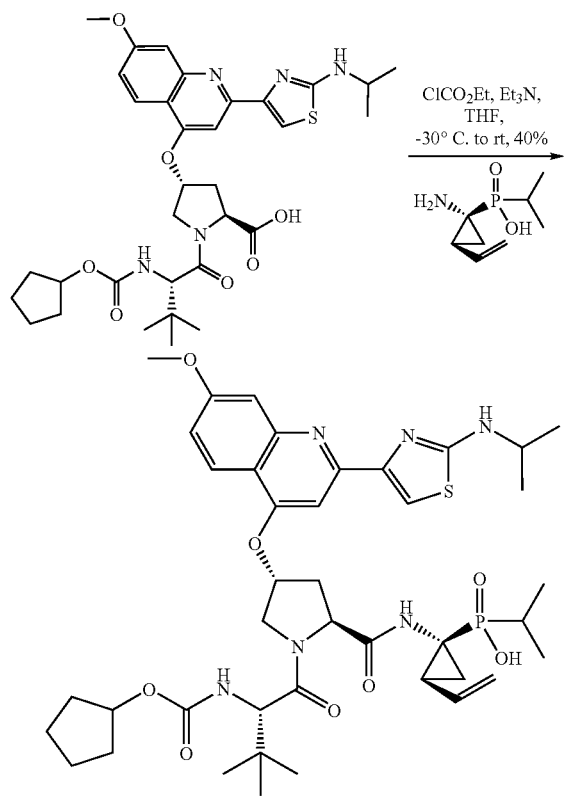

Step 1. A solution of (1-Benzyloxycarbonylamino-2-vinyl-cyclopropyl)-isopropyl-phosphinic acid ethyl ester (108 mg, 0.308 mmol) in ACN (7.7 mL) was cooled to 0° C. and TMSI (220 ●L, 1.54 mmol) was added in a drop-wise fashion. The reaction was warmed to rt and stirred for an hour. The reaction was then cooled to 0° C. and additional TMSI (110 ●L, 0.77 mmol) was added in a drop-wise fashion. The reaction was warmed to rt and stirred for 30 min. The reaction was cooled back to 0° C. and 2,6-lutidine (360 ●L, 3.1 mmol) was added in a drop-wise fashion. This was followed by the addition of Et$_3$N (1 mL, 7.2 mmol) and MeOH (4 mL). The reaction was then concentrated in vacuum and crude was used directly in the next reaction.

Step 2. A solution of 6 (81 mg, 0.123 mmol) in THF (2 mL) was cooled to −30° C. Et$_3$N (34 ●L, 0.246 mmol) was added to this solution followed by ClCO$_2$Et (18 ●L, 0.185 mmol). The reaction was stirred at a temperature between −20° C. and −30° C. for 30 min. Additional Et$_3$N (34 ●L, 0.246 mmol) and ClCO$_2$Et (18 ●L, 0.185 mmol) was added to the reaction. The reaction was stirred for an additional 30 min at a temperature between −20° C. and −30° C. A solution of crude product from step 1 in CH$_2$Cl$_2$ (2 mL) was added in a drop-wise fashion at −30° C. and the reaction was warmed to rt and stirred for 2 hours. The reaction was quenched by the addition of sat. NH$_4$Cl$_{(aq.)}$. The organic phase was diluted with EtOAc and extracted with sat. NH$_4$Cl$_{(aq.)}$, H$_2$O, and brine. The organic phase was then dried over Na$_2$SO$_4$, which was subsequently removed by vacuum filtration. The filtrate was concentrated in vacuum and the residue was dissolved in MeOH (1.5 mL). Compound 3 was isolated from this solution by reverse-phase HPLC as a yellow solid (40 mg, 40%).

$^1$H NMR (300 MHz, CD$_3$CN) δ 8.27 (d, J=9.6 Hz, 1H), 8.11 (m, 1H), 8.05 (s, 1H), 7.75 (d, J=2.1 Hz, 1H), 7.53 (d, J=3.9 Hz, 1H), 7.31 (dd, J=2.1, 9.3 Hz, 1H), 6.75 (m, 1H), 6.06 (dt, J=6.9, 17.1 Hz, 1H), 5.77 (m, 2H), 5.26 (d, J=17.1 Hz, 1H), 5.08 (d, J=11.4 Hz, 1H), 4.63 (m, 2H), 4.17 (m, 2H), 4.08 (s, 1H), 4.04 (s, 3H), 2.74 (dd, J=7.2, 14.1 Hz, 1H), 2.53 (ddd, J=3.3, 10.5, 13.8 Hz, 1H), 2.21 (m, 1H), 2.08 (m, 1H), 1.42-1.78 (m, 8H), 1.34 (d, J=6.3 Hz, 6H), 1.34 (m, 2H) 1.15 (m, 5H), 1.04 (s, 9H), 0.99-1.03 (m, 3H)

$^{31}$P NMR (121.4 MHz, CD$_3$CN) δ 50.6

LC/MS=825 (M$^+$+1), 847 (M$^+$+Na)

Example 4

Preparation of Compound 4

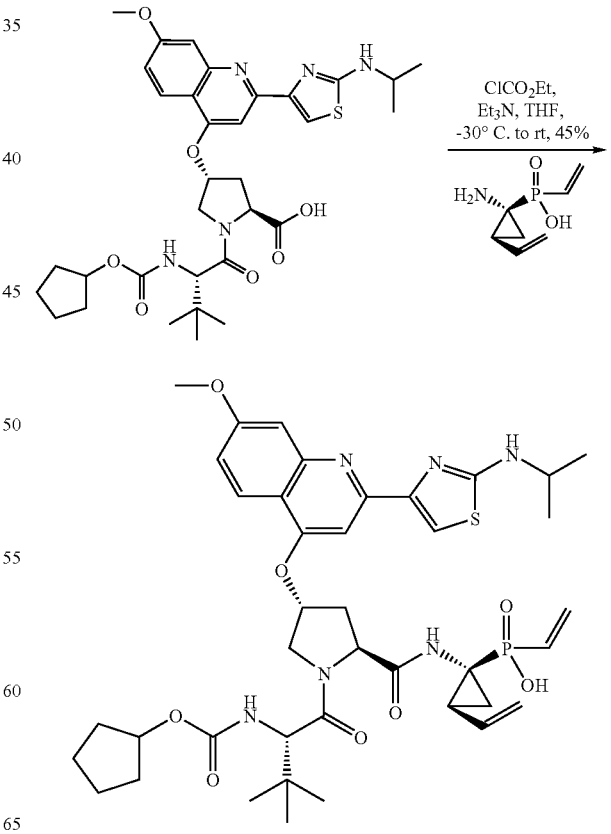

Step 1. A solution of (1-Benzyloxycarbonylamino-2-vinyl-cyclopropyl)-vinyl-phosphinic acid ethyl ester (103 mg, 0.308 mmol) in ACN (7.7 mL) was cooled to 0° C. and TMSI (220 ⊚L, 1.54 mmol) was added in a drop-wise fashion. The reaction was warmed to rt and stirred for an hour. The reaction was then cooled to 0° C. and additional TMSI (110 ⊚L, 0.77 mmol) was added in a drop-wise fashion. The reaction was warmed to rt and stirred for 30 min. The reaction was cooled back to 0° C. and 2,6-lutidine (360 ⊚L, 3.1 mmol) was added in a drop-wise fashion. This was followed by the addition of Et₃N (1 mL, 7.2 mmol) and MeOH (4 mL). The reaction was then concentrated in vacuum and crude was used directly in the next reaction.

Step 2. A solution of dipeptide (81 mg, 0.123 mmol) in THF (2 mL) was cooled to −30° C. Et₃N (34 ⊚L, 0.246 mmol) was added to this solution followed by ClCO₂Et (18 ⊚L, 0.185 mmol). The reaction was stirred at a temperature between −20° C. and −30° C. for 30 min. Additional Et₃N (34 ⊚L, 0.246 mmol) and ClCO₂Et (18 ⊚L, 0.185 mmol) was added to the reaction. The reaction was stirred for an additional 30 min at a temperature between −20° C. and −30° C. A solution of crude from step 1 in CH₂Cl₂ (2 mL) was added in a drop-wise fashion at −30° C. and the reaction was warmed to rt and stirred for 2 hours. The reaction was quenched by the addition of sat. NH₄Cl$_{(aq.)}$. The organic phase was diluted with EtOAc and extracted with sat. NH₄Cl$_{(aq.)}$, H₂O, and brine. The organic phase was then dried over Na₂SO₄, which was subsequently removed by vacuum filtration. The filtrate was concentrated in vacuum and the residue was dissolved in MeOH (1.5 mL). Compound 4 was isolated from this solution by reverse-phase HPLC as a yellow solid (45 mg, 45%).

¹H NMR (300 MHz, CD₃CN) δ 8.25 (br, 1H), 8.20 (d, J=9.6 Hz, 1H), 8.02 (s, 1H), 7.75 (s, 1H), 7.39 (s, 1H), 7.23 (dd, J=2.1, 9.3 Hz, 1H), 6.84 (br, 1H), 6.35 (m, 2H), 5.97 (m, 3H), 5.77 (m, 1H), 5.61 (s, 1H), 5.26 (d, J=17.1 Hz, 1H), 5.08 (d, J=11.4 Hz, 1H), 4.63 (m, 2H), 4.44 (s, 1H), 4.17 (m, 2H), 4.08 (s, 1H), 4.04 (s, 3H), 2.74 (dd, J=7.2, 14.1 Hz, 1H), 2.43 (ddd, J=3.3, 10.5, 13.8 Hz, 1H), 1.41-1.78 (m, 8H), 1.34 (d, J=6.3 Hz, 6H), 1.34 (m, 2H), 1.15 (m, 1H), 1.04 (s, 9H)

³¹P NMR (121.4 MHz, CD₃CN) δ 30.2
LC/MS=809 (M⁺+1), 831 (M⁺+Na)

Example 5

Preparation of Compound 5

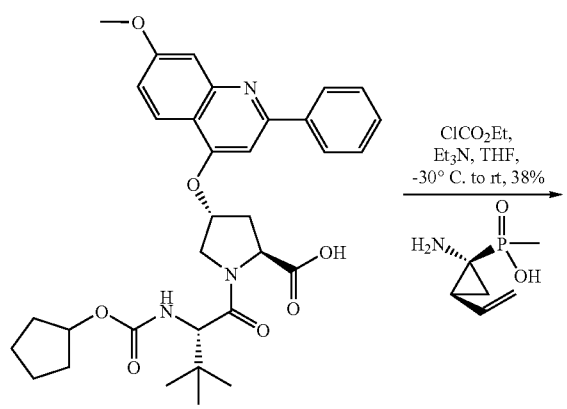

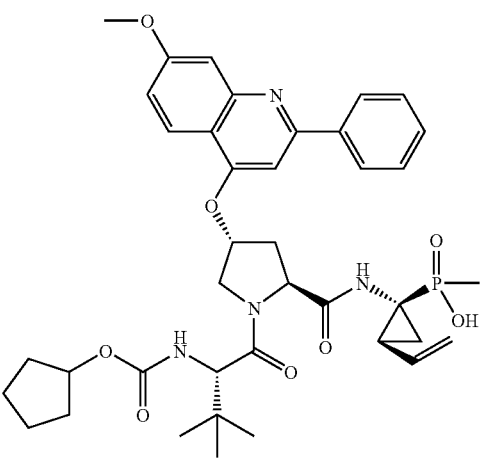

Step 1. A solution of (1-Benzyloxycarbonylamino-2-vinyl-cyclopropyl)-methyl-phosphinic acid ethyl ester (100 mg, 0.308 mmol) in ACN (7.7 mL) was cooled to 0° C. and TMSI (220 ⊚L, 1.54 mmol) was added in a drop-wise fashion. The reaction was warmed to rt and stirred for an hour. The reaction was then cooled to 0° C. and additional TMSI (110 ⊚L, 0.77 mmol) was added in a drop-wise fashion. The reaction was warmed to rt and stirred for 30 min. The reaction was cooled back to 0° C. and 2,6-lutidine (360 ⊚L, 3.1 mmol) was added in a drop-wise fashion. This was followed by the addition of Et₃N (1 mL, 7.2 mmol) and MeOH (4 mL). The reaction was then concentrated in vacuum and crude was used directly in the next reaction.

Step 2. A solution of 15 (72 mg, 0.123 mmol) in THF (2 mL) was cooled to −30° C. Et₃N (34 ⊚L, 0.246 mmol) was added to this solution followed by ClCO₂Et (18 ⊚L, 0.185 mmol). The reaction was stirred at a temperature between −20° C. and −30° C. for 30 min. Additional Et₃N (34 ⊚L, 0.246 mmol) and ClCO₂Et (18 ⊚L, 0.185 mmol) was added to the reaction. The reaction was stirred for an additional 30 min at a temperature between −20° C. and −30° C. A solution of crude product from step 1 in CH₂Cl₂ (2 mL) was added in a drop-wise fashion at −30° C. and the reaction was warmed to rt and stirred for 2 hours. The reaction was quenched by the addition of sat. NH₄Cl$_{(aq.)}$. The organic phase was diluted with EtOAc and extracted with sat. NH₄Cl$_{(aq.)}$, H₂O, and brine. The organic phase was then dried over Na₂SO₄, which was subsequently removed by vacuum filtration. The filtrate was concentrated in vacuum and the residue was dissolved in MeOH (1.5 mL). Compound 5 was isolated from this solution by reverse-phase HPLC as a yellow solid (35 mg, 38%).

¹H NMR (300 MHz, CD₃OD) δ 8.25 (d, J=9.3 Hz, 1H), 8.16 (m, 2H), 7.68 (m, 3H), 7.49 (m 1H), 7.39 (m 1H), 7.24 (dd, J=2.1, 9.3 Hz, 1H), 6.45 (m, 1H), 5.97 (m, 2H), 5.69 (s, 1H), 5.26 (d, J=17.1 Hz, 1H), 5.08 (d, J=11.4 Hz, 1H), 4.63 (m, 2H), 4.24 (m, 1H), 4.08 (m, 1H), 4.04 (s, 3H), 2.76 (dd, J=7.2, 14.1 Hz, 1H), 2.43 (ddd, J=3.3, 10.5, 13.8 Hz, 1H), 1.42-1.78 (m, 8H), 1.34 (d, J=6.3 Hz, 3H), 1.34 (m, 1H), 1.15 (m, 1H), 1.04 (s, 9H)

³¹P NMR (121.4 MHz, CD₃OD) δ 41.2
LC/MS=733 (M⁺+1), 755 (M⁺+Na)

Example 6

Preparation of Compound 6

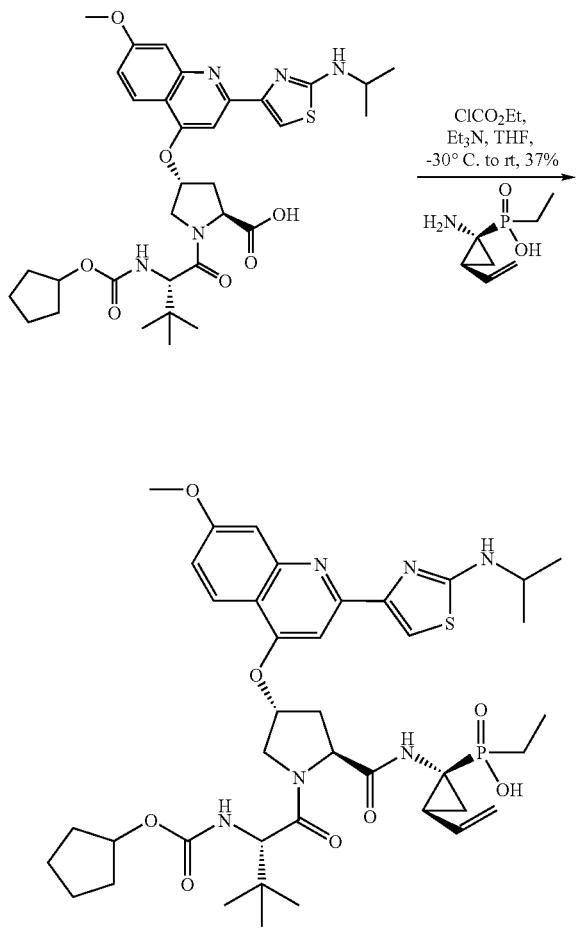

Step 1. A solution of (1-Benzyloxycarbonylamino-2-vinyl-cyclopropyl)-ethyl-phosphinic acid ethyl ester (104 mg, 0.308 mmol) in ACN (7.7 mL) was cooled to 0° C. and TMSI (220 µL, 1.54 mmol) was added in a drop-wise fashion. The reaction was warmed to rt and stirred for an hour. The reaction was then cooled to 0° C. and additional TMSI (110 µL, 0.77 mmol) was added in a drop-wise fashion. The reaction was warmed to rt and stirred for 30 min. The reaction was cooled back to 0° C. and 2,6-lutidine (360 µL, 3.1 mmol) was added in a drop-wise fashion. This was followed by the addition of $Et_3N$ (1 mL, 7.2 mmol) and MeOH (4 mL). The reaction was then concentrated in vacuo and the crude material was used directly in the next reaction.

Step 2. A solution of dipeptide (81 mg, 0.123 mmol) in THF (2 mL) was cooled to −30° C. $Et_3N$ (34 µL, 0.246 mmol) was added to this solution followed by $ClCO_2Et$ (18 µL, 0.185 mmol). The reaction was stirred at a temperature between −20° C. and −30° C. for 30 min. Additional $Et_3N$ (34 µL, 0.246 mmol) and $ClCO_2Et$ (18 µL, 0.185 mmol) was added to the reaction. The reaction was stirred for an additional 30 min at a temperature between −20° C. and −30° C. A solution of the crude product from step 1 in $CH_2Cl_2$ (2 mL) was added in a drop-wise fashion at −30° C. and the reaction was warmed to rt. The reaction was quenched by the addition of sat. $NH_4Cl_{(aq.)}$. The organic phase was diluted with EtOAc and extracted with sat. $NH_4Cl_{(aq.)}$, $H_2O$, and brine. The organic phase was then dried over $Na_2SO_4$, which was subsequently removed by vacuum filtration. The filtrate was concentrated in vacuum and the residue was dissolved in MeOH (1.5 mL). Compound 6 was isolated from this solution by reverse-phase HPLC as a yellow solid (37 mg, 37%).

$^1H$ NMR (300 MHz, $CDCl_3$) δ 8.27 (d, J=9.6 Hz, 1H), 8.18 (s, 1H), 7.75 (d, J=2.1 Hz, 1H), 7.73 (d, J=3.9 Hz, 1H), 7.31 (dd, J=2.1, 9.3 Hz, 1H), 5.97 (dt, J=6.9, 17.1 Hz, 1H), 5.77 (s, 1H), 5.26 (d, J=17.1 Hz, 1H), 5.08 (d, J=11.4 Hz, 1H), 4.63 (m, 2H), 4.44 (s, 1H), 4.17 (m, 2H), 4.08 (s, 1H), 4.04 (s, 3H), 2.74 (dd, J=7.2, 14.1 Hz, 1H), 2.43 (ddd, J=3.3, 10.5, 13.8 Hz, 1H), 2.08 (m, 1H), 1.84 (m, 2H), 1.54 (m, 8H), 1.34 (d, J=6.3 Hz, 6H), 1.34 (m, 2H), 1.15 (dt, J=7.8, 18.3 Hz, 3H), 1.04 (s, 9H)

$^{31}P$ NMR (121.4 MHz, $CDCl_3$) δ 50.6

LC/MS=811 ($M^+$+1), 834 ($M^+$+Na)

Example 7

Preparation of Compound 7

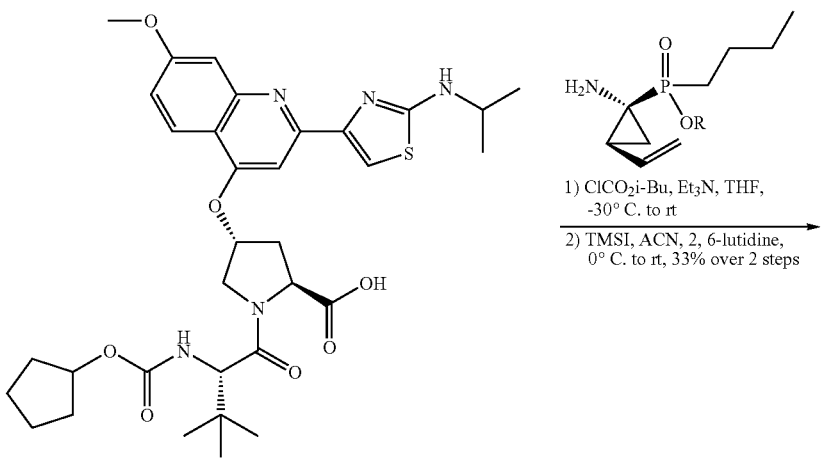

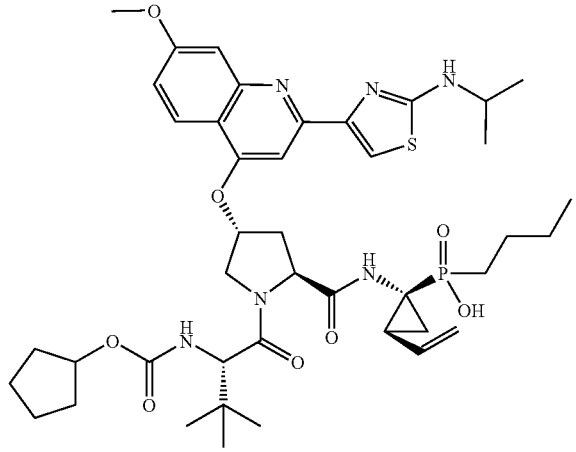

Step 1. A solution of (1-Benzyloxycarbonylamino-2-vinyl-cyclopropyl)-butyl-phosphinic acid ethyl ester (364 mg, 0.996 mmol) in ACN (25 mL) was cooled to 0° C. and TMSI (220 ◦L, 1.54 mmol) was added in a drop-wise fashion. The reaction was warmed to rt and stirred for an hour. The reaction was then cooled to 0° C. and additional TMSI (711 ◦L, 4.98 mmol) was added in a drop-wise fashion. The reaction was warmed to rt and stirred for 1 h. The reaction was cooled back to 0° C. and 2,6-lutidine (1 mL, 10.1 mmol) was added in a drop-wise fashion. This was followed by the addition of $Et_3N$ (1 mL, 7.2 mmol) and MeOH (4 mL). The reaction was warmed to rt then concentrated in vacuo. The crude mixtures were used directly in the next reaction.

Step 2. A solution of the starting dipeptide (100 mg, 0.153 mmol) in THF (2 mL) was cooled to −30° C. $Et_3N$ (32 ◦L, 0.230 mmol) was added to this solution followed by $ClCO_2Et$ (22 ◦L, 0.23 mmol). The reaction was stirred at a temperature between −20° C. and −30° C. for 30 min. Additional $Et_3N$ (32 ◦L, 0.23 mmol) and $ClCO_2Et$ (22 ◦L, 0.23 mmol) was added to the reaction. The reaction was stirred for an additional 30 min at a temperature between −20° C. and −30° C. A solution of crude product from step 1 in $CH_2Cl_2$ (2 mL) was added in a drop-wise fashion at −30° C. and the reaction was warmed to rt. The reaction was quenched by the addition of sat. $NH_4Cl_{(aq.)}$. The organic phase was diluted with EtOAc and extracted with sat. $NH_4Cl_{(aq.)}$, $H_2O$, and brine. The organic phase was then dried over $Na_2SO_4$, which was subsequently removed by vacuum filtration. The filtrate was concentrated in vacuo and the residue was dissolved in MeOH (1.5 mL). A mixture of products from the coupling was isolated by reverse-phase HPLC. This coupling reaction was repeated once more on the same scale and the isolated mixture of products from both reaction runs were combined.

The mixture of products from the coupling was dissolved in ACN (5.4 mL) and 2,6-lutidine (149 ◦L, 1.29 mmol) was then added. This solution was cooled to 0° C. and TMSI (184 ◦L, 1.29 mmol) was added in a drop-wise fashion. The reaction was stirred at rt for 1 h and then cooled to 0° C. Additional 2,6-lutidine (125 ◦L, 0.645 mmol) and TMSI (92 ◦L, 0.645 mmol) was added and the reaction was warmed to rt. The reaction was then cooled to 0° C. and $Et_3N$ (1.5 mL, 20.4 mmol) was added in a drop-wise fashion followed by MeOH (5 mL). The reaction was evaporated in vacuo and then dissolved in MeOH (1.5 mL). Compound 7 was isolated from this solution by reverse-phase HPLC as a yellow solid (86 mg, 33% over 2 steps).

$^1$H NMR (300 MHz, $CDCl_3$) δ 8.26 (d, J=9 Hz, 1H), 8.15 (s, 1H), 7.70 (d, J=2.1 Hz, 2H), 7.24 (dd, j=2.1, 9 Hz, 1H), 5.93 (dt, J=9.6, 19.5 Hz, 1H), 5.71 (s, 1H), 5.11 (d, J=16.8 Hz, 1H), 4.95 (d, J=12.3 Hz, 1H), 4.70 (d, J=12.3 Hz, 1H), 4.62 (dd, I=7.2, 9.3 Hz, 1H), 4.51 (s, 1H), 4.21 (s, 1H), 4.14 (q, I=6.6 Hz, 1H), 4.07 (dd, J=2.4, 9.9 Hz, 1H), 4.02 (s, 3H), 2.82 (dd, J=7.5, 14.4 Hz, 1H), 2.45 (ddd, J 3.9, 10.2, 14.1 Hz, 1H), 1.98 (m, 1H), 1.40-1.80 (m, 13H), 1.34 (d, J=6.3 Hz, 6H), 1.14-1.32 (m, 3H), 1.01 (s, 9H), 0.86 (t, J=7.2 Hz, 3H), $^{31}$P NMR (121.4 MHz, $CDCl_3$) δ 43.1

LC/MS=839 ($M^+$+1), 861 ($M^+$+Na)

Example 8

Preparation of Compound 8

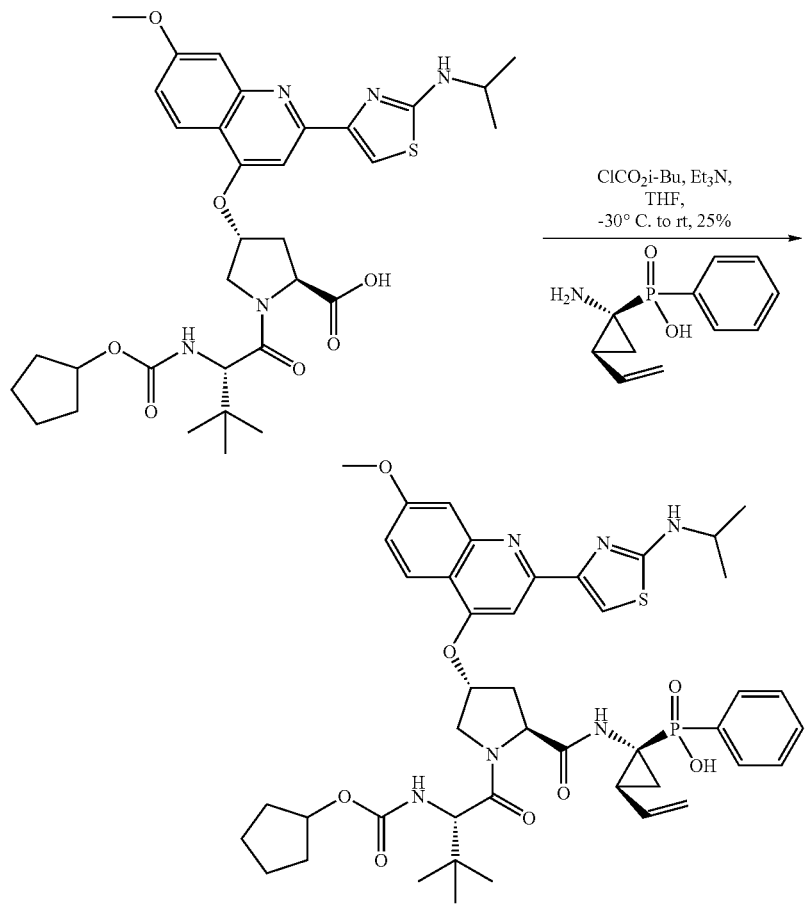

Step 1. A solution of (1-Benzyloxycarbonylamino-2-vinyl-cyclopropyl)-phenyl-phosphinic acid ethyl ester (150 mg, 0.389 mmol) in ACN (10 mL) was cooled to 0° C. and TMSI (278 μL, 1.95 mmol) was added in a drop-wise fashion. The reaction was warmed to rt and stirred for an hour. The reaction was cooled back to 0° C. and Et$_3$N (1.5 mL, 20.4 mmol) and MeOH (5 mL) were added in a drop-wise fashion. The reaction was then concentrated in vacuo and the crude product was used directly in the next reaction.

Step 2. A solution of dipeptide (50 mg, 0.076 mmol) in THF (2 mL) was cooled to −30° C. Et$_3$N (16 μL, 0.114 mmol) was added to this solution followed by ClCO$_2$Et (15 μL/0.114 mmol). The reaction was stirred at a temperature between −20° C. and −30° C. for 30 min. Additional Et$_3$N (16 μL, 0.114 mmol) and ClCO$_2$Et (15 μL, 0.114 mmol) was added to the reaction. The reaction was stirred for an additional 30 min at a temperature between −20° C. and −30° C. A solution of the crude product from step 1 in CH$_2$Cl$_2$ (2 mL) was added in a drop-wise fashion at −30° C. and the reaction was warmed to rt. The reaction was quenched by the addition of sat. NH$_4$Cl$_{(aq.)}$. The organic phase was diluted with EtOAc and extracted with sat. NH$_4$Cl$_{(aq.)}$, dH$_2$O, and brine. The organic phase was then dried over Na$_2$SO$_4$, which was subsequently removed by vacuum filtration. The filtrate was concentrated in vacuo and the residue was dissolved in MeOH (1.5 mL). Compound 8 was isolated from this solution by reverse-phase HPLC as a yellow solid (17 mg, 25%).

$^1$H NMR (300 MHz, CDCl$_3$) δ 8.22 (d, J=9.6 Hz, 1H), 8.18 (s, 1H), 7.89 (dd, J=6.9, 11.7 Hz, 2H), 7.74 (d, J=2.1 Hz, 1H), 7.72 (s, 1H), 7.53 (m, 3H), 7.30 (dd, J=2.1, 9 Hz, 1H), 6.14 (dt, J=10.2, 19.5 Hz, 1H), 5.71 (s, 1H),), 5.22 (d, J=17.1 Hz, 1H), 5.02 (d, J=10.2 Hz, 1H), 4.55 (m, 2H), 4.40 (s, 1H), 4.18 (quint., J=6.6 Hz, 1H), 4.11 (s, 1H), 4.04 (m, 4H), 5.60 (dd, J=6.9, 14.1 Hz, 1H), 2.23 (ddd, J=3.6, 10.2, 13.8 Hz, 1H), 2.12 (m, 1H), 1.72 (m, 1H), 1.40-1.66 (m, 9H), 1.34 (d, J=6.3 Hz, 6H), 1.03 (s, 9H)

$^{31}$P NMR (121.4 MHz, CDCl$_3$) δ 34.0
LC/MS=859 (M$^+$+1), 881 (M$^+$+Na)

Example 9

Preparation of Compound 9

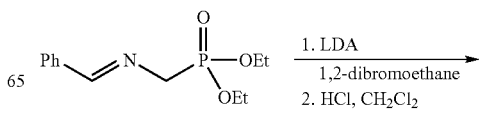

-continued

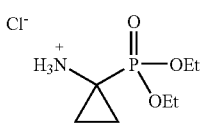

Step 1. A 100 ml round bottomed flask was charged with LDA (8.5 mL of a 1.8M solution, 15.3 mmol) in THF (35 mL) under argon. The flask was cooled to −78° C. and the iminophosphonate (1.96 g, 7.67 mmol) was added. The mixture was stirred for 10 minutes and then 1,2-dibromoethane (3.95 mL, 46 mmol) was added. The reaction was stirred at −78° C. for 6 hours then warmed to room temperature and stirred 12 h. The mixture was then concentrated and quenched with saturated ammonium chloride solution. The mixture was extracted with ether, washed with water and then concentrated to provide 1.86 g of alkylation product which contained approximately 50% impurity of unreacted iminophosphonate. The imine was then taken up in dichloromethane (25 mL) and 1M HCl (25 mL). The mixture was stirred at room temperature for 3 hours. The layers were then separated and the organic layer was washed with water. The aqueous layers were combined and concentrated to remove the water and provide the desired HCl salt (1.27 g which contains approx 50% impurity of unsubstituted aminophosphonate).

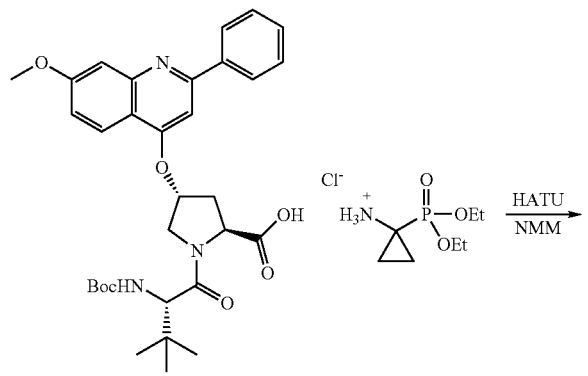

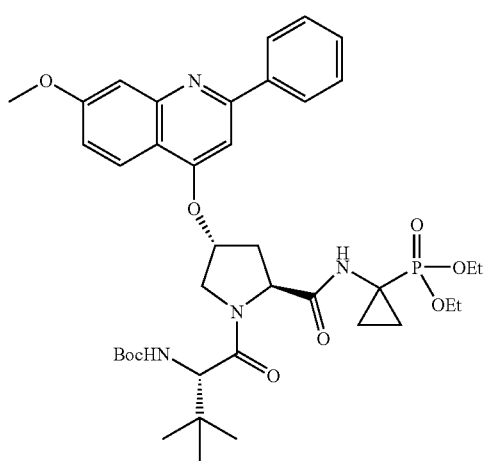

Step 2. In a 50 mL round bottomed flask was placed dipeptide carboxylic acid (1.13 g, 1.96 mmol), aminophosphonate from step 1 (0.436 g, 1.90 mmol), and HATU (1.04 g, 2.74 mmol) in dichloromethane (20 mL). The reaction was stirred at room temperature and NMM (0.65 mL, 5.88 mmol) was added. The mixture was stirred 12 h and then water was added. The layers were separated and the organic layer was washed with saturate sodium bicarbonate solution then dried and concentrated. The crude mixture was purified via flash column chromatography (EtOAC/Hex) to provide the desired product which also contained an impurity of unsubstituted aminophosphonate product. This impurity was removed by performing flash chromatography using 24% $CH_2Cl_2$/38% EtOAc/38% acetone as eluent to provide the desired product in 30% yield.

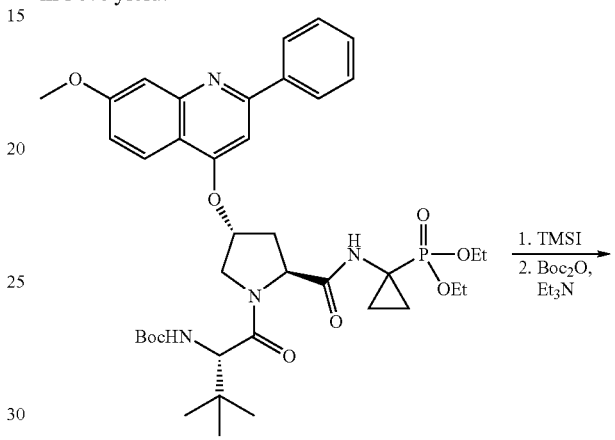

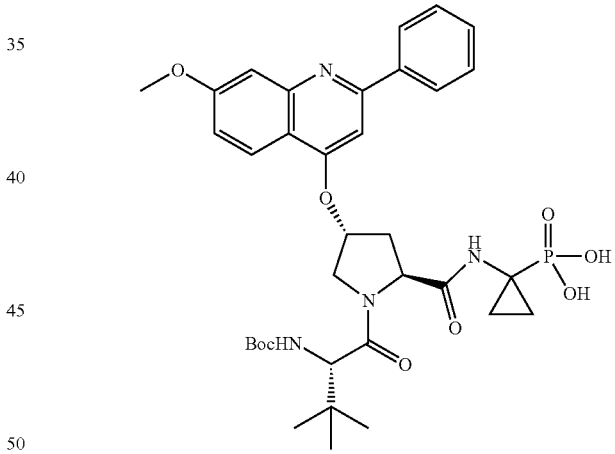

Step 3. The diethyl phosphonate from step 2 (27 mg, 0.036 mmol) was azeotroped with toluene 3 times and then taken up in acetonitrile (2 mL). TMSI (0.02 mL, 0.144 mmol) was then added and the reaction was stirred at room temperature for 1 h. Another 0.02 mL of TMSI was then added and the reaction stirred an additional 1 h. The mixture was then concentrated and azeotroped 3× with toluene. The crude reaction mixture was then taken up in dichloromethane (1 mL) and Boc anhydride (40 mg, 0.180 mmol), and Triethylamine (0.035 mL, 0.252 mmol) was added. The mixture was stirred at room temperature for 1 h and then concentrated. The reaction was purified via HPLC to provide the desired compound 9 (8 mg, 31%). $^1$H NMR (300 MHz, $CD_3OD$) δ 1.05 (s, 9H), 1.19 (s, 9H), 1.28 (m, 3H), 2.5 (m, 1H), 2.8 (m, 1H), 4.07 (s, 3H), 4.12

(m, 2H), 4.7 (m, 2H), 5.82 (s, 1H), 7.38 (m, 1H), 7.5 (m, 1H), 7.65 (s, 1H), 7.75 (m, 3H), 8.08 (m, 2H), 8.38 (d, 1H).

Example 10

Preparation of Compound 10

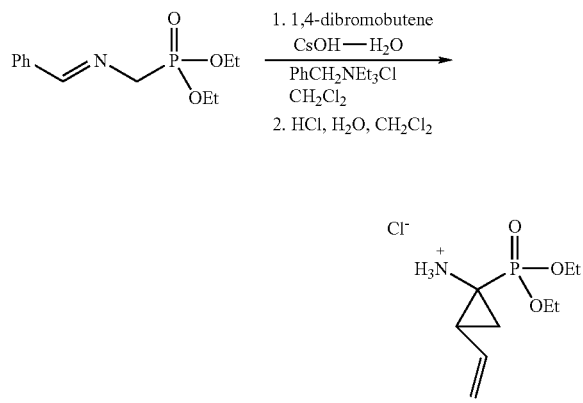

Step 1. In a 1 L two-necked round bottomed flask was placed iminophosphonate (10 g, 39.2 mmol), 1,4-dibromobutene (20 g, 96 mmol), and benzyl triethyl ammonium chloride (892 mg, 3.92 mmol) in dichloromethane (400 mL). The reaction was stirred with a mechanical stirrer and CsOH—H₂O (33 g, 196 mmol) was added. The reaction was stirred at room temperature for 2 days until complete as observed via TLC. The reaction was then filtered, concentrated, and purified via flash chromatography to provide the desired alkylation product (5.4 g, 17.6 mmol). This alkylation product (1.50 g, 4.88 mmol) was then taken up in dichloromethane (30 mL) and 1M HCl (30 mL) was added. The reaction was stirred at room temperature for 3 h. Ether (60 mL) was then added and the layers separated. The organic layer was extracted with water and the aqueous extracts were combined and concentrated to provide the desired aminophosphonate salt (1.07 g, 4.46 mmol).

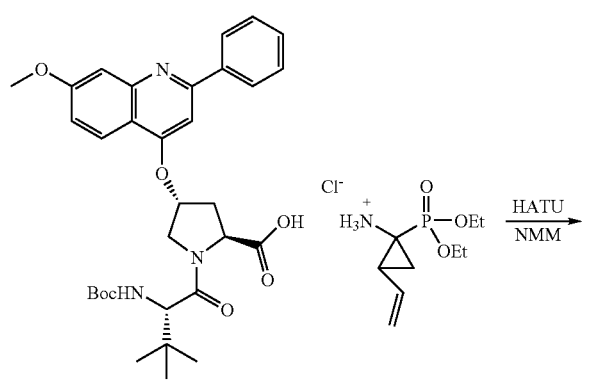

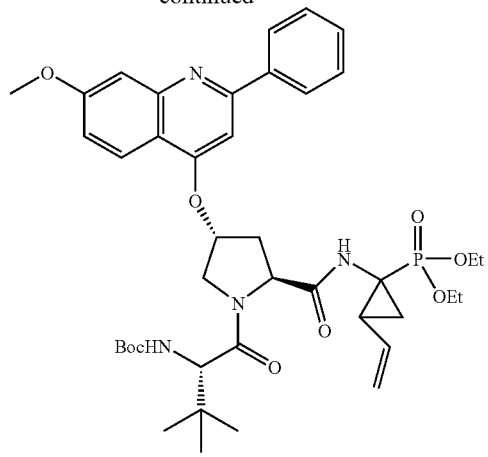

Step 2. In a 50 mL round bottomed flask was placed dipeptide carboxylic acid (1.2 g, 2.08 mmol), aminophosphonate (0.455 g, 2.08 mmol), and HATU (1.011 g, 2.91 mmol) in dichloromethane (30 mL). The reaction was stirred at room temperature and NMM (1.2 mL, 10.4 mmol) was added. The mixture was stirred 12 h and then water was added. The layers were separated and the organic layer was washed with saturate sodium bicarbonate solution then dried and concentrated. The crude mixture was purified via flash column chromatography (EtOAC/Hex) to provide the desired product.

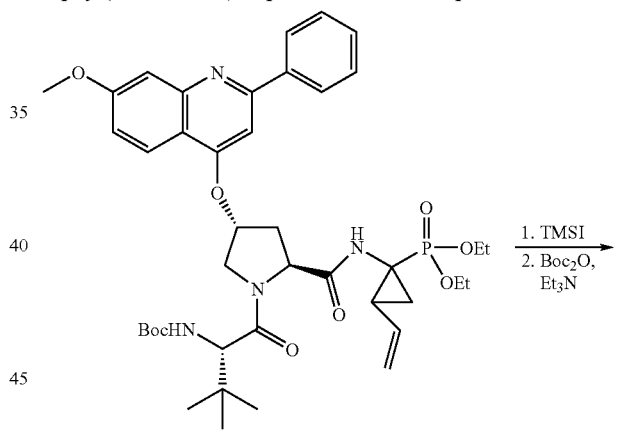

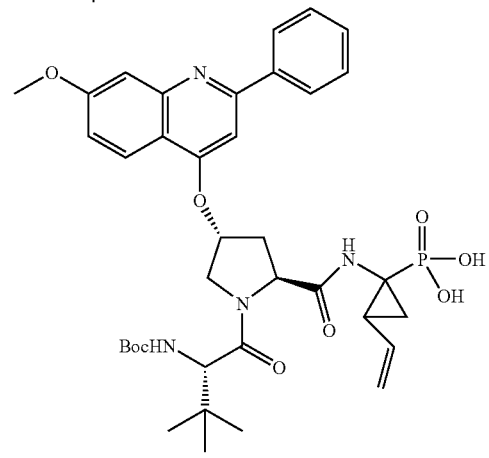

Step 3. The diethyl phosphonate (41 mg, 0.052 mmol) was azeotroped with toluene 3 times and then taken up in acetonitrile (2 mL). TMSI (0.03 mL, 0.21 mmol) was then added and the reaction was stirred at room temperature for 1 h. The mixture was then concentrated and azeotroped 3× with toluene. The crude reaction mixture was then taken up in dichloromethane (1 mL) and Boc anhydride (57 mg, 0.26 mmol), and triethylamine (0.050 mL, 0.37 mmol) was added. The mixture was stirred at room temperature for 1 h and then concentrated. The reaction was purified via HPLC to provide the desired compound 10 (14 mg, 0.019 mmol). $^1$H NMR (300 MHz, CD$_3$OD) b 0.94 (s, 9H), 1.08 (m, 9H), 2.42 (m, 1H), 2.68 (m, 1H), 3.95 (s, 3H), 4.03 (m, 2H), 4.59 (m, 2H), 4.98 (d, 1H), 5.19 (d, 1H), 5.74 (br s, 1H), 5.9 (m, 1H), 7.1 (m, 1H), 7.28 (m, 1H), 7.43 (d, 1H), 7.54 (s, 1H), 7.64 (m, 3H), 7.98 (m, 2H), 8.28 (d, 1H).

Example 11

Preparation of Compound 11

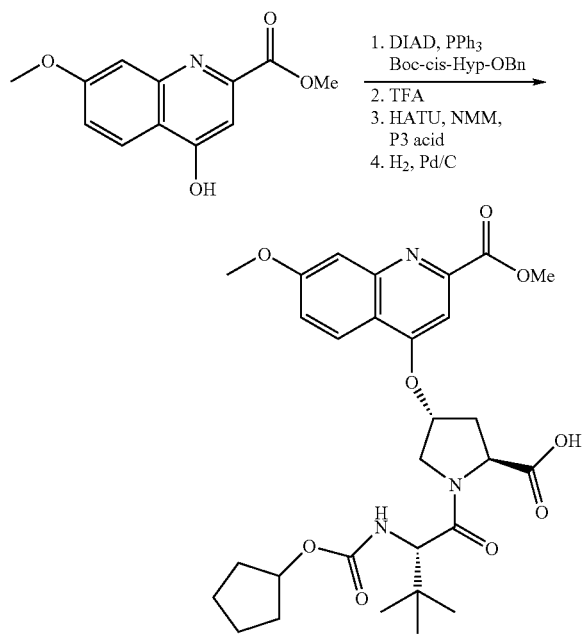

Step 1. The quinoline (2.33 g, 10 mmol) and Boc-cis-hydroxyproline benzyl ester (3.6 g, 11 mmol) were taken up in THF (100 mL). To this mixture was added DIAD (4.3 mL, 22 mmol), and triphenylphosphine (5.8 g, 22 mmol). The reaction was stirred at room temperature overnight then concentrated and purified via flash chromatography to provide the Mitsunobu product (1.66 g, 30%). This Boc-amine (3.1 mmol) was taken up in DCM (30 mL) and treated with TFA (30 mL). The reaction was stirred at room temp for 1 h, concentrated and azeotroped with toluene (3×50 mL). The residue was then taken up in DCM. HATU (1.65 g, 4.35 mmol), NMM (1.02 mL. 9.3 mmol), and the P3 carboxylic acid (0.83 g, 3.41 mmol) were added and the reaction was stirred at room temp for 15 h. The mixture was then concentrated and purified via flash chromatography to provide the dipeptide (1.71 g, 83%). This benzyl ester was then taken up in methanol and ethyl acetate (10 mL each). Palladium on carbon (250 mg) was added and the mixture was stirred under hydrogen balloon for 1.5 h. The mixture was then filtered and concentrated to provide the desired carboxylic acid 32 (1.2 g, 81%).

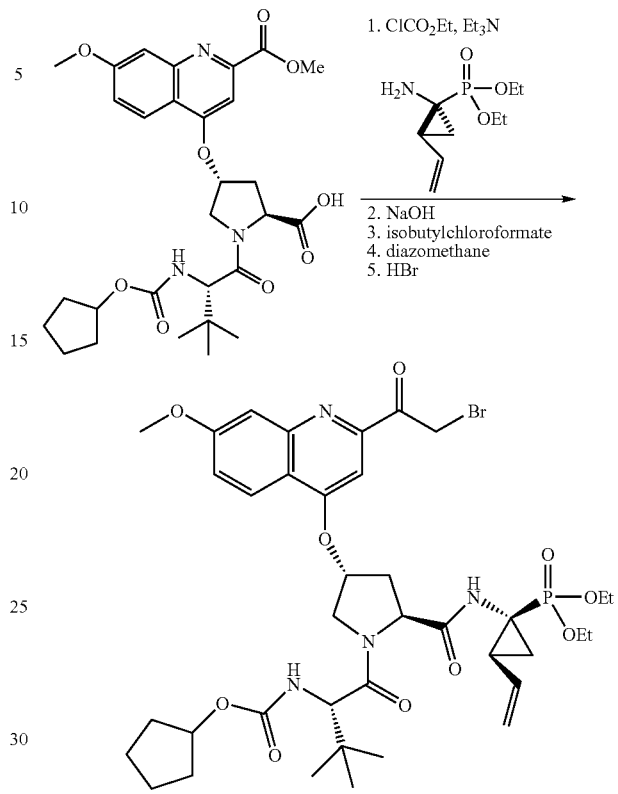

Step 2. Dipeptide carboxylic acid 32 (2 g, 3.5 mmol) was taken up in THF (35 mL) and cooled to −40. Triethylamine (0.98 mL, 7.0 mmol), and ethylchloroformate (0.67 mL, 7.0 mmol) were added. The reaction was monitored by LC/MS for the disappearance of starting material. Aminophosphonate 33 (844 mg, 3.85 mmol) was then added in THF (10 mL) and the reaction was warmed to room temperature. The reaction was quenched with sat NH$_4$Cl and extracted with EtOAc. The organic layer was dried, concentrated and purified via flash chromatography to provide the tripeptide (2.1 g, 78%). This methyl ester was taken up in THF (30 mL), MeOH (10 mL), and water (10 mL) and cooled to 0° C. NaOH (54 mL of 1M solution) was added and the mixture was monitored for disappearance of starting material. The reaction was then diluted with water and pH adjusted to 2 using 1N HCl. The mixture was then extracted with EtOAc and concentrated to provide the carboxylic acid (2.0 g, 98%). The carboxylic acid (2 g, 2.6 mmol) was taken up in THF at 0° C. and triethylamine (0.4 mL, 2.9 mmol) and isobutylchloroformate (0.38 mL, 2.9 mmol) were added. The reaction was stirred for 40 minutes. Diazonmethane (5.2 mmol) was added and the reaction was warmed to room temp and stirred for 2 h. The mixture was extracted with EtOAc, washed with NaHCO$_3$ and brine, then dried, concentrated, and purified via flash chromatography to provide the diazoketone (1.12 g, 43%). The diazoketone (500 mg, 0.64 mmol) was taken up in THF (10 mL) and cooled to 0° C. HBr (0.41 mL of 48% HBr) was added and the reaction was monitored via LC/MS. After 1 h, the mixture was extracted with EtOAc, washed with NaHCO$_3$, dried and concentrated to provide the α-bromoketone intermediate (490 mg, 92%).

187

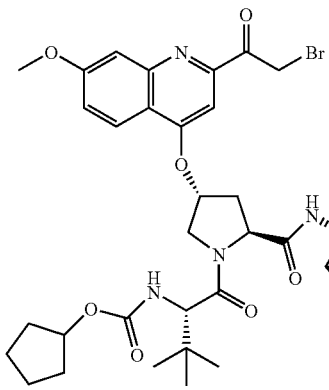

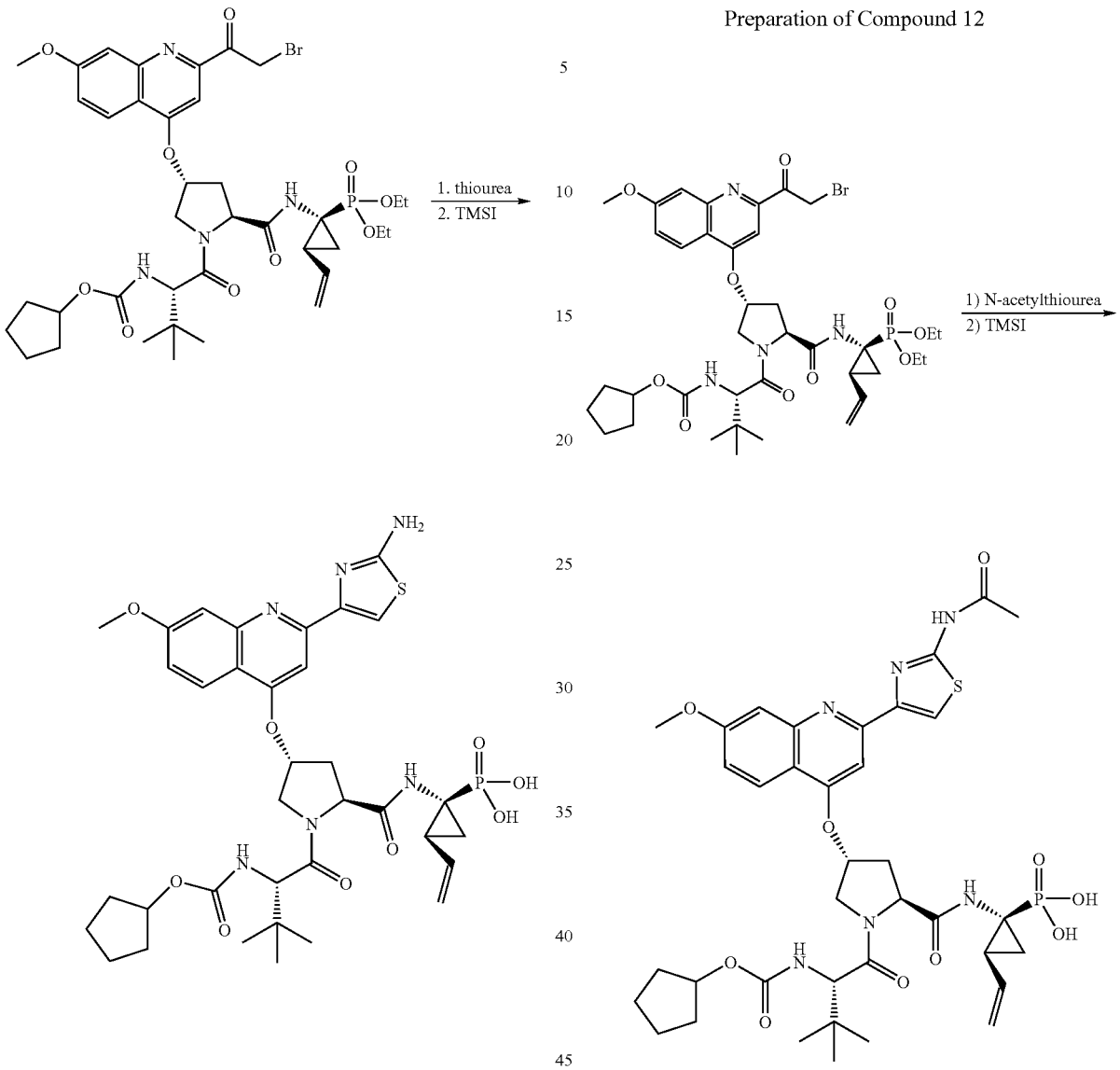

188

Example 12

Preparation of Compound 12

Step 3. α-bromoketone (173 mg, 0.2 mmol) was taken up in isopropanol (3 mL) and thiourea (32 mg, 0.42 mmol) was added. The reaction was heated to 75° C. for 1 h, the cooled and concentrated. The residue was taken up in ethyl acetate, washed with sat NaHCO$_3$ and brine, and then concentrated to provide the aminothiazole (141 mg, 84%). This diethylphosphonate was then taken up in CH$_3$CN (5 mL) and 2,6-lutidine (58 mg, 0.55 mmol) was added. TMSI (0.078 mL, 0.55 mmol) was added and the reaction was stirred at room temp for 1 h. The reaction was then quenched with TEA followed by methanol. The mixture was then concentrated and purified via HPLC to provide the compound 11 (48.8 mg, 71%). $^1$H NMR (300 MHz, CD$_3$OD) δ 1.02 (s, 9H), 1.26-1.48 (m, 15H), 2.06 (m, 1H), 2.52 (m, 1H), 2.77 (m, 1H), 3.35 (s, 1H), 4.10 (m, 1H), 4.43 (s, 1H), 4.91 (m, 1H), 5.27 (m, 1H), 5.67 (s, 1H), 5.95 (m, 1H), 6.72 (d, 1H, J=8.7 Hz), 7.30 (d, 1H, J=9.3 Hz), 7.61 (s, 1H), 7.68 (s, 1H), 8.14 (s, 1H), 8.23 (d, 1H, J=9.6 Hz). $^{31}$P NMR (300 MHz) δ20.42. LC/MS: 757 (M+1).

α-bromoketone intermediate from example 11 (173 mg, 0.2 mmol) was taken up in isopropanol (3 mL) and acteylthiourea (49 mg, 0.42 mmol) was added. The reaction was heated to 75° C. for 1 h, the cooled and concentrated. The residue was taken up in ethyl acetate, washed with sat NaHCO$_3$ and brine, and then concentrated to provide the acetylaminothiazole (160 mg, 90%). This diethylphosphonate intermediate (80 mg) was then taken up in CH$_3$CN (5 mL) and 2,6-lutidine (58 mg, 0.55 mmol) was added. TMSI (0.078 mL, 0.55 mmol) was added and the reaction was stirred at room temp for 1 h. The reaction was then quenched with TEA followed by methanol. The mixture was then concentrated and purified via HPLC to provide the compound 12 (45.9 mg, 64%). $^1$H NMR (300 MHz, CD$_3$OD) δ 1.02 (m, 11H), 1.25-1.72 (m, 15H), 2.08 (m, 1H), 2.35 (s, 3H), 2.58 (m, 1H), 2.83 (m, 1H), 3.2 (m, 4H), 4.15 (m, 1H), 4.42 (s, 1H), 4.68 (m, 1H), 5.08 (d, 1H J=9.9 Hz), 5.23 (d, 1H, J=17 Hz), 5.81 (s, 1H), 5.98 (m, 1H), 7.33 (d, 1H, J=7.2 Hz), 7.64 (s, 1H), 7.83 (s, 1H), 8.30 (d, 1H, J=9.4 Hz), 8.63 (s, 1H). $^{31}$P NMR (300 MHz) δ 20.30. LC/MS: 799 (M+1).

Example 13

Preparation of Compound 13

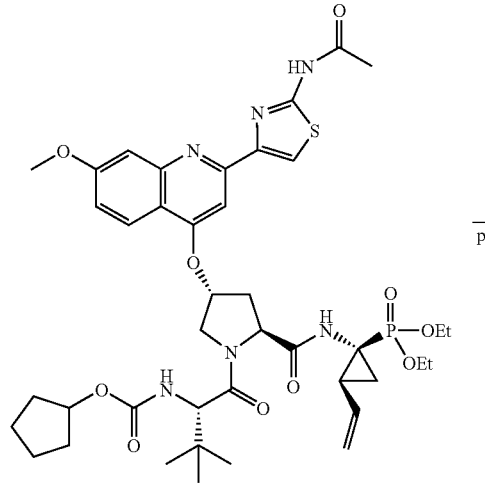

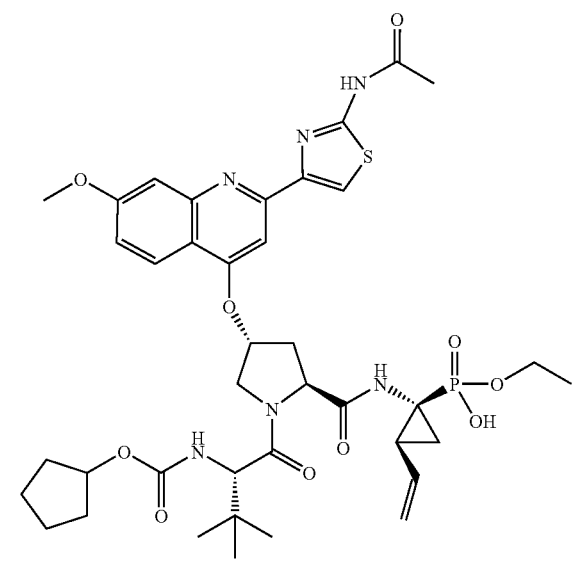

The diethylphosphonate intermediate from example 12 (80 mg, 0.09 mmol) was taken up in pyridine (5 mL) and NaI (67 mg, 0.45 mmol) was added. The reaction was heated to 95° C. until complete after 8 h. The reaction was then concentrated and the residue taken up in EtOAc. The organics were washed with 1M HCl, dried, concentrated, and purified via HPLC to provide the compound 13 (36 mg, 48%). $^1$H NMR (300 MHz, CD$_3$OD) δ 1.05 (m, 9H), 1.26-1.61 (m, 14H), 2.11 (m, 1H), 2.32 (s, 3H), 2.50 (m, 1H), 2.77 (m, 1H), 3.10 (s, 1H), 3.98-4.18 (m, 6H), 4.41 (s, 1H), 4.66 (m, 2H), 5.08 (d, 1H, J=11.7 Hz), 5.26 (d, 1H, J=17.4 Hz), 5.80 (s, 1H), 5.97 (m, 1H), 7.35 (dd, 1H, J=9.6 Hz, 2 Hz), 7.64 (d, 1H, J=2 Hz), 7.86 (s, 1H), 8.30 (d, 1H, 9.3 Hz), 8.63 (s, 1H). $^{31}$P NMR (300 MHz) δ 21.54. LC/MS: 827 (M+1).

Example 14

Preparation of Compound 14

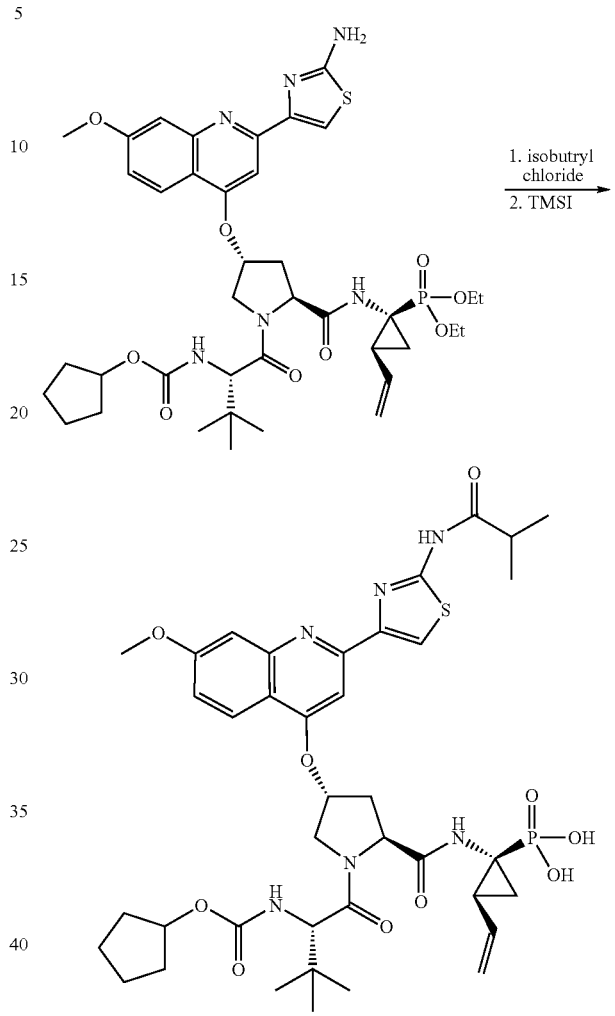

Aminothiazole intermediate from example 11 (152 mg, 0.19 mmol) was taken up in DCM (3 mL) and cooled to 0° C. Triethylamine (21 mg, 0.21 mmol) and isobutyryl chloride (22 mg, 0.21 mmol) were added. The reaction was warmed to room temp and stirred for 1 h. The reaction was diluted with DCM, washed with NaHCO$_3$ and brine, concentrated and purified via flash chromatography to provide the desired product (87 mg, 52%). The diethyl phosphonate 77 mg, 0.087 mmol) was taken up in CH$_3$CN. 2,6-lutidine (56 mg, 0.52 mmol), and TMSI (105 mg, 0.52 mmol) were added. The reaction was stirred at room temp for 1 h and then quenched with triethylamine and methanol. The mixture was then concentrated and purified via HPLC to provide the desired compound 14 (38.9 mg, 54%). $^1$H NMR (300 MHz, CD$_3$OD) b 1.02 (s, 11H), 1.20-1.73 (m, 16H), 2.08 (m, 1H), 2.58 (m, 1H), 2.82 (m, 2H), 3.37 (m, 1H), 4.18 (m, 1H), 4.43 (s, 1-H), 4.67 (m, 2H), 5.07 (d, 1H, J=9.9 Hz), 5.23 (d, 1H, J=18.2 Hz), 5.81 (s, 1H), 5.99 (m, 1H), 7.35 (dd, 1H, J=9.4 Hz, 2.3 Hz), 7.64 (d, 1H, J=2.4 Hz), 7.85 (s, 1H), 8.3 (d, 1H, J=9.5 Hz), 8.63 (s, 1H). $^{31}$P NMR (300 MHz) δ 20.39. LC/MS: 827 (M+1).

Example 15

Preparation of Compound 15

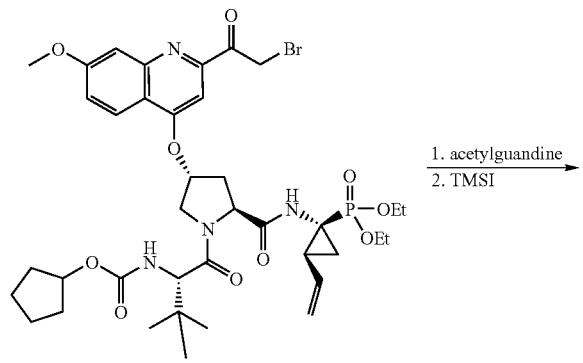

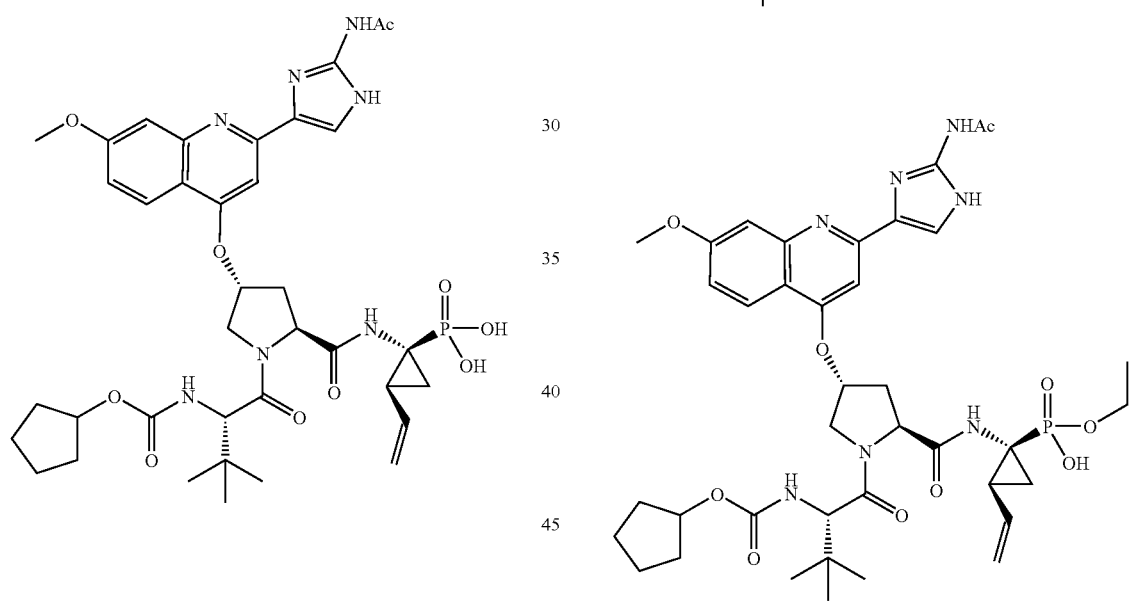

1-acetylguanidine (92 mg, 0.91 mmol) was taken up in DMF (1 mL). Bromoketone from example 11 (254 mg, 0.30 mmol) was added in DMF (1 mL). This reaction was then stirred at room temperature for 5 days, then concentrated and purified via flash chromatography (MeOH: EtOAc) to provide the acetylaminoimidzole (146 mg, 57%). This diethylphosphonate (131 mg, 0.16 mmol) was then taken up in CH$_3$CN (9 mL). 2,6-lutidine (0.1 mL, 0.94 mmol) and TMSI (0.13 mL, 0.94 mmol) were added at the reaction stirred at room temperature for 1 h. The reaction was then quenched with triethylamine followed by methanol and then concentrated and purified via HPLC to provide the desired diacid 15 (19.5 mg, 16%). $^1$H NMR (300 MHz, CD$_3$OD) δ1.02 (s, 12H), 1.22-1.78 (m, 14H), 2.08 (m, 1H), 2.25 (s, 3H), 2.56 (m, 1H), 2.78 (m, 1H), 4.02-4.09 (m, 6H), 4.45 (s, 1H), 4.65 (m, 2H), 5.07 (d, 1H, J=10.6 Hz), 5.25 (d, 1H, J=17.2 Hz), 5.5.72 (s, 1H), 5.95 (m, 1H), 7.30 (d, 1H, J=9.3 Hz), 7.49 (d, 1H, J=1.9 Hz), 7.65 (s, 1H), 8.23 (d, 1H, J=9.2 Hz), 8.29 (s, 1H). $^{31}$P NMR δ 20.67. LC/MS: 782 (M+1).

Example 16

Preparation of Compound 16

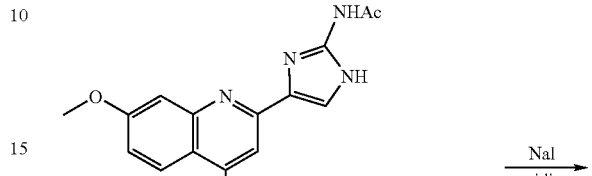

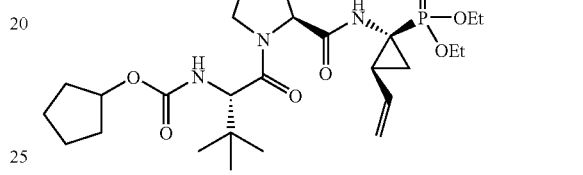

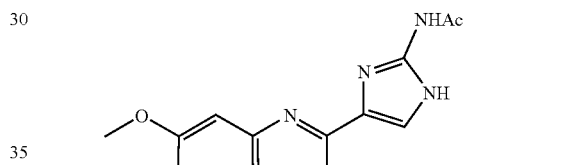

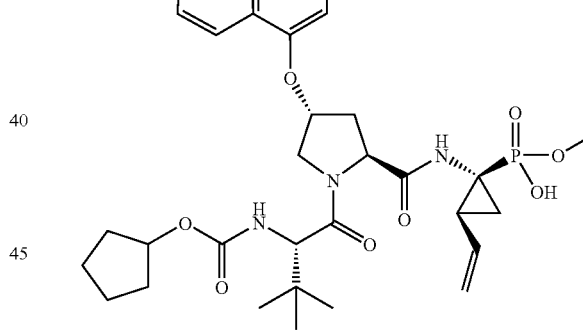

The diethylphosphonate from example 15 (95 mg, 0.11 mmol) was taken up in pyridine (5 mL) and NaI (85 mg, 0.57 mmol) was added. The reaction was heated to 95° C. until complete after 8 h. The reaction was then concentrated and the residue taken up in EtOAc. The organics were washed with 1M HCl, dried, concentrated, and purified via HPLC to provide the monoacid 16 (17.5 mg. 19%). $^1$H NMR (300 MHz, CD$_3$OD) b 1.05 (s, 12H), 1.26-1.62 (m, 15H), 2.11 (m, 1H), 2.24 (s, 3H), 2.43 (m, 1H), 2.74 (m, 1H), 3.98-4.19 (m, 8H), 4.45 (s, 1H), 4.65 (m, 2H), 5.09 (d, 1H, J=11.7 Hz), 5.26 (d, 1H, J=16 Hz), 5.71 (s, 1H), 5.98 (m, 1H), 7.28 (dd, 1H, J=9.3 Hz, 2.4 Hz), 7.49 (d, 1H, J=2.4 Hz), 7.66 (s, 1H), 8.23 (d, 1H, J=9 Hz), 8.32 (s, 1H). $^{31}$P NMR (300 MHz) δ 21.66. LC/MS: 810 (M+1).

Example 17

Preparation of Compound 17

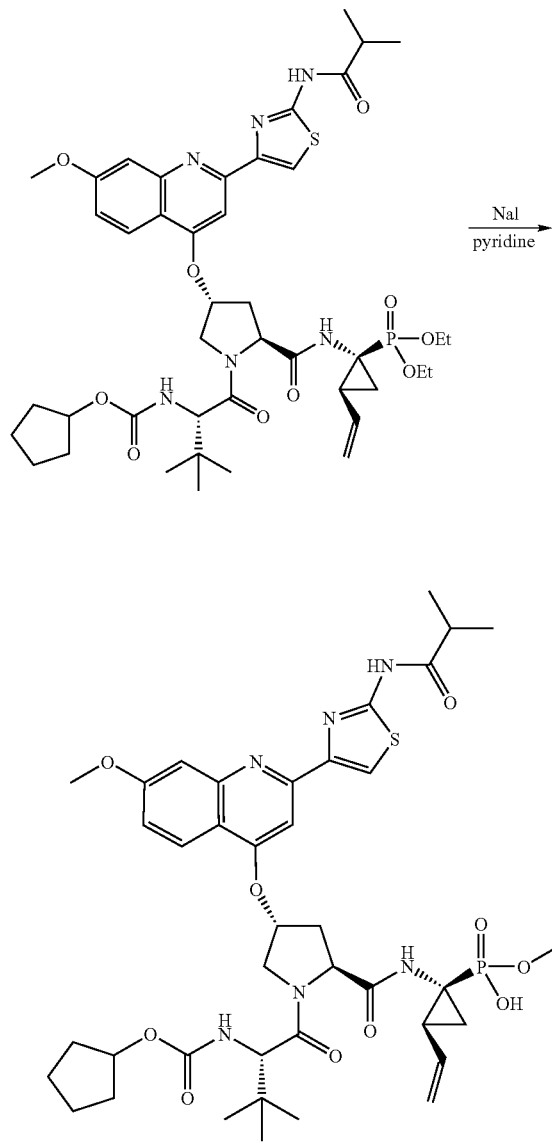

The diethylphosphonate from example 14 (100 mg, 0.11 mmol)) was taken up in pyridine (5 mL) and NaI (85 mg, 0.57 mmol) was added. The reaction was heated to 95° C. until complete after 8 h. The reaction was then concentrated and the residue taken up in EtOAc. The organics were washed with 1M HCl, dried, concentrated, and purified via HPLC to provide the monoacid 17 (28 mg, 29%). $^1$H NMR (300 MHz, CD$_3$OD) δ 1.05 (m, 12H), 1.15-1.61 (m, 17H), 2.11 (m, 1H), 2.51 (m, 1H), 2.82 (m, 2H), 3.31 (m, 1H), 4.06-4.17 (m, 7H), 4.41 (s, 1H), 4.64 (m, 2H), 5.09 (d, 1H, J=9.9 Hz), 5.25 (d, 1H, J=17 Hz), 5.8 (s, 1H), 5.97 (m, 1H), 7.35 (dd, 1H, J=9.3 Hz, 2.1 Hz), 7.63 (d, 1H, J=2.4 Hz), 7.87 (s, 1H), 8.32 (d, 1H, J=9.3 Hz), 8.63 (s, 1H). $^{31}$P δ 21.58. LC/MS: 855 (M+1).

Example 18

Preparation of Compound 18

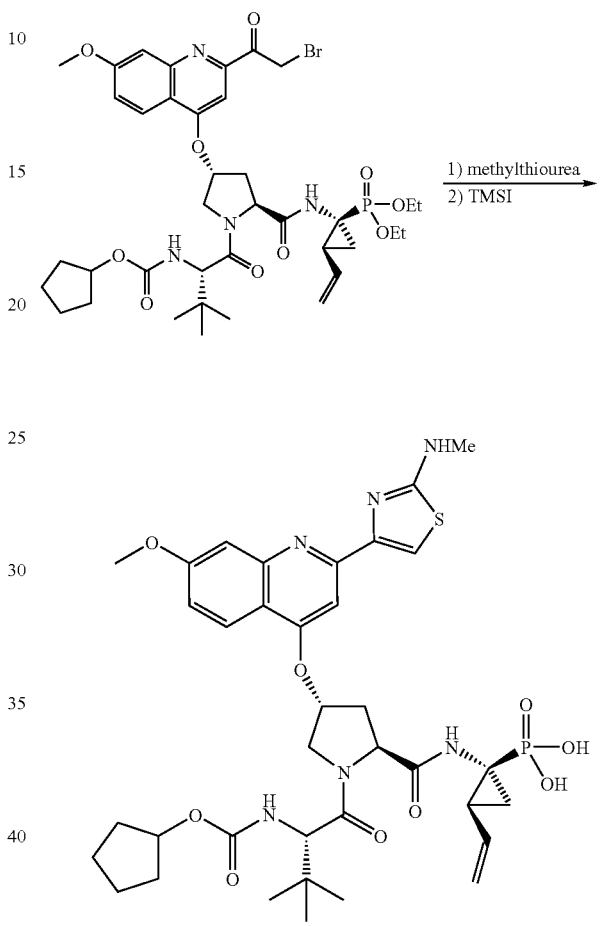

α-bromoketone from example 11 (135 mg, 0.16 mmol) was taken up in isopropanol (3 mL) and methylthiourea (29 mg, 0.32 mmol) was added. The reaction was heated to 75° C. for 1 h, the cooled and concentrated. The residue was taken up in ethyl acetate, washed with sat NaHCO$_3$ and brine, and then concentrated to provide the methylaminothiazole (121 mg, 90%). This diethylphosphonate (100 mg) was then taken up in CH$_3$CN (5 mL) and 2,6-lutidine (78 mg, 0.73 mmol) was added. TMSI (0.1 mL, 0.73 mmol) was added and the reaction was stirred at room temp for 1 h. The reaction was then quenched with TEA followed by methanol. The mixture was then concentrated and purified via HPLC to provide the diacid 18 (60.5 mg, 65%). $^1$H NMR (300 MHz, CD$_3$OD) δ 1.02 (s, 9H), 1.29-1.65 (m, 10H), 2.08 (m, 1H), 2.53 (m, 1H), 2.75 (m, 1H), 3.13 (s, 3H), 4.08-4.16 (m, 5H), 4.45 (s, 1H), 4.67 (m, 2H), 5.08 (d, 1H, J=10.4 Hz), 5.25 (d, 1H, J=17 Hz), 5.78 (s, 1H), 5.97 (m, 1H), 7.32 (dd, 1H, J=9.2 Hz, 2.4 Hz), 7.75 (s, 1H), 8.20 (s, 1H), 8.26 (d, 1H, J=9.2 Hz). $^{31}$P NMR (300 MHz) δ 20.65. LC/MS: 771 (M+1).

Example 19

Preparation of Compound 19

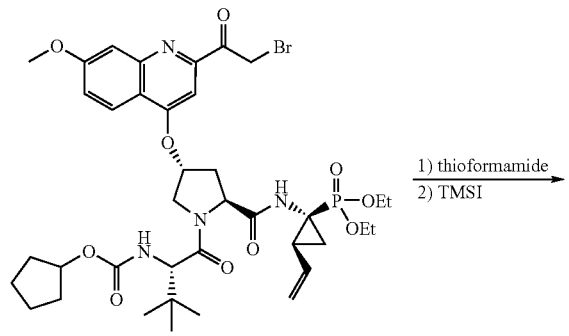

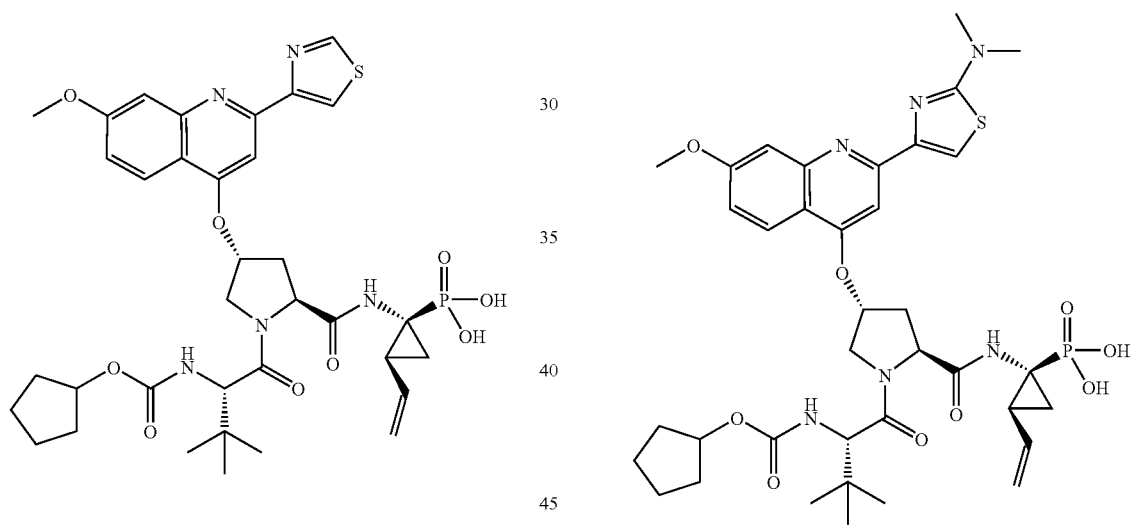

α-bromoketone (135 mg, 0.16 mmol) was taken up in isopropanol (3 mL) and thioformamide (20 mg, 0.32 mmol) was added. The reaction was heated to 75° C. for 1 h, the cooled and concentrated. The residue was taken up in ethyl acetate, washed with sat NaHCO$_3$ and brine then concentrated to provide the thiazole (115 mg, 89%). This diethylphosphonate (100 mg) was then taken up in CH$_3$CN (5 mL) and 2,6-lutidine (80 mg, 0.75 mmol) was added. TMSI (0.1 mL, 0.75 mmol) was added and the reaction was stirred at room temp for 1 h. The reaction was then quenched with TEA followed by methanol. The mixture was then concentrated and purified via HPLC to provide the compound 19 (42 mg, 45%). $^1$H NMR (300 MHz, CD$_3$OD) δ 1.02 (s, 10H), 1.04-1.61 (m, 10H), 2.07 (m, 1H), 2.55 (m, 1H), 2.80 (m, 1H), 4.06-4.15 (m, 6H), 4.40 (s, 1H), 4.70 (m, 2H), 5.08 (d, 1 h, J=11.9 Hz), 5.25 (d, 1H, J=17.2 Hz), 5.84 (m, 1H), 5.97 (m, 1H), 7.37 (dd, 1H, J=9.3 Hz, 2.3 Hz), 7.73 (d, 1H, J=2.2 Hz), 7.97 (s, 1H), 8.33 (d, 1H, J=9.3 Hz), 9.13 (d, 1H, J=1.8 Hz), 9.36 (d, 1H, J=1.5 Hz). $^{31}$P NMR (300 MHz) b 20.66. LC/MS: 742 (M+1).

Example 20

Preparation of Compound 20

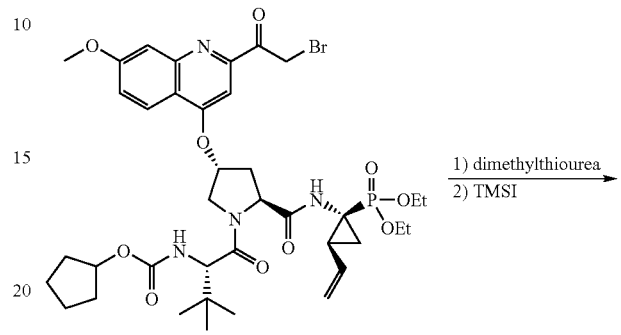

α-bromoketone (149 mg, 0.18 mmol) was taken up in isopropanol (3 mL) and N,N-dimethylthiourea (37 mg, 0.36 mmol) was added. The reaction was heated to 75° C. for 1 h, the cooled and concentrated. The residue was taken up in ethyl acetate, washed with sat NaHCO$_3$ and brine then concentrated to provide the dimethylaminothiazole (135 mg, 90%). This diethylphosphonate (115 mg) was then taken up in CH$_3$CN (5 mL) and 2,6-lutidine (88 mg, 0.82 mmol) was added. TMSI (0.12 mL, 0.82 mmol) was added and the reaction was stirred at room temp for 1 h. The reaction was then quenched with TEA followed by methanol. The mixture was then concentrated and purified via HPLC to provide the diacid 20 (53 mg, 49%). $^1$H NMR (300 MHz, CD$_3$OD) b 1.03 (s, 9H), 1.32-1.60 (m, 9H), 2.07 (m, 1H), 2.57 (m, 1H), 2.80 (m, 1H), 4.11-4.17 (m, 5H), 4.60 (m, 1H), 4.67 (m, 2H), 5.06-5.31 (m, 2H), 5.80 (m, 1H), 5.97 (m, 1H), 7.31 (dd, 1H, J=9 Hz, 2.2 Hz), 7.74 (s, 1H), 7.79 (d, 1H, J=2.5 Hz), 8.24 (s, 1H). $^{31}$P NMR (300 MHz) δ 20.49. LC/MS: 785 (M+1).

Example 21

Preparation of Compound 21

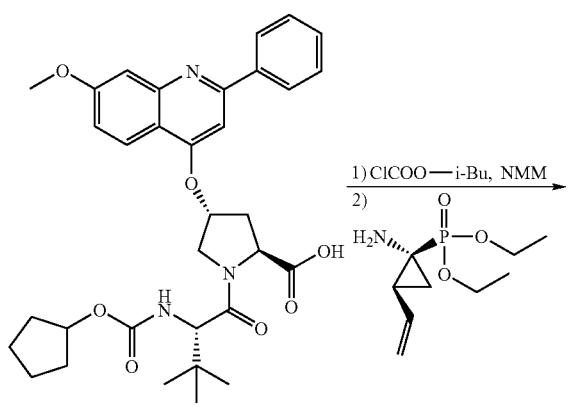

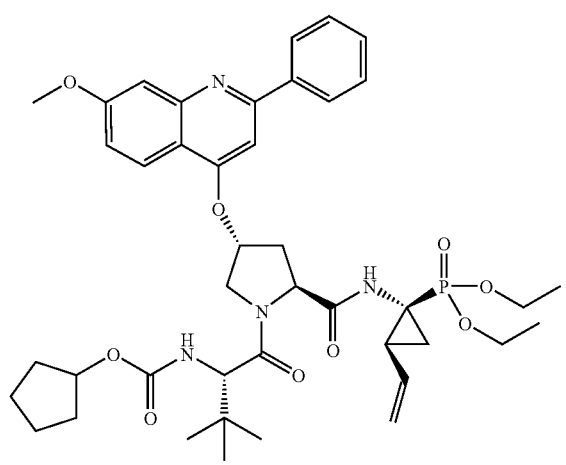

The dibenzoyltartrate salt (4.053 g, 7.80 mmol) of the amino phosphonate was dissolved in a mixture of saturated aq. sodium bicarbonate solution (45 mL) and brine (45 mL). After the free amine was extracted with dichloromethane (45 mL×2), the extracts were washed with a mixture of saturated aq. sodium bicarbonate solution (45 mL) and brine (45 mL), followed by brine (30 mL), dried (MgSO$_4$), and concentrated to obtain 1.63 g (95% recovery) of the free amine.

A solution of 2.80 g (4.75 mmol) of the reactant dipeptide and 0.65 mL (5.91 mmol) of N-methylmorpholine in THF (50 mL) was stirred at ice-salt bath as 0.70 mL (5.40 mmol) of isobutyl chloroformate was added dropwise. After 30 min, a solution of 1.25 g (5.70 mmol) of the free amine in THF (5 mL) was added by canula. The resulting mixture was stirred at the ice-salt bath for 1 h and stored in a freezer overnight. The resulting mixture was concentrated and the residue was dissolved in 5% citric acid (50 mL) before the product was extracted with ethyl acetate (70 mL×2). The extracts were washed with saturated aq. sodium bicarbonate solution (50 mL), dried (MgSO4), and concentrated. The product was purified by chromatography using 120 g silica gel column using combi-flash by gradient elution with ethyl acetate-hexane (1:1) to ethyl acetate (100%) to obtain 2.08 g (56%): $^1$H NMR (300 MHz, CDCl$_3$): δ 8.01-8.09 (m, 3H), 7.46-7.56 (m, 3H), 7.44 (d, J=2.4 Hz, 1H), 7.36 (br, 1H), 7.08 (d, j=2.4 Hz, 1H), 7.06 (s, 1H), 5.99 (dt, J=16.8 and 9.9 Hz, 1H), 5.26-5.42 (m, 2H), 5.08-5.15 (m, 1H), 4.88-5.03 (m, 2H), 4.76 (t, J=7.2 Hz, 1H), 4.47 (br d, J=11.4 Hz, 1H), 4.39 (d, J=9.3 Hz, 1H), 4.00-4.21 (m, 5H), 3.96 (s, 3H), 2.94 (dt, J=14.1 and 5.7 Hz, 1H), 2.37-2.47 (m, 1H), 1.50-2.10 (m, 5H), 1.34-1.44 (m, 1H), 1.20-1.34 (m, 10H), 0.98-1.07 (m, 1H), 1.04 (s, 9H); $^{31}$P NMR (75 MHz, CDCl$_3$) δ 22.74; LC/MS: 791 (M$^+$+1).

Example 22

Preparation of Compound 22

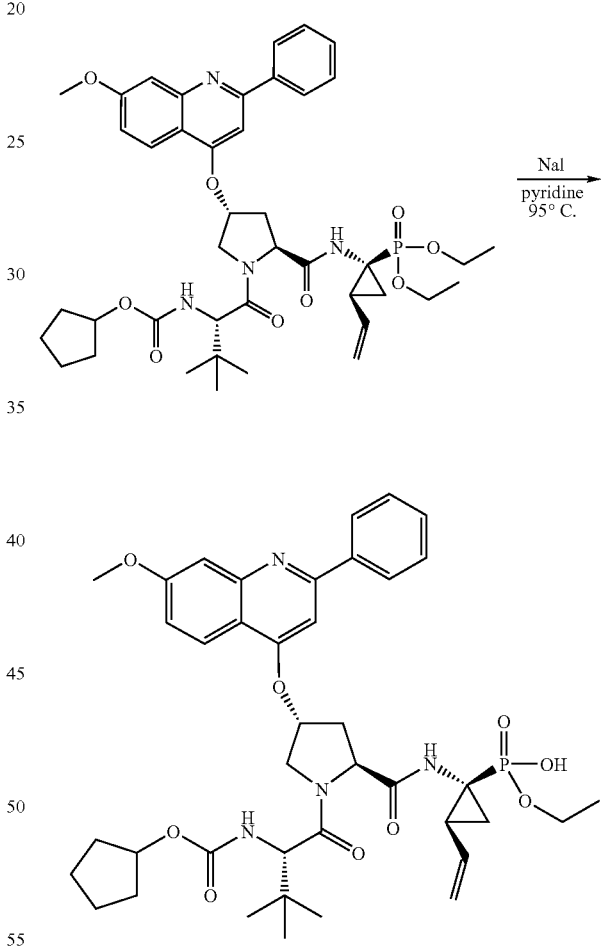

See example 17.

$^1$H NMR (300 MHz, CD$_3$OD): δ 8.36 (d, J=9.0 Hz, 1H), 8.06-8.11 (m, 2H), 7.70-7.82 (m, 3H), 7.66 (s, 1H), 7.54 (d, J=2.1 Hz, 1H), 7.39 (dd, J=9.3 and 2.1 Hz, 1H), 5.98 (dt, J=17.1 and 9.9 Hz, 1H), 5.83 (br, 1H), 5.25 (d, J=17.1 Hz, 1H), 5.08 (d, J=9.9 Hz, 1H), 4.62-4.72 (m, 2H), 4.45 (br, 1H), 4.17 (s, 1H), 4.06-4.20 (m, 3H), 4.06 (s, 3H), 2.73-2.83 (m, 1H), 2.43-2.54 (m, 1H), 2.05-2.17 (m, 1H), 1.31-1.70 (m, 12H), 1.28 (t, J=7.1 Hz, 3H), 1.01-1.08 (m, 2H), 1.05 (s, 9H); $^{31}$P NMR (75 MHz, CD$_3$OD) δ 21.30; LC/MS: 763 (M$^+$+1).

Example 23

Preparation of Compound 23

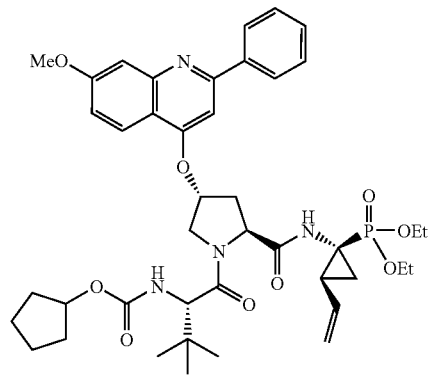

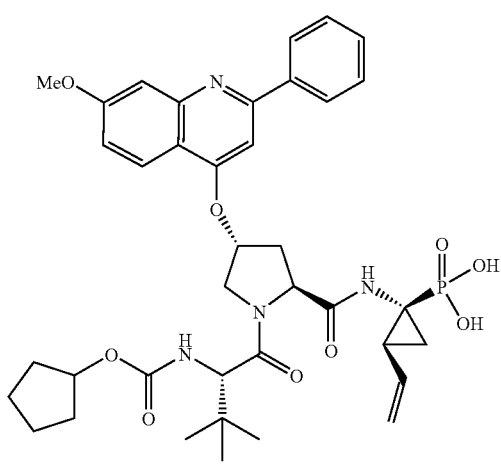

To a solution of diethyl phosphonate (3.60 g, 4.55 mmol) in 30 mL of $CH_3CN$ at 0° C. was added iodotrimethylsilane (3.24 mL, 22.78 mmol) and 2,6-lutidine. The reaction mixture was stirred at 0° C. for 1 h, concentrated, and co-evaporated with toluene. The residue was treated with methanol and evaporated. The crude product was purified by Gilson (0.1% $TFA/CH_3CN/H_2O$) to give the phosphonic acid 23 (1.68 g, 50%) as a white solid: $^1HNMR$ ($CD_3OD$) δ 8.40 (d, J=9.0 Hz, 1H), 8.10 (m; 2H), 7.75 (m, 3H), 7.68 (s, 1H), 7.58 (s, 1H), 7.40 (d, J=7.5 Hz, 1H), 6.00 (m, 1H), 5.80 (s, broad, 1H), 5.25 (d, J=14.4 Hz, 1H), 5.08 (d, J=12 Hz, 1H), 4.70 (d, J=10.2 Hz, 2H), 4.50 (s, broad, 1H), 4.20 (s, 1H), 4.05 (s, 3H), 2.80 (m, 1H), 2.55 (m, 1H), 2.10 (m, 1H), 1.80-1.40 (m, 12H), 1.00 (m, 9H); $^{31}P$ NMR ($CD_3OD$) δ 20.10.

Example 24

Preparation of Compound 24

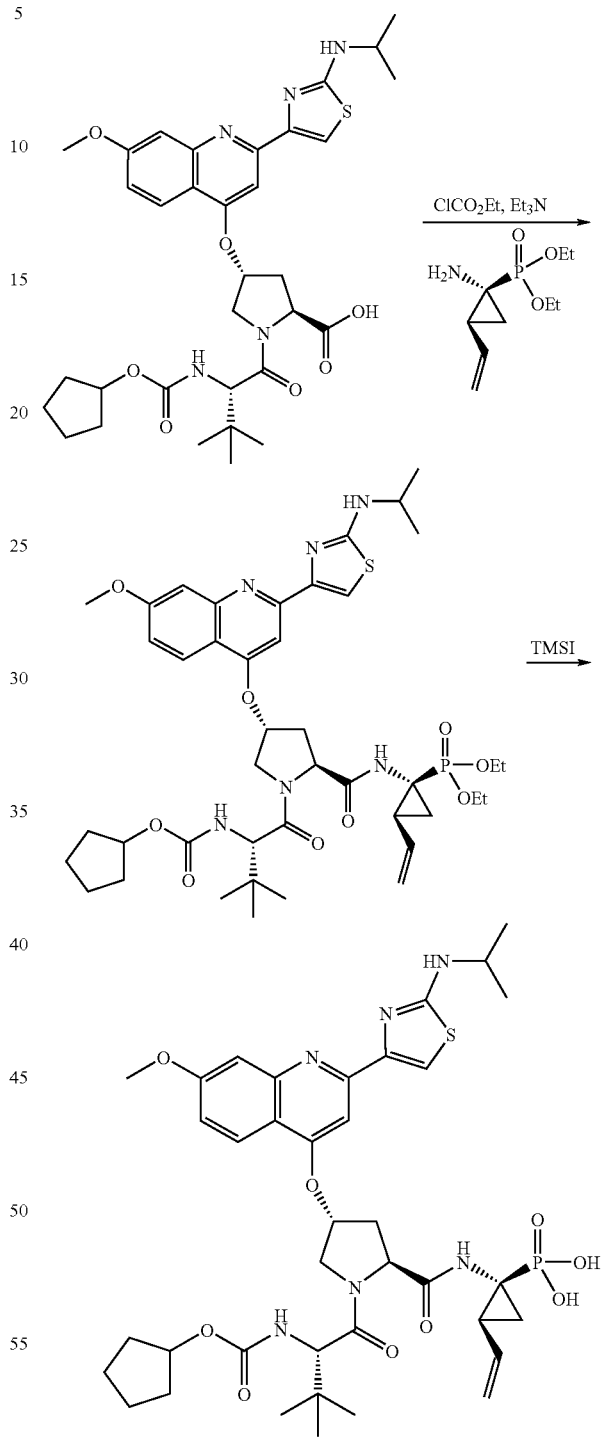

Carboxylic acid (2.24 g, 3.42 mmol) was taken up in anhydrous THF (30 mL) in a round bottomed flask and cooled to ~30° C. Ethyl chloroformate (0.65 mL, 6.84 mmol), and triethylamine (1.4 mL, 10.26 mmol) were added and the reaction was stirred with temperature maintained between −20 to −30 for 30 minutes. The disappearance of starting material was monitored via LC/MS. The aminophosphonate B (0.93 g, 4.25 mmol) was added in THF (5 mL) and the reaction was warmed to room temperature and stirred for 1 h. The reaction was then quenched with sat NH₄Cl solution and extracted with ethyl acetate. The organic layer was dried, concentrated, and purified via flash chromatography to provide the tripeptide (1.4 g, 48%). ¹H NMR (300 MHz, CD₃OD) δ 1.05 (s, 9H), 1.33 (m, 15H), 1.50-1.62 (m, 8H), 2.15 (m, 1H), 2.46 (m, 1H), 2.75 (m, 1H), 4.04-4.24 (m, 10H), 4.42 (m, 1H), 4.63 (m, 2H), 5.13 (dd, 1H, J=10.5 Hz, 1.5 Hz), 5.30 (dd, 1H, J=17 Hz, 1.5 Hz), 5.77 (m, 1H), 5.95 (m, 1H), 7.31 (dd, 1H, J=9 Hz, 2.2 Hz), 7.75 (m, 2H), 8.18 (s, 1H), 8.27 (d, 1H, J=9.3 Hz), 8.54 (s, 1H). ³¹P NMR (CD₃OD, 300 MHz) b 23.39. LC/MS: 856 (M+1).

To a solution of tripeptide (50 mg, 0.059 mmol) in 1 mL of pyridine was added one portion of NaI (45 mg, 0.029 mmol). The solution mixture was stirred at 95° C. for 1 h. The second portion of NaI (45 mg, 0.029 mmol) was then added and the reaction mixture was stirred at 95° C. for another 6 h. The mixture was concentrated in vacuo using high vacuum pump at 40° C. and three drops of a 1M solution of HCl was added. The crude mixture was dissolved in 1 mL of MeOH. The mixture was concentrated in vacuo, dissolved in 1 mL of MeOH and purified by reverse phase HPLC (eluted with 10% to 75% H₂O/CH₃CN) to give 24 as a yellow solid (18 mg, 37%). ¹H NMR (300 MHz, CD₃OD): δ 8.27 (d, J=9.1 Hz, 1H), 8.18 (s, 1H), 7.75 (s, 2H), 7.33 (dd, J=9.2, 2.7 Hz, 1H), 6.05-5.90 (m, 1H), 5.76 (bs, 1H), 5.25 (d, J=18 Hz, 1H), 5.08 (d, J=11.9 Hz, 1H), 4.73-4.60 (m, 2H), 4.50-4.40 (m, 1H), 4.25-4.05 (m, 4H), 4.04 (s, 3H), 2.82-2.75 (m, 1H), 2.58-2.40 (m, 1H), 2.20-2.00 (m, 1H), 1.70-1.40 (m, 9H), 1.34 (d, J=6.4 Hz, 6H), 1.28 (t, J=7.0 Hz, 3H), 1.05 (s, 9H), 0.97 (s, 1H). ³¹P NMR (300 MHz, CD₃OD): δ 21.3. LC/MS: 827 (M⁺+1).

Example 25

Preparation of Compound 25

The diethyl phosphonate from example 24 (380 mg, 0.45 mmol) was taken up in acetonitrile (5 mL) and treated with TMSI (0.32 mL, 2.23 mmol). The reaction was stirred at room temp for 20 minutes and monitored via LC/MS. 2,6-lutidine (1.5 mL) was then added, followed by methanol (2 mL). The mixture was concentrated and evaporated with toluene (3×20 mL). The residue was then purified via HPLC to provide the diacid 25 (240 mg, 67%). ¹H NMR (300 MHz, CD₃OD) δ 1.04 (s, 9H), 1.34 (d, 6H, J=6.3 Hz), 1.37-1.62 (m, 11H), 2.05 (m, 1H), 2.53 (m, 1H), 2.77 (m, 1H), 4.04 (s, 3H), 4.09-4.19 (m, 3H), 4.46 (m, 1H), 4.65 (m, 2H), 5.05 (dd, 1H, J=10.2 Hz, 1.5 Hz), 5.21 (dd, 1H, J=17 Hz, J=1.5 Hz), 5.76 (m, 1H), 6.00 (m, 1H), 7.30 (dd, 1H, J=9 Hz, 2.2 Hz), 7.74 (m, 1H), 8.19 (s, 1H), 8.26 (d, 1H, J=9.6 Hz). ³¹P NMR (300 MHz, CD₃OD) δ 20.03. LC/MS: 799 (M+1).

Example 26

Preparation of Compound 26

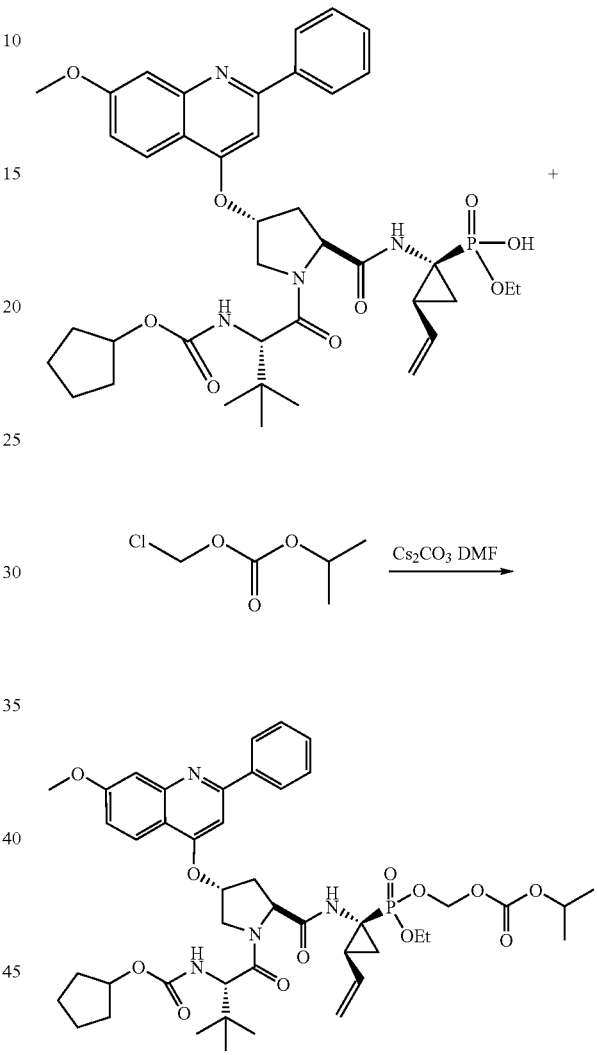

The mono acid precursor of compound 22 (200 mg, 0.262 mmol) was suspended in 6 mL of DMF under N₂. Cs₂CO₃ (427 mg, 1.31 mmol) followed by chloromethyl isopropyl carbonate (199 mg, 1.31 mmol) and tetrabutyl ammonium iodide (TBAI) (9.6 mg, 0.026 mmol) was added. The solution was heated at 55° C. for 2 hours. The solution was concentrated and purified using a reverse phase Gilson HPLC to yield compound 26 (30 mg, 13%) as a light yellow solid. ¹H NMR (300 MHz, CD₃OD): δ 8.10 (m, 3H), 7.59 (m, 3H), 7.40 (s, 1H), 7.21 (s, 1H), 7.10 (d, J=8.8 Hz, 1H), 6.80 (d, J=9.2 Hz, 1H), 5.90 (m, 1H), 5.60 (m, 3H), 5.30 (d, J=9.6 Hz, 1H), 5.18 (d, J=9.0 Hz, 1H) 4.78 (m, 3H), 4.58 (m, 2H), 4.30 (m, 3H), 4.20 (q, 2H), 4.05 (m, 2H), 3.98 (s, 3H), 2.70 (m, 1H), 2.40 (m, 1H), 2.20 (m, 1H), 1.62 (m, 2H,) 1.50 (m, 2H) 1.40 (t, 3H), 1.3-1.2 (m, 6H), 1.05 (s, 9H). ³¹P (75 MHz, CD₃OD): δ 22.843, 22.717 (diastereomers)

Example 27

Preparation of Compound 27

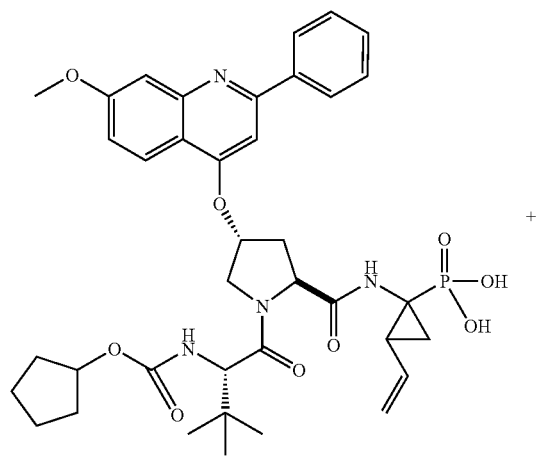

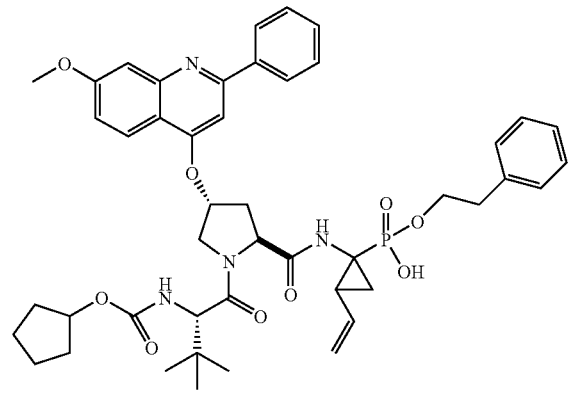

The diacid of compound 23 (22.8 mg, 0.03 mmol) was suspended in 1 mL of DMF under $N_2$. $Cs_2CO_3$ (17 mg, 0.05 mmol), tetrabutyl ammonium iodide (TBAI) (5 mg, 0.015 mmol) and (2-bromo-ethyl)-benzene (7 μl, 0.05 mmol) were added and the solution stirred at ambient temperature. After 1 hour, (2-bromo-ethyl)-benzene (35 μl. 0.25 mmol) was added and the solution was heated at 70° C. for 8 hours. The reaction was cooled to room temperature and purified using a reverse phase Gilson HPLC to yield compound 27 (2.2 mg, 8%). $^1$H NMR (300 MHz, $CD_3OD$): δ 8.40 (d, J=9.0 Hz, 1H) 8.10 (d, J=8.8 Hz, 2H), 7.78 (m, 3H) 7.62 (s, 1H), 7.50 (s, 1H), 7.40 (d, J=9.0 Hz, 1H) 7.23 (s, 1H), 7.20 (m 1H), 5.90 (m, 1H), 5.80 (s, 1H) 5.60 (m, 3H), 5.30 (t, 1H), 5.18 (d, J=9.0 Hz, 1H) 4.78 (m, 2H), 4.58 (s, 1H), 4.30 (m, 3H), 4.20 (m, 3H), 4.05 (s, 3H), 2.92 (q, 2H), 2.70-2.6 (m, 1H), 2.43-2.40 (m, 1H), 2.18-2.05 (m, 1H), 1.62 (m, 2H, 1.50 (m, 2H)m 1.40 (t, 3H), 1.3-1.2 (m, 6H), 1.05 (s, 9H). $^{31}$P (75 MHz, $CD_3OD$): δ 20.702 (s, 1P)

Example 28

Preparation of Compound 28

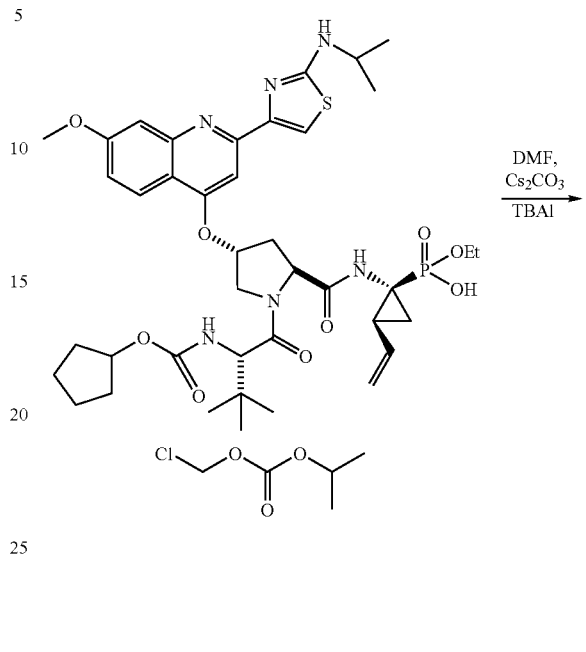

The mono acid (200 mg, 0.24 mmol) was suspended in 8 mL of DMF under $N_2$. $Cs_2CO_3$ (394 mg, 1.21 mmol) followed by chloromethyl ethyl chloroformate (8) (167 mg, 1.21 mmol) and tetrabutyl ammonium iodide (TBAI) (8.8 mg, 0.024 mmol) were added. The solution was heated at 55° C. for 2 hours. The solution was concentrated and purified using a reverse phase Gilson HPLC to yield compound 28 (32.5 mg, 15%). $^1$H NMR (300 MHz, $CD_3OD$): δ 8.10 (d, J=9.5 Hz, 2H), 7.42 (d, J=8.8 Hz, 2H), 7.38 (s, 1H), 7.10 (d, J=8.8 Hz, 1H), 6.78 (d, J=9.2 Hz, 1H), 5.90 (m, 1H), 5.60 (m, 2H), 5.45 (s, 1H) 5.30 (d, J=9.6 Hz, 1H), 5.18 (d, J=9.0 Hz, 1H) 4.78 (s, 1H), 4.58 (m, 1H), 4.30 (m, 1H), 4.20 (q, 2H), 4.05 (m, 2H), 3.98 (s, 3H), 2.70 (m, 1H), 2.40 (m, 1H), 2.20 (m, 1H), 1.62 (m, 2H), 1.50 (m, 2H) 1.40 (t, 3H), 1.3-1.2 (m, 9H), 1.05 (s, 9H). $^{31}$P (75 MHz; $CD_3OD$): δ 22.813, 22.697 (diastereomers)

Example 29

Preparation of Compound 29

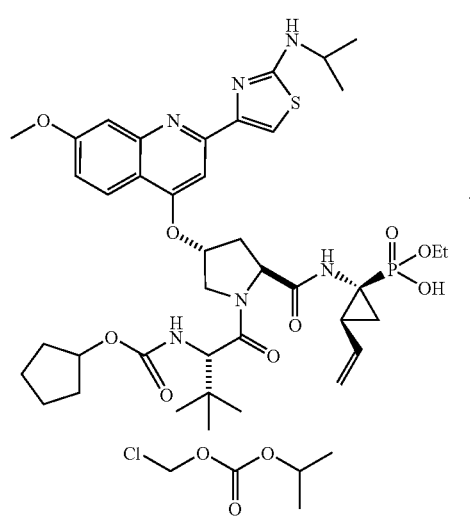

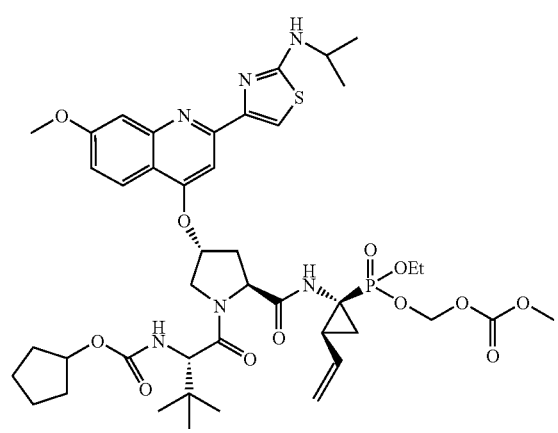

The mono acid (220 mg, 0.26 mmol) was suspended in 7 mL of DMF. $Cs_2CO_3$ (433 mg, 1.33 mmol) followed by carbonic acid chloromethyl ester methyl ester (184 mg, 1.33 mmol) and tetrabutyl ammonium iodide (TBAI) (9.6 mg, 0.026 mmol) were added. The solution was heated at 55° C. for 2 hours and stirred for 8 hours at ambient temperature. The solution was purified using a reverse phase Gilson HPLC to yield compound 29 (9 mg, 4%). $^1$H NMR (300 MHz, CDCl$_3$): δ 8.00 (d, J=9.5 Hz, 1H), 7.42 (d, J=8.8 Hz, 3H), 7.10 (d, J=8.8 Hz, 1H), 6.10-5.82 (m, 1H), 5.63 (t, 2H), 5.45 (s, 1H) 5.30 (d, J=9.6 Hz, 1H), 5.20 (d, J=9.0 Hz, 1H), 5.00 (s, 1H), 4.70 (m, 1H) 4.43 (m, 1H), 4.20 (q, 2H), 4.05 (m, 2H), 3.98 (s, 3H), 2.90 (m, 1H), 2.40 (m, 1H), 2.10 (m, 1H), 1.39 (d, J=8.8 Hz, 6H), 1.30 (t, 3H), 1.05 (s, 9H). $^{31}$P (75 MHz, CD$_3$OD): δ 22.466, 22.059 (diastereomers).

Example 30

Preparation of Compound 30

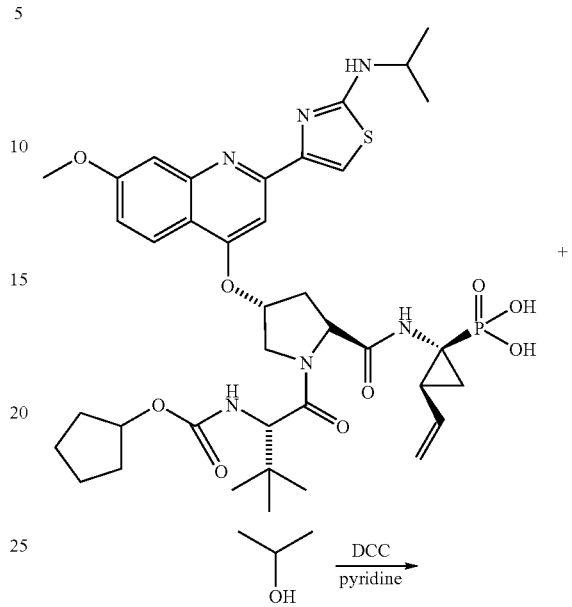

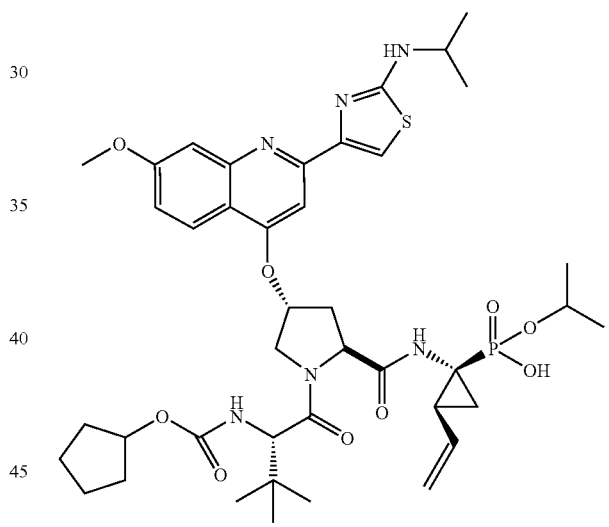

The diacid (220 mg, 0.27 mmol) was suspended in 6 mL of pyridine and isopropanol (49 mg, 0.83 mmol) was added. The solution was heated at 55° C. and DCC (11 mg, 0.54 mmol) was added. After 2 hours, there was no product formation and the solution was heated at 80° C. After 1 hour, DCC (28 mg, 0.13 mmol) was added with continued stirring at 80° C. After 10 hours, DCC (28 mg, 0.13 mmol) was added. After 3 hours, the solution was concentrated and purified using reverse phase Gilson HPLC to yield compound 30 (60 mg, 27%). $^1$H NMR (300 MHz, CD$_3$OD): δ 8.21 (d, J=9.2 Hz, 1H), 8.10 (s, 1H), 7.70 (m, 2H), 7.21 (d, J=9.0 Hz, 1H), 7.10 (d, J=8.8 Hz, 1H), 6.80 (d, J=9.2 Hz, 1H), 6.20-6.10 (m, 1H), 5.60 (s, 1H), 5.20 (d, J=9.6 Hz, 1H), 4.98 (d, J=9.0 Hz, 1H) 4.61-4.25 (m, 3H), 4.20 (d, 1H), 4.18 (m, 2H), 4.05 (s, 3H), 3.42 (m, 2H), 3.22 (m, 2H), 2.80 (m, 1H), 2.60 (m, 1H), 2.10 (m, 1H), 1.9 (m, 2H), 1.39 (d, J=8.8 Hz, 6H), 1.30 (t, 3H), 1.05 (s, 9H). $^{31}$P (75 MHz, CD$_3$OD): δ 15.575.

Example 31 and 32

Preparation of Compound 31 and 32

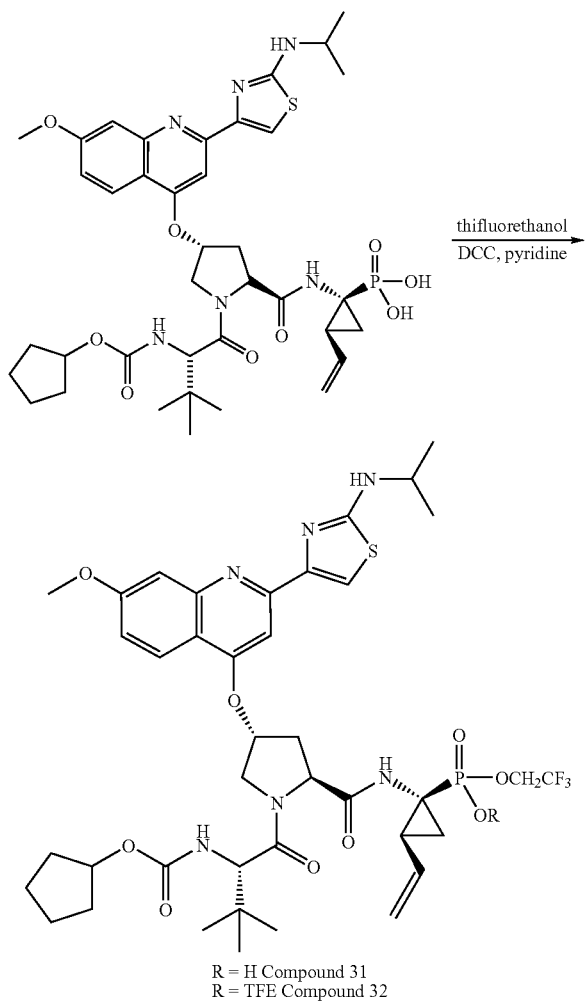

R = H Compound 31
R = TFE Compound 32

To a round bottomed flask was added diacid (112 mg, 0.14 mmol) in pyridine (2 mL). Trifluoroethanol (0.081 mL, 1.12 mmol) and DCC (0.7 mL, 0.7 mmol) were added and the reaction was heated to 70° C. The reaction was monitored via LC/MS and stopped when the ration of mono-trifluoroethyl to bis-trifluoroethyl was approximately 1:1. The reaction was quenched with water, extracted with ethyl acetate, washed with 0.5M HCl, the with saturated sodium bicarbonate solution. The organic layer was then dried, concentrated and purified via HPLC to provide mono TFE product 31 (16.5 mg, 12% yield) and bis-TFE product 32 (20 mg, 16% yield).

31: $^1$H NMR (300 MHz, CD$_3$OD) δ 0.97-1.83 (m, 22H), 1.83-1.87 (m, 4H), 2.06 (m, 1H), 2.51 (m, 1H), 2.77 (m, 1H), 3.45 (m, 1H), 4.04-4.19 (m, 7H), 4.29 (m, 1H), 4.50 (br s, 2H), 4.67 (m, 2H), 5.03 (d, 1H, J=10.2 Hz), 5.18 (d, 1H, J=17.4 Hz), 5.75 (s, 1H), 5.99 (m, 1H), 7.31 (d, 1H, J=9 Hz), 7.73 (s, 2H), 8.20 (s, 1H), 8.27 (d, 1H. J=9.6 Hz). $^{31}$P NMR (300 MHz) δ 18.89.

32: $^1$H NMR (300 MHz) δ 1.03 (s, 9H), 1.48 (d, 9H, J=6.3 Hz), 1.47-1.80 (m, 17H), 2.14 (m, 1H), 2.48 (m, 1H), 2.91 (m, 1H), 3.75 (m, 1H), 3.94 (s, 4H), 4.24-4.45 (m, 7H), 4.71 (m, 1H), 4.98 (m, 1H), 5.09 (d, 1H, J=7.2 Hz), 5.20-5.41 (m, 5H), 5.85 (m, 1H), 7.02 (dd, 1H, J=9 Hz, 2.1 Hz), 7.38 (s, 1H), 7.46 (s, 1H), 7.55 (s, 1H), 7.99 (d, 1H, J=8.4 Hz). $^{31}$P NMR δ 26.07.

Example 33

Preparation of Compound 33

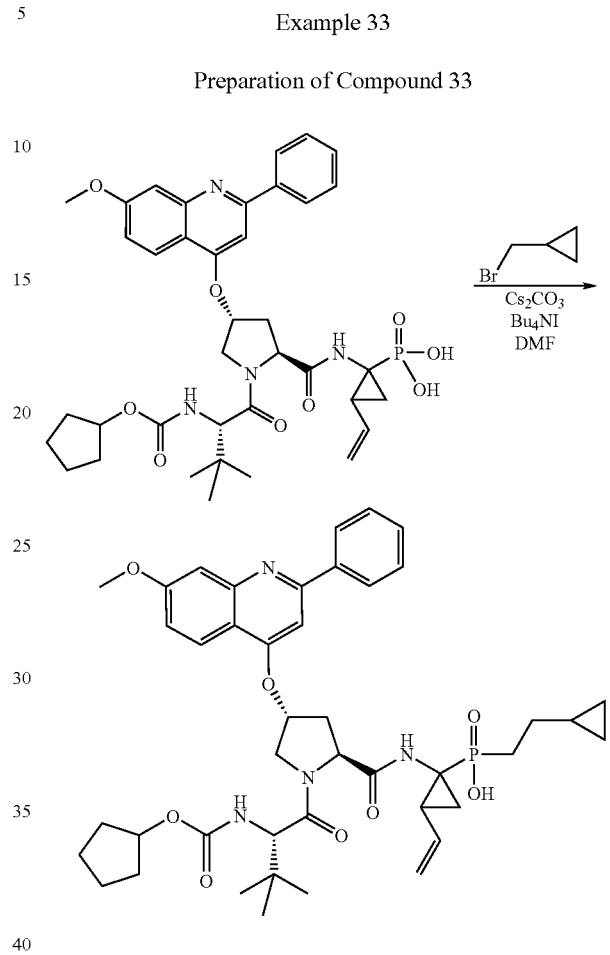

A mixture of 24.5 mg (33.3 mmol) of the diastereomeric mixture of the diacid, 6.1 mg (16.5 mmol) of tetra-n-butylammonium iodide, 16.2 mg (49.7 mmol) of cesium carbonate in 1 mL of DMF was stirred at rt as 5 uL (51.6 mmol) of cyclopropylmethyl bromide was added. After the mixture was stirred at rt for 18 h and at 70° C. for 4 h, 5 uL (51.6 mmol) of the bromide was added more and the mixture was stirred at 70° C. for 20 h. Additional 12.0 mg (36.8 mmol) of cesium carbonate was added and the mixture was stirred at 70° C. for 3.5 h, before 12 uL (123.7 mmol) of the bromide was added and stirred at 70° C. for 1.5 h. After further addition of 10 uL (103.1 mmol) of the bromide and stirring the mixture at 70° C. for 1.5 h, the mixture was filtered. The product in the filtrate was purified by HPLC and 6.2 mg (24%) of the compound 33 was obtained after lyophilization as a mixture of two diastereomers: $^1$H NMR (300 MHz, CD$_3$OD): δ 8.37 (br d, J=9.3 Hz, 1H), 8.08-8.11 (m, 2H), 7.71-7.81 (m, 3H), 7.67 (s, 1H), 7.54 (br d, J=2.1 Hz, 1H), 7.40 (br d, J=9.0 Hz, 1H), 5.90-6.04 (m, 1H), 5.83 (br, 1H), 5.27 (t, J=17.5 Hz, 1H), 5.06 (d, J=10.2 Hz, 1H), 4.62-4.71 (m, 2H), 4.46 (br, 1H), 4.18 (s, 1H), 4.04-4.12 (br, 1H), 4.06 (s, 3H), 3.78-3.95 (m, 2H), 2.75-2.83 (m, 1H), 2.46-2.57 (m, 1H), 1.98-2.15 (m, 1H), 1.28-1.68 (m, 10H), 1.05-1.20 (m, 1H), 1.05 and 1.03 (two s, 9H), 0.46-0.55 (m, 2H), 0.26-0.32 (m, 2H); $^{31}$P NMR (75 MHz, CD$_3$OD) δ 20.41, 20.55; LC/MS: 789 (M$^+$+1).

Example 34

Preparation of Compound 34

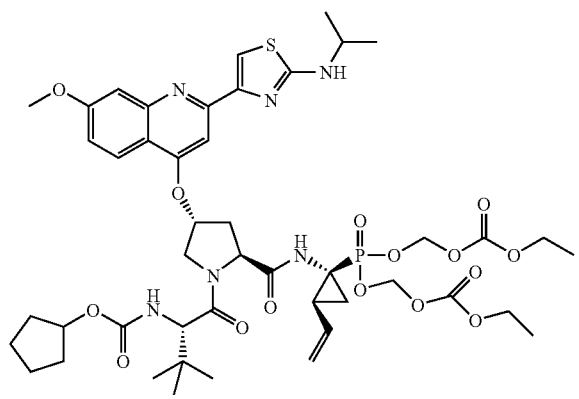

A solution of 1.028 g (1.29 mmol) of the diacid, 118.2 mg (0.32 mmol), and 2.7 mL (19.4 mmol) of triethylamine in 20 mL N-methylpyrrolidone (20 mL) was stirred at rt as 2.054 g (14.8 mmol) of carbonic acid chloromethyl ester ethyl ester was added. The mixture was stirred at 50° C. for 22 h and cooled to rt before filtration through a membrane filter. The filtrate was purified by preparative HPLC and the pure product containing fractions were freeze-dried to obtain 284 mg (22%) of compound 34: $^1$H NMR (300 MHz, CDCl$_3$): δ 7.99 (d, J=9.3 Hz, 1H), 7.46 (s, 1H), 7.40 (s, 1H), 7.37 (br, 1H), 7.31 (br, 1H), 7.02 (d, J=8.4 Hz, 1H), 5.94 (dt, J=17.1 and 9.7 Hz, 1H), 5.60-5.74 (m, 4H), 5.15-5.44 (m, 5H), 5.00 (br, 1H), 4.65 (t, J=7.1 Hz, 1H), 4.35-4.44 (m, 2H), 4.13-4.26 (m, 4H), 3.96-4.05 (m, 1H), 3.94 (s, 3H), 3.66-3.77 (m, 1H), 2.81-2.90 (m, 1H), 2.40-2.49 (m, 1H), 2.00-2.21 (m, 1H), 1.47-1.88 (m, 10H), 1.35 (d, J=6.3 Hz, 6H), 1.20-1.38 (m, 6H), 1.04 (s, 9H); $^{31}$P NMR (75 MHz, CDCl$_3$) δ 22.32 (~0.1P), 21.78 (~0.9P); LC/MS: 1003 (M$^+$+1).

Example 35

Preparation of Compound 35

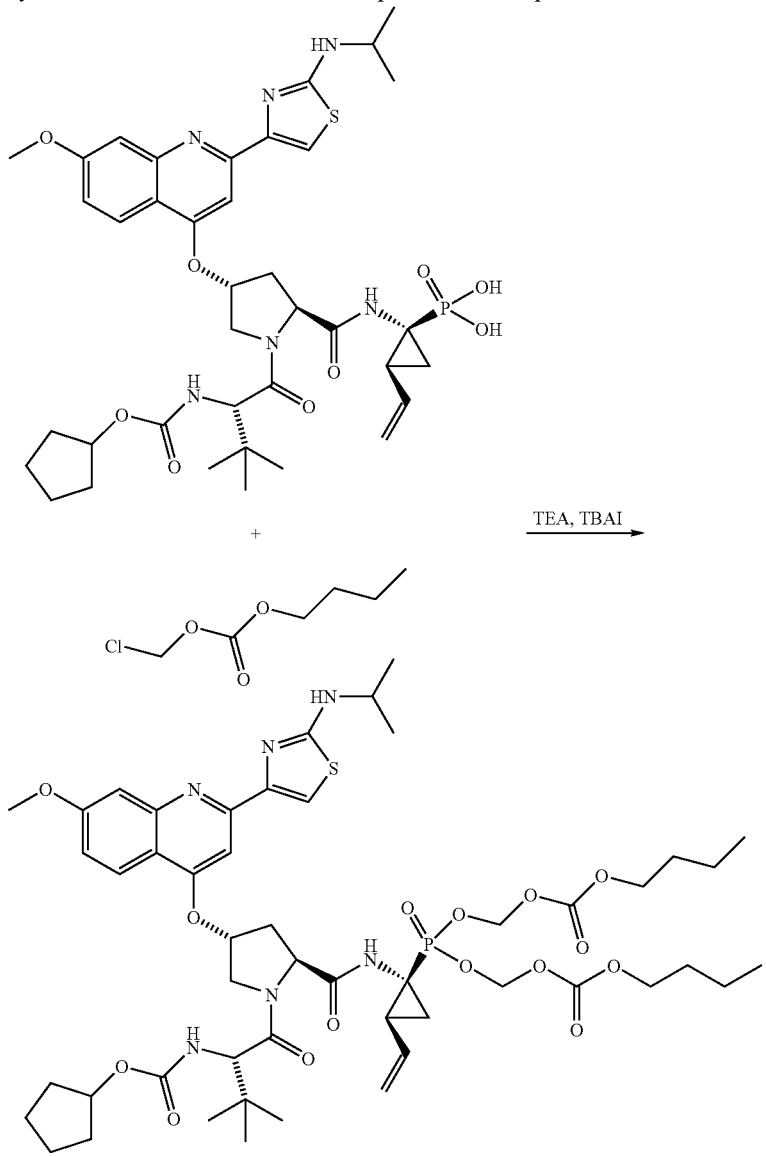

The diacid (150 mg, 0.187 mmol) was suspended in 3 mL of DMF. Butyl chloromethyl carbonate (311 mg, 1.87 mmol), triethylamine (390 μl, 2.80 mmol) and tetrabutyl ammonium iodide (TBAI) (17 mg, 0.05 mmol) were added. The solution was heated at 50° C. for 6 hours and at 70° C. for 3 hours. The solution was cooled to room temperature, purified using a Reverse Phase Gilson HPLC to yield compound 35 as a light yellow solid (45 mg, 23%). $^1$H NMR (300 MHz, CD$_3$OD): δ 8.07 (d, J=8.8 Hz, 1H), 7.50 (s, 1H), 7.43 (s, 1H), 7.36 (s, 1H), 7.06 (d, J=9.5 Hz, 1H), 6.00-5.84 (m, 1H), 5.68 (dd, 4H), 5.5 (s, 1H), 5.36 (d, J=9.8 Hz, 1H), 5.18 (d, J=10 Hz, 1H), 4.79 (s, 1H), 4.56-4.47 (m, 1H), 4.29 (s, 1H), 4.15-4.13 (m, 2H), 3.95 (s, 3H), 2.71-2.66 (m, 1H), 2.40-2.32 (m, 1H), 2.25-2.20 (m, 1H), 1.64-1.54 (m, 7H), 1.33-1.31 (m, 8H), 1.06 (s, 9H), 0.93-0.87 (m, 6H). $^{31}$P (75 MHz, CD$_3$OD): δ 23.245, 22.280

Example 36

Preparation of Compound 36

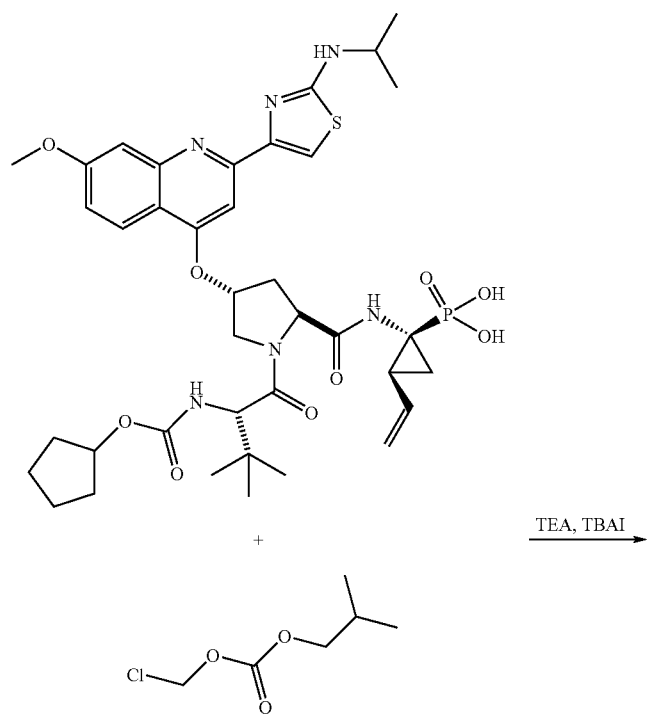

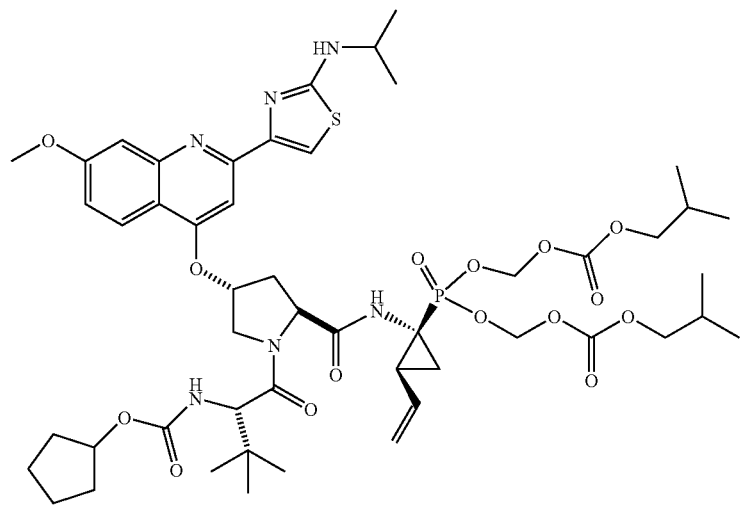

The diacid (150 mg, 0.187 mmol) was suspended in 3 mL of DMF. Chloromethyl isobutyl carbonate (311 mg, 1.87 mmol), triethylamine (390 μl, 2.80 mmol) and tetrabutyl ammonium iodide (TBAI) (17 mg, 0.05 mmol) were added. The solution was heated at 70° C. for 5 hours. The solution was cooled to room temperature, purified using a Reverse Phase Gilson HPLC to yield compound 36 (30 mg, 15%) as a light yellow solid. $^1$H NMR (300 MHz, CDCl$_3$): δ 8.02 (d, J=9.2 Hz, 1H), 7.43 (s, 1H), 7.34 (s, 1H), 7.06 (d, J=9.7 Hz, 1H), 5.97-5.88 (m, 1H), 5.70-5.62 (m, 4H), 5.5 (s, 1H), 5.39 (d, J=9.8 Hz, 1H), 5.18 (d, J=10 Hz, 1H), 4.79 (s, 1H), 4.56 (m, 1H), 4.29 (s, 1H), 4.17 (m, 2H), 3.95 (s, 3H), 3.80 (m, 2H) 2.90 (m, 1H), 2.43 (m, 1H), 2.18 (m, 1H), 1.64 (m, 7H), 1.33 (m, 8H), (1.06) (s, 9H), 0.88 (m, 6H). $^{31}$P (75 MHz, CD$_3$OD): δ 22.406, 21.777.

Example 37

Preparation of Compound 37

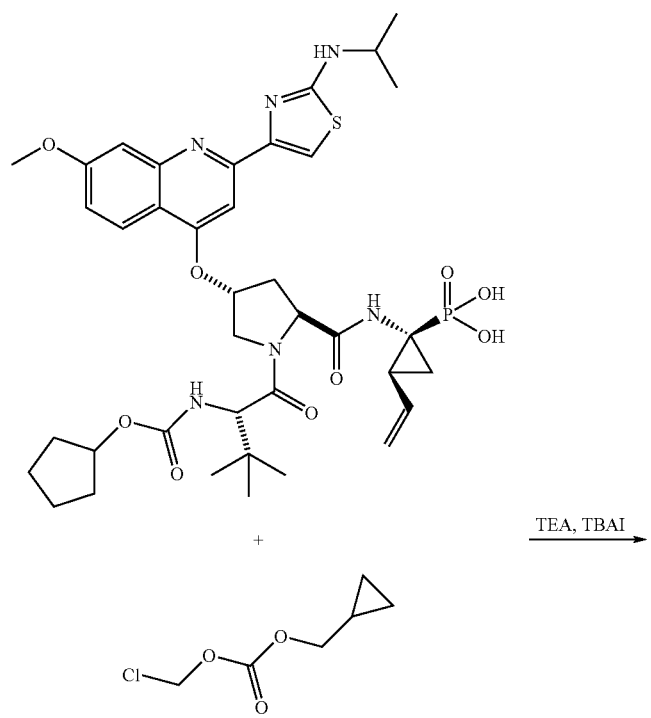

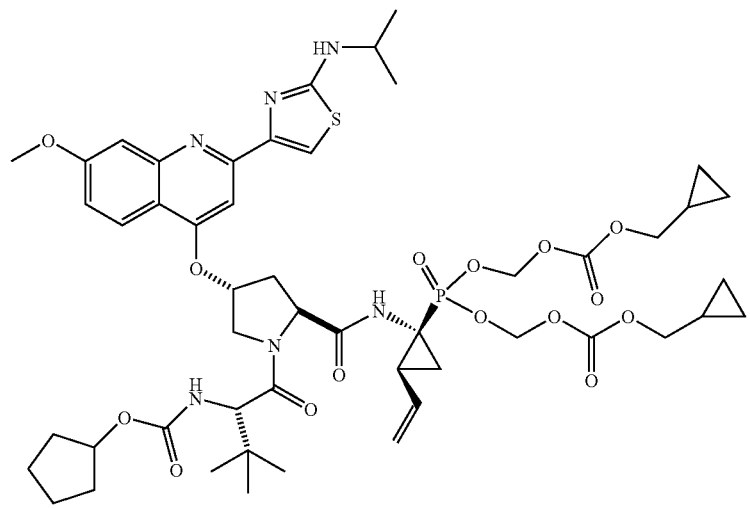

The diacid (150 mg, 0.187 mmol) was suspended in 3 mL of DMF. Chloromethyl cyclopropyl methyl carbonate (307 mg, 1.87 mmol), triethylamine (390 μl, 2.80 mmol) and tetrabutyl ammonium iodide (TBAI) (17 mg, 0.05 mmol) were added. The solution was heated at 70° C. for 5 hours. The solution was cooled to room temperature, purified using a Reverse Phase Gilson HPLC to yield compound 37 (35 mg, 18%) as a light yellow solid. $^1$H NMR (300 MHz, CDCl$_3$): δ 8.00 (d, J=9.2 Hz, 1H), 7.43 (s, 1H), 7.34 (s, 1H), 7.06 (d, J=9.7 Hz, 1H), 5.97-5.88 (m, 1H), 5.70-5.62 (m, 4H), 5.50 (s, 1H), 5.26 (d, J=9.8 Hz, 1H), 4.98 (s, 1H), 4.67 (t, 1H), 4.42 (m, 2H), 4.17 (m, 2H), 3.95 (s, 3H), 2.90 (m, 1H), 2.47 (m, 1H), 2.18 (m, 1H), 1.64 (m, 7H), 1.35 (d, 6H), 1.09 (s, 9H), 0.59 (t, 2H), 0.29 (m, 2H). $^{31}$P (75 MHz, CD$_3$OD): δ 21.772.

Example 38

Preparation of Compound 38

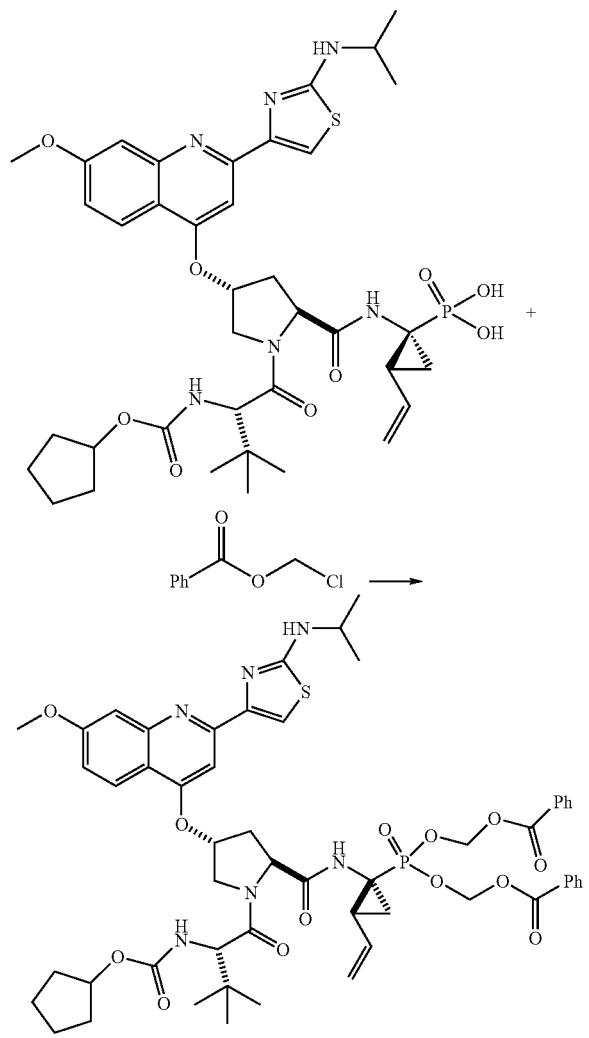

The diacid (150 mg, 0.187 mmol) was suspended in 3 mL of DMF. Chloromethyl benzoate (319 mg, 1.87 mmol), triethylamine (390 μl, 2.80 mmol) and tetrabutyl ammonium iodide (TBAI) (17 mg, 0.05 mmol) were added. The solution was heated at 70° C. for 5 hours. The solution was cooled to room temperature, purified using a Reverse Phase Gilson HPLC to yield compound 38 (60 mg, 30%) as a light yellow solid. $^1$H NMR (300 MHz, CDCl$_3$): δ 8.01 (d, J=7.0 Hz, 1H), 7.95 (d, J=8.2 Hz, 2H) 7.48 (dd, 2H), 7.06 (d, J=9.7 Hz, 1H), 5.99 (m, 3H), 5.40 (s, 1H), 5.15 (d, J=10 Hz, 1H), 4.87 (s, 1H), 4.56 (t, 1H), 4.47 (d, 2H), 4.27 (s, 1H), 3.94 (s, 3H), 2.58 (m, 1H), 2.37 (m, 1H), 2.24 (m, 1H), 1.64 (m, 6H), 1.29 (d, 6H), 1.04 (s, 9H). $^{31}$P (75 MHz, CD$_3$OD): δ 23.662, 22.873.

Example 39

Preparation of Compound 39

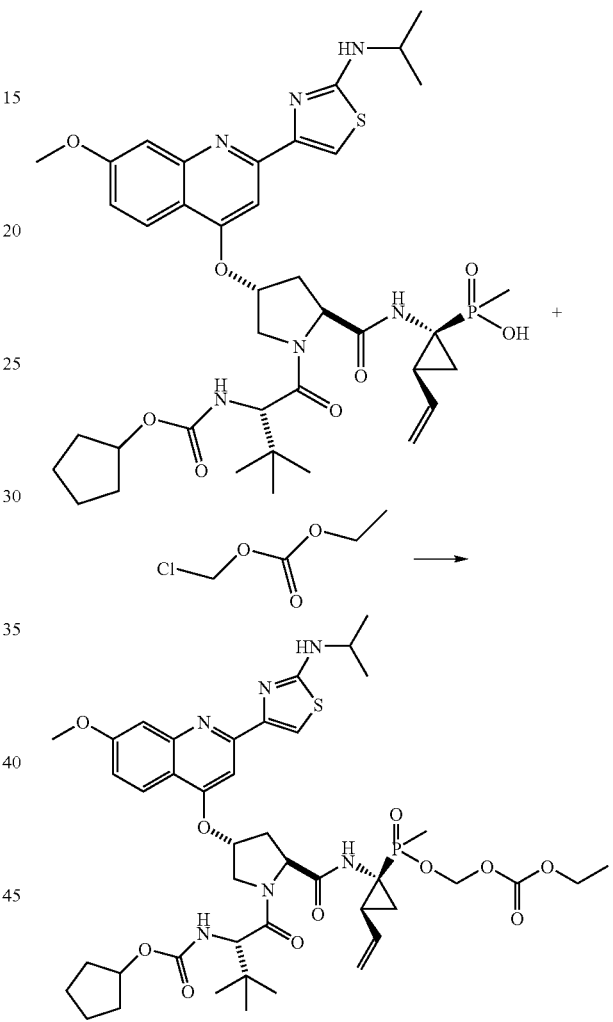

The phosphinic acid (83 mg, 0.102) was suspended in 1.5 mL of DMF. chloromethyl ethyl chloroformate (142 mg, 1.02 mmol), triethylamine (213 μl, 1.53 mmol) and tetrabutyl ammonium iodide (TBAI) (9 mg, 0.02 mmol) were added. The solution was heated at 70° C. for 2 hours. The solution was cooled to room temperature, purified using a Reverse Phase Gilson HPLC to yield compound 39 $^1$H NMR (300 MHz, CD$_3$OD): δ 8.03 (d, J=8.8 Hz, 1H), 7.43 (s, 2H) 7.33 (s, 1H), 7.03 (d, J=9.2 Hz, 1H), 5.98 (m, 1H), 5.95 (m, 1H), 5.60 (d, 2H), 5.44 (s, 1H), 5.33 (dd, 1H), 5.17 (t, 1H), 4.87 (s, 1H), 4.52 (d, J=9.4, 1H), 4.56 (t, 1H), 4.47 (d, 2H), 4.27 (s, 1H), 4.24 (m, 3H), 3.94 (s, 3H), 2.66 (m, 1H), 2.58 (m, 1H), 2.37 (m, 1H), 2.14 (m, 1H), 1.64 (m, 6H), 1.33 (d, 6H), 1.20 (t, 3H), 1.29 (d, 6H), 1.04 (s, 9H). $^{31}$P (75 MHz, CD$_3$OD): δ 53.082, 57.428.

Example 40

Preparation of Compound 40

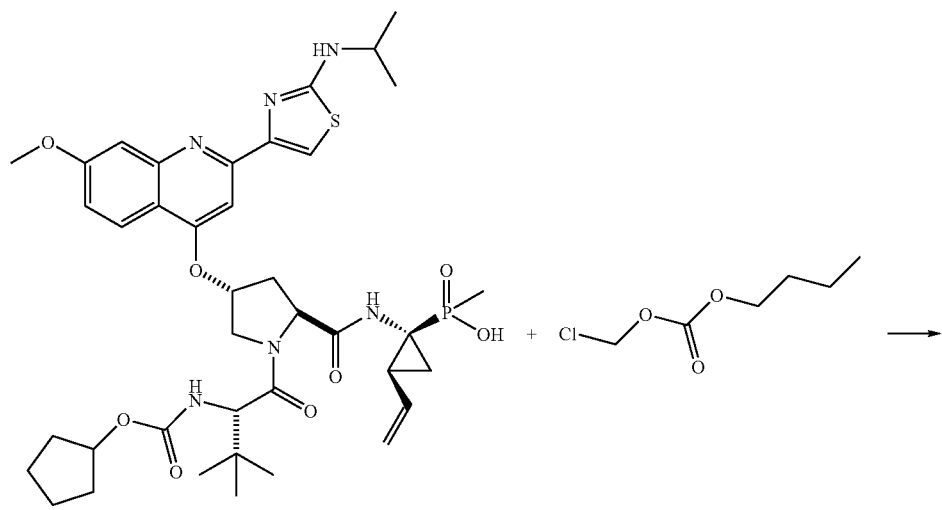

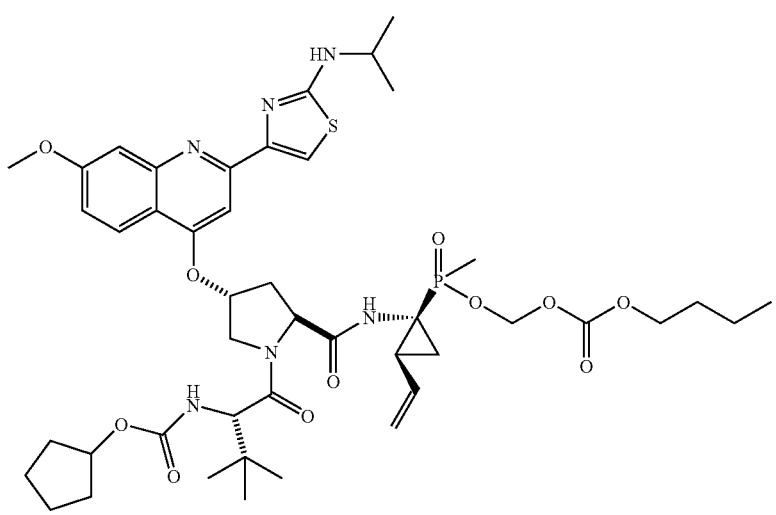

The phosphinic acid (63 mg, 0.079 mmol) was suspended in 1 mL of DMF. Butyl chloromethyl carbonate (131 mg, 0.79 mmol), triethylamine (165 µl, 1.18 mmol) and tetrabutyl ammonium iodide (TBAI) (7 mg, 0.01 mmol) were added. The solution was heated at 70° C. for 2 hours. The solution was cooled to room temperature, purified using a Reverse Phase Gilson HPLC to yield compound 40. $^1$H NMR (300 MHz, CD$_3$OD): δ 8.06 (d, J=9.2 Hz, 1H), 7.48 (d, J=6.4 Hz, 1H) 7.43 (s, 1H), 7.35 (s, 1H), 7.04 (d, J=8.5 Hz, 1H), 5.98 (m, 1H), 5.95 (m, 1H), 5.60 (d, 2H), 5.44 (s, 1H), 5.33 (dd, 1H), 5.17 (t, 1H), 4.87 (s, 1H), 4.52 (d, J=9.4, 1H), 4.56 (t, 1H), 4.47 (d, 2H), 4.27 (s, 1H), 4.24 (m, 3H), 3.94 (s, 3H), 2.66 (m, 1H), 2.58 (m, 1H), 2.37 (m, 1H), 2.14 (m, 1H), 1.64 (m, 6H), 1.33 (d, 6H), 1.20 (t, 3H), 1.29 (d, 6H), 1.04 (s, 9H). $^{31}$P (75 MHz, CD$_3$OD): δ 53.060, 57.414.

Example 41

Preparation of Compound 41

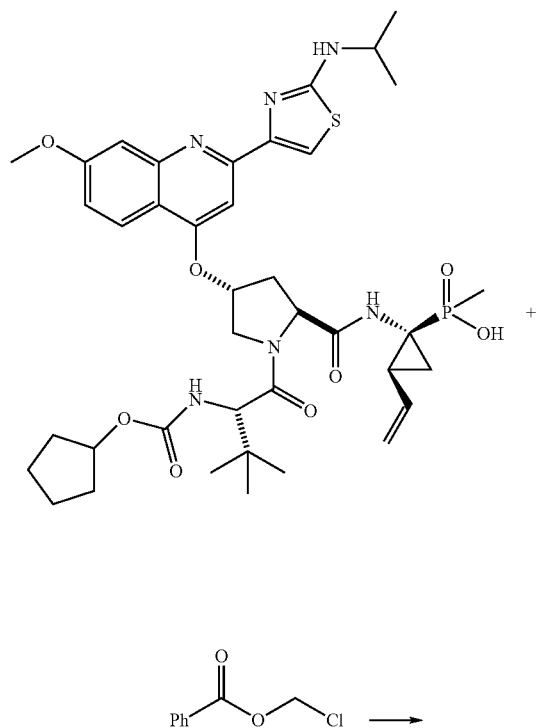

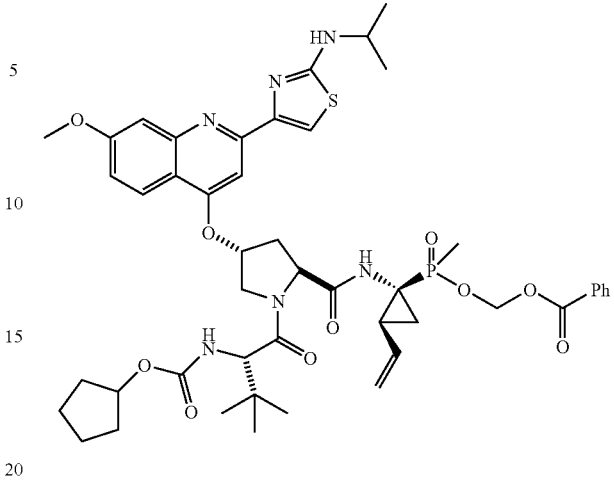

The phosphinic acid (65 mg, 0.08 mmol) was suspended in 1.5 mL of DMF. Chloromethyl benzoate (113 mg, 0.81 mmol), triethylamine (167 µl, 1.20 mmol) and tetrabutyl ammonium iodide (TBAI) (7 mg, 0.02 mmol) were added. The solution was heated at 70° C. for 3 hours. The solution was cooled to room temperature, purified using a Reverse Phase Gilson HPLC to yield compound 41 (20 mg, 27%). $^1$H NMR (300 MHz, CD$_3$OD): δ 8.08 (dd, 2H), 7.63 (d, J=7.3 Hz, 1H), 7.48 (d, J=6.4 Hz, 1H) 7.42 (s, 1H), 7.35 (s, 1H), 7.04 (d, J=9.1 Hz, 1H), 5.98 (m, 1H), 5.95 (m, 1H), 5.60 (d, 2H), 5.44 (s, 1H), 5.33 (d, 1H), 5.18 (d, J=9.1 Hz, 1H), 5.14 (d, J=9.1, 1H), 4.87 (s, 1H), 4.52 (d, J=9.4, 1H), 4.56 (d, 1H), 4.27 (s, 1H), 3.94 (s, 3H), 2.66 (m, 1H), 2.58 (m, 1H), 2.37 (m, 1H), 2.14 (m, 1H), 1.64 (m, 6H), 1.33 (d, 6H), 1.04 (s, 9H). $^{31}$P (75 MHz, CD$_3$OD): δ 52.994, 57.542.

Example 42

Preparation of Compound 42

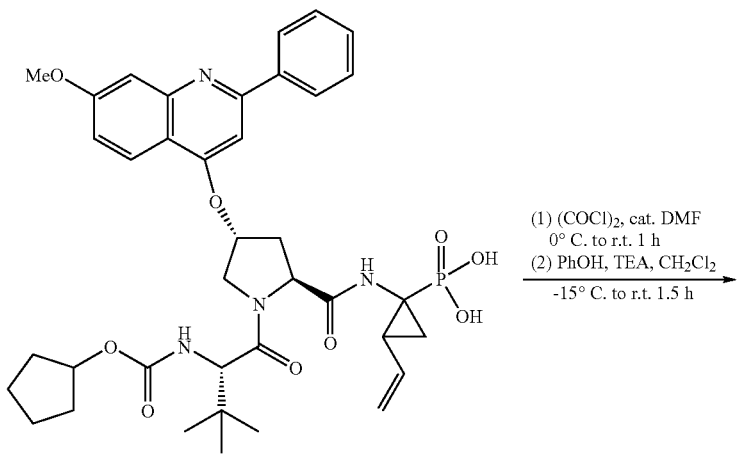

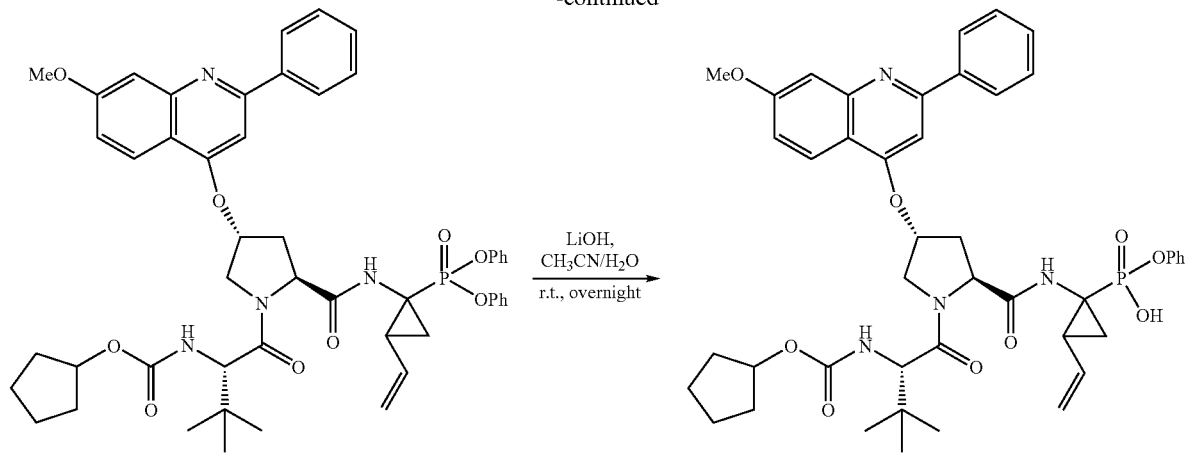

To a solution of diacid (0.448 g, 6.10 mmol) in 6 mL of CH₂Cl₂ at 0° C. was added oxalyl chloride (0.55 mL, 0.122 mol) and catalytic amount of DMF (150 μL). The reaction mixture was stirred at 0° C. for 1 h and warmed to room temperature for 1 h. The solvent was removed on rotavap, co-evaporated with toluene, and dried under vacuum to give a pale yellow solid which was dissolved in 8 mL of CH₂Cl₂ and cooled to −15° C. Triethylamine (0.43 mL, 30.50 mmol) and phenol (0.574 g, 61.00 mmol) were added. The reaction mixture was stirred at −15° C. for 1 h and warmed to room temperature overnight. The reaction mixture was poured into aqueous NH₄Cl and extracted with CH₂Cl₂ (3×). The organic layers were washed with H₂O, dried with Na₂SO₄, filtered and concentrated. The crude product was purified by column chromatography on silica gel (3% MeOH/CH₂Cl₂) to give the diphenyl phosphonate 42 (0.360 g, 67%, 1:1 diastereomeric mixture) as an off-white solid: $^1$H NMR (CDCl₃) b 8.06 (m, 3H), 7.50 (m, 5H), 7.30-7.03 (m, 11H), 5.93 (m, 1H), 5.36 (m, 2H), 5.02 (m, 1H), 4.80 (m, 1H), 4.50-4.30 (m, 2H), 4.00 (s, 3H), 2.95 (m, 1H), 2.45 (m, 1H), 2.20 (m, 1H), 1.82-1.50 (m, 12H), 1.00 (s, 9H); $^{31}$P NMR (CDCl₃) δ 16.18, 15.49. LC/MS: 888 (M⁺+1).

Example 43

Preparation of Compound 43

To a solution of diphenyl phosphonate 42 (25 mg, 0.028 mmol) in 3 mL solvents (1:1 CH₃CN/H₂O) at r.t. was added LiOH (10 mg, 0.42 mmol). The reaction mixture was stirred at room temperature overnight, acidified with 6N HCl, and concentrated. The crude product was purified by Gilson HPLC (0.1% TFA/CH₃CN/H₂O) to give the monophenyl phosphonate 43 (13 mg, 60%) as a white solid: $^1$H NMR (CD₃OD) δ 8.37 (m, 1H), 8.09 (m, 2H), 7.78 (m, 3H), 7.63 (m, 1H), 7.54 (m, 1H), 7.40 (m, 1H), 7.24 (m, 4H), 7.05 (m, 1H), 6.01 (m, 1H), 5.80 (m, 1H), 5.25 (m, 1H), 5.02 (m, 1H), 4.70 (m, 2H), 4.50 (m, 1H), 4.05 (m, 3H), 2.76 (m, 1H), 2.45 (m, 1H), 2.15 (m, 1H), 1.70-1.30 (m, 12H), 1.00 (m, 9H); $^{31}$P NMR (CD₃OD) δ 16.69.

LC/MS: 811 (M⁺+1).

Example 44

Preparation of Compound 44

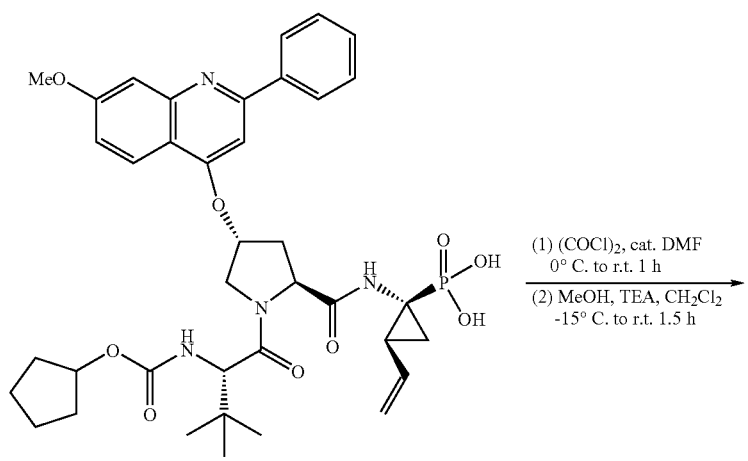

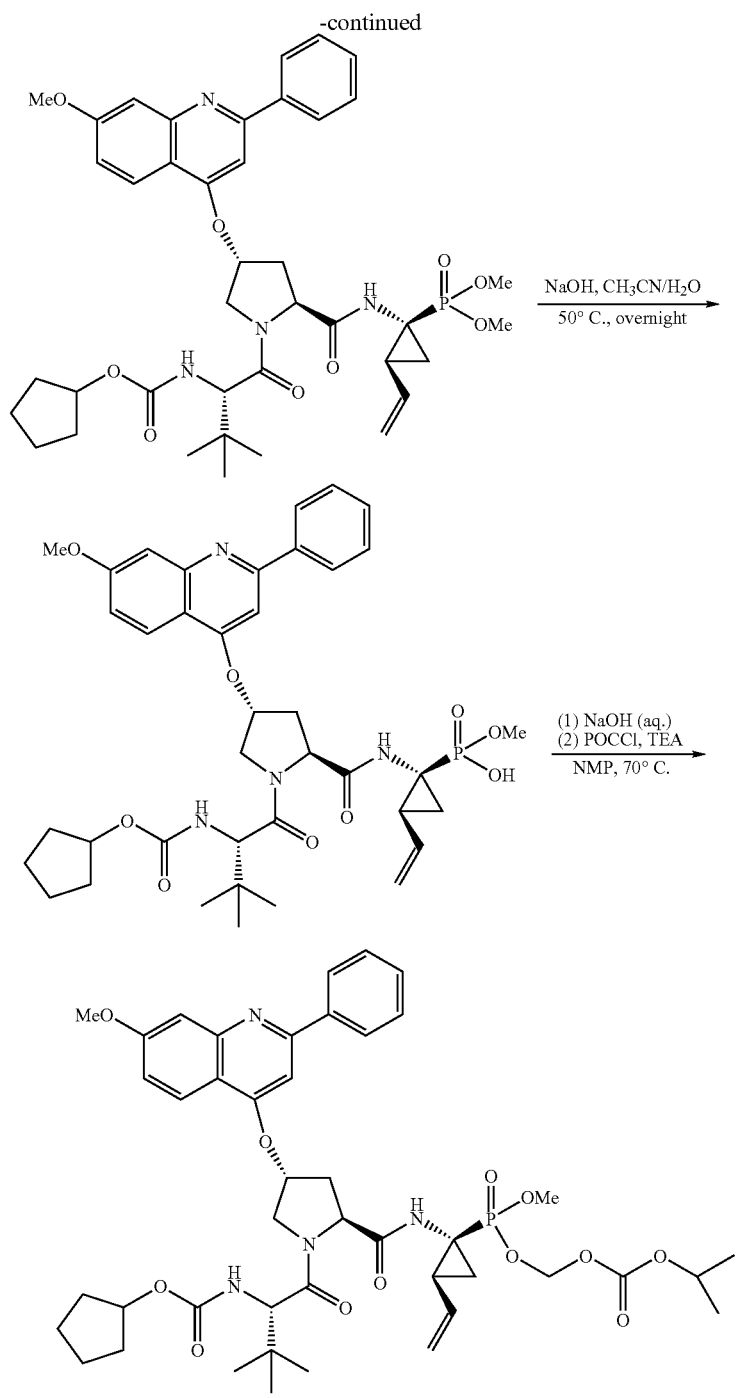

To a solution of diacid (0.15 g, 0.20 mmol) in 2 mL of CH$_2$Cl$_2$ at 0° C. was added oxalyl chloride (0.36 mL, 4.00 mmol) and catalytic amount of DMF (70 αL). The reaction mixture was stirred at 0° C. for 1 h and warmed to room temperature for 1 h. The solvent was removed on rotavap, co-evaporated with toluene, and dried under vacuum to give a pale yellow solid which was dissolved in 8 mL of CH$_2$Cl$_2$ and cooled to −15° C. Triethylamine (0.14 mL, 1.00 mmol) and methanol (1.00 mL) were added. The reaction mixture was stirred at −15° C. for 0.5 h and warmed to room temperature for 1 h. The reaction mixture was poured into aqueous NH$_4$Cl and extracted with EtOAc (3×). The organic layers were washed with H$_2$O, dried with Na$_2$SO$_4$, filtered and concentrated. The crude product was purified by column chromatography on silica gel (3% MeOH/CH$_2$Cl$_2$) to give the dimethyl phosphonate 44 (0.132 g, 85%) as a white solid: $^1$H NMR (CDCl$_3$) δ 8.05 (m, 2H), 7.50 (m, 5H), 7.02 (m, 2H), 6.00 (m, 1H), 5.36 (m, 2H), 5.10-4.90 (m, 2H), 4.70 (m, 1H), 4.50-4.30 (m, 1H), 3.98 (s, 3H), 3.70 (m, 6H), 3.00 (m, 2H), 2.45 (m, 1H), 2.00 (m, 1H), 1.80-1.40 (m, 12H), 1.00 (s, 9H); $^{31}$P NMR (CDCl$_3$) δ 25.67.

LC/MS: 863 (M$^+$+1).

Example 45

Preparation of Compound 45

To a solution of dimethyl phosphonate 44 (0.11 g, 0.14 mmol) in 3 mL solvents (1:1 $CH_3CN/H_2O$) at r.t. was added NaOH (0.11 g, 2.80 mmol). The reaction mixture was heated to 50° C. and stirred overnight, acidified with 6N HCl, and concentrated. The crude product was purified by Gilson HPLC (0.1% TFA/$CH_3CN/H_2O$) to give the monomethyl phosphonate 45 (70 mg, 68%) as a white solid: $^1$H NMR ($CD_3OD$) δ 8.37 (d, J=9.0 Hz, 1H), 8.10 (m, 2H), 7.78 (m, 3H), 7.66 (s, 1H), 7.50 (m, 1H), 7.37 (m, 1H), 6.00 (m, 1H), 5.80 (s, broad, 1H), 5.20 (m, 1H), 5.08 (m, 1H), 4.70 (m, 2H), 4.47 (m, 1H), 4.18 (m, 1H), 4.00 (s, 3H), 3.70 (m, 3H), 2.80 (m, 1H), 2.45 (m, 1H), 2.05 (m, 1H), 1.60-1.30 (m, 12H), 1.00 (s, 9H); $^{31}$P NMR ($CD_3OD$) b 22.49.
LC/MS: 749 (M$^+$+1).

Example 46

Preparation of Compound 46

To a solution of monomethyl phosphonate 45 (50 mg, 0.07 mmol) in 0.3 mL of $CH_3CN$ was treated with 1.0 N NaOH (0.14 mL, 0.14 mmol) and stirred at r.t. for 0.5 h and lyophilized. The sodium salt was suspended in 1.0 mL N-methylpyrrolidinone and heated to 70° C. Triethylamine (37 μL, 0.27 mmol) and POCCl were added. The reaction mixture was stirred at 70° C. for 2 h, cooled to room temperature, and concentrated. The crude product was purified by Gilson ($CH_3CN/H_2O$) to give the monomethyl monoPOC phosphonate 46 (8 mg, 13%, 1:1 diastereomeric mixture) as a white solid: $^1$H NMR ($CDCl_3$) δ 8.10 (m, 2H), 7.58-7.23 (m, 5H), 7.06 (m, 2H), 6.00 (m, 1H), 5.65 (m, 2H), 5.30 (m, 2H), 5.17 (m, 1H), 5.00 (s, broad, 1H), 4.90-4.60 (m, 2H), 4.40 (m, 1H), 4.00 (s, 3H), 3.80 (m, 3H), 2.95 (m, 1H), 2.40 (m, 1H), 2.05 (m, 1H), 1.80-1.40 (m, 12H), 1.20 (m, 6H), 1.00 (s, 9H); $^{31}$P NMR ($CDCl_3$) δ 23.83, 23.23. LC/MS: 865 (M$^+$+1).

Example 47

Preparation of Compound 47

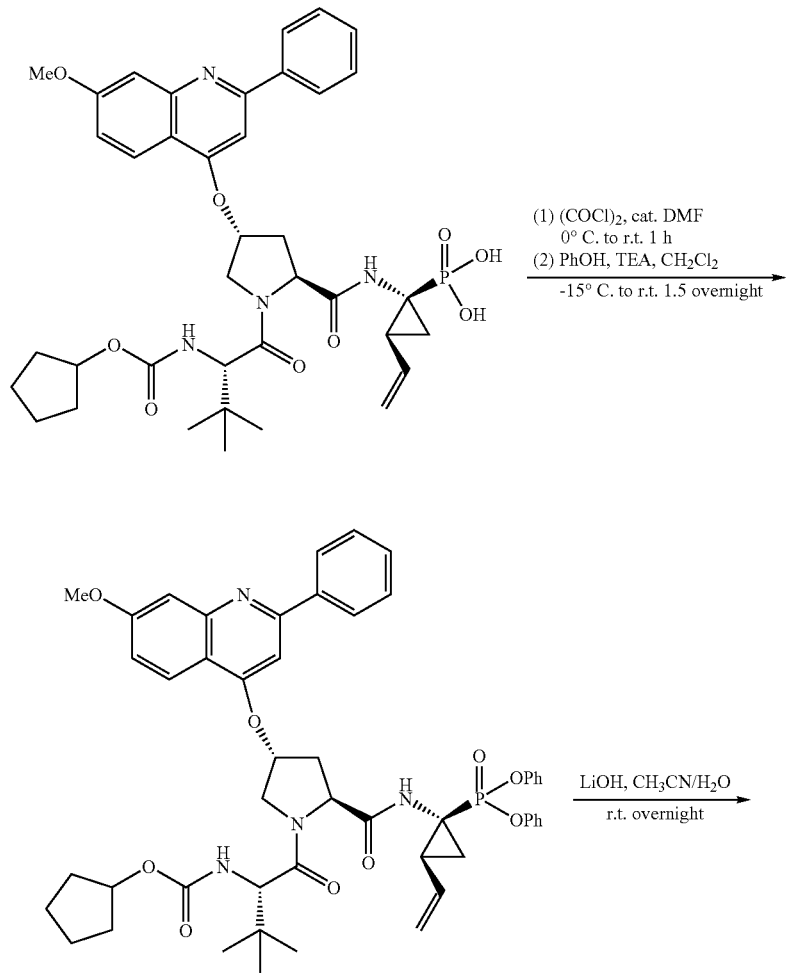

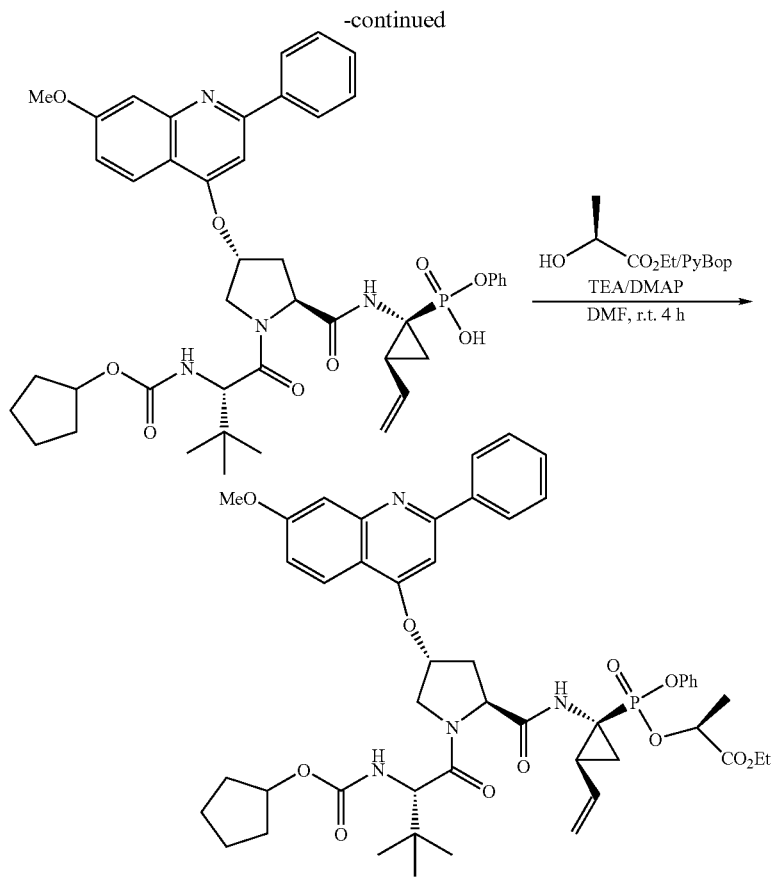

To a solution of diacid (0.50 g, 0.68 mmol) in 10 mL of CH$_2$Cl$_2$ at 0° C. was added oxalyl chloride (1.22 mL, 13.60 mmol) and catalytic amount of DMF (180 μL). The reaction mixture was stirred at 0° C. for 0.5 h and warmed to room temperature for 0.5 h. The solvent was removed on rotavap, co-evaporated with toluene, and dried under vacuum to give the dichloridate as a pale yellow solid which was dissolved in 5 mL of CH$_2$Cl$_2$ and cooled to −15° C. Triethylamine (0.47 mL, 3.40 mmol) and phenol (0.64 g, 6.80 mmol) were added. The reaction mixture was stirred at −15° C. for 0.5 h and warmed to room temperature overnight. The reaction mixture was poured into aqueous NH$_4$Cl and extracted with EtOAc (3×). The organic layers were washed with H$_2$O, dried with Na$_2$SO$_4$, filtered and concentrated. The crude product was purified by column chromatography on silica gel (3% MeOH/ CH$_2$Cl$_2$) to give the diphenyl phosphonate 47 (0.392 g, 65%) as a white solid: $^1$H NMR (CDCl$_3$) b 8.06 (m, 3H), 7.50 (m, 3H), 7.30-7.03 (m, 13H), 5.93 (m, 1H), 5.36 (m, 2H), 5.02 (m, 1H), 4.80 (m, 1H), 4.50-4.30 (m, 2H), 4.00 (s, 3H), 2.95 (m, 1H), 2.45 (m, 1H), 2.20 (m, 1H), 1.82-1.50 (m, 12H), 1.00 (s, 9H); $^{31}$P NMR (CDCl$_3$) δ 16.10. LC/MS: 888 (M$^+$+1).

Example 48

Preparation of Compound 48

To a solution of diphenyl phosphonate (0.392 g, 0.44 mmol) in 6 mL solvents (1:1 CH$_3$CN/H$_2$O) at r.t. was added LiOH (0.11 g, 4.40 mmol). The reaction mixture was stirred at room temperature overnight, acidified with 6N HCl, and concentrated. The crude product was purified by Gilson HPLC (0.1% TFA/CH$_3$CN/H$_2$O) to give the monophenyl phosphonate 48 (0.197 g, 55%) as a white solid: $^1$H NMR (CD$_3$OD) b 8.37 (d, J=9.3 Hz, 1H), 8.09 (d, J=6.0 Hz, 2H), 7.78 (m, 3H), 7.63 (s, 1H), 7.50 (m, 1H), 7.40 (m, 1H), 7.24 (m, 4H), 7.05 (m, 1H), 6.01 (m, 1H), 5.80 (m, 1H), 5.25 (m, 1H), 5.02 (m, 1H), 4.70 (m, 2H), 4.50 (m, 1H), 4.20 (s, 1H), 4.05 (s, 3H), 2.86 (m, 1H), 2.45 (m, 1H), 2.15 (m, 1H), 1.70-1.30 (m, 12H), 1.00 (s, 9H); $^{31}$P NMR (CD$_3$OD) δ 17.08. LC/MS: 811 (M$^+$+1).

Example 49

Preparation of Compound 49

To a solution of monophenyl phosphonate 48 (85 mg, 0.10 mmol) and ethyl (S)-(−)-lactate in 1 mL of DMF was added PyBop (0.273 g, 0.52 mmol), triethylamine (73 ●L, 0.52 mmol), and DMAP (3 mg). The reaction mixture was stirred at r.t. for 4 h and the solvent was removed on rotavap. The reaction mixture was poured into aqueous NH$_4$Cl and extracted with EtOAc (3×). The product was partitioned between EtOAc (3×) and brine and the organic layer was concentrated. The crude product was purified by Gilson (CH$_3$CN/H$_2$O) to give the monolactate 49 (60 mg, 63%, 1:4 diastereomeric mixture, GS 331031) as an off-white solid: $^1$H NMR (CDCl$_3$) δ 8.06 (m, 3H), 7.50 (m, 4H), 7.30 (m, 4H), 7.06 (m, 3H), 5.93 (m, 1H), 5.36 (m, 2H), 5.02 (m, 2H), 4.80 (m, 1H), 4.50-4.30 (m, 2H), 4.08-3.95 (m, 5H), 2.98 (m, 1H), 2.45 (m, 1H), 2.20 (m, 1H), 1.82-1.50 (m, 15H), 1.30-1.00 (m, 12H); $^{31}$P NMR (CDCl$_3$) δ 19.72, 19.48. LC/MS: 911 (M$^+$+1).

Example 50

Preparation of Compound 50

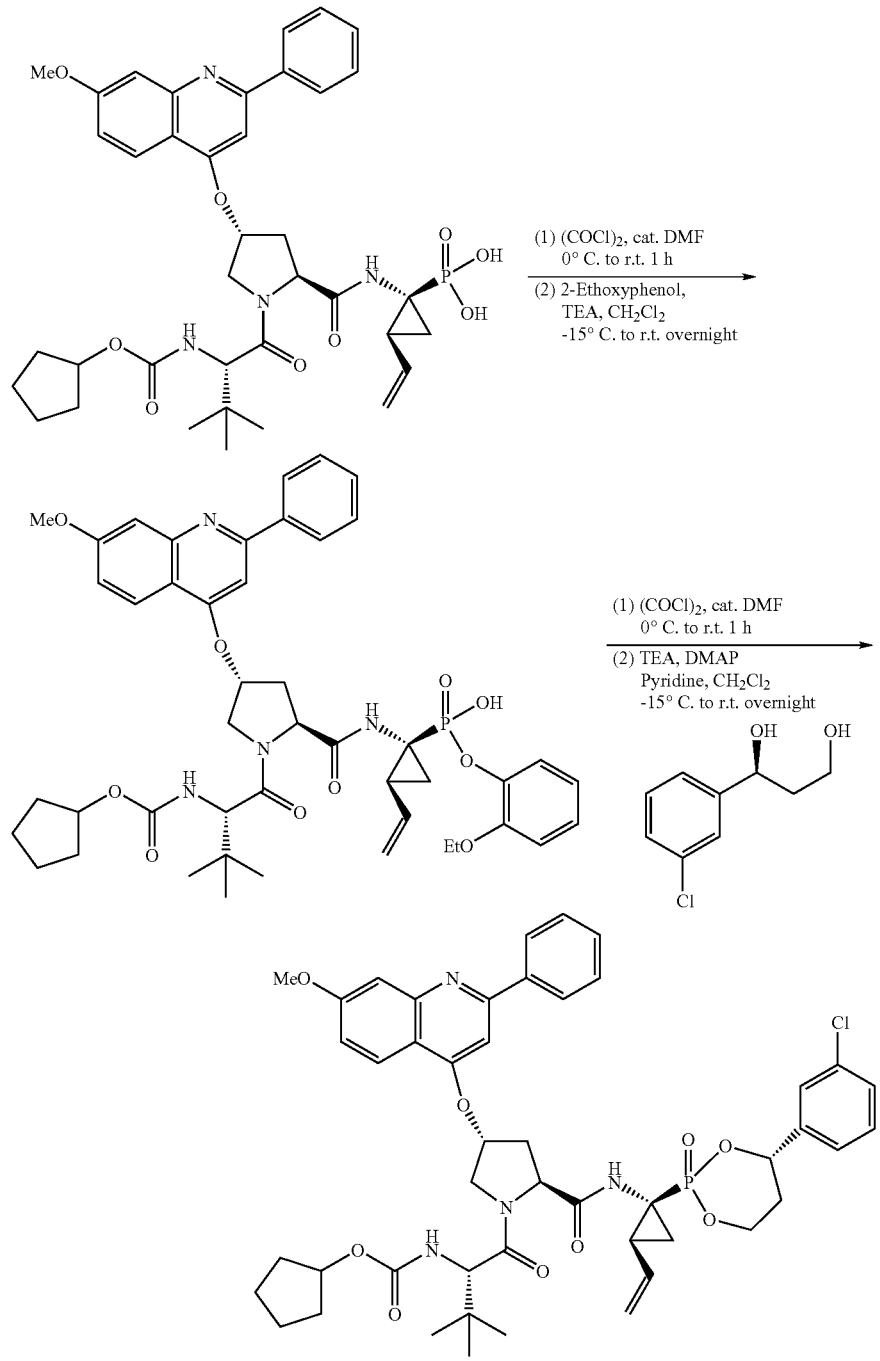

To a solution of diacid (0.10 g, 0.14 mmol) in 1 mL of CH$_2$Cl$_2$ at 0° C. was added oxalyl chloride (0.25 mL, 2.80 mmol) and catalytic amount of DMF (50 μL). The reaction mixture was stirred at 0° C. for 0.5 h and warmed to room temperature for 0.5 h. The solvent was removed on rotavap, co-evaporated with toluene, and dried under vacuum to give the dichloridate as a pale yellow solid which was dissolved in 1.0 mL of CH$_2$Cl$_2$ and cooled to −15° C. Triethylamine (95 μL, 0.40 mmol) and 2-ethoxyphenol (0.188 g, 1.40 mmol) were added. The reaction mixture was stirred at −15° C. for 0.5 h and warmed to room temperature overnight. The reaction mixture was poured into aqueous NH$_4$Cl and extracted with 15% MeOH/CH$_2$Cl$_2$ (3×). The organic layers were washed with H$_2$O and concentrated. The crude product was purified by Gilson (0.1% TFA/MeCN/H$_2$O) to give 2-ethoxyphenyl monoacid 50 (23 mg, 20%) as a white solid: $^1$H NMR (CD$_3$OD) b 8.37 (d, J=9.3 Hz, 1H), 8.09 (d, J=6.3 Hz, 2H), 7.78 (m, 2H), 7.63 (s, 1H), 7.50 (m, 1H), 7.40 (m, 2H), 7.00-6.75 (m, 4H), 6.00 (m, 1H), 5.80 (s, broad, 1H), 5.25 (m, 1H), 5.02 (m, 1H), 4.70 (m, 2H), 4.50 (m, 1H), 4.05 (m, 5H), 2.70 (m, 1H), 2.55 (m, 1H), 2.20 (m, 1H), 1.70-1.30 (m, 15H), 1.00 (s, 9H); $^{31}$P NMR (CD$_3$OD) b 16.68. LC/MS: 855 (M$^+$+1).

Example 51 and 52

Preparation of Compound 51 and 52

To a solution of diacid (0.30 g, 0.41 mmol) in 3 mL of CH$_2$Cl$_2$ at 0° C. was added oxalyl chloride (0.74 mL, 8.20 mmol) and catalytic amount of DMF (100 µL). The reaction mixture was stirred at 0° C. for 0.5 h and warmed to room temperature for 0.5 h. The solvent was removed on rotavap, co-evaporated with toluene, and dried under vacuum to give the dichloridate as a pale yellow solid which was dissolved in 2.0 mL of CH$_2$Cl$_2$, cooled to 0° C., and treated slowly with pyridine (67 µL, 0.82 mmol). The above cold solution was then added slowly to a −78° C. solution of diol (0.23 g, 1.23 mmol) and triethylamine (0.40 mL, 2.87 mmol) in 1.0 mL CH$_2$Cl$_2$ followed by addition of DMAP (10 mg). The reaction mixture was stirred at −78° C. for 0.5 h, warmed to 0° C. for 1 h, and then warmed to room temperature and stirred overnight. The reaction mixture was poured into aqueous NH$_4$Cl and extracted with CH$_2$Cl$_2$ (3×). The organic layers were washed with brine, dried with Na$_2$SO$_4$, filtered and concentrated. The crude product was purified by column chromatography on silica gel (2% MeOH/CH$_2$Cl$_2$) to give isomer A, compound 51 (50 mg, 14%) and isomer B, compound 52 (50 mg, 14%). $^1$H NMR (CD$_3$OD) for compound 51: δ 8.10 (m, 3H), 7.57 (m, 4H), 7.38 (m, 4H), 7.23 (s, 1H), 7.05 (m, 1H), 6.70 (m, 1H), 5.95 (m, 2H), 5.57 (s, broad, 1H), 5.30 (m, 1H), 5.10 (m, 1H), 4.85 (m, 1H), 4.70 (m, 1H), 4.60 (m, 2H), 4.30 (d, J=9.3 Hz, 1H), 4.00 (m, 4H), 2.75 (m, 1H), 2.30 (m, 2H), 2.10 (m, 1H), 1.60 (m, 12H), 1.00 (s, 9H); $^{31}$P NMR (CD$_3$OD) b 15.98. LC/MS: 885 (M$^+$+1). $^1$H NMR (CD$_3$OD) for compound 52: b 8.10 (m, 3H), 7.57 (m, 4H), 7.38 (m, 4H), 7.23 (s, 1H), 7.05 (m, 1H), 6.70 (m, 1H), 5.95 (m, 1H), 5.58 (m, 2H), 5.30 (m, 1H), 5.10 (m, 1H), 4.70 (m, 1H), 4.60 (m, 2H), 4.30 (d, J=9.3 Hz, 1H), 4.00 (m, 4H), 2.70 (m, 1H), 2.50-2.08 (m, 3H), 1.60 (m, 12H), 1.00 (s, 9H); $^{31}$P NMR (CD$_3$OD) b 23.19. LC/MS: 885 (M$^+$+1).

Example 53

Preparation of Compound 53

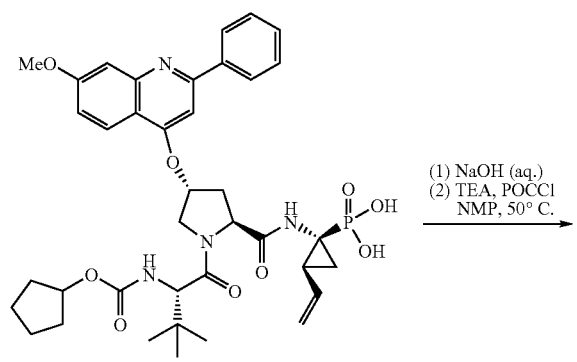

(1) NaOH (aq.)
(2) TEA, POCCl NMP, 50° C.

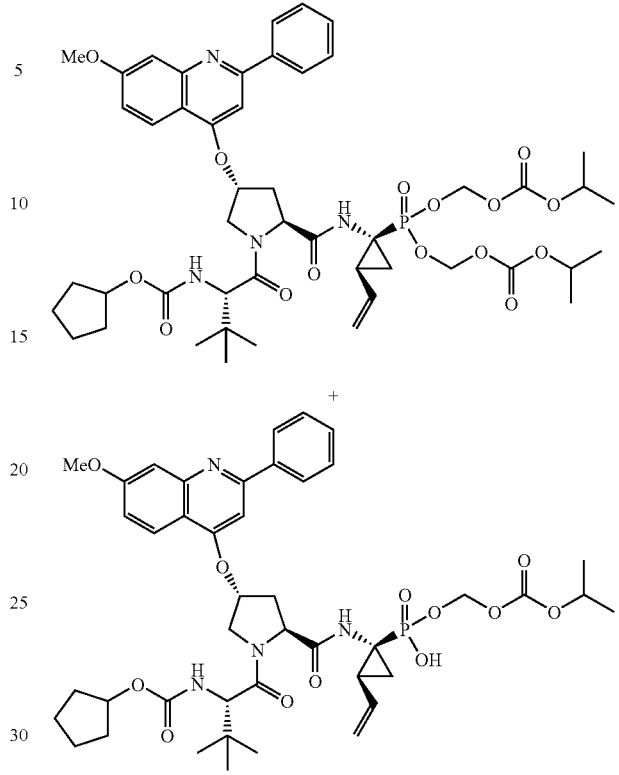

To a solution of diacid (0.20 g, 0.27 mmol) in 1.0 mL of CH$_3$CN was treated with 1.0 N NaOH (0.55 mL, 0.55 mmol) and stirred at r.t. for 0.5 h and lyophilized. The sodium salt was suspended in 2.0 mL N-methyl pyrrolidinone and heated to 70° C. Triethylamine (0.15 mL, 1.08 mmol) and POCCl (0.415 g, 2.70 mmol) were added. The reaction mixture was stirred at 70° C. for 2 h, cooled to room temperature, and concentrated. The crude product was purified by Gilson (0.1% TFA/CH$_3$CN/H$_2$O) to give bis POC phosphonate compound 53 (50 mg, 19%). $^1$H NMR (CDCl$_3$) for bis POC phosphonate: δ 8.05 (m, 3H), 7.50 (m, 4H), 7.30 (m, 1H), 7.03 (m, 1H), 5.97 (m, 1H), 5.65 (m, 4H), 5.40-5.20 (m, 3H), 5.00 (m, 1H), 4.85 (m, 1H), 4.65 (m, 1H), 4.40 (m, 1H), 4.00 (m, 4H), 2.85 (m, 1H), 2.45 (m, 1H), 2.17 (m, 1H), 1.80-1.50 (m, 12H), 1.25 (m, 12H), 1.03 (s, 9H); $^{31}$P NMR (CDCl$_3$) b 21.60.

Example 54

Preparation of Compound 54

From the reaction mixture mentioned for example 53, monoPOC phosphonate was isolated by Gilson (0.1% TFA/CH$_3$CN/H$_2$O) to give 54.

LC/MS: 967 (M$^+$+1). $^1$H NMR (CD$_3$OD) for monoPOC phosphonate: δ 8.40 (m, 1H), 8.05 (m, 2H), 7.75 (m, 3H), 7.65 (s, 1H), 7.55 (m, 1H), 7.40 (m, 1H), 6.00 (m, 1H), 5.82 (s, broad, 1H), 5.60 (m, 1H), 5.20-5.00 (m, 2H), 4.95-4.50 (m, 4H), 4.20-4.00 (m, 4H), 2.80 (m, 1H), 2.60 (m, 1H), 2.10 (m, 1H), 1.65 (m, 12H), 1.2 (m, 6H), 1.00 (s, 9H); $^{31}$P NMR (CD$_3$OD) b 17.59.

LC/MS: 851 (M$^+$+1).

Example 55

Preparation of Compound 55

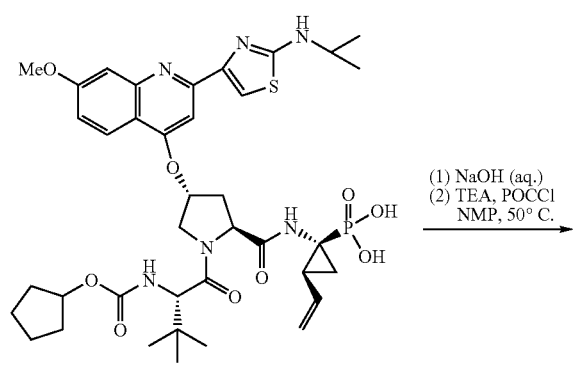

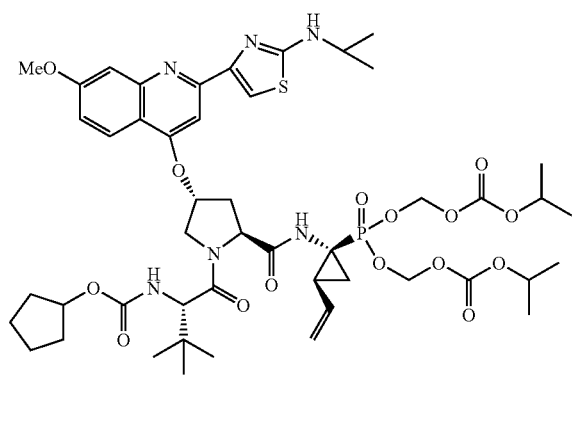

To a solution of diacid (0.15 g, 0.19 mmol) in 1.0 mL of CH$_3$CN was treated with 1.0 N NaOH (0.38 mL, 0.38 mmol) and stirred at r.t. for 0.5 h and lyophilized. The sodium salt was suspended in 1.5 mL N-methyl pyrrolidinone and heated to 70° C. Triethylamine (0.10 mL, 0.76 mmol) and POCCl (0.286 g, 1.90 mmol) were added. The reaction mixture was stirred at 70° C. for 2 h, cooled to room temperature, and concentrated. The crude product was purified by Gilson (0.1% TFA/CH$_3$CN/H$_2$O) to give bisPOC phosphonate 55 (35 mg, 18%) as a pale yellow solid: $^1$H NMR (CDCl$_3$) b 8.00 (d, J=9.9 Hz, 1H), 7.50-7.40 (m, 3H), 7.05 (m, 1H), 6.00 (m, 1H), 5.70 (m, 4H), 5.45-5.20 (m, 3H), 4.90 (m, 2H), 4.63 (m, 1H), 4.40 (m, 2H), 4.00 (m, 4H), 3.90 (m, 1H), 2.90 (m, 1H), 2.45 (m, 1H), 2.20 (m, 1H), 1.80 (m, 12H), 1.40 (m, 18H), 1.00 (s, 9H); $^{31}$P NMR (CDCl$_3$) δ 21.55.

LC/MS: 1032 (M$^+$+1).

Example 56

Preparation of Compound 56

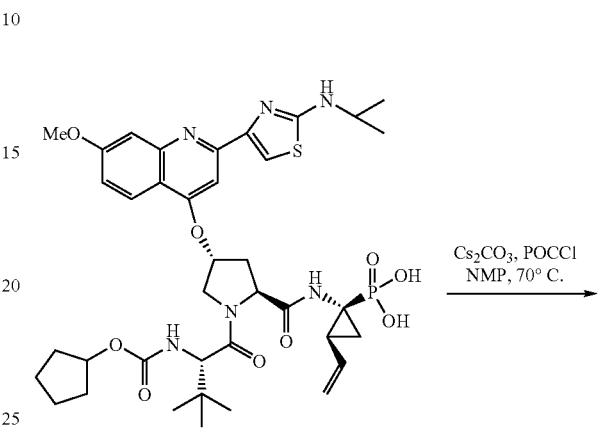

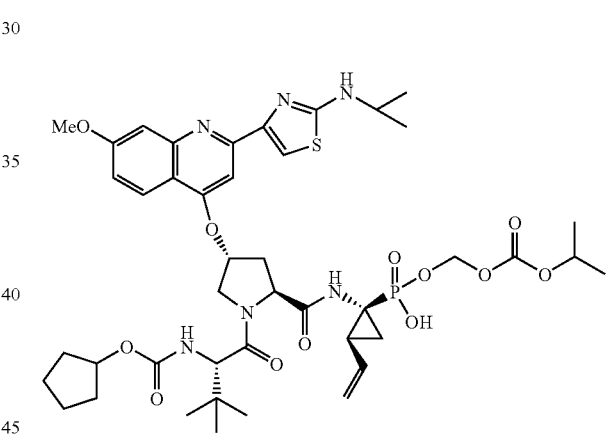

The diacid (50 mg, 0.06 mmol) in 1.0 mL N-methyl pyrrolidinone was treated with cesium carbonate (82 mg, 0.25 mmol) and heated to 70° C. POCCl (48 mg, 0.31 mmol) was added. The reaction mixture was stirred at 70° C. for 2 h, cooled to room temperature, and concentrated. The crude product was purified by Gilson (0.1% TFA/CH$_3$CN/H$_2$O) to give monoPOC phosphonate 56 (11 mg, 19%, GS 330334) as a pale yellow solid: $^1$H NMR (CD$_3$OD) δ 8.30 (d, J=9.6 Hz, 1H), 8.20 (s, 1H), 7.70 (m, 2H), 7.35 (m, 1H), 6.00 (m, 1H), 5.80 (m, 1H), 5.60 (m, 2H), 5.30 (m, 1H), 5.10 (m, 1H), 4.85 (m, 1H), 4.60 (m, 3H), 4.20 (m, 2H), 4.00 (s, 3H), 2.80-2.60 (m, 2H), 2.10 (m, 1H), 1.60 (m, 12H), 1.40-1.20 (m, 12H), 1.00 (s, 9H); $^{31}$P NMR (CD$_3$OD) b 18.70.

LC/MS: 915 (M$^+$+1).

Example 57
Preparation of Compound 57
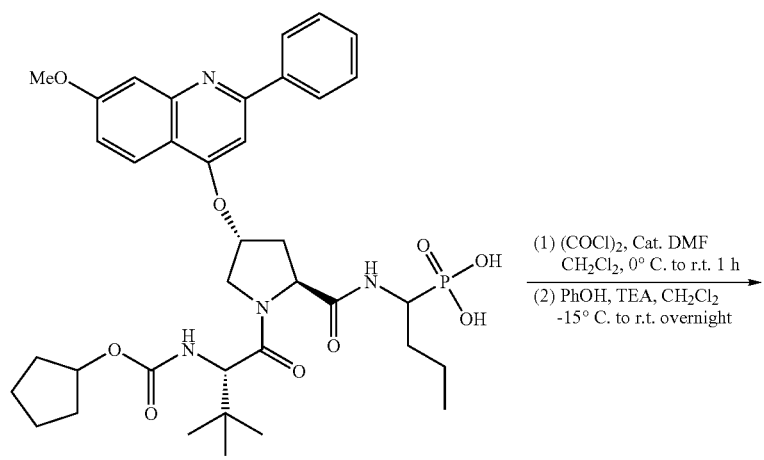
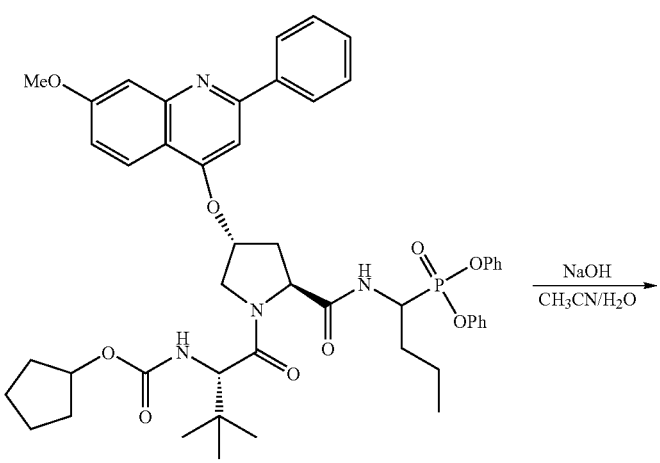
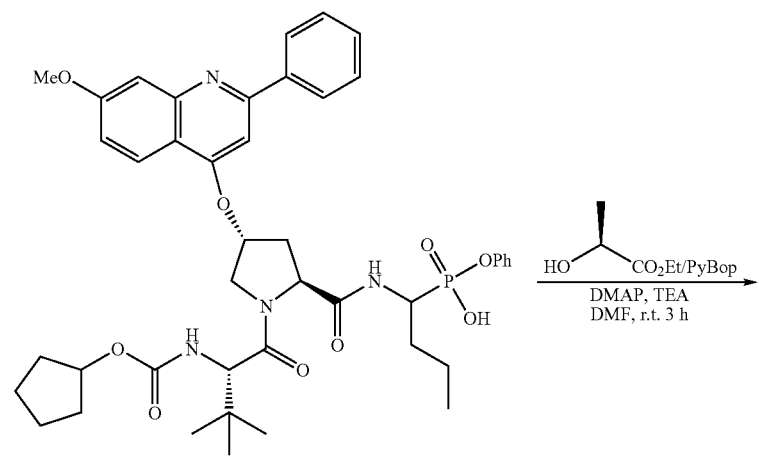

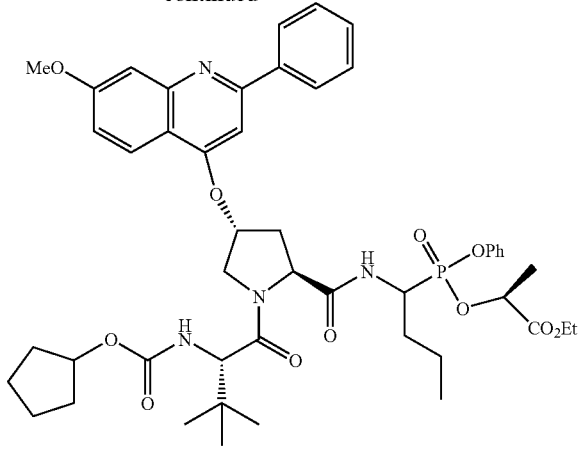

To a solution of diacid (0.26 g, 0.36 mmol) in 3 mL of $CH_2Cl_2$ at 0° C. was added oxalyl chloride (0.65 mL, 7.20 mmol) and catalytic amount of DMF (100 μL). The reaction mixture was stirred at 0° C. for 0.5 h and warmed to room temperature for 0.5 h. The solvent was removed on rotavap, co-evaporated with toluene, and dried under vacuum to give the dichloridate as a pale yellow solid which was dissolved in 3 mL of $CH_2Cl_2$ and cooled to −15° C. Triethylamine (0.50 mL, 3.60 mmol) and phenol (0.338 g, 3.60 mmol) were added. The reaction mixture was stirred at −15° C. for 0.5 h and warmed to room temperature for 4 h. The reaction mixture was poured into aqueous $NH_4Cl$, extracted with EtOAc (3×), and concentrated to give diphenyl phosphonate as crude product which was carried on for next step reaction without purification.

To a solution of crude diphenyl phosphonate in 4 mL solvents (1:1 $CH_3CN/H_2O$) at r.t. was added NaOH (0.143 g, 3.60 mmol). The reaction mixture was stirred at room temperature for 1 h, acidified with 6N HCl, and concentrated. The crude product was purified by Gilson HPLC (0.1% TFA/$CH_3CN/H_2O$) to give the monophenyl phosphonate 57 (0.129 g, 45%) as a pale yellow solid: $^1$H NMR ($CD_3OD$) δ 8.40 (d, J=9.3 Hz, 1H), 8.10 (m, 2H), 7.80 (m, 3H), 7.60 (s, 1H), 7.55 (s, broad, 1H), 7.40 (m, 1H), 7.20 (m, 4H), 7.00 (m, 1H), 5.80 (s, 1H), 4.80 (m, 1H), 4.67 (m, 1H), 4.55 (s, broad, 1H), 4.40 (m, 1H), 4.20 (s, 1H), 4.00 (s, 3H), 2.70 (m, 1H), 2.43 (m, 1H), 1.90-1.60 (m, 14H), 1.00 (s, 9H), 0.90 (t, J=7.5 Hz, 3H); $^{31}$P NMR ($CD_3OD$) b 17.67.

LC/MS: 801 ($M^+$+1).

Example 58

Preparation of Compound 58

To a solution of monophenyl phosphonate (0.10 g, 0.12 mmol) and ethyl (S)-(−)-lactate (0.148 g, 1.20 mmol) in 1 mL of DMF was added PyBop (0.325 g, 0.60 mmol), triethylamine (87 μL, 0.60 mmol), and DMAP (3 mg). The reaction mixture was stirred at r.t. for 3 h and the solvent was removed on rotavap. The reaction mixture was poured into aqueous $NH_4Cl$ and extracted with EtOAc (3×). The organic layer was washed with brine, dried with $Na_2SO_4$, filtered and concentrated. The crude product was purified by column chromatography on silica gel (3% MeOH/$CH_2Cl_2$) to give the monolactate 58 (28 mg, 25%) as an off-white solid: $^1$H NMR ($CDCl_3$) δ 8.10 (m, 2H), 7.50 (m, 3H), 7.40-7.00 (m, 9H), 5.40 (m, 2H), 5.00 (s, 1H), 4.90 (m, 1H), 4.70 (m, 2H), 4.40 (m, 2H), 4.10 (m, 1H), 4.00 (m, 4H), 2.65-2.40 (m, 2H), 2.00-1.50 (m, 14H), 1.30 (m, 4H), 1.10-0.97 (m, 12H); $^{31}$P NMR ($CDCl_3$) δ 22.38.

LC/MS: 901 ($M^+$+1).

Example 59

Preparation of Compound 59

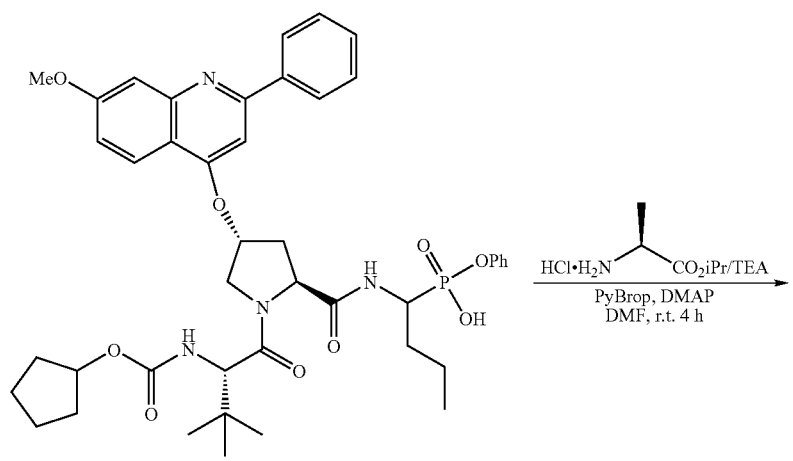

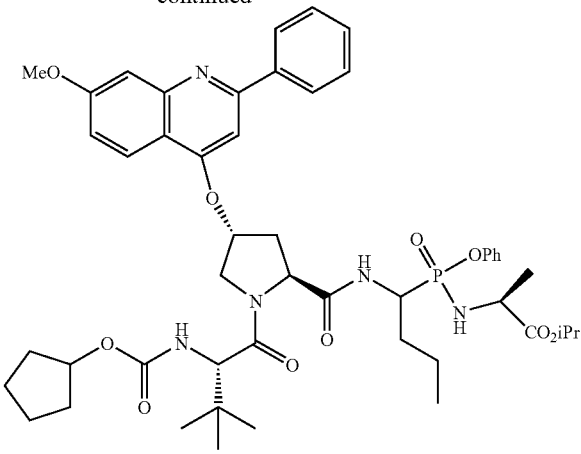

To a solution of monophenyl phosphonate from example 57 (30 mg, 0.04 mmol) and L-alanine isopropyl ester hydrochloride (50 mg, 0.30 mmol) in 0.5 mL of DMF was added PyBrop (84 mg, 0.19 mmol), triethylamine (52 ⊕L, 0.37 mmol), and DMAP (3 mg). The reaction mixture was stirred at r.t. for 4 h and the solvent was removed on rotavap. The residue was dissolved in EtOAc and poured into aqueous NH$_4$Cl. The product was extracted with EtOAc (3×) and concentrated. The crude product was purified by Gilson (CH$_3$CN/H$_2$O) to give the monophosphoamidate 59 (5 mg, 15%) as a white solid: $^1$H NMR (CDCl$_3$) δ 8.05 (m, 3H), 7.50 (m, 4H), 7.24 (m, 4H), 7.06 (m, 3H), 5.40 (m, 2H), 5.00-4.80 (m, 2H), 4.40 (m, 2H), 4.10-3.90 (m, 4H), 3.45 (m, 1H), 2.80 (m, 1H), 2.50 (m, 1H), 1.90-1.45 (m, 14H), 1.30 (m, 6H), 1.10 (m, 3H), 1.05 (s, 9H), 0.96 (m, 3H); $^{31}$P NMR (CDCl$_3$) δ 25.48.

LC/MS: 914 (M$^+$+1).

Example 60

Preparation of Compound 60

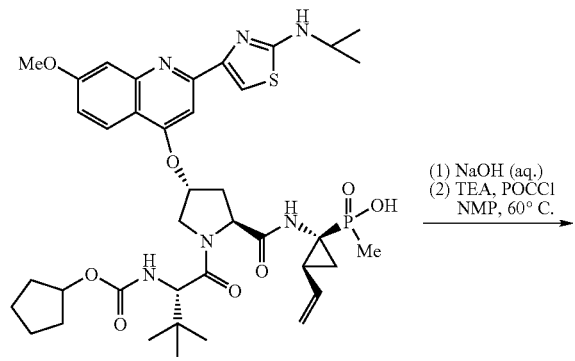

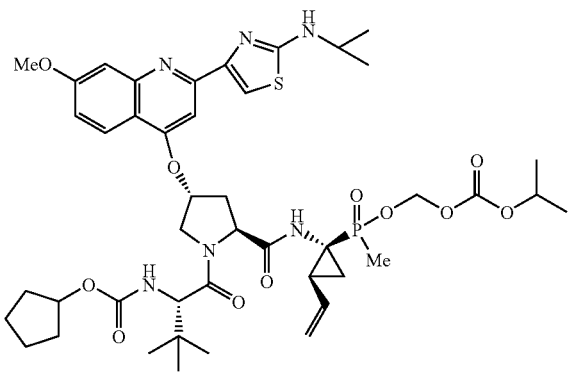

To a solution of phosphinic acid (10 mg, 0.001 mmol) in 0.2 mL of CH$_3$CN was treated with 1.0 N NaOH (50 µL, 0.004 mmol) and stirred at r.t. for 0.5 h and lyophilized. The sodium salt was suspended in 0.3 mL N-methyl pyrrolidinone and heated to 70° C. Triethylamine (7 µL, 0.004 mmol) and POCCl (19 mg, 0.01 mmol) were added. The reaction mixture was stirred at 60° C. for 1 h, cooled to room temperature, and concentrated. The crude product was purified by Gilson (0.1% TFA/CH$_3$CN/H$_2$O) to give POC phosphinate 60 (4.5 mg, 39%, 1:1 diastereomeric mixture) as a pale yellow solid: $^1$H NMR (CD$_3$OD) δ 8.25 (d, J=9.3 Hz, 1H), 8.20 (s, 1H), 7.76 (s, 2H), 7.30 (m, 1H), 6.00 (m, 1H), 5.80-5.60 (m, 2H), 5.30 (m, 1H), 5.17 (m, 1H), 4.60 (m, 2H), 4.45 (m, 1H), 4.20 (m, 2H), 4.00 (s, 3H), 2.78 (m, 1H), 2.40 (m, 1H), 2.17 (m, 1H), 1.60 (m, 12H), 1.30 (m, 14H), 1.02 (m, 12H); $^{31}$P NMR (CDCl$_3$) δ 57.17, 52.94.

LC/MS: 913 (M$^+$+1).

Example 61

Preparation of Compound 61

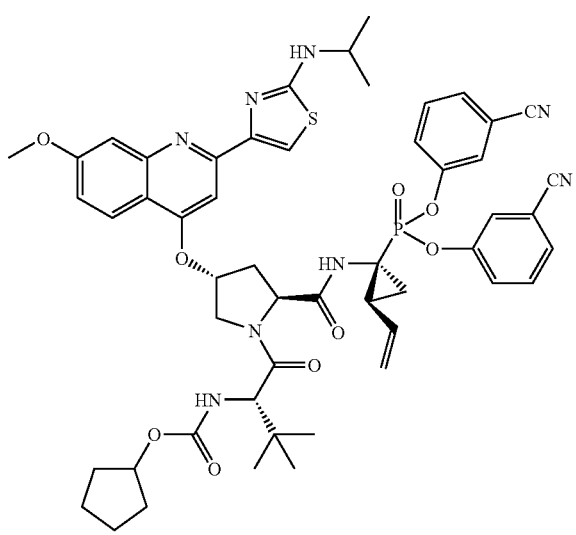

To a solution of the phosphonic diacid precursor (200 mg, 0.250 mmol) in 3 mL of pyridine was added meta-cyanophenol (350 mg, 2.5 mmol). The solution mixture was heated at 60° C. in an oil bath for 10 min. To the acid solution was added dicyclohexylcarbodiimide (310 mg, 1.50 mmol). The reaction mixture was heated at 60° C. for 2 h using an oil bath. The reaction mixture was then cooled to room temperature and the solvent was removed under reduced pressure. The crude mixture was dissolved in ethyl acetate and extracted with saturated sodium bicarbonate followed by brine. The organics were separated and dried over $MgSO_4$, filtered and solvent removed under reduced pressure. The crude mixture was purified by silica gel chromatography (eluted with 0% to 10% methanol/dichloromethane). The purified material was then repurified by reverse phase prep HPLC (ACN/Water) to afford 61 as a yellow solid (42 mg, 17%). $^1$H NMR (300 MHz, $CDCl_3$): δ 8.85 (s, 1H), 8.18 (d, J=9.1 Hz, 1H), 7.91 (s, 1H), 7.78 (s, 1H), 7.28 (bs, 10H), 5.92 (m, 2H), 5.37 (d, J=17.1, 1H), 5.13 (m, 2H), 4.85-4.40 (bs, 3H), 4.14 (d, J=9.2 Hz 1H), 4.02 (s, 3H), 2.98 (m, 1H), 2.77 (m, 1H), 2.23 (q, J=8.7 Hz, 1H), 1.85-1.63 (bs, 7H), 1.48 (d, J=6.4 Hz, 6H), 1.35 (m, 5H), 0.94 (s, 9H). $^{31}$P NMR (300 MHz, $CDCl_3$): δ ppm: 17.76 (s, 1P). LC/MS: 1001 ($M^+$+1).

Example 62

Preparation of Compound 62

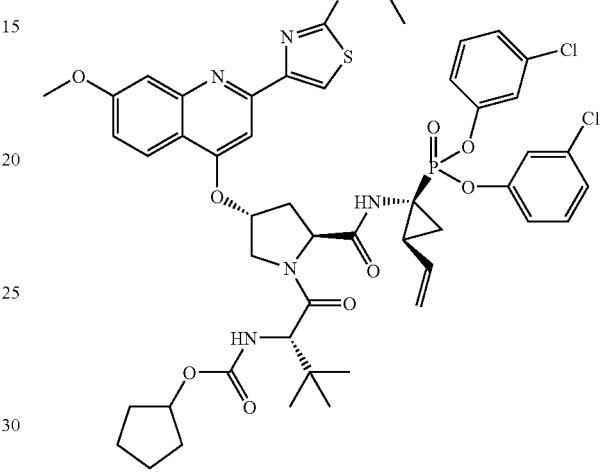

To a solution of the phosphonic diacid precursor (100 mg, 0.125 mmol) in 1.5 mL of pyridine was added meta-chlorophenol (160 mg, 1.25 mmol). The solution mixture was heated at 60° C. in an oil bath for 10 min. To the acid solution was added dicyclohexylcarbodiimide (154 mg, 0.75 mmol). The reaction mixture was heated at 60° C. for 2 h using oil bath. The reaction mixture was cooled to room temperature and the solvent was removed under reduced pressure. The crude mixture was dissolved in ethyl acetate and extracted with saturated sodium bicarbonate followed by brine. The organics were separated and dried over $MgSO_4$, filtered and solvent removed under reduced pressure. The crude mixture was purified by silica gel chromatography (eluted with 0% to 10% methanol/dichloromethane). The purified material was then repurified by reverse phase prep HPLC (ACN/Water) to afford 62 as a yellow solid (15 mg, 12%). $^1$H NMR (300 MHz, $CDCl_3$): δ 8.84 (s, 1H), 8.21 (d, J=9.1 Hz, 1H), 7.91 (s, 1H), 7.77 (d, J=10.7 Hz, 1H), 7.52-7.45 (bs, 10H), 7.23 (m, 1H), 5.78 (m, 2H), 5.37 (d, J=16.8, 1H), 5.19 (d, J=9.2 Hz, 1H), 5.11 (d, J=11 Hz, 1H), 4.82 (t, J=9.6 Hz, 1H), 4.68 (m, 1H), 4.20 (m, 1H), 4.01 (s, 3H), 3.92 (d, J=11 Hz), 3.58 (m, 2H), 3.01 (m, 1H), 2.60 (m, 1H), 2.22 (q, J=8.3 Hz, 1H), 1.88 (m, 1H), 1.67-1.26 (bs, 13H), 0.94 (s, 9H). $^{31}$P NMR (300 MHz, $CDCl_3$): δ ppm: 16.78 (s, 1P). LC/MS: 1019 ($M^+$+1).

Example 63

Preparation of Compound 63

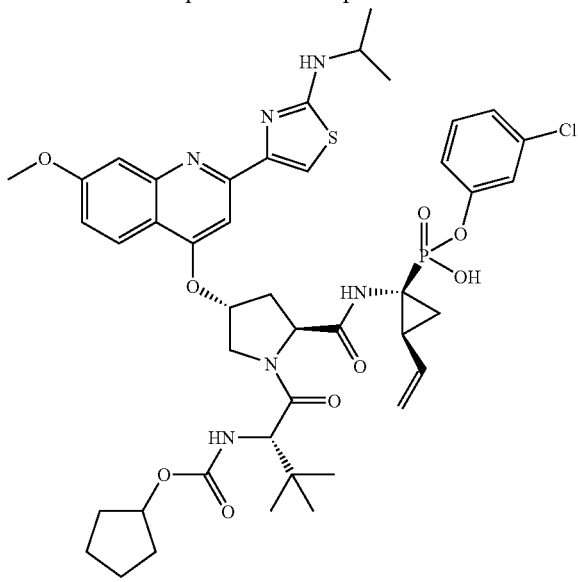

To a solution of compound 62 (50 mg, 0.049 mmol) in 3 mL ACN at 0° C. was added 1 mL 1.0 M NaOH in water. The solution mixture was allowed to come to room temperature and stirred for 2 h. The reaction mixture was adjusted to pH=2 with 10% HCl in water. The crude mixture was diluted in ethyl acetate and extracted with 10% HCl in water, followed by brine. The organics were separated and dried over MgSO$_4$, filtered and solvent removed under reduced pressure. The crude mixture was purified by reverse phase prep HPLC (ACN/Water) to afford 63 as a yellow solid (13 mg, 30%). $^1$H NMR (300 MHz, CD$_3$OD): δ 8.12 (m, 2H), 7.58-7.36 (bs, 4H), 7.19-6.94 (bs, 5H), 6.77 (m, 1H), 6.11 (m, 1H), 5.46 (m, 1H), 5.22 (d, J=19 Hz, 1H), 4.99 (d, J=11.9 Hz, 1H), 4.75-4.44 (bs, 3H), 4.28-3.92 (bs, 7H), 3.16 (m, 1H), 2.62 (m, 1H), 2.35 (m, 1H), 2.08 (m, 1H), 1.90-1.30 (bs, 21H), 1.04 (s, 9H), 0.97 (m, 2H). $^{31}$P NMR (300 MHz, CD$_3$OD): δ ppm: 13.75 (s, 1P). LC/MS: 909 (M$^+$+1).

Example 64

Preparation of Compound 64

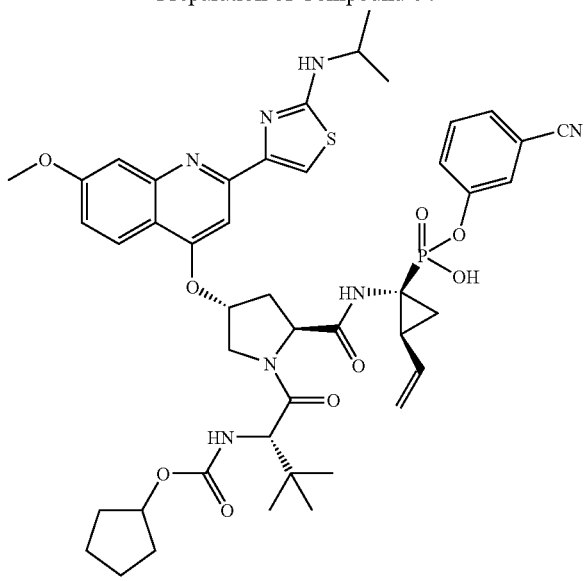

To a solution of 61 (50 mg, 0.049 mmol) in 3 mL ACN at 0° C. was added 1 mL 1.0 M NaOH in water. The solution mixture was allowed to come to room temperature and stirred for 2 h. The reaction mixture was adjusted to pH=2 with 10% HCl in water. The crude mixture was diluted in ethyl acetate and extracted with 10% HCl in water, followed by brine. The organics were separated and dried over MgSO$_4$, filtered and solvent removed under reduced pressure. The crude mixture was purified by reverse phase prep HPLC (ACN/Water) to afford 64 as a yellow solid (6 mg, 13%). $^1$H NMR (300 MHz, CD$_3$OD): δ 8.25 (d, J=9.1 Hz, 1H), 8.06 (m, 2H), 7.73-7.24 (bs, 5H), 6.77 (d, J=7.9 Hz, 1H), 6.01 (m, 1H), 5.65 (m, 1H), 5.20 (d, J=17.7 Hz, 1H), 4.94 (m, 2H), 4.63-4.23 (bs, 3H), 4.12-3.98 (bs, 7H), 3.64 (s, 1H), 2.65-2.12 (bs, 3H), 1.92-0.99 (bs, 15H). $^{31}$P NMR (300 MHz, CD$_3$OD): δ ppm: 14.45 (s, 1P). LC/MS: 900 (M$^+$+1).

Example 65

Preparation of Compound 65

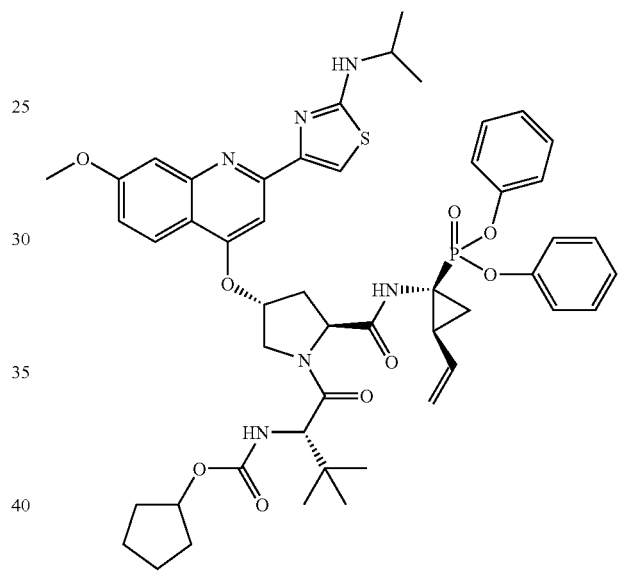

To a solution of aminothiazolequinoline dipeptide carboxylic acid (150 mgs, 0.229 mmol) in 10 mL THF at −50° C. for 1 h was added TEA (81 μL, 0.572 mmol) followed by ethylchloroformate (32 μL, 0.240 mmol). After 1 h amino vinylcyclopropyl diphenylphosphonate was added and the reaction was warmed to room temperature slowly and stirred overnight. The solvent was removed under reduced pressure and diluted with ethyl acetate. The crude mixture was extracted with ethyl acetate and 10% HCl followed by brine. The layers were separated and the organics were dried over MgSO$_4$, filtered and evaporated. The crude material was then purified on reverse phase prep HPLC (ACN/Water) to afford 65 as a yellow solid (65 mgs, 30%). $^1$H NMR (300 MHz, CDCl$_3$): δ 8.84 (s, 1H), 8.16 (d, J=9.2 Hz, 1H), 7.90 (s, 1H), 7.79 (s, 1H), 7.63 (s, 1H) 7.33-7.14 (bs, 10H), 5.95 (m, 1H), 5.86 (s, 1H), 5.35 (d, J=16.4, 1H), 5.13 (m, 2H), 4.87 (t, J=10.5 Hz, 1H), 4.68 (d, J=12.8 Hz, 1H), 4.35 (s, 1H), 4.13 (d, J=9.1 Hz, 1H), 4.01 (s, 3H), 3.92 (d, J=10.1 Hz, 1H), 3.58 (t, J=6.7 Hz, 1H), 2.98 (m, 1H), 2.63 (m, 1H), 2.27 (q, J=8.7 Hz, 1H), 1.87 (m, 1H), 1.64-1.26 (bs, 8H), 0.93 (s, 9H). $^{31}$P NMR (300 MHz, CDCl$_3$): δ ppm: 16.13 (s, 1P).

LC/MS: 951 (M$^+$+1).

Example 66

Preparation of Compound 66

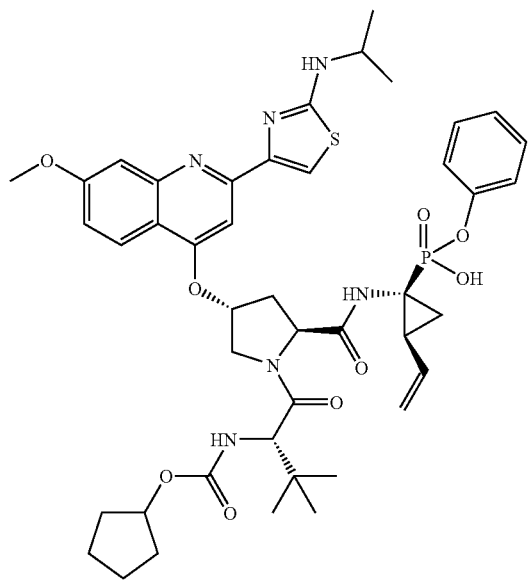

To a solution of 65 (36 mg, 0.038 mmol) in 5 mL ACN at 0° C. was added 0.54 mL 1.0 M NaOH in water. The solution mixture was allowed to come to room temperature and stirred for 2 h. The reaction mixture was adjusted to pH=2 with 10% HCl in water. The crude mixture was diluted in ethyl acetate and extracted with 10% HCl in water, followed by brine. The organics were separated and dried over MgSO$_4$, filtered and solvent removed under reduced pressure. The crude mixture was purified by reverse phase prep HPLC (ACN/Water) to afford 66 as a yellow solid (13 mg, 39%). $^1$H NMR (300 MHz, CD$_3$OD): δ ppm: 8.29 (d, J=9.1 Hz, 1H), 8.16 (s, 1H), 7.74 (m, 2H), 7.33-7.10 (bs, 8H), 6.01 (m, 1H) 5.74 (s, 1H), 5.29 (d, J=17.4 Hz, 1H), 5.07 (d, J=10.4 Hz, 1H), 4.68 (m, 2H), 4.48 (s, 1H), 4.17-4.04 (bs, 7H), 4.13 (d, J=9.1 Hz, 1H), 2.70 (m, 1H), 2.51 (m, 1H), 2.19 (m, 1H), 1.63-1.33 (bs, 13H), 1.03 (s, 9H), 0.99 (s, 1H). $^{31}$P NMR (300 MHz, CD$_3$OD): δ ppm: 17.57 (s, 1P). LC/MS: 875 (M$^+$+1).

Example 67

Preparation of Compound 67

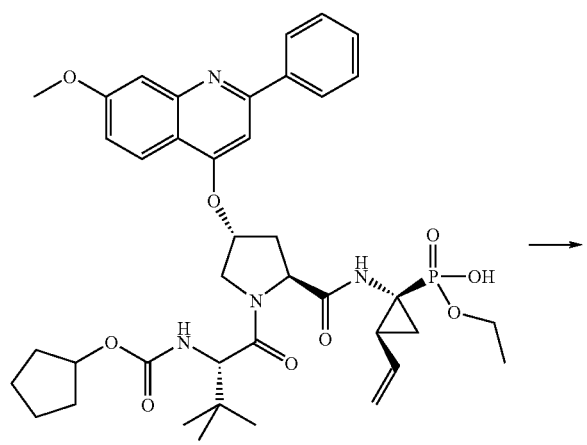

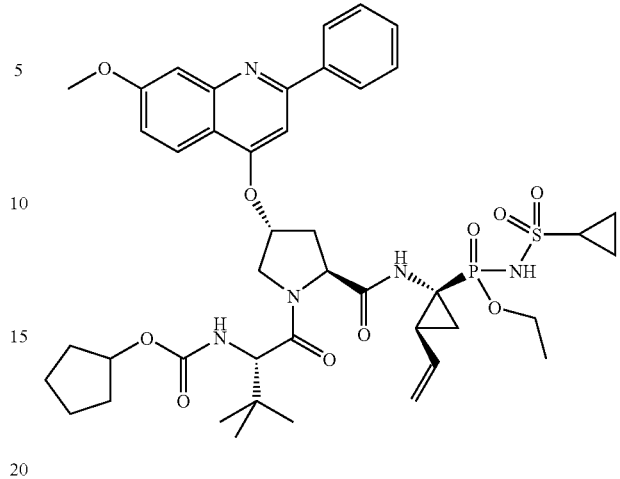

A solution of 125.2 mg (164.1 mmol) of the monoacid and 20 uL (258.3 mmol) of DMF in dichloromethane (1.5 mL) was stirred at 0° C. bath as 145 uL (1.66 mmol) of oxalyl chloride was added dropwise. After stirring for 30 min at 0° C., the solution was diluted with toluene and concentrated. The residue was dried in vacuum for 30 min, dissolved in acetonitrile (1.5 mL), and stirred at 0° C. as 99.8 mg (823.7 mmol) of cyclopropylsulfonamide and 0.13 mL (869.3 mmol) of DBU were added. After 1 h at 0° C., 67 uL (869.7 mmol) of trifluoroacetic acid was added at 0° C. and the mixture was filtered through a membrane filter. The filtrate was purified by preparative HPLC followed by silica gel chromatography using 12 g column to obtain 64.8 mg (46%) of the compound 67: $^1$H NMR (300 MHz, CD$_3$OD): δ 8.19-8.26 (m, 1H), 8.05-8.12 (m, 2H), 7.59-7.67 (br, 3H), 7.42-7.48 (br, 2H), 7.23 (br d, J=9.3 Hz, 1H), 5.95-6.15 (m, 1H), 5.71 (br, 1H), 54.97-5.33 (m, 2H), 4.53-4.67 (m, 2H), 4.25 (br, 1H), 4.02-4.21 (m, 3H), 4.00 (s, 3H), 2.7-2.9 (m, 1H), 2.45-2.7 (m, 2H), 1.27-2.04 (m, 13H), 1.24 (t, J=6.3 Hz, 3H), 1.5 (s, 9H), 0.94-1.00 (m, 1H), 0.79-0.89 (m, 2H); $^{31}$P NMR (75 MHz, CD$_3$OD) δ 17.21, 14.83 (~0.9P); LC/MS: 866 (M$^+$+1).

Example 68

Preparation of Compound 68

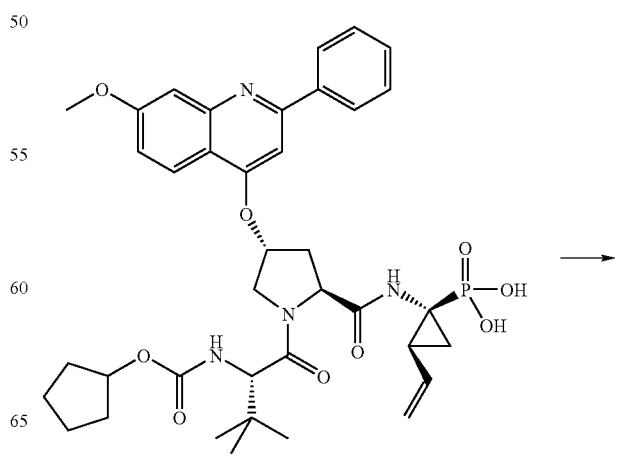

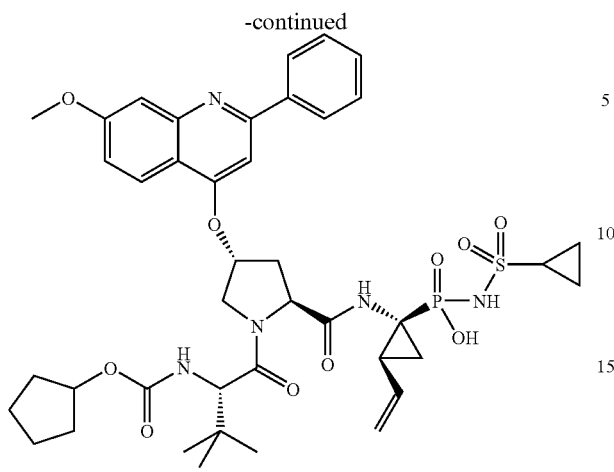

A suspension of 102.4 mg (139.4 mmol) of the diacid and 25 uL (323 mmol) of DMF in dichloromethane (1.5 mL) was stirred at 0° C. as 0.25 mL (2.87 mmol) of oxalyl chloride was added. After the mixture was stirred for 30 min at 0° C. and for 1 h at rt, it was diluted with toluene (1 mL) and concentrated. The residue was dissolved in acetonitrile, diluted with toluene, and concentrated. After the residue was dried in vacuum for 30 min, the residue was dissolved in acetonitrile (1 mL) and stirred at 0° C., as 17 mg (140.3 mmol) of cyclopropylsulfonamide was added. After 30 min, 0.1 mL (668.7 mmol) of DBU was added. After 1.5 h at 0° C., several drops of water were added to the mixture followed by 50 uL (649 mmol) of trifluoroacetic acid. The mixture was filtered through a membrane filter and the filtrate was purified by preparative HPLC to obtain 15.0 mg (13%) of the compound 68: $^1$H NMR (300 MHz, CD$_3$OD): δ 8.38 (d, J=9.3 Hz, 1H), 8.07-8.12 (m, 2H), 7.71-7.82 (m, 3H), 7.66 (s, 1H), 7.55 (d, J=2.1 Hz, 1H), 7.38 (dd, J=9.3 and 2.1 Hz, 1H), 5.98 (dt, J=17.1 and 10.0 Hz, 1H), 5.84 (br, 1H), 5.17 (d, J=17.1 Hz, 1H), 5.02 (d, J=10.0 Hz, 1H), 4.65-4.73 (m, 2H), 4.51 (br, 1H), 4.20 (s, 1H), 4.07-4.18 (m, 1H), 4.06 (s, 3H), 3.39-3.52 (m, 1H), 2.77-3.03 (m, 2H), 2.46-2.70 (m, 1H), 1.98-2.13 (m, 1H), 1.32-1.98 (m, 10H), 0.96-1.26 (m, 3H), 1.05 (s, 9H); $^{31}$P NMR (75 MHz, CD$_3$OD) δ 12.81; LC/MS: 838 (M$^+$+1).

Example 69

Preparation of Compound 69

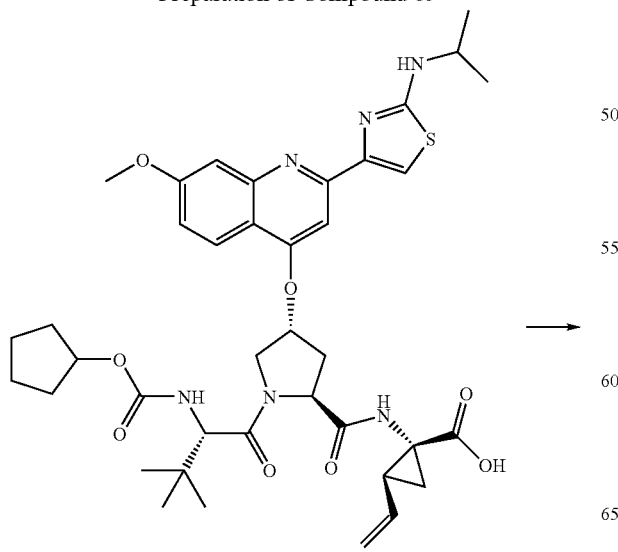

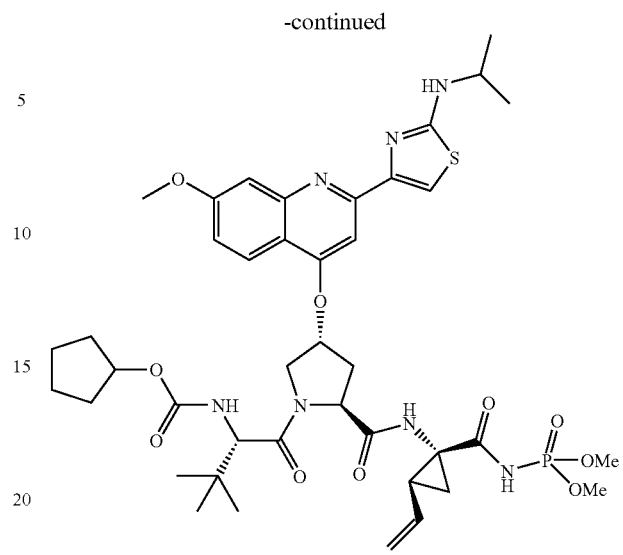

To a solution of tripeptide acid (75 mg, 0.0983 mmol) in 2 mL of THF was added CDI (40 mg, 0.246 mmol). The solution mixture was refluxed for 2 h. To the cooled mixture was added the phosphoramidate (49 mg, 0.392 mmol) followed by DBU (103 μL, 0.69 mmol) and refluxed for 2 h. The mixture was concentrated in vacuo, dissolved in 1 mL of MeOH and purified by reverse phase HPLC (eluted with 10% to 75% H$_2$O/CH$_3$CN) to give 69 as a yellow solid (24 mg, 28%). $^1$H NMR (300 MHz, CDCl$_3$): δ 8.60-8.45 (m, 1H), 8.10 (d, 1H), 7.83 (s, 1H), 7.65 (s, 1H), 7.60-7.45 (m, 1H), 7.18 (d, 1H), 5.85-5.70 (m, 2H), 5.55-5.30 (m, 2H), 5.25 (d, J=18 Hz, 1H), 5.11 (d, J=11.9 Hz, 1H), 4.73-4.50 (m, 3H), 4.22 (d, 1H), 4.10-4.00 (m, 1H), 4.02 (s, 3H), 3.85-3.70 (m, 6H), 3.60-3.50 (m, 1H), 2.78-2.58 (m, 2H), 2.15-2.05 (m, 1H), 2.00-1.85 (m, 1H), 1.80-1.40 (m, 9H), 1.43 (d, J=6.4 Hz, 6H), 1.05 (s, 9H). $^{31}$P NMR (300 MHz, CDCl$_3$): δ 0.44. LC/MS: 871 (M$^+$+1).

Example 70

Preparation of Compound 70

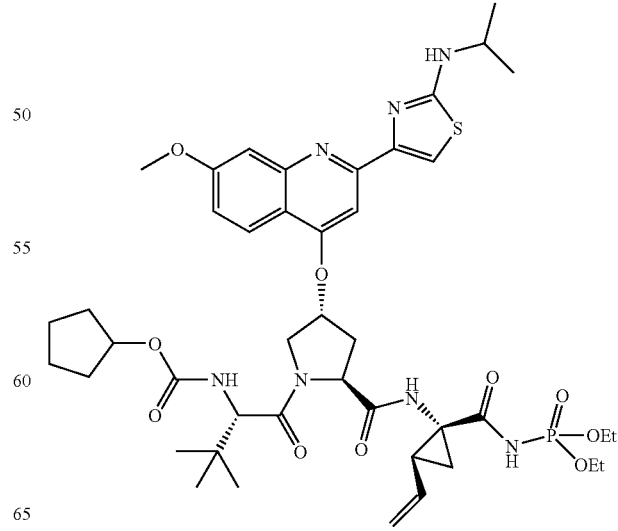

249

To a solution of acid (150 mg, 0.197 mmol) in 3 mL of THF was added CDI (80 mg, 0.49 mmol). The solution mixture was refluxed for 2 h. To the cooled mixture was added the phosphoramidate (121 mg, 0.79 mmol) followed by DBU (200 µL, 1.38 mmol) and refluxed for 4 h. The mixture was concentrated in vacuo, dissolved in 1 mL of MeOH and purified by reverse phase HPLC (eluted with 10% to 75% H$_2$O/CH$_3$CN) to give 70 as a yellow solid (60 mg, 34%). $^1$H NMR (300 MHz, CDCl$_3$): δ8.70 (bs, 1H), 8.50 (d, 1H), 8.10 (d, 1H), 7.90 (s, 1H), 7.67 (s, 1H), 7.42-7.33 (m, 1H), 7.21 (d, 1H), 5.85-5.70 (m, 2H), 5.50-5.40 (d, 1H), 5.25 (d, J=18 Hz, 1H), 5.11 (d, J=11.9 Hz, 1H), 4.65-4.55 (m, 3H), 4.30-4.00 (m, 10H), 4.02 (s, 3H), 3.65-3.50 (m, 2H), 2.75-2.65 (m, 2H), 2.15-2.05 (m, 1H), 2.02-1.95 (m, 1H), 1.80-1.40 (m, 6H), 1.42 (d, 6H), 1.40-1.25 (m, 6H), 1.05 (s, 9H). $^{31}$P NMR (300 MHz, CDCl$_3$): δ −2.7. LC/MS: 899 (M$^+$+1).

Example 71

Preparation of Compound 71

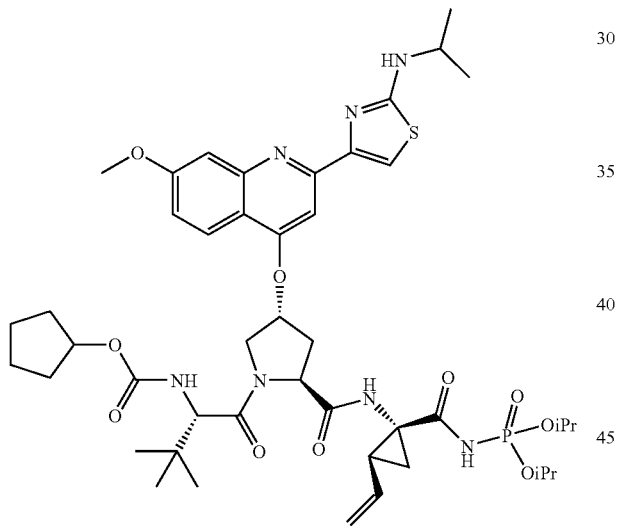

To a solution of acid (200 mg, 0.262 mmol) in 3 mL of THF was added CDI (85 mg, 0.52 mmol). The solution mixture was refluxed for 2 h. To the cooled mixture was added the phosphoramidate (142 mg, 0.79 mmol) followed by DBU (275 µL, 1.83 mmol) and refluxed for 4 h. The mixture was concentrated in vacuo, dissolved in 1 mL of MeOH and purified by reverse phase HPLC (eluted with 10% to 95% H$_2$O/CH$_3$CN) to give 71 as a yellow solid (100 mg, 41%). $^1$H NMR (300 MHz, CDCl$_3$): δ 8.48-8.27 (m, 1H), 8.20-8.00 (m, 1H), 7.70-7.60 (m, 1H), 7.58 (s, 1H), 7.15 (d, 1H), 5.90-5.70 (m, 1H), 5.60 (bs, 1H), 5.50-5.05 (m, 3H), 4.85-4.55 (m, 3H), 4.35-4.25 (m, 1H), 4.20-3.95 (m, 2H), 4.02 (s, 3H), 3.80-3.50 (m, 2H), 2.75-2.60 (m, 2H), 1.80-1.50 (m, 8H), 1.42 (d, 6H), 1.35-1.20 (m, 12H), 1.05 (s, 9H). $^{31}$P NMR (300 MHz, CDCl$_3$): δ −4.9 and −5.2. LC/MS: 926 (M$^+$).

250

Example 72

Preparation of Compound 72

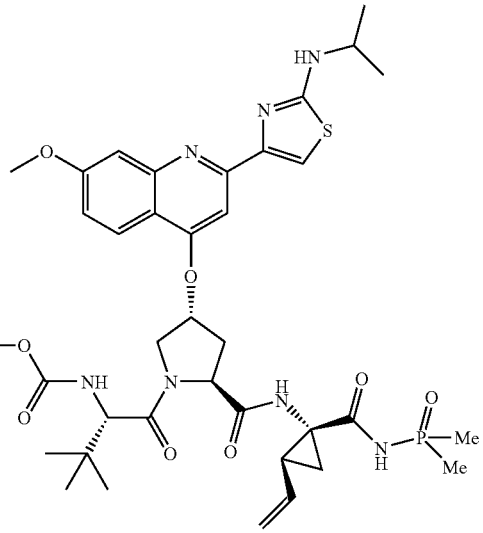

To a solution of acid (200 mg, 0.262 mmol) in 2 mL of DCM was added CDI (88 mg, 0.524 mmol). The solution mixture was refluxed for 2 h. To the cooled mixture was added the freshly made phosphoramide (2.62 mmol) followed by DBU (195 µL, 1.31 mmol) and refluxed for 2 h. The mixture was concentrated in vacuo, dissolved in 1 mL of MeOH and purified by reverse phase HPLC (eluted with 10% to 75% H$_2$O/CH$_3$CN) to give 72 as a yellow solid (9 mg, 4%). $^1$H NMR (300 MHz, CDCl$_3$): δ 11.2 (bs, 1H), 8.62 (bs, 1H), 8.41 (d, 1H), 8.09 (d, 1H), 7.90 (bs, 1H), 7.64 (s, 1H), 7.63-7.50 (m, 1H), 7.21 (d, 1H), 5.93-5.63 (m, 2H), 5.30 (d, J=18 Hz, 1H), 5.15 (d, J=11.9 Hz, 1H), 4.65-4.55 (m, 2H), 4.22 (d, 1H), 4.10-4.00 (m, 1H), 4.02 (s, 3H), 3.60-3.00 (m, 8H), 2.78-2.58 (m, 2H), 2.10-2.03 (m, 1H), 2.00-1.95 (m, 1H), 1.80-1.60 (m, 6H), 1.65-1.15 (m, 4H), 1.43 (d, J=6.4 Hz, 6H), 1.05 (s, 9H). $^{31}$P NMR (300 MHz, CDCl$_3$): δ 49.8. LC/MS: 839 (M$^+$+1).

Example 73

Preparation of Compound 73

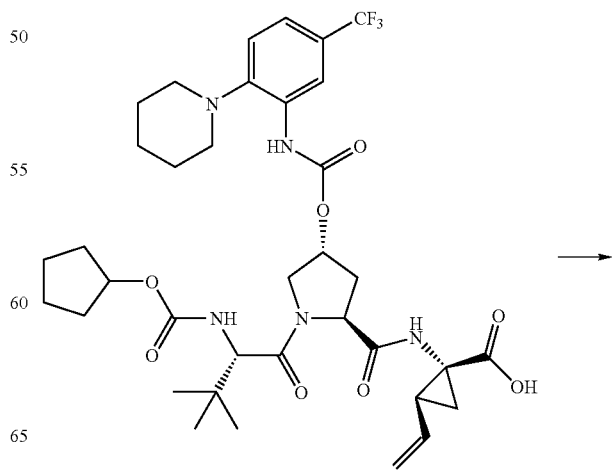

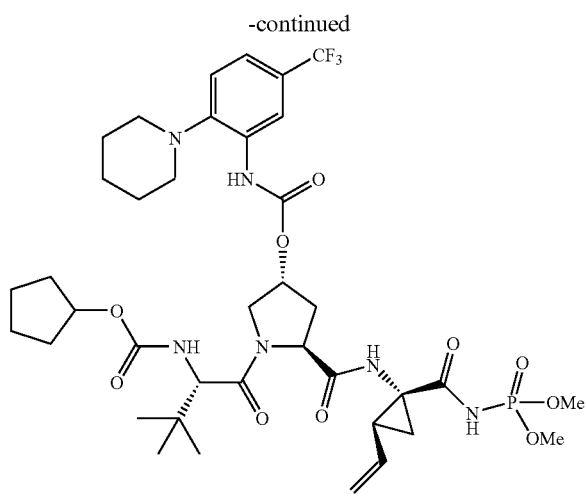

To a solution of acid (270 mg, 0.367 mmol) in 4 mL of DCM was added CDI (120 mg, 0.734 mmol). The solution mixture was refluxed for 2 h. To the cooled mixture was added the phosphoramidate (185 mg, 1.47 mmol) followed by DBU (385 μL, 2.57 mmol) and refluxed for 2 h. The mixture was concentrated in vacuo, dissolved in 1 mL of MeOH and purified by reverse phase HPLC (eluted with 10% to 95% $H_2O/CH_3CN$) to give 73 as a white solid (120 mg, 39%). $^1H$ NMR (300 MHz, $CDCl_3$): δ 8.65 (d, 1H), 8.40 (s, 1H), 8.02 (s, 1H), 7.35-7.20 (m, 3H), 5.85-5.75 (m, 5H), 5.43 (bs, 2H), 5.28 (d, J=17.1 Hz, 1H), 5.14 (d, J=11.9 Hz, 1H), 4.95-4.87 (m, 1H), 4.43 (t, 1H), 4.35-4.18 (m, 2H), 4.02-3.90 (m, 1H), 3.90-3.75 (m, 6H), 2.95-2.80 (m, 6H), 2.45-2.35 (m, 2H), 2.17-2.07 (m, 1H), 2.02-1.96 (m, 1H), 1.85-1.75 (m, 6H), 1.75-1.55 (m, 8H), 1.55-1.43 (m, 3H), 1.02 (s, 9H). $^{31}P$ NMR (300 MHz, $CD_3OD$): δ 0.58. LC/MS: 844 ($M^+$+1).

Example 74

Preparation of Compound 74

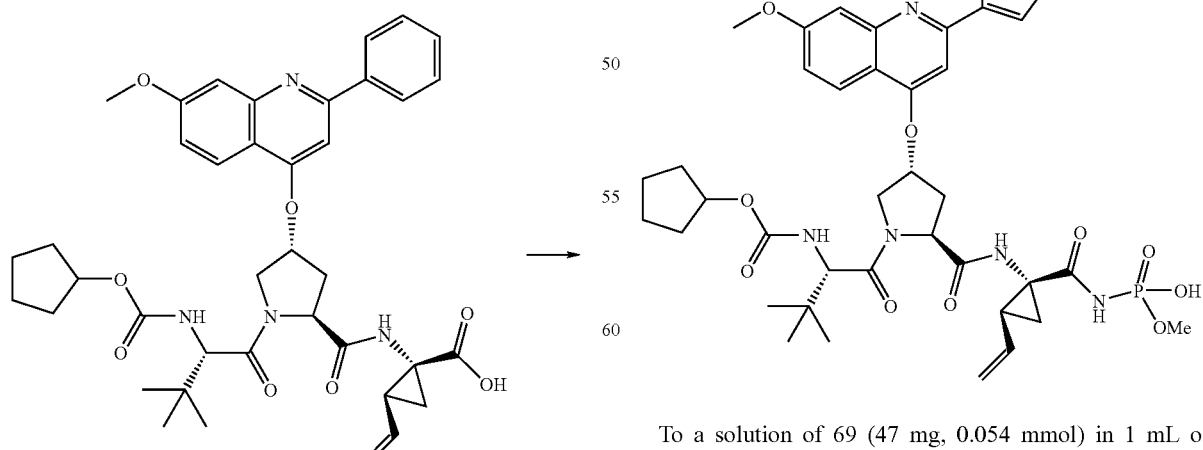

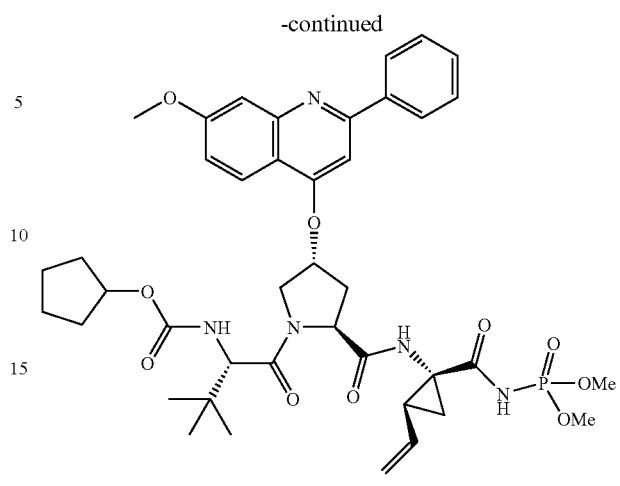

To a solution of acid (200 mg, 0.287 mmol) in 2 mL of DCM was added CDI (93 mg, 0.574 mmol). The solution mixture was refluxed for 1 h30. To the cooled mixture was added the phosphoramidate (72 mg, 0.392 mmol) followed by DBU (245 μL, 1.43 mmol) and refluxed for 2 h. The mixture was concentrated in vacuo, dissolved in 1 mL of MeOH and purified by reverse phase HPLC (eluted with 10% to 75% $H_2O/CH_3CN$) to give 74 as a white solid (103 mg, 45%). $^1H$ NMR (300 MHz, $CDCl_3$): δ 8.50 (d, 1H), 8.18 (d, 1H), 7.90 (bs, 2H), 7.80 (s, 1H), 7.75 (bs, 1H), 7.42 (bs, 3H), 7.19 (d, 1H), 7.07 (bs, 1H), 5.74 (qu, 1H), 5.58 (bs, 1H), 5.45 (d, 1H), 5.25 (d, J=18 Hz, 1H), 5.15 (d, J=11.9 Hz, 1H), 4.90-4.80 (m, 1H), 4.75-4.60 (m, 2H), 4.25 (d, 1H), 4.15-4.05 (m, 1H), 4.00 (s, 3H), 3.95-3.75 (m, 6H), 2.85-2.75 (m, 1H), 2.73-2.60 (m, 1H), 2.20-2.10 (m, 1H), 2.00-1.90 (m, 1H), 1.80-1.50 (m, 8H), 1.50-1.40 (m, 1H), 1.05 (s, 9H). $^{31}P$ NMR (300 MHz, $CDCl_3$): δ 0.4. LC/MS: 807 ($M^+$+1).

Example 75

Preparation of Compound 75

To a solution of 69 (47 mg, 0.054 mmol) in 1 mL of pyridine was added one portion of NaI (40 mg, 0.270 mmol). The solution mixture was stirred at 95° C. for 1 h. The second portion of NaI (40 mg, 0.270 mmol) was then added and the reaction mixture was stirred at 95° C. for another 1 h. The mixture was concentrated in vacuo using high vacuum pump at 40° C. and three drops of a 1M solution of HCl was added. The crude mixture was dissolved in 1 mL of MeOH. The mixture was concentrated in vacuo, dissolved in 1 mL of MeOH and purified by reverse phase HPLC (eluted with 10% to 75% H$_2$O/CH$_3$CN) to give 75 as a yellow solid (27 mg, 58%). $^1$H NMR (300 MHz, CD$_3$OD): δ 9.23 (s, 1H), 8.25 (d, 1H), 8.20 (s, 1H), 7.77 (s, 2H), 7.35 (dd, 1H), 5.85-5.76 (m, 2H), 5.27 (d, J=18 Hz, 1H), 5.09 (d, J=11.9 Hz, 1H), 4.65-4.50 (m, 3H), 4.15-4.05 (m, 3H), 4.10-4.00 (m, 1H), 4.05 (s, 3H), 3.70-3.60 (m, 3H), 2.80-2.70 (m, 1H), 2.55-2.40 (m, 1H), 2.20-2.10 (m, 1H), 1.90-1.80 (m, 1H), 1.75-1.43 (m, 6H), 1.50-1.30 (m, 3H), 1.35 (d, J=6.4 Hz, 6H), 1.05 (s, 9H). $^{31}$P NMR (300 MHz, CDCl$_3$): δ2.78. LC/MS: 856 (M$^+$+1).

1H), 1.75-1.45 (m, 6H), 1.45-1.18 (m, 5H), 1.38 (d, 6H), 1.05 (s, 9H). $^{31}$P NMR (300 MHz, CDCl$_3$): δ −4.5. LC/MS: 871 (M$^+$+1).

Example 77

Preparation of Compound 77

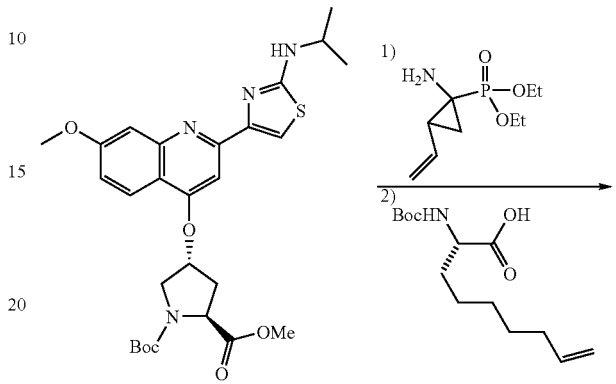

Example 76

Preparation of Compound 76

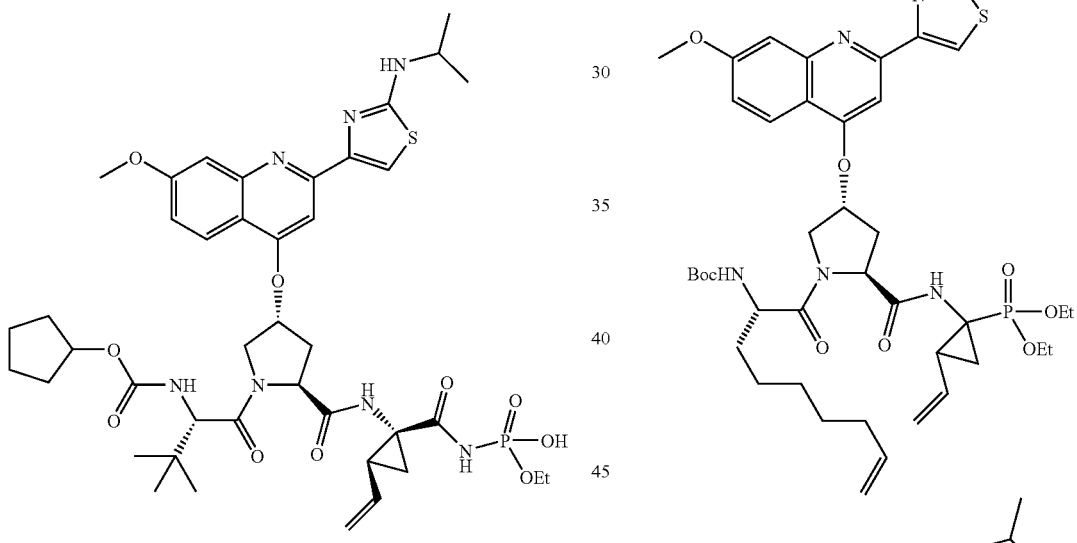

To a solution of 70 (7 mg, 0.008 mmol) in 0.5 mL of pyridine was added one portion of NaI (6 mg, 0.039 mmol). The solution mixture was stirred at 95° C. for 1 h. The second portion of NaI (6 mg, 0.039 mmol) was then added and the reaction mixture was stirred at 95° C. for ON. The mixture was concentrated in vacuo using high vacuum pump at 40° C. and three drops of a 1M solution of HCl was added. The crude mixture was dissolved in 1 mL of MeOH. The mixture was concentrated in vacuo, dissolved in 1 mL of MeOH and purified by reverse phase HPLC (eluted with 10% to 75% H$_2$O/CH$_3$CN) to give 76 as a yellow solid (2 mg, 29%). $^1$H NMR (300 MHz, CD$_3$OD): δ 9.20 (bs, 1H), 8.25 (d, 1H), 8.20 (s, 1H), 7.78 (s, 1H), 7.35 (d, 1H), 5.85-5.78 (m, 2H), 5.27 (d, J=18 Hz, 1H), 5.09 (d, J=11.9 Hz, 1H), 4.70-4.50 (m, 4H), 4.30-4.10 (m, 4H), 4.10-3.95 (m, 3H), 4.04 (s, 3H), 2.80-2.70 (m, 1H), 2.60-2.40 (m, 1H), 2.10-2.05 (m, 1H), 1.90-1.80 (m,

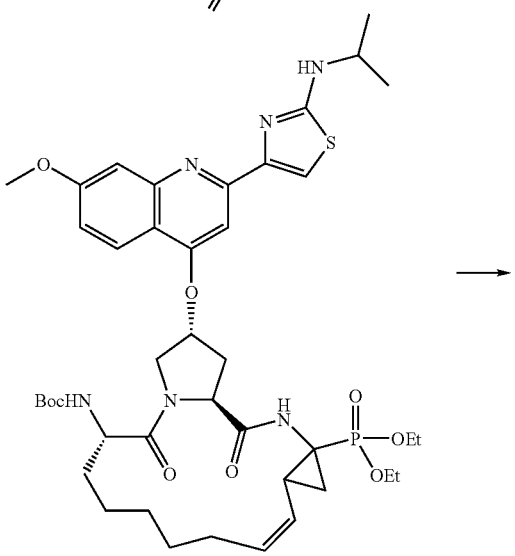

-continued

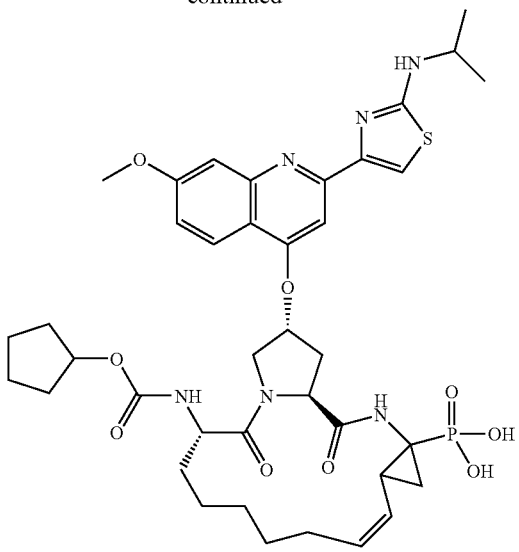

Step 1. To methyl ester (1.3 g, 2.39 mmol) dissolved in 45 mL of a 3/2/1 solution mixture of THF/MeOH/H$_2$O was added LiOH (500 mg, 11.95 mmol. The mixture was stirred at rt for 1 h. The reaction was then acidified to pH 4 using a 37% solution of HCl in H$_2$O and extracted 3× by DCM. The organic phase was evaporated in vacuo and azeotroped 3× with toluene to give the acid intermediate. To the acid (2.39 mmol) in 40 mL of THF at –40° C. was added TEA (500 μL, 3.58 mmol) followed by ethylchloroformate (345 μL, 3.58 mmol). The solution was stirred for 30 min at –40° C. and one more equivalent of TEA (333 μL, 2.39 mmol) and ethylchloroformate (228 μL, 2.39 mmol) was added. The mixture was stirred for another 30 min and a solution of amino phosphonate (915 mg, 3.58 mmol) with TEA (500 μL, 3.58 mmol) in 10 mL of THF was added. The solvent was evaporated under vacuo and the mixture was purified by silica gel chromatography using SiO$_2$ (eluted with 0% to 100% EtOAc/hexane) to give P1 phosphonate intermediate as a dark orange solid (870 mg, 50%). LC/MS: 730 (M$^+$+1). Step 2. To the P1 phosphonate (450 mg, 0.617 mmol) dissolved in 10 mL of DCM was added 5 mL of TFA. The reaction mixture was stirred for 30 min and the solvent was concentrated in vacuo using high vacuum pump at 30° C. and azeotroped 3× with toluene to give the free amine. To the amine (0.617) in 30 mL of THF was added NMM (200 μL, 1.85 mmol) followed by HATU (350 mg, 0.92 mmol) and acid (200 mg, 0.74 mmol). The solution was stirred for 6 h, quenched by a saturated solution of NH$_4$Cl in H$_2$O, extracted by DCM and evaporated under vacuo. The crude product was dissolved in 100 mL EtOAC and washed by a saturated solution of NaHCO$_3$ in H$_2$O 3×. The EtOAC was removed under vacuo and the crude product was purified by silica gel chromatography using SiO$_2$ (eluted with 0% to 100% EtOAc/hexane) to give P3 phosphonate intermediate as a dark orange solid (510 mg, 94%). $^1$H-NMR (300 MHz, CD$_3$OD): δ 8.24 (d, 1H), 7.95 (bs, 1H), 7.65-7.58 (m, 2H), 7.25 (dd, 1H), 6.00-5.90 (m, 2H), 5.67 (bs, 1H), 5.32 (dd, 1H), 5.15 (dd, 1H), 5.05-4.90 (m, 1H), 4.70-4.50 (m, 1H), 4.33-3.90 (m, 8H), 2.85-2.65 (m, 1H), 2.35-2.45 (m, 1H), 2.25-2.00 (m, 3H), 1.80-1.65 (m, 1H), 1.65-1.15 (m, 16H), 1.22 (s, 9H). $^{31}$P NMR (300 MHz, CD$_3$OD): δ 23.5 and 23.2 (both diastereomer). LC/MS: 883 (M$^+$+1).

Step 3. To P3 phosphonate intermediate (200 mg, 0.227 mmol) and G1 Grubb catalyst (56 mg, 0.068 mmol) under argon was added 24 mL of degassed DCM. The reaction was refluxed for 3 h. The mixture was concentrated in vacuo, dried loaded onto SiO$_2$ and purified by silica gel chromatography using SiO$_2$ (eluted with 0% to 100% EtOAc/hexane) to give cyclized product as a dark orange solid (64 mg, 32%). $^1$H NMR (300 MHz, CD$_3$OD): δ 8.73 (s, 1H), 8.33 (d, 1H), 7.75 (s, 2H), 7.25 (dd, 1H), 5.82 (bs, 1H), 5.70 (q, 1H), 5.35 (t, 1H), 4.62 (t, 1H), 4.38-4.03 (m, 7H), 4.04 (s, 3H), 3.00-2.82 (m, 1H), 2.82-2.72 (m, 1H), 2.62-2.50 (m, 1H), 2.35-2.20 (m, 1H), 1.90-1.70 (m, 2H), 1.62-1.38 (m, 8H), 1.40-1.25 (m, 16H), 1.08 (s, 9H). LC/MS: 855 (M$^+$+1).

Step 4. To a solution of cyclopentanol (3 eq.) in 10 mL of THF was added a of 20% phosgene solution in toluene (5 eq.). The reaction mixture was stirred at rt for 1 h. The ⅔ of the mixture was concentrated in vacuo at 40° C. and dissolved in 2 mL of DCM. This process was repeated 3×.

To a solution of cyclized product (120 mg, 0.140 mmol) in 2 mL of DCM at 0° C. was added TMSI (160 μL, 1.12 mmol). The solution mixture was stirred at rt for 1 h. The mixture was concentrated in vacuo using high vacuum pump at 30° C. and azeotroped 3× with toluene. The crude mixture was dissolved in 1 mL of DCM. One third of TEA (52 μL, 0.373 mmol) was added to it followed by slow addition of the chloroformate prepared above. The balance of TEA (104 μL, 0.746 mmol) was then added to the mixture. The reaction mixture was quenched by adding a 1M solution of HCl in water until pH 3 was reached. The mixture was extracted with DCM, concentrated in vacuo, dissolved in 1 mL of MeOH and purified by reverse phase HPLC (eluted with 0% to 60% H$_2$O/CH$_3$CN) to give diethyl phosphonate 77 as a yellow solid (3 mg, 3%). $^1$H NMR (300 MHz, CD$_3$OD): δ 8.31 (d, J=9.1 Hz, 1H), 8.16 (s, 1H), 7.76-7.72 (m, 2H), 7.33 (bdd, 1H), 5.84 (bs, 1H), 5.70-5.60 (m, 1H), 5.38-5.25 (m, 1H), 4.80-4.68 (m, 1H), 4.38-4.10 (m, 2H), 4.04 (s, 3H), 2.85-2.73 (m, 1H), 2.73-2.50 (m, 1H), 1.65-1.30 (m, 9H), 1.34 (d, J=6.4 Hz, 6H). $^{31}$P NMR (300 MHz, CD$_3$OD): δ 21.2. LC/MS: 812 (M$^+$+1).

Example 78

Preparation of Compound 78

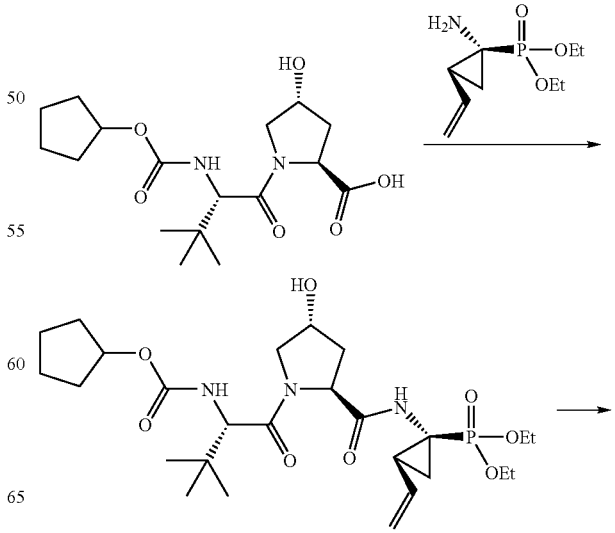

-continued

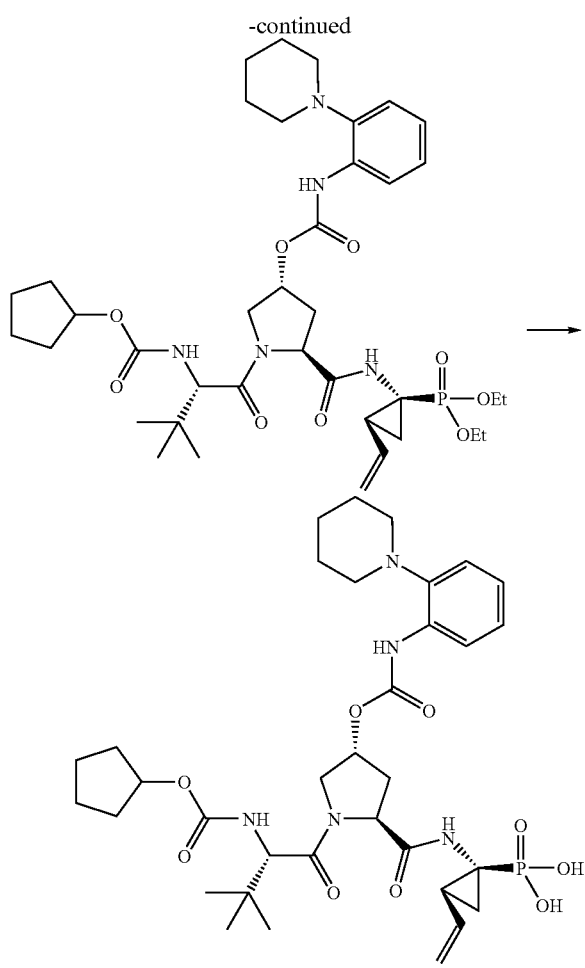

Step 1. To starting acid (1.2 g, 3.36 mmol) dissolved in 30 mL of DMF was added amine (880 mg, 4.03 mmol), TBTU (2.16 g, 6.72 mmol) and DIPEA (1.14 mL, 10.08 mmol). The mixture was stirred at rt for 4 h, quenched by a saturated solution of NH$_4$Cl in H$_2$O, extracted by DCM and evaporated under vacuo. The crude product was dissolved in 100 mL EtOAC and washed by a saturated solution of NaHCO$_3$ in H$_2$O 3×. The EtOAC was removed under vacuo and the crude product was purified by silica gel chromatography using SiO$_2$ (eluted with 0% to 100% EtOAc/hexane) to give crude product as a yellow solid (950 mg, 51%). $^1$H-NMR (300 MHz, CDCl$_3$): δ 7.55 (s, 1H), 6.03-5.88 (m, 1H), 5.43 (t, 1H), 5.33-5.20 (m, 1H), 5.13-4.98 (m, 2H), 4.62-4.45 (m, 2H), 4.30-3.93 (m, 7H), 3.62-3.50 (m, 1H), 3.45-3.33 (m, 1H), 2.50-2.20 (m, 2H), 1.90-1.50 (m, 11H), 1.38-1.20 (m, 9H), 1.02 (s, 9H). LC/MS: 558 (M$^+$+1).

Step 2. To crude obtained above (130 mg, 0.233 mmol) dissolved in 5 mL of THF was added DSC (120 mg, 0.466 mmol) followed by NaH (60% dispersion in mineral oil) (18 mg, 0.466 mmol). The reaction was refluxed for 6 h, quenched by 30 mL of 1M solution of HCl in water, extracted by EtOAc and dried using anhydrous magnesium sulfate. The organic phase was concentrated in vacuo, dissolved in 1.5 mL of DCM and added to a microwave flask. To the solution was added 2-piperidin-1-yl-phenylamine (82 mg, 0.466 mmol). The microwave flask was sealed and put on the microwave apparatus. The reaction was heated to 65° C. for 1 h. The reaction was purified by silica gel chromatography using SiO$_2$ (eluted with 0% to 100% EtOAc/hexane) to give carbamate as a yellow solid (146 mg, 83%).

Step 3. To a solution of carbamate (146 mg, 0.192 mmol) in 5 mL of CH$_3$CN at 0° C. was added TMSI (220 μL, 1.15 mmol) followed by 2,6-lutidine (178 μL, 1.53 mmol). The solution mixture was stirred at rt for 1 h. The mixture was concentrated in vacuo using high vacuum pump at 30° C. and azeotroped 3× with toluene. The reaction mixture was then quenched by MeOH. The MeOH was evaporated in vacuo. The crude mixture was dissolved in 1 mL of MeOH and purified by reverse phase HPLC (eluted with 10% to 75% H$_2$O/CH$_3$CN) to give 78 as a white solid (45 mg, 33%). $^1$H NMR (300 MHz, CD$_3$OD): δ 7.62-7.58 (m, 2H), 7.40-7.22 (m, 3H), 6.05-5.90 (m, 1H), 5.43 (bs, 1H), 5.25 (dd, J=17, 1.5 Hz, 1H), 5.06 (dd, J=10.4, 1.8 Hz, 1H), 4.51 (bt, 1H), 4.35 (bd, 1H), 4.25 (s, 1H), 4.00-3.95 (m, 1H), 2.55-2.43 (m, 1H), 2.38-2.24 (m, 1H), 2.10-2.00 (m, 1H), 1.99-1.83 (m, 5H), 1.80-1.60 (m, 9H), 1.60-1.40 (m, 5H), 1.06 (s, 9H), 1.05 (s, 9H). $^{31}$P NMR (300 MHz, CD$_3$OD): δ 20.7. LC/MS: 704 (M$^+$+1).

Example 79

Preparation of Compound 79

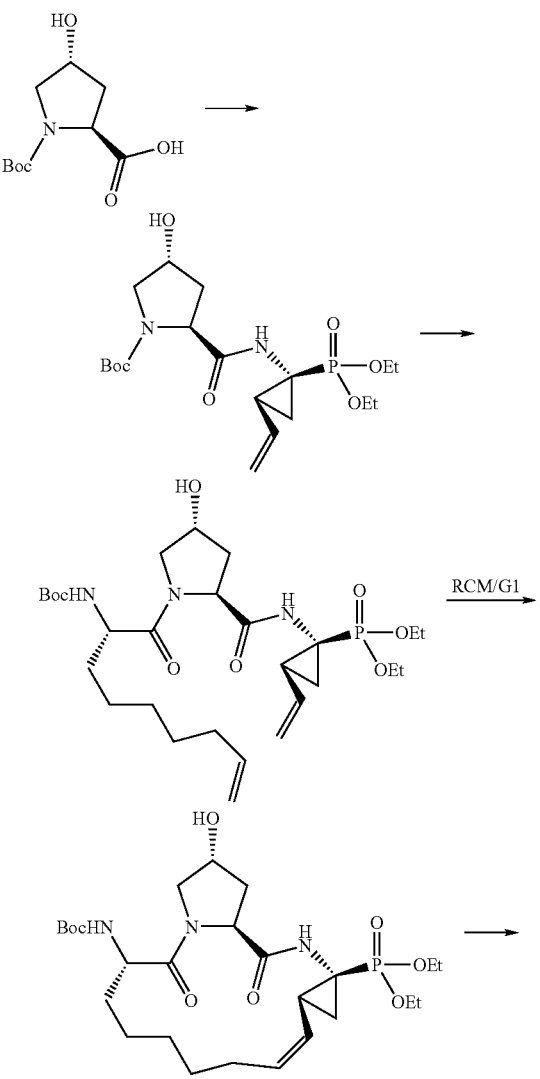

-continued

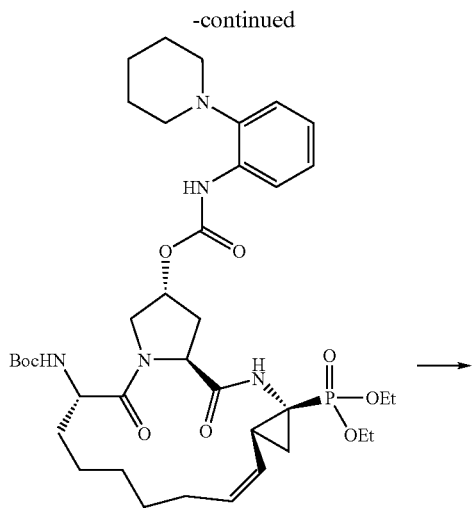

Step 1. To proline acid (905 mg, 3.92 mmol) dissolved in 40 mL of DMF was added diethyl aminophosphonate (1.03 g, 4.7 mmol), TBTU (2.2 g, 6.86 mmol) and DIPEA (1.8 mL, 15.68 mmol). The mixture was stirred at rt for 1 h, quenched by a saturated solution of NH$_4$Cl in H$_2$O, extracted by DCM and evaporated under vacuo. The crude product was dissolved in 100 mL EtOAC and washed by a saturated solution of NaHCO$_3$ in H$_2$O 3×. The EtOAC was removed under vacuo and the crude product was purified by silica gel chromatography using SiO$_2$ (eluted with 0% to 100% EtOAc/hexane) to give the P1 intermediate as a yellow solid (470 mg, 28%). To the P1 phosphonate (470 mg, 0.73 mmol) dissolved in 10 mL of DCM was added 5 mL of TFA. The reaction mixture was stirred for 30 min and the solvent was concentrated in vacuo using high vacuum pump at 30° C. and azeotroped 3× with toluene to give the free amine. To the amine (0.73 mmol) in 30 mL of THF was added NMM (240 μL, 2.19 mmol) followed by HATU (415 mg, 1.095 mmol) and carboxylic acid (275 mg, 1.22 mmol). The solution was stirred for 6 h, quenched by a saturated solution of NH$_4$Cl in H$_2$O, extracted by DCM and evaporated under vacuo. The crude product was dissolved in 100 mL EtOAC and washed by a saturated solution of NaHCO$_3$ in H$_2$O 3×. The EtOAC was removed under vacuo and the crude product was purified by silica gel chromatography using SiO$_2$ (eluted with 0% to 100% EtOAc/hexane) to give tripeptide intermediate as a dark orange solid (187 mg, 43%).

Step 2. To tripeptide intermediate (137 mg, 0.234 mmol) and G1 Grubb catalyst (56 mg, 0.058 mmol) under argon was added 25 mL of degassed DCM. The reaction was refluxed for 3 h. The mixture was concentrated in vacuo, dried loaded onto SiO$_2$ and purified by silica gel chromatography using SiO$_2$ (eluted with 0% to 100% EtOAc/hexane) to give the macrocyclic product as a yellow solid (93 mg, 71%).

Step 3. To macrocyclic product (110 mg, 0.197 mmol) dissolved in 5 mL of THF was added DSC (101 mg, 0.394 mmol) followed by NaH (60% dispersion in mineral oil) (15 mg, 0.394 mmol). The reaction was refluxed for 6 h, quenched by 30 mL of 1M solution of HCl in water, extracted by EtOAc and dried using anhydrous magnesium sulfate. The organic phase was concentrated in vacuo, dissolved in 1.5 mL of DCM and added to a microwave flask. To the solution was added 2-piperidin-1-yl-phenylamine (69 mg, 0.394 mmol). The microwave flask was sealed and put on the microwave apparatus. The reaction was heated to 65° C. for 1 h. The reaction was purified by silica gel chromatography using SiO$_2$ (eluted with 0% to 100% EtOAc/hexane) to give carbamate as a yellow solid (50 mg, 33%). $^1$H NMR (300 MHz, CDCl$_3$): δ 8.10-7.90 (m, 2H), 7.18-7.06 (m, 2H), 7.05-6.96 (m, 1H), 6.80 (bs, 1H), 5.75-5.60 (m, 1H), 5.50-5.33 (m, 2H), 4.63-4.40 (m, 2H), 4.22-4.07 (m, 4H), 4.05-3.93 (m, 2H), 2.59-2.40 (m, 3H), 2.20-1.80 (m, 5H), 1.80-1.50 (m, 10H), 1.38 (s, 9H), 1.28 (t, 6H), 1.60-1.40 (m, 8H). LC/MS: 761 (M$^+$+1).

Step 4. To a solution of carbamate (70 mg, 0.092 mmol) in 3 mL of CH$_3$CN at 0° C. was added TMSI (105 μL, 0.736 mmol). The solution mixture was stirred at rt for ¾ h. The mixture was concentrated in vacuo using high vacuum pump at 30° C. and azeotroped 3× with toluene. The crude mixture was dissolved in 1 mL of DCM. One third of TEA (38 μL, 0.276 mmol) was added to it followed by slow addition of chloroformate. The balance of TEA (76 μL, 0.552 mmol) was then added to the mixture. The reaction mixture was quenched by adding two drops of a 1M solution of HCl. The mixture was concentrated in vacuo, dissolved in 1 mL of MeOH and purified by reverse phase HPLC (eluted with 10% to 75% H$_2$O/CH$_3$CN) to give 79 as a white solid (32 mg, 49%). $^1$H NMR (300 MHz, CD$_3$OD): δ 7.73 (d, J=7.9 Hz, 1H), 7.50-7.38 (m, 3H), 5.65-5.58 (m, 1H), 5.51 (bs, 1H), 5.30 (bt, 1H), 4.85 (bs, 1H), 4.62-4.50 (m, 2H), 4.30-4.22 (m, 1H), 4.00-3.90 (m, 1H), 3.65-3.50 (m, 4H), 2.50-2.40 (m, 3H), 2.22-2.10 (m, 1H), 2.08-1.98 (m, 5H), 1.98-1.78 (m, 5H), 1.80-1.60 (m, 6H), 1.70-1.60 (m, 6H), 1.60-1.40 (m, 8H). $^{31}$P NMR (300 MHz, CD$_3$OD): δ 21.3. LC/MS: 716 (M$^+$+1).

Example 80

Preparation of Compound 80

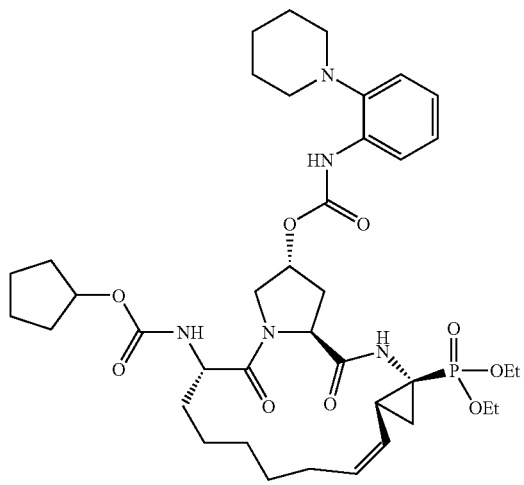

To a solution of N-Boc tripeptide obtained for example 79 (125 mg, 0.164 mmol) in 3 mL of DCM was added 3 mL of TFA. The solution mixture was stirred at rt for ¾ h. The mixture was concentrated in vacuo using high vacuum pump at 40° C. and azeotroped 3× with toluene. The crude mixture was dissolved in 1 mL of DCM. One third of TEA (38 μL, 0.276 mmol) was added to it followed by slow addition of chloroformate. The balance of TEA (76 μL, 0.552 mmol) was then added to the mixture. The reaction mixture was quenched by adding two drops of a 1M solution of HCl. The mixture was concentrated in vacuo, dissolved in 1 mL of MeOH and purified by reverse phase HPLC (eluted with 10% to 95% $H_2O/CH_3CN$) to give 80 as a white solid (42 mg, 33%). $^1$H NMR (300 MHz, $CD_3OD$): δ 8.66 (s, 1H), 7.75 (bs, 1H), 7.40 (bs, 1H), 7.22 (bs, 2H), 5.67 (q, J=9.5 Hz, 1H), 5.47 (bs, 1H), 5.37 (t, J=10.0 Hz, 1H), 4.55-4.45 (m, 2H), 4.30-4.00 (m, 5H), 3.95 (dd, J=3.9 Hz, 1H), 3.30-3.00 (m, 2H), 2.85-2.75 (m, 1H), 2.50-2.40 (m, 2H), 2.00-1.80 (m, 5H), 1.75-1.40 (m, 15H), 1.33 (t, J=7.0 Hz, 3H), 1.26 (t, J=7.1 Hz, 3H). $^{31}$P NMR (300 MHz, $CD_3OD$): δ 23.8. LC/MS: 772 (M$^+$+1).

Example 81

Preparation of Compound 81

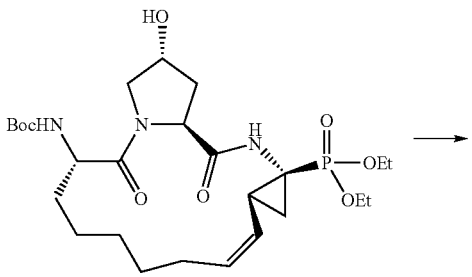

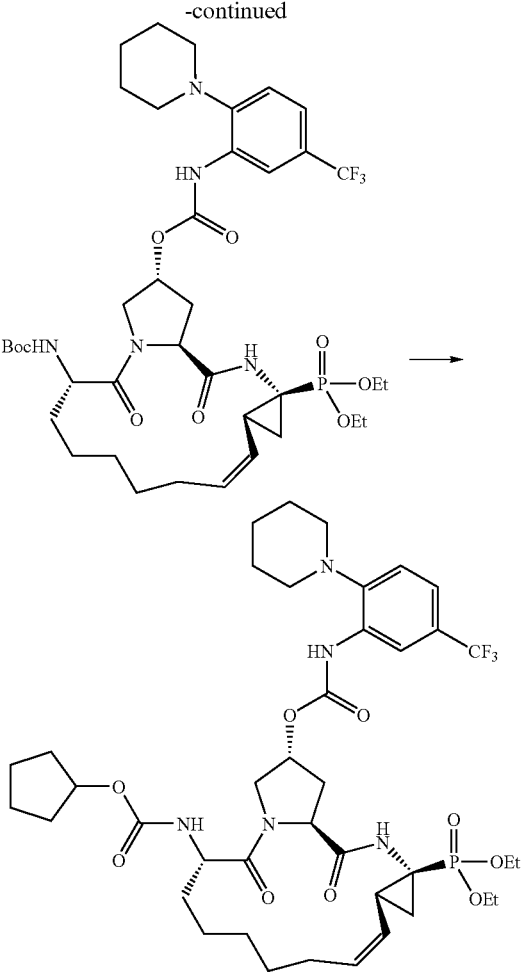

Step 1. To macrocyclic alcohol (300 mg, 0.538 mmol) dissolved in 20 mL of THF was added DSC (275 mg, 1.076 mmol) followed by NaH (60% dispersion in mineral oil) (15 mg, 1.345 mmol). The reaction was refluxed for 6 h, quenched by 30 mL of 1M solution of HCl in water, extracted by EtOAc and dried using anhydrous magnesium sulfate. The organic phase was concentrated in vacuo, dissolved in 3 mL of DCM and added to a microwave flask. To the solution was added 2-piperidin-1-yl-5-trifluoromethyl-phenylamine (394 mg, 1.61 mmol). The microwave flask was sealed and put on the microwave apparatus. The reaction was heated to 65° C. for 7 h. The reaction was purified by silica gel using $SiO_2$ (eluted with 0% to 100% EtOAc/hexane) to give desired product as a yellow solid (350 mg, 79%).

Step 2. To a solution of carbamate (350 mg, 0.423 mmol) in 3 mL of DCM was added 3 mL of TFA. The solution mixture was stirred at rt for ¾ h. The mixture was concentrated in vacuo using high vacuum pump at 40° C. and azeotroped 3× with toluene. The crude mixture was dissolved in 1 mL of DCM. One third of TEA (200 μL, 1.4 mmol) was added to it followed by slow addition of chloroformate. The balance of TEA (400 μL, 2.8 mmol) was then added to the mixture. The reaction mixture was quenched after 2 h by adding a saturated solution of $NaHCO_3$ in water. The mixture was extracted by DCM, concentrated and purified by normal phase chromatography using $SiO_2$ to give desired product as a white solid (270 mg, 76%). $^1$H NMR (300 MHz, $CD_3OD$): δ 8.64 (s, 1H), 8.26 (s, 1H), 7.33 (s, 2H), 5.65 (q, J=10.1 Hz, 1H), 5.44 (bs, 1H), 5.34 (t, J=9.7 Hz, 1H), 4.77 (bs, 1H), 4.55-4.45 (m, 2H), 4.30-4.00 (m, 5H), 3.93 (dd, J=11.3, 3.3 Hz, 1H), 3.00-2.75

(m, 5H), 2.50-2.40 (m, 1H), 2.40-2.20 (m, 2H), 1.90-1.70 (m, 5H), 1.70-1.38 (m, 13H), 1.34 (t, J=7.1 Hz, 3H), 1.26 (t, J=7.0 Hz, 3H). ³¹P NMR (300 MHz, CD₃OD): δ 23.7. LC/MS: 840 (M⁺+1).

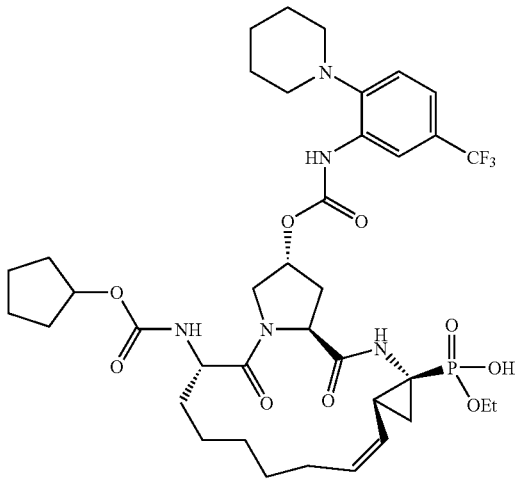

Step 3. To a solution of carbamate (120 mg, 0.143 mmol) in 2 mL of pyridine was added one portion of NaI (110 mg, 0.71 mmol). The solution mixture was stirred at 95° C. for 1 h. The second portion of NaI (110 mg, 0.71 mmol) was then added and the reaction mixture was stirred at 95° C. for another 6 h. The mixture was concentrated in vacuo using high vacuum pump at 40° C. and three drops of a 1M solution of HCl was added. The crude mixture was dissolved in 1 mL of MeOH. The mixture was concentrated in vacuo, dissolved in 1 mL of MeOH and purified by reverse phase HPLC (eluted with 10% to 95% H₂O/CH₃CN) to give 81 as a white solid (20 mg, 17%). ¹H NMR (300 MHz, CD₃OD): δ 8.26 (s, 1H), 7.33 (s, 2H), 5.65 (q, J=9.5 Hz, 1H), 5.45 (bs, 1H), 5.34 (t, J=10.1 Hz, 1H), 4.76 (bs, 1H), 4.60-4.50 (m, 2H), 4.30-4.15 (m, 2H), 4.10-4.00 (m, 1H), 3.92 (dd, J=11.9, 3.6 Hz, 1H), 2.95-2.80 (m, 4H), 2.80-2.60 (m, 1H), 2.50-2.40 (m, 1H), 2.40-2.30 (m, 1H), 2.25-2.15 (m, 1H), 1.95-1.70 (m, 5H), 1.65-1.30 (m, 16H), 1.27 (t, J=7.0 Hz, 3H). ³¹P NMR (300 MHz, CD₃OD): δ 22.4. LC/MS: 812 (M⁺+1).

Example 82

Preparation of Compound 82

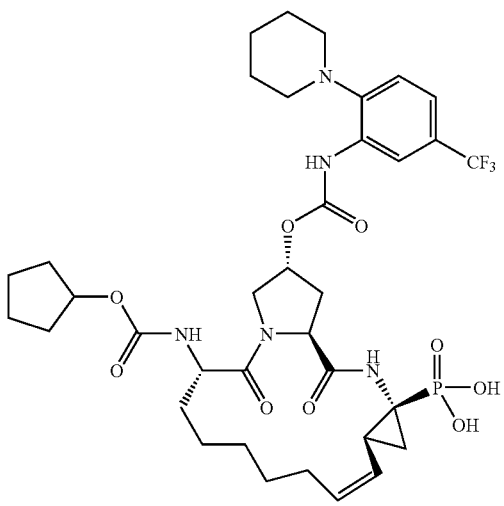

To a solution of diethyl phosphonate (150 mg, 0.179 mmol) in 3 mL of CH₃CN at 0° C. was added TMSI (125 µL, 1.07 mmol). The solution mixture was stirred at rt for ¾ h. The mixture was concentrated in vacuo using high vacuum pump at 30° C. and azeotroped 3× with toluene. The crude mixture was dissolved in 1 mL of MeOH, evaporated and dissolved in 1 mL of MeOH and purified by reverse phase HPLC (eluted with 10% to 95% H₂O/CH₃CN) to give 82 as a white solid (20 mg, 14%). ¹H NMR (300 MHz, CD₃OD): δ 8.25 (s, 1H), 7.35 (s, 2H), 5.62 (q, J=9.8 Hz, 1H), 5.46 (bs, 1H), 5.30 (t, J=9.1 Hz, 1H), 4.76 (bs, 1H), 4.65-4.50 (m, 2H), 4.25 (bd, J=8.3 Hz, 1H), 3.92 (dd, J=11.6, 3.1 Hz, 1H), 3.00-2.80 (m, 4H), 2.55-2.35 (m, 3H), 2.30-2.10 (m, 1H), 2.10-1.90 (m, 1H), 1.85-1.70 (m, 5H), 1.65-1.10 (m, 17H). ³¹P NMR (300 MHz, CD₃OD): δ 21.5. LC/MS: 784 (M⁺+1).

Example 83

Preparation of Compound 83

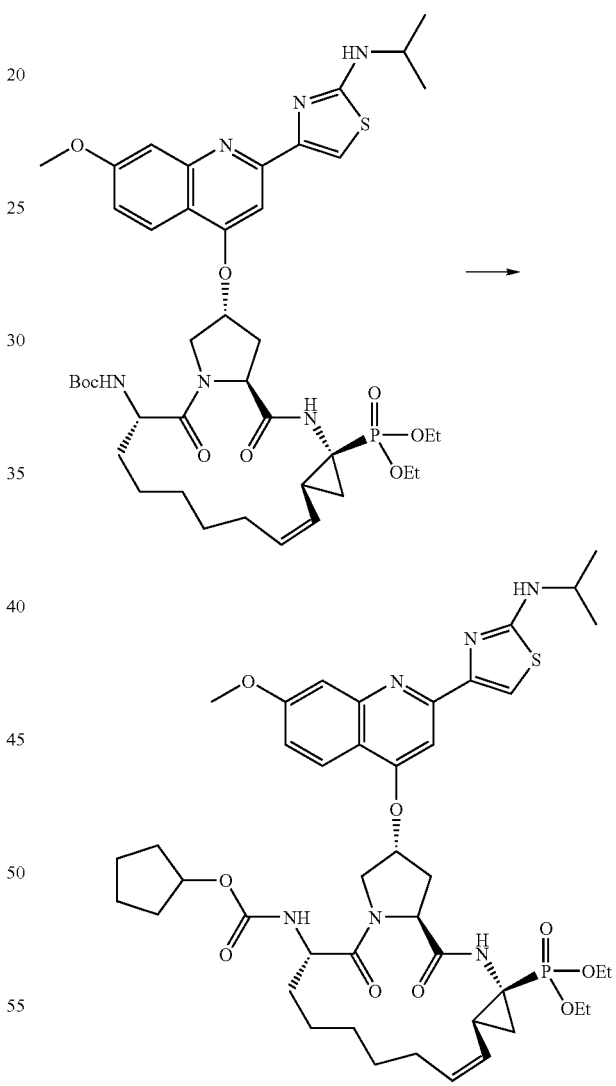

Step 1. To a solution of macrocyclic diethyl phosphonate (240 mg, 0.281 mmol) in 3 mL of DCM was added 3 mL of TFA. The solution mixture was stirred at rt for ¾ h. The mixture was concentrated in vacuo using high vacuum pump at 40° C. and azeotroped 3× with toluene. The crude mixture was dissolved in 1 mL of DCM. One third of TEA (131 µL, 0.94 mmol) was added to it followed by slow addition of chloroformate. The balance of TEA (262 µL, 1.87 mmol) was then added to the mixture. The reaction mixture was quenched after 2 h by adding a saturated solution of NaHCO$_3$ in water. The mixture was extracted by DCM, concentrated, dissolved by 1 mL of MeOH and purified by reverse phase HPLC (eluted with 10% to 75% H$_2$O/CH$_3$CN) to give desired product as a yellow solid (77 mg, 32%). LC/MS: 840 (M$^+$−1).

Step 2. To a solution of intermediate obtained above (62 mg, 0.072 mmol) in 1 mL of pyridine was added one portion of NaI (55 mg, 0.036 mmol). The solution mixture was stirred at 95° C. for 1 h. The second portion of NaI (55 mg, 0.036 mmol) was then added and the reaction mixture was stirred at 95° C. for another 6 h. The mixture was concentrated in vacuo using high vacuum pump at 40° C. and three drops of a 1M solution of HCl was added. The crude mixture was dissolved in 1 mL of MeOH. The mixture was concentrated in vacuo, dissolved in 1 mL of MeOH and purified by reverse phase HPLC (eluted with 10% to 75% H$_2$O/CH$_3$CN) to give 83 as a yellow solid (33 mg, 55%). LC/MS: 838 (M).

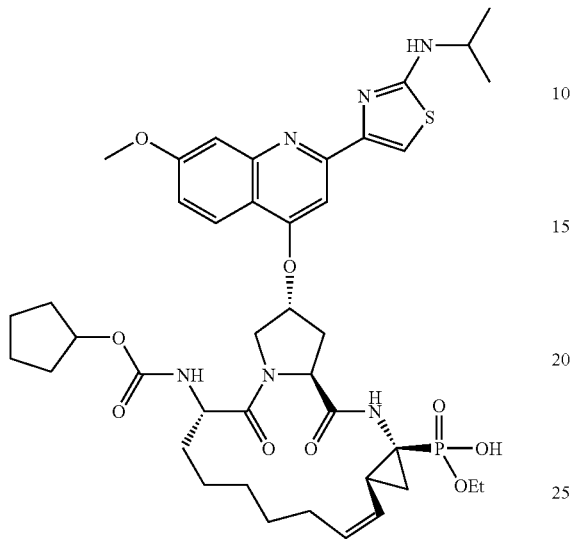

Example 84

Preparation of Compound 84

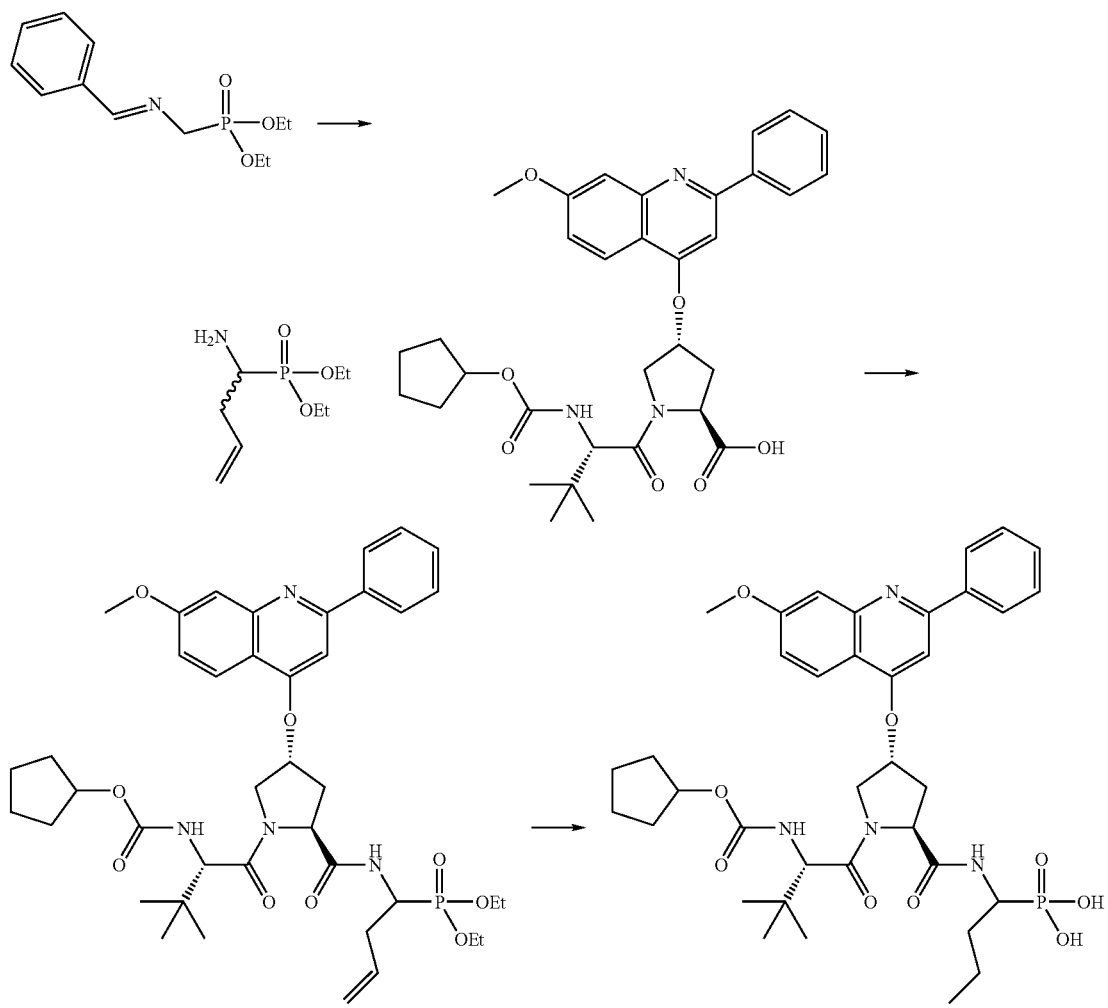

Step 1. To a −78° C. solution of diethyl-(N-benzylidene-aminomethyl)phosphonate (12.9 g, 50.5 mmol) in 100 mL of THF was added LDA (30.8 mL, 55.6 mmol). The mixture was stirred from −78° C. to rt for 10 min and cooled back −78° C. To the mixture was added allyl bromide (5.7 mL, 65.6 mmol) in 20 mL of THF. The solution was stirred for ON from −78° C. to rt, quenched by EtOH and purified by silica gel chromatography using $SiO_2$ (pretreated by 2% TEA/hexane) (eluted with 0% to 60% EtOAc/hexane) to give intermediate as a pale yellow liquid (3.3 g, 32%). The imine was dissolved in DCM 20 mL and hydrolyzed using 20 mL of 1M solution of HCl in water to give amine. $^1$H-NMR (300 MHz, $CDCl_3$): δ 5.91-5.75 (m, 1H), 5.21 (d, 1H), 5.13 (s, 1H), 4.23-4.10 (m, 4H), 3.12-2.99 (m, 1H), 2.70-2.53 (m, 1H), 2.33-2.18 (m, 1H), 1.62 (s, 2H), 1.36 (t, 6H). $^{19}$P NMR (300 MHz, $CDCl_3$): δ 28.4.

Step 2. The coupling reaction was done the same was as described before. The crude product was purified by silica gel chromatography using $SiO_2$ (eluted with 0% to 100% EtOAc/hexane) to give desired product as a yellow solid (1.14 g, 35%). $^{31}$P NMR (300 MHz, $CDCl_3$): δ 23.4, 23.6.

Step 3. To a purged flask of product obtained above (385 mg, 0.495 mmol) and Pd/C under argon was added 4 mL of MeOH. The reaction was completed after 40 min. The reaction mixture was filtered through celite and the filtrate was evaporated under vacuo. To the product in 3 mL of $CH_3CN$ at 0° C. was added TMSI (425 μL, 2.97 mmol) followed by 2,6-lutidine (345 μL, 2.97 mmol). The solution mixture was stirred at rt for ¾ h. The mixture was concentrated in vacuo using high vacuum pump at 30° C. and azeotroped 3× with toluene. The crude mixture was dissolved in 1 mL of MeOH, evaporated and dissolved in 1 mL of MeOH and purified by reverse phase HPLC (eluted with 10% to 95% $H_2O/CH_3CN$) to give 84 as a white solid (185 mg, 51%). $^1$H NMR (300 MHz, DMSO): δ 8.25 (d, J=9.2 Hz, 1H), 8.25-8.15 (m, 2H), 7.75 (d, J=9.5 Hz, 1H), 7.70-7.60 (m, 3H), 7.55 (bs, 1H), 7.26 (d, J=9.5 Hz, 1H), 7.07 (d, J=8.0 Hz, 1H), 5.78 (bs, 1H), 4.66 (t, J=9.2 Hz, 1H), 4.55-4.45 (m, 1H), 4.10-4.05 (m, 1H), 3.96 (s, 3H), 3.95-2.85 (m, 1H), 2.70-2.60 (m, 1H), 2.25-2.15 (m, 1H), 1.70-1.30 (m, 10H), 1.28-1.10 (m, 1H), 0.95 (s, 9H), 0.82 (t, J=7.3 Hz, 3H). $^{31}$P NMR (300 MHz, DMSO): δ 20.8. LC/MS: 725 (M$^+$+1).

Example 85

Preparation of Compound 85

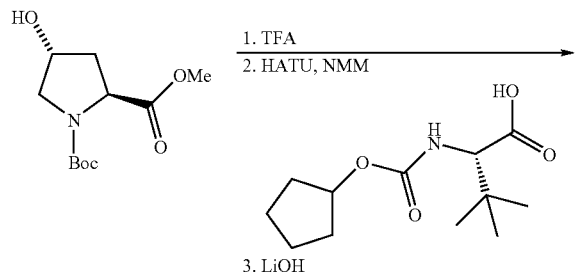

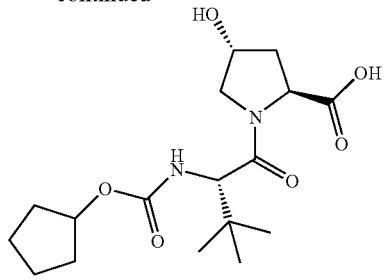

Step 1. Boc-aminoproline methyl ester (20 g, 81.5 mmol) was dissolved in DCM (100 mL) in a round bottomed flask. TFA (200 mL) was added and the reaction was stirred at room temp for 1 h. The mixture was then concentrated and azeotroped with toluene (2×100 mL). The crude mixture was then taken up in DCM (600 mL). HATU (46.5 g, 122 mmol), NMM (28.9 g, 285 mmol), and acid (23.8 g, 97.8 mmol) were added. The reaction mixture was stirred at room temperature for 15 h. The reaction was then quenched with water, diluted with DCM, washed with sat. $NaHCO_3$, and sat. $NH_4Cl$. The organic layer was then dried, concentrated, and purified via flash chromatography to provide the coupling product (21.6 g, 73%). This methyl ester (21.6 g, 58.3 mmol) was then taken up in THF (100 mL), MeOH (100 mL), and water (100 mL). LiOH (12.2 g, 292 mmol) was added and the mixture was stirred at room temperature for 1 h. The reaction was then diluted with water and the pH was adjusted to 3 using 1N HCl. The mixture was then extracted with EtOAc, dried, and concentrated to provide carboxylic acid (20.2 g, 97%).

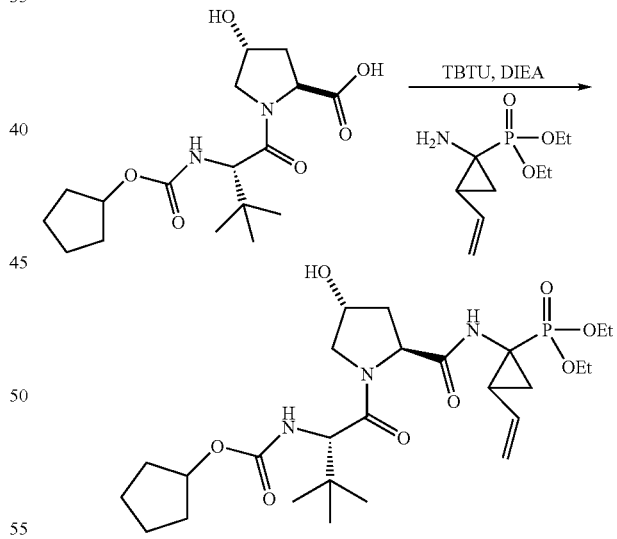

Step 2. Carboxylic acid (7 g, 19.6 mmol) and aminophosphonate (5.6 g, 25.5 mmol) were taken up in DMF (200 mL). TBTU (12.6 g, 39 mmol), and DIEA (10.1 g, 78.4 mmol) were added and the reaction was stirred at room temp and monitored via LC/MS until complete. The mixture was then quenched with water, diluted with DCM and washed with $NaHCO_3$. The organic layer was further washed with $NH_4Cl$, 1M HCl, and brine, then dried, concentrated, and purified via flash chromatography (hexanes/ethyl acetate/methanol) to provide tripeptide (4.3 g, 39%).

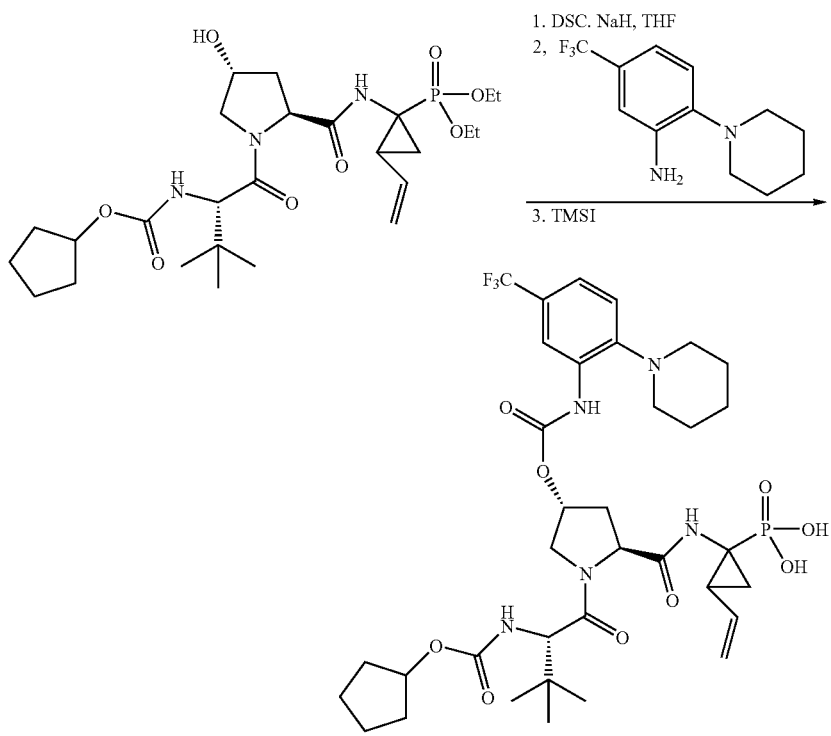

Step 3. Alcohol (200 mg, 0.36 mmol) was taken up in THF (5 mL). NaH (43 mg, 1.08 mmol), and disuccinimidecarbonyl (276 mg, 1.08 mmol) were added. The reaction was refluxed for 6 h until complete via LC/MS analysis. Ethyl acetate and 1M HCl were added. The organic layer was separated and washed with brine, dried, and concentrated. The residue was then taken up in DCM (1 mL) and the aniline (175 mg, 0.72 mmol) was added. The mixture was heated in the microwave at 65° C. for 1 h. The reaction was then concentrated and purified via flash chromatography to provide the desired carbamate (30 mg). This diethylphosphonate was then taken up in acetonitrile (1 mL) and 2,6-lutidine (11.6 mg, 0.11 mmol) was added. The mixture was cooled to 0° C. and then TMSI (22 mg, 0.11 mmol) was added. The reaction was warmed to room temp and stirred for 2 h. The reaction was then quenched with triethylamine, then methanol and concentrated. The residue was purified via HPLC (acetonitrile:water) to provide the desired diacid 85 (1.6 mg). $^1$H NMR (300 MHz, CD$_3$OD) δ 1.05 (m, 12H), 1.35-1.83 (m, 19H), 2.11 (m, 1H), 2.32 (m, 1H), 2.48 (m, 1H), 2.89 (m, 2H), 3.95 (m, 1H), 4.38 (m, 1H), 4.53 (m, 1H), 5.08 (m, 1H), 5.25 (m, 1H), 5.41 (m, 1H), 5.98 (m, 1H), 7.37 (s, 2H), 8.23 (s, 1H). $^{31}$P NMR (300 MHz) δ 20.08. LC/MS: 772 (M+1).

Example 86

Preparation of Compound 86

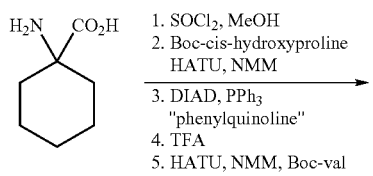

1. SOCl$_2$, MeOH
2. Boc-cis-hydroxyproline HATU, NMM
3. DIAD, PPh$_3$ "phenylquinoline"
4. TFA
5. HATU, NMM, Boc-val -continued 1-aminocyclohexanecarboxylic acid (2.03 g, 14 mmol) was taken up in MeOH (50 mL). Thionyl chloride (2.04 mL) was added drop-wise at 0° C. The reaction was warmed to room temp and stirred for 3 days after which time it was concentrated then diluted with water. The pH was adjusted to 9 with saturated Na$_2$CO$_3$ and then the mixture was extracted with DCM. The organic layer was dried and concentrated to provide the methyl ester. This amino-ester (0.56 g, 3.6 mmol) was taken up in DCM in a round bottomed flask. Boc-cis-hydroxyproline (0.84 g, 3.6 mmol), HATU (1.9 g, 5.1 mmol), and NMM (1.2 mL), 10.8 mmol) were added and the reaction was stirred at room temp for 15 h. The reaction was then quenched with sat NH$_4$Cl. The organic layer was dried, concentrated, and purified via flash chromatography to provide the dipeptide (0.59 g, 44%). This alcohol (1.6 mmol) was taken up in THF (16 mL). The phenylquinoline (0.4 g), DIAD (0.31 g), and PPh$_3$ (0.42 g) were added. The reaction was stirred at room temp for 15 h then concentrated and purified via flash chromatography to provide desired intermediate (200 mg, 21%). This Boc-amine (0.33 mmol) was taken up in DCM (3 mL) and TFA (6 mL) was added. The reaction was monitored by LC/MS until complete and then concentrated and azeotroped with toluene (2×15 mL). The residue was then taken up in DCM. HATU (189 mg, 0.5 mmol), NMM (1.5 mL), and Boc-valine (86 mg, 0.4 mmol) were added and the reaction was stirred at room temp for 15 h. The reaction was quenched with water and diluted with DCM. The organic layer was washed with NaHCO$_3$, dried, concentrated and purified via flash chromatography to provide the tripeptide (93 mg, 40%). This methyl ester tripeptide (0.13 mmol) was taken up in THF:water:methanol (0.5 mL each) and LiOH (218 mg, 5.2 mmol) was added. The reaction was stirred at room temp for 2 h and then diluted with water. The pH was adjusted to 2 using 1N HCl and the mixture was then extracted with ethyl acetate. The organic layer was dried, concentrated, and purified via HPLC to provide the desired acid 86 (21 mg, 23% yield). $^1$H NMR (300 MHz, CD$_3$OD) δ 0.97 (m, 7H), 1.08 (s, 9H), 1.25-1.99 (m, 10H), 2.06 (m, 1H), 2.51 (m, 1H), 2.78 (m, 1H), 3.25 (m, 1H), 3.95-4.06 (m, 5H), 4.76 (m, 1H), 5.78 (m, 1H), 7.38 (dd, 1H), 7.52 (d, 1H), 7.75 (m, 4H), 8.03 (m, 1H), 8.38 (d, 1H). LC/MS: 689 (M+1).

Example 87

Preparation of Compound 87

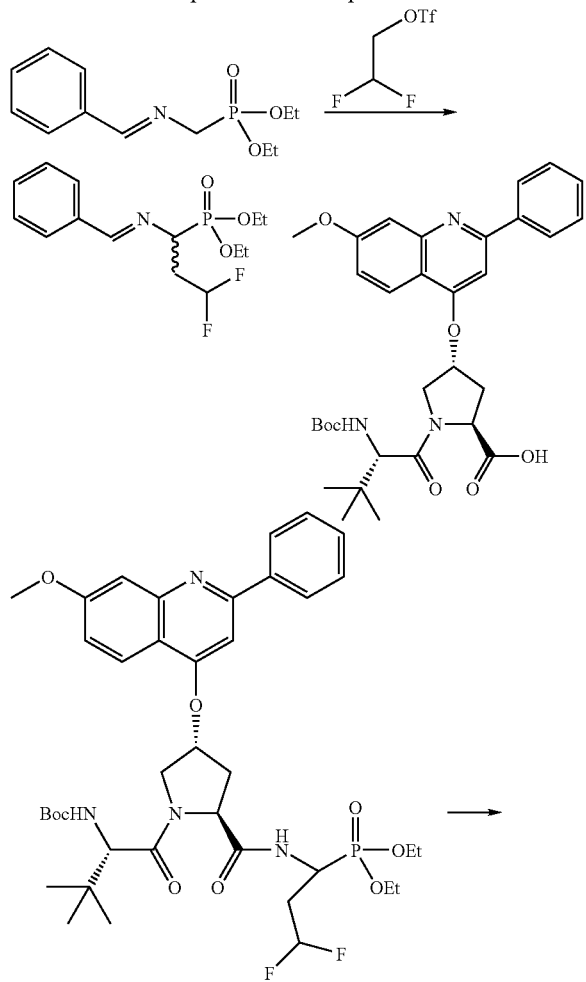

-continued

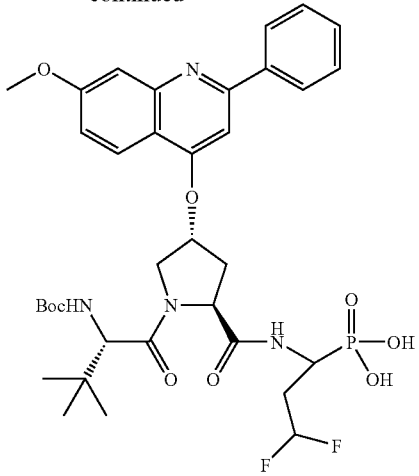

Step 1. To a −78° C. solution of diethyl-(N-benzylidene-aminomethyl) phosphonate (200 mg, 0.784 mmol) in 1 mL of THF was added LDA (480 μL, 0.863 mmol). The mixture was stirred from −78° C. to rt for 10 min and cooled back −78° C. To the mixture was added triflate (251 mg, 1.176 mmol) in 0.5 mL of THF. The solution was stirred for 20 min from −78° C. to rt, quenched by EtOH and purified by silica gel chromatography using SiO$_2$ (pretreated by 2% TEA/hexane) (eluted with 20% to 60% EtOAc/hexane) to give alkylated product as a pale yellow liquid (150 mg, 60%). $^1$H-NMR (300 MHz, CDCl$_3$): δ 8.38 (dd, 1H), 7.83-7.70 (m, 2H), 7.50-7.35 (m, 3H), 6.20-5.58 (m, 1H), 4.30-4.07 (m, 4H), 4.00-3.60 (m, 1H), 2.75-2.40 (m, 2H), 1.45-1.30 (m, 6H). LC/MS: 320 (M$^+$+1).

Step 2. Imine hydrolysis and HATU/coupling experimental were described before.

The crude product was purified by silica gel chromatography using SiO$_2$ (eluted with 20% to 100% EtOAc/Hex) to give coupled tripeptide as a pale yellow solid (310 mg, 45%). Both diastereomer were separated and isolated. $^{31}$P NMR (300 MHz, CDCl$_3$): δ 21.7 (A) and 22.1 (B). LC/MS: 791 (M$^+$+1). Step 3. To a solution of dry tripeptide (120 mg, 0.139 mmol) in 2 mL of CH$_3$CN at 0° C. was added TMSI (81 μL, 0.556 mmol). The solution mixture was stirred at rt for ½ h. The mixture was concentrated in vacuo using high vacuum pump at 30° C. and azeotroped 3× with toluene. The reaction mixture was then dissolved in 3 mL of DCM followed by addition Boc)$_2$O (175 μL, 0.695 mmol). The solution mixture was stirred 10 min and TEA (148 μL, 0.973 mmol) was added over 20 min and the mixture was stirred for another 30 min. The reaction was then acidified to pH 3 using a 1M solution of HCl in H$_2$O and extracted 3× by 10% EtOH in DCM. The organic phase was evaporated in vacuo. The crude mixture was dissolved in 1 mL of MeOH and purified by reverse phase HPLC (eluted with 0% to 100% H$_2$O/CH$_3$CN) to give 87 as a white solid (30 mg, 29%). $^1$H NMR (300 MHz, CD$_3$OD): δ 8.40 (d, J=9.5 Hz, 1H), 8.08 (d, J=6.5 Hz, 2H), 7.80-7.70 (m, 3H), 7.67 (s, 1H), 7.54 (d, J=2.1 Hz, 1H), 7.40 (dd, J=9.5, 2.1 Hz, 1H), 6.13 (td, 1H), 5.82 (bs, 1H), 4.80-4.70 (m, 2H), 4.50-4.35 (m, 1H), 4.20-4.05 (m, 1H), 4.16 (s, 1H), 4.06 (s, 3H), 2.90-2.77 (m, 1H), 2.65-2.10 (m, 3H), 1.19 (s, 9H), 1.05 (s, 9H). LC/MS: 735 (M$^+$+1).

Example 88

Preparation of Compound 88

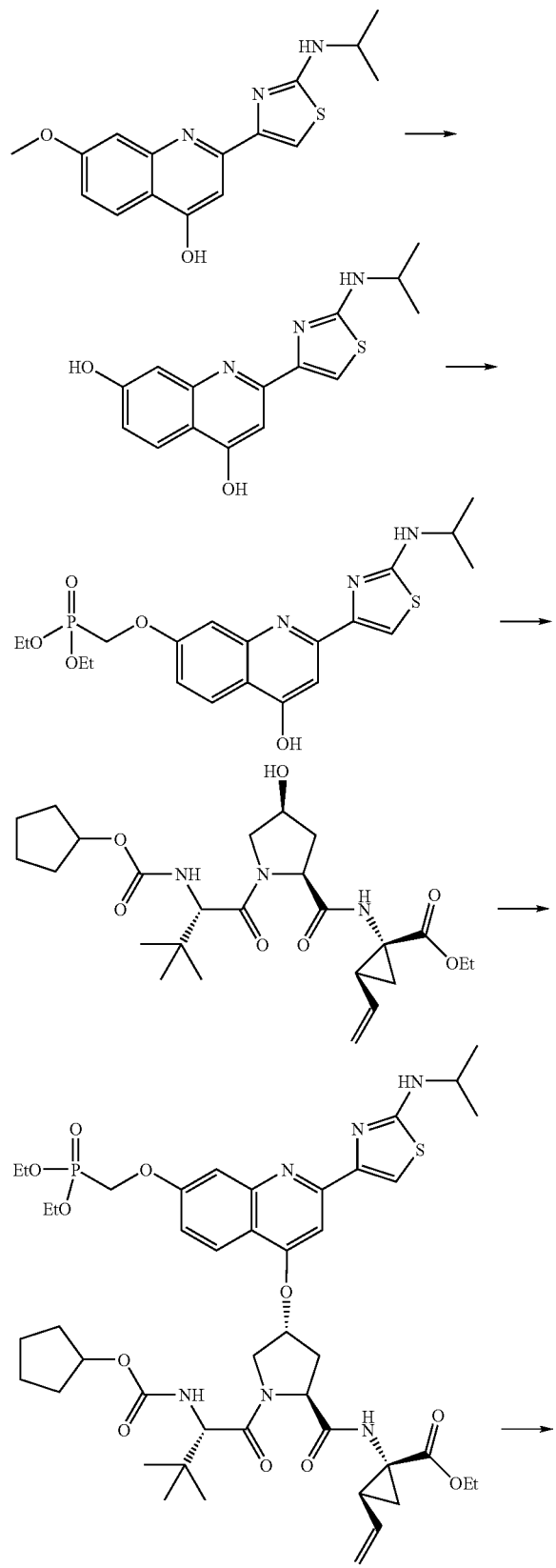

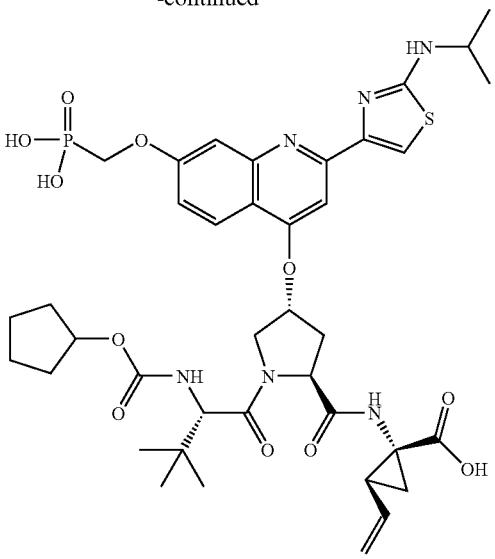

Step 1. To a solution of quinoline (2 g, 6 mmol) in 100 mL of DCM at rt was added 1M solution of BBr$_3$ in DCM (30 mL, 30 mmol). The solution mixture was stirred at reflux for ON. The mixture was poured on ice and then basified to pH 14 using a 10M solution of NaOH in H$_2$O. The product was dissolved in the aqueous. The aqueous layer was extracted 2× by DCM and then acidified to pH 5-6 using a 37% solution of HCl in H$_2$O. The product crashed out the aqueous solution. The precipitate was filtered using a Buchner funnel. The solid was transferred to a 500 mL flask, dissolved in 50 mL of MeOH, concentrated in vacuo using high vacuum pump at 40° C. (this process was repeated 3×) and azeotroped 1× with toluene to give the diol compound as a dark orange solid (1.7 g, 95%).

Step 2. To NaH (60% dispersion in mineral oil) (146 mg, 3.65 mmol) at −5° C. was added quinoline (500 mg, 1.66 mmol) in 4 mL of DMF. The suspension was stirred at −5° C. for 15 min and diethylphosphonatetriflate (520 mg, 1.74 mmol) was added. The solution was stirred for 5 min at rt, quenched by H$_2$O and acidified to pH 3 using a 1M solution of HCl in water. The solution was extracted with DCM and evaporated under vacuo. The crude product was purified by silica gel chromatography using SiO$_2$ (eluted with 0% to 10% MeOH/DCM) to give desired product as a dark orange solid (435 mg, 58%). $^1$H-NMR (300 MHz, CDCl$_3$): δ 8.24 (d, 1H), 7.11 (s, 1H), 6.96 (s, 1H), 6.92 (dd, 1H), 6.68 (s, 1H), 5.85 (bs, 1H), 4.33 (d, 2H), 4.22 (qu, 4H), 3.80-3.70 (m, 1H), 1.33 (t, 6H), 1.27 (d, 6H). LC/MS: 453 (M$^+$+1).

Step 3. Mitsunobu reaction was described before. The crude product was purified by silica gel chromatography using SiO$_2$ (eluted with 20% to 100% EtOAc/Hex) to give intermediate as a dark orange solid (120 mg, 40%). Step 3. To a solution of dry intermediate (110 mg, 0.119 mmol) in 3 mL of CH$_3$CN at 0° C. was added TMSI (68 μL, 0.476 mmol). The solution mixture was stirred at rt for ½ h. The mixture was concentrated in vacuo using high vacuum pump at 30° C. and azeotroped 3× with toluene. The reaction mixture was then dissolved by 6 mL of a 3/2/1 solution mixture of THF/EtOH/H$_2$O followed by addition of LiOH (50 mg, 1.12 mmol). The reaction was stirred at rt for ON. The mixture was then acidified to pH 4 using a 1M solution of HCl in H$_2$O and extracted 3× by 10% EtOH in DCM. The organic phase was evaporated in vacuo. The crude mixture was dissolved in 1 mL of MeOH and purified by reverse phase HPLC (eluted with 0% to 60% H₂O/CH₃CN) to give 88 as a yellow solid (4 mg, 4%). ¹H NMR (300 MHz, CD₃OD): δ 8.73 (s, 1H), 8.29 (bs, 1H), 8.19 (s, 1H), 7.83 (s, 1H), 7.74 (s, 1H), 7.40 (bs, 1H), 5.90-5.80 (m, 1H), 5.77 (bs, 1H), 527 (d, J=17.6 Hz, 1H), 5.10 (d, J=9.9 Hz, 1H), 4.78-4.60 (m, 2H), 4.53-4.35 (m, 2H), 4.17 (s, 1H), 4.07 (d, J=12.1 Hz, 1H), 2.82-2.73 (m, 1H), 2.62-2.55 (m, 1H), 2.25-2.15 (m, 1H), 1.80-1.60 (m, 11H), 1.40-1.30 (m, 2H), 1.37 (bs, 6H), 1.04 (s, 9H). LC/MS: 843 (M⁺+1).

Example 89

Preparation of Compound 89

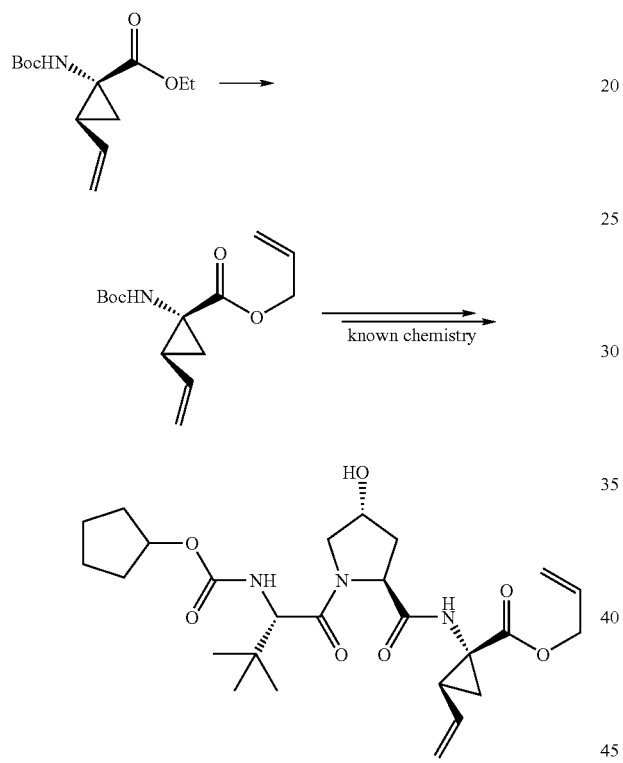

Step 1. Synthesis of 1-tert-Butoxycarbonylamino-2-vinyl-cyclopropanecarboxylic acid allyl ester. 1-tert-Butoxycarbonylamino-2-vinyl-cyclopropanecarboxylic acid ethyl ester (2.9 g, 11.3 mmol) was dissolved by 120 mL of a 3/2/1 solution mixture of THF/EtOH/H₂O followed by addition of LiOH (2.4 g, 56.5 mmol). The reaction mixture was stirred at rt for ON. The mixture was then acidified to pH 4 using a 37% solution of HCl in H₂O and extracted 3× by 10% EtOH in DCM. The organic phase was evaporated in vacuo. The crude intermediate was dissolved by 80 mL of a 3/1 solution mixture of DCM/H₂O. To this solution was added K₂CO₃ (15.6 g, 113 mmol), allylbromide (5 mL, 56.5 mmol) and catalytic amount of Aliquat 336. The reaction mixture was stirred for 2 days, extracted with DCM and evaporated under vacuo. The crude product was purified by silica gel chromatography using SiO₂ (eluted with 0% to 60% EtOAc/Hex) to give product as a pale yellow solid (3 g, 100%). ¹H NMR (300 MHz, CDCl₃): δ 5.98-5.70 (m, 2H), 5.40-5.10 (m, 6H), 4.65-4.60 (m, 2H), 2.15 (q, 1H), 1.82 (bs, 1H), 1.44 (s, 9H).

Step 2. Coupling to dipeptide was described before.

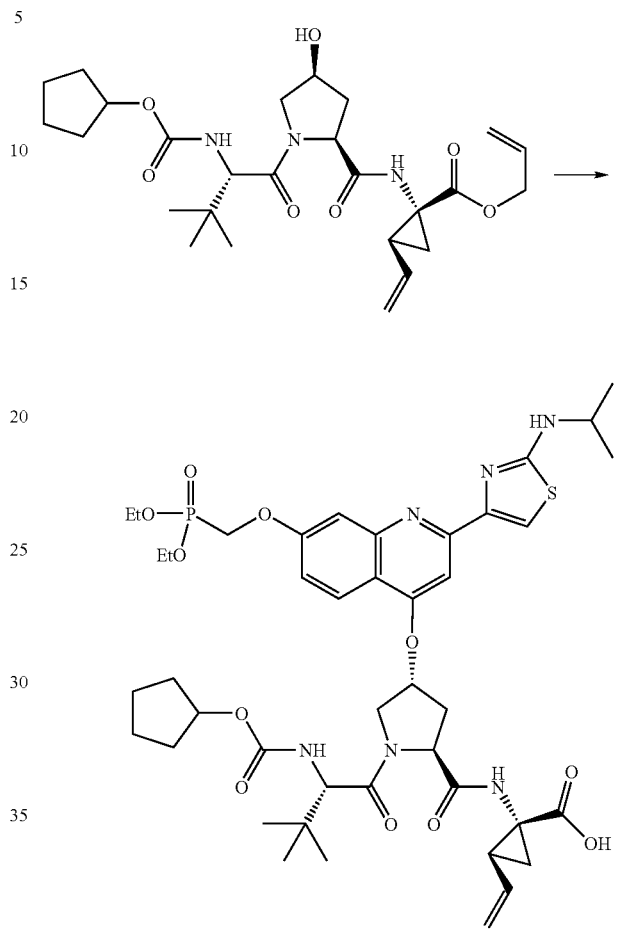

To a solution of dry tripeptide (153 mg, 0.302 mmol) in 20 mL of THF was added [4-Hydroxy-2-(2-isopropylamino-thiazol-4-yl)-quinolin-7-yloxymethyl]-phosphonic acid diethyl ester (150 mg, 0.332 mmol), PPh₃ (174 mg, 0.664 mmol) followed by slow addition of DIAD (128 μL, 0.664 mmol). The solution mixture was stirred at rt for ON. The mixture was concentrated in vacuo and purified by normal phase chromatography using SiO₂ (eluted with 0% to 20% MeOH/EtOAc) to give the intermediate as a yellow solid (25 mg, 10%). The intermediate (25 mg, 0.0266 mmol) was then dissolved in 2 mL of THF and piperidine (13 μL, 0.133 mmol) was added followed by addition Pd(PPh₃)₄ (6 mg, 0.016 mmol). The solution mixture was stirred 20 min, filtered and evaporated in vacuo. The crude mixture was dissolved in 1 mL of MeOH, acidified to pH 4 using a 1M solution of HCl in water and purified by reverse phase HPLC (eluted with 10% to 75% H₂O/CH₃CN) to give 89 as a yellow solid (2.7 mg, 11%). ¹H NMR (500 MHz, CD₃OD): δ 8.32 (d, 1H), 8.22 (s, 1H), 7.83 (s, 1H), 7.73 (s, 1H), 7.41 (dd, 1H), 5.90-5.80 (m, 1H), 5.78 (bs, 1H), 5.27 (dd, J=17.6 Hz, 1H), 5.10 (dd, J=9.9 Hz, 1H), 4.76-4.60 (m, 3H), 4.46 (bs, 1H), 4.27 (qu, 4H), 4.17 (s, 1H), 4.08 (dd, J=12.1 Hz, 1H), 2.82-2.74 (m, 1H), 2.65-2.56 (m, 1H), 2.20 (q, 1H), 1.76-1.42 (m, 8H), 1.40 (t, 6H), 1.30 (d, 6H), 1.44 (bs, 6H), 1.04 (s, 9H). LC/MS: 900 (M⁺+1).

Example 90

Preparation of Compound 90

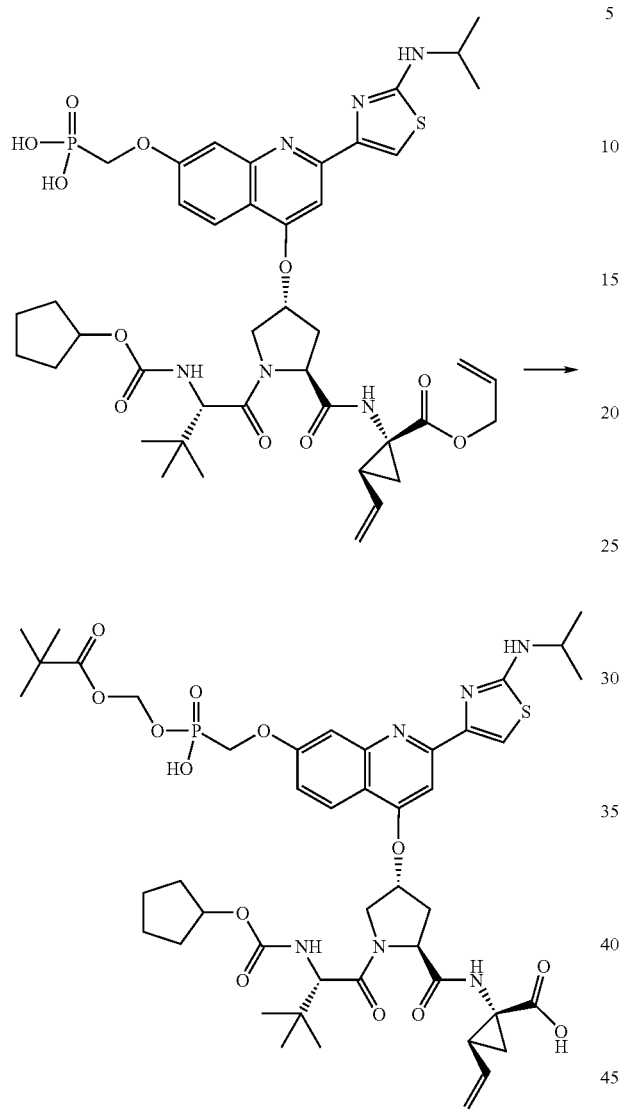

Step 1. TMSI reaction was described before. To a solution of dry phosphonic diacid (105 mg, 0.112 mmol) in 0.5 mL of DMF was added CMIC (81 μL, 0.560 mmol) followed by TEA (156 μL, 1.11 mmol). The solution mixture was stirred at 60° C. for ON. The mixture was dissolved in 1 mL of MeOH and purified by reverse phase HPLC (eluted with 10% to 100% H$_2$O/CH$_3$CN) to give the intermediate as a yellow solid (15 mg, 13%). The intermediate (15 mg, 0.0151 mmol) was then dissolved in 1 mL of THF and piperidine (8 μL, 0.075 mmol) was added followed by addition Pd(PPh$_3$)$_4$ (7 mg, 0.006 mmol). The solution mixture was stirred 20 min, filtered and evaporated in vacuo. The crude mixture was dissolved in 1 mL of MeOH, acidified to pH 4 using a 1M solution of HCl in water and purified by reverse phase HPLC (eluted with 10% to 75% H$_2$O/CH$_3$CN) to give 90 as a yellow solid (1.4 mg, 10%). LC/MS: 958 (M$^+$+1).

Example 91

Preparation of Compound 91

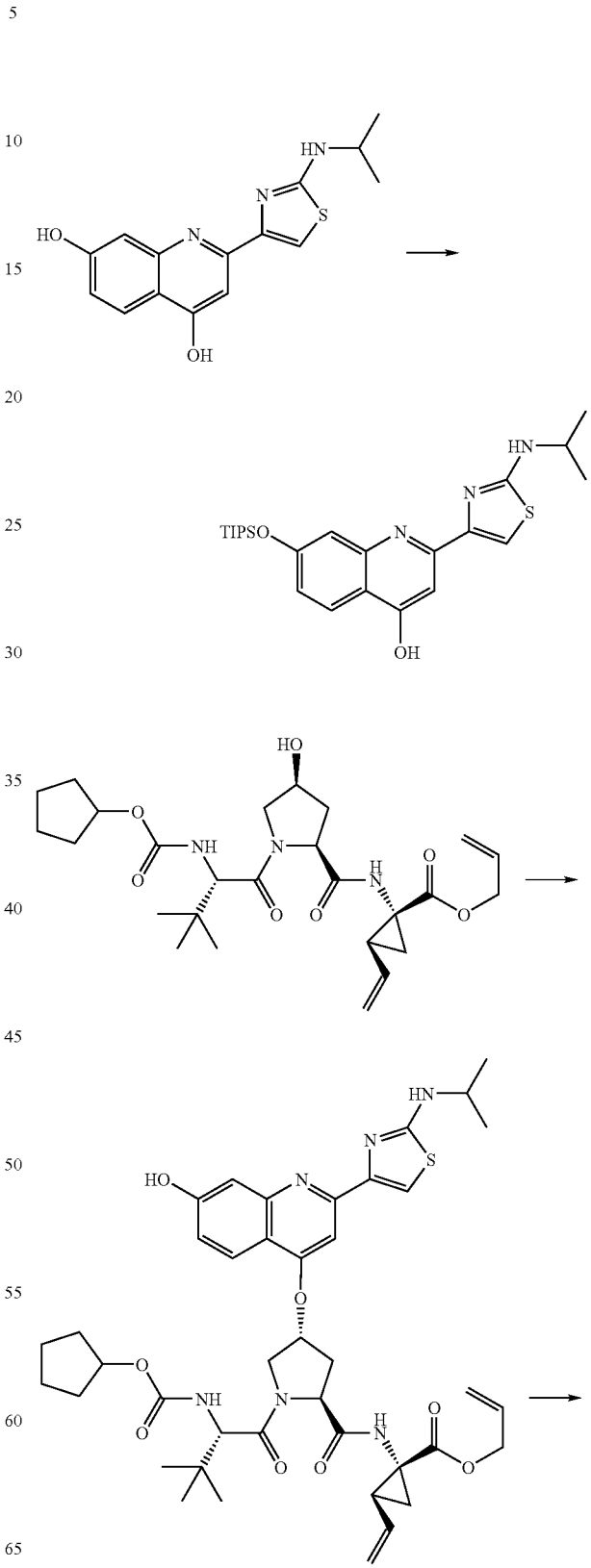

-continued

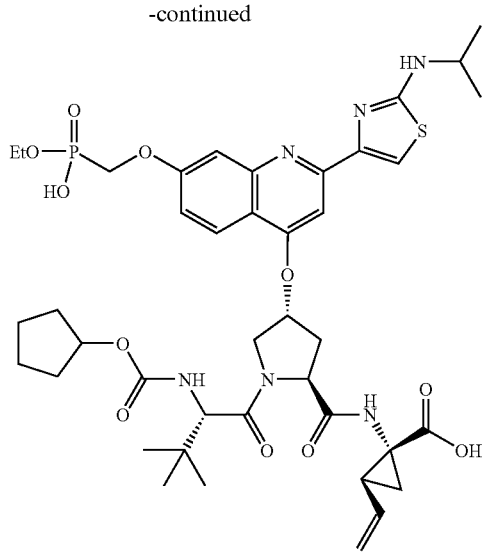

Step 1. To a solution of 2-(2-Isopropylamino-thiazol-4-yl)-quinoline-4,7-diol (1.27 g, 4.2 mmol) in 4 mL of DMF was added TIPSCl (2.67 mL, 12.6 mmol) followed by imidazole (2.86 g, 42 mmol). The solution was stirred for 5 min at rt, dissolved in 20 mL EtOAC, quenched by saturated solution of NH$_4$Cl in H$_2$O. The solution was extracted and evaporated under vacuo. The crude product was purified by silica gel chromatography using SiO$_2$ (eluted with 5% to 20% MeOH/DCM) to give 2-(2-Isopropylamino-thiazol-4-yl)-7-triisopropylsilanyloxy-quinolin-4-ol as a dark orange solid (1.9 g, 99%). $^1$H-NMR (300 MHz, DMSO): δ 11.0 (bs, 1H), 7.93 (d, 1H), 7.70 (bs, 1H), 7.42 (s, 1H), 7.25 (s, 1H), 6.81 (dd, 1H), 6.49 (s, 1H), 3.97-3.87 (m, 1H), 1.38-1.25 (m, 1H), 1.22 (d, 6H), 1.07 (d, 6H).

Step 2. Mitsunobu reaction was described before. The crude product was purified by silica gel chromatography using SiO$_2$ (treated by 2% TEA in hexane) (eluted with 50% to 100% EtOAc/Hex) to give intermediate as a dark orange solid. This intermediate was dissolved in 1 mL of THF and 1 mL of TBAF was added. The reaction was completed after 2 min. To the reaction mixture was added MeOH and the solvent was evaporated. The crude mixture was purified by silica gel chromatography using SiO$_2$ (eluted with 0% to 20% MeOH/DCM) to give desired product as a dark orange solid (260 mg, 23% over 2 steps).

Step 3. To a solution of dry intermediate (40 mg, 0.05 mmol) in 0.1 mL of DMF and 1 mL of THF was added CsCO$_3$ (83 mg, 0.25 mmol) followed by diethylphosphonatetriflate (30 mg, 0.1 mmol). The solution mixture was stirred at rt for 10 min. To the mixture was added in 1 mL of 1N solution of NaOH in water. The mixture was acidified to pH 4 using a 10M solution of HCl in water and purified by reverse phase HPLC (eluted with 10% to 75% H$_2$O/CH$_3$CN) to give 91 as a yellow solid (5 mg, 11%). $^1$H NMR (300 MHz, CD$_3$OD): δ 8.78 (s, 1H), 8.30 (dd, 1H), 8.19 (s, 1H), 7.83 (d, 1H), 7.74 (s, 1H), 7.40 (dd, 1H), 5.93-5.80 (m, 1H), 5.77 (bs, 1H), 5.25 (dd, 1H), 5.11 (dd, 1H), 4.78-4.60 (m, 2H), 4.49 (bs, 1H), 4.40 (d, 1H), 4.20-4.00 (m, 4H), 2.83-2.73 (m, 1H), 2.64-2.55 (m, 1H), 2.20 (q, 1H), 1.80-1.40 (m, 8H), 1.40-1.30 (m, 4H), 1.37 (d, 6H), 1.04 (s, 9H). $^{31}$P NMR (300 MHz, CD$_3$OD): δ 13.8. LC/MS: 871 (M$^+$+1).

Example 92

Preparation of Compound 92

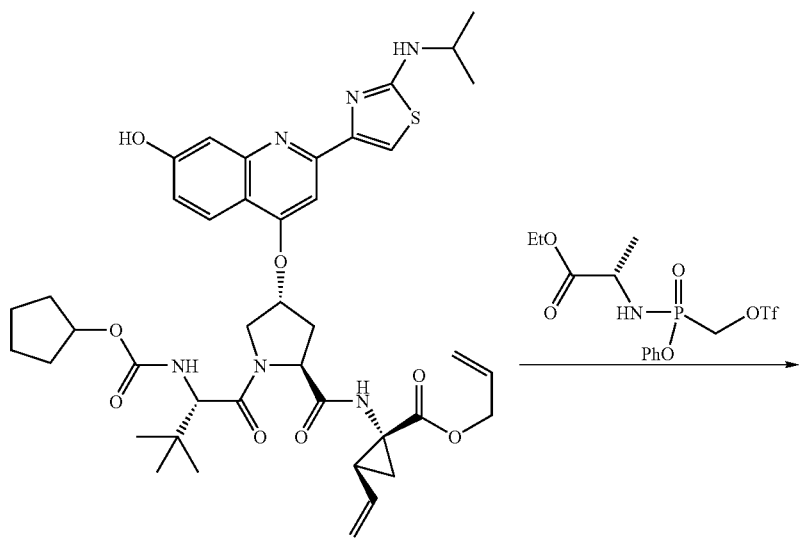

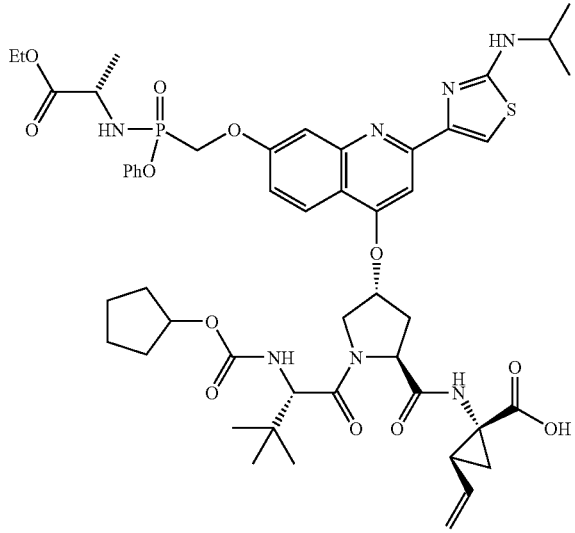

To a solution of dry starting material (55 mg, 0.07 mmol) in 0.1 mL of DMF and 1 mL of THF was added CsCO$_3$ (68 mg, 0.21 mmol) followed by triflate (45 mg, 0.1 mmol). The solution mixture was stirred at rt for 10 min. The mixture was concentrated under vacuo, dissolved in 1 mL of MeOH and purified by reverse phase HPLC (eluted with 10% to 100% H$_2$O/CH$_3$CN) to give the intermediate as a yellow solid (10 mg, 14%). The intermediate (10 mg, 0.095 mmol) was then dissolved in 1 mL of THF and piperidine (6 μL, 0.048 mmol) was added followed by addition Pd(PPh$_3$)$_4$ (4 mg, 0.0004 mmol). The solution mixture was stirred 20 min, filtered and evaporated in vacuo. The crude mixture was dissolved in 1 mL of MeOH, acidified to pH 4 using a 1M solution of HCl in water and purified by reverse phase HPLC (eluted with 10% to 75% H$_2$O/CH$_3$CN) to give 92 as a yellow solid (4 mg, 41%). $^1$H NMR (300 MHz, CD$_3$OD): δ 8.78 (s, 1H), 8.35 (d, 1H), 8.21 (s, 1H), 7.83 (bs, 1H), 7.78 (s, 1H), 7.50-7.35 (m, 3H), 7.38-7.20 (m, 2H), 5.93-5.80 (m, 1H), 5.79 (bs, 1H), 5.30 (d, 1H), 5.11 (d, 1H), 4.78-4.60 (m, 2H), 4.50 (bs, 1H), 4.22-4.00 (m, 4H), 2.83-2.76 (m, 1H), 2.64-2.57 (m, 1H), 2.22-2.15 (m, 1H), 1.78-1.40 (m, 10H), 1.40-1.28 (m, 5H), 1.37 (d, 6H), 1.28-1.15 (m, 3H), 1.04 (s, 9H). $^{31}$P NMR (300 MHz, CD$_3$OD): δ 20.9 and 19.5. LC/MS: 1019 (M$^+$+1).

Example 93

Preparation of Compound 93

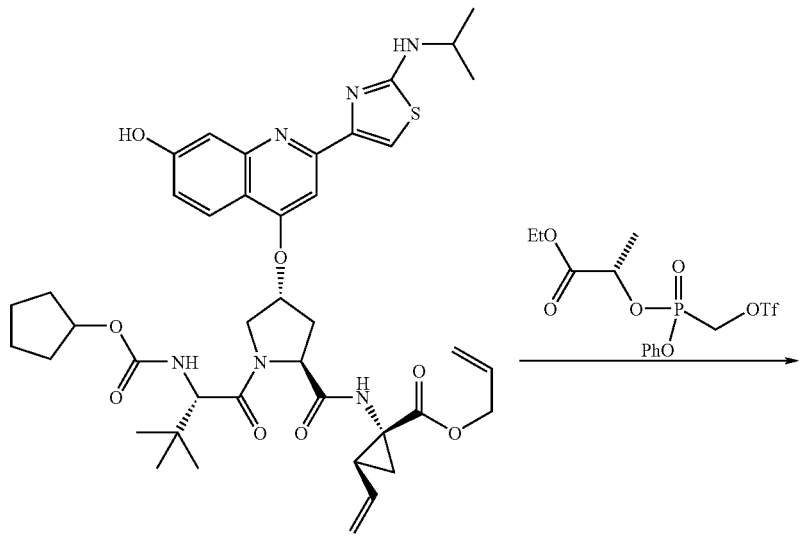

-continued

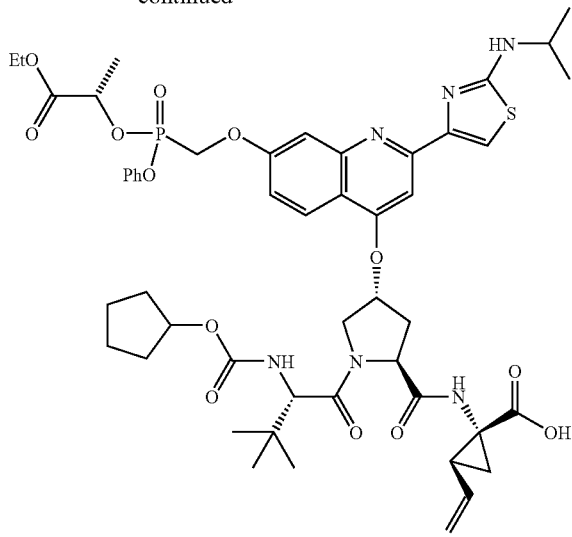

To a solution of dry starting material (40 mg, 0.05 mmol) in 0.1 mL of DMF and 1 mL of THF was added $CsCO_3$ (83 mg, 0.25 mmol) followed by triflate (42 mg, 0.1 mmol). The solution mixture was stirred at rt for 1 h. The mixture was concentrated under vacuo, dissolved in 1 mL of MeOH and purified by reverse phase HPLC (eluted with 10% to 100% $H_2O/CH_3CN$) to give the intermediate as a yellow solid (21 mg, 40%). The intermediate (21 mg, 0.02 mmol) was then dissolved in 1 mL of THF and piperidine (10 μL, 0.1 mmol) was added followed by addition $Pd(PPh_3)_4$ (9 mg, 0.008 mmol). The solution mixture was stirred 20 min, filtered and evaporated in vacuo. The crude mixture was dissolved in 1 mL of MeOH, acidified to pH 4 using a 1M solution of HCl in water and purified by reverse phase HPLC (eluted with 10% to 75% $H_2O/CH_3CN$) to give 93 as a yellow solid (6 mg, 49%). $^1H$ NMR (300 MHz, $CD_3OD$): δ 8.78 (s, 1H), 8.35 (d, 1H), 8.21 (s, 1H), 7.83 (bs, 1H), 7.78 (s, 1H), 7.50-7.35 (m, 3H), 7.38-7.20 (m, 2H), 5.93-5.80 (m, 1H), 5.79 (bs, 1H), 5.30 (d, 1H), 5.11 (d, 1H), 4.78-4.60 (m, 2H), 4.50 (bs, 1H), 4.22-4.00 (m, 4H), 2.83-2.76 (m, 1H), 2.64-2.57 (m, 1H), 2.22-2.15 (m, 1H), 1.78-1.40 (m, 10H), 1.40-1.28 (m, 5H), 1.37 (d, 6H), 1.28-1.15 (m, 3H), 1.04 (s, 9H). $^{31}P$ NMR (300 MHz, $CD_3OD$): δ 20.9 and 19.5. LC/MS: 1019 ($M^++1$).

Example 94

Preparation of Compound 94

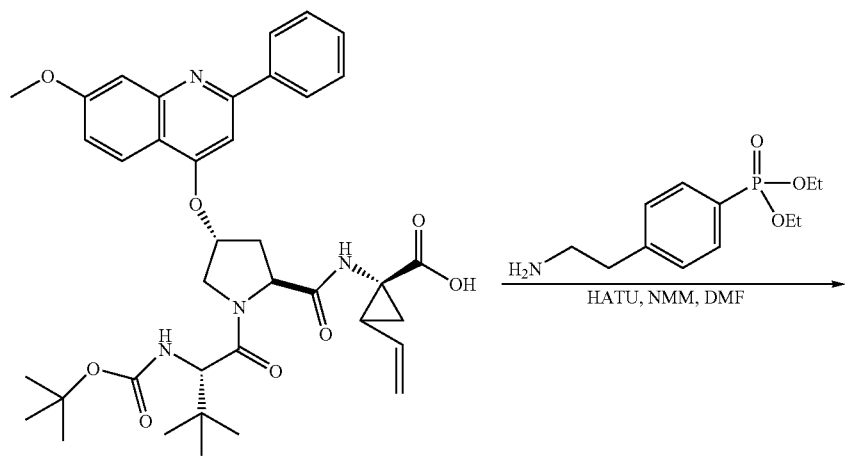

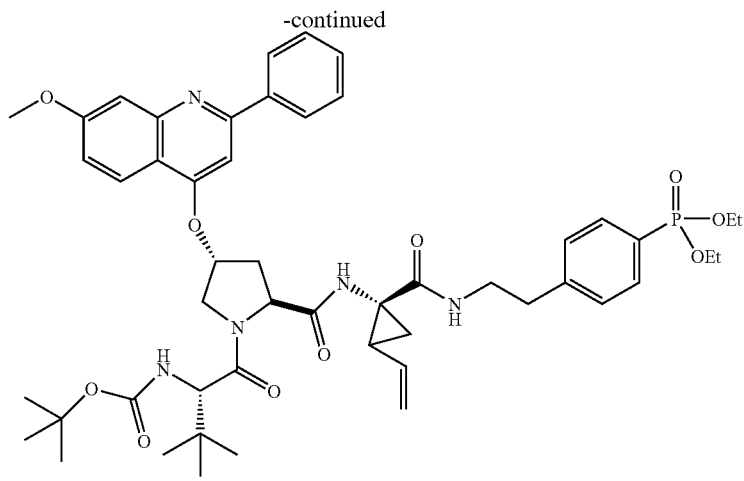

Carboxylic acid (45 mg, 0.068 mmol) was taken up in DMF (0.8 mL). HATU, 38 mg, 0.12 mmol), NMM (0.25 mL, 0.92 mmol), and amine (31 mg, 0.12 mmol) were added. The reaction was stirred at room temp for 1 h and the quenched with water and diluted with DCM. The organic layer was washed with sat $NaHCO_3$, dried, concentrated, and purified via HPLC to provide 94 (18 mg, 29%). $^1$H NMR (300 MHz, $CD_3OD$) δ 0.98 m, 4H), 1.06 (s, 6H), 1.05 (m, 5H), 1.78 (m, 1H), 2.0 (m, 1H), 2.41 (m, 1H), 2.73 (m, 1H), 2.91 (m, 2H), 3.58 (m, 1H), 3.94 (d, 1H), 4.05 (m, 5H), 4.59 (m, 1H), 5.0 (d, 1H), 5.19 (d, 1H), 5.78 (m, 2H), 7.19 (m, 4H), 7.65 (m, 6), 8.03 (m, 2H), 8.29 (m, 1H). $^{31}$P NMR δ 19.98. LC/MS: 913, 935 (M+1, M+23).

Example 95

Preparation of Compound 95

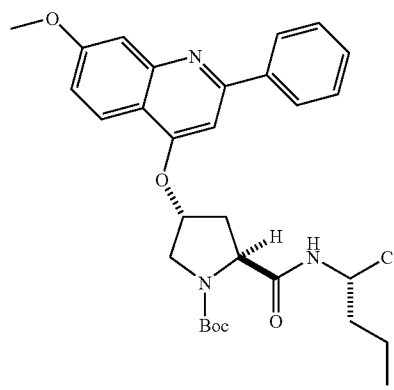

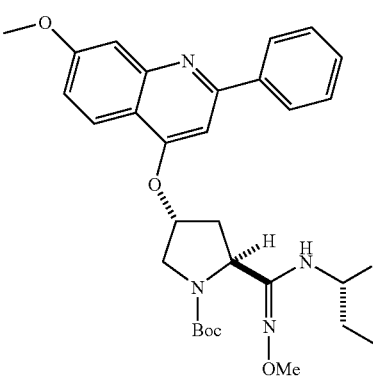

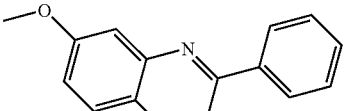

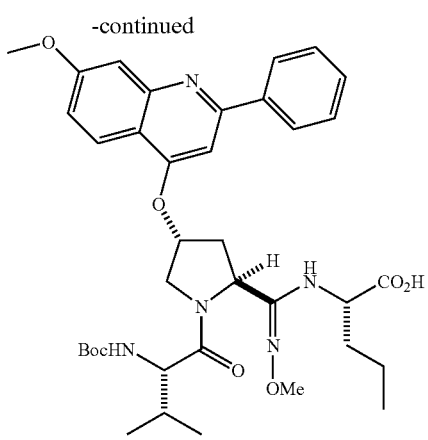

Example 96

Preparation of Compound 96

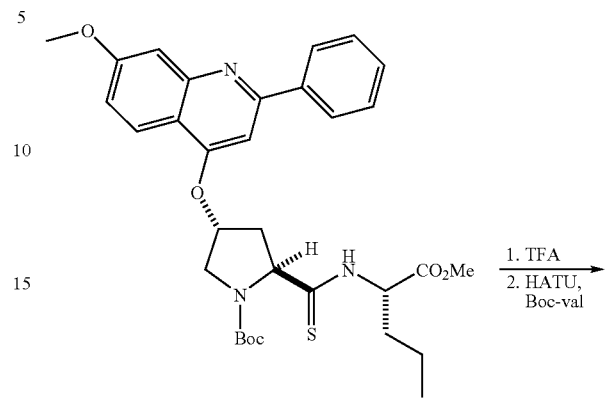

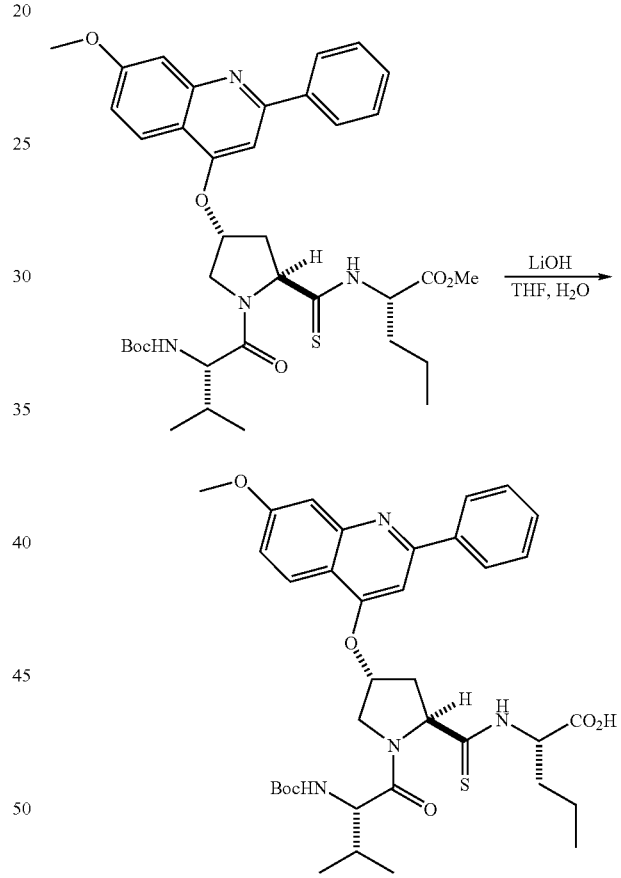

Step 1. The aryl dipeptide (0.599 g, 1.04 mmol) was taken up in toluene (10 mL) in a round bottomed flask equipped with reflux condenser. Lawesson's reagent (0.428 g, 1.06 mmol) was added. The reaction was refluxed 1.5 h and then concentrated. Flash chromatography (10% EtOAc/Hex) gave the desired thioamide (0.49 g, 79%).

Step 2. The thioamide (0.114 g, 0.192 mmol) was taken up in acetonitrile (10 mL) in a round bottomed flask equipped with magnetic stir bar. Triethylamine (0.08 mL, 0.576 mmol) was added, followed by methoxylamine hydrochloride (24 mg, 0.288 mmol). Mercuric acetate (67 mg, 0.211 mmol) was then added and the reaction was allowed to stir under argon atmosphere at room temperature overnight. The reaction mixture was then quenched with saturated aqueous ammonium chloride solution and extracted with dichloromethane. The organic layer was dried with sodium sulfate, concentrated, and purified via flash chromatography (15% EtOAc/Hex) to give the desired methoxyamidine (31.2 mg, 27%).

Step 3. The Boc-amine (9.3 mg, 0.015 mmol) was dissolved in dichloromethane (2 mL) and placed in a round bottomed flask equipped with magnetic stir bar. TFA (1 m L) was added and the reaction was stirred at room temperature. Monitoring the reaction by LC/MS showed complete conversion after 30 minutes. The reaction was then concentrated and then azeotroped with toluene (4 mL) twice. Dichloromethane was then added (2 mL) and the mixture stirred at room temperature. HATU (8.7 mg, 0.023 mmol), Boc-valine (4 mg, 0.018 mmol), and N-methylmorpholine (0.05 mL) were added and the reaction was stirred for 45 minutes. The mixture was then quenched with water, diluted with dichloromethane, and washed with saturated sodium bicarbonate solution. The organic layer was dried with sodium sulfate, concentrated and purified via flash chromatography to provide the tripeptide (7.7 mg, 71%). This methyl ester was then taken up in THF (0.25 mL) and water (0.2 mL). LiOH (10 equiv) was then added and the reaction stirred for 1 h. Water (5 mL) was then added and the pH was adjusted to pH 4-5 using acetic acid. The mixture was then extracted with ethyl acetate, concentrated and purified via HPLC to give the desired carboxylic acid 95. $^1$H NMR (300 MHz, CDCl$_3$) δ 0.80-1.06 (m, 16H), 1.09-1.52 (m, 21H), 1.63 (m, 1H), 1.85 (m, 1H), 2.10 (m, 2H), 2.45 (m, 1H), 2.80 (m, 1H), 3.72 (m, 4H), 3.99 (s, 3H), 4.18 (m, 1H), 4.29 (m, 1H), 4.42 (m, 1H), 5.15 (m, 1H), 5.59 (m, 2H), 7.10 (m, 1H), 7.50 (m, 4H), 8.05 (m, 3H).

Boc amine 2-(1-Methoxycarbonyl-butylthiocarbamoyl)-4-(7-methoxy-2-phenyl-quinolin-4-yloxy)-pyrrolidine-1-carboxylic acid tert-butyl ester (19 mg, 0.032 mmol) was dissolved in dichloromethane (2 mL) and placed in a round bottomed flask equipped with magnetic stir bar. TFA (1 mL) was added and the reaction was stirred at room temperature. Monitoring the reaction by LC/MS showed complete conversion after 30 minutes. The reaction was then concentrated and then azeotroped with toluene (4 mL) twice. Dichloromethane was then added (4 mL) and the mixture stirred at room temperature. HATU (18.2 mg, 0.048 mmol), Boc-valine (7.6 mg, 0.035 mmol), and N-methylmorpholine (0.05 mL) were added and the reaction was stirred for 1 h. The mixture was then quenched with water, diluted with dichloromethane, and washed with saturated sodium bicarbonate solution. The organic layer was dried with sodium sulfate, concentrated and purified via flash chromatography to provide the tripeptide (8 mg, 36%). This methyl ester was then taken up in THF (0.25 mL) and water (0.2 mL). LiOH (10 equiv) was then added and the reaction stirred for 1 h. Water (5 mL) was then added and the pH was adjusted to pH 4-5 using acetic acid. The mixture was then extracted with ethyl acetate, concentrated and purified via HPLC to give the desired carboxylic acid 96 (4 mg). $^1$H NMR (300 MHz, CDCl$_3$) δ 0.86 (m, 3H), 0.96 (m, 6H), 1.33 (m, 2H), 1.38 (m, 9H), 1.63 (m, 1H), 1.78 (m, 1H), 1.99 (m, 1H), 2.44 (m, 1H), 2.76 (m, 1H), 3.95 (s, 3H), 4.02 (m, 1H), 4.41 (m, 1H), 4.26 (m, 1H), 4.48 (m, 1H), 4.79 (m, 1H), 5.39 (m, 1H), 6.99 (s, 1H), 7.10 (m, 1H), 7.42 (m, 1H), 7.48 (m, 2H), 7.60 (m, 1H), 8.03 (m, 1H). LC/MS: 663 (M+1).

Example 97

Preparation of Compound 97

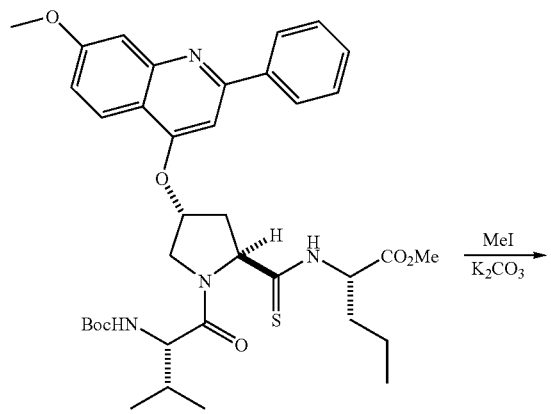

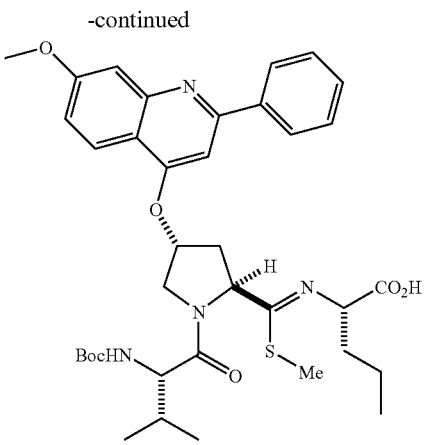

Step 1. Thioamide 2-{[1-(2-tert-Butoxycarbonylamino-3-methyl-butyryl)-4-(7-methoxy-2-phenyl-quinolin-4-yloxy)-pyrrolidine-2-carbothioyl]-amino}-pentanoic acid methyl ester (28 mg, 0.041 mmol) was taken up in acetone (1.5 mL) in a round bottomed flask equipped with reflux condenser. Potassium carbonate (11 mg, 0.082 mmol), and iodomethane (1 mL) was added. The reaction was refluxed for 2 h until complete by LC/MS. The mixture was then concentrated and purified via flash chromatography to provide methyl ester (23 mg, 80%).

Step 2. The methyl ester (14.2 mg, 0.02 mmol) was taken up in THF (0.5 mL) and water (0.5 mL). LiOH (10 equiv) was then added and the reaction stirred for 30 min. Water (5 mL) was then added and the pH was adjusted to pH 4-5 using acetic acid. The mixture was then extracted with ethyl acetate, dried with sodium sulfate, concentrated and purified via HPLC to give the desired carboxylic acid 97. $^1$H NMR δ 0.56-1.11 (m, 12H), 1.16-1.52 (m, 18H), 1.75-2.30 (m, 11H), 2.42 (m, 4H), 3.89 (m, 5H), 4.15 (m, 2H), 4.41-4.53 (m, 2H), 5.32 (m, 2H), 5.59 (m, 1H), 6.42 (m, 1H), 6.95 (m, 2H), 7.09 (m, 1H), 7.49 (m, 3H), 8.02 (m, 2H). LC/MS: 693 (M+1).

Example 98

Preparation of Compound 98

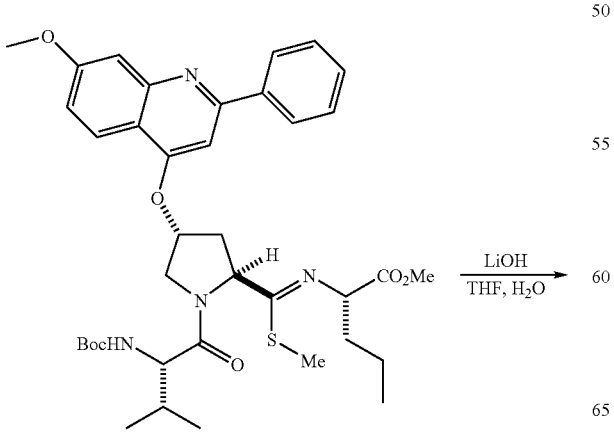

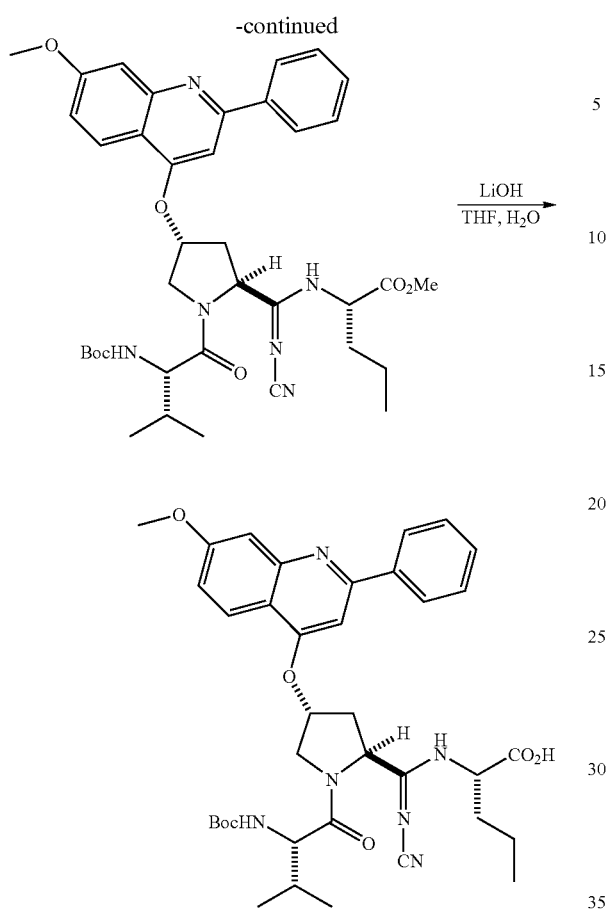

Example 99

Preparation of Compound 99

Step 1. Thioamide 2-{[1-(2-tert-Butoxycarbonylamino-3-methyl-butyryl)-4-(7-methoxy-2-phenyl-quinolin-4-yloxy)-pyrrolidine-2-carbothioyl]-amino}-pentanoic acid methyl ester (37 mg, 0.053 mmol) was taken up in acetonitrile (4 mL) in a round bottomed flask. Cyanamide (3.3 mg, 0.079 mmol) and mercuric acetate (18.5 mg, 0.058 mmol) were added. The reaction was heated to 50° C. for 12 hours. The reaction mixture was then quenched with saturated aqueous ammonium chloride solution and extracted with dichloromethane. The organic layer was dried with sodium sulfate, concentrated, and purified via flash chromatography to give the desired cyanoamidine (14.1 mg, 38%).

Step 2. The methyl ester (14.1 mg, 0.02 mmol) was taken up in THF (0.5 mL) and water (0.5 mL) and LiOH (8.4 mg, 0.2 mmol) was added. The reaction was stirred at room temperature for 1 h. Water (5 mL) was then added and the pH was adjusted to pH 4-5 using acetic acid. The mixture was then extracted with ethyl acetate, dried with sodium sulfate, concentrated and purified via HPLC to give the desired carboxylic acid 98 (5 mg, 36%). $^1$H NMR (300 MHz, CD$_3$OD) δ 0.96 (m, 12H), 1.11 (s, 10H), 1.55 (m, 3H), 1.81 (m, 1H), 1.90 (m, 1H), 2.05 (m, 1H), 2.75 (m, 1H), 2.91 (m, 1H), 4.02 (m, 5H), 4.41 (m, 1H), 4.52 (m, 1H), 5.07 (m, 1H), 5.95 (m, 1H), 7.40 (m, 1H), 7.55 (s, 1H), 7.75 (m, 5H), 8.08 (d, 1H), 8.39 (d, 1H). LC/MS: 687 (M+1).

Thioamide 2-{[1-(2-tert-Butoxycarbonylamino-3-methyl-butyryl)-4-(7-methoxy-2-phenyl-quinolin-4-yloxy)-pyrrolidine-2-carbothioyl]-amino}1-pentanoic acid methyl ester (40 mg, 0.058 mmol) was taken up in acetonitrile (4 mL) in a round bottomed flask. Ammonia (0.2 mL of 7N MeOH solution) and mercuric acetate (20 mg, 0.064 mmol) were added. The reaction was heated to 80° C. for 12 hours. The reaction mixture was then quenched with saturated aqueous ammonium chloride solution and extracted with dichloromethane. The organic layer was dried with sodium sulfate, concentrated, and purified via flash chromatography to give the desired amidine (5 mg, 13%). The methyl ester (5 mg, 0.007 mmol) was taken up in THF (0.5 mL) and water (0.5 mL) and LiOH (3.1 mg, 0.07 mmol) was added. The reaction was stirred at room temperature for 1 h. Water (5 mL) was then added and the pH was adjusted to pH 4-5 using acetic acid. The mixture was then extracted with ethyl acetate, dried with sodium sulfate, concentrated and purified via HPLC to give the desired carboxylic acid 99 (3.5 mg, 70%). $^1$H NMR (CD$_3$OD, 300 MHz) δ 0.98 (m, 11H), 1.08 (s, 9H), 1.31 (m, 4H), 1.55 (m, 3H), 1.72 (m, 1H), 1.85 (m, 1H), 1.96 (m, 1H), 2.56 (m, 1H), 2.85 (m, 1H), 3.95 (d, 1H), 1.11 (m, 5H), 4.42 (m, 1H), 4.81 (d, 1H), 5.80 (m, 1H), 7.40 (dd, 1H), 7.53 (d, 1H), 7.78 (m, 4H), 8.07 (d, 1H), 8.41 (m, 2H). LC/MS: 663 (M+1).

Example 100

Preparation of Compound 100

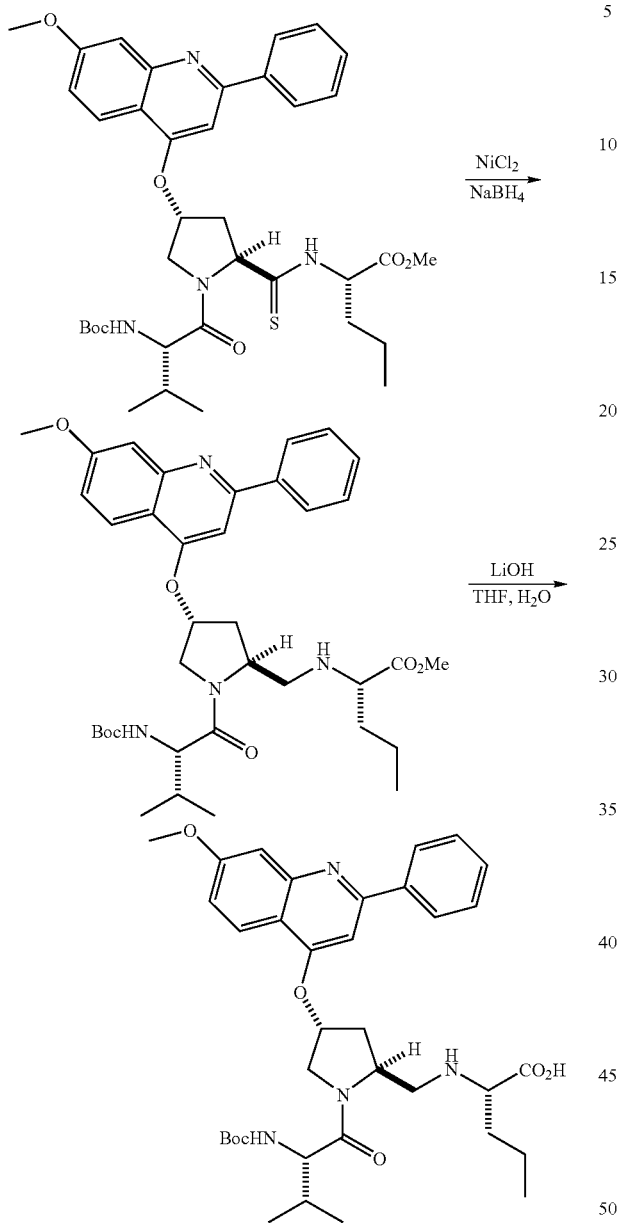

Thioamide 2-{[1-(2-tert-Butoxycarbonylamino-3-methyl-butyryl)-4-(7-methoxy-2-phenyl-quinolin-4-yloxy)-pyrrolidine-2-carbothioyl]-amino}-pentanoic acid methyl ester (35 mg, 0.05 mmol) was taken up in THF (1 mL) and methanol (1 mL). The reaction was cooled to 0° C. and Nickel (II) chloride hexahydrate (96 mg, 0.4 mmol) was added and the reaction mixture turned green. Sodium borohydride (4.6 mg, 0.12 mmol) was added and the reaction mixture turned black. The reaction was warmed to room temperature and stirred for 5 h. The mixture was then filtered through celite and purified via flash chromatography to provide the desired amine (14.2 mg, 43%). The methyl ester (14.2 mg, 0.021 mmol) was taken up in THF (1 mL) and water (1 mL). LiOH (9 mg, 0.21 mmol) was added and the reaction was stirred for 1 h. Water (5 mL) was then added and the pH was adjusted to pH 4-5 using acetic acid. The mixture was then extracted with ethyl acetate, dried with sodium sulfate, concentrated and purified via HPLC to give the desired carboxylic acid 100 (6.4 mg, 47%). $^1$H NMR (300 MHz, CD$_3$OD) δ 1.03 (m, 11H), 1.11 (m, 9H), 1.31 (m, 1H), 1.52 (m, 3H), 2.00 (m, 3H), 2.39 (m, 1H), 2.90 (m, 1H), 3.58 (m, 1H), 4.03 (m, 7H), 4.62 (m, 1H), 5.78 (m, 1H), 7.40 (dd, 1H), 7.58 (d, 1H), 7.62 (s, 1H), 7.78 (m, 3H), 8.05 (m, 2H), 8.40 (d, 1H). LC/MS: 649 (M+1).

Example 101

Preparation of Compound 101

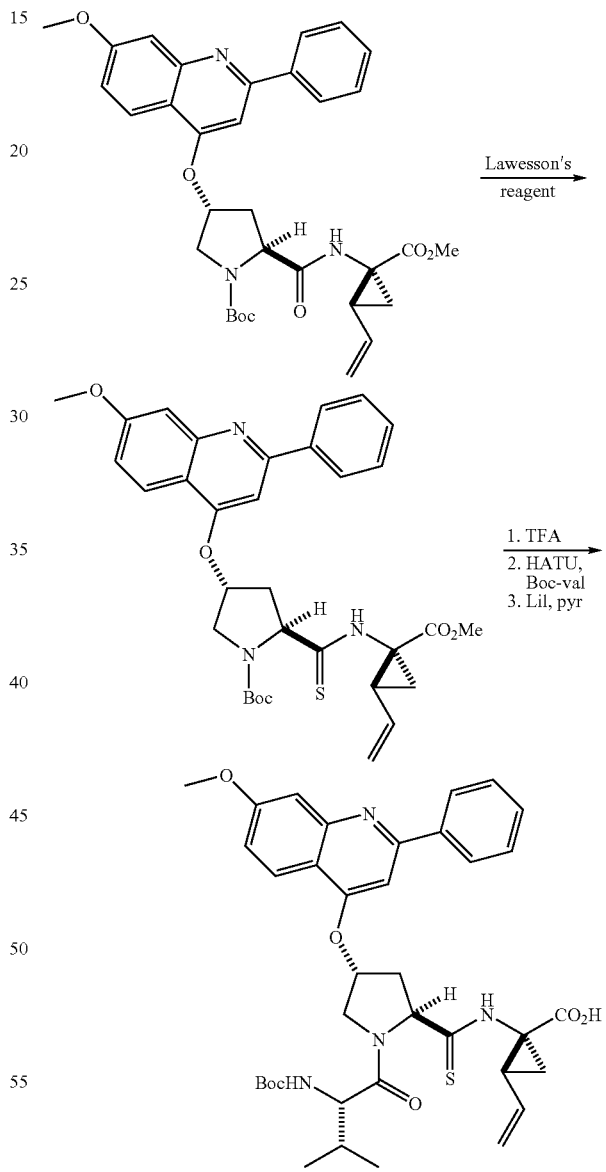

Step 1. The amide 2-(1-Methoxycarbonyl-2-vinyl-cyclopropylcarbamoyl)-4-(7-methoxy-2-phenyl-quinolin-4-yloxy)-pyrrolidine-1-carboxylic acid tert-butyl ester (0.135 g, 0.23 mmol) was taken up in toluene (6 mL) and Lawesson's reagent (94 mg, 0.23 mmol) was added. The reaction was refluxed for 30 minutes, concentrated, and purified via flash chromatography to provide the thioamide (48 mg, 35%).

Step 2. Boc-amine (36 mg, 0.043 mmol) was taken up in dichloromethane (2 mL) and placed in a round bottomed flask equipped with magnetic stir bar. TFA (1 mL) was added and the reaction was stirred at room temperature. Monitoring the reaction by LC/MS showed complete conversion after 30 minutes. The reaction was then concentrated and then azeotroped with toluene (4 mL) twice. Dichloromethane was then added (4 mL) and the mixture stirred at room temperature. HATU (23 mg, 0.060 mmol), Boc-valine (11 mg, 0.056 mmol), and N-methylmorpholine (0.01 mL) were added and the reaction was stirred for 2 h. The mixture was then quenched with water, diluted with dichloromethane, and washed with saturated sodium bicarbonate solution. The organic layer was dried with sodium sulfate, concentrated and purified via flash chromatography to provide the tripeptide (10 mg, 34%). The tripeptide (10 mg, 0.014 mmol) was taken up in pyridine (2 mL) and lithium iodide (10 equiv) was added. The mixture was refluxed for 1.5 h and then concentrated. Water was then added and the pH was adjusted to pH 4 using acetic acid. The reaction mixture was then extracted with ethyl acetate, concentrated and purified via HPLC to provide the desired carboxylic acid 101 (2 mg). $^1$H NMR (300 MHz, CD$_3$OD) δ 0.90 (m, 11H), 1.05 (m, 11H), 1.21 (m, 8H), 1.38 (s, 1H), 1.42 (m, 1H), 1.73 (m, 1H), 2.25 (m, 1H), 2.75 (m, 2H), 3.99 (m, 6H), 4.15 (m, 1H), 4.68 (d, 1H), 5.03 (m, 2H), 5.22 (d, 1H), 5.78 (m, 2H), 7.32 (dd, 1H), 7.55 (s, 1H), 7.64 (m, 4H), 7.99 (m, 2H), 8.29 (d, 1H). LC/MS: 689 (M+1).

Example 102

Preparation of Compound 102

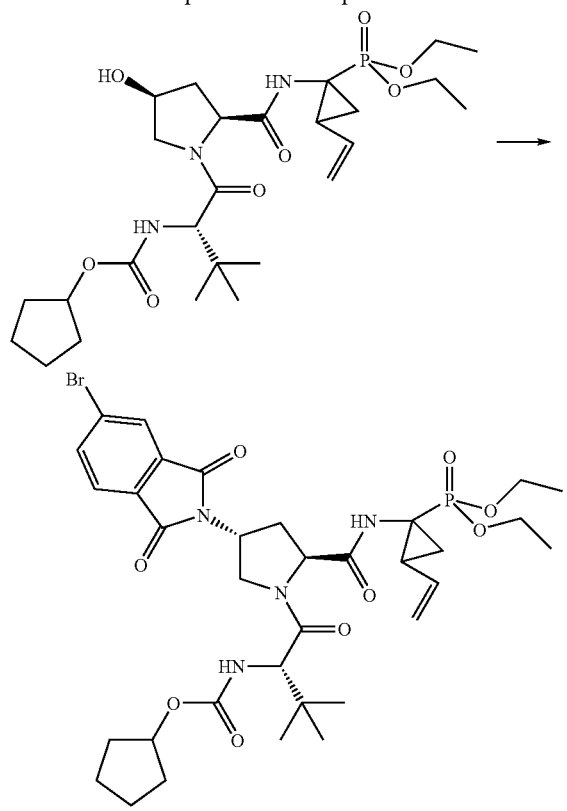

Step 1. To a solution of cis-hydroxyprolinemethyl ester (20 g, 81 mmol) in DCM (200 mL) was added TFA (40 mL). The reaction was stirred for 2 h with monitoring by LC/MS. Strip solvent and coevaporate with toluene 2× then chloroform 3×. Remove excess TFA by placing the reaction mixture under high vacuum for 5 h which afforded TFA salt (21 g) as an orange viscous oil. LC/MS: 260 (M$^+$+1).

To a solution of TFA salt (10.0 g, 40.7 mmol) in DMF (125 mL) was added cyclopentyloxycarbonyl-tert-leucinecarboxylic acid (12 g, 48 mmol), and HATU (23 g, 61 mmol). The reaction mixture was cooled to 0° C. and Hunig's base (28 mL, 163 mmol) was added slowly over 5 min. The reaction was allowed to warm to room temperature and stirred for 1 h. Remove solvent under reduced pressure and dilute with ethyl acetate. Extract the organics with sat sodium bicarb, water and brine. Purification of the product on silica gel (10-100% ethyl acetate/hexane) to afford dipeptide (14.2 g, 94%) as a white solid. $^1$H NMR (300 MHz, CDCl$_3$): δ 5.51 (d, J=8.7 Hz, 1H), 5.02 (m, 1H), 4.68 (m, 1H), 4.56 (m, 1H), 4.44 (d, J=9.1 Hz, 1H), 3.96-3.91 (bs, 4H), 3.83 (m, 1H), 2.47 (m, 2H), 1.89-1.47 (bs, 10H), 1.09 (s, 9H). LC/MS: 371 (M$^+$+1).

Step 2. To a solution of methyl ester (15.2 g, 41 mmol) in 200 mL THF, and 20 mL methanol was added lithium hydroxide (4 g, 167 mmol) in 120 mL water. The reaction mixture was stirred at room temperature overnight. The organics were removed under reduced pressure and the pH was adjusted to 2-3 using 10% HCl. Extract the acidic solution with ethyl acetate, dry over MgSO$_4$, filter and remove solvent under reduced pressure to afford acid (14.6 g, 100%) as a white solid. The product was used as is for the next reaction. $^1$H NMR (300 MHz, CDCl$_3$): δ 5.51 (d, J=8.7 Hz, 1H), 5.02 (m, 1H), 4.68 (m, 1H), 4.56 (m, 1H), 4.44 (d, J=9.1 Hz, 1H), 3.96-3.91 (m, 1H), 3.83 (m, 1H), 2.47 (m, 2H), 1.89-1.47 (bs, 10H), 1.09 (s, 9H). LC/MS: 357 (M$^+$+1).

Step 3. To a solution of acid (2.0 g, 5.61 mmol) in DMF (20 mL) was added racemic vinyl cyclopropylamino diethylphosphonate (1.20 g, 5.1 mmol) and HATU (2.32 g, 6.12 mmol). The reaction was cooled to 0° C. for 10 min then Hunig's base (3.1 mL, 17.8 mmol) was added over 5 min. The reaction was allowed to warm to room temperature and stirring continued for 1 h. Remove solvent under reduced pressure and dilute with ethyl acetate. Extract the organics with sat bicarb, water then brine. Dry organics over MgSO$_4$, filter and remove solvent under reduced pressure. Purify on silica (0-5% methanol/DCM) to afford tripeptide (694 mgs, 23%) as a white solid. $^1$H NMR (300 MHz, CDCl$_3$): δ 5.99 (m, 1H), 5.37-5.02 (bs, 5H), 4.66 (m, 1H), 4.52 (m, 1H), 4.36-4.01 (bs, 6H), 3.94 (m, 1H), 3.83 (m, 1H), 2.47 (m, 2H), 2.01-1.47 (bs, 10H), 1.36 (m, 7H), 1.04 (s, 9H). LC/MS: 558 (M$^+$+1).

Step 4. To a solution of hydroxyproline tripeptide precursor (200 mgs, 0.359 mmol) in 4 mL of DMF at room temperature was added 4-bromophthalimide (97 mgs, 0.430 mmol) and triphenyl phosphine (206 mgs, 0.789 mmol). Sonicate until dissolved and add DIAD (152 μL, 0.789 mmol). Stir at room temperature overnight. Remove solvent under reduced pressure and extract with ethyl acetate and water. Separate the layers and dry over MgSO$_4$, filter and strip. Purify using silica gel chromatography eluting (10-100% ethyl acetate in hexane). Further purify on reverse phase HPLC (ACN/Water) to afford 102 as a white solid (98 mgs, 36%). $^1$H NMR (300 MHz, CDCl$_3$): δ 7.95 (s, 1H), 7.88 (d, J=7.9 Hz, 1H), 7.71 (d, J=7.7 Hz, 1H), 7.65 (s, 1H), 7.43 (s, 1H), 6.03 (m, 1H), 5.37 (d, J=15.5 1H), 5.31-5.07 (bs, 5H), 4.91 (m, 1H), 4.77 (m, 1H), 4.23-4.03 (bs, 7H), 3.81 (t, J=7.9 Hz, 1H), 2.75 (m, 2H), 2.01 (m, 1H), 1.68-1.50 (bs, 8H), 1.30 (q, J=7.0 Hz, 6H), 1.10 (s, 1H), 0.99 (s, 9H). $^{31}$P NMR (300 MHz, CDCl$_3$): δ 22.92 (s, 1P), 22.75 (s, 1P). LC/MS: 766 (M$^+$+1).

Example 103

Preparation of Compound 103

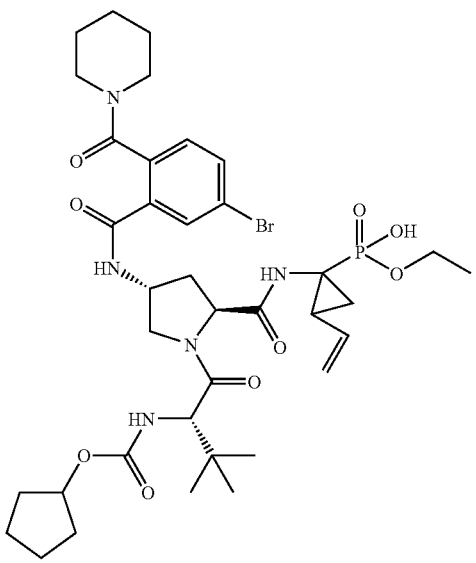

A solution of 102 (85 mgs, 0.111 mmol) in 2 mL piperidine was heated at 80° C. overnight in a pressure vessel. The solvent was removed under reduced pressure and purified on reverse phase prep HPLC (ACN/Water) to afford 103 (48.5 mgs, 53%) as a white solid. $^1$H NMR (300 MHz, CDCl$_3$): δ 7.71 (s, 1H), 7.48 (m, 2H), 7.29 (m, 1H), 7.01 (m, 1H), 6.11 (m, 1H), 5.30-5.15 (bs, 2H), 4.97 (d, J=11.3 Hz, 2H), 4.62 (s, 2H), 4.15 (m, 1H), 3.98-3.71 (bs, 3H), 3.16-3.05 (bs, 3H), 2.40-2.20 (bs, 2H), 2.15-1.15 (bs, 8H), 1.02 (s, 9H), $^{31}$P NMR (300 MHz, CDCl$_3$): δ 15.86 (s, 1P), 14.91 (s, 1P). LC/MS: 824 (M$^+$+1).

Example 104

Preparation of Compound 104

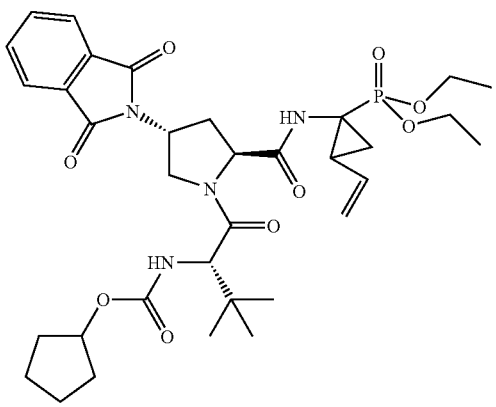

To a solution of hydroxyproline tripeptide (50 mgs, 0.08 mmol) in 1 mL of DMF at room temperature was added phthalimide (16 mgs, 0.107 mmol) and triphenyl phosphine (46 mgs, 0.176 mmol). Sonicate until dissolved and add DIAD (34 μL, 0.176 mmol). Stir at room temperature overnight. Remove solvent under reduced pressure and extract with ethyl acetate and water. Separate the layers and dry over MgSO$_4$, filter and strip. Purify using silica gel chromatography eluting (10-100% ethyl acetate in hexane). Further purify on reverse phase HPLC (ACN/Water) to afford 104 as a white solid (37.4 mgs, 69%). $^1$H NMR (300 MHz, CDCl$_3$): δ 7.85 (m, 2H), 7.74 (m, 2H), 7.43 (s, 1H), 7.27 (s, 1H), 6.08 (m, 1H), 5.31-5.12 (bs, 3H), 4.89 (m, 1H), 4.26-4.08 (bs, 3H), 3.88 (m, 1H), 2.76 (m, 2H), 1.96 (m, 1H), 1.87-1.25 (bs, 10H), 1.10 (s, 1H), 1.00 (s, 9H). $^{31}$P NMR (300 MHz, CDCl$_3$): δ@ppm: 22.95 (s, 1P), 22.76 (s, 1P). LC/MS: 687 (M$^+$+1).

Example 105

Preparation of Compound 105

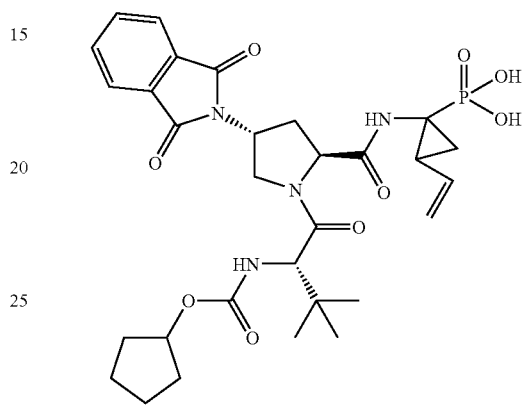

To a solution of 104 (30 mgs, 0.04 mmol) in 1.0 mL of acetonitrile, 2,6-lutidine (25 μL, 7 eq) was added and the solution was cooled to 0° C. with stirring. TMS-I (20 μL, 5 eq) was added slowly and the reaction mixture was allowed to warm to room temperature of the course of 1 h. The reaction was monitored by LCMS. Quench the reaction with 1.0 mL of methanol, stirring for 30 min. Strip the solvents and dilute with acetonitrile. Purify on reverse phase prep HPLC (ACN/Water) to afford 105 as a white solid (6 mgs, 24%). $^1$H NMR (300 MHz, CD$_3$OD): δ 7.88 (m, 4H), 7.57 (s, 1H), 7.53 (d, J=5.5 Hz, 1H), 6.70 (m, 1H), 6.08 (m, 2H), 5.27-4.77 (bs, 5H), 4.28 (m, 2H), 4.07-3.89 (bs, 3H), 2.82 (m, 2H), 2.42 (m, 2H) 2.03 (m, 1H), 1.68-1.24 (bs, 10H), 1.03 (s, 9H). $^{31}$P NMR (300 MHz, CDCl$_3$): δ@ppm: 18.82 (s, 1P), 18.48 (s, 1P). LC/MS: 631 (M$^+$+1).

Example 106

Preparation of Compound 106

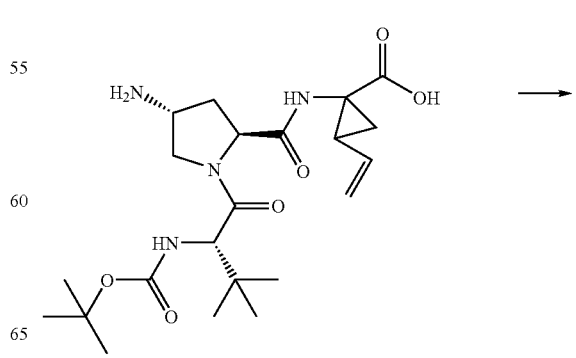

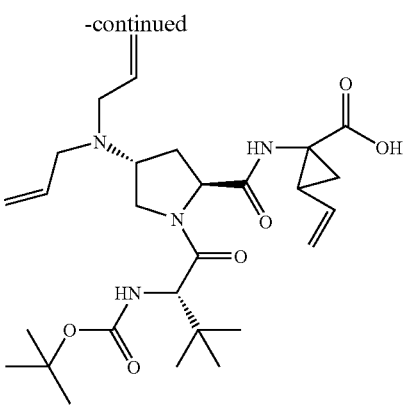

Step 1. To a solution of cis-Boc-aminoprolinemethyl ester (43.5 g, 155 mmol) in 750 mL THF, and 63 mL methanol was added lithium hydroxide (17.95 g, 750 mmol) in 500 mL water. The reaction mixture was stirred at room temperature overnight. The organics were removed under reduced pressure and the pH was adjusted to 5-6 using 10% HCl. The aqueous solution was used as is for the next step. LC/MS: 231 ($M^+$+1).

To a solution of cis-Boc-aminoprolinecarboxylic acid (≈40 g, 174 mmol) as a crude reaction mixture from previous step cooled to 0° C. was added sodium carbonate (32.76 g, 309 mmol). Dissolve FMOC-Cl (46 g, 178 mmol) in 1,4-dioxane (500 mL). Combine the dioxane solution to the aqueous solution. Stir the reaction mixture at room temperature for 5 h. Remove organics under reduced pressure. Extract the aqueous solution with ether to remove excess FMOC-Cl and discard organic layer. Adjust pH to 2-3 with con HCl. Extract aqueous with ethyl acetate 3×400 mL, combine fractions and dry over $MgSO_4$, filter and remove solvent under reduced pressure. Coevaporate the material 3× with chloroform to afford desired product (78.8 g, 100%) as a white solid and use as is for the next step. $^1$H NMR (300 MHz, $CDCl_3$): δ 7.78 (d, J=9.1 Hz, 2H), 7.59 (d, J=9.2 Hz, 2H), 7.45 (m, 4H), 5.11-4.92 (bs, 1H), 4.58-4.18 (bs, 6H), 3.81 (m, 1H), 3.42 (m, 1H), 2.50-2.15 (bs, 2H), 1.43 (s, 9H). LC/MS: 453 ($M^+$+1).

Step 2. To a solution of crude product from step 1 (12.0 g, 26.5 mmol) in DMF (100 mL) was added racemic vinylcyclopropylaminocarboxylicethyl ester (4.93 g, 31.8 mmol), and TBTU (15 g, 46.7 mmol). The reaction mixture was cooled to 0° C. and Hunig's base (18.6 mL, 106 mmol) was added slowly over 5 min. The reaction was allowed to warm to room temperature and stirred for 3 h. Remove solvent under reduced pressure and dilute with ethyl acetate. Extract the organics with sat sodium bicarb, water and brine. Purification of product on silica gel (10-100% ethyl acetate/hexane) to afford dipeptide intermediate (11.9 g, 76%) as an off-white solid mixture of diastereomers. $^1$H NMR (300 MHz, $CDCl_3$): δ 7.79 (d, J=9.1 Hz, 2H), 7.61 (d, J=9.0 Hz, 2H), 7.47 (m, 4H), 5.83 (m, 1H), 5.37 (m, 1H), 5.14 (m, 1H), 4.83 (m, 1H), 4.58-4.18 (bs, 8H), 3.78 (m, 1H), 3.37 (m, 1H), 2.59 (m, 1H), 2.13-1.82 (bs, 4H) 1.41 (s, 9H), 1.32 (m, 4H). LC/MS: 590 ($M^+$+1).

Step 3. To a solution of dipeptide intermediate (24.2 g, 41.0 mmol) in DCM (200 mL) was added TFA (40 mL). The reaction was stirred for 2.5 h with monitoring by LC/MS. Strip solvent and coevaporate with toluene 2× then chloroform 3×. Remove excess TFA by placing the reaction mixture under high vacuum for 5 h which afforded the TFA salt (≈25 g) as an orange viscous oil. LC/MS: 490 ($M^+$+1).

Step 4. To a solution of the TFA salt (25 g, 41 mmol) in DCM (200 mL) was added Boc-tert-leucinecarboxylic acid (11.5, 49 mmol), and TBTU (19.96 g, 62 mmol). The reaction mixture was stirred for 10 min then Hunig's base (28.8 mL, 165 mmol) was added over a period of 5 min. The reaction was allowed to stir at room temperature for 3 h. Solvent was removed under reduced pressure and diluted with ethyl acetate. The solution was extracted with sat bicarb, water, then brine. The organics were then dried over $MgSO_4$, filtered and solvent removed under reduced pressure. The crude material was purified on silica gel (10-100% ethyl acetate/hexane) to afford tripeptide (18 g, 63%) as an off-white solid. $^1$H NMR (300 MHz, $CDCl_3$): δ 7.79 (m, 2H), 7.63 (m, 2H), 7.47 (m, 4H), 6.18 (m, 1H), 5.78 (m, 1H), 5.37-5.21 (m, 1H), 5.14 (d, J=8.7 Hz, 1H), 4.76 (m, 1H), 4.62-4.09 (bs, 8H), 3.94 (m, 1H), 3.77 (m, 1H), 2.63 (m, 1H), 2.31-2.05 (bs, 2H), 1.89 (m, 2H) 1.41 (s, 9H), 1.32 (t, J=7.6 Hz, 3H), 1.06 (s, 9H). LC/MS: 703 ($M^+$+1).

Step 5. To a solution of tripeptide (19 g, 27 mmol) in DCM (250 mL) was added piperidine (70 mL). The reaction was stirred at room temperature and monitored by LC/MS. Complete conversion to product was observed after 2 h. Remove solvent under reduced pressure and dilute with ethyl acetate. Extract the organic mixture with sat bicarb, followed by brine. Dry organics over $MgSO_4$, filter and remove solvent under reduced pressure. The product was purified on silica (10-100% ethyl acetate/hexane) to afford amine (9.0 g, 70%) as a white solid. $^1$H NMR (300 MHz, $CDCl_3$): δ 5.79 (m, 1H), 5.32-5.18 (bs, 3H), 4.72 (m, 1H), 4.29-4.11 (bs, 3H), 3.83 (m, 1H), 2.47 (m, 1H), 2.06 (m, 1H), 1.89-1.47 (bs, 3H), 1.41 (s, 9H), 1.24 (m, 3H), 1.03 (s, 9H). LC/MS: 481 ($M^+$+1).

To a solution of amine (1.066 g, 2.22 mmol) in DMF (10 mL) was added potassium carbonate (0.460 g, 3.33 mmol) and allyl bromide (0.200 mL, 2.33 mmol). The reaction was stirred at room temperature overnight. The solvent was removed under reduced pressure and the crude mixture was extracted with ethyl acetate and water. The organics were dried over $MgSO_4$, filtered and solvent removed under reduced pressure. The mixture was purified on silica (10-100% ethyl acetate/hexane) to afford nearly a 1:1 mixture of mono allyl (250 mgs, 22%) and bisallyl amine product (200 mgs, 16%) both as white solids. Monoallyl amine $^1$H NMR (300 MHz, $CDCl_3$): δ 5.93-5.72 (bs, 4H), 5.32-5.08 (bs, 5H), 4.72 (m, 1H), 4.29-4.11 (bs, 3H), 3.83 (m, 1H), 2.47 (m, 1H), 2.06 (m, 1H), 1.89-1.47 (bs, 3H), 1.41 (s, 9H), 1.24 (m, 3H), 1.03 (s, 9H). LC/MS: 521 ($M^+$+1). Bisallyl amine product $^1$H NMR (300 MHz, $CDCl_3$): δ 5.96-5.72 (bs, 6H), 5.32-5.08 (bs, 7H), 4.72 (m, 1H), 4.29-4.11 (bs, 3H), 3.83 (m, 1H), 2.47 (m, 1H), 2.04 (m, 1H), 1.87-1.45 (bs, 3H), 1.39 (s, 9H), 1.26 (m, 3H), 1.02 (s, 9H). LC/MS: 561 ($M^+$+1).

Step 6. To a solution of the bis-allyl tripeptide ethyl ester precursor to, (200 mgs, 0.357 mmol) in 3.0 mL water, 5.0 mL THF, and 0.5 mL methanol was added 50 mgs of lithium hydroxide. The reaction mixture was stirred at room temperature overnight. The organics were removed under reduced pressure and the pH was adjusted to 2 using 10% HCl. The aqueous solution was extracted 3×50 mL ethyl acetate. The organics were combined and dried over $MgSO_4$. The solids were filtered off and the organics were removed under reduced pressure. The crude material was diluted with acetonitrile and purified on reverse phase prep HPLC (ACN/Water) to afford 106 as a white solid (71 mgs, 38%). $^1$H NMR (300 MHz, $CDCl_3$): δ 7.63 (s, 1H), 7.56 (s, 1H), 5.90-5.70 (bs, 7H), 5.49-5.10 (bs, 8H), 4.64 (m, 1H), 4.31 (m, 1H), 3.88 (d, J=11.9 Hz, 1H), 3.68 (m, 2H), 3.21 (m, 4H) 2.50-2.39 (m, 2H), 2.09-1.80 (bs, 4H), 1.41 (s, 9H), 0.98 (s, 9H). LC/MS: 533 (M$^+$+1).

Example 107

Preparation of Compound 107

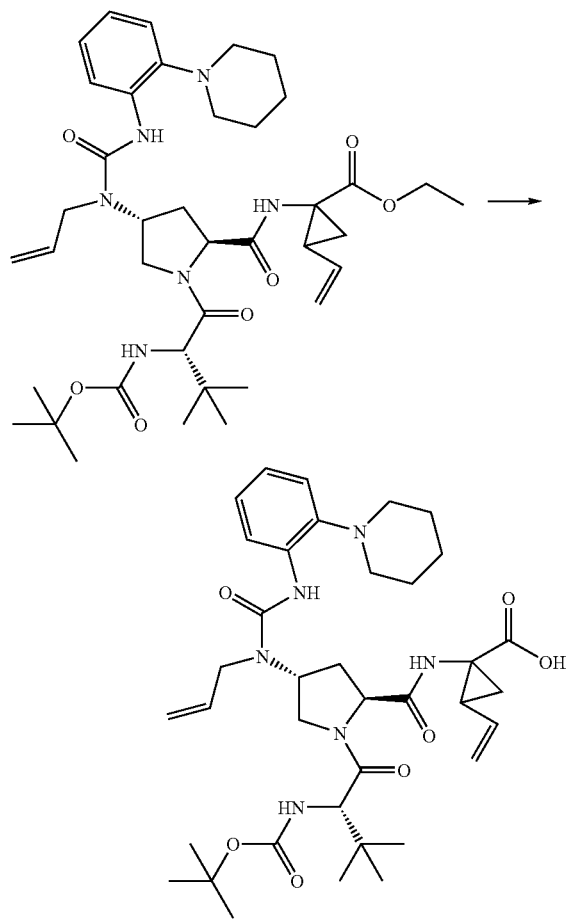

Step 1. To a solution of o-piperidinoaniline (250 mgs, 1.41 mmol) and 5.0 mL DMF, was added carbonyl diimidazole (229 mgs, 1.41 mmol). The solution was heated to 80° C. for 1 h. Then add the mono-allyl amine precursor to (example 106) (110 mgs, 0.21 mmol) and continue heating at 80° C. overnight. The organics were removed under reduced pressure and the crude material was extracted with EtOAc and water, followed by brine. The organics were combined and dried over MgSO$_4$. The solids were filtered off and the organics were removed under reduced pressure. The crude material was diluted with dichloromethane and purified on silica EtOAc/Hexane to afford ester as a white solid (90 mgs, 60%). $^1$H NMR (300 MHz, CDCl$_3$): δ 8.26 (s, 1H), 8.21 (d, J=7.9 Hz, 1H), 7.47 (d, J=10.9 Hz, 1H), 7.14 (m, 2H), 6.97 (m, 1H), 6.02 (m, 1H), 5.75 (m, 1H), 5.42-5.10 (bs, 8H), 4.73 (t, J=7 Hz, 1H), 4.28-3.80 (m, 8H), 2.73-2.59 (bs, 6H), 2.13-2.01 (m, 2H), 1.89-1.57 (bs, 9H), 1.43 (s, 9H), 1.28 (m, 4H), 1.09 (d, J=7.7, 9H). LC/MS: 723 (M$^+$+1).

Step 2. To a solution of ester (90 mgs, 0.125 mmol) in 2.0 mL water, 3.0 mL THF, and 1.0 mL methanol was added 50 mgs of lithium hydroxide. The reaction mixture was stirred at room temperature overnight. The organics were removed under reduced pressure and the pH was adjusted to 2 using 10% HCl. The aqueous solution was extracted 3×50 mL ethyl acetate. The organics were combined and dried over MgSO$_4$. The solids were filtered off and the organics were removed under reduced pressure. The crude material was diluted with acetonitrile and purified on reverse phase prep HPLC (ACN/Water) to afford 107 as a white solid (31 mgs, 36%). $^1$H NMR (300 MHz, CDCl$_3$): δ 8.26 (s, 1H), 8.20 (d, J=8.6 Hz, 1H), 7.56 (d, J=13.4 Hz, 1H), 7.16 (m, 2H), 5.97 (m, 2H), 5.75 (m, 1H), 5.42-5.13 (bs, 8H), 4.73 (t, J=7 Hz, 1H), 4.28-3.80 (m, 8H), 2.73-2.59 (bs, 6H), 2.13-2.01 (bs, 2H), 1.89-1.57 (bs, 9H), 1.43 (s, 9H), 1.00 (s, 9H). LC/MS: 695 (M$^+$+1).

Example 108

Preparation of Compound 108

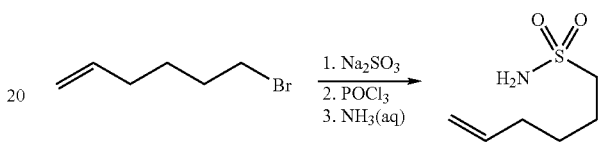

Step 1. To a solution of Na$_2$SO$_3$ (6 g, 48 mmol) in H$_2$O (28 mL) was added 6-bromo-1-hexene (5.4 mL, 40 mmol). The reaction mixture was heated to reflux for 4 hr. The reaction mixture was cooled to rt, and extracted with Et$_2$O (20 mL). The aqueous phase was evaporated to a white solid, and dried at 130° C. under vacuum for 2 hr. The resulting white solid was treated with POCl$_3$ (40 mL) for 4 hr at 130° C. Solvent was evaporated to dryness. The residue was taken up in CH$_3$CN (50 mL) and cooled to 0° C. To this solution was added aqueous NH$_3$ (100 mL, 28%) in CH$_3$CN (40 mL) dropwise. After the addition, CH$_2$Cl$_2$ (100 mL) was added, and the two phases were separated. The organic phase was washed with H$_2$O (50 mL), brine (50 mL) and dried over Na$_2$SO$_4$. The crude product was collected after evaporation of the solvent.

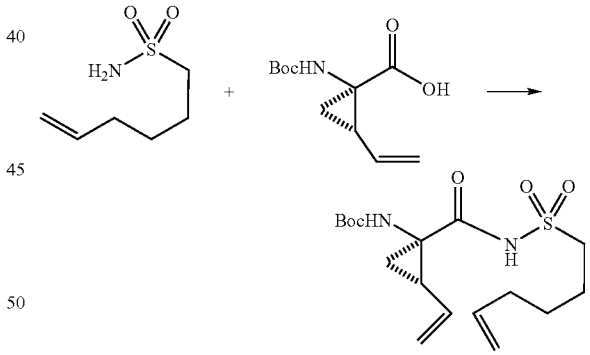

Step 2. To a solution of acid (2.0 g, 8.8 mmol) in THF (30 mL) stirred at rt was added CDI (1.6 g, 9.7 mmol). The reaction mixture was heated to 65° C. for 2 hr. A solution of sulfonamide (2.6 g, 15.3 mmol) in THF (5.0 mL) was added, followed by DBU (2.0 mL). After the addition, the reaction mixture was heated for 14 hr at 65° C. The reaction mixture was cooled to rt and diluted with EtOAc, washed with saturated NH$_4$Cl, brine and dried over Na$_2$SO$_4$. The drying agent was filtered off and the solvent was evaporated. The residue was purified by SiO$_2$ column (10-20-35% EtOAc in hexanes) to give the desired product (1.1 g). HNMR (300 MHz, CDCl$_3$): δ 5.44-5.76 (m, 2H), 5.21 (d, 1H), 5.06 (d, 1H), 4.96-4.86 (m, 2H), 3.4-3.34 (m, 2H), 2.14-1.92 (m, 2H), 1.86-1.66 (m, 2H), 1.38 (s, 9H).

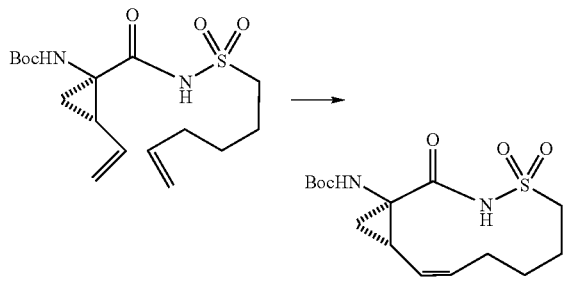

Step 3. A solution of starting material (210 mg, 0.57 mmol) in CH$_2$Cl$_2$ (130 mL) was degassed with a gentle stream of N$_2$ for 40 min. Grubbs catalyst (G1, 93 mg, 0.11 mmol) was added and degassed for 30 min. The reaction mixture was then heated at 65° C. for 6 hr. The reaction mixture was cooled to rt and solvent was evaporated off. The residue was purified by SiO$_2$ column (20-35-45% EtOAc in hexanes) to give the desired product (40 mg, 19%). HNMR (300 MHz, CDCl$_3$): δ 10.2 (bs, 1H), 5.51-5.22 (m, 1H), 5.25 (s, 1H), 3.33-3.23 (t, 1H), 3.01-2.88 (m, 1H), 2.28-1.7 (m, 6H), 1.43 (s, 9H), 1.4-1.15 (m, 2H).

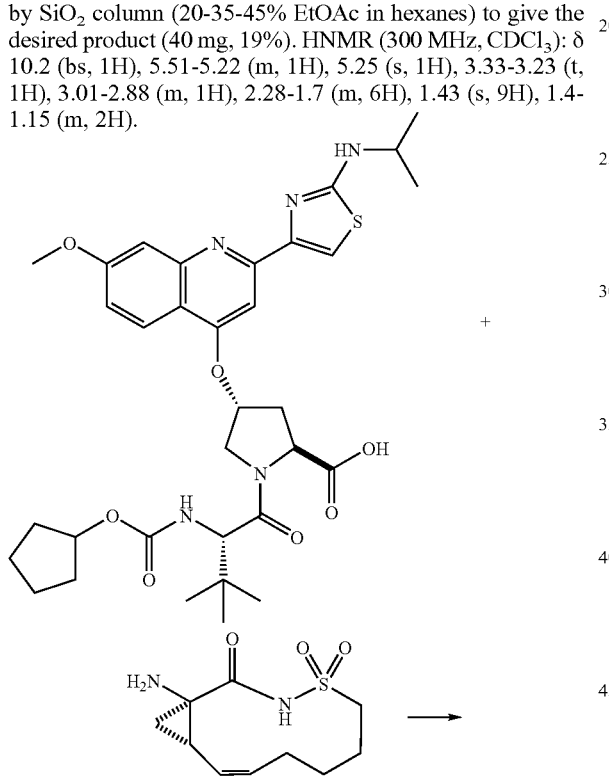

Step 4. To a solution of cyclic acylsulfonamide (100 mg) in CH$_2$Cl$_2$ (5 mL) was added TFA (2.0 (mL). The reaction mixture was stirred at rt for 3 hr. Solvent was removed under vacuum. The residue was azeotroped with PhMe three times. The crude TFA salt was diluted with DMF (2.0 mL), to this solution was added acid (100 mg, 0.15 mmol), HATU (87 mg, 0.23 mmol) and NMM (62 mg, 0.61 mmol). The resulting reaction mixture was stirred at rt for 14 hr. Diluted with EtOAc and washed with saturated NH$_4$Cl, brine and dried over Na$_2$SO$_4$. The drying agent was filtered off and the solvent was evaporated. The crude product was purified by HPLC to give compound 108 as a yellow solid (15 mg, 11%). HNMR (300 MHz, CDCl$_3$): δ 10.02 (bs, 1H), 8.76 (s, 1H), 7.82-7.52 (m, 5H), 5.74 (s, 1H), 5.6-5.5 (m, 1H), 5.24-5.02 (m, 2H), 4.73 (t, J=8.2 Hz, 1H), 4.61 (d, J=12.3 Hz, 1H), 4.38 (s, 1H), 3.95 (s, 3H), 3.6-3.5 (m, 1H), 3.2 (t, J=12 Hz, 1H), 2.9-2.6 (m, 3H), 2.3-1.5 (m, 6H), 1.42 (d, J=6.6 Hz, 6H), 0.95 (s, 9H).

Example 109

Preparation of Compound 109

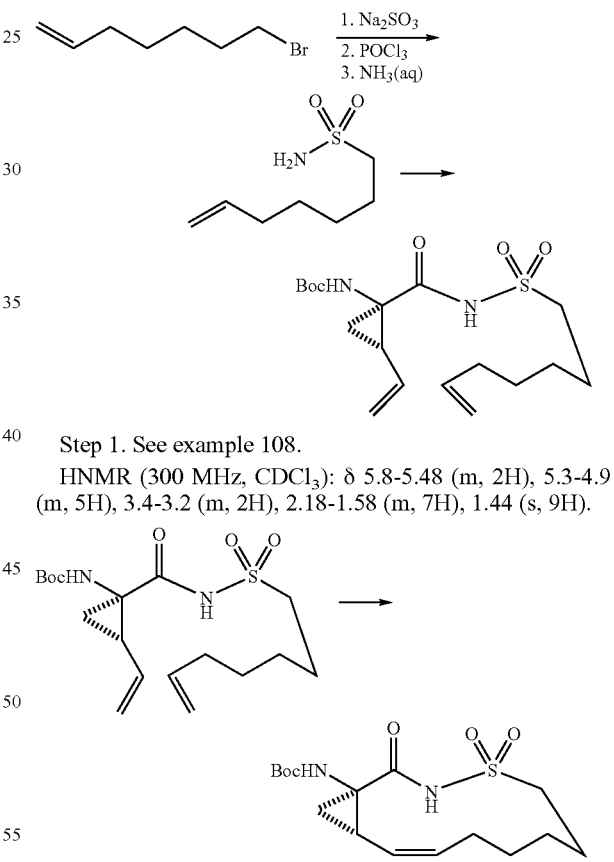

Step 1. See example 108.
HNMR (300 MHz, CDCl$_3$): δ 5.8-5.48 (m, 2H), 5.3-4.9 (m, 5H), 3.4-3.2 (m, 2H), 2.18-1.58 (m, 7H), 1.44 (s, 9H).

Step 2. A solution of starting material (982 mg, 2.54 mmol) in CH$_2$Cl$_2$ (100 mL) was degassed with a gentle stream of N$_2$ for 40 min. Grubbs catalyst (312 mg, 0.38 mmol) was added and degassed for 30 min. The reaction mixture was then heated at 65° C. for 24 hr. The reaction mixture was cooled to rt and solvent was evaporated off. The residue was purified by SiO$_2$ column (20-35-45% EtOAc in hexanes) to give the desired product (510 mg, 56%). HNMR (300 MHz, CDCl$_3$): δ 9.9 (s, 1H), 5.72-5.6 (m, 1H), 5.44-5.28 (m, 2H), 3.7-3.6 (m, 1H), 3.04-2.9 (m, 1H)2.2-1.6 (m, 4H), 1.42 9 s, 9H), 1.22-1.14 (m, 2H).

4.75-4.63 (m, 2H), 4.12-4.04 (m, 1H), 3.95 (s, 3H), 3.56-3.54 (m, 1H), 2.9-2.67 (m, 2H), 2.05-1.21 (m, 8H), 0.93 (s, 9H).

Example 110

Preparation of Compound 110

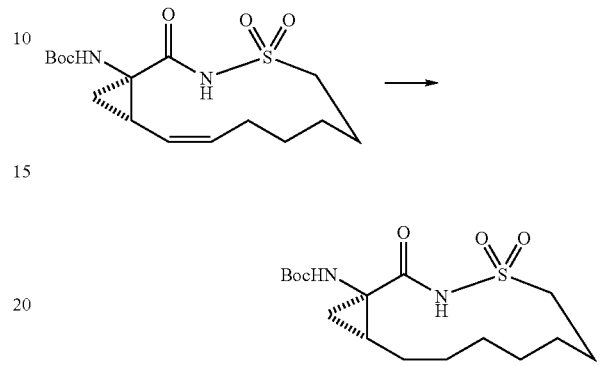

Step 1. To a solution of cyclic acylsulfonamide (230 mg, 0.64 mmol) in THF (2.0 mL) was added 2,4,6-triiospropyl-benzenesulphonyl hydrazide (1.1 g, 3.85 mmol). The reaction flask was then placed in a preheated 65° C. oil bath. Et₃N (388 mg, 3.85 mmol) was added slowly. After the addition, the reaction mixture was cooled to rt, diluted with EtOAc, and washed with NH₄Cl, NaHCO₃, brine. The organic phase was dried over Na₂SO₄. The residue was purified by SiO₂ column (20-35-45% EtOAc in hexanes) to give the desired product (162 mg, 70%). HNMR (300 MHz, CDCl₃): δ 9.8 (s, 1H), 4.1-3.84 (m, 2H), 3.14-3.02 (m, 1H), 2.86-2.74 (m, 1H)1.75-1.22 (m, 8H), 1.21 (9s, 9H).

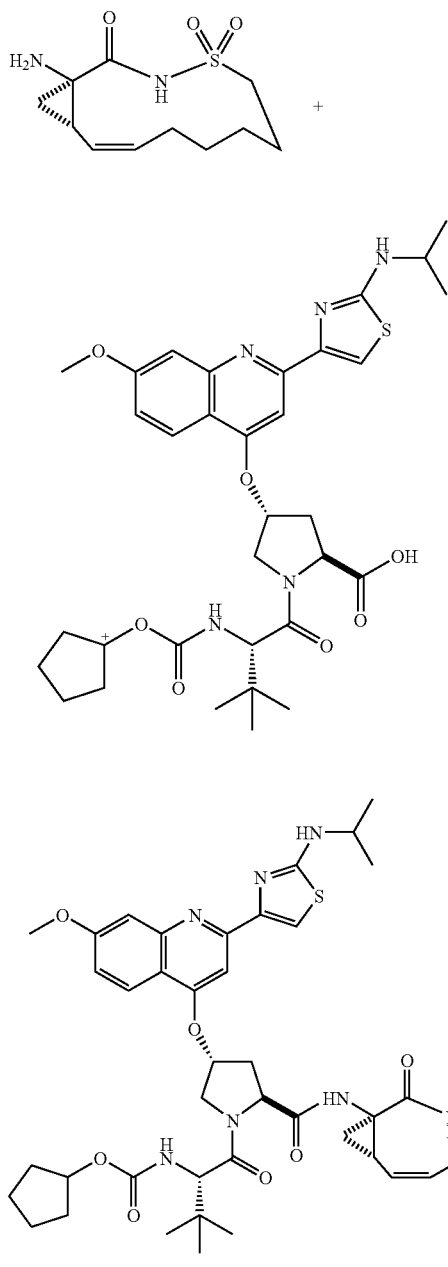

Step 3. To a solution of cyclic acylsulfonamide (92 mg) in CH₂Cl₂ (4.0 mL) was added TFA (2.0 (mL). The reaction mixture was stirred at rt for 3 hr. Solvent was removed under vacuum. The residue was azeotroped with PhMe three times. The crude TFA salt was diluted with DMF (2.0 mL), to this solution was added acid (100 mg, 0.15 mmol), HATU (87 mg, 0.23 mmol) and NMM (62 mg, 0.61 mmol). The resulting reaction mixture was stirred at rt for 14 hr. Diluted with EtOAc and washed with saturated NH₄Cl, brine and dried over Na₂SO₄. The drying agent was filtered off and the solvent was evaporated. The crude product was purified by HPLC to give compound 109 as a yellow solid (38 mg, 16%). HNMR (300 MHz, CDCl₃): δ 9.8 (s, 1H), 8.66 (s, 1H), 8.13 (d, J=9.4 Hz, 1H), 7.76-7.7 (m, 2H), 5.76 (s, 1H), 5.7-5.62 (m, 1H), 5.31 (dd, J=16.5, 7.3 Hz, 1H), 5.18 (s, 1H), 5.04 (s, 1H),

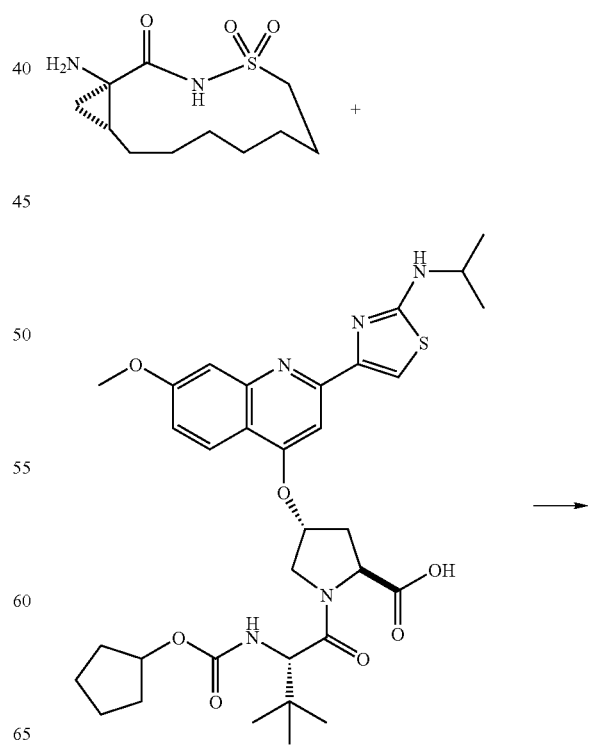

-continued

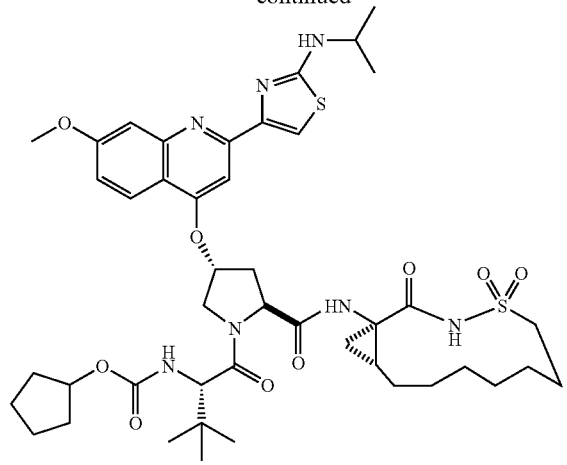

Step 2. To a solution of cyclic acylsulfonamide (80 mg, 0.22 mmol) in CH$_2$Cl$_2$ (4.0 mL) was added TFA (2.0 mL). The reaction mixture was stirred at rt for 3 hr. Solvent was removed under vacuum. The residue was azeotroped with PhMe three times. The crude TFA salt was diluted with DMF (2.0 mL), to this solution was added acid (217 mg, 0.33 mmol), HATU (117 mg, 0.31 mmol) and NMM (89 mg, 0.88 mmol). The resulting reaction mixture was stirred at rt for 14 hr. Diluted with EtOAc and washed with saturated NH$_4$Cl, brine and dried over Na$_2$SO$_4$. The drying agent was filtered off and the solvent was evaporated. The crude product was purified by HPLC to give a yellow solid (39 mg, 16%). HNMR (300 MHz, CDCl$_3$): δ 9.82 (bs, 1H), 8.66 (s, 1H), 8.13 (d, J=9.4, 1H), 7.76 (d, J=3.2 Hz, 1H), 7.76 (s, 1H), 7.4 (s, 1H), 5.73 (s, 1H), 5.25 (d, J=8.8 Hz, 1H), 4.64-4.59 (m, 2H), 4.45 (s, 1H), 4.09-3.93 (m, 2H), 3.91 (s, 3H), 3.56-3.45 (m, 1H), 3.02-2.63 (m, 3H), 2.04-1.96 (m, 2H), 1.71-1.08 (m, 8H), 0.97 (s, 9H). Methylmorpholine (395 μL, 3.59 mmol), the TFA salt of the amino ester (191 mg, 1.23 mmol) and the resultant solution was allowed to stir at room temperature for 16 hours. The reaction mixture was diluted with dichloromethane (50 mL), washed with water (20 mL), saturated sodium bicarbonate (20 mL), saturated ammonium chloride (20 mL), dried (Na$_2$SO$_4$), purified by silica gel chromatography (eluted with 50% EtOAc in hexanes) to supply the tripeptide as a white solid (545 mg, 0.87 mmol, 85%). $^1$H NMR (300 MHz, MeOD) δ 0.96-1.02 (m, 1H), 1.19 (t, J=7-Hz, 3H), 1.35-1.39 (m, 1H), 1.53-1.75 (m, 9H), 2.09-2.26 (m, 2H), 2.37-2.42 (m, 1H), 3.93-4.13 (m, 4H), 4.25-4.50 (m, 3H), 4.56-4.75 (m, 1H), 4.96-5.16 (m, 2H), 5.18-5.24 (m, 1H), 5.67-5.79 (m, 1H), 6.73-6.76 (m, 1H), 6.85-6.90 (m, 1H), 7.06-7.13 (m, 2H). LC-MS 624 (M$^+$+1).

Step 2. To a solution of tripeptide (150 mg, 0.24 mmol) in 3 mL of THF, 3 mL water, and 3 mL methanol stirred at room temperature was added lithium hydroxide (51 mg, 21.2 mmol). The resulting solution was stirred for 2 hours. The reaction mixture was diluted EtOAc (100 mL) and the pH of the solution was adjusted to 4 using 1 M solution of hydrochloric acid. The aqueous fraction was extracted with EtOAc (2×100 mL), and the combined organic fractions were concentrated under reduced pressure followed by purification by HPLC to afford the desired compound 112 as a white solid (40 mg, 0.07 mmol, 29%). $^1$H NMR (300 MHz, MeOD) δ 0.96-1.01 (m, 11H), 1.36-1.41 (m, 1H), 1.52-1.80 (m, 9H), 2.09-2.17 (m, 1H), 2.23-2.43 (m, 2H), 3.93-4.10 (m, 2H), 4.25-4.50 (m, 3H), 4.58-4.62 (m, 1H), 4.93-4.96 (m, 1H), 5.16-5.19 (m, 1H), 5.21-5.25 (m, 2H), 5.72-5.84 (m, 1H), 6.73-6.76 (m, 1H), 6.85-6.90 (m, 1H), 7.09-7.13 (m, 2H). LC-MS 596 (M$^+$+1).

Biological Assay Description

Evaluation of Protease Inhibitors:

NS3 Enzymatic Potency:

Purified NS3 protease is complexed with NS4A peptide and then incubated with serial dilutions of compound (DMSO used as solvent). Reactions are started by addition of dual-labeled peptide substrate and the resulting kinetic increase in fluorescence is measured. Non-linear regression of velocity data is performed to calculate IC$_{50}$s. Activity is initially be tested against genotype 1b protease. Depending on the potency obtained against genotype 1b, additional genotypes (1a, 2a, 3) and or protease inhibitor resistant enzymes (D168Y, D168V, or A156T mutants) may be tested. BILN-2061 is used as a control during all assays.

Replicon Potency and Cytotoxicity:

Huh-luc cells (stably replicating Bartenschlager's I389luc-ubi-neo/NS3-3'/ET genotype 1b replicon) is treated with serial dilutions of compound (DMSO is used as solvent) for 72 hours. Replicon copy number is measured by bioluminescence and non-linear regression is performed to calculate EC$_{50}$s. Parallel plates treated with the same drug dilutions are assayed for cytotoxicity using the Promega CellTiter-Glo cell viability assay. Depending on the potency achieved against the 1b replicon, compounds may be tested against a genotype 1a replicon and/or inhibitor resistant replicons encoding D168Y or A156T mutations. BILN-2061 is used as a control during all assays.

Effect of Serum Proteins on Replicon Potency:

Replicon assays are conducted in normal cell culture medium (DMEM+10% FBS) supplemented with physiologic concentrations of human serum albumin (40 mg/mL) or α-acid glycoprotein (1 mg/mL). EC$_{50}$s in the presence of human serum proteins are compared to the EC$_{50}$ in normal medium to determine the fold shift in potency.

Enzymatic Selectivity:

The inhibition of mammalian proteases including Porcine Pancreatic Elastase, Human Leukocyte Elastase, Protease 3, and Cathepsin D are measured at K$_m$ for the respective substrates for each enzyme. IC$_{50}$ for each enzyme is compared to the IC$_{50}$ obtained with NS3 1b protease to calculate selectivity. Representative compounds of the invention have shown activity.

MT-4 Cell Cytotoxicity:

MT4 cells are treated with serial dilutions of compounds for a five day period. Cell viability is measured at the end of the treatment period using the Promega CellTiter-Glo assay and non-linear regression is performed to calculate CC$_{50}$.

Compound Concentration Associated with Cells at EC$_{50}$:

Huh-luc cultures are incubated with compound at concentrations equal to EC$_{50}$. At multiple time points (0-72 hours), cells are washed 2× with cold medium and extracted with 85% acetonitrile; a sample of the media at each time-point will also be extracted. Cell and media extracts are analyzed by LC/MS/MS to determine the Molar concentration of compounds in each fraction. Representative compounds of the invention have shown activity.

Solubility and Stability:

Solubility is determined by taking an aliquot of 10 mM DMSO stock solution and preparing the compound at a final concentration of 100 µM in the test media solutions (PBS, pH 7.4 and 0.1 N HCl, pH 1.5) with a total DMSO concentration of 1%. The test media solutions are incubated at room temperature with shaking for 1 hr. The solutions will then be centrifuged and the recovered supernatants are assayed on the HPLC/UV. Solubility will be calculated by comparing the amount of compound detected in the defined test solution compared to the amount detected in DMSO at the same concentration. Stability of compounds after an 1 hour incubation with PBS at 37° C. will also be determined.

Stability in Cryopreserved Human, Dog, and Rat Hepatocytes:

Each compound is incubated for up to 1 hour in hepatocyte suspensions (100 µl, 80,000 cells per well) at 37° C. Cryopreserved hepatocytes are reconstituted in the serum-free incubation medium. The suspension is transferred into 96-well plates (50 µL/well). The compounds are diluted to 2 µM in incubation medium and then are added to hepatocyte suspensions to start the incubation. Samples are taken at 0, 10, 30 and 60 minutes after the start of incubation and reaction will be quenched with a mixture consisting of 0.3% formic acid in 90% acetonitrile/10% water. The concentration of the compound in each sample is analyzed using LC/MS/MS. The disappearance half-life of the compound in hepatocyte suspension is determined by fitting the concentration-time data with a monophasic exponential equation. The data will also be scaled up to represent intrinsic hepatic clearance and/or total hepatic clearance.

Stability in Hepatic S9 Fraction from Human, Dog, and Rat:

Each compound is incubated for up to 1 hour in S9 suspension (500 µl, 3 mg protein/mL) at 37° C. (n=3). The compounds are added to the S9 suspension to start the incubation. Samples are taken at 0, 10, 30, and 60 minutes after the start of incubation. The concentration of the compound in each sample is analyzed using LC/MS/MS. The disappearance half-life of the compound in S9 suspension is determined by fitting the concentration-time data with a monophasic exponential equation.

Caco-2 Permeability:

Compounds are assayed via a contract service (Absorption Systems, Exton, Pa.). Compounds are provided to the contractor in a blinded manner. Both forward (A-to-B) and reverse (B-to-A) permeability will be measured. Caco-2 monolayers are grown to confluence on collagen-coated, microporous, polycarbonate membranes in 12-well Costar Transwell® plates. The compounds are dosed on the apical side for forward permeability (A-to-B), and are dosed on the basolateral side for reverse permeability (B-to-A). The cells are incubated at 37° C. with 5% $CO_2$ in a humidified incubator. At the beginning of incubation and at 1 hr and 2 hr after incubation, a 200-µL aliquot is taken from the receiver chamber and replaced with fresh assay buffer. The concentration of the compound in each sample is determined with LC/MS/MS. The apparent permeability, Papp, is calculated.

Plasma Protein Binding:

Plasma protein binding is measured by equilibrium dialysis. Each compound is spiked into blank plasma at a final concentration of 2 µM. The spiked plasma and phosphate buffer is placed into opposite sides of the assembled dialysis cells, which will then be rotated slowly in a 37° C. water bath. At the end of the incubation, the concentration of the compound in plasma and phosphate buffer is determined. The percent unbound is calculated using the following equation:

$$\% \text{ Unbound} = 100 \cdot \left( \frac{C_f}{C_b + C_f} \right)$$

Where $C_f$ and $C_b$ are free and bound concentrations determined as the post-dialysis buffer and plasma concentrations, respectively CYP450 Profiling:

Each compound is incubated with each of 5 recombinant human CYP450 enzymes, including CYP1A2, CYP2C9, CYP3A4, CYP2D6 and CYP2C19 in the presence and absence of NADPH. Serial samples will be taken from the incubation mixture at the beginning of the incubation and at 5, 15, 30, 45 and 60 min after the start of the incubation. The concentration of the compound in the incubation mixture is determined by LC/MS/MS. The percentage of the compound remaining after incubation at each time point is calculated by comparing with the sampling at the start of incubation.

Stability in Rat, Dog, Monkey and Human Plasma:

Compounds will be incubated for up to 2 hour in plasma (rat, dog, monkey, or human) at 37° C. Compounds are added to the plasma at final concentrations of 1 and 10 ug/mL. Aliquots are taken at 0, 5, 15, 30, 60, and 120 min after adding the compound. Concentration of compounds and major metabolites at each timepoint are measured by LC/MS/MS.

Exemplary PRT's

By way of example and not limitation, embodiments of the invention are named below in tabular format. The definitions used within this section ("Exemplary PRTs") are applicable only to the structures within this section. Exemplary PRT includes $R^x$.

By way of example and not limitation, embodiments of the invention are named below in tabular format (Table Y). These embodiments are of the general formula "MBF3"

MBF3: Sc.K1.K2.K3

Each embodiment of MBF3, is depicted as a substituted nucleus (Sc). Sc is described in Tables 1.3 to 1.6 below. Sc is also described by any formula presented herein that bears at least one K1, K2, and K3 wherein each is a point of covalent attachment to Sc. For those embodiments-described in Table Y, Sc is a nucleus designated by a number and each substituent is designated in order by number. Tables 1.3 to 1.6 are a schedule of nuclei used in forming the embodiments of Table Y. Each nucleus (Sc) is given a number designation from Table 1.3 to 1.6 and this designation appears first in each embodiment name as numbers 9 thru 40. Similarly, Tables 2a to 6k list the selected substituent groups by number designation, and are understood to be attached to Sc at K1, K2, or K3 as listed. It is understood that K1, K2, K3 do not represent atoms, but only points of connection to the parent scaffold Sc. Accordingly, a compound of the formula MBF3 includes compounds having Sc groups based on compounds according to Table Y below. In all cases the compounds of the formula MBF3 have groups K1, K2, and K3 on nucleus Sc, and the corresponding groups K1, K2, and K3 are listed, as set forth in the Tables below.

Accordingly, each named embodiment of Table Y is depicted by a number designating the nucleus from Tables 1.3 to 1.6, followed by a number designating each substituent group K1, followed by the designation of substituent K2, followed by the designation of substituent K3, as incorporated from Table 1.7. In graphical tabular form, each embodiment of Table Y appears as a name having the syntax:

Each Sc group is shown having various substituents K1, K2, and K3. Each group K1, K2, and K3 as listed in Table Y, is a substituent, as listed, of the Sc nucleus listed in Table Y. K1, K2, and K3, it should be understood, do not represent groups or atoms but are simply connectivity designations. The site of the covalent bond to the nucleus (Sc) is designated as K1, K2, and K3 of formula MBF3. Embodiments of K1, K2, and K3 in Tables 1.7 are designated as numbers 1 to 4. For example there are 32 Table 1.3 to 1.6 entries for Sc are numbered 9 to 40. Each is designated as the Sc identifier (ie. 9-40). In any event, entries of Table 1.7 always begin with a number. Selection of the point of attachment is described herein. By way of example and not limitation, the point of attachment is selected from those depicted in the schemes and examples.

TABLE 1.3

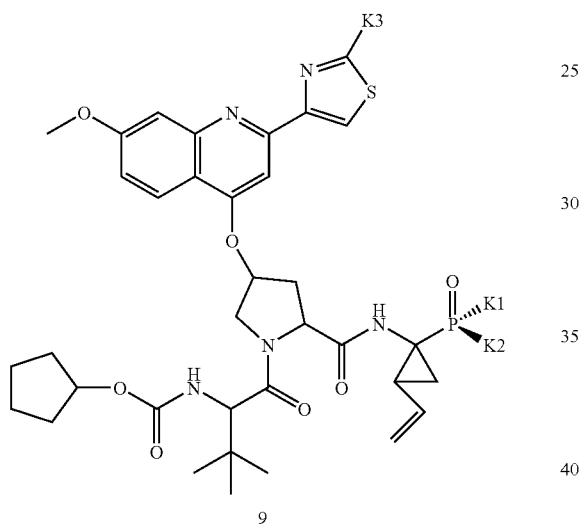

9

TABLE 1.3-continued

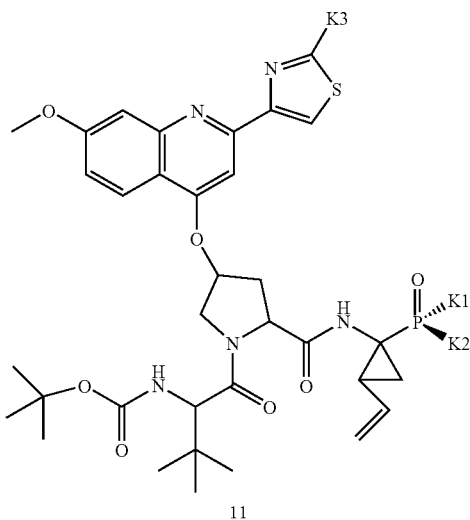

11

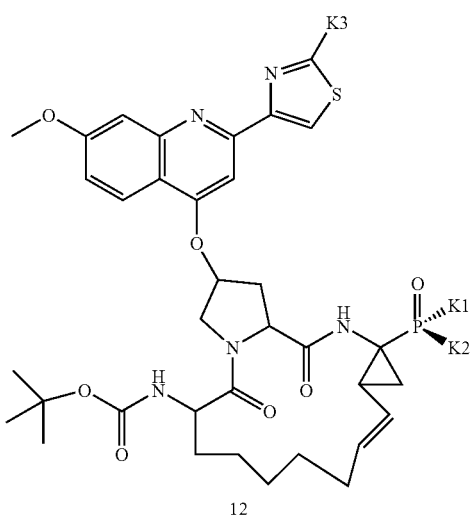

12

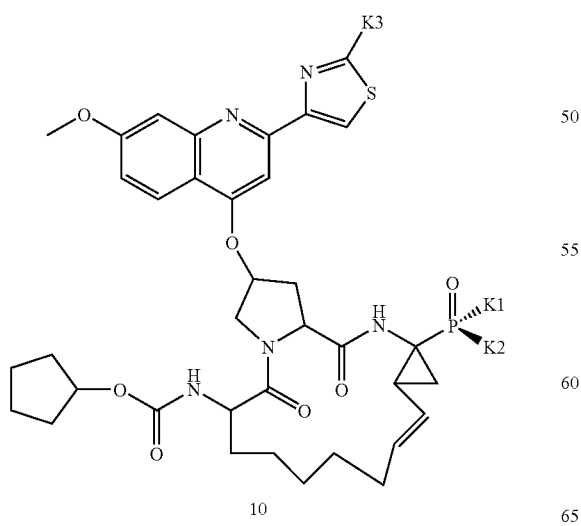

10

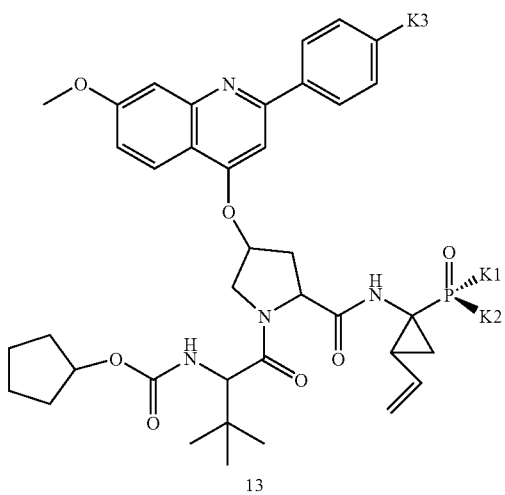

13

TABLE 1.3-continued
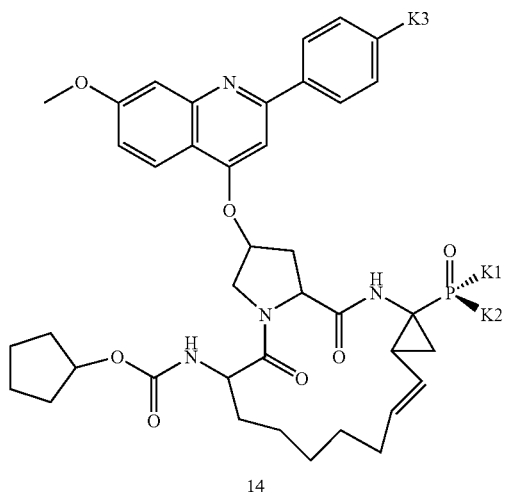
14
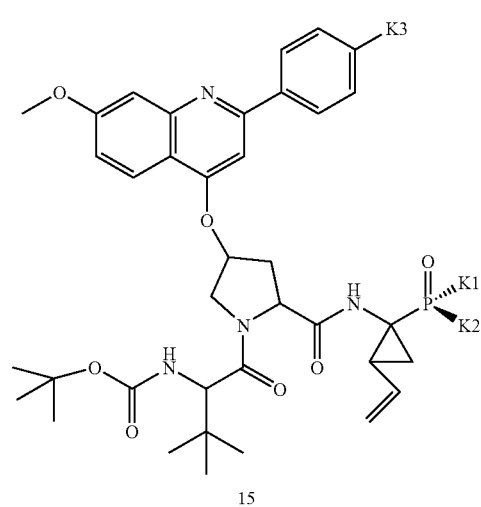
15
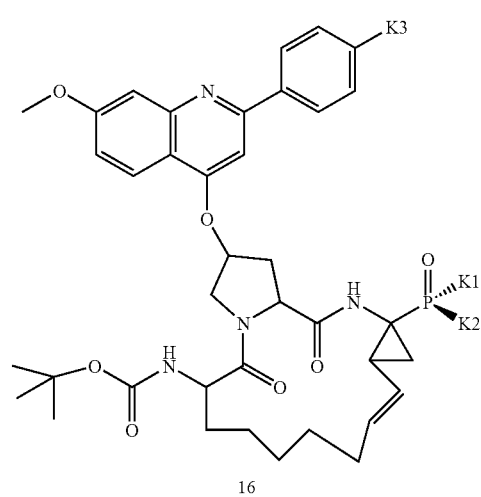
16
TABLE 1.4
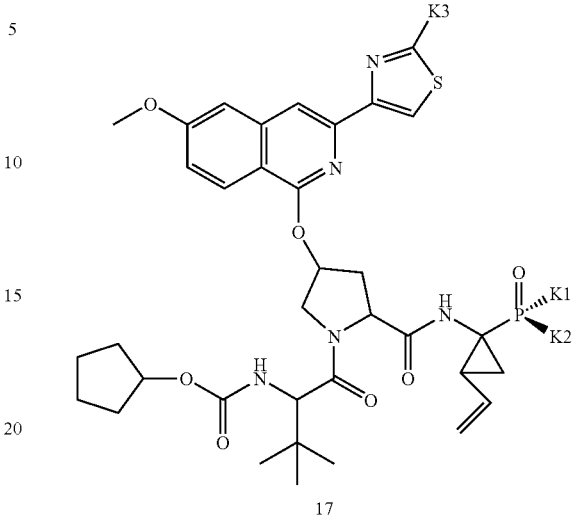
17
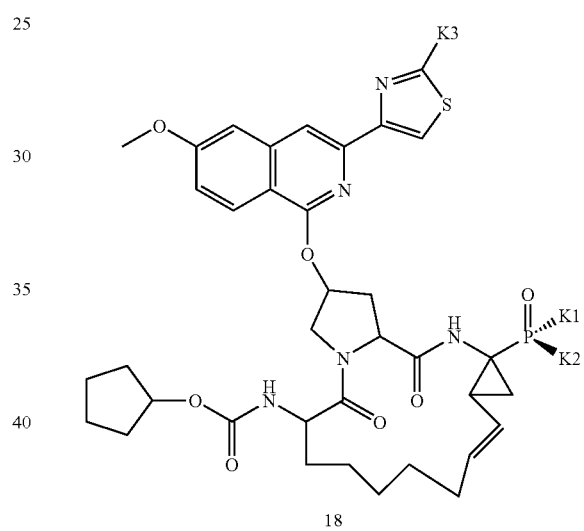
18
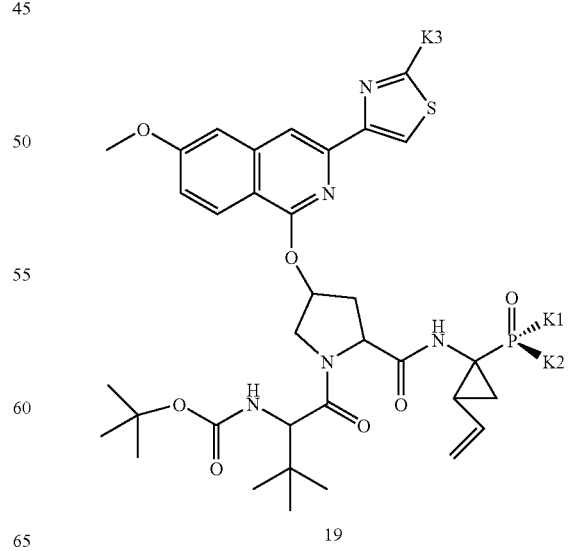
19

TABLE 1.4-continued
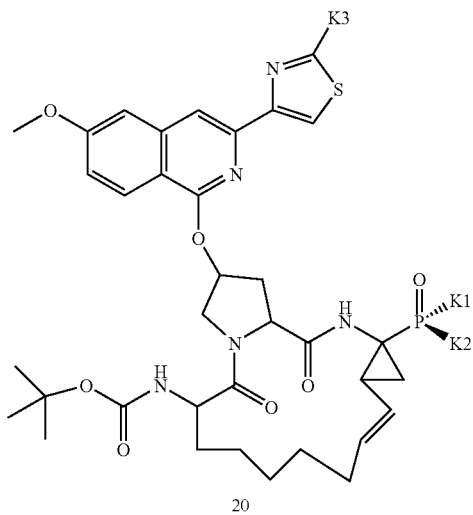
20
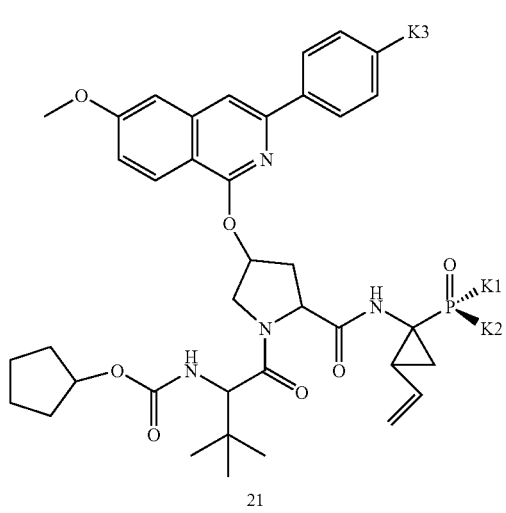
21
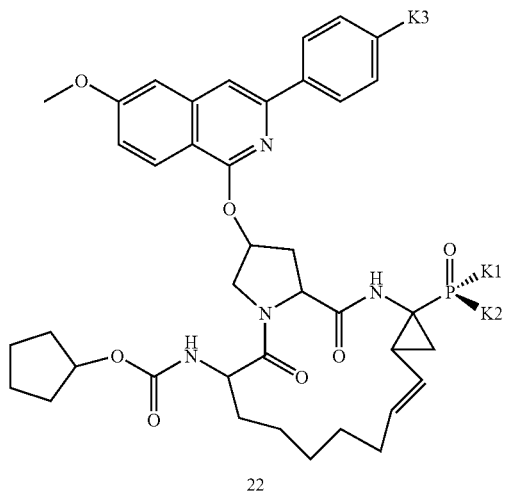
22
TABLE 1.4-continued
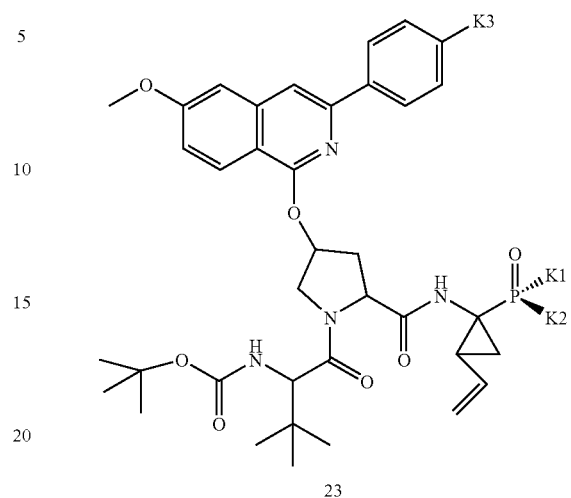
23
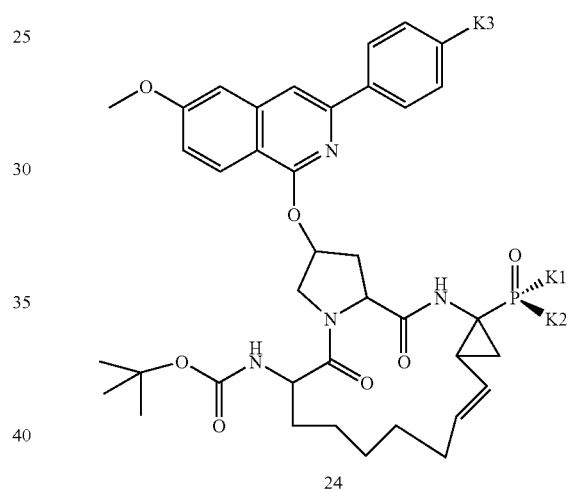
24
TABLE 1.5
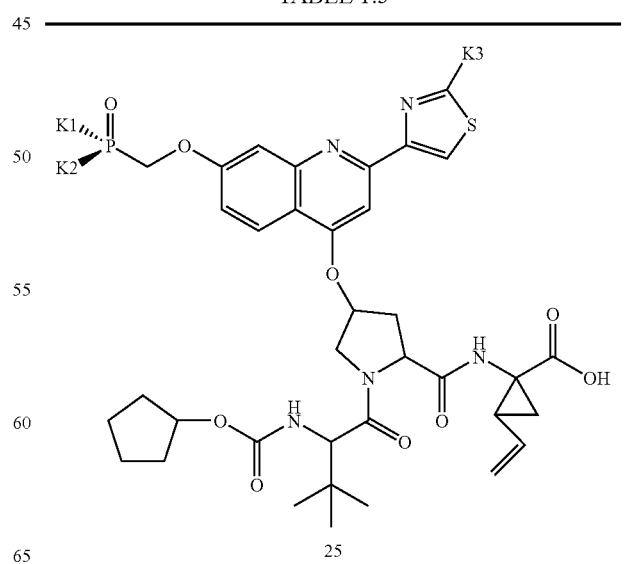
25

TABLE 1.5-continued
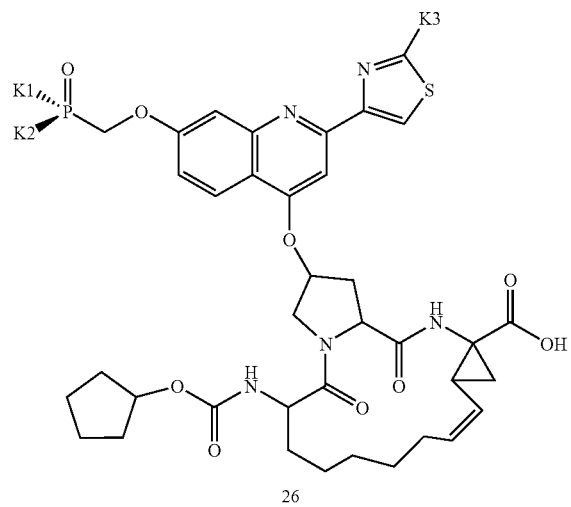
26
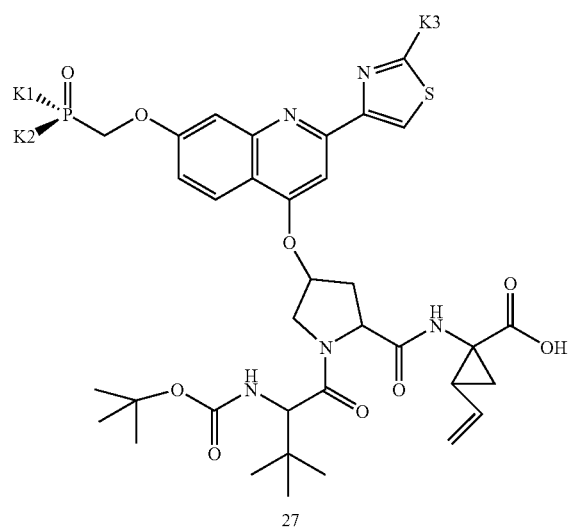
27
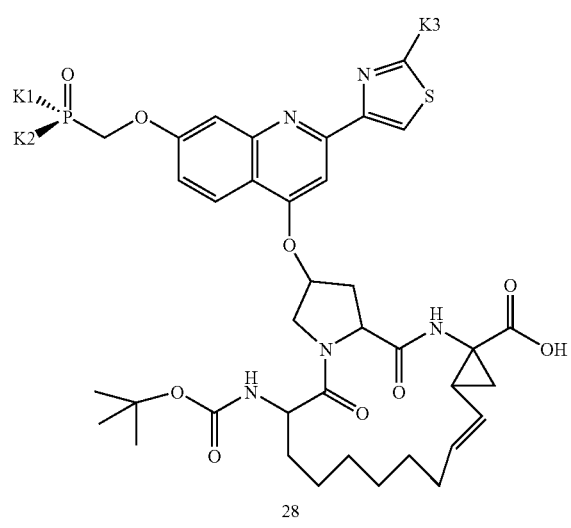
28
TABLE 1.5-continued
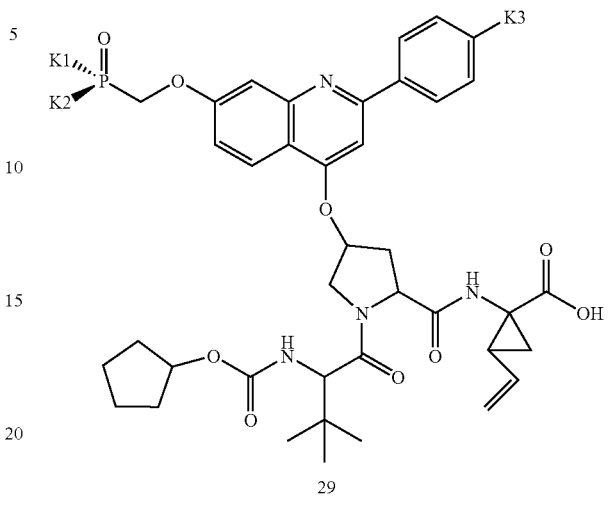
29
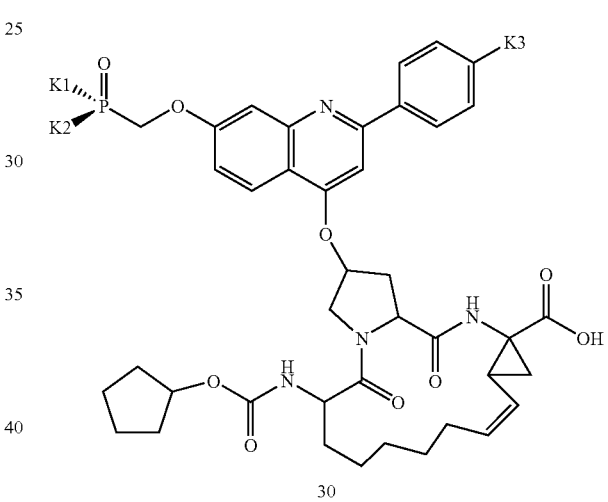
30
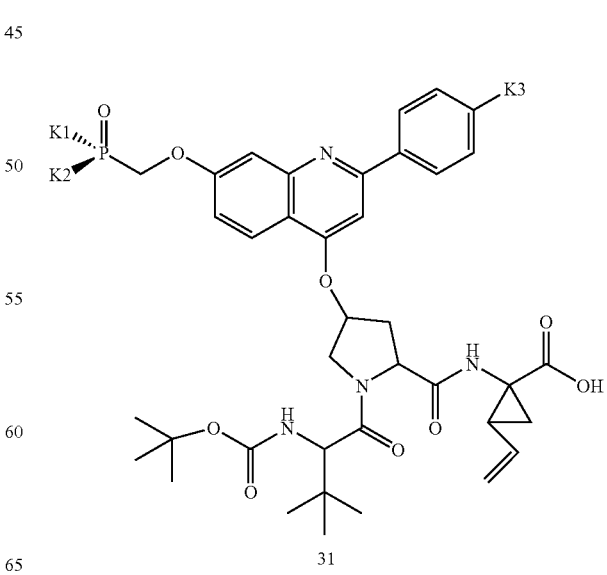
31

TABLE 1.5-continued
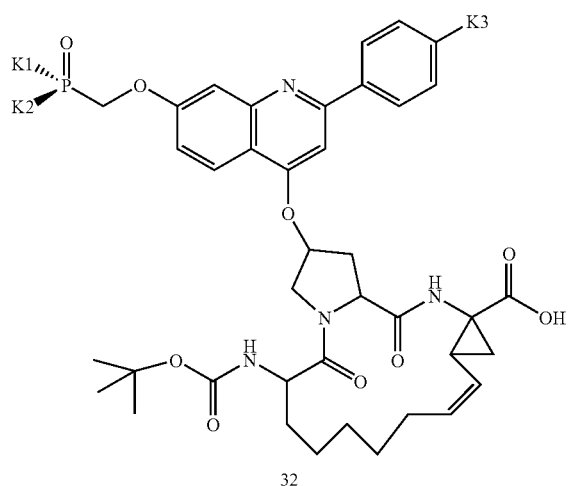
32
TABLE 1.6
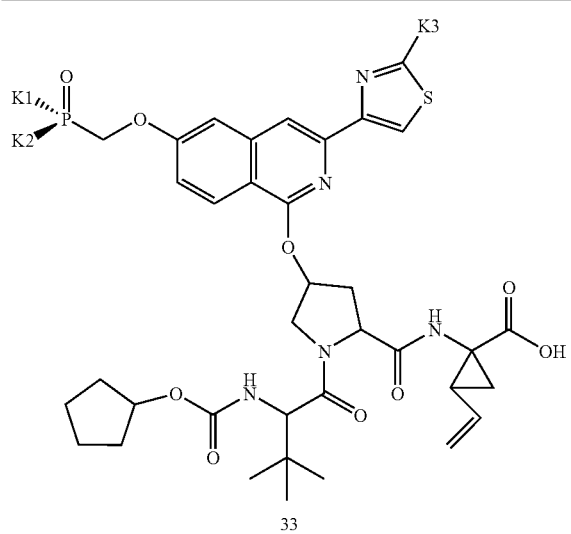
33
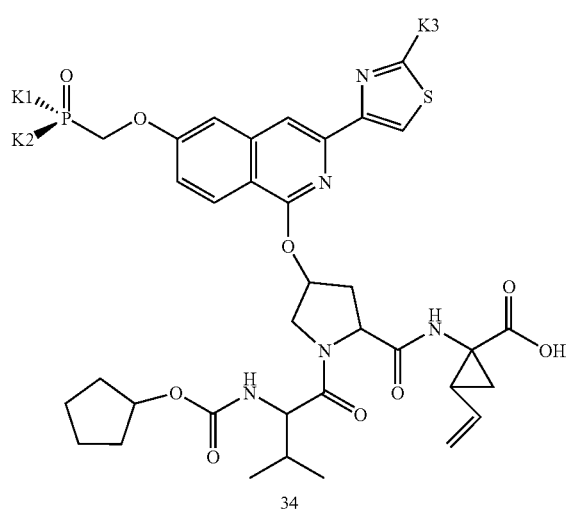
34
TABLE 1.6-continued
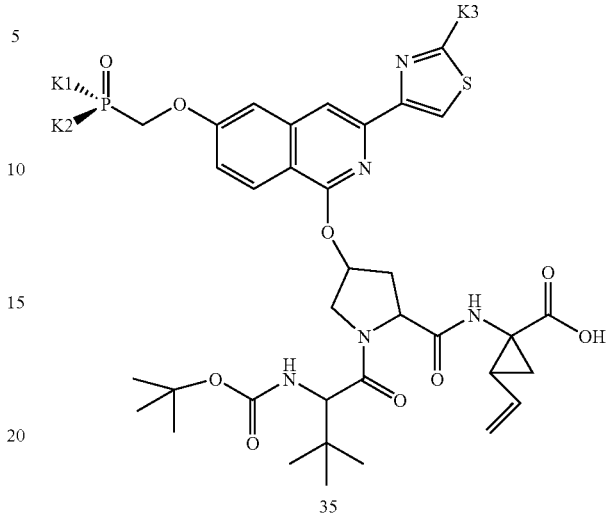
35
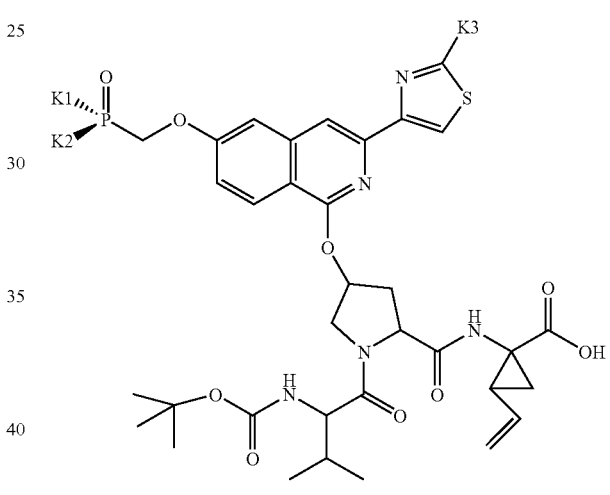
36
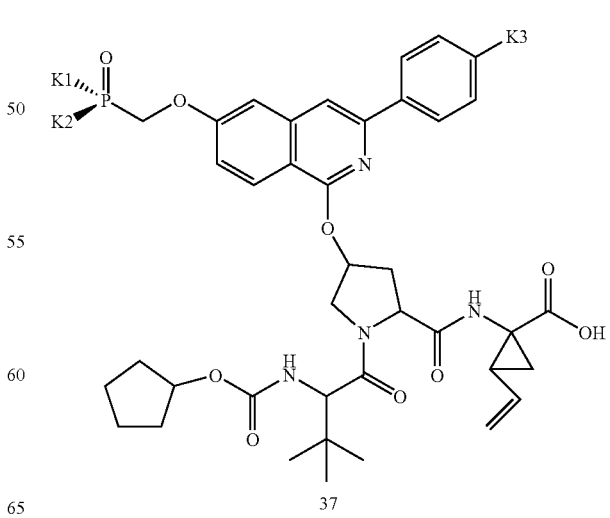
37

TABLE 1.6-continued

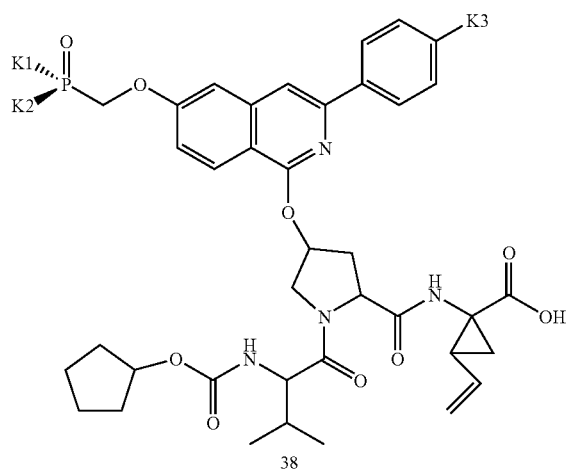

38

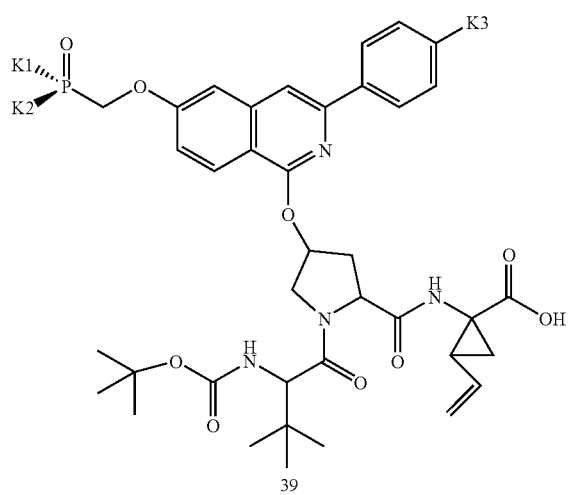

39

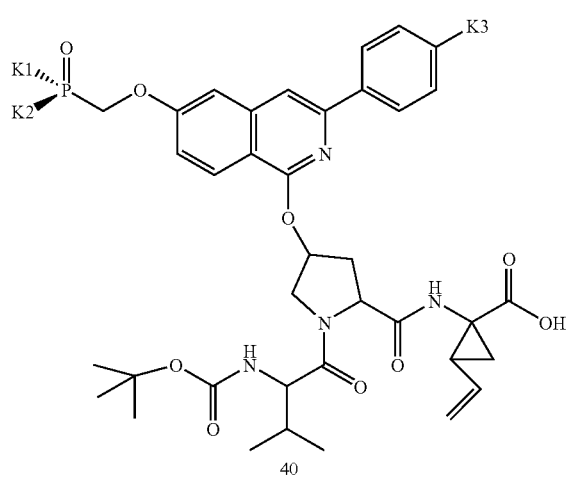

40

TABLE 1.7

| | K1 | |
|---|---|---|
| 1 | | —OH |
| 2 | | —PRT |
| 3 | | —$R^x$ |
| 4 | | —H |

TABLE 1.7-continued

| | K2 | |
|---|---|---|
| 1 | | —OH |
| 2 | | —PRT |
| 3 | | —$R^x$ |
| 4 | | —H |
| | K3 | |
| 1 | | —H |
| 2 | | —R3 |
| 3 | | —Rx |
| 4 | | —$Y^1R^2$ |

$R^x$ is independently H, $R^1$, $R^2$, $W^3$, a protecting group, or the formula:

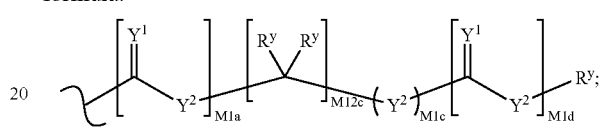

wherein:
$A^3$ is:

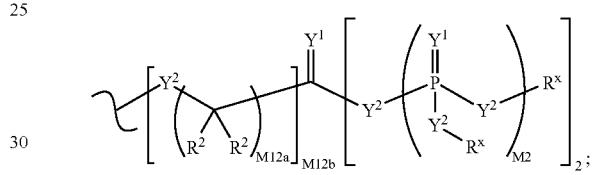

$Y^1$ is independently O, S, N($R^x$), N(O)($R^x$), N(O$R^x$), N(O)(O$R^x$), or N(N($R^x$)($R^x$));

$Y^2$ is independently a bond, O, N($R^x$), N(O)($R^x$), N(O$R^x$), N(O)(O$R^x$), N(N($R^x$)($R^x$)), —S(O)$_{M2}$—, or —S(O)$_{M2}$—S(O)$_{M2}$—; and when $Y^2$ joins two phosphorous atoms $Y^2$ can also be C($R^2$)($R^2$);

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, $N_3$ or —$NO_2$;

$R^{3b}$ is $Y^1$;

$R^{3c}$ is $R^x$, —N($R^x$)($R^x$), —S$R^x$, —S(O)$R^x$, —S(O)$_2R^x$, —S(O)(O$R^x$), —S(O)$_2$(O$R^x$), —OC($Y^1$)$R^x$, —OC($Y^1$)O$R^x$, —OC($Y^1$)(N($R^x$)($R^x$)), —SC($Y^1$)$R^x$, —SC($Y^1$)O$R^x$, —SC($Y^1$)(N($R^x$)($R^x$)), —N($R^x$)C($Y^1$)$R^x$, —N($R^x$)C($Y^1$)O$R^x$, or —N($R^x$)C($Y^1$)N($R^x$)($R^x$));

$R^{3d}$ is —C($Y^1$)$R^x$, —C($Y^1$)O$R^x$ or —C($Y^1$)(N($R^x$)($R^x$));

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$W^3$ is $W^4$ or $W^5$;

$W^4$ is $R^5$, —C($Y^1$)$R^5$, —C($Y^1$)$W^5$, —SO$_{M2}R^5$, or —SO$_{M2}W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;
M12b is 0, 1, 2, 3, 4, 5, 6, 7, 8, 9, 10, 11 or 12;
M1a, M1c, and M1d are independently 0 or 1; and
M12c is 0, 1, 2, 3, 4, 5, 6, 7, 8, 9, 10, 11 or 12.

TABLE Y 9.1.1.1
9.1.1.2
9.1.1.3
9.1.1.4
9.2.1.1
9.2.1.2
9.2.1.3
9.2.1.4
9.3.1.1
9.3.1.2
9.3.1.3
9.3.1.4
9.4.1.1
9.4.1.2
9.4.1.3
9.4.1.4
9.1.2.1
9.1.2.2
9.1.2.3
9.1.2.4
9.2.2.1
9.2.2.2
9.2.2.3
9.2.2.4
9.3.2.1
9.3.2.2
9.3.2.3
9.3.2.4
9.4.2.1
9.4.2.2
9.4.2.3
9.4.2.4
9.1.3.1
9.1.3.2
9.1.3.3
9.1.3.4
9.2.3.1
9.2.3.2
9.2.3.3
9.2.3.4
9.3.3.1
9.3.3.2
9.3.3.3
9.3.3.4
9.4.3.1
9.4.3.2
9.4.3.3
9.4.3.4
9.1.4.1
9.1.4.2
9.1.4.3
9.1.4.4
9.2.4.1
9.2.4.2
9.2.4.3
9.2.4.4
9.3.4.1
9.3.4.2
9.3.4.3
9.3.4.4
9.4.4.1
9.4.4.2
9.4.4.3
9.4.4.4
10.1.1.1
10.1.1.2
10.1.1.3
10.1.1.4
10.2.1.1
10.2.1.2
10.2.1.3
10.2.1.4
10.3.1.1
10.3.1.2

TABLE Y-continued 10.3.1.3
10.3.1.4
10.4.1.1
10.4.1.2
10.4.1.3
10.4.1.4
10.1.2.1
10.1.2.2
10.1.2.3
10.1.2.4
10.2.2.1
10.2.2.2
10.2.2.3
10.2.2.4
10.3.2.1
10.3.2.2
10.3.2.3
10.3.2.4
10.4.2.1
10.4.2.2
10.4.2.3
10.4.2.4
10.1.3.1
10.1.3.2
10.1.3.3
10.1.3.4
10.2.3.1
10.2.3.2
10.2.3.3
10.2.3.4
10.3.3.1
10.3.3.2
10.3.3.3
10.3.3.4
10.4.3.1
10.4.3.2
10.4.3.3
10.4.3.4
10.1.4.1
10.1.4.2
10.1.4.3
10.1.4.4
10.2.4.1
10.2.4.2
10.2.4.3
10.2.4.4
10.3.4.1
10.3.4.2
10.3.4.3
10.3.4.4
10.4.4.1
10.4.4.2
10.4.4.3
10.4.4.4
11.1.1.1
11.1.1.2
11.1.1.3
11.1.1.4
11.2.1.1
11.2.1.2
11.2.1.3
11.2.1.4
11.3.1.1
11.3.1.2
11.3.1.3
11.3.1.4
11.4.1.1
11.4.1.2
11.4.1.3
11.4.1.4
11.1.2.1
11.1.2.2
11.1.2.3
11.1.2.4
11.2.2.1
11.2.2.2
11.2.2.3
11.2.2.4
11.3.2.1

TABLE Y-continued

| |
|---|
| 11.3.2.2 |
| 11.3.2.3 |
| 11.3.2.4 |
| 11.4.2.1 |
| 11.4.2.2 |
| 11.4.2.3 |
| 11.4.2.4 |
| 11.1.3.1 |
| 11.1.3.2 |
| 11.1.3.3 |
| 11.1.3.4 |
| 11.2.3.1 |
| 11.2.3.2 |
| 11.2.3.3 |
| 11.2.3.4 |
| 11.3.3.1 |
| 11.3.3.2 |
| 11.3.3.3 |
| 11.3.3.4 |
| 11.4.3.1 |
| 11.4.3.2 |
| 11.4.3.3 |
| 11.4.3.4 |
| 11.1.4.1 |
| 11.1.4.2 |
| 11.1.4.3 |
| 11.1.4.4 |
| 11.2.4.1 |
| 11.2.4.2 |
| 11.2.4.3 |
| 11.2.4.4 |
| 11.3.4.1 |
| 11.3.4.2 |
| 11.3.4.3 |
| 11.3.4.4 |
| 11.4.4.1 |
| 11.4.4.2 |
| 11.4.4.3 |
| 11.4.4.4 |
| 12.1.1.1 |
| 12.1.1.2 |
| 12.1.1.3 |
| 12.1.1.4 |
| 12.2.1.1 |
| 12.2.1.2 |
| 12.2.1.3 |
| 12.2.1.4 |
| 12.3.1.1 |
| 12.3.1.2 |
| 12.3.1.3 |
| 12.3.1.4 |
| 12.4.1.1 |
| 12.4.1.2 |
| 12.4.1.3 |
| 12.4.1.4 |
| 12.1.2.1 |
| 12.1.2.2 |
| 12.1.2.3 |
| 12.1.2.4 |
| 12.2.2.1 |
| 12.2.2.2 |
| 12.2.2.3 |
| 12.2.2.4 |
| 12.3.2.1 |
| 12.3.2.2 |
| 12.3.2.3 |
| 12.3.2.4 |
| 12.4.2.1 |
| 12.4.2.2 |
| 12.4.2.3 |
| 12.4.2.4 |
| 12.1.3.1 |
| 12.1.3.2 |
| 12.1.3.3 |
| 12.1.3.4 |
| 12.2.3.1 |
| 12.2.3.2 |
| 12.2.3.3 |
| 12.2.3.4 |
| 12.3.3.1 |
| 12.3.3.2 |
| 12.3.3.3 |
| 12.3.3.4 |
| 12.4.3.1 |
| 12.4.3.2 |
| 12.4.3.3 |
| 12.4.3.4 |
| 12.1.4.1 |
| 12.1.4.2 |
| 12.1.4.3 |
| 12.1.4.4 |
| 12.2.4.1 |
| 12.2.4.2 |
| 12.2.4.3 |
| 12.2.4.4 |
| 12.3.4.1 |
| 12.3.4.2 |
| 12.3.4.3 |
| 12.3.4.4 |
| 12.4.4.1 |
| 12.4.4.2 |
| 12.4.4.3 |
| 12.4.4.4 |
| 13.1.1.1 |
| 13.1.1.2 |
| 13.1.1.3 |
| 13.1.1.4 |
| 13.2.1.1 |
| 13.2.1.2 |
| 13.2.1.3 |
| 13.2.1.4 |
| 13.3.1.1 |
| 13.3.1.2 |
| 13.3.1.3 |
| 13.3.1.4 |
| 13.4.1.1 |
| 13.4.1.2 |
| 13.4.1.3 |
| 13.4.1.4 |
| 13.1.2.1 |
| 13.1.2.2 |
| 13.1.2.3 |
| 13.1.2.4 |
| 13.2.2.1 |
| 13.2.2.2 |
| 13.2.2.3 |
| 13.2.2.4 |
| 13.3.2.1 |
| 13.3.2.2 |
| 13.3.2.3 |
| 13.3.2.4 |
| 13.4.2.1 |
| 13.4.2.2 |
| 13.4.2.3 |
| 13.4.2.4 |
| 13.1.3.1 |
| 13.1.3.2 |
| 13.1.3.3 |
| 13.1.3.4 |
| 13.2.3.1 |
| 13.2.3.2 |
| 13.2.3.3 |
| 13.2.3.4 |
| 13.3.3.1 |
| 13.3.3.2 |
| 13.3.3.3 |
| 13.3.3.4 |
| 13.4.3.1 |
| 13.4.3.2 |
| 13.4.3.3 |
| 13.4.3.4 |
| 13.1.4.1 |
| 13.1.4.2 |
| 13.1.4.3 |
| 13.1.4.4 |
| 13.2.4.1 |
| 13.2.4.2 |
| 13.2.4.3 |

TABLE Y-continued 13.2.4.4
13.3.4.1
13.3.4.2
13.3.4.3
13.3.4.4
13.4.4.1
13.4.4.2
13.4.4.3
13.4.4.4
14.1.1.1
14.1.1.2
14.1.1.3
14.1.1.4
14.2.1.1
14.2.1.2
14.2.1.3
14.2.1.4
14.3.1.1
14.3.1.2
14.3.1.3
14.3.1.4
14.4.1.1
14.4.1.2
14.4.1.3
14.4.1.4
14.1.2.1
14.1.2.2
14.1.2.3
14.1.2.4
14.2.2.1
14.2.2.2
14.2.2.3
14.2.2.4
14.3.2.1
14.3.2.2
14.3.2.3
14.3.2.4
14.4.2.1
14.4.2.2
14.4.2.3
14.4.2.4
14.1.3.1
14.1.3.2
14.1.3.3
14.1.3.4
14.2.3.1
14.2.3.2
14.2.3.3
14.2.3.4
14.3.3.1
14.3.3.2
14.3.3.3
14.3.3.4
14.4.3.1
14.4.3.2
14.4.3.3
14.4.3.4
14.1.4.1
14.1.4.2
14.1.4.3
14.1.4.4
14.2.4.1
14.2.4.2
14.2.4.3
14.2.4.4
14.3.4.1
14.3.4.2
14.3.4.3
14.3.4.4
14.4.4.1
14.4.4.2
14.4.4.3
14.4.4.4
15.1.1.1
15.1.1.2
15.1.1.3
15.1.1.4
15.2.1.1
15.2.1.2

TABLE Y-continued 15.2.1.3
15.2.1.4
15.3.1.1
15.3.1.2
15.3.1.3
15.3.1.4
15.4.1.1
15.4.1.2
15.4.1.3
15.4.1.4
15.1.2.1
15.1.2.2
15.1.2.3
15.1.2.4
15.2.2.1
15.2.2.2
15.2.2.3
15.2.2.4
15.3.2.1
15.3.2.2
15.3.2.3
15.3.2.4
15.4.2.1
15.4.2.2
15.4.2.3
15.4.2.4
15.1.3.1
15.1.3.2
15.1.3.3
15.1.3.4
15.2.3.1
15.2.3.2
15.2.3.3
15.2.3.4
15.3.3.1
15.3.3.2
15.3.3.3
15.3.3.4
15.4.3.1
15.4.3.2
15.4.3.3
15.4.3.4
15.1.4.1
15.1.4.2
15.1.4.3
15.1.4.4
15.2.4.1
15.2.4.2
15.2.4.3
15.2.4.4
15.3.4.1
15.3.4.2
15.3.4.3
15.3.4.4
15.4.4.1
15.4.4.2
15.4.4.3
15.4.4.4
16.1.1.1
16.1.1.2
16.1.1.3
16.1.1.4
16.2.1.1
16.2.1.2
16.2.1.3
16.2.1.4
16.3.1.1
16.3.1.2
16.3.1.3
16.3.1.4
16.4.1.1
16.4.1.2
16.4.1.3
16.4.1.4
16.1.2.1
16.1.2.2
16.1.2.3
16.1.2.4
16.2.2.1

TABLE Y-continued 16.2.2.2
16.2.2.3
16.2.2.4
16.3.2.1
16.3.2.2
16.3.2.3
16.3.2.4
16.4.2.1
16.4.2.2
16.4.2.3
16.4.2.4
16.1.3.1
16.1.3.2
16.1.3.3
16.1.3.4
16.2.3.1
16.2.3.2
16.2.3.3
16.2.3.4
16.3.3.1
16.3.3.2
16.3.3.3
16.3.3.4
16.4.3.1
16.4.3.2
16.4.3.3
16.4.3.4
16.1.4.1
16.1.4.2
16.1.4.3
16.1.4.4
16.2.4.1
16.2.4.2
16.2.4.3
16.2.4.4
16.3.4.1
16.3.4.2
16.3.4.3
16.3.4.4
16.4.4.1
16.4.4.2
16.4.4.3
16.4.4.4
17.1.1.1
17.1.1.2
17.1.1.3
17.1.1.4
17.2.1.1
17.2.1.2
17.2.1.3
17.2.1.4
17.3.1.1
17.3.1.2
17.3.1.3
17.3.1.4
17.4.1.1
17.4.1.2
17.4.1.3
17.4.1.4
17.1.2.1
17.1.2.2
17.1.2.3
17.1.2.4
17.2.2.1
17.2.2.2
17.2.2.3
17.2.2.4
17.3.2.1
17.3.2.2
17.3.2.3
17.3.2.4
17.4.2.1
17.4.2.2
17.4.2.3
17.4.2.4
17.1.3.1
17.1.3.2
17.1.3.3
17.1.3.4

TABLE Y-continued 17.2.3.1
17.2.3.2
17.2.3.3
17.2.3.4
17.3.3.1
17.3.3.2
17.3.3.3
17.3.3.4
17.4.3.1
17.4.3.2
17.4.3.3
17.4.3.4
17.1.4.1
17.1.4.2
17.1.4.3
17.1.4.4
17.2.4.1
17.2.4.2
17.2.4.3
17.2.4.4
17.3.4.1
17.3.4.2
17.3.4.3
17.3.4.4
17.4.4.1
17.4.4.2
17.4.4.3
17.4.4.4
18.1.1.1
18.1.1.2
18.1.1.3
18.1.1.4
18.2.1.1
18.2.1.2
18.2.1.3
18.2.1.4
18.3.1.1
18.3.1.2
18.3.1.3
18.3.1.4
18.4.1.1
18.4.1.2
18.4.1.3
18.4.1.4
18.1.2.1
18.1.2.2
18.1.2.3
18.1.2.4
18.2.2.1
18.2.2.2
18.2.2.3
18.2.2.4
18.3.2.1
18.3.2.2
18.3.2.3
18.3.2.4
18.4.2.1
18.4.2.2
18.4.2.3
18.4.2.4
18.1.3.1
18.1.3.2
18.1.3.3
18.1.3.4
18.2.3.1
18.2.3.2
18.2.3.3
18.2.3.4
18.3.3.1
18.3.3.2
18.3.3.3
18.3.3.4
18.4.3.1
18.4.3.2
18.4.3.3
18.4.3.4
18.1.4.1
18.1.4.2
18.1.4.3

TABLE Y-continued 18.1.4.4
18.2.4.1
18.2.4.2
18.2.4.3
18.2.4.4
18.3.4.1
18.3.4.2
18.3.4.3
18.3.4.4
18.4.4.1
18.4.4.2
18.4.4.3
18.4.4.4
19.1.1.1
19.1.1.2
19.1.1.3
19.1.1.4
19.2.1.1
19.2.1.2
19.2.1.3
19.2.1.4
19.3.1.1
19.3.1.2
19.3.1.3
19.3.1.4
19.4.1.1
19.4.1.2
19.4.1.3
19.4.1.4
19.1.2.1
19.1.2.2
19.1.2.3
19.1.2.4
19.2.2.1
19.2.2.2
19.2.2.3
19.2.2.4
19.3.2.1
19.3.2.2
19.3.2.3
19.3.2.4
19.4.2.1
19.4.2.2
19.4.2.3
19.4.2.4
19.1.3.1
19.1.3.2
19.1.3.3
19.1.3.4
19.2.3.1
19.2.3.2
19.2.3.3
19.2.3.4
19.3.3.1
19.3.3.2
19.3.3.3
19.3.3.4
19.4.3.1
19.4.3.2
19.4.3.3
19.4.3.4
19.1.4.1
19.1.4.2
19.1.4.3
19.1.4.4
19.2.4.1
19.2.4.2
19.2.4.3
19.2.4.4
19.3.4.1
19.3.4.2
19.3.4.3
19.3.4.4
19.4.4.1
19.4.4.2
19.4.4.3
19.4.4.4
20.1.1.1
20.1.1.2

TABLE Y-continued 20.1.1.3
20.1.1.4
20.2.1.1
20.2.1.2
20.2.1.3
20.2.1.4
20.3.1.1
20.3.1.2
20.3.1.3
20.3.1.4
20.4.1.1
20.4.1.2
20.4.1.3
20.4.1.4
20.1.2.1
20.1.2.2
20.1.2.3
20.1.2.4
20.2.2.1
20.2.2.2
20.2.2.3
20.2.2.4
20.3.2.1
20.3.2.2
20.3.2.3
20.3.2.4
20.4.2.1
20.4.2.2
20.4.2.3
20.4.2.4
20.1.3.1
20.1.3.2
20.1.3.3
20.1.3.4
20.2.3.1
20.2.3.2
20.2.3.3
20.2.3.4
20.3.3.1
20.3.3.2
20.3.3.3
20.3.3.4
20.4.3.1
20.4.3.2
20.4.3.3
20.4.3.4
20.1.4.1
20.1.4.2
20.1.4.3
20.1.4.4
20.2.4.1
20.2.4.2
20.2.4.3
20.2.4.4
20.3.4.1
20.3.4.2
20.3.4.3
20.3.4.4
20.4.4.1
20.4.4.2
20.4.4.3
20.4.4.4
21.1.1.1
21.1.1.2
21.1.1.3
21.1.1.4
21.2.1.1
21.2.1.2
21.2.1.3
21.2.1.4
21.3.1.1
21.3.1.2
21.3.1.3
21.3.1.4
21.4.1.1
21.4.1.2
21.4.1.3
21.4.1.4
21.1.2.1

TABLE Y-continued

| |
|---|
| 21.1.2.2 |
| 21.1.2.3 |
| 21.1.2.4 |
| 21.2.2.1 |
| 21.2.2.2 |
| 21.2.2.3 |
| 21.2.2.4 |
| 21.3.2.1 |
| 21.3.2.2 |
| 21.3.2.3 |
| 21.3.2.4 |
| 21.4.2.1 |
| 21.4.2.2 |
| 21.4.2.3 |
| 21.4.2.4 |
| 21.1.3.1 |
| 21.1.3.2 |
| 21.1.3.3 |
| 21.1.3.4 |
| 21.2.3.1 |
| 21.2.3.2 |
| 21.2.3.3 |
| 21.2.3.4 |
| 21.3.3.1 |
| 21.3.3.2 |
| 21.3.3.3 |
| 21.3.3.4 |
| 21.4.3.1 |
| 21.4.3.2 |
| 21.4.3.3 |
| 21.4.3.4 |
| 21.1.4.1 |
| 21.1.4.2 |
| 21.1.4.3 |
| 21.1.4.4 |
| 21.2.4.1 |
| 21.2.4.2 |
| 21.2.4.3 |
| 21.2.4.4 |
| 21.3.4.1 |
| 21.3.4.2 |
| 21.3.4.3 |
| 21.3.4.4 |
| 21.4.4.1 |
| 21.4.4.2 |
| 21.4.4.3 |
| 21.4.4.4 |
| 22.1.1.1 |
| 22.1.1.2 |
| 22.1.1.3 |
| 22.1.1.4 |
| 22.2.1.1 |
| 22.2.1.2 |
| 22.2.1.3 |
| 22.2.1.4 |
| 22.3.1.1 |
| 22.3.1.2 |
| 22.3.1.3 |
| 22.3.1.4 |
| 22.4.1.1 |
| 22.4.1.2 |
| 22.4.1.3 |
| 22.4.1.4 |
| 22.1.2.1 |
| 22.1.2.2 |
| 22.1.2.3 |
| 22.1.2.4 |
| 22.2.2.1 |
| 22.2.2.2 |
| 22.2.2.3 |
| 22.2.2.4 |
| 22.3.2.1 |
| 22.3.2.2 |
| 22.3.2.3 |
| 22.3.2.4 |
| 22.4.2.1 |
| 22.4.2.2 |
| 22.4.2.3 |
| 22.4.2.4 |

TABLE Y-continued

| |
|---|
| 22.1.3.1 |
| 22.1.3.2 |
| 22.1.3.3 |
| 22.1.3.4 |
| 22.2.3.1 |
| 22.2.3.2 |
| 22.2.3.3 |
| 22.2.3.4 |
| 22.3.3.1 |
| 22.3.3.2 |
| 22.3.3.3 |
| 22.3.3.4 |
| 22.4.3.1 |
| 22.4.3.2 |
| 22.4.3.3 |
| 22.4.3.4 |
| 22.1.4.1 |
| 22.1.4.2 |
| 22.1.4.3 |
| 22.1.4.4 |
| 22.2.4.1 |
| 22.2.4.2 |
| 22.2.4.3 |
| 22.2.4.4 |
| 22.3.4.1 |
| 22.3.4.2 |
| 22.3.4.3 |
| 22.3.4.4 |
| 22.4.4.1 |
| 22.4.4.2 |
| 22.4.4.3 |
| 22.4.4.4 |
| 23.1.1.1 |
| 23.1.1.2 |
| 23.1.1.3 |
| 23.1.1.4 |
| 23.2.1.1 |
| 23.2.1.2 |
| 23.2.1.3 |
| 23.2.1.4 |
| 23.3.1.1 |
| 23.3.1.2 |
| 23.3.1.3 |
| 23.3.1.4 |
| 23.4.1.1 |
| 23.4.1.2 |
| 23.4.1.3 |
| 23.4.1.4 |
| 23.1.2.1 |
| 23.1.2.2 |
| 23.1.2.3 |
| 23.1.2.4 |
| 23.2.2.1 |
| 23.2.2.2 |
| 23.2.2.3 |
| 23.2.2.4 |
| 23.3.2.1 |
| 23.3.2.2 |
| 23.3.2.3 |
| 23.3.2.4 |
| 23.4.2.1 |
| 23.4.2.2 |
| 23.4.2.3 |
| 23.4.2.4 |
| 23.1.3.1 |
| 23.1.3.2 |
| 23.1.3.3 |
| 23.1.3.4 |
| 23.2.3.1 |
| 23.2.3.2 |
| 23.2.3.3 |
| 23.2.3.4 |
| 23.3.3.1 |
| 23.3.3.2 |
| 23.3.3.3 |
| 23.3.3.4 |
| 23.4.3.1 |
| 23.4.3.2 |
| 23.4.3.3 |

TABLE Y-continued 23.4.3.4
23.1.4.1
23.1.4.2
23.1.4.3
23.1.4.4
23.2.4.1
23.2.4.2
23.2.4.3
23.2.4.4
23.3.4.1
23.3.4.2
23.3.4.3
23.3.4.4
23.4.4.1
23.4.4.2
23.4.4.3
23.4.4.4
24.1.1.1
24.1.1.2
24.1.1.3
24.1.1.4
24.2.1.1
24.2.1.2
24.2.1.3
24.2.1.4
24.3.1.1
24.3.1.2
24.3.1.3
24.3.1.4
24.4.1.1
24.4.1.2
24.4.1.3
24.4.1.4
24.1.2.1
24.1.2.2
24.1.2.3
24.1.2.4
24.2.2.1
24.2.2.2
24.2.2.3
24.2.2.4
24.3.2.1
24.3.2.2
24.3.2.3
24.3.2.4
24.4.2.1
24.4.2.2
24.4.2.3
24.4.2.4
24.1.3.1
24.1.3.2
24.1.3.3
24.1.3.4
24.2.3.1
24.2.3.2
24.2.3.3
24.2.3.4
24.3.3.1
24.3.3.2
24.3.3.3
24.3.3.4
24.4.3.1
24.4.3.2
24.4.3.3
24.4.3.4
24.1.4.1
24.1.4.2
24.1.4.3
24.1.4.4
24.2.4.1
24.2.4.2
24.2.4.3
24.2.4.4
24.3.4.1
24.3.4.2
24.3.4.3
24.3.4.4
24.4.4.1
24.4.4.2

TABLE Y-continued 24.4.4.3
24.4.4.4
25.1.1.1
25.1.1.2
25.1.1.3
25.1.1.4
25.2.1.1
25.2.1.2
25.2.1.3
25.2.1.4
25.3.1.1
25.3.1.2
25.3.1.3
25.3.1.4
25.4.1.1
25.4.1.2
25.4.1.3
25.4.1.4
25.1.2.1
25.1.2.2
25.1.2.3
25.1.2.4
25.2.2.1
25.2.2.2
25.2.2.3
25.2.2.4
25.3.2.1
25.3.2.2
25.3.2.3
25.3.2.4
25.4.2.1
25.4.2.2
25.4.2.3
25.4.2.4
25.1.3.1
25.1.3.2
25.1.3.3
25.1.3.4
25.2.3.1
25.2.3.2
25.2.3.3
25.2.3.4
25.3.3.1
25.3.3.2
25.3.3.3
25.3.3.4
25.4.3.1
25.4.3.2
25.4.3.3
25.4.3.4
25.1.4.1
25.1.4.2
25.1.4.3
25.1.4.4
25.2.4.1
25.2.4.2
25.2.4.3
25.2.4.4
25.3.4.1
25.3.4.2
25.3.4.3
25.3.4.4
25.4.4.1
25.4.4.2
25.4.4.3
25.4.4.4
26.1.1.1
26.1.1.2
26.1.1.3
26.1.1.4
26.2.1.1
26.2.1.2
26.2.1.3
26.2.1.4
26.3.1.1
26.3.1.2
26.3.1.3
26.3.1.4
26.4.1.1

TABLE Y-continued 26.4.1.2
26.4.1.3
26.4.1.4
26.1.2.1
26.1.2.2
26.1.2.3
26.1.2.4
26.2.2.1
26.2.2.2
26.2.2.3
26.2.2.4
26.3.2.1
26.3.2.2
26.3.2.3
26.3.2.4
26.4.2.1
26.4.2.2
26.4.2.3
26.4.2.4
26.1.3.1
26.1.3.2
26.1.3.3
26.1.3.4
26.2.3.1
26.2.3.2
26.2.3.3
26.2.3.4
26.3.3.1
26.3.3.2
26.3.3.3
26.3.3.4
26.4.3.1
26.4.3.2
26.4.3.3
26.4.3.4
26.1.4.1
26.1.4.2
26.1.4.3
26.1.4.4
26.2.4.1
26.2.4.2
26.2.4.3
26.2.4.4
26.3.4.1
26.3.4.2
26.3.4.3
26.3.4.4
26.4.4.1
26.4.4.2
26.4.4.3
26.4.4.4
27.1.1.1
27.1.1.2
27.1.1.3
27.1.1.4
27.2.1.1
27.2.1.2
27.2.1.3
27.2.1.4
27.3.1.1
27.3.1.2
27.3.1.3
27.3.1.4
27.4.1.1
27.4.1.2
27.4.1.3
27.4.1.4
27.1.2.1
27.1.2.2
27.1.2.3
27.1.2.4
27.2.2.1
27.2.2.2
27.2.2.3
27.2.2.4
27.3.2.1
27.3.2.2
27.3.2.3
27.3.2.4

TABLE Y-continued 27.4.2.1
27.4.2.2
27.4.2.3
27.4.2.4
27.1.3.1
27.1.3.2
27.1.3.3
27.1.3.4
27.2.3.1
27.2.3.2
27.2.3.3
27.2.3.4
27.3.3.1
27.3.3.2
27.3.3.3
27.3.3.4
27.4.3.1
27.4.3.2
27.4.3.3
27.4.3.4
27.1.4.1
27.1.4.2
27.1.4.3
27.1.4.4
27.2.4.1
27.2.4.2
27.2.4.3
27.2.4.4
27.3.4.1
27.3.4.2
27.3.4.3
27.3.4.4
27.4.4.1
27.4.4.2
27.4.4.3
27.4.4.4
28.1.1.1
28.1.1.2
28.1.1.3
28.1.1.4
28.2.1.1
28.2.1.2
28.2.1.3
28.2.1.4
28.3.1.1
28.3.1.2
28.3.1.3
28.3.1.4
28.4.1.1
28.4.1.2
28.4.1.3
28.4.1.4
28.1.2.1
28.1.2.2
28.1.2.3
28.1.2.4
28.2.2.1
28.2.2.2
28.2.2.3
28.2.2.4
28.3.2.1
28.3.2.2
28.3.2.3
28.3.2.4
28.4.2.1
28.4.2.2
28.4.2.3
28.4.2.4
28.1.3.1
28.1.3.2
28.1.3.3
28.1.3.4
28.2.3.1
28.2.3.2
28.2.3.3
28.2.3.4
28.3.3.1
28.3.3.2
28.3.3.3

TABLE Y-continued 28.3.3.4
28.4.3.1
28.4.3.2
28.4.3.3
28.4.3.4
28.1.4.1
28.1.4.2
28.1.4.3
28.1.4.4
28.2.4.1
28.2.4.2
28.2.4.3
28.2.4.4
28.3.4.1
28.3.4.2
28.3.4.3
28.3.4.4
28.4.4.1
28.4.4.2
28.4.4.3
28.4.4.4
29.1.1.1
29.1.1.2
29.1.1.3
29.1.1.4
29.2.1.1
29.2.1.2
29.2.1.3
29.2.1.4
29.3.1.1
29.3.1.2
29.3.1.3
29.3.1.4
29.4.1.1
29.4.1.2
29.4.1.3
29.4.1.4
29.1.2.1
29.1.2.2
29.1.2.3
29.1.2.4
29.2.2.1
29.2.2.2
29.2.2.3
29.2.2.4
29.3.2.1
29.3.2.2
29.3.2.3
29.3.2.4
29.4.2.1
29.4.2.2
29.4.2.3
29.4.2.4
29.1.3.1
29.1.3.2
29.1.3.3
29.1.3.4
29.2.3.1
29.2.3.2
29.2.3.3
29.2.3.4
29.3.3.1
29.3.3.2
29.3.3.3
29.3.3.4
29.4.3.1
29.4.3.2
29.4.3.3
29.4.3.4
29.1.4.1
29.1.4.2
29.1.4.3
29.1.4.4
29.2.4.1
29.2.4.2
29.2.4.3
29.2.4.4
29.3.4.1
29.3.4.2

TABLE Y-continued 29.3.4.3
29.3.4.4
29.4.4.1
29.4.4.2
29.4.4.3
29.4.4.4
30.1.1.1
30.1.1.2
30.1.1.3
30.1.1.4
30.2.1.1
30.2.1.2
30.2.1.3
30.2.1.4
30.3.1.1
30.3.1.2
30.3.1.3
30.3.1.4
30.4.1.1
30.4.1.2
30.4.1.3
30.4.1.4
30.1.2.1
30.1.2.2
30.1.2.3
30.1.2.4
30.2.2.1
30.2.2.2
30.2.2.3
30.2.2.4
30.3.2.1
30.3.2.2
30.3.2.3
30.3.2.4
30.4.2.1
30.4.2.2
30.4.2.3
30.4.2.4
30.1.3.1
30.1.3.2
30.1.3.3
30.1.3.4
30.2.3.1
30.2.3.2
30.2.3.3
30.2.3.4
30.3.3.1
30.3.3.2
30.3.3.3
30.3.3.4
30.4.3.1
30.4.3.2
30.4.3.3
30.4.3.4
30.1.4.1
30.1.4.2
30.1.4.3
30.1.4.4
30.2.4.1
30.2.4.2
30.2.4.3
30.2.4.4
30.3.4.1
30.3.4.2
30.3.4.3
30.3.4.4
30.4.4.1
30.4.4.2
30.4.4.3
30.4.4.4
31.1.1.1
31.1.1.2
31.1.1.3
31.1.1.4
31.2.1.1
31.2.1.2
31.2.1.3
31.2.1.4
31.3.1.1

TABLE Y-continued

| | |
|---|---|
| 31.3.1.2 | |
| 31.3.1.3 | |
| 31.3.1.4 | |
| 31.4.1.1 | |
| 31.4.1.2 | |
| 31.4.1.3 | |
| 31.4.1.4 | |
| 31.1.2.1 | |
| 31.1.2.2 | |
| 31.1.2.3 | |
| 31.1.2.4 | |
| 31.2.2.1 | |
| 31.2.2.2 | |
| 31.2.2.3 | |
| 31.2.2.4 | |
| 31.3.2.1 | |
| 31.3.2.2 | |
| 31.3.2.3 | |
| 31.3.2.4 | |
| 31.4.2.1 | |
| 31.4.2.2 | |
| 31.4.2.3 | |
| 31.4.2.4 | |
| 31.1.3.1 | |
| 31.1.3.2 | |
| 31.1.3.3 | |
| 31.1.3.4 | |
| 31.2.3.1 | |
| 31.2.3.2 | |
| 31.2.3.3 | |
| 31.2.3.4 | |
| 31.3.3.1 | |
| 31.3.3.2 | |
| 31.3.3.3 | |
| 31.3.3.4 | |
| 31.4.3.1 | |
| 31.4.3.2 | |
| 31.4.3.3 | |
| 31.4.3.4 | |
| 31.1.4.1 | |
| 31.1.4.2 | |
| 31.1.4.3 | |
| 31.1.4.4 | |
| 31.2.4.1 | |
| 31.2.4.2 | |
| 31.2.4.3 | |
| 31.2.4.4 | |
| 31.3.4.1 | |
| 31.3.4.2 | |
| 31.3.4.3 | |
| 31.3.4.4 | |
| 31.4.4.1 | |
| 31.4.4.2 | |
| 31.4.4.3 | |
| 31.4.4.4 | |
| 32.1.1.1 | |
| 32.1.1.2 | |
| 32.1.1.3 | |
| 32.1.1.4 | |
| 32.2.1.1 | |
| 32.2.1.2 | |
| 32.2.1.3 | |
| 32.2.1.4 | |
| 32.3.1.1 | |
| 32.3.1.2 | |
| 32.3.1.3 | |
| 32.3.1.4 | |
| 32.4.1.1 | |
| 32.4.1.2 | |
| 32.4.1.3 | |
| 32.4.1.4 | |
| 32.1.2.1 | |
| 32.1.2.2 | |
| 32.1.2.3 | |
| 32.1.2.4 | |
| 32.2.2.1 | |
| 32.2.2.2 | |
| 32.2.2.3 | |
| 32.2.2.4 | |

TABLE Y-continued

| | |
|---|---|
| 32.3.2.1 | |
| 32.3.2.2 | |
| 32.3.2.3 | |
| 32.3.2.4 | |
| 32.4.2.1 | |
| 32.4.2.2 | |
| 32.4.2.3 | |
| 32.4.2.4 | |
| 32.1.3.1 | |
| 32.1.3.2 | |
| 32.1.3.3 | |
| 32.1.3.4 | |
| 32.2.3.1 | |
| 32.2.3.2 | |
| 32.2.3.3 | |
| 32.2.3.4 | |
| 32.3.3.1 | |
| 32.3.3.2 | |
| 32.3.3.3 | |
| 32.3.3.4 | |
| 32.4.3.1 | |
| 32.4.3.2 | |
| 32.4.3.3 | |
| 32.4.3.4 | |
| 32.1.4.1 | |
| 32.1.4.2 | |
| 32.1.4.3 | |
| 32.1.4.4 | |
| 32.2.4.1 | |
| 32.2.4.2 | |
| 32.2.4.3 | |
| 32.2.4.4 | |
| 32.3.4.1 | |
| 32.3.4.2 | |
| 32.3.4.3 | |
| 32.3.4.4 | |
| 32.4.4.1 | |
| 32.4.4.2 | |
| 32.4.4.3 | |
| 32.4.4.4 | |
| 33.1.1.1 | |
| 33.1.1.2 | |
| 33.1.1.3 | |
| 33.1.1.4 | |
| 33.2.1.1 | |
| 33.2.1.2 | |
| 33.2.1.3 | |
| 33.2.1.4 | |
| 33.3.1.1 | |
| 33.3.1.2 | |
| 33.3.1.3 | |
| 33.3.1.4 | |
| 33.4.1.1 | |
| 33.4.1.2 | |
| 33.4.1.3 | |
| 33.4.1.4 | |
| 33.1.2.1 | |
| 33.1.2.2 | |
| 33.1.2.3 | |
| 33.1.2.4 | |
| 33.2.2.1 | |
| 33.2.2.2 | |
| 33.2.2.3 | |
| 33.2.2.4 | |
| 33.3.2.1 | |
| 33.3.2.2 | |
| 33.3.2.3 | |
| 33.3.2.4 | |
| 33.4.2.1 | |
| 33.4.2.2 | |
| 33.4.2.3 | |
| 33.4.2.4 | |
| 33.1.3.1 | |
| 33.1.3.2 | |
| 33.1.3.3 | |
| 33.1.3.4 | |
| 33.2.3.1 | |
| 33.2.3.2 | |
| 33.2.3.3 | |

TABLE Y-continued 33.2.3.4
33.3.3.1
33.3.3.2
33.3.3.3
33.3.3.4
33.4.3.1
33.4.3.2
33.4.3.3
33.4.3.4
33.1.4.1
33.1.4.2
33.1.4.3
33.1.4.4
33.2.4.1
33.2.4.2
33.2.4.3
33.2.4.4
33.3.4.1
33.3.4.2
33.3.4.3
33.3.4.4
33.4.4.1
33.4.4.2
33.4.4.3
33.4.4.4
34.1.1.1
34.1.1.2
34.1.1.3
34.1.1.4
34.2.1.1
34.2.1.2
34.2.1.3
34.2.1.4
34.3.1.1
34.3.1.2
34.3.1.3
34.3.1.4
34.4.1.1
34.4.1.2
34.4.1.3
34.4.1.4
34.1.2.1
34.1.2.2
34.1.2.3
34.1.2.4
34.2.2.1
34.2.2.2
34.2.2.3
34.2.2.4
34.3.2.1
34.3.2.2
34.3.2.3
34.3.2.4
34.4.2.1
34.4.2.2
34.4.2.3
34.4.2.4
34.1.3.1
34.1.3.2
34.1.3.3
34.1.3.4
34.2.3.1
34.2.3.2
34.2.3.3
34.2.3.4
34.3.3.1
34.3.3.2
34.3.3.3
34.3.3.4
34.4.3.1
34.4.3.2
34.4.3.3
34.4.3.4
34.1.4.1
34.1.4.2
34.1.4.3
34.1.4.4
34.2.4.1
34.2.4.2

TABLE Y-continued 34.2.4.3
34.2.4.4
34.3.4.1
34.3.4.2
34.3.4.3
34.3.4.4
34.4.4.1
34.4.4.2
34.4.4.3
34.4.4.4
35.1.1.1
35.1.1.2
35.1.1.3
35.1.1.4
35.2.1.1
35.2.1.2
35.2.1.3
35.2.1.4
35.3.1.1
35.3.1.2
35.3.1.3
35.3.1.4
35.4.1.1
35.4.1.2
35.4.1.3
35.4.1.4
35.1.2.1
35.1.2.2
35.1.2.3
35.1.2.4
35.2.2.1
35.2.2.2
35.2.2.3
35.2.2.4
35.3.2.1
35.3.2.2
35.3.2.3
35.3.2.4
35.4.2.1
35.4.2.2
35.4.2.3
35.4.2.4
35.1.3.1
35.1.3.2
35.1.3.3
35.1.3.4
35.2.3.1
35.2.3.2
35.2.3.3
35.2.3.4
35.3.3.1
35.3.3.2
35.3.3.3
35.3.3.4
35.4.3.1
35.4.3.2
35.4.3.3
35.4.3.4
35.1.4.1
35.1.4.2
35.1.4.3
35.1.4.4
35.2.4.1
35.2.4.2
35.2.4.3
35.2.4.4
35.3.4.1
35.3.4.2
35.3.4.3
35.3.4.4
35.4.4.1
35.4.4.2
35.4.4.3
35.4.4.4
36.1.1.1
36.1.1.2
36.1.1.3
36.1.1.4
36.2.1.1

TABLE Y-continued

| |
|---|
| 36.2.1.2 |
| 36.2.1.3 |
| 36.2.1.4 |
| 36.3.1.1 |
| 36.3.1.2 |
| 36.3.1.3 |
| 36.3.1.4 |
| 36.4.1.1 |
| 36.4.1.2 |
| 36.4.1.3 |
| 36.4.1.4 |
| 36.1.2.1 |
| 36.1.2.2 |
| 36.1.2.3 |
| 36.1.2.4 |
| 36.2.2.1 |
| 36.2.2.2 |
| 36.2.2.3 |
| 36.2.2.4 |
| 36.3.2.1 |
| 36.3.2.2 |
| 36.3.2.3 |
| 36.3.2.4 |
| 36.4.2.1 |
| 36.4.2.2 |
| 36.4.2.3 |
| 36.4.2.4 |
| 36.1.3.1 |
| 36.1.3.2 |
| 36.1.3.3 |
| 36.1.3.4 |
| 36.2.3.1 |
| 36.2.3.2 |
| 36.2.3.3 |
| 36.2.3.4 |
| 36.3.3.1 |
| 36.3.3.2 |
| 36.3.3.3 |
| 36.3.3.4 |
| 36.4.3.1 |
| 36.4.3.2 |
| 36.4.3.3 |
| 36.4.3.4 |
| 36.1.4.1 |
| 36.1.4.2 |
| 36.1.4.3 |
| 36.1.4.4 |
| 36.2.4.1 |
| 36.2.4.2 |
| 36.2.4.3 |
| 36.2.4.4 |
| 36.3.4.1 |
| 36.3.4.2 |
| 36.3.4.3 |
| 36.3.4.4 |
| 36.4.4.1 |
| 36.4.4.2 |
| 36.4.4.3 |
| 36.4.4.4 |
| 37.1.1.1 |
| 37.1.1.2 |
| 37.1.1.3 |
| 37.1.1.4 |
| 37.2.1.1 |
| 37.2.1.2 |
| 37.2.1.3 |
| 37.2.1.4 |
| 37.3.1.1 |
| 37.3.1.2 |
| 37.3.1.3 |
| 37.3.1.4 |
| 37.4.1.1 |
| 37.4.1.2 |
| 37.4.1.3 |
| 37.4.1.4 |
| 37.1.2.1 |
| 37.1.2.2 |
| 37.1.2.3 |
| 37.1.2.4 |

TABLE Y-continued

| |
|---|
| 37.2.2.1 |
| 37.2.2.2 |
| 37.2.2.3 |
| 37.2.2.4 |
| 37.3.2.1 |
| 37.3.2.2 |
| 37.3.2.3 |
| 37.3.2.4 |
| 37.4.2.1 |
| 37.4.2.2 |
| 37.4.2.3 |
| 37.4.2.4 |
| 37.1.3.1 |
| 37.1.3.2 |
| 37.1.3.3 |
| 37.1.3.4 |
| 37.2.3.1 |
| 37.2.3.2 |
| 37.2.3.3 |
| 37.2.3.4 |
| 37.3.3.1 |
| 37.3.3.2 |
| 37.3.3.3 |
| 37.3.3.4 |
| 37.4.3.1 |
| 37.4.3.2 |
| 37.4.3.3 |
| 37.4.3.4 |
| 37.1.4.1 |
| 37.1.4.2 |
| 37.1.4.3 |
| 37.1.4.4 |
| 37.2.4.1 |
| 37.2.4.2 |
| 37.2.4.3 |
| 37.2.4.4 |
| 37.3.4.1 |
| 37.3.4.2 |
| 37.3.4.3 |
| 37.3.4.4 |
| 37.4.4.1 |
| 37.4.4.2 |
| 37.4.4.3 |
| 37.4.4.4 |
| 38.1.1.1 |
| 38.1.1.2 |
| 38.1.1.3 |
| 38.1.1.4 |
| 38.2.1.1 |
| 38.2.1.2 |
| 38.2.1.3 |
| 38.2.1.4 |
| 38.3.1.1 |
| 38.3.1.2 |
| 38.3.1.3 |
| 38.3.1.4 |
| 38.4.1.1 |
| 38.4.1.2 |
| 38.4.1.3 |
| 38.4.1.4 |
| 38.1.2.1 |
| 38.1.2.2 |
| 38.1.2.3 |
| 38.1.2.4 |
| 38.2.2.1 |
| 38.2.2.2 |
| 38.2.2.3 |
| 38.2.2.4 |
| 38.3.2.1 |
| 38.3.2.2 |
| 38.3.2.3 |
| 38.3.2.4 |
| 38.4.2.1 |
| 38.4.2.2 |
| 38.4.2.3 |
| 38.4.2.4 |
| 38.1.3.1 |
| 38.1.3.2 |
| 38.1.3.3 |

TABLE Y-continued 38.1.3.4
38.2.3.1
38.2.3.2
38.2.3.3
38.2.3.4
38.3.3.1
38.3.3.2
38.3.3.3
38.3.3.4
38.4.3.1
38.4.3.2
38.4.3.3
38.4.3.4
38.1.4.1
38.1.4.2
38.1.4.3
38.1.4.4
38.2.4.1
38.2.4.2
38.2.4.3
38.2.4.4
38.3.4.1
38.3.4.2
38.3.4.3
38.3.4.4
38.4.4.1
38.4.4.2
38.4.4.3
38.4.4.4
39.1.1.1
39.1.1.2
39.1.1.3
39.1.1.4
39.2.1.1
39.2.1.2
39.2.1.3
39.2.1.4
39.3.1.1
39.3.1.2
39.3.1.3
39.3.1.4
39.4.1.1
39.4.1.2
39.4.1.3
39.4.1.4
39.1.2.1
39.1.2.2
39.1.2.3
39.1.2.4
39.2.2.1
39.2.2.2
39.2.2.3
39.2.2.4
39.3.2.1
39.3.2.2
39.3.2.3
39.3.2.4
39.4.2.1
39.4.2.2
39.4.2.3
39.4.2.4
39.1.3.1
39.1.3.2
39.1.3.3
39.1.3.4
39.2.3.1
39.2.3.2
39.2.3.3
39.2.3.4
39.3.3.1
39.3.3.2
39.3.3.3
39.3.3.4
39.4.3.1
39.4.3.2
39.4.3.3
39.4.3.4
39.1.4.1
39.1.4.2

TABLE Y-continued 39.1.4.3
39.1.4.4
39.2.4.1
39.2.4.2
39.2.4.3
39.2.4.4
39.3.4.1
39.3.4.2
39.3.4.3
39.3.4.4
39.4.4.1
39.4.4.2
39.4.4.3
39.4.4.4
40.1.1.1
40.1.1.2
40.1.1.3
40.1.1.4
40.2.1.1
40.2.1.2
40.2.1.3
40.2.1.4
40.3.1.1
40.3.1.2
40.3.1.3
40.3.1.4
40.4.1.1
40.4.1.2
40.4.1.3
40.4.1.4
40.1.2.1
40.1.2.2
40.1.2.3
40.1.2.4
40.2.2.1
40.2.2.2
40.2.2.3
40.2.2.4
40.3.2.1
40.3.2.2
40.3.2.3
40.3.2.4
40.4.2.1
40.4.2.2
40.4.2.3
40.4.2.4
40.1.3.1
40.1.3.2
40.1.3.3
40.1.3.4
40.2.3.1
40.2.3.2
40.2.3.3
40.2.3.4
40.3.3.1
40.3.3.2
40.3.3.3
40.3.3.4
40.4.3.1
40.4.3.2
40.4.3.3
40.4.3.4
40.1.4.1
40.1.4.2
40.1.4.3
40.1.4.4
40.2.4.1
40.2.4.2
40.2.4.3
40.2.4.4
40.3.4.1
40.3.4.2
40.3.4.3
40.3.4.4
40.4.4.1
40.4.4.2
40.4.4.3
40.4.4.4

The section directed to "Exemplary PRT's" is concluded at this point.

Exemplary Embodiments of the Invention

1. Exemplary Embodiments of a Compound of Formula I:

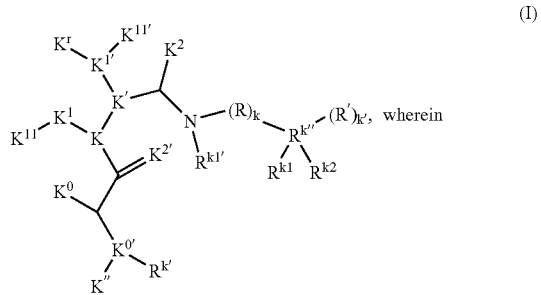

(I)

wherein

K" and $R^{k'}$ are independently absent or selected from a bond, H, —OH, alkyl, aryl, aralkyl, alkenyl, alkynyl, alkoxy, aryloxy, —C(W)$_2$, —C(O)W, —C(O)OW, —O(W), —N(W)$_2$, —S(W), CH$_2$P(O)(OW$_1$)(OW$_2$), —OCH$_2$P(O)(OW$_1$)(OW$_2$), —C(O)OCH$_2$P(O)(OW$_1$)(OW$_2$), CH$_2$P(O)(OW$_1$)(NW$_2$), —OCH$_2$P(O)(OW$_1$)(NW$_2$), —C(O)OCH$_2$P(O)(OW$_1$)(NW$_2$), CH$_2$P(O)(NW$_1$)(NW$_2$), —C(O)OCH$_2$P(O)(NW$_1$)(NW$_2$), and —OCH$_2$P(O)(NW$_1$)(NW$_2$), are optionally substituted with 0-3 W, W$_1$, or W$_2$, optionally form a bond, through themselves or any substituents thereof, to $K^r$, $K^1$, $K^{1'}$, $K^2$, $R^{k1}$, $R^{k1'}$, R, R', $R^{k2}$, or any substituents thereof, with the proviso that when either $R^{k1}$ or $R^{k2}$ are alkyl, alkenyl, or alkynyl, and the other of $R^{k1}$ or $R^{k2}$ is H, and the other of K" or $R^{k'}$ are H or C$_{1-3}$ alkyl, and $K^2$ and $K^{2'}$ are both oxygen, and $K^{0'}$ is N, the other of K" or $R^{k'}$ is alkyl and optionally substituted with 0-3 W, W$_1$, or W$_2$;

$K^{0'}$ is N, —CH, —S(O)$_2$, —C(O)NHS(O)$_2$K$^3$W or —P(O);

$K^0$ is selected from a bond, H, —OH, alkyl, aryl, aralkyl, alkenyl, alkynyl, alkoxy, aryloxy, —C(W)$_2$, —C(O)W, —C(O)OW, —O(W), —N(W)$_2$, —S(W), W, W$_1$, W$_2$, P(O)(OW$_1$)(OW$_2$), —P(O)(OW$_1$)(NW$_2$), —P(O)(NW$_1$)(NW$_2$), —OP(O)(OW$_1$)(OW$_2$), —OP(O)(OW$_1$)(NW$_2$), —OP(O)(NW$_1$)(NW$_2$), —OCH$_2$P(O)(OW$_1$)(OW$_2$), —C(O)OCH$_2$P(O)(OW$_1$)(OW$_2$), CH$_2$P(O)(OW$_1$)(NW$_2$), —OCH$_2$P(O)(OW$_1$)(NW$_2$), —C(O)OCH$_2$P(O)(OW$_1$)(NW$_2$), CH$_2$P(O)(NW$_1$)(NW$_2$), —C(O)OCH$_2$P(O)(NW$_1$)(NW$_2$), and —OCH$_2$P(O)(NW$_1$)(NW$_2$), are optionally substituted with 0-3 W, W$_1$, or W$_2$, optionally forms a bond, through itself or any substituent thereof, to $K^r$, $K^1$, $K^{1'}$, $K^2$, $R^{k1}$, $R^{k1'}$, R, R', $R^{k2}$, or any substituent thereof, with the proviso that if $K^0$ is connected to $R^{k''}$ or substitutents thereof via an optionally substituted alkyl, alkenyl, or alkynyl chain, via substituents thereof or in combination, and $R^{k''}$ is part of a spirocyclic ring system wherein the ring is not substituted with P(O)(OW$_1$)(OW$_2$), —P(O)(OW$_1$)(NW$_2$), or —P(O)(NW$_1$)(NW$_2$), at least one carbon in said chain therein is substituted with P(O)(OW$_1$)(OW$_2$), P(O)(OW$_1$)(NW$_2$), or —P(O)(NW$_1$)(NW$_2$);

$K^{2'}$ is oxygen, sulfur, —NW, —C(W)$_2$;

K is N;

K' is CH;

$K^{11}$ and $K^{11'}$ are independently absent, a bond, H, together form, or are each independently selected from H, alkyl, alkoxy, aryl, aryloxy, halogen, CF$_3$, CH$_2$CF$_3$, $K^{1'}$ is CH, optionally substituted with 0-3 W, W$_1$, —OR$^{k''}$ or W$_2$;

$K^1$ is CH, optionally substituted with 0-3 W, W$_1$, or W$_2$, optionally forms a bond, through itself or any substituent thereof, to K", $K^r$, $K^2$, $R^{k1}$, or $R^{k1'}$, or any substituent thereof;

$R^{k1'}$ is absent or H, alkyl, or aryl optionally substituted with 0-3 W, W$_1$, or W$_2$;

$R^{k''}$ is absent, a bond, H, C, CH, P(O), —C(O)NHS(O)$_2$K$^3$W, or C(O)NHS(O)$_2$K$^3$, wherein K$^3$ is alkyl, aryl, cycloalkyl, heteroaryl, heterocyclic, spirocyclic or heterospirocyclic ring optionally substituted with one or more W, optionally substituted with one or more W optionally substituted, with the proviso that when k is 1 and R is a member of a spirocarbocyclic or spiroheterocyclic ring, $R^{k''}$ is —P(O) and two of $R^{k1}$, $R^{k2}$, and R', are independently —OW$_1$ or —NW$_1$, and the third of $R^{k1}$, $R^{k2'}$; and R' is absent, and also with the proviso that when k is 2 and two consecutive R are C and are substituted such that together they form a ring, then $R^{k''}$ is not H;

k is 0 to 6, with the proviso that k is not 2 if two consecutive groups R are jointly substituted to form a ring;

k' is 0 to 6;

$K^r$ is CH, optionally substituted with 0-3 W, W$_1$, —OK$^{1'''}$ or W$_2$, optionally forms an additional bond, through itself or any substituent thereof, to K", $K^1$, $K^2$, $R^{k1}$, or $R^{k1'}$, or any substituent thereof, with the proviso that when none of $K^1$, $K^{1'}$, and $K^r$ are substituted with —OR$^{k''}$, $R^{k1}$ and $R^{k2}$ or $R^{k1}$ and R', or R' and $R^{k2}$, together form optionally substituted —C(O)NHS(O)$_2$K$^3$W, —C(O)NHS(O)$_2$, —S(O)$_2$ or a carbocyclic ring, optionally substituted with 0-3 W, W$_1$, or W$_2$, or 0-3 H, —OH, alkyl, aryl, aralkyl, alkenyl, alkynyl, alkoxy, aryloxy, —C(W)$_2$, —C(O)W, —C(O)OW, —O(W), —N(W)$_2$, —S(W), (O)(OW$_1$)(OW$_2$), P(O)(OW$_1$)(OW$_2$), —P(O)(OW$_1$)(NW$_2$), —P(O)(NW$_1$)(NW$_2$), —OP(O)(OW$_1$)(OW$_2$), —OP(O)(OW$_1$)(NW$_2$), —OP(O)(NW$_1$)(NW$_2$), —OCH$_2$P(O)(OW$_1$)(OW$_2$), —C(O)OCH$_2$P(O)(OW$_1$)(OW$_2$), CH$_2$P(O)(OW$_1$)(NW$_2$), —OCH$_2$P(O)(OW$_1$)(NW$_2$), —C(O)OCH$_2$P(O)(OW$_1$)(NW$_2$), CH$_2$P(O)(NW$_1$)(NW$_2$), —C(O)OCH$_2$P(O)(NW$_1$)(NW$_2$), and —OCH$_2$P(O)(NW$_1$)(NW$_2$), wherein third member of $R^{k2}$, $R^{k1}$, and R' that is not a member of the carbocyclic ring is P(O)(OW$_1$)(OW$_2$), —P(O)(OW$_1$)(NW$_2$), or —P(O)(NW$_1$)(NW$_2$);

$R^{k1}$, $R^{k2}$, and R' are independently absent or, when $R^{k''}$ is C, selected from optionally substituted C(O)NHS(O)$_2$K$^3$W, P(O)(OW$_1$)(OW$_2$), —P(O)(OW$_1$)(NW$_2$), and —P(O)(NW$_1$)(NW$_2$), and when $R^{k''}$ is —P(O), $R^{k1}$, $R^{k2}$, and R' are independently absent or selected from —OH, —OW$_1$, —NW$_1$, or —W$_1$, optionally substituted with 0-3 W, W$_1$, or W$_2$, and optionally form a bond, through themselves or any substituent thereof, to K", $K^r$, $K^2$, or another of R', $R^{k1}$, or $R^{k2}$, or any substituent thereof, and when $R^{k''}$ is C(O)NHS(O)$_2$K$^3$W, R', $R^{k1}$, and $R^{k2}$ are absent or selected from W, W$_1$, or W$_2$, —OH, alkyl, aryl, aralkyl, alkenyl, alkynyl, alkoxy, aryloxy, C(W)$_2$, —C(O)W, —C(O)OW, —O(W), —N(W)$_2$, —S(W), (O)(OW$_1$)(OW$_2$), P(O)(OW$_1$)(OW$_2$), —P(O)(OW$_1$)(NW$_2$), —P(O)(NW$_1$)(NW$_2$), —OP(O)(OW$_1$)(OW$_2$), —OP(O)(OW$_1$)(NW$_2$), —OP(O)(NW$_1$)(NW$_2$), —OCH$_2$P(O)(OW$_1$)(OW$_2$), —C(O)OCH$_2$P(O)(OW$_1$)(OW$_2$), CH$_2$P(O)(OW$_1$)(NW$_2$), —OCH$_2$P(O)(OW$_1$)(NW$_2$), —C(O)OCH$_2$P(O)(OW$_1$)(NW$_2$), CH$_2$P(O)(NW$_1$)(NW$_2$), —C(O)OCH$_2$P(O)(NW$_1$)(NW$_2$), and —OCH$_2$P(O)(NW$_1$)(NW$_2$), with the proviso that when $K^0$ is N, $R^{k''}$ is C, and either $R^{k'}$ or K" are one or more units of substituted or unsubstituted —C(O)CHNH—, any two of R', $R^{k1}$, and $R^{k2}$ together form with $R^{k''}$ a spirocyclic ring, and also with the proviso that when k is 0 and R$^{k''}$ is C, none of R', R$^{k1}$, and R$^{k2}$ are (C(O))$_{k''}$, wherein k'' is 2-3, also with the proviso that when 0-2 R, 0-1 R$^{k'}$, and 0-2 R', R$^{k1}$, or R$^{k1'}$ are C and substituted such that together they form a ring, then R', R$^{k1}$, and R$^{k2}$ are not H, also with the proviso that when K$^r$ is CH, bound to K$^1$, that is CH$_2$, and not substituted with —OK$^{1''}$, then k is 0, and two of R', R$^{k1}$, or R$^{k2}$, together with R$^{k''}$, form a spirocyclic ring with the remaining R', R$^{k1}$, or R$^{k2}$, being P(O)(OW$_1$)(OW$_2$), —P(O)(OW$_1$)(NW$_2$), or —P(O)(NW$_1$)(NW$_2$);

K$^{1''}$ is, when R$^{k''}$ is part of a spirocyclic ring and any of R, K'', R$^{k1'}$, K$^0$, K$^r$, K$^1$, K$^{1'}$, K$^2$, R$^{k1}$, R', or R$^{k2}$ are or are substituted with —P(O)(OW$_1$)(OW$_2$), —P(O)(OW$_1$)(NW$_2$), or P(O)(NW$_1$)(NW$_2$), alkyl, aryl, heteroaryl, carbocycle, heterocycle, aralkyl, heterocyclic aryl, heterocyclic aralkyl, alkyl heterocyclic aryl, alkyl heterocyclic alkyl, alkyl heterocyclic aryloxyalkyl, alkyl heterocyclic alkyloxyalky, alkyl heterocyclic alkyloxyaryl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, or alkyloxy arylsulfonamide, optionally and optionally multiply, and optionally absent, substituted with —P(O)(OW$_1$)(OW$_2$), —P(O)(OW$_1$)(NW$_2$), or P(O)(NW$_1$)(NW$_2$), alkyl, aryl, heteroaryl, carbocycle, heterocycle, aralkyl, heterocyclic aryl, heterocyclic aralkyl, alkyl heterocyclic aryl, alkyl heterocyclic alkyl, alkyl heterocyclic aryloxyalkyl, alkyl heterocyclic alkyloxyalky, alkyl heterocyclic alkyloxyaryl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, or alkyloxy arylsulfonamide;

R is C, —C(O)NHS(O)$_2$K$^3$W, or —S(O)$_2$—, optionally substituted with one or more W, W$_1$, or W$_2$;

W is absent or 0-3 W$_1$ or W$_2$;

W$_1$ and W$_2$ are independently absent, together form, or are independently selected from a bond, H, —OH, —C(O), —C(O)O—, alkyl, amino, amido, imido, imino, halogen, CF$_3$, CH$_2$CF$_3$, aryl, aralkyl, alkenyl, alkynyl, alkoxy, aryloxy, —C(W)$_2$, —C(O)W, —C(O)OW, —O(W), —N(W)$_2$, —S(W), CH$_2$P(O)(OW$_1$)(OW$_2$), —OCH$_2$P(O)(OW$_1$)(OW$_2$), —C(O)OCH$_2$P(O)(OW$_1$)(OW$_2$), CH$_2$P(O)(OW$_1$)(NW$_2$), —OCH$_2$P(O)(OW$_1$)(NW$_2$), —C(O)OCH$_2$P(O)(OW$_1$)(NW$_2$), CH$_2$P(O)(NW$_1$)(NW$_2$), —C(O)OCH$_2$P(O)(NW$_1$)(NW$_2$), and —OCH$_2$P(O)(NW$_1$)(NW$_2$), heteroaryl, carbocycle, heterocycle, aralkyl, heterocyclic aryl, heterocyclic aralkyl, alkyl heterocyclic aryl, alkyl heterocyclic alkyl, alkyl heterocyclic aryloxyalkyl, alkyl heterocyclic alkyloxyalky, alkyl heterocyclic alkyloxyaryl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, or alkyloxy arylsulfonamide, optionally and optionally multiply, and optionally absent, substituted with —P(O)(OW$_1$)(OW$_2$), —P(O)(OW$_1$)(NW$_2$), or P(O)(NW$_1$)(NW$_2$), alkyl, aryl, heteroaryl, carbocycle, heterocycle, aralkyl, heterocyclic aryl, heterocyclic aralkyl, alkyl heterocyclic aryl, alkyl heterocyclic alkyl, alkyl heterocyclic aryloxyalkyl, alkyl heterocyclic alkyloxyalky, alkyl heterocyclic alkyloxyaryl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, or alkyloxy arylsulfonamide.

2. A Compound of Embodiment 1 wherein Formula I is

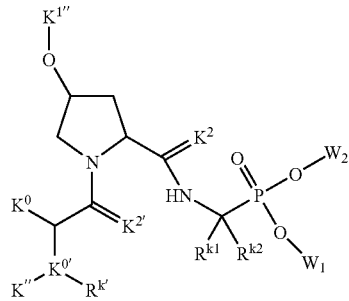

3. A Compound of Embodiment 1 wherein Formula I is

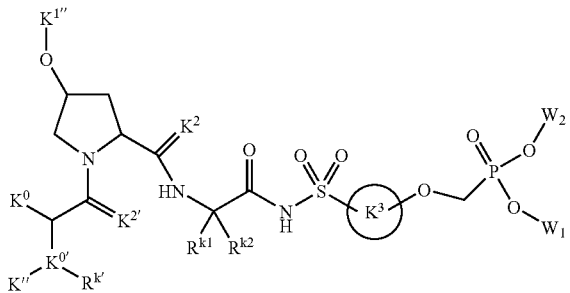

4. A Compound of Embodiment 1 wherein Formula I is

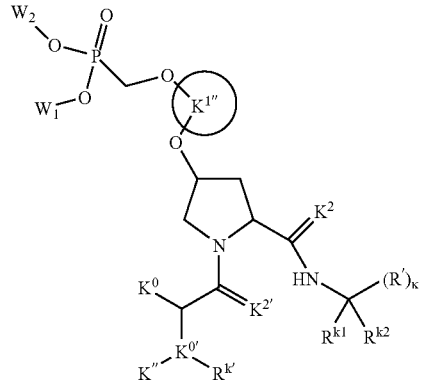

5. A Compound of Embodiment 1 wherein Formula I is

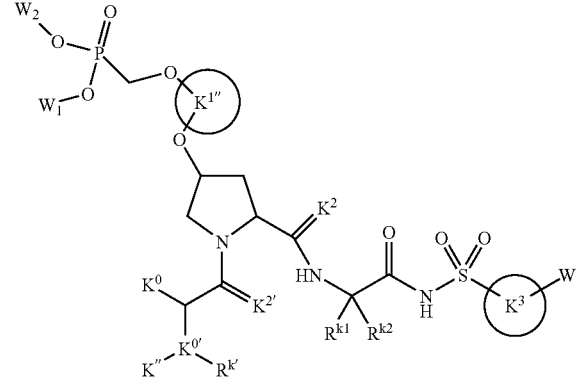

6. A Compound of Embodiment 1 wherein Formula I is

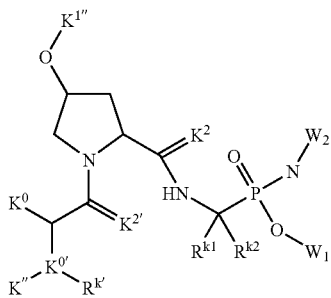

7. A Compound of Embodiment 1 wherein Formula I is

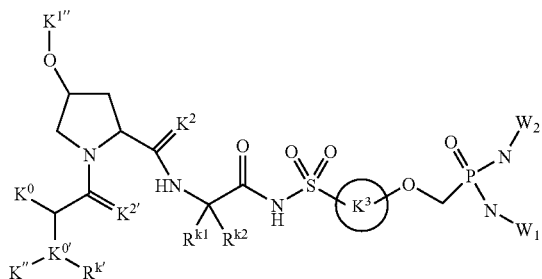

8. A Compound of Embodiment 1 wherein Formula I is

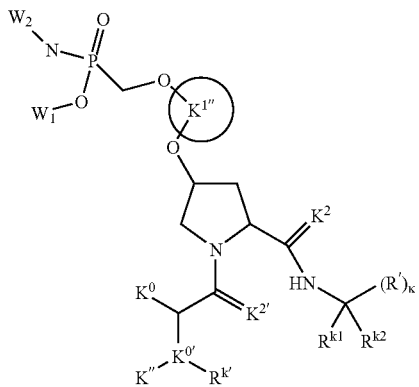

9. A Compound of Embodiment 1 wherein Formula I is

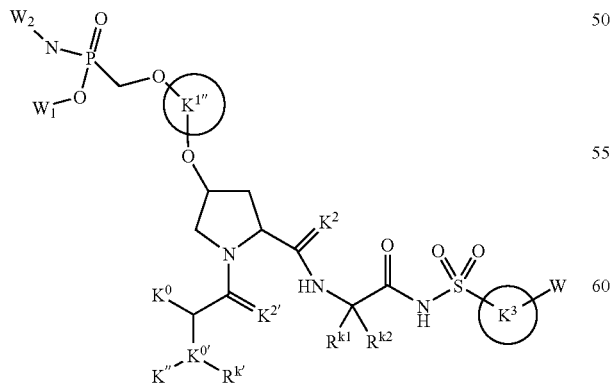

10. A Compound of Embodiment 1 wherein Formula I is

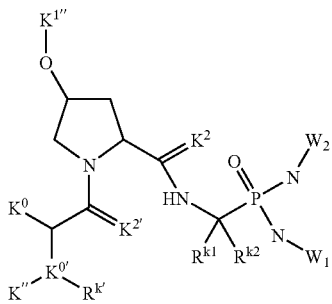

11. A Compound of Embodiment 1 wherein Formula I is

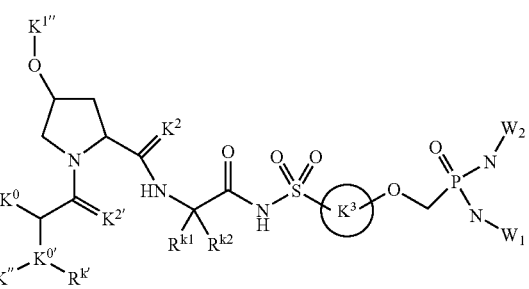

12. A Compound of Embodiment 1 wherein Formula I is

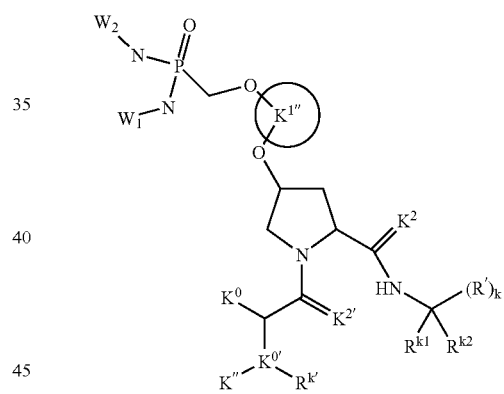

13. A Compound of Embodiment 1 wherein Formula I is

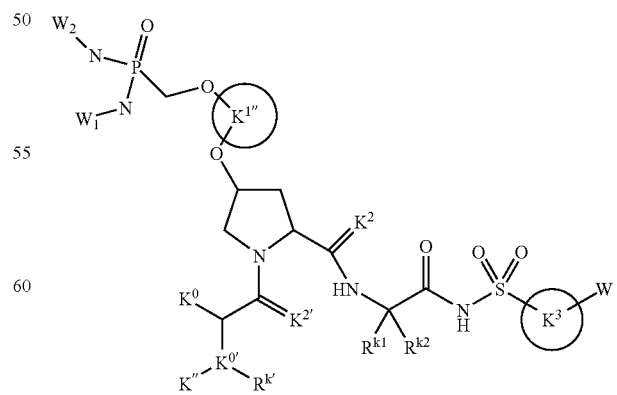

Further Exemplary Embodiments

1. A Compound of Formula I or II:

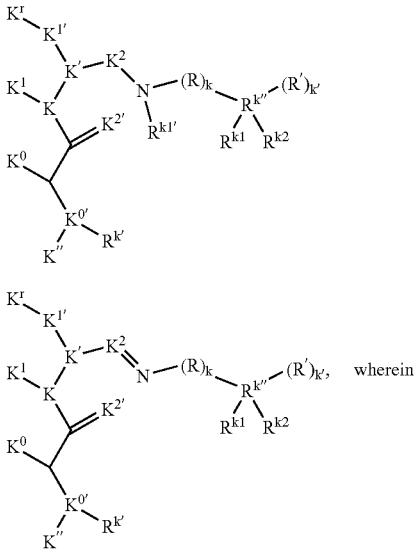

K" and $R^{k'}$ are independently absent or selected from a bond, H, —OH, alkyl, aryl, aralkyl, alkenyl, alkynyl, alkoxy, aryloxy, —C(W)$_2$, —C(O)W, —C(O)OW, —O(W), —N(W)$_2$, —S(W), CH$_2$P(O)(OW$_1$)(OW$_2$), —OCH$_2$P(O)(OW$_1$)(OW$_2$), —C(O)OCH$_2$P(O)(OW$_1$)(OW$_2$), CH$_2$P(O)(OW$_1$)(NW$_2$), —OCH$_2$P(O)(OW$_1$)(NW$_2$), —C(O)OCH$_2$P(O)(OW$_1$)(NW$_2$), CH$_2$P(O)(NW$_1$)(NW$_2$), —C(O)OCH$_2$P(O)(NW$_1$)(NW$_2$), —OCH$_2$P(O)(NW$_1$)(NW$_2$), and —P(O)(W)$_k$, are optionally substituted with 0-3 W, W$_1$, or W$_2$, optionally form a bond, through themselves or any substituents thereof, to K$^r$, K$^1$, K$^{1'}$, K$^2$, R$^{k1}$, R$^{k1'}$, R, R', R$^{k2}$, or any substituents thereof, with the proviso that when either R$^{k1}$ or R$^{k2}$ are alkyl, alkenyl, or alkynyl, and the other of R$^{k1}$ or R$^{k2}$ is H, and the other of K" or R$^{k'}$ are H or C1-3 alkyl, and K$^2$ and K$^{2'}$ are both oxygen, and K$^{0'}$ is N, the other of K" or R$^{k'}$ is alkyl and optionally substituted with 0-3 W, W$_1$, or W$_2$;

K$^{0'}$ is N, —CH, —S(O)$_2$, —C(O)NHS(O)$_2$K$^3$W or and —P(O)(W)$_k$;

K$^0$ is selected from a bond, H, —OH, alkyl, aryl, aralkyl, alkenyl, alkynyl, alkoxy, aryloxy, —C(W)$_2$, —C(O)W, —C(O)OW, —O(W), —N(W)$_2$, —NC(O)OW, —S(W), W, W$_1$, W$_2$, P(O)(OW$_1$)(OW$_2$), —P(O)(OW$_1$)(NW$_2$), —P(O)(NW$_1$)(NW$_2$), —P(O)(W)$_k$, —OP(O)(OW$_1$)(OW$_2$), —OP(O)(OW$_1$)(NW$_2$), —OP(O)(NW$_1$)(NW$_2$), —OCH$_2$P(O)(OW$_1$)(OW$_2$), —C(O)OCH$_2$P(O)(OW$_1$)(OW$_2$), CH$_2$P(O)(OW$_1$)(NW$_2$), —OCH$_2$P(O)(OW$_1$)(NW$_2$), —C(O)OCH$_2$P(O)(OW$_1$)(NW$_2$), CH$_2$P(O)(NW$_1$)(NW$_2$), —C(O)OCH$_2$P(O)(NW$_1$)(NW$_2$), and —OCH$_2$P(O)(NW)(NW$_2$), are optionally substituted with 0-3 W, W$_1$, or W$_2$, optionally forms a bond, through itself or any substituent thereof, to K$^r$, K$^1$, K$^{1'}$, K$^2$, R$^{k1}$, R$^{k1'}$, R, R', R$^{k2}$, or any substituent thereof, with the proviso that if K$^0$ is connected to R$^{k''}$ or substitutents thereof via an optionally substituted alkyl, alkenyl, or alkynyl chain, via substituents thereof or in combination, and R$^{k''}$ is part of a spirocyclic ring system wherein the ring is not substituted with P(O)(OW$_1$)(OW$_2$), —P(O)(OW$_1$)(NW$_2$), or —P(O)(NW$_1$)(NW$_2$), at least one carbon in said chain therein is substituted with P(O)(OW$_1$)(OW$_2$), P(O)(OW$_1$)(NW$_2$), —P(O)(NW$_1$)(NW$_2$), or —P(O)(W)$_k$;

K$^2$ is absent, a bond, —C(O)—, —C(NW$_2$)—, —C(NW$_1$)—, —C(S)—, —CH—, —CH$_2$—, —C(W)$_k$—, —O—, —S—, W, —NCN, SMe, C(SC(W)$_2$C(O)N(H)C(H)$_2$C(H)C(H)C(W)$_2$O—)—, —C(SC(W)$_2$C(O)N(W)C(W)$_2$C(W)C(W)C(W)$_2$O—)—, or —CH$_2$—, wherein K$^2$ is optionally substituted with 0-3 W, and wherein a bond is optionally formed through K$^2$, or any substituent thereof, to K", R$^{k'}$, or K$^{0'}$;

K$^{2'}$ is oxygen, sulfur, —NW, —C(W)$_2$;

K is N;

K' is CH or C(W);

K$^{1'}$ and K$^{1''}$ are independently absent, a bond, H, together form, or are each independently selected from H, alkyl, alkoxy, aryl, aryloxy, halogen, CF$_3$, CH$_2$CF$_3$;

K$^{1'}$ is CH, optionally substituted with 0-3 W, W$_1$, —OR$^{k''}$ or W$_2$;

K$^1$ is CH, optionally substituted with 0-3 W, W$_1$, or W$_2$, optionally forms a bond, through itself or any substituent thereof, to K", K$^r$, K$^2$, R$^{k1}$, or R$^{k1'}$, or any substituent thereof;

R$^{k1'}$ is absent or H, alkyl, or aryl optionally substituted with 0-3 W, W$_1$, or W$_2$;

R$^{k''}$ is absent, a bond, H, C, CH, P(O), —P(O)(W)$_k$, —C(O)NHS(O)$_2$K$^3$W, or C(O)NHS(O)$_2$K$^3$, wherein K$^3$ is absent, a bond, H, —OH, —C(O)OW, alkyl, aryl, cycloalkyl, heteroaryl, heterocyclic, spirocyclic or heterospirocyclic ring optionally substituted with one or more W, optionally substituted with one or more W optionally substituted, with the proviso that when k is 1 and R is a member of a spirocarbocyclic or spiroheterocyclic ring, R$^{k''}$ is —P(O) and two of R$^{k1}$, R$^{k2}$, and R', are independently —OW, or —NW$_1$, and the third of R$^{k1}$, R$^{k2}$, and R' is absent, and also with the proviso that when k is 2 and two consecutive R are C and are substituted such that together they form a ring, then R$^{k''}$ is not H;

k is 0 to 6, with the proviso that k is not 2 if two consecutive groups R are jointly substituted to form a ring;

k' is 0 to 6;

K$^r$ is CH, optionally substituted with 0-3 W, W$_1$, —OK$^{1''}$ or W$_2$, optionally forms an additional bond, through itself or any substituent thereof, to K", K$^1$, K$^2$, R$^{k1}$, or R$^{k1'}$, or any substituent thereof, with the proviso that when none of K$^1$, K$^{1'}$, and K$^r$ are substituted with —OR$^{k''}$, R$^{k1}$ and R$^{k2}$ or R$^{k1}$ and R', or R' and R$^{k2}$, together form optionally substituted —C(O)NHS(O)$_2$K$^3$W, —C(O)NHS(O)$_2$, —S(O)$_2$ or a carbocyclic ring, optionally substituted with 0-3 W, W$_1$, or W$_2$, or 0-3 H, —OH, alkyl, aryl, aralkyl, alkenyl, alkynyl, alkoxy, aryloxy, —C(W)$_2$, —C(O)W, —C(O)OW, —O(W), —N(W)$_2$, —S(W), (O)(OW$_1$)(OW$_2$), P(O)(OW$_1$)(OW$_2$), —P(O)(OW$_1$)(NW$_2$), —P(O)(NW$_1$)(NW$_2$), —OP(O)(OW$_1$)(OW$_2$), —OP(O)(OW$_1$)(NW$_2$), —OP(O)(NW$_1$)(NW$_2$), —OCH$_2$P(O)(OW$_1$)(OW$_2$), —C(O)OCH$_2$P(O)(OW$_1$)(OW$_2$), CH$_2$P(O)(OW$_1$)(NW$_2$), —OCH$_2$P(O)(OW$_1$)(NW$_2$), —C(O)OCH$_2$P(O)(OW$_1$)(NW$_2$), CH$_2$P(O)(NW$_1$)(NW$_2$), —C(O)OCH$_2$P(O)(NW$_1$)(NW$_2$), —OCH$_2$P(O)(NW$_1$)(NW$_2$), and —P(O)(W)$_k$, wherein third member of R$^{k2}$, R$^{k1}$, and R' that is not a member of the carbocyclic ring is P(O)(OW$_1$)(OW$_2$), —P(O)(OW$_1$)(NW$_2$), —P(O)(NW$_1$)(NW$_2$) or —P(O)(W)$_k$;

R$^{k1}$, R$^{k2}$, and R' are independently absent or, when R$^{k''}$ is C, selected from optionally substituted C(O)NHS(O)$_2$K$^3$W, P(O)(OW$_1$)(OW$_2$), —P(O)(OW$_1$)(NW$_2$), —P(O)(NW$_1$)(NW$_2$), and —P(O)(W)$_k$, and when R is —P(O), R$^{k1}$, R$^{k2}$, and R' are independently absent or selected from —OH, —OW$_1$, —NW$_1$, or —W$_1$, optionally substituted with 0-3 W, W$_1$, or W$_2$, and optionally form a bond, through themselves or any substituent thereof, to K'', K$^r$, K$^2$, or another of R', R$^{k1}$, or R$^{k2}$, or any substituent thereof, and when R$^{k''}$ is C(O)NHS(O)$_2$K$^3$W, R', R$^{k1}$, and R$^{k2}$ are absent or selected from W, W$_1$, or W$_2$, —OH, alkyl, aryl, aralkyl, alkenyl, alkynyl, alkoxy, aryloxy, —C(W)$_2$, —C(O)W, —C(O)OW, —O(W), —N(W)$_2$, —S(W), (O)(OW$_1$)(OW$_2$), P(O)(OW$_1$)(OW$_2$), —P(O)(OW$_1$)(NW$_2$), —P(O)(NW$_1$)(NW$_2$), —OP(O)(OW$_1$)(OW$_2$), —OP(O)(OW$_1$)(NW$_2$), —OP(O)(NW$_1$)(NW$_2$), —OCH$_2$P(O)(OW$_1$)(OW$_2$), —C(O)OCH$_2$P(O)(OW$_1$)(OW$_2$), CH$_2$P(O)(OW$_1$)(NW$_2$), —OCH$_2$P(O)(OW$_1$)(NW$_2$), —C(O)OCH$_2$P(O)(OW$_1$)(NW$_2$), CH$_2$P(O)(NW$_1$)(NW$_2$), —C(O)OCH$_2$P(O)(NW$_1$)(NW$_2$), —OCH$_2$P(O)(NW$_1$)(NW$_2$), and —P(O)(W)$_k$, with the proviso that when K$^0$ is N, R$^{k''}$ is C, and either R$^{k'}$ or K'' are one or more units of substituted or unsubstituted —C(O)CHNH—, any two of R', R$^{k1}$, and R$^{k2}$ together form with R$^{k''}$ a spirocyclic ring, and also with the proviso that when k is 0 and R$^{k''}$ is C, none of R', R$^{k1}$, and R$^{k2}$ are (C(O))$_{k'''}$, wherein k'' is 2-3, also with the proviso that when 0-2 R, 0-1 R$^{k''}$, and 0-2 R', R$^{k1}$, or R$^{k1'}$ are C and substituted such that together they form a ring, then R', R$^{k1}$, and R$^{k2}$ are not H, also with the proviso that when K$^r$ is CH, bound to K$^1$, that is CH$_2$, and not substituted with —OK$^{1''}$, then k is 0, and two of R', R$^{k1}$, or R$^{k2}$, together with R$^{k''}$, form a spirocyclic ring with the remaining R', R$^{k1}$, or R$^{k2}$, being P(O)(OW$_1$)(OW$_2$), —P(O)(OW$_1$)(NW$_2$), or —P(O)(NW$_1$)(NW$_2$);

K$^{1''}$ is absent, (W)$_k$, alkyl, aryl, heteroaryl, carbocycle, heterocycle, aralkyl, heterocyclic aryl, heterocyclic aralkyl, alkyl heterocyclic aryl, alkyl heterocyclic alkyl, alkyl heterocyclic aryloxyalkyl, alkyl heterocyclic alkyloxyalky, alkyl heterocyclic alkyloxyaryl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, or alkyloxy arylsulfonamide, optionally and optionally multiply, and optionally absent, substituted with —P(O)(OW$_1$)(OW$_2$), —P(O)(OW$_1$)(NW$_2$), or P(O)(NW$_1$)(NW$_2$), alkyl, aryl, heteroaryl, carbocycle, heterocycle, aralkyl, heterocyclic aryl, heterocyclic aralkyl, alkyl heterocyclic aryl, alkyl heterocyclic alkyl, alkyl heterocyclic aryloxyalkyl, alkyl heterocyclic alkyloxyalky, alkyl heterocyclic alkyloxyaryl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, or alkyloxy arylsulfonamide;

R is C, —C(O)NHS(O)$_2$K$^3$W, or —S(O)$_2$—, optionally substituted with one or more W, W$_1$, or W$_2$;

W is absent or 0-3 W$_1$ or W$_2$;

W$_1$ and W$_2$ are independently absent, together form, or are independently selected from a bond, H, —OH, —C(O), —C(O)OH, —(CH$_k$)$_k$—, —C(O)O—, —NH—, alkyl, alkenyl, alkynyl, amino, amido, imido, imino, halogen, CF$_3$, CH$_2$CF$_3$, cycloalkyl, spirocycloalkyl, aryl, aralkyl, alkoxy, aryloxy, —C(W)$_2$, —C(O)W, —C(O)OW, —O(W), —N(W)$_2$, —S(W), CH$_2$P(O)(OW$_1$)(OW$_2$), —OCH$_2$P(O)(OW$_1$)(OW$_2$), —C(O)OCH$_2$P(O)(OW$_1$)(OW$_2$), CH$_2$P(O)(OW$_1$)(NW$_2$), —OCH$_2$P(O)(OW$_1$)(NW$_2$), —C(O)OCH$_2$P(O)(OW$_1$)(NW$_2$), CH$_2$P(O)(NW$_1$)(NW$_2$), —C(O)OCH$_2$P(O)(NW$_1$)(NW$_2$), and OCH$_2$P(O)(NW$_1$)(NW$_2$), heteroaryl, carbocycle, heterocycle, aralkyl, heterocyclic aryl, heterocyclic aralkyl, alkyl heterocyclic aryl, alkyl heterocyclic alkyl, alkyl heterocyclic aryloxyalkyl, alkyl heterocyclic alkyloxyalky, alkyl heterocyclic alkyloxyaryl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, or alkyloxy arylsulfonamide, optionally and optionally multiply, and optionally absent, substituted with —P(O)(OW$_1$)(OW$_2$), —P(O)(OW$_1$)(NW$_2$), or P(O)(NW$_1$)(NW$_2$), alkyl, aryl, heteroaryl, carbocycle, heterocycle, aralkyl, heterocyclic aryl, heterocyclic aralkyl, alkyl heterocyclic aryl, alkyl heterocyclic alkyl, alkyl heterocyclic aryloxyalkyl, alkyl heterocyclic alkyloxyalky, alkyl heterocyclic alkyloxyaryl, aryl sulfonamide, aryl alkylsulfonamide, aryloxy sulfonamide, aryloxy alkylsulfonamide, aryloxy arylsulfonamide, alkyl sulfonamide, alkyloxy sulfonamide, alkyloxy alkylsulfonamide, or alkyloxy arylsulfonamide.

2. A Compound of Embodiment 1 wherein Formula I is

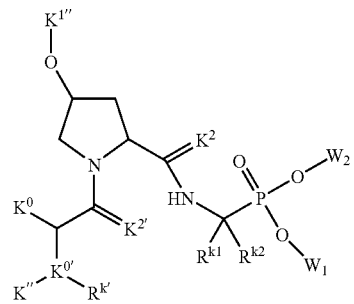

3. A Compound of Embodiment 1 wherein Formula I is

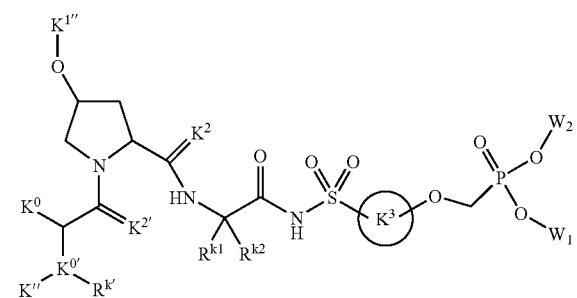

4. A Compound of Embodiment 1 wherein Formula I is

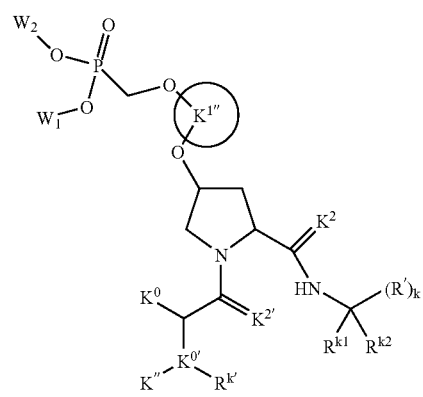

5. A Compound of Embodiment 1 wherein Formula I is

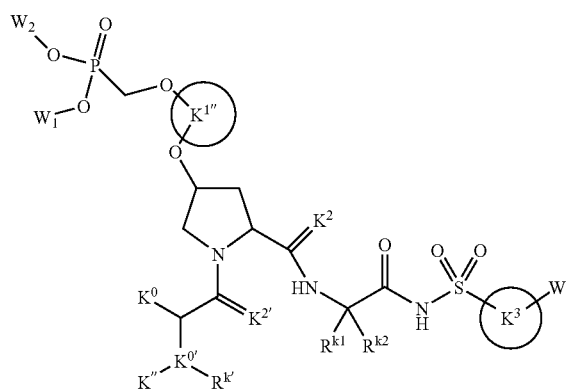

6. A Compound of Embodiment 1 wherein Formula I is

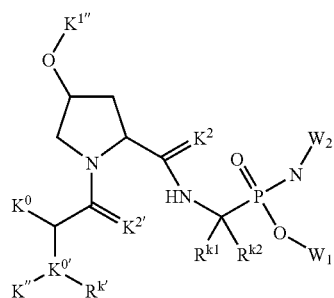

7. A Compound of Embodiment 1 wherein Formula I is

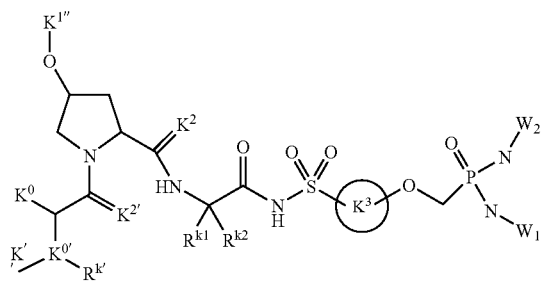

8. A Compound of Embodiment 1 wherein Formula I is

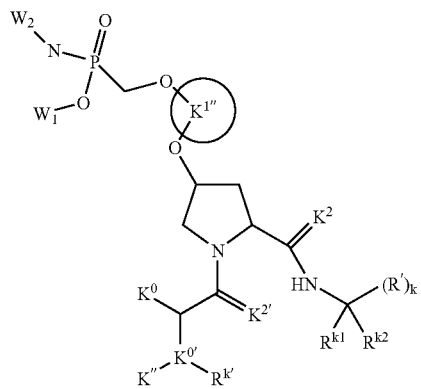

9. A Compound of Embodiment 1 wherein Formula I is

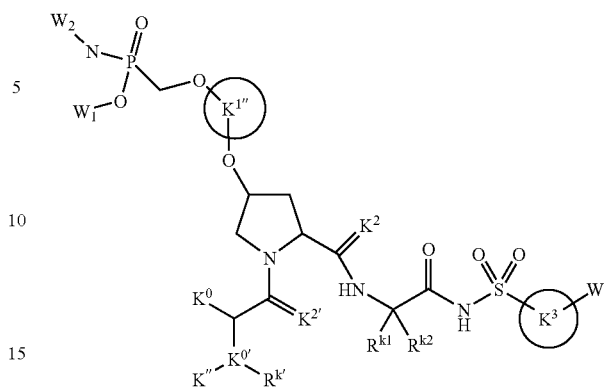

10. A Compound of Embodiment 1 wherein Formula I is

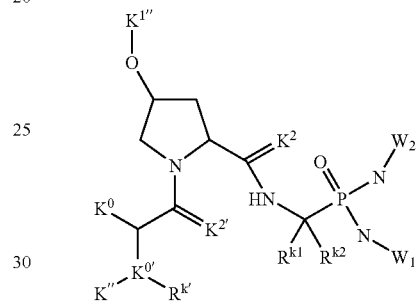

11. A Compound of Embodiment 1 wherein Formula I is

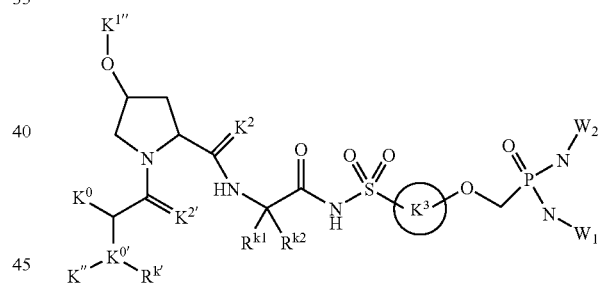

12. A Compound of Embodiment 1 wherein Formula I is

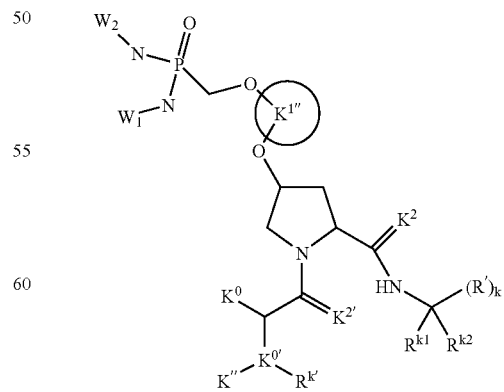

13. A Compound of Embodiment 1 wherein Formula I is
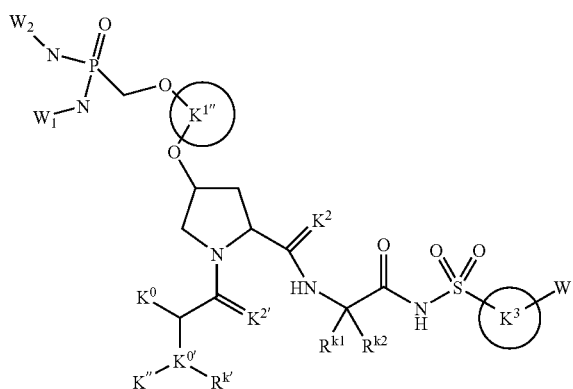
14. A Compound of Embodiment 1 wherein Formula I is
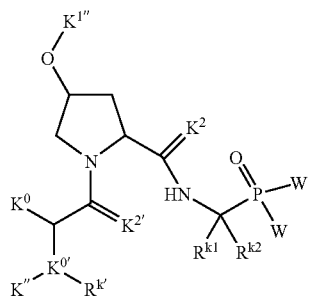
15. A Compound of Embodiment 1 wherein Formula II is
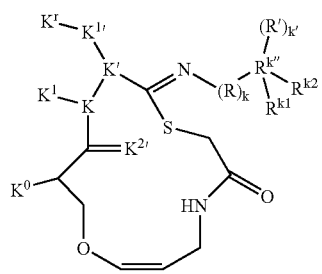
16. A Compound of Embodiment 1 wherein Formula I is
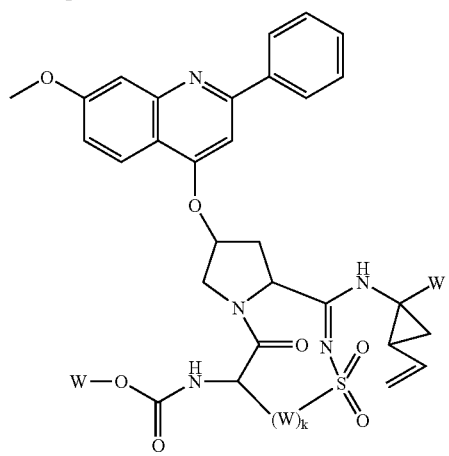
17. A Compound of Embodiment 1 wherein Formula I is
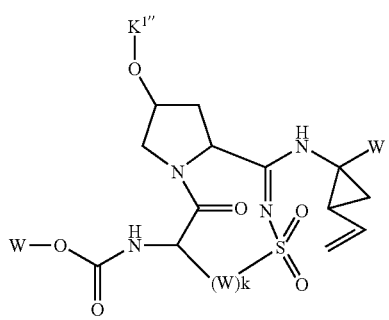
18. A Compound of Embodiment 1 wherein Formula I is
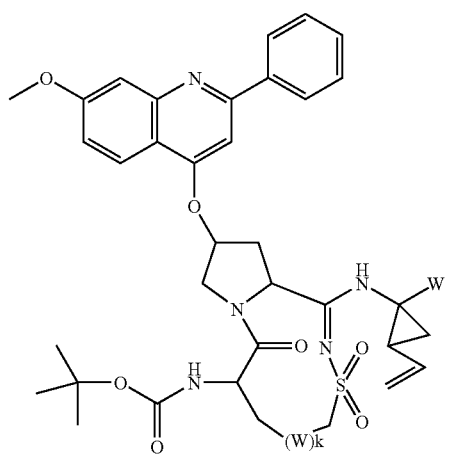
19. A Compound of Embodiment 1 wherein Formula I is
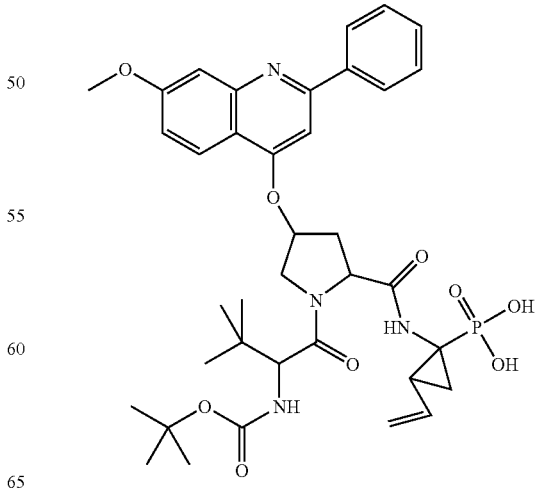

20. A Compound of Embodiment 1 wherein Formula I is
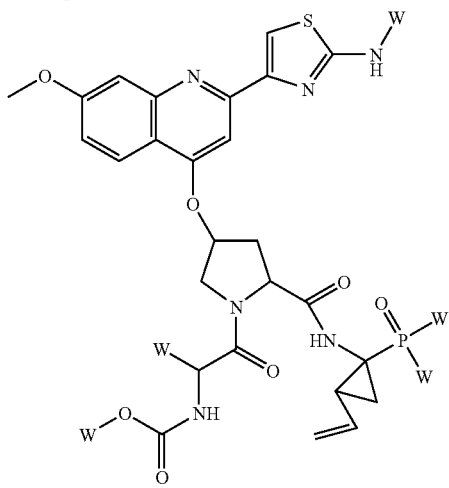
21. A Compound of Embodiment 1 wherein Formula I is
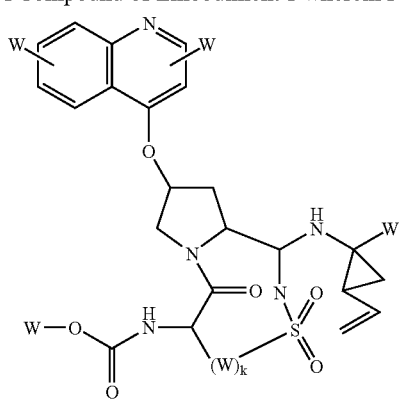
22. A Compound of Embodiment 1 wherein Formula I is
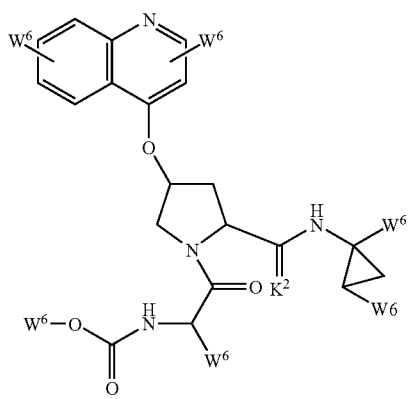
What is claimed:
1. A compound selected from the group consisting of:
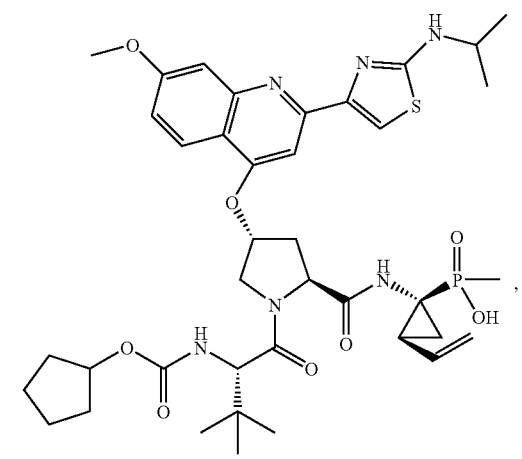
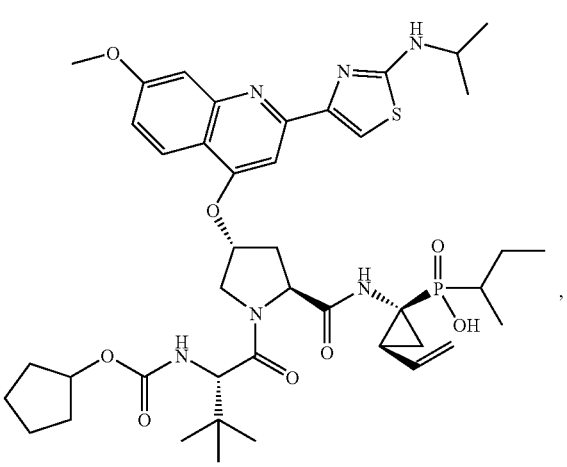
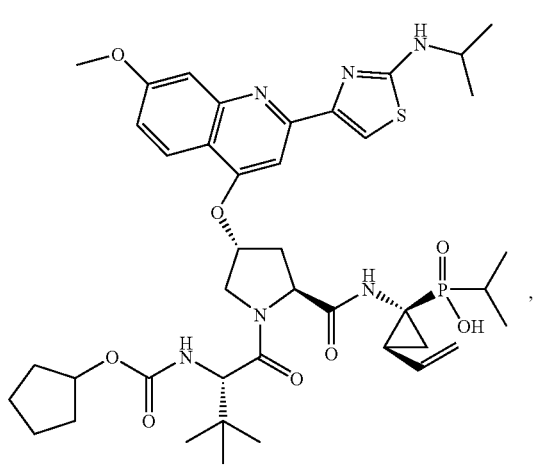

365
-continued
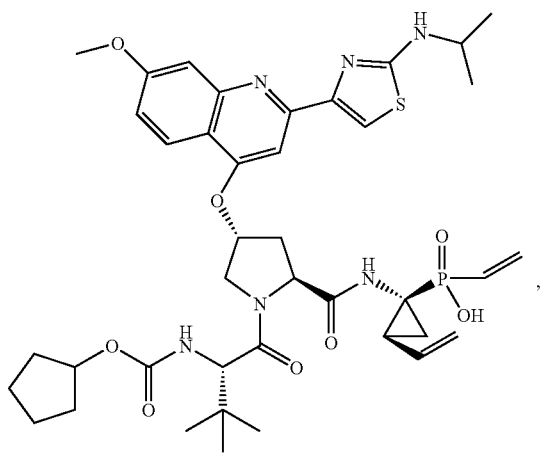
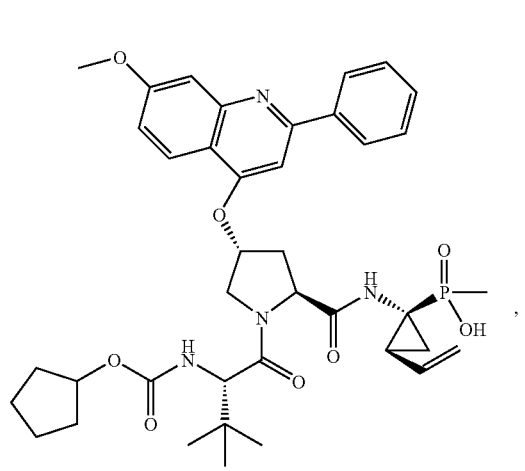
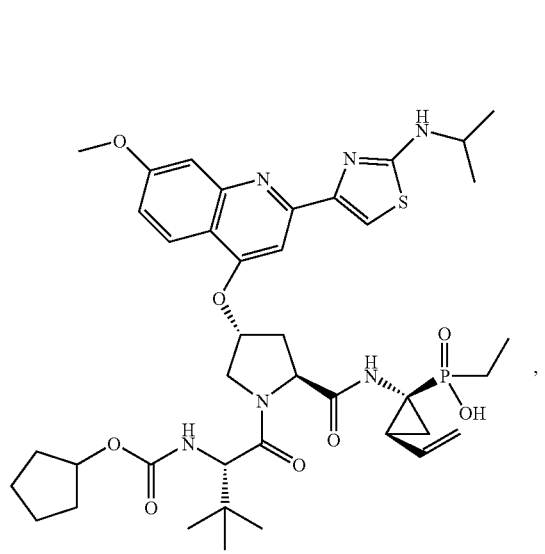
366
-continued
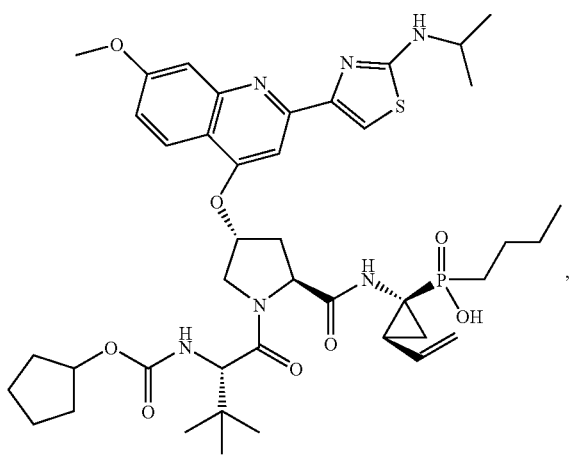
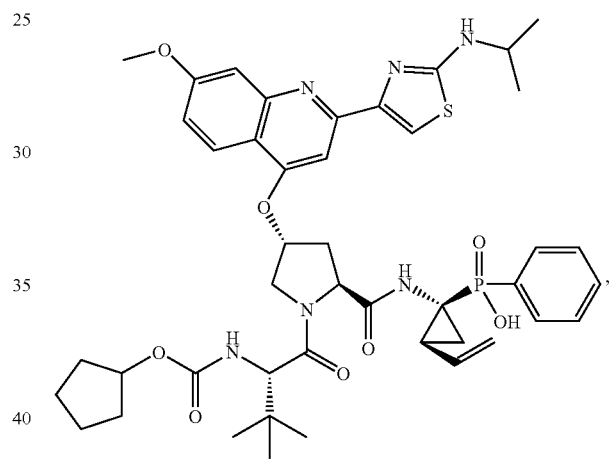
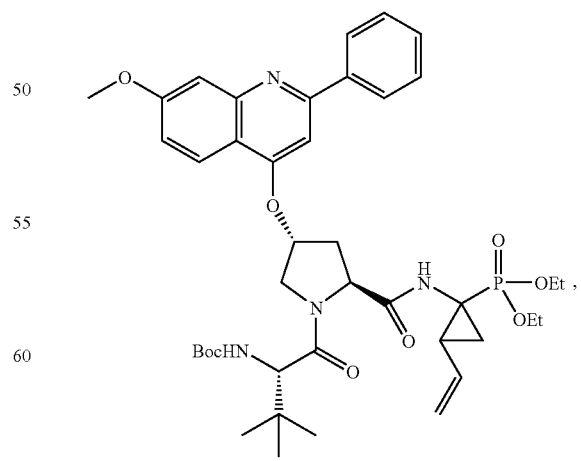

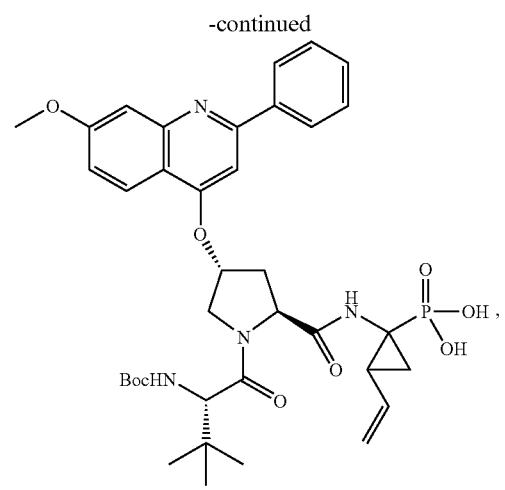
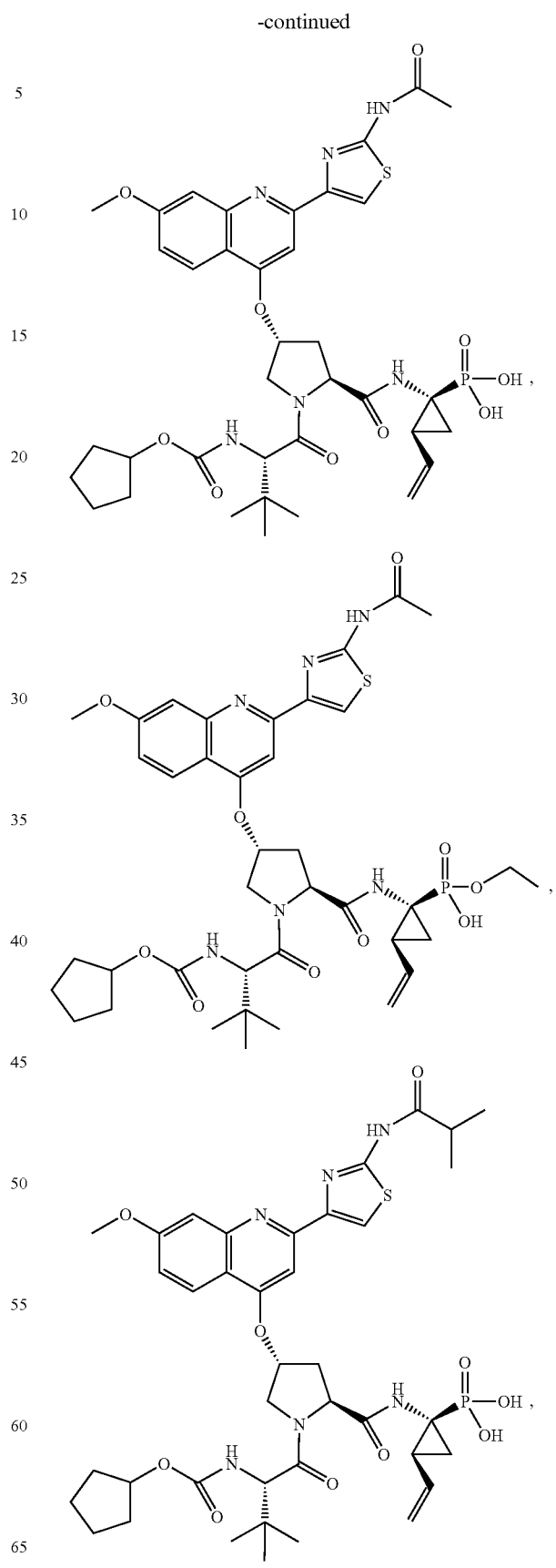

369
-continued
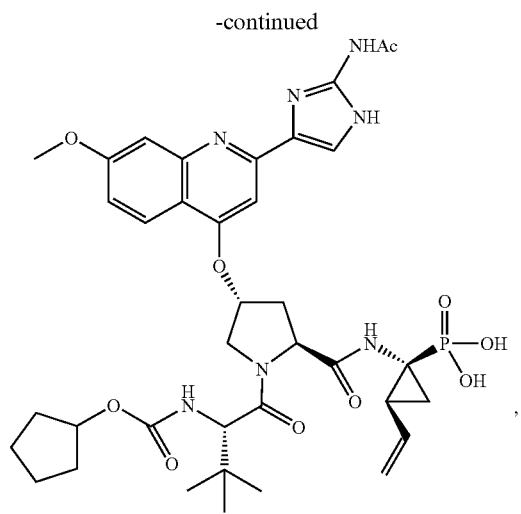
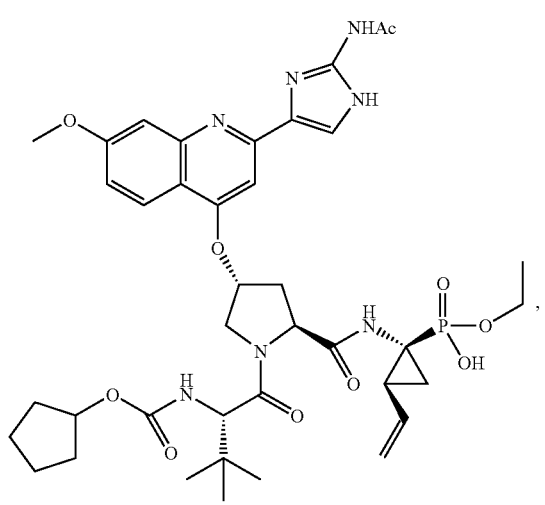
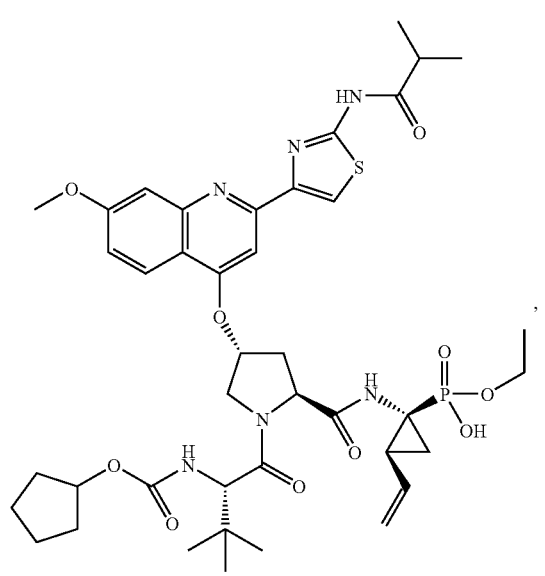
370
-continued
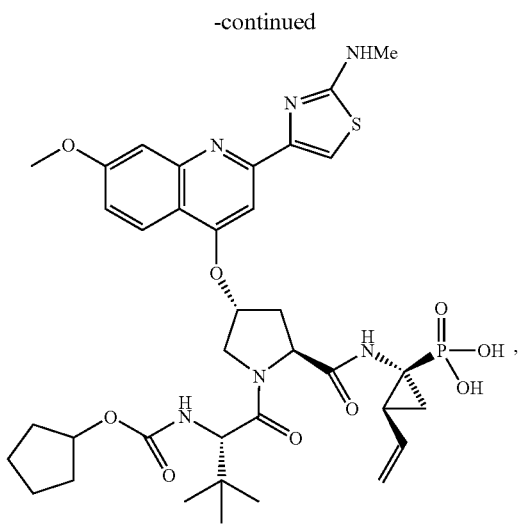
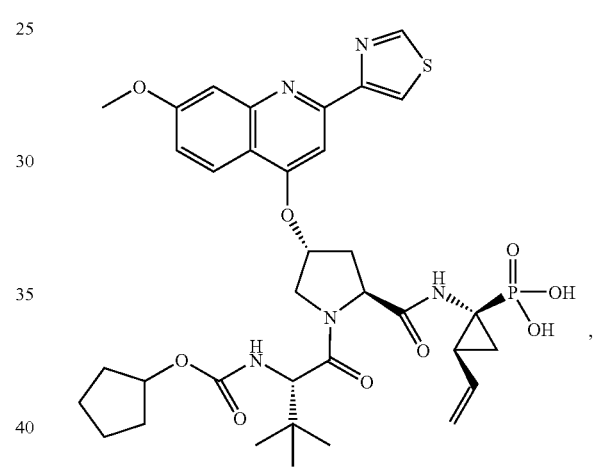
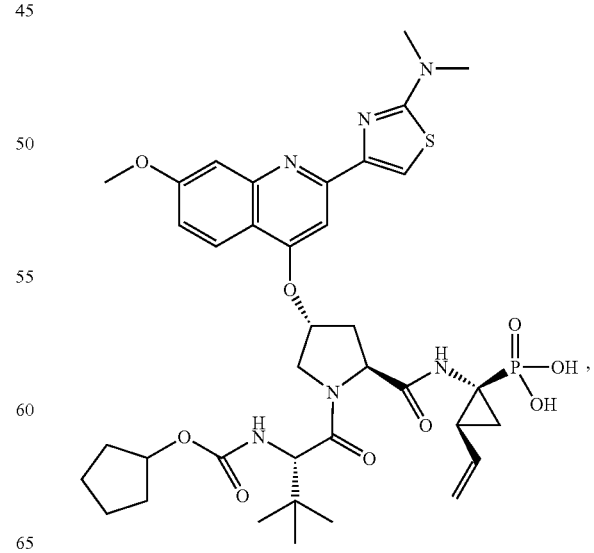

371
-continued
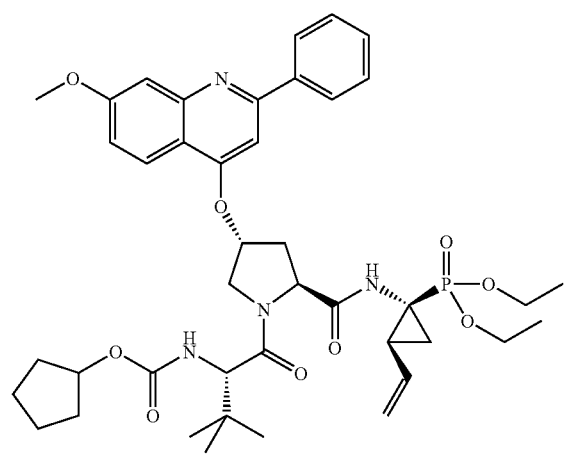
372
-continued
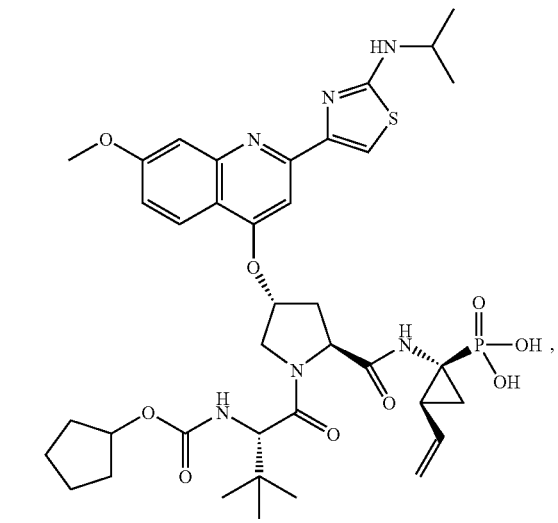
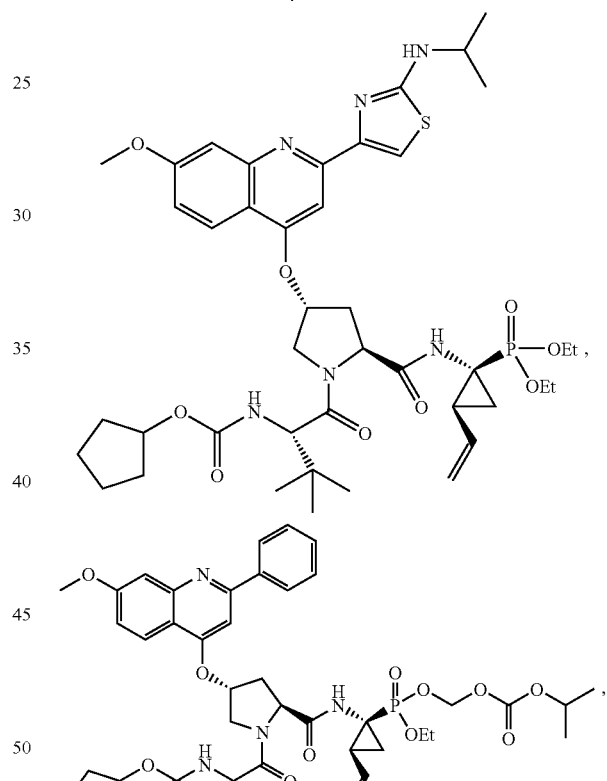
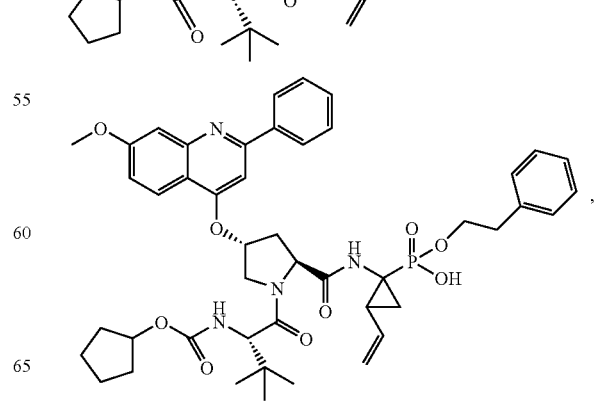

373
-continued
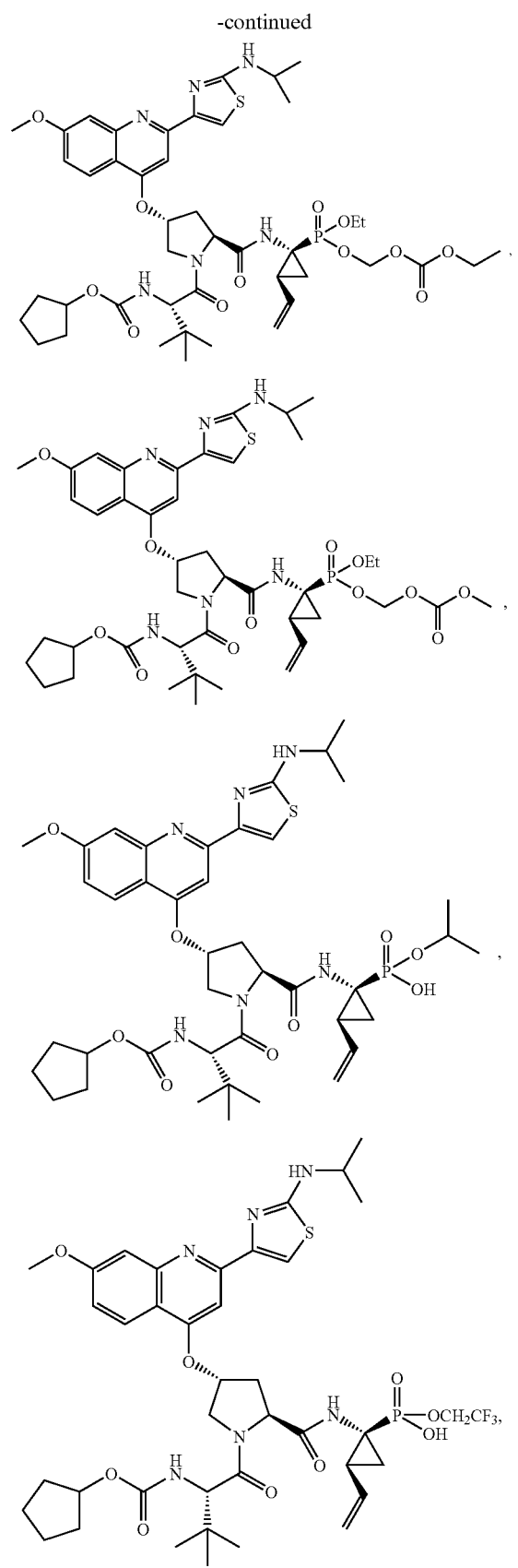
374
-continued
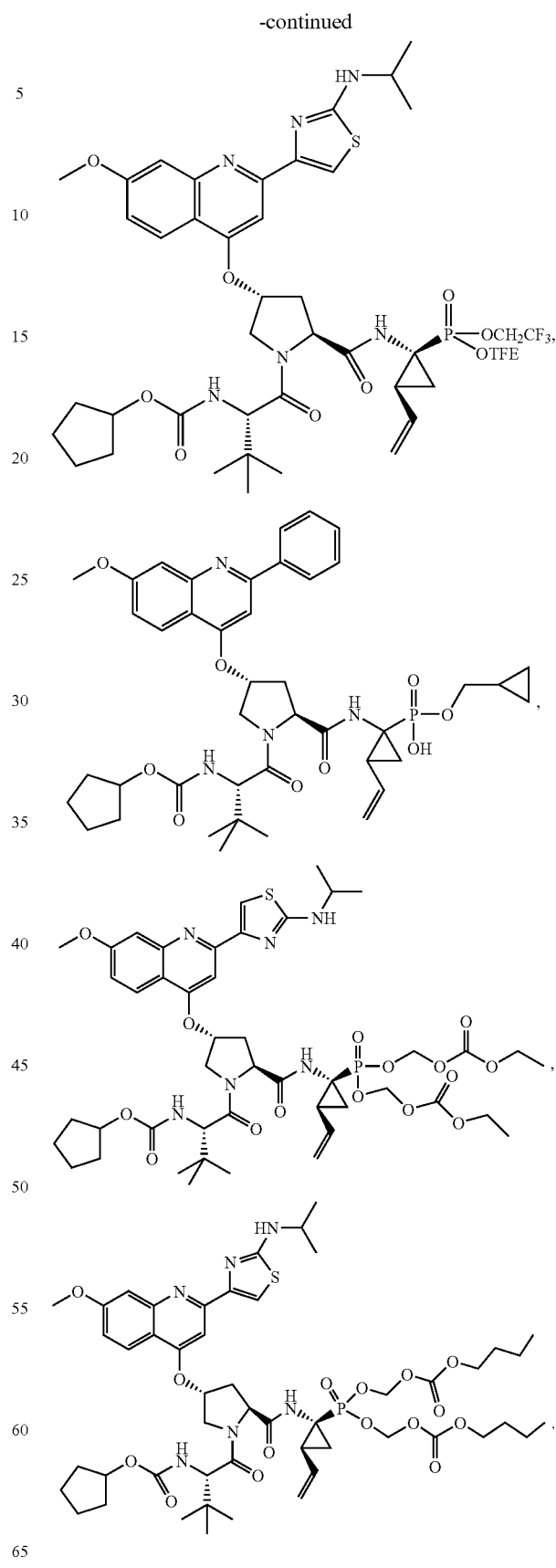

375
-continued
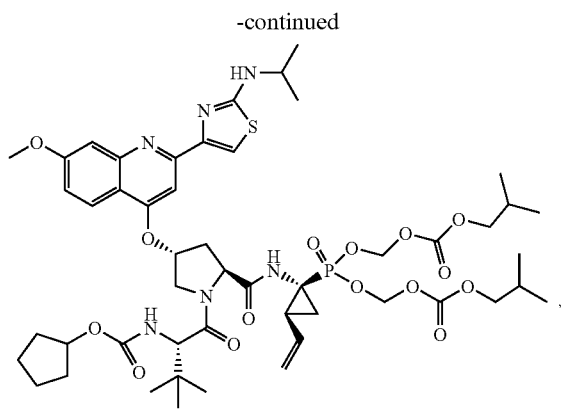
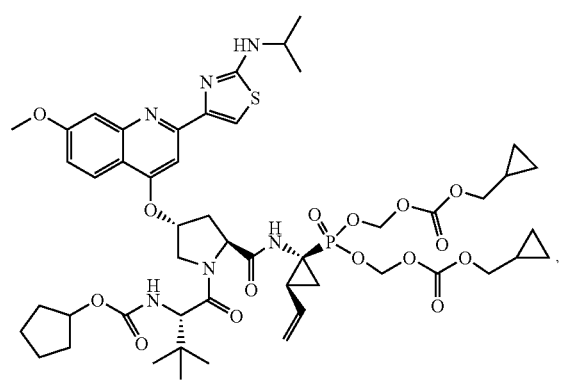
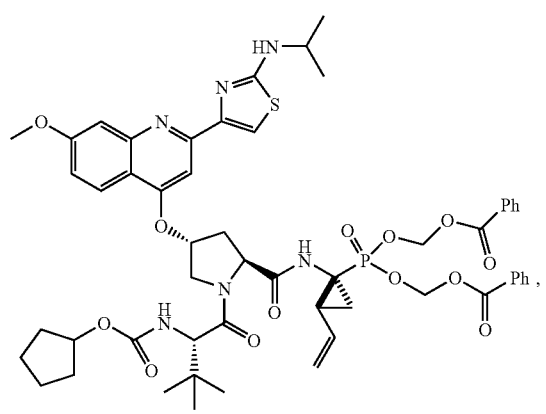
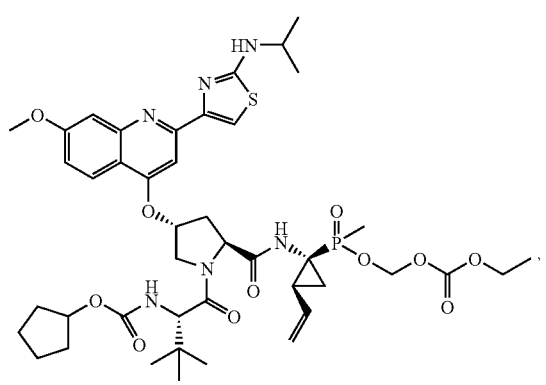
376
-continued
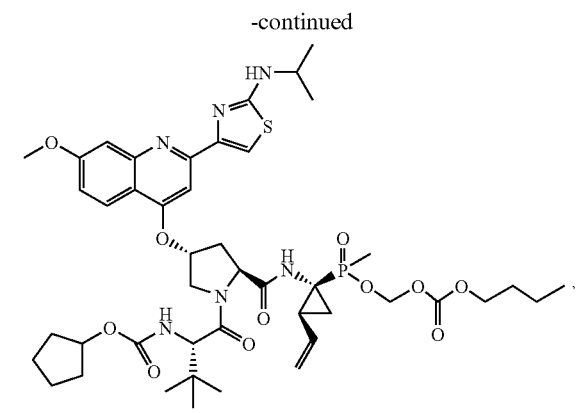
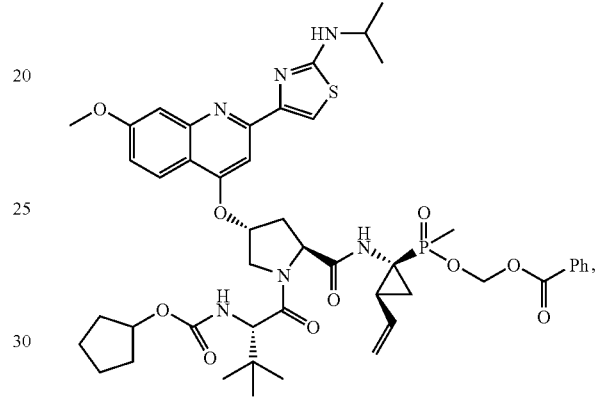
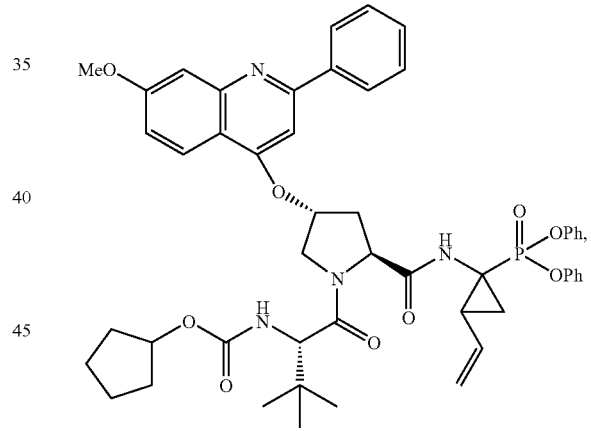
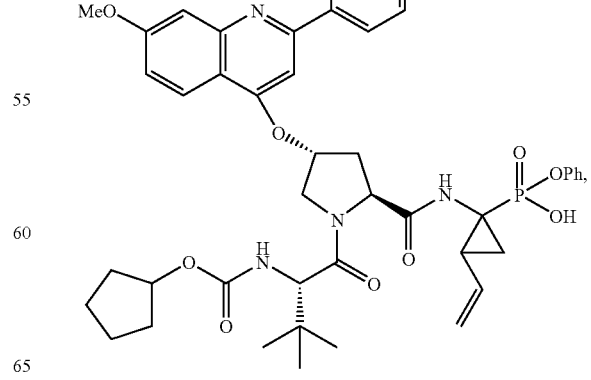

-continued
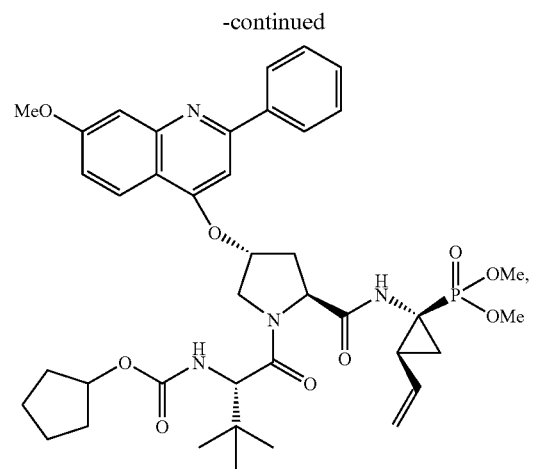
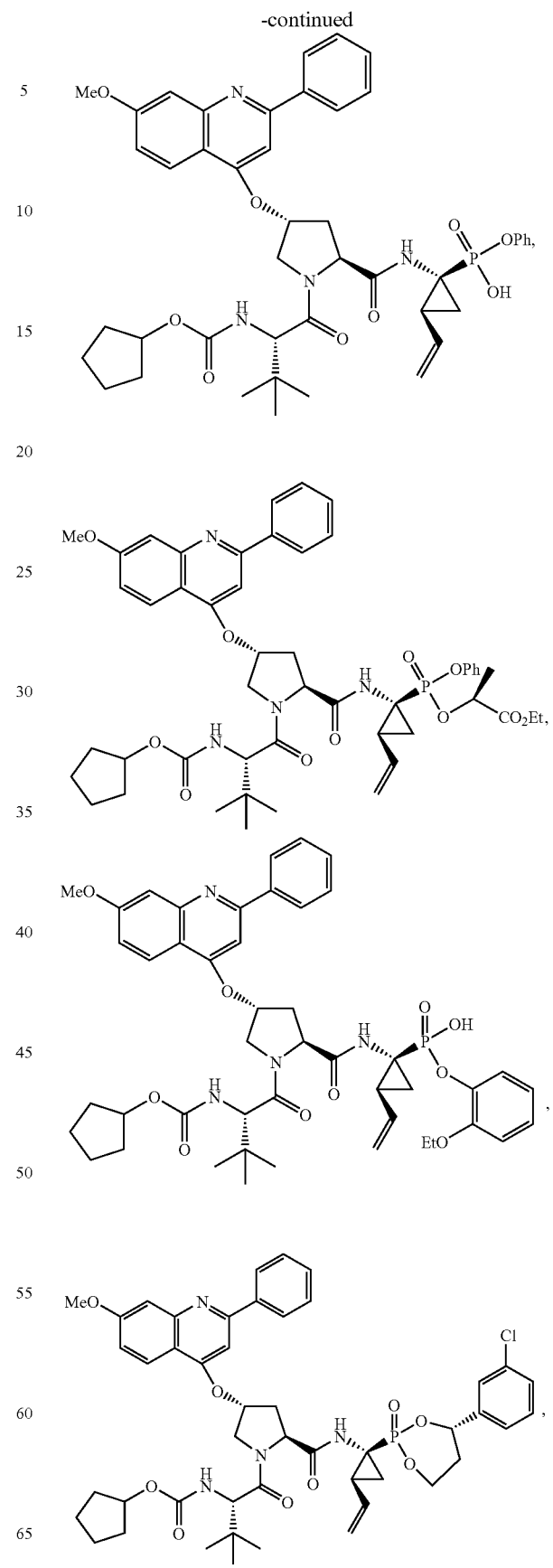

-continued
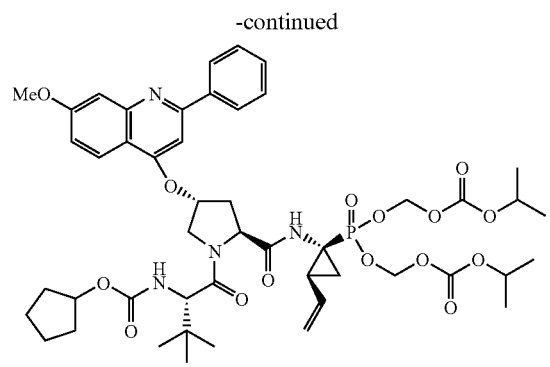
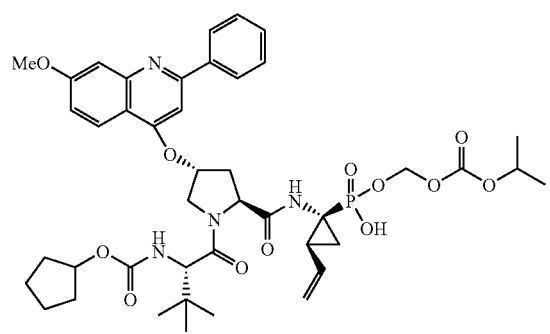
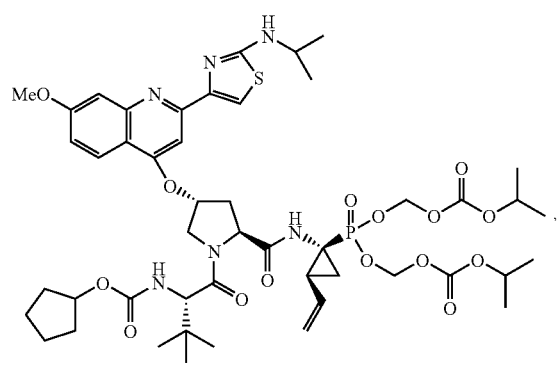
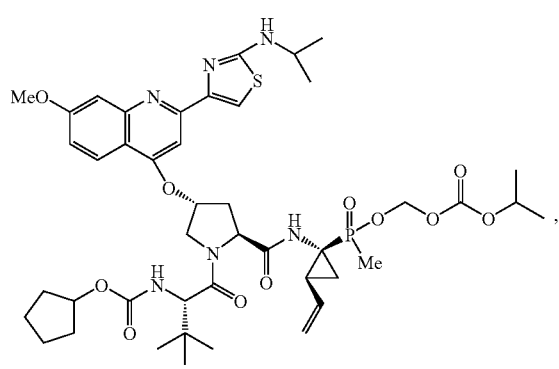
-continued
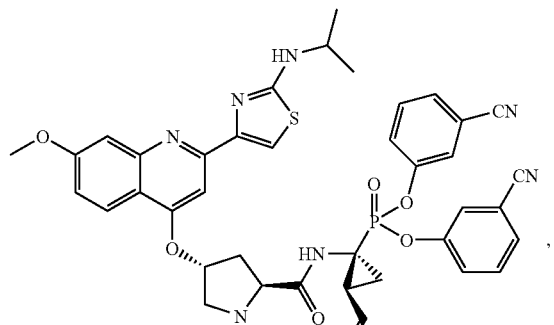
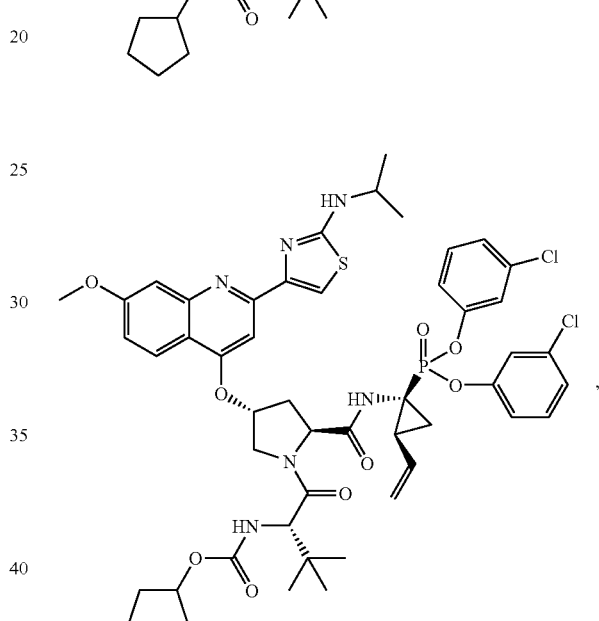
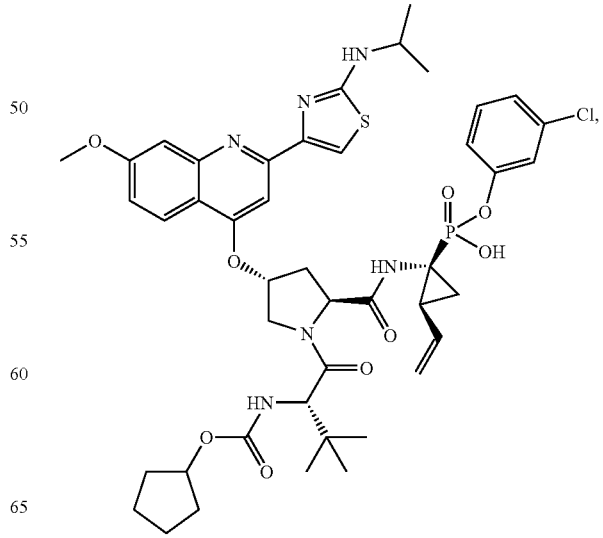

-continued
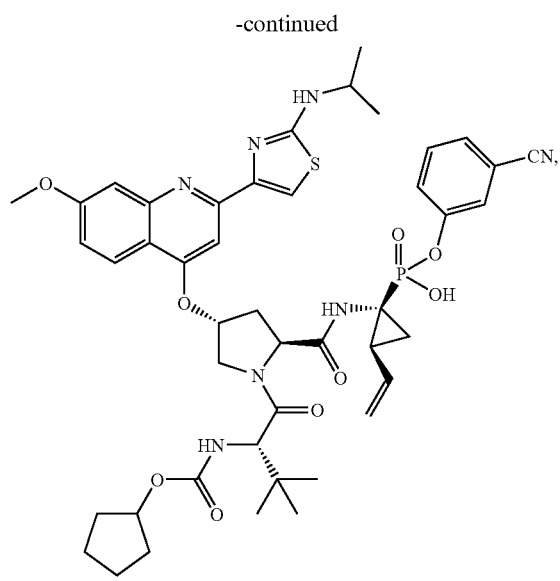
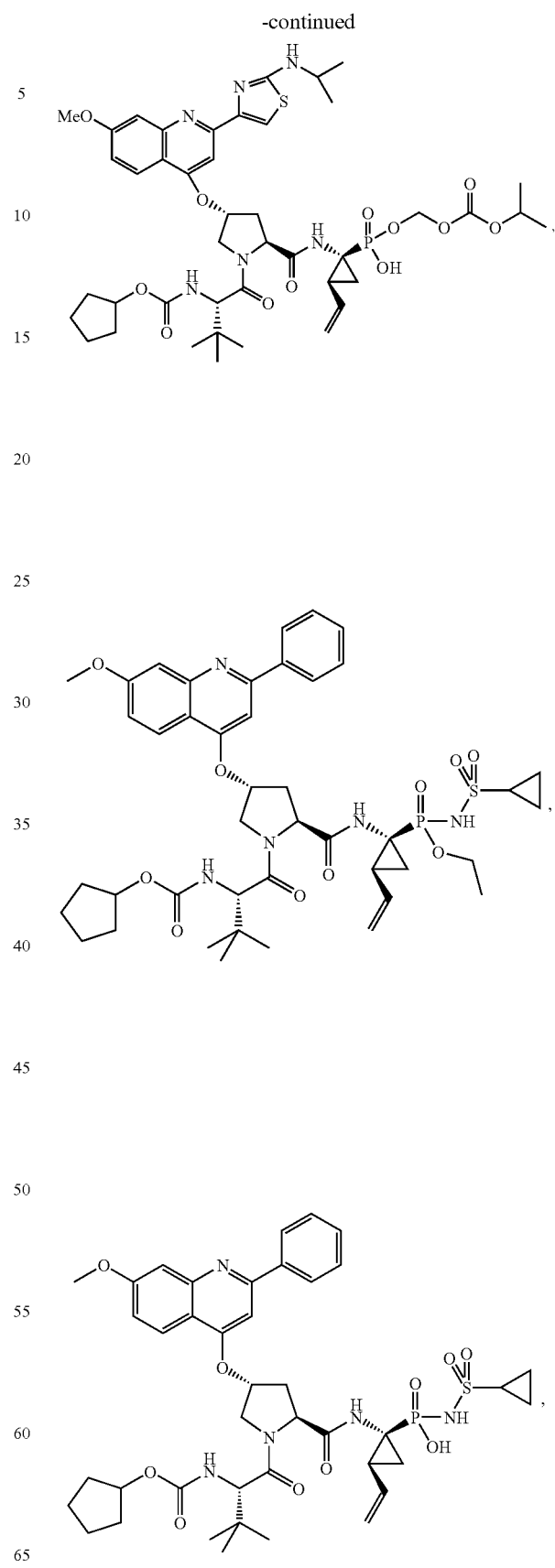

383    384
-continued    -continued
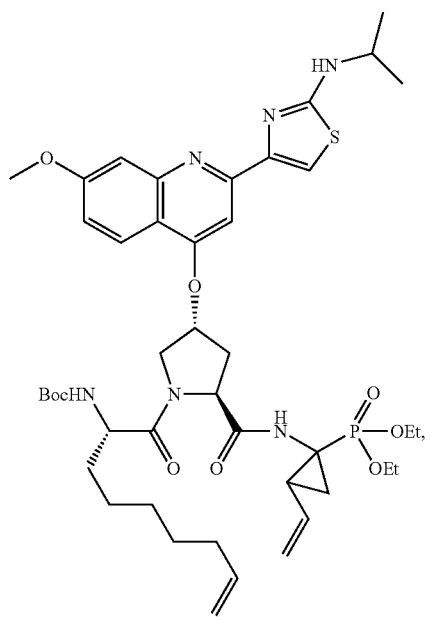
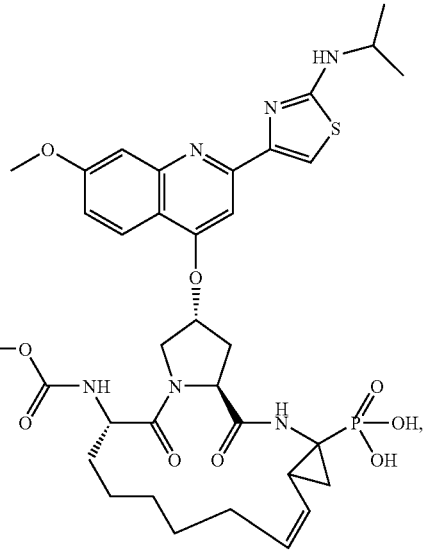
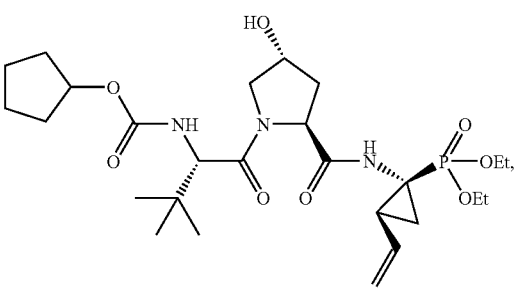
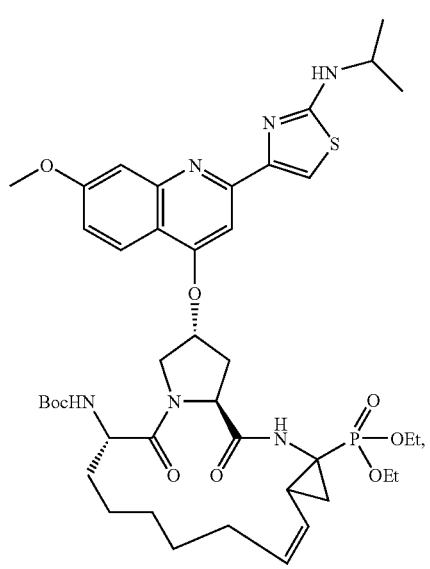
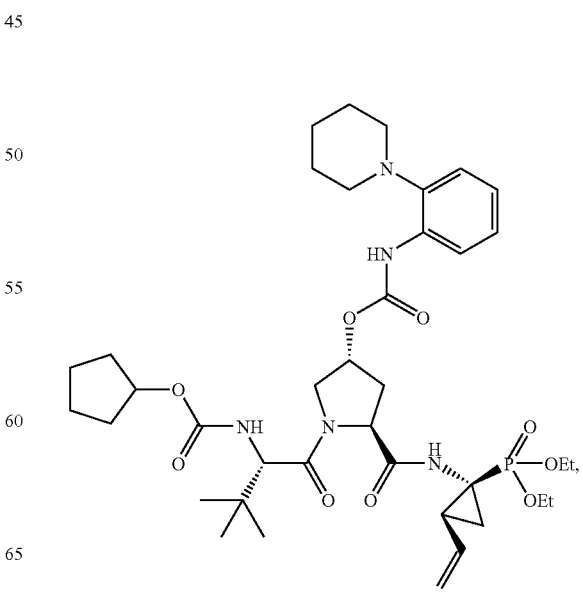

385
-continued
386
-continued
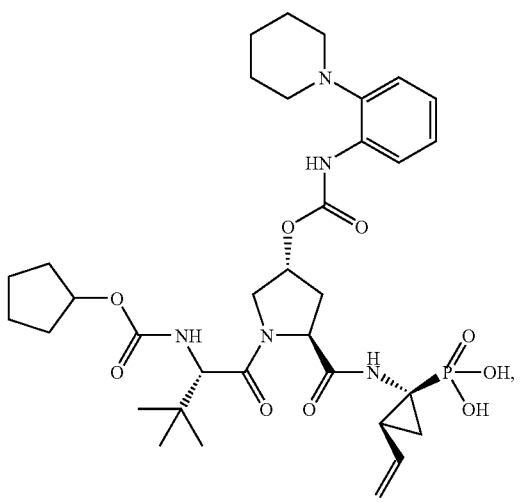
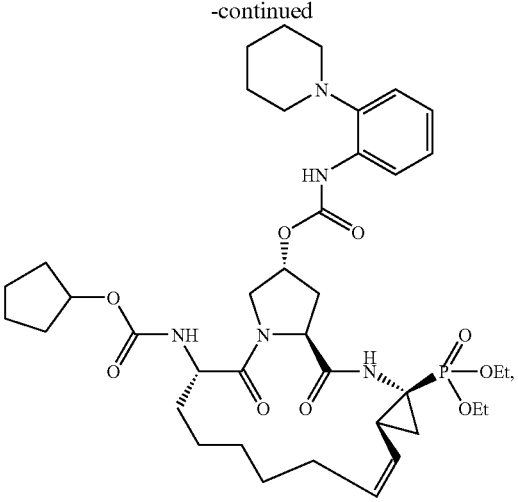

-continued
387
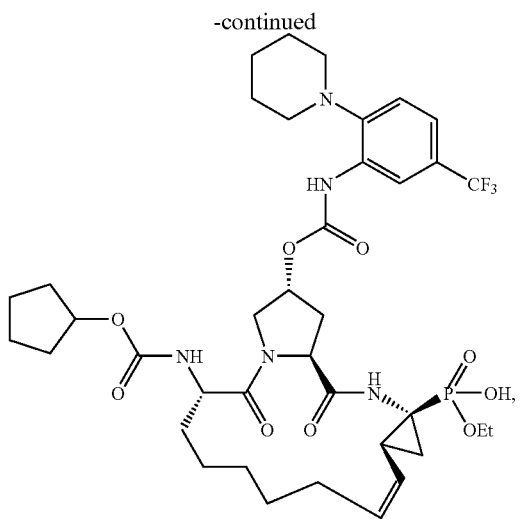
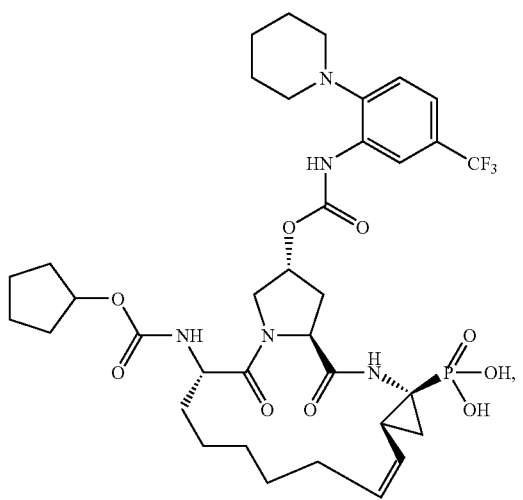
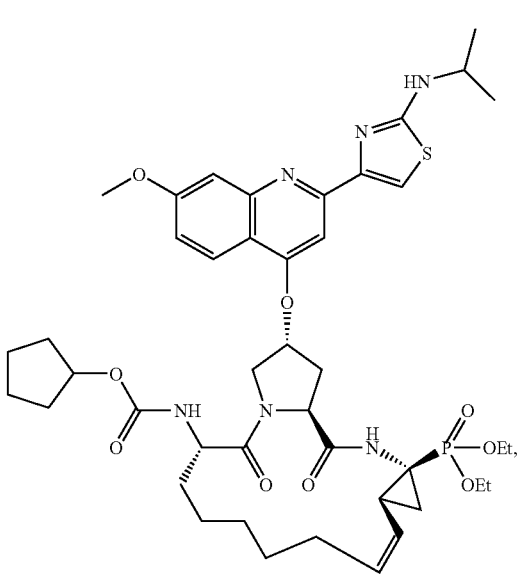
388
-continued
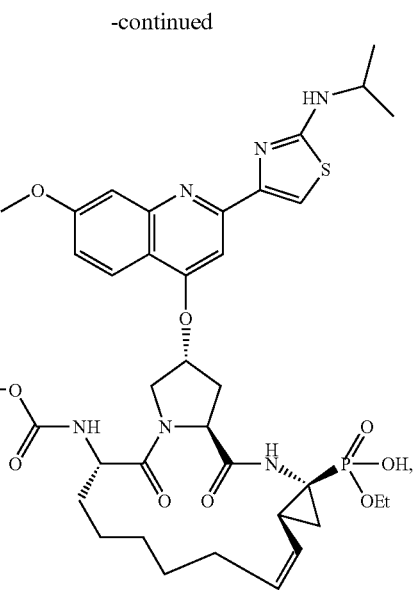
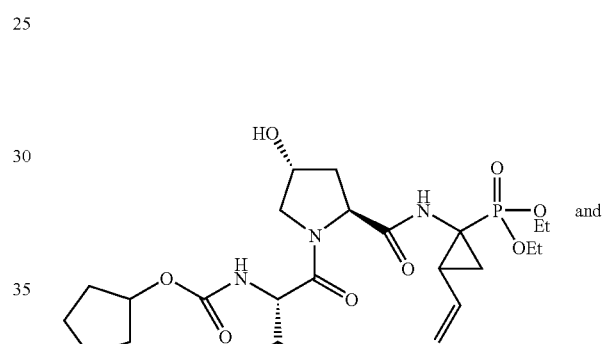 and
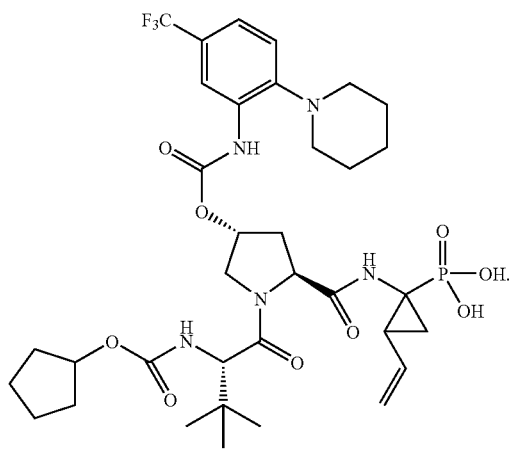

2. A compound selected from the group consisting of:
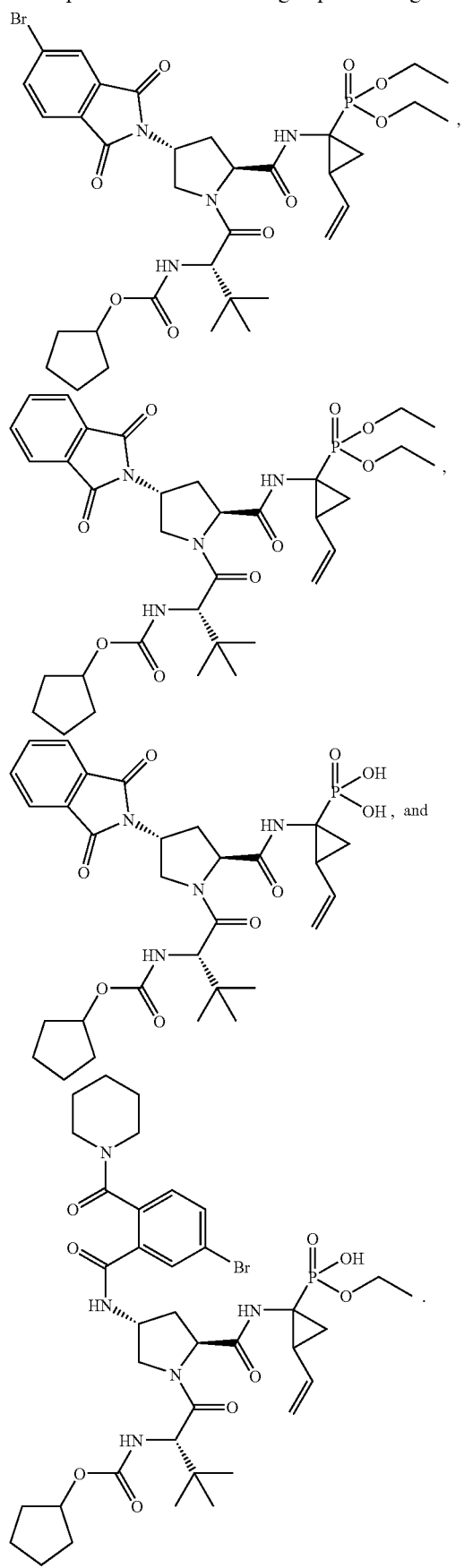
3. A compound selected from the group consisting of:
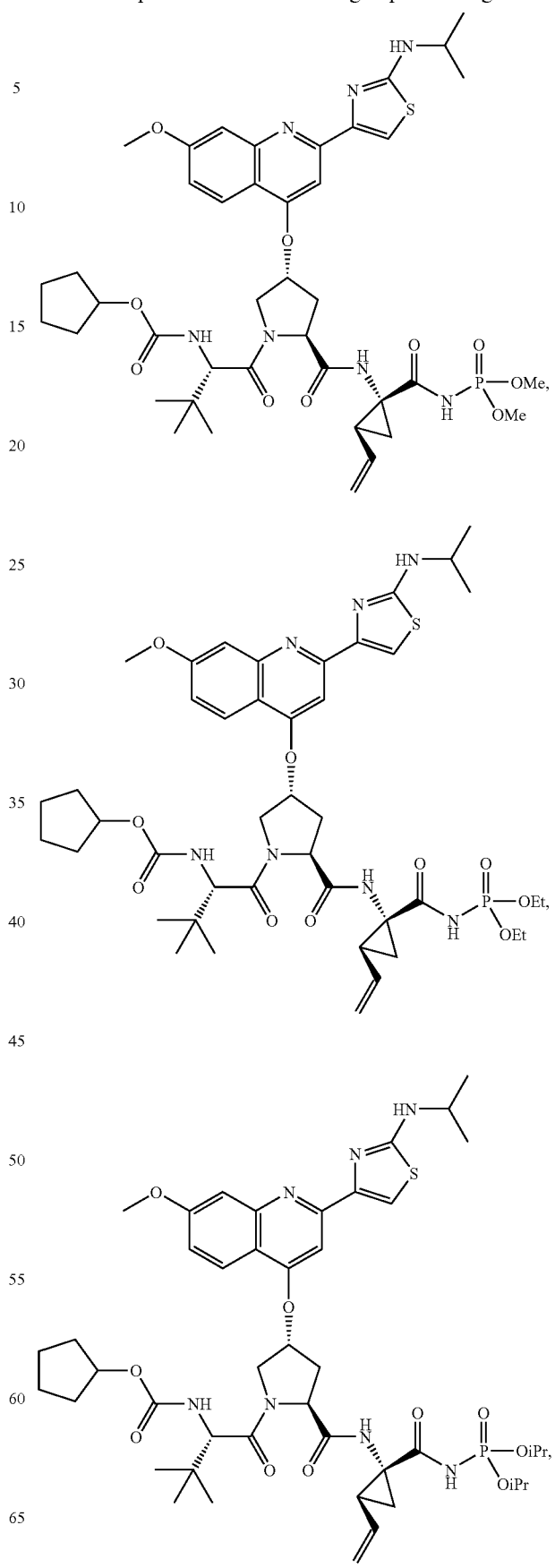

391
-continued
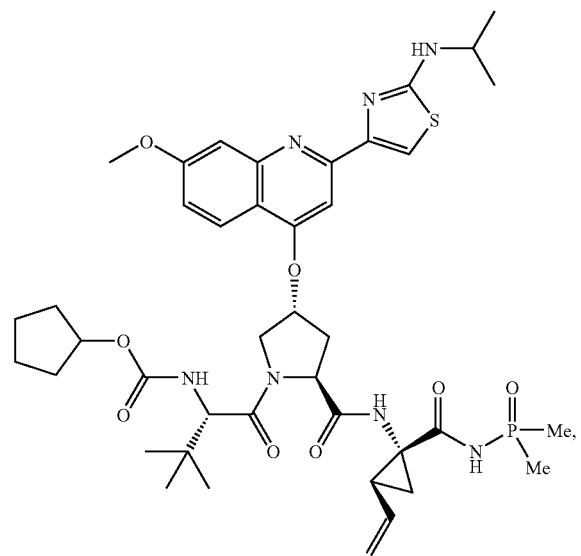
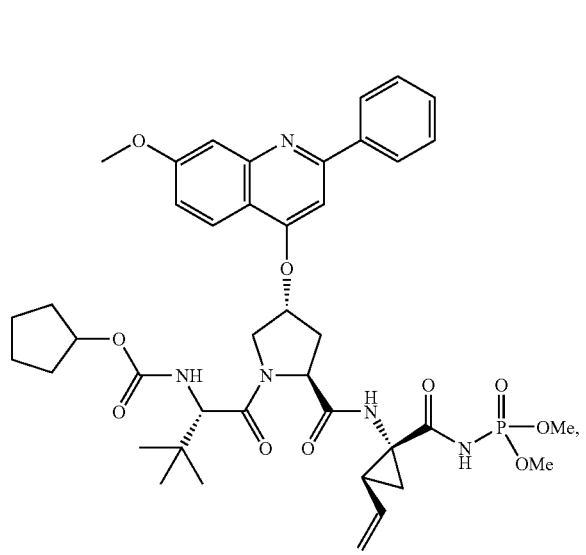
392
-continued
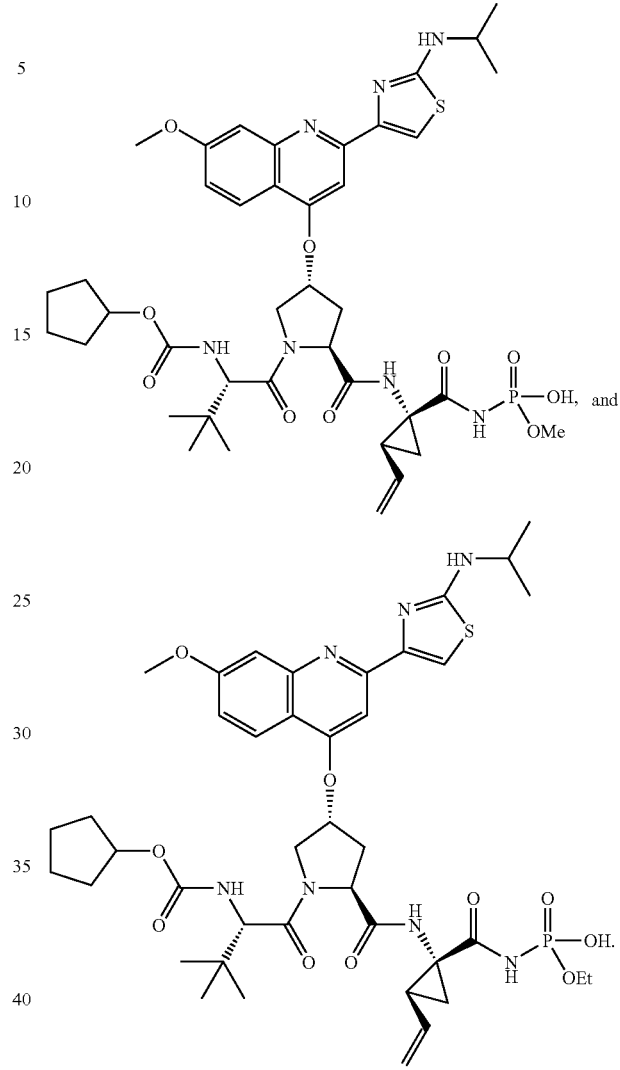
4. A compound selected from the group consisting of:
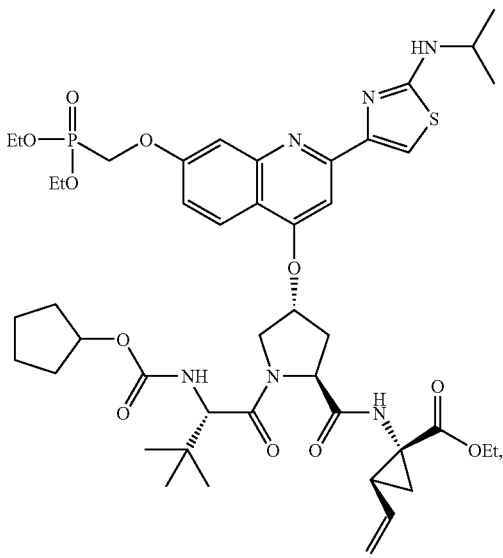

393
-continued
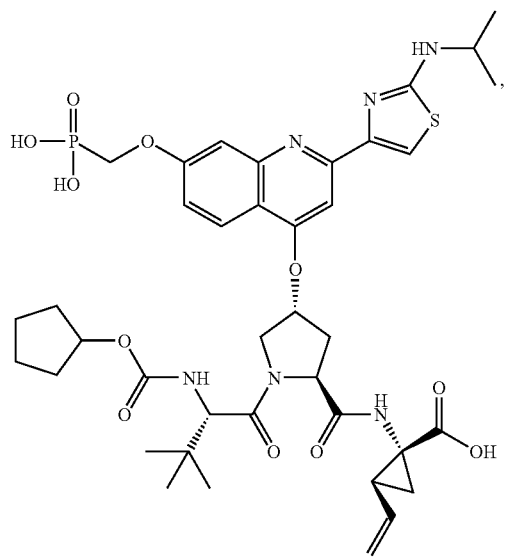
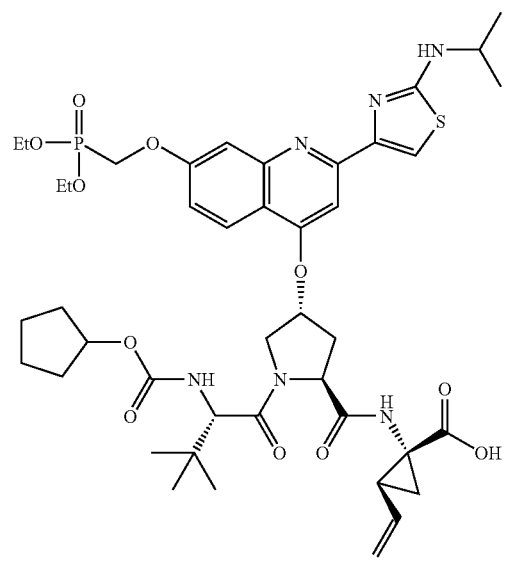
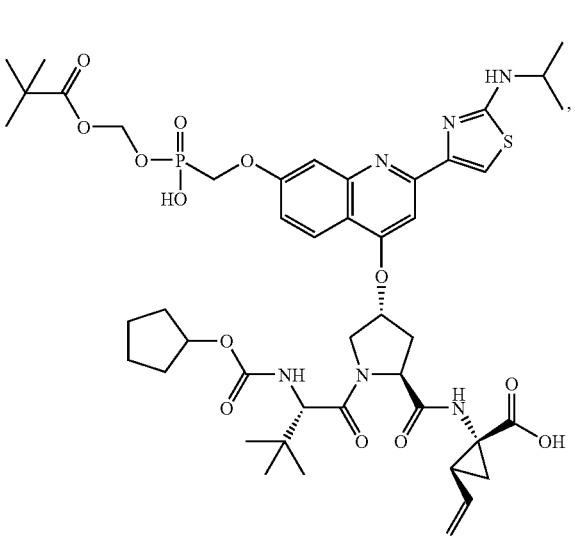
394
-continued
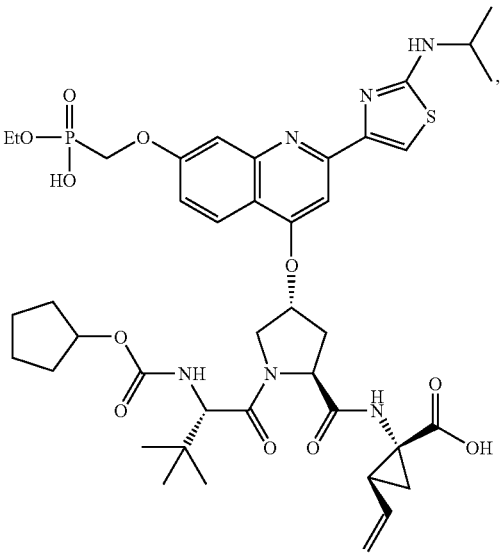
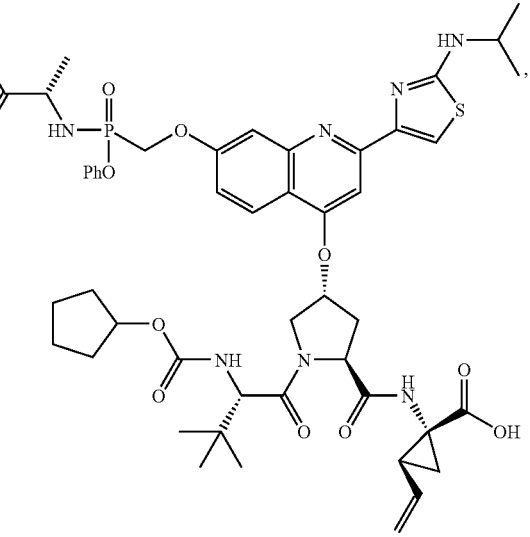
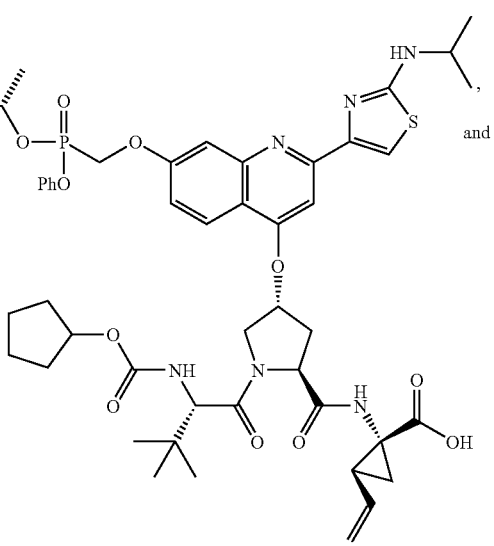
and -continued

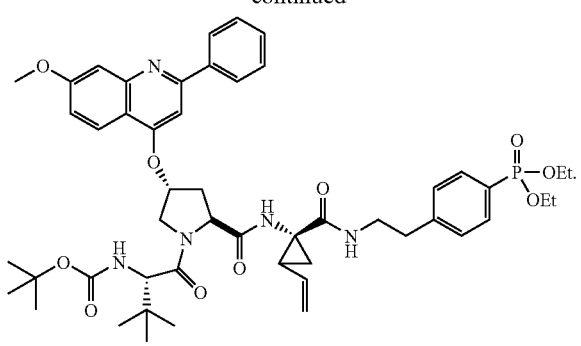

5. A pharmaceutical composition comprising a compound of claim 1, 2, 3, or 4 and at least one pharmaceutically acceptable carrier.

6. The pharmaceutical composition according to claim 5, additionally containing a nucleoside analogue.

7. The pharmaceutical composition according to claim 5, additionally containing an interferon or pegylated interferon.

8. The pharmaceutical composition according to claim 6, wherein said nucleoside analogue is selected from ribavirin, viramidine, levovirin, a L-nucleoside, and isatoribine and said interferon is α-interferon or pegylated interferon.

9. A method of treating hepatitis C, said method comprising administering to an individual a pharmaceutical composition which comprises a therapeutically effective amount of a compound of claim 1, 2, 3, or 4.

* * * * *

UNITED STATES PATENT AND TRADEMARK OFFICE
CERTIFICATE OF CORRECTION

PATENT NO. : 7,642,339 B2  Page 1 of 1
APPLICATION NO. : 11/184429
DATED : January 5, 2010
INVENTOR(S) : Chaudhary et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 490 days.

Signed and Sealed this

Sixteenth Day of November, 2010

David J. Kappos
*Director of the United States Patent and Trademark Office*